(12) United States Patent
Rearick et al.

(10) Patent No.: US 8,776,573 B2
(45) Date of Patent: Jul. 15, 2014

(54) METHODS AND APPARATUS FOR MEASURING ANALYTES

(75) Inventors: Todd Rearick, Cheshire, CT (US);
Melville Davey, Westbrook, CT (US);
Mark Beauchemin, S. Glastonbury, CT (US)

(73) Assignee: Life Technologies Corporation, Carlsbad, CA (US)

( * ) Notice: Subject to any disclaimer, the term of this patent is extended or adjusted under 35 U.S.C. 154(b) by 362 days.

(21) Appl. No.: 13/333,602

(22) Filed: Dec. 21, 2011

(65) Prior Publication Data

US 2012/0265474 A1    Oct. 18, 2012

Related U.S. Application Data

(63) Continuation-in-part of application No. 12/475,311, filed on May 29, 2009, now abandoned.

(60) Provisional application No. 61/428,733, filed on Dec. 30, 2010.

(51) Int. Cl.
*G01N 21/00* (2006.01)

(52) U.S. Cl.
USPC .......................................................... 73/1.02

(58) Field of Classification Search
None
See application file for complete search history.

(56) References Cited

U.S. PATENT DOCUMENTS

| | | | |
|---|---|---|---|
| 4,086,642 A | 4/1978 | Yoshida et al. | |
| 4,411,741 A | 10/1983 | Janata | |
| 4,437,969 A | 3/1984 | Covington et al. | |
| 4,490,678 A | 12/1984 | Kuisl et al. | |
| 4,641,084 A | 2/1987 | Komatsu | |
| 4,660,063 A | 4/1987 | Anthony | |
| 4,691,167 A | 9/1987 | Vlekkert et al. | |
| 4,701,253 A | 10/1987 | Ligtenberg et al. | |
| 4,722,830 A | 2/1988 | Urie et al. | |
| 4,743,954 A | 5/1988 | Brown | |
| 4,764,797 A | 8/1988 | Shaw et al. | |
| 4,777,019 A | 10/1988 | Dandekar | |
| 4,822,566 A | 4/1989 | Newman | |

(Continued)

FOREIGN PATENT DOCUMENTS

| | | |
|---|---|---|
| CN | 102203282 | 9/2011 |
| DE | 19512117 | 10/1996 |

(Continued)

OTHER PUBLICATIONS

[No Author Listed], "ISFET Wikipedia article", *Wikipedia*, Last modified Nov. 7, 2006, 2006.

(Continued)

*Primary Examiner* — Robert R Raevis

(57) ABSTRACT

A method, computer program product, and system are provided to calibrate a sensor array with a plurality of sensors. The method can include sweeping a voltage of a reference electrode from a first voltage to a second voltage, where the reference electrode is in fluid communication with the sensor array. The output voltage of each of the plurality of sensors can be monitored at one or more voltages within the first and second voltages. An overall average gain of the plurality of sensors can be calculated at each of the one or more voltages. Further, an acquisition window for the sensor may can be determined. The acquisition window can include a maximum distribution of sensors that provides a maximal overall average gain at a particular reference electrode voltage.

20 Claims, 132 Drawing Sheets

(56) References Cited

U.S. PATENT DOCUMENTS

| | | |
|---|---|---|
| 4,863,849 A | 9/1989 | Melamede |
| 4,864,229 A | 9/1989 | Lauks et al. |
| 4,874,499 A | 10/1989 | Smith et al. |
| 4,971,903 A | 11/1990 | Hyman |
| 5,009,766 A | 4/1991 | Lauks |
| 5,038,192 A | 8/1991 | Bonneau |
| 5,110,441 A | 5/1992 | Kinlen et al. |
| 5,113,870 A | 5/1992 | Rossenfeld |
| 5,138,251 A | 8/1992 | Koshiishi et al. |
| 5,151,759 A | 9/1992 | Vinal |
| 5,164,319 A | 11/1992 | Hafeman et al. |
| 5,284,566 A | 2/1994 | Cuomo et al. |
| 5,317,407 A | 5/1994 | Michon |
| 5,319,226 A | 6/1994 | Sohn et al. |
| 5,407,854 A | 4/1995 | Baxter et al. |
| 5,436,149 A | 7/1995 | Barnes |
| 5,439,839 A | 8/1995 | Jang |
| 5,466,348 A | 11/1995 | Holm-Kennedy |
| 5,490,971 A | 2/1996 | Gifford et al. |
| 5,554,339 A | 9/1996 | Cozzette et al. |
| 5,583,462 A | 12/1996 | Grasshoff |
| 5,593,838 A | 1/1997 | Zanzucchi et al. |
| 5,600,451 A | 2/1997 | Maki |
| 5,631,704 A | 5/1997 | Dickinson et al. |
| 5,637,469 A | 6/1997 | Wilding et al. |
| 5,702,964 A | 12/1997 | Lee |
| 5,793,230 A | 8/1998 | Chu et al. |
| 5,846,708 A | 12/1998 | Hollis et al. |
| 5,911,873 A | 6/1999 | McCarron et al. |
| 5,912,560 A | 6/1999 | Pasternak |
| 5,922,591 A | 7/1999 | Anderson et al. |
| 5,923,421 A | 7/1999 | Rajic et al. |
| 5,958,703 A | 9/1999 | Dower et al. |
| 5,965,452 A | 10/1999 | Kovacs |
| 6,002,299 A | 12/1999 | Thomsen |
| 6,107,032 A | 8/2000 | Kilger et al. |
| 6,195,585 B1 | 2/2001 | Karunasiri et al. |
| 6,210,891 B1 | 4/2001 | Nyren et al. |
| 6,255,678 B1 | 7/2001 | Sawada et al. |
| 6,274,320 B1 | 8/2001 | Rothberg et al. |
| 6,327,410 B1 | 12/2001 | Walt et al. |
| 6,355,431 B1 | 3/2002 | Chee et al. |
| 6,361,671 B1 | 3/2002 | Mathies et al. |
| 6,384,684 B1 | 5/2002 | Redman-White |
| 6,403,957 B1 | 6/2002 | Fodor et al. |
| 6,406,848 B1 | 6/2002 | Bridgham et al. |
| 6,413,792 B1 | 7/2002 | Sauer et al. |
| 6,429,027 B1 | 8/2002 | Chee et al. |
| 6,432,360 B1 | 8/2002 | Church |
| 6,433,386 B1 | 8/2002 | Yun et al. |
| 6,459,398 B1 | 10/2002 | Gureshnik et al. |
| 6,465,178 B2 | 10/2002 | Chappa et al. |
| 6,475,728 B1 | 11/2002 | Martin et al. |
| 6,482,639 B2 | 11/2002 | Snow et al. |
| 6,485,944 B1 | 11/2002 | Church et al. |
| 6,499,499 B2 | 12/2002 | Dantsker et al. |
| 6,511,803 B1 | 1/2003 | Church et al. |
| 6,518,024 B2 | 2/2003 | Choong et al. |
| 6,518,146 B1 | 2/2003 | Singh et al. |
| 6,535,824 B1 | 3/2003 | Mansky et al. |
| 6,537,881 B1 | 3/2003 | Rangarajan et al. |
| 6,538,593 B2 | 3/2003 | Yang et al. |
| 6,545,620 B2 | 4/2003 | Groeneweg |
| 6,602,702 B1 | 8/2003 | McDevitt et al. |
| 6,605,428 B2 | 8/2003 | Klinger et al. |
| 6,613,513 B1 | 9/2003 | Parce et al. |
| 6,624,637 B1 | 9/2003 | Pechstein |
| 6,627,154 B1 | 9/2003 | Goodman et al. |
| 6,654,505 B2 | 11/2003 | Bridgham et al. |
| 6,682,899 B2 | 1/2004 | Bryan et al. |
| 6,682,936 B2 | 1/2004 | Kovacs |
| 6,700,814 B1 | 3/2004 | Nahas et al. |
| 6,780,591 B2 | 8/2004 | Williams et al. |
| 6,806,052 B2 | 10/2004 | Bridgham et al. |
| 6,828,100 B1 | 12/2004 | Ronaghi |
| 6,831,994 B2 | 12/2004 | Bridgham et al. |
| 6,859,570 B2 | 2/2005 | Walt et al. |
| 6,888,194 B2 | 5/2005 | Yoshino |
| 6,919,211 B1 | 7/2005 | Fodor et al. |
| 6,926,865 B2 | 8/2005 | Howard |
| 6,939,451 B2 | 9/2005 | Zhao et al. |
| 6,953,958 B2 | 10/2005 | Baxter et al. |
| 6,969,488 B2 | 11/2005 | Bridgham et al. |
| 6,998,274 B2 | 2/2006 | Chee et al. |
| 7,019,305 B2 | 3/2006 | Eversmann et al. |
| 7,022,288 B1 | 4/2006 | Boss |
| 7,033,754 B2 | 4/2006 | Chee et al. |
| 7,037,687 B2 | 5/2006 | Williams et al. |
| 7,049,645 B2 | 5/2006 | Sawada et al. |
| 7,060,431 B2 | 6/2006 | Chee et al. |
| 7,085,502 B2 | 8/2006 | Shushakov et al. |
| 7,087,387 B2 | 8/2006 | Gerdes et al. |
| 7,090,975 B2 | 8/2006 | Shultz et al. |
| 7,097,973 B1 | 8/2006 | Zenhausern |
| 7,105,300 B2 | 9/2006 | Parce et al. |
| 7,169,560 B2 | 1/2007 | Lapidus et al. |
| 7,190,026 B2 | 3/2007 | Lotfi et al. |
| 7,192,745 B2 | 3/2007 | Jaeger |
| 7,193,453 B2 | 3/2007 | Wei et al. |
| 7,211,390 B2 | 5/2007 | Rothberg |
| 7,223,540 B2 | 5/2007 | Pourmand et al. |
| 7,226,734 B2 | 6/2007 | Chee et al. |
| 7,238,323 B2 | 7/2007 | Knapp et al. |
| 7,244,559 B2 | 7/2007 | Rothberg et al. |
| 7,244,567 B2 | 7/2007 | Chen et al. |
| 7,264,929 B2 | 9/2007 | Rothberg et al. |
| 7,264,934 B2 | 9/2007 | Fuller |
| 7,265,929 B2 | 9/2007 | Umeda et al. |
| 7,276,749 B2 | 10/2007 | Martin et al. |
| 7,282,370 B2 | 10/2007 | Bridgham et al. |
| 7,291,496 B2 | 11/2007 | Holm-Kennedy |
| 7,297,518 B2 | 11/2007 | Quake et al. |
| 7,298,475 B2 | 11/2007 | Gandhi et al. |
| 7,303,875 B1 | 12/2007 | Bock et al. |
| 7,317,216 B2 | 1/2008 | Holm-Kennedy |
| 7,323,305 B2 | 1/2008 | Leamon et al. |
| 7,335,762 B2 | 2/2008 | Rothberg et al. |
| 7,359,058 B2 | 4/2008 | Kranz et al. |
| 7,363,717 B2 * | 4/2008 | Ekseth et al. ............... 33/304 |
| 7,381,936 B2 | 6/2008 | Tan et al. |
| 7,394,263 B2 | 7/2008 | Pechstein et al. |
| 7,419,636 B2 | 9/2008 | Aker et al. |
| 7,455,971 B2 | 11/2008 | Chee et al. |
| 7,462,512 B2 | 12/2008 | Levon et al. |
| 7,465,512 B2 | 12/2008 | Wright et al. |
| 7,466,258 B1 | 12/2008 | Akopyan et al. |
| 7,470,352 B2 | 12/2008 | Eversmann et al. |
| 7,482,153 B2 | 1/2009 | Okada et al. |
| 7,515,124 B2 | 4/2009 | Yaguma et al. |
| 7,575,865 B2 | 8/2009 | Leamon et al. |
| 7,595,883 B1 | 9/2009 | El Gamal et al. |
| 7,605,650 B2 | 10/2009 | Forbes |
| 7,608,810 B2 | 10/2009 | Yamada |
| 7,609,303 B1 | 10/2009 | Lee |
| 7,612,817 B2 | 11/2009 | Tay |
| 7,667,501 B2 | 2/2010 | Surendranath et al. |
| 7,686,929 B2 | 3/2010 | Toumazou et al. |
| 7,695,907 B2 | 4/2010 | Miyahara et al. |
| 7,733,401 B2 | 6/2010 | Takeda |
| 7,785,790 B1 | 8/2010 | Church et al. |
| 7,859,029 B2 | 12/2010 | Lee et al. |
| 7,885,490 B2 | 2/2011 | Heideman et al. |
| 7,888,013 B2 | 2/2011 | Miyahara et al. |
| 7,888,708 B2 | 2/2011 | Yazawa et al. |
| 7,923,240 B2 | 4/2011 | Xu |
| 7,932,034 B2 | 4/2011 | Esfandyarpour et al. |
| 7,948,015 B2 | 5/2011 | Rothberg et al. |
| 8,067,731 B2 | 11/2011 | Matyjaszczyk et al. |
| 8,124,936 B1 | 2/2012 | Lagna |
| 8,199,859 B2 | 6/2012 | Zerbe et al. |
| 8,217,433 B1 | 7/2012 | Fife |
| 8,231,831 B2 | 7/2012 | Hartzell et al. |
| 8,232,813 B2 | 7/2012 | Burdett et al. |
| 8,247,849 B2 | 8/2012 | Fife et al. |

(56) References Cited

U.S. PATENT DOCUMENTS

| | | |
|---|---|---|
| 8,262,900 B2 | 9/2012 | Rothberg et al. |
| 8,263,336 B2 | 9/2012 | Rothberg et al. |
| 8,264,014 B2 | 9/2012 | Rothberg et al. |
| 8,269,261 B2 | 9/2012 | Rothberg et al. |
| 8,293,082 B2 | 10/2012 | Rothberg et al. |
| 8,306,757 B2 | 11/2012 | Rothberg et al. |
| 8,313,625 B2 | 11/2012 | Rothberg et al. |
| 8,313,639 B2 | 11/2012 | Rothberg et al. |
| 8,317,999 B2 | 11/2012 | Rothberg et al. |
| 8,426,898 B2 | 4/2013 | Rothberg et al. |
| 8,449,824 B2 | 5/2013 | Sun |
| 8,558,288 B2 | 10/2013 | Rothberg et al. |
| 2001/0007418 A1 | 7/2001 | Komatsu et al. |
| 2001/0024790 A1 | 9/2001 | Kambara et al. |
| 2002/0001801 A1 | 1/2002 | Fan et al. |
| 2002/0012930 A1 | 1/2002 | Rothberg et al. |
| 2002/0012933 A1 | 1/2002 | Rothberg et al. |
| 2002/0042059 A1 | 4/2002 | Makarov et al. |
| 2002/0042388 A1 | 4/2002 | Cooper et al. |
| 2002/0050611 A1 | 5/2002 | Yitzchaik et al. |
| 2002/0061529 A1 | 5/2002 | Bridgham et al. |
| 2002/0086318 A1 | 7/2002 | Manalis et al. |
| 2002/0094533 A1 | 7/2002 | Hess et al. |
| 2002/0117659 A1 | 8/2002 | Lieber et al. |
| 2002/0117694 A1 | 8/2002 | Migliorato et al. |
| 2002/0131899 A1 | 9/2002 | Kovacs |
| 2002/0132221 A1 | 9/2002 | Chee et al. |
| 2002/0137062 A1 | 9/2002 | Williams et al. |
| 2002/0150909 A1 | 10/2002 | Stuelpnagel et al. |
| 2002/0168678 A1 | 11/2002 | Williams et al. |
| 2002/0169574 A1* | 11/2002 | Jensen et al. .............. 702/104 |
| 2002/0172963 A1 | 11/2002 | Kelley et al. |
| 2002/0187515 A1 | 12/2002 | Chee et al. |
| 2003/0032052 A1 | 2/2003 | Hadd et al. |
| 2003/0044799 A1 | 3/2003 | Matson |
| 2003/0049624 A1 | 3/2003 | Shultz et al. |
| 2003/0054396 A1 | 3/2003 | Weiner |
| 2003/0064366 A1 | 4/2003 | Hardin et al. |
| 2003/0068629 A1 | 4/2003 | Rothberg et al. |
| 2003/0077615 A1 | 4/2003 | Bridgham et al. |
| 2003/0100102 A1 | 5/2003 | Rothberg et al. |
| 2003/0102510 A1 | 6/2003 | Lim et al. |
| 2003/0108867 A1 | 6/2003 | Chee et al. |
| 2003/0124572 A1 | 7/2003 | Umek et al. |
| 2003/0124599 A1 | 7/2003 | Chen et al. |
| 2003/0138809 A1 | 7/2003 | Williams et al. |
| 2003/0141928 A1 | 7/2003 | Lee |
| 2003/0141929 A1 | 7/2003 | Casper et al. |
| 2003/0148301 A1 | 8/2003 | Aono et al. |
| 2003/0148344 A1 | 8/2003 | Rothberg et al. |
| 2003/0157504 A1 | 8/2003 | Chee et al. |
| 2003/0186262 A1 | 10/2003 | Cailloux |
| 2003/0194740 A1 | 10/2003 | Williams |
| 2003/0211502 A1 | 11/2003 | Sauer et al. |
| 2003/0215857 A1 | 11/2003 | Kilger et al. |
| 2003/0224419 A1 | 12/2003 | Corcoran et al. |
| 2003/0231531 A1 | 12/2003 | Baxter et al. |
| 2004/0012998 A1 | 1/2004 | Chien et al. |
| 2004/0023253 A1 | 2/2004 | Kunwar et al. |
| 2004/0038420 A1 | 2/2004 | Gelbart et al. |
| 2004/0049237 A1 | 3/2004 | Larson et al. |
| 2004/0079636 A1 | 4/2004 | Hsia et al. |
| 2004/0106211 A1* | 6/2004 | Kauer et al. ............... 436/169 |
| 2004/0134798 A1 | 7/2004 | Toumazou et al. |
| 2004/0136866 A1 | 7/2004 | Pontis et al. |
| 2004/0146849 A1 | 7/2004 | Huang et al. |
| 2004/0185484 A1 | 9/2004 | Costa et al. |
| 2004/0197803 A1 | 10/2004 | Yaku et al. |
| 2004/0207384 A1 | 10/2004 | Brederlow et al. |
| 2004/0235216 A1 | 11/2004 | Rhodes |
| 2004/0248161 A1 | 12/2004 | Rothberg et al. |
| 2005/0006234 A1 | 1/2005 | Hassibi |
| 2005/0009022 A1 | 1/2005 | Weiner et al. |
| 2005/0017190 A1 | 1/2005 | Eversmann et al. |
| 2005/0031490 A1 | 2/2005 | Gumbrecht et al. |
| 2005/0032075 A1 | 2/2005 | Yaku et al. |
| 2005/0032076 A1 | 2/2005 | Williams et al. |
| 2005/0042627 A1 | 2/2005 | Chakrabarti et al. |
| 2005/0058990 A1 | 3/2005 | Guia et al. |
| 2005/0062093 A1 | 3/2005 | Sawada et al. |
| 2005/0079510 A1 | 4/2005 | Berka et al. |
| 2005/0093072 A1 | 5/2005 | Bonges et al. |
| 2005/0106587 A1 | 5/2005 | Klapproth et al. |
| 2005/0119497 A1 | 6/2005 | Hong et al. |
| 2005/0130173 A1 | 6/2005 | Leamon et al. |
| 2005/0130188 A1 | 6/2005 | Walt et al. |
| 2005/0142033 A1 | 6/2005 | Glezer et al. |
| 2005/0156207 A1 | 7/2005 | Yazawa et al. |
| 2005/0181440 A1 | 8/2005 | Chee et al. |
| 2005/0191698 A1 | 9/2005 | Chee et al. |
| 2005/0212016 A1 | 9/2005 | Brunner et al. |
| 2005/0221473 A1 | 10/2005 | Dubin et al. |
| 2005/0224346 A1 | 10/2005 | Holm-Kennedy |
| 2005/0227264 A1 | 10/2005 | Nobile et al. |
| 2005/0230245 A1 | 10/2005 | Morgenshtein et al. |
| 2005/0230271 A1 | 10/2005 | Levon et al. |
| 2005/0233318 A1 | 10/2005 | Chee et al. |
| 2005/0239132 A1 | 10/2005 | Klapprith |
| 2005/0266456 A1 | 12/2005 | Williams et al. |
| 2006/0016699 A1 | 1/2006 | Kamahori et al. |
| 2006/0024711 A1 | 2/2006 | Lapidus et al. |
| 2006/0040297 A1 | 2/2006 | Leamon et al. |
| 2006/0051807 A1 | 3/2006 | Fuller |
| 2006/0057604 A1 | 3/2006 | Chen et al. |
| 2006/0073513 A1 | 4/2006 | Chee et al. |
| 2006/0093488 A1 | 5/2006 | Wong et al. |
| 2006/0105373 A1 | 5/2006 | Pourmand et al. |
| 2006/0115857 A1 | 6/2006 | Keen |
| 2006/0121670 A1 | 6/2006 | Stasiak |
| 2006/0134633 A1 | 6/2006 | Chen et al. |
| 2006/0141474 A1 | 6/2006 | Miyahara et al. |
| 2006/0154399 A1 | 7/2006 | Sauer et al. |
| 2006/0166203 A1 | 7/2006 | Tooke et al. |
| 2006/0182664 A1 | 8/2006 | Peck et al. |
| 2006/0183145 A1 | 8/2006 | Turner |
| 2006/0197118 A1 | 9/2006 | Migliorato et al. |
| 2006/0199193 A1 | 9/2006 | Koo et al. |
| 2006/0199493 A1 | 9/2006 | Hartmann et al. |
| 2006/0205061 A1 | 9/2006 | Roukes |
| 2006/0219558 A1 | 10/2006 | Hafeman et al. |
| 2006/0228721 A1 | 10/2006 | Leamon et al. |
| 2006/0244147 A1 | 11/2006 | Lee et al. |
| 2006/0246497 A1 | 11/2006 | Huang et al. |
| 2006/0269927 A1 | 11/2006 | Lieber et al. |
| 2007/0059741 A1 | 3/2007 | Kamahori et al. |
| 2007/0069291 A1 | 3/2007 | Stuber et al. |
| 2007/0087362 A1 | 4/2007 | Church et al. |
| 2007/0087401 A1 | 4/2007 | Neilson et al. |
| 2007/0092872 A1 | 4/2007 | Rothberg et al. |
| 2007/0095663 A1 | 5/2007 | Chou et al. |
| 2007/0099208 A1 | 5/2007 | Drmanac et al. |
| 2007/0099351 A1 | 5/2007 | Peters et al. |
| 2007/0109454 A1 | 5/2007 | Chou |
| 2007/0117099 A1 | 5/2007 | Engelhardt et al. |
| 2007/0117137 A1 | 5/2007 | Jaeger |
| 2007/0138028 A1 | 6/2007 | Chodavarapu et al. |
| 2007/0138132 A1 | 6/2007 | Barth |
| 2007/0172865 A1 | 7/2007 | Hardin et al. |
| 2007/0212681 A1 | 9/2007 | Shapiro et al. |
| 2007/0217963 A1 | 9/2007 | Elizarov et al. |
| 2007/0231824 A1 | 10/2007 | Chee et al. |
| 2007/0233477 A1 | 10/2007 | Halowani et al. |
| 2007/0252176 A1 | 11/2007 | Shim et al. |
| 2007/0262363 A1 | 11/2007 | Tao et al. |
| 2007/0278488 A1 | 12/2007 | Hirabayashi et al. |
| 2008/0003142 A1 | 1/2008 | Link et al. |
| 2008/0012007 A1 | 1/2008 | Li et al. |
| 2008/0014589 A1 | 1/2008 | Link et al. |
| 2008/0032295 A1 | 2/2008 | Toumazou et al. |
| 2008/0035494 A1 | 2/2008 | Gomez et al. |
| 2008/0096216 A1 | 4/2008 | Quake |
| 2008/0115361 A1 | 5/2008 | Santini et al. |
| 2008/0121946 A1 | 5/2008 | Youn et al. |
| 2008/0132693 A1 | 6/2008 | Berka et al. |

(56) References Cited

U.S. PATENT DOCUMENTS

| | | |
|---|---|---|
| 2008/0145910 A1 | 6/2008 | Ward et al. |
| 2008/0166727 A1 | 7/2008 | Esfandyarpour et al. |
| 2008/0176271 A1 | 7/2008 | Silver et al. |
| 2008/0186093 A1 | 8/2008 | Forbes |
| 2008/0197022 A1 | 8/2008 | Suzuki et al. |
| 2008/0213770 A1 | 9/2008 | Williams et al. |
| 2008/0230386 A1 | 9/2008 | Srinivasan et al. |
| 2008/0265985 A1 | 10/2008 | Toumazou et al. |
| 2008/0286762 A1 | 11/2008 | Miyahara et al. |
| 2008/0286767 A1 | 11/2008 | Miyahara et al. |
| 2009/0026082 A1 | 1/2009 | Rothberg et al. |
| 2009/0030117 A1 | 1/2009 | Lanphere et al. |
| 2009/0032401 A1 | 2/2009 | Ronaghi et al. |
| 2009/0033370 A1 | 2/2009 | Sarig et al. |
| 2009/0048124 A1 | 2/2009 | Leamon et al. |
| 2009/0062132 A1 | 3/2009 | Borner |
| 2009/0079414 A1 | 3/2009 | Levon et al. |
| 2009/0108831 A1 | 4/2009 | Levon et al. |
| 2009/0127589 A1 | 5/2009 | Rothberg et al. |
| 2009/0140763 A1 | 6/2009 | Kim |
| 2009/0143244 A1 | 6/2009 | Bridgham et al. |
| 2009/0156425 A1 | 6/2009 | Walt et al. |
| 2009/0170728 A1 | 7/2009 | Walt et al. |
| 2009/0194416 A1 | 8/2009 | Hsiung et al. |
| 2009/0316477 A1 | 12/2009 | Horiuchi |
| 2010/0007326 A1 | 1/2010 | Nakazato |
| 2010/0137143 A1 | 6/2010 | Rothberg et al. |
| 2010/0156454 A1 | 6/2010 | Weir |
| 2010/0188073 A1 | 7/2010 | Rothberg et al. |
| 2010/0197507 A1 | 8/2010 | Rothberg et al. |
| 2010/0244106 A1 | 9/2010 | Parker et al. |
| 2010/0255595 A1 | 10/2010 | Toumazou et al. |
| 2010/0282617 A1 | 11/2010 | Rothberg et al. |
| 2010/0300895 A1 | 12/2010 | Nobile et al. |
| 2010/0301398 A1 | 12/2010 | Rothberg et al. |
| 2011/0037121 A1 | 2/2011 | Lee et al. |
| 2011/0062972 A1 | 3/2011 | Je et al. |
| 2011/0165557 A1 | 7/2011 | Ah et al. |
| 2011/0181253 A1 | 7/2011 | Isham et al. |
| 2011/0217697 A1 | 9/2011 | Rothberg et al. |
| 2011/0230375 A1 | 9/2011 | Rothberg et al. |
| 2011/0236263 A1 | 9/2011 | Sawada et al. |
| 2011/0247933 A1 | 10/2011 | Rothberg et al. |
| 2011/0263463 A1 | 10/2011 | Rothberg et al. |
| 2011/0275522 A1 | 11/2011 | Rothberg et al. |
| 2011/0281737 A1 | 11/2011 | Rothberg et al. |
| 2011/0281741 A1 | 11/2011 | Rothberg et al. |
| 2011/0287945 A1 | 11/2011 | Rothberg et al. |
| 2012/0000274 A1 | 1/2012 | Fife |
| 2012/0001056 A1 | 1/2012 | Fife et al. |
| 2012/0001235 A1 | 1/2012 | Fife |
| 2012/0001236 A1 | 1/2012 | Fife et al. |
| 2012/0001237 A1 | 1/2012 | Fife et al. |
| 2012/0001615 A1 | 1/2012 | Levine et al. |
| 2012/0001646 A1 | 1/2012 | Bolander et al. |
| 2012/0001685 A1 | 1/2012 | Levine et al. |
| 2012/0001779 A1 | 1/2012 | Fife et al. |
| 2012/0013392 A1 | 1/2012 | Rothberg et al. |
| 2012/0022795 A1 | 1/2012 | Johnson et al. |
| 2012/0034607 A1 | 2/2012 | Rothberg et al. |
| 2012/0037961 A1 | 2/2012 | Rothberg et al. |
| 2012/0040844 A1 | 2/2012 | Rothberg et al. |
| 2012/0045844 A1 | 2/2012 | Rothberg et al. |
| 2012/0055811 A1 | 3/2012 | Rothberg et al. |
| 2012/0055813 A1 | 3/2012 | Rothberg et al. |
| 2012/0056248 A1 | 3/2012 | Fife |
| 2012/0074956 A1 | 3/2012 | Fife et al. |
| 2012/0129703 A1 | 5/2012 | Rothberg et al. |
| 2012/0129728 A1 | 5/2012 | Rothberg et al. |
| 2012/0129732 A1 | 5/2012 | Rothberg et al. |
| 2012/0135870 A1 | 5/2012 | Rothberg et al. |
| 2012/0143531 A1 | 6/2012 | Davey et al. |
| 2012/0168307 A1 | 7/2012 | Fife |
| 2012/0173159 A1 | 7/2012 | Davey et al. |
| 2012/0247977 A1 | 10/2012 | Rothberg et al. |
| 2012/0261274 A1 | 10/2012 | Rearick et al. |
| 2012/0265474 A1 | 10/2012 | Rearick et al. |
| 2012/0279859 A1 | 11/2012 | Rothberg et al. |
| 2012/0280285 A1 | 11/2012 | Rothberg et al. |
| 2012/0280286 A1 | 11/2012 | Rothberg et al. |
| 2012/0283146 A1 | 11/2012 | Rothberg et al. |
| 2012/0286332 A1 | 11/2012 | Rothberg et al. |
| 2012/0286333 A1 | 11/2012 | Rothberg et al. |
| 2012/0286771 A1 | 11/2012 | Rothberg et al. |
| 2012/0288853 A1 | 11/2012 | Rothberg et al. |
| 2012/0288976 A1 | 11/2012 | Rothberg et al. |
| 2012/0289413 A1 | 11/2012 | Rothberg et al. |
| 2012/0293158 A1 | 11/2012 | Rothberg et al. |
| 2012/0295795 A1 | 11/2012 | Rothberg et al. |
| 2012/0322054 A1 | 12/2012 | Rothberg et al. |
| 2012/0325683 A1 | 12/2012 | Milgrew |
| 2012/0326213 A1 | 12/2012 | Bustillo et al. |
| 2012/0326767 A1 | 12/2012 | Milgrew |
| 2012/0329043 A1 | 12/2012 | Milgrew |
| 2012/0329044 A1 | 12/2012 | Milgrew |
| 2012/0329192 A1 | 12/2012 | Bustillo et al. |
| 2013/0001653 A1 | 1/2013 | Milgrew et al. |
| 2013/0004948 A1 | 1/2013 | Milgrew |
| 2013/0004949 A1 | 1/2013 | Rearick et al. |
| 2013/0009214 A1 | 1/2013 | Bustillo et al. |
| 2013/0015505 A1 | 1/2013 | Rothberg et al. |
| 2013/0015506 A1 | 1/2013 | Rothberg et al. |
| 2013/0017959 A1 | 1/2013 | Rothberg et al. |

FOREIGN PATENT DOCUMENTS

| | | |
|---|---|---|
| DE | 102008012899 | 9/2009 |
| EP | 1975246 | 3/1984 |
| EP | 0223618 | 5/1987 |
| EP | 1371974 | 12/2003 |
| EP | 1432818 | 6/2004 |
| EP | 1542009 | 6/2005 |
| EP | 1557884 | 7/2005 |
| EP | 1870703 | 12/2007 |
| EP | 2307577 | 4/2011 |
| GB | 2457851 | 9/2009 |
| GB | 2461127 B | 7/2010 |
| JP | 2000055874 | 2/2000 |
| JP | 2002272463 | 9/2002 |
| JP | 20052183310 | 8/2004 |
| JP | 2005-518541 | 6/2005 |
| JP | 2011-525810 | 9/2011 |
| KR | 10-0442838 | 7/2004 |
| KR | 10-0455283 | 10/2004 |
| WO | WO-89/09283 | 10/1989 |
| WO | WO-98/13523 | 4/1998 |
| WO | WO-98/46797 | 10/1998 |
| WO | WO-01/20039 | 3/2001 |
| WO | WO-01/42498 | 6/2001 |
| WO | WO-01/81896 | 11/2001 |
| WO | WO-02/077287 | 10/2002 |
| WO | WO-02/086162 | 10/2002 |
| WO | WO-03/073088 | 9/2003 |
| WO | WO-2004/040291 | 5/2004 |
| WO | WO2004040291 | 5/2004 |
| WO | WO2004048962 | 6/2004 |
| WO | WO2005015156 | 2/2005 |
| WO | WO-2005/047878 | 5/2005 |
| WO | WO2005043160 | 5/2005 |
| WO | WO-2005/054431 | 6/2005 |
| WO | WO2005602049 | 7/2005 |
| WO | WO-2005/084367 | 9/2005 |
| WO | WO2005090961 | 9/2005 |
| WO | WO-2006/005967 | 1/2006 |
| WO | WO-2006/022370 | 3/2006 |
| WO | WO2007002204 | 1/2007 |
| WO | WO-2007/086935 | 8/2007 |
| WO | WO-2008/007716 | 1/2008 |
| WO | WO-2008/058282 | 5/2008 |
| WO | WO-2008/076406 | 6/2008 |
| WO | WO-2008/107014 | 9/2008 |
| WO | WO-2009/012112 | 1/2009 |
| WO | WO2009041917 | 4/2009 |
| WO | WO2009074926 | 6/2009 |

(56) References Cited

FOREIGN PATENT DOCUMENTS

| WO | WO2009081890 | 7/2009 |
|---|---|---|
| WO | WO-2009/158006 | 12/2009 |
| WO | WO-2010/008480 | 1/2010 |
| WO | WO-2010/047804 | 4/2010 |
| WO | WO-2010/047804 A8 | 4/2010 |
| WO | WO-2010/138182 | 12/2010 |
| WO | WO-2010/138188 | 12/2010 |
| WO | WO-2012/003359 | 1/2012 |
| WO | WO-2012/003363 | 1/2012 |
| WO | WO-2012/003368 | 1/2012 |
| WO | WO-2012/003380 | 1/2012 |
| WO | WO-2012/006222 | 1/2012 |

OTHER PUBLICATIONS

Ahmadian, A. et al., "Single-nucleotide polymorphism analysis by pyrosequencing", *Anal. Biochem*, vol. 280, 2000, pp. 103-110.

Akiyama, T et al., "Ion-Sensitive Field-Effect Transistors with Inorganic Gate Oxide for pH Sensing", *IEE Transactions on Electron Devices*, vol. ED-20(12), 1982, pp. 1936-1941.

AU2011226767 Search Information Statement Mailed Oct. 26, 2011, pp. 1-3.

Bandiera, L et al., "A fully electronic sensor for the measurement of cDNA hybridization kinetics", *Biosens Bioelectron*, vol. 22, 2007, pp. 2108-2114.

Barbaro, M et al., "A Charge-Modulated FET for Detection of Biomolecular Processes: Conception, Modeling, and Simulation", *IEEE Transactions on Electron Devices*, vol. 53(1), 2006, pp. 158-166.

Barbaro, M et al., "A CMOS, Fully Integrated Sensor for Electronic Detection of DNA Hybridization", *IEEE Electron Device Letters*, vol. 27(7), 2006, pp. 595-597.

Barbaro, M et al., "Fully electronic DNA hybridization detection by a standard CMOS biochip", *Sensors and Actuators B Chemical*, vol. 118, 2006, pp. 41-46.

Bashford, G et al., "Automated bead-trapping apparatus and control system for single-molecule DNA sequencing", *Optics Express*, vol. 16(5), Mar. 3, 2008, pp. 3445-3455.

Baumann, W et al., "Microelectronic sensor system for microphysiological application on living cells", *Sensors Actuators B*, vol. 55, 1999, pp. 77-89.

Bausells, J et al., "Ion-sensitive field-effect transistors fabricated in a commercial CMOS technology", *Sensors and Actuators B Chemical*, vol. 57, 1999, pp. 56-62.

Bergveld, P., "ISFET, Theory and Practice", *IEEE Sensor Conference*, Toronto, Oct. 2003, 2003, pp. 1-26.

Bergveld, P., "Thirty years of ISFETOLOGY What happened in the past 30 years and what may happen in the next 30 years", *Sensors and Actuators B*, vol. 88, vol. 88, 2003, pp. 1-20.

Besselink, G et al., "ISFET Affinity Sensor", *Methods in Biotechnology*, vol. 7: Affinity Biosensors: Techniques and Protocols, 1998, pp. 173-185.

Bobrov, P et al., "Chemical sensitivity of an ISFET with Ta2O5 membrane in strong acid and alkaline solutions", *Sensors and Actuators B*, vol. 3, 1991, pp. 75-81.

Bousse, L et al., "A process for the combined fabrication of ion sensors and CMOS circuits", *IEEE Electron Device Letters*, vol. 9(1), 1988, pp. 44-46.

Bousse, L et al., "Zeta potential measurements of Ta2O5 and SiO2 thin films", *J. Colloid Interface Sci.*, vol. 147(1), 1991, pp. 22-32.

Chen, et al., "Nanoscale field effect transistor for biomolecular signal amplification", *App Phys Letter*, vol. 91, 2007, pp. 243511-1-243511-3.

Chen, et al., "Silicon-based nanoelectronic field-effect pH sensor with local gate control", *App Phys Letter*, vol. 89, 2006, pp. 223512-1-223512-3.

Chou, J. et al., "Letter to the Editor on Simulation of Ta2O5 gate ISFET temperature characteristics", *Sensors and Actuators B*, vol. 80, 2001, pp. 290-291.

Chou, J. et al., "Simulation of Ta2O5 gate ISFET temperature characteristics", *Sensor and Actuators B, vol. 71, Letter to the Editor*, 2000, pp. 73-61.

Chung, W-Y et al., "ISFET interface circuit embedded with noise rejection capability", *Electronics Letters*, vol. 40(18), e-pub ; 2 pages, 2004.

Chung, W-Y et al., "ISFET performance enhancement by using the improved circuit techniques", *Sensors and Actuators B*, vol. 113, 2006, pp. 555-562.

Eijkel, J. et al., "Measuring Donnan-related phenomena using a solid-state ion sensor and a concentration-step method", *J. Membrane Sci.*, vol. 127, 1997, pp. 203-221.

Eijkel, J., "Potentiometric detection and characterization of adsorbed protein using stimulus-response measurement techniques", *Thesis*, Sep. 3, 1955, pp. 1-147; 160-192.

Eltoukhy, H et al., "A 0.18um CMOS 10-6 lux Bioluminescence Detection System-on-Chip", *ISSCC 2004/Session12/Biomicrosystems/12.3*, 2004, pp. 1-3.

Eltoukhy, H. et al., "A. 0.18-um CMOS Bioluminescence Detection Lab-on-Chip", *IEEE J Solid-State Circuits*, vol. 41(3), 2006, pp. 651-662.

Eriksson, J et al., "Pyrosequencing technology at elevated temperature", *Electrophoresis*, vol. 25, 2004, pp. 20-27.

Esfandyarpour, H. et al., "Gate-controlled microfluidic chamber with magnetic bead for DNA sequencing-by-synthesis technology", *Proc 5th Intl Conf Nanochannels, Microchannels, Minnichannels*, Puebla, Mexico (Jun. 18-20, 2007), Jun. 18, 2007, pp. 1-5.

Eversmann, B. et al., "A 128×128 CMOS Biosensor Array for Extracellular Recording of Neural Activity", *IEEE J. Solid-State Circ.*, vol. 38(12), Dec. 12, 2003, pp. 2306-2317.

Faramarzpour, N. et al., "CMOS-Based Active Pixel for Low-Light Level Detection: Analysis and Measurements", *IEEE Trans Electron Devices*, vol. 54(12), Dec. 2007, pp. 3229-3237.

Finn, A et al., "Towards an Optimization of FET-Based Bio-Sensors", *European Cells and Materials*, vol. 4, Sup 2, 2002, pp. 21-23.

Fraden, J., "Handbook of Modern Sensors—Physics, Designs, and Applications . . . ", *17.3.2 CHEMFET Sensors*, 1996, pp. 499-501.

Fritz, et al., "Electronic detection of DNA by its intrinsic molecular charge", *PNAS*, vol. 99(22), 2002, pp. 14142-14146.

GB0811656.8 Search and Examination Report Mailed Mar. 12, 2010.

GB0811656.8 Search Report Mailed Sep. 21, 2009.

GB0811657.6 Examination Report Mailed Jun. 30, 2010.

GB0811657.6 Search Report under Section 17 Mailed Oct. 26, 2009.

Gracia, I. et al., "Test Structures for ISFET Chemical Sensors", *Proc IEEE 1992 Intl Conf Microelec Test Struct*, vol. 5, 1992, pp. 156-159.

Hammond, P et al., "A System-on-Chip Digital pH Meter for Use in a Wireless Diagnostic Capsule", *IEEE Transactons on Biomedical Engineering*, vol. 52(4), 2005, pp. 687-694.

Hammond, P et al., "Design of a Single-Chip pH Sensor Using a Conventional 0.6-μm CMOS Process", *IEEE Sensors Journal*, vol. 4(6), 2004, pp. 706-712.

Hammond, P et al., "Encapsulation of a liquid-sensing microchip using SU-8 photoresist", *MicoElectronic Engineering*, vol. 73-74, 2004, pp. 893-897.

Hammond, S. et al., "Genomic sequencing and analysis of a Chinese Hampster ovary cell line using Illumina sequencing technology", *BMC Genomics*, 12:67, 2011, pp. 1-8.

Han, Y., "Label-free detection of biomolecules by a field-effect transistor microarray biosensor with bio-functionalized gate surfaces", Masters Dissertation, 2006, pp. 1-63.

Hara, H. et al., "Dynamic response of a Ta2O5-gate pH-sensitive field-effect transistor", *Sensors Actuators B*, vol. 32, 1996, pp. 115-119.

Hermon, Z. et al., "Miniaturized bio-electronic hybrid for chemical sensing applications", *Tech Connect News*, Apr. 22, 2008, pp. 1.

Hideshima, S. et al., "Detection of tumor marker in blood serum using antibody-modified field effect ransistor with optimized BSA blocking", *Sensors and Actuations B: Chemical*, vol. 161, 2012, pp. 146-150.

(56) References Cited

OTHER PUBLICATIONS

Hijikata, M. et al., "Identification of a Single Nucleotide Polymorphism in the MXA Gene Promoter (T/T at nt-88) Correlated with the Response of Hepatitis C Patients to Interferon", *Intervirology*, vol. 43, 2000, pp. 124-127.
Hizawa, T et al., "Fabrication of a two-dimensional pH image sensor using a charge transfer technique", *Sensors and Actuators B Chemical*, 117, 2006, pp. 509-515.
Hizawa, T. et al., "32×32 pH Image Sensors for Real Time Observation of Biochemical Phenomena", *Transducers & Eurosensors '07*, 14th International Conference on Solid-State, Actuators and Microsystems, Lyon, France, Jun. 10-14, 2007, 2007, pp. 1311-1312.
Jakobson, C. et al., "Low frequency noise and drift in Ion Senstive Field Effect Transistors", *Sensors Actuators B*, vol. 68, 2000, pp. 134-139.
Ji, H. et al., "A CMOS contact imager for locating individual cells", *ISCAS*, 2006, pp. 3357-3360.
Ji, H. et al., "Contact Imaging: Simulation and Experiment", *IEEE Trans Circuits Systems-I: Regular Papers*, vol. 54(8), 2007, pp. 1698-1710.
Kim, D. et al., "An FET-type charger sensor for highly sensitive detection of DNA sequence", *Biosens Bioelectron*, vol. 20(1), Jul. 30, 2004, pp. 69-74.
Klein, M., "Time effects of ion-sensitive field-effect transistors", *Sens Act B*, vol. 17, 1989, pp. 203-208.
Koch, S et al., "Protein detection with a novel ISFET-based zeta potential analyzer", *Biosensors & Bioelectronics*, vol. 14, 1999, pp. 413-421.
Kruise, J. et al., "Detection of protein concentrations using a pH-step titration method", *Sensors Actuators B*, vol. 44, 1997, pp. 297-303.
Leamon, J et al., "A Massively Parallel PicoTiterPlate Based Platform for Discrete Picoliter-Scale Polymerase Chain Reactions", *Electrophoresis*, vol. 24, Nov. 24, 2003, pp. 3769-3777.
Leamon, J. et al., "Cramming More Sequening Reactions onto Microreactor Chips", *Chemical Reviews*, 107:, 2007, 3367-3376.
Lee, C-S et al., "Ion-sensitive Field-Effect Transistor for Biological Sensing", *Sensors*, vol. 9, 2009, pp. 7111-7131.
Li, et al., "Sequence-Specific Label-Free DNA Sensors Based on Silico Nanowires", *Nano Letters,*, vol. 4(2), 2004, pp. 245-247.
Lohrengel, M. et al., "A new microcell or microreactor for material surface investigations at large current densities", *Electrochimica Acta*, vol. 49, 2004, pp. 2863-2870.
Lui, A. et al., "A Test Chip for ISFET/CMNOS Technology Development", *Prooceedings of the 1996 IEEE International Conference on Microelectronic Test Structures*, vol. 9, 1996, pp. 123-128.
Margulies, M. et al., "Genome sequencing in microfabricated high-density picolitre reactors", *Nature*, vol. 437, 2005, pp. 376-380.
Marshall, A. et al., "DNA chips: an array of possibilities", *Nature Biotechnology*, vol. 16, Jan. 1998, pp. 27-31.
Martinoia, S. et al., "A behavioral macromodel of the ISFET in SPICE", *Sensors Actuators B*, vol. 62, 2000, pp. 182-189.
Martinoia, S., "Development of ISFET Array-Based Microsystems for Bioelectrochemical measurements of cell populations", *Biosensors & Bioelectronics*, vol. 16, 2001, pp. 1043-1050.
Medoro, G. et al., "A Lab-on-a-Chip for Cell Detection and Manipulation", *IEEE Sensors J*, vol. 3(3), 2003, pp. 317-325.
Meyburg, S. et al., "N-Channel field-effect transistors with floating gates for extracellular recordings", *Biosens Bioelectron*, vol. 21(7), Jan. 15, 2006, pp. 1037-1044.
Milgrew, M et al., "A large transistor based sensor array chip for direct extracellular imaging", *Sensors and Actuators B Chemical*, vol. 111-112, 2005, pp. 347-353.
Milgrew, M et al. al., "Microsensor Array Technology for Direct Extracellular Imaging", Apr. 5, 2006, pp. 1-23.
Milgrew, M et al., "The development of scalable sensor arrays using standard CMOS technology", *Sensors and Actuators B*, 103, 2004, pp. 37-42.
Milgrew, M et al., "The fabrication of scalable multi-sensor arrays using standard CMOS technology", 2003 *IEEE Custom Integrated Circuits Conference*, 2003, pp. 513-516.
Milgrew, M. et al., "A 16×16 CMOS proton camera array for direct extracellular imaging of hydrogen-ion activity", *IEEE Intl Solid-State Circuits Conf*, Session 32:24, 2008, pp. 590-591; 638.
Milgrew, M. et al., "Matching the transconductance characteristics of CMOS ESFET arrays by removing trapped charge", *IEEE Trans Electron Devices*, vol. 55(4), 2008, pp. 1074-1079.
Miyahara, Y et al., "Direct Transduction of Primer Extension into Electrical Signal Using Genetic Field Effect Transistor", *Micro Total Analysis Systems 2004*, vol. 1, Proceedings of uTAS 2004, 8th International Conference on Miniaturized Systems for Chemistry and Life Sciences, Malmo, Sweden, Sep. 26-30, 2004, pp. 303-305.
Miyahara, Y. et al., "Biochip Using Micromatchining Technology", *J. Institute of Electrostatics*, Japan, vol. 27(6), 2003, pp. 268-272.
Miyahara, Y. et al., "Potentiometric Detection of DNA Molecules Using Field Effect Transistor", *The Japan Society of Applied Physics*, No. 3 (Translation included), 2003, pp. 1180, 30A-S2.
Nyren, P. et al., "Enzymatic Method for Continuous Monitoring of Inorganic Pyrophosphate Synthesis", *Analytical Biochemistry*, vol. 151, 1985, 504-509.
Oelbner, W. et al., "Encapsulation of ESFET sensor chips", *Sensors Actuators B*, vol. 105, 2005, pp. 104-117.
Oelbner, W. et al., "Investigation of the dynamic response behaviour of ISFET pH sensors by means of laser Doppler velocimetry (LDV)", *Sensors Actuators B*, vol. 26-27, 1995, pp. 345-348.
Offenhausser, A. et al., "Field-Effect transistor array for monitoring electrical activity from mammalian neurons in culture", *Biosensors & Bioelectronics*, vol. 12(8), 1997, pp. 819-826.
Ohno, Y. et al., "Electrolyte-Gated Graphene Field-Effect Transistors for Detecting pH and Protein Adsorption", *Nano Letters*, vol. 9(9), Jul. 28, 2009, pp. 3318-3322.
Patolsky, F. et al., "Nanowire-Based Biosensors", *Analyt Chem 1*, vol. 78(13), Jul. 1, 2006, pp. 4261-4269.
PCT/JP2005/001987 International Search Report Mailed Apr. 5, 2005.
PCT/JP2005/015522 International Search Report (includes English translation) Mailed Sep. 27, 2005.
PCT/US2007/025721 Declaration of Non-Establishment of International Search Report Mailed Jul. 15, 2008.
PCT/US2007/025721 International Prelimary Report on Patentability Mailed Jun. 16, 2009.
PCT/US2007/025721 Written Opinion Mailed Jun. 16, 2009.
PCT/US2009/003766 International Preliminary Report on Patentability Mailed Jan. 5, 2011.
PCT/US2009/003766 International Search Report Mailed Apr. 8, 2010.
PCT/US2009/003766 Written Opinion Mailed Apr. 8, 2010.
PCT/US2009/003797 International Search Report Mailed Mar. 12, 2010.
PCT/US2010/001543 International Preliminary Report on Patentability Mailed Nov. 29, 2011, pp. 1-8.
PCT/US2010/001543 International Search Report and Written Opinion Mailed Oct. 13, 2010, pp. 1-12.
PCT/US2010/001553 International Preliminary Report on Patentability Mailed Dec. 8, 2011, pp. 1-10.
PCT/US2010/001553 International Search Report Mailed Jul. 28, 2010, pp. 1-2.
PCT/US2010/001553 Written Opinion Mailed Jul. 14, 2010, pp. 1-6.
PCT/US2010/48835 International Search Report and Written Opinion Mailed Dec. 16, 2010, pp. 1-12.
PCT/US2011/042655 International Search Report Mailed Oct. 21, 2011, pp. 1-2.
PCT/US2011/042660 International Search Report Mailed Nov. 2, 2011.
PCT/US2011/42669 International Search Report Mailed Jan. 9, 2012, pp. 1-5.
PCT/US2011/42669 Written Opinion Mailed Jan. 9, 2012, pp. 1-5.
PCT/US2011/42683 International Search Report Mailed Feb. 16, 2012.
PCT/US2011/42683 Written Opinon Mailed Feb. 16, 2012.
Poghossian, A. et al., "Functional testing and characterization of ISFETs on wafer level by means of a micro-droplet cell", *Sensors*, vol. 6, 2006, pp. 397-404.

(56) References Cited

OTHER PUBLICATIONS

Pourmand, N et al., "Direct electrical detection of DNA synthesis", *PNAS*, vol. 103(17), 2006, pp. 6466-6470.

Pouthas, F. et al., "Spatially resolved electronic detection of biopolymers", *Phys Rev*, vol. 70, 2004, pp. 031906-1-031906-8.

Premanode, B. et al., "A composite ISFED readout circuit employing current feedback", *Sensors Actuators B*, vol. 127, 2007, pp. 486-490.

Premanode, B. et al., "A novel, low power biosensor for real time monitoring of creatine and urea in peritoneal dialysis", *Sensors Actuators B*, vol. 120, 2007, pp. 732-735.

Premanode, B. et al., "Ultra-low power precision ISFET readout using global current feedback", *Electronic Lett*, vol. 42(22), Oct. 26, 2006, 2 pages.

Purushothaman, S. et al., "Protons and single nucleotide polymorphism detection: A simple use for the Ion Sensitive Field Effect Transistor", *Sensors and Actuators B Chemical*, vol. 114, 2006, pp. 964-968.

Purushothaman, S. et al., "Towards Fast Solid State DNA Sequencing", *IEEE ISCAS 2002 Proceedings*, 2002, pp. IV-169-IV-172.

Rodriguez-Villegas, E., "Solution to trapped charge in FGMOS transistors, vol. 39(19)", *Electronics Letters*, 2003.

Ronaghi, M. et al., "A Sequencing Method Based on Real-Time Pyrophosphate", *Science*, vol. 281, Jul. 17, 1998, pp. 363-365.

Sakata, T. et al., "Cell-based field effect devices fo cell adhesion analysis", *International Conference on Microtechnologies in Medicine and Biology*, May 9-12, 2006, Okinawa, Japan, 2006, pp. 177-179.

Sakata, T. et al., "Detection of DNA recognition events using multi-well field effect transistor", *Biosensors and Bioelectronics* vol. 21, 2005, pp. 827-832.

Sakata, T. et al., "Detection sensitivity of genetic field effect transistor combined with charged nanoparticle-DNA conjugate", *Proceedings of 2006 International Conference on Microtechnologies in Medicine and Biology*, May 9-12, 2005, Okinawa, Japan, 2006, pp. 97-100.

Sakata, T. et al., "Direct detection of single nucleotide polymorphism using genetic field effect transistor", *Digest of Papers Microprocesses and Nanotechnology 2004*, Osaka, Japan, 2004 International Microprocesses and Nanotechnology Conference, 2004, pp. 226-227.

Sakata, T. et al., "Direct Detection of Single-Base Extension Reaction Using Genetic Field Effect Transistor", *Proceedings of 3rd Annual International IEEE EMBS Special Topic Conference on Microtechnologies in Medicine and Biology*, Kahuku, Oahu, HI, May 12-15, 2005, 2005, pp. 219-222.

Sakata, T. et al., "Direct transduction of allele-specific primer extension into electrical signal using genetic field effect transitor", *Biosensors and Bioelectric* vol. 22, 2007, pp. 1311-1316.

Sakata, T. et al., "DNA Analysis Chip Based on Field-Effect Transistors", *Japanese Journal of Applied Physics*, vol. 44, No. 4B, 2005, pp. 2854-2859.

Sakata, T. et al., "DNA Sequencing Based on Intrinsic Molecular Charges", *Angewandte Chemie International Edition*, 2006, vol. 45, 2006, pp. 2225-2228.

Sakata, T. et al., "DNA Sequencing Based on Intrinsic Molecular Charges", *Angewandte Chemie International Edition*, 2006, vol. 118, 2006, pp. 2283-2286.

Sakata, T. et al., "DNA Sequencing Using Genetic Field Effect Transistor", *13th International Conference on Solid-State Sensors, Actuators and Microsystems*, Jun. 5-9, 2005, Seoul, Korea, 2005, pp. 1676-1679.

Sakata, T. et al., "Immobilization of oligonucleotide probes on Si3N4 surface and its application to genetic field effect transistor", *Materials Science and Engineering: C*, vol. 24, 2004, pp. 827-832.

Sakata, T. et al., "Potential Behavior of Biochemically Modified Gold Electrode for Extended-Gate Field-Effect Transistor", *Japanese Journal of Applied Physics*, vol. 44, No. 4B, 2005, 2005, pp. 2860-2863.

Sakata, T. et al., "Potential Response of Genetic Field Effect Transistor to Charged Nanoparticle-DNA Conjugate", *Digest of Papers Microprocesses and Nanotechnology 2005*, Tokyo, Japan, 2005 Intl Microprocesses and Nanotech Conference, Hotel Bellclassic, 2005, pp. 42-43.

Sakata, T. et al., "Potentiometric Detection of Allele Specific Oligonucleotide Hybridization Using Genetic Field Effect Transistor", *Micro Total Anslysis Systems 2004*, vol. 1, 8th International Conference on Miniaturized Systems for Chemistry and Life Sciences, Sep. 26-30, 2004, Malmo, Sweden, 2004, pp. 300-302.

Sakata, T. et al., "Potentiometric Detection of DNA Molecules Hybridization Using Gene Field Effect Transistor and Intercalator", *Materials Research Society Symposium Proceedings*, vol. 782, *Micro- and Nanosystems*, Dec. 1-3, 2003, Boston, Massachusetts, 2004, pp. 393-398.

Sakata, T. et al., "Potentiometric Detection of DNA Using Genetic Transistor", *Denki Gakkai Kenkyukai Shiryo Chemical Sensor Kenkyukai*, CHS-03-51-55, 2003, pp. 1-5.

Sakata, T. et al., "Potentiometric Detection of Single Nucleotide Polymorphism by Using a Genetic Field-effect transistor", *ChemBioChem 2005*, vol. 6, 2005, pp. 703-710.

Sakurai, T. et al., "Real-Time Monitoring of DNA Polymerase Reactions by a Micro ISFET pH Sensor", *Anal Chem*, vol. 64(17), 1992, pp. 1996-1997.

Salama, K., "CMOS luminescence detection lab-on-chip: modeling, design, and characterization", *Thesis*, Presented at Stanford University, 2005, pp. ii-78.

Salama, K., "Modeling and simulation of luminescence detection platforms", *Biosensors & Bioelectronics*, 2004, 1377-1386.

Sawada, K. et al., "A novel fused sensor for photo- and ion-sensing", *Sensors Actuators B*, vol. 106, 2005, pp. 614-618.

Sawada, K. et al., "Highly sensitive ion sensors using charge transfer technique", *Sensors Actuators B*, vol. 98, 2004, pp. 69-72.

Schasfoort, B. et al., "A new approach to immunoFET operation", *Biosensors & Bioelectronics*, vol. 5, 1990, pp. 103-124.

Schasfoort, RB et al., "Field-effect flow control for microfabricated fluidic networks", *Science*, vol. 286(5441), Oct. 29, 1999, pp. 942-945.

Schoning, M. et al., "Bio FEDs (Field-Effect Devices): State-of-the-Art and New Directions", *Electroanalysis*, vol. 18(19-20), 2006, pp. 1893-1900.

SG200903992-6 Search and Examination Report (Favourable) Mailed Jan. 20, 2011.

Shah, N., "Microfabrication of a parellel-array DNA pyrosequencing chip", *NNIN REU Research Accomplishments*, 2005, pp. 130-131.

Shepherd, L. et al., "A biochemical translinear principle with weak inversion ISFETs", *IEEE Trans Circuits Syst-I*, vol. 52(12), Dec. 2005, pp. 2614-2619.

Shepherd, L. et al., "A novel voltage-clamped CMOS ISFET sensor interface", *IEEE*, 2007, pp. 3331-3334.

Shepherd, L. et al., "Towards direct biochemical analysis with weak inversion ISFETS", *Intl Workshop on Biomedical . . .* , 2004, S1.5-5-S1.5-8.

Shepherd, L. et al., "Weak inversion ISFETs for ultra-low power biochemical sensing and real-time analysis", *Sensors Actuators B*, vol. 107, 2005, pp. 468-473.

Shi, Y. et al., "Radical Capillary Array Electrophoresis Microplace and Scanner for High-Performance Nucleic Acid Analysis", *Anal. Chem.*, vol. 71(23), 1999, pp. 5354-5361.

Simonian, A. L. et al., "FET bases biosensors for the direct detection of organophosphate neurotoxins", *Electroanalysis*, vol. 16(22), 2004, pp. 1896-1906.

Souteyrand, E. et al., "Direct detection of the hybridization of synthetic homo-oligomer DNA sequences by field effect", *J Phys Chem B*, vol. 101(15), 1997, pp. 2980-2985.

Starodub, N. et al., "Immunosensor for the determination of the herbicide simazine based on an ion-selective field-effect transistor", *Analytica Chimica Acta*, vol. 424, 2000, pp. 37-43.

Takenaka, S. et al., "DNA Sensing on a DNA Probe-Modified Electrode Using Ferrocenylnaphthalene Dimide as the Electrochemically Active Ligand", *Anal. Chem.*, vol. 72(6), 2000, pp. 1334-1341.

Tomaszewski, D. et al., "Electrical characterization of ISFETs", *J Telecomm Info Technol*, Mar. 2007, pp. 55-60.

Toumazou, C. et al., "Using transistors to linearase biochemistry", *Electronics Letters*, vol. 43(2), Jan. 18, 2007, 3 pages.

(56) References Cited

OTHER PUBLICATIONS

Truman, P., "Monitoring liquid transport and chemical composition in lab on . . . ", *Lab on a Chip*, vol. 6, 2006, pp. 1220-1228.
Uslu, F. et al., "Labelfree fully electronic nucleic acid detection system based on a field-effect transistor device", *Biosens & Bioelectron*, vol. 19(12), 2004, pp. 1723-1731.
Van Der Wouden, E. et al., "Directional flow induced by synchronized longitudinal and zeta-potential controlling AC-electrical fields", *Lab Chip*, vol. 6(10), 2006, pp. 1300-1305.
Van Hal, R.E.G. et al., "A general model to describe the electrostatic potential at electrolyte oxide interfaces", *Advances in Colloid and Interface Science*, vol. 69, 1996, pp. 31-62.
Van Kerkhof, J et al., "The ISFET based heparin sensor with a monolayer of protamine as affinity ligand", *Biosensors & Bioelectronics*, vol. 10(3), 1995, pp. 269-282.
Van Kerkhof, J. et al., "ISFET Responses on a stepwise change in electrolyte concentration at constant pH", *Sensors Actuators B: Chemical*, vol. 18-19, Mar. 1994, pp. 56-59.
Van Kerkhof, J., "The Development of an ISFET-based Heparin Sensor", *Thesis*, 1994.
Wagner, T et al., "All-in-one solid-state device based on a light-addressable potentiometric sensor platform", *Sensors and Actuators B*, vol. 117, 2006, pp. 472-479.
Wang, W. et al., "Label-free detection of small-molecule-protein interactions by using nanowire nanosensors", *Proceedings of the National Academy of Sciences (PNAS)*, vol. 102,(9), 2005, pp. 3208-3212.
Woias, P., "Modelling the short time response of ISFET sensors", *Sensors and Actuators B*, vol. 24-25, 1995, pp. 211-217.
Woias, P. et al., "Slow pH response effects of silicon nitride ISFET sensors", *Sensors and Actuators B*, vol. 48, 1998, pp. 501-504.
Wu, P. et al., "DNA and protein microarray printing on silicon nitride waveguide surfaces", *Biosensens Bioelectron*, vol. 21(7), 2006, pp. 1252-1263.
Xu, J-J et al., "Analytical Aspects of FET-Based Biosensors", *Frontiers in Bioscience*, 10, 2005, pp. 420-430.
Yeow, T.C.W., "A very large integrated pH-ISFET sensor array chip compatible with standard CMOS processes", *Sensor and Actuators B*, vol. 44, 1997, pp. 434-440.
Yuqing, M. et al., "Ion sensitive field effect trnasducer-based biosensors", *Biotechnology Advances*, vol. 21, 2003, 527-534.
Zhang, X et al., "32-Channel Full Customized Cmos Biosensor Chip for Extracellular neural Signal Recording", *Proceedings of the 2nd International IEEE EMBs Conference on Neural Engineering*, Arlington, VA-, 2005, pp. v-viii.
Zhou, G. et al., "Quantitative detection of single nucleotide polymorphisms for a pooled sample by a bioluminometric assay coupled with modified primer extension reactions (BAMPER)", *Nuc. Acids Res.*, vol. 29(19), e93, 2001, pp. 1-11.
Chan, Wai P. et al., "An Integrated ISFETs Instrumentation System in Standard CMOS Technology", IEEE Journal of Solid-State Circuits, vol. 45, No. 9, 2010, pp. 1923-1934.
Chinese Patent Application 200780051353.2 Second Office Action dated Mar. 5, 2013.
Chung, W-Y et al., "New ISFET Interface Circuit Design with Temperature Compensation", Microelectronics Journal, vol. 37(10), 2006, pp. 1105-1114.
Chung, W-Y et al., "Temperature Compensation Electronics for ISFET Readout Applications", Biomedical Circuits and Systems, IEEE International Workshop Singapore, 2004, pp. 305-308.
EP7867780.4 Patent Application Examination Report dated Jul. 3, 2012.
Krause, M. et al., "Extended Gate Electrode Arrays for Extracellular Signal Recordings", Sensors and Actuators B, vol. 70, 2000, pp. 101-107.
Park, K-Y et al., "ISFET Glucose Sensor System With Fast Recovery Characteristics by Employing Electrolysis", Sensors and Actuators B: Chemical, vol. 83 (1-3), 2002, pp. 90-97.
PCT/JP2005/015522 International Preliminary Report on Patentability dated Mar. 19, 2007.
PCT/US2010/048835 International Preliminary Report on Patentability dated Mar. 19, 2013.
PCT/US2011/042665 International Search Report dated Nov. 2, 2011.
PCT/US2011/042668 International Search Report dated Oct. 28, 2011.
PCT/US2012/058996 International Search Report and Written Opinion dated Jan. 22, 2013.
PCT/US2012/071471 International Search Report and Written Opinion dated Apr. 24, 2013.
PCT/US2013/022140 International Search Report and Written Opinion dated May 2, 2013.
U.S. Appl. No. 13/033,147 Non-Final Office Action dated Apr. 25, 2013.
U.S. Appl. No. 13/603,631 Final Office Action dated Apr. 30, 2013.
Dazhong, Z. et al. "Research of CMOS Biosensor IC for Extracellular Electrophysiological Signal Recording and pH value Measuring" Solid-State and Integrated Circuit Technology, 9th International Conference, Oct. 20, 2008, pp. 2557-2560.
EP11801437.2 Extended European Search Report dated Jul. 25, 2013.
EP11804218.3 Extended European Search Report dated Jul. 11, 2013.
EP11804218.3 First Office Action dated Jul. 29, 2013.
EP11827128.7 European Search Report dated Aug. 1, 2013.
EP13163995.7 Extended European Search Report dated Aug. 20, 2013.
Eriksson, J. et al. "Pyrosequencing Technology at Elevated Temperature" Electrophoresis, vol. 25, 2004, pp. 20-27.
Hizawa, et al. "Sensing Characteristics of Charge Transfer Type pH Sensor by Accumulative Operation" IEEE Sensors, EXCO, Daegu, Korea, 2006, pp. 144-147.
JP2012246413 First Office Action dated Jun. 28, 2013.
Lee, S. et al. "An Enhanced Glucose Biosensor Using Charge Transfer Techniques" Biosensors and Bioelectronics, vol. 24, 2008, pp. 650-656.
Matsuo, J. et al. "Charge Transfer Type pH Sensor with Super High Sensitivity" 14th International Conference on Solid-State Sensors Actuators and Microsystems, France, Jun. 10-14, 2007, pp. 1881-1884.
Milgrew, M. et al. "A Proton Camera Array Technology for Direct Extracellular Ion Imaging" IEEE International Symposium on Industrial Electronics, 2008, pp. 2051-255.
Milgrew, M.J. et al., "The Development of Scalable Sensor Arrays Using Standard CMOS Technology" ScienceDirect, Sensors and Actuators, vol. 103, 2004, pp. 37-42.
PCT/US2011/042668 International Preliminary Report on Patentability Mailed Mar. 26, 2013.
PCT/US2011/042683 International Preliminary Report on Patentability Mailed Jun. 4, 2013.
PCT/US2012/071482 International Search Report and Written Opinion Mailed May 23, 2013.
Pollack, J. et al. "Genome-Wide Analysis of DNA copy-number changes using cDNA Microarrays", Nature Genetics, vol. 23, 1999, pp. 41-46.
Premanode, B. et al. "Drift Reduction in Ion-Sensitive FETs Using Correlated Double Sampling", Electronics Letters, IEEE Stevenage, GB, vol. 43 (16) Aug. 2, 2007.
Seong-Jin, K. et al. "Label-Free CMOS DNA Quantification With On-Chip Noise Reduction Schemes" Solid-State Sensors, Actuators and Microsystems Conference, IEEE, Jun. 10, 2013, pp. 947-950.
Voigt, H. et al. "Diamond-like carbon-gate pH-ISFET" Sensors and Actuators B., vol. 44, 1997, pp. 441-445.
EP13174555.6 EP Extended Search Report Dec. 12, 2013.
EP13174555.6 EP Search Report Nov. 21, 2013.
EP13177039.8 EP Search Report Nov. 21, 2013.
EP13177590.0 EP Search Report Nov. 20, 2013.
Hammond, et al., "Performance and System-On-Chip Integration of an Unmodified CMOS ISFET", Science Direct, Sensors and Actuators vol. 111-112, 2005, pp. 254-258.
Ingebrandt, Sven et al., "Label-free Detection of DNA using Field-Effect Transistors", Phys. stat. sol. (a) 203, No. 14, 2006, pp. 3399-3411.

(56) References Cited

OTHER PUBLICATIONS

Wood, et al. "Base composition-independent hybridization in tetramethylammonium chloride: a method for oligonucleotide screening of highly complex gene libraries" Proc. Nat. Acad. Sci., 1985, pp. 1585-1588.

EP09798251.6 Extended European Search Report dated Aug. 27, 2013.

EP13161312.7 Extended European Search Report dated Oct. 15, 2013.

EP13163995.7 First Office Action dated Aug. 30, 2013.

EP13164768.7 Extended European Search Report dated Aug. 20, 2013.

EP13164768.7 First Office Action dated Aug. 30, 2013.

Hanshaw, R. et al., "An indicator displacement system for fluorescent detection of phosphate oxyanions under physiological conditions" Science Direct, Tetrahedron Ltrs., vol. 45, 2004, pp. 8721-8724.

JP20120246413 First Office Action dated Jun. 28, 2013.

Maki, W et al., "Nanowire-transistor based ultra-sensitive DNA methylation detection", Biosensors & Bioelectronics, vol. 23, 2008, pp. 780-787.

PCT/US2013/022129 International Search Report and Written Opinion dated Aug. 9, 2013.

Rothberg, J. et al., "An integrated semiconductor device enabling non-optical genome sequencing" Nature, vol. 475, No. 7356, 2011, pp. 348-352.

* cited by examiner

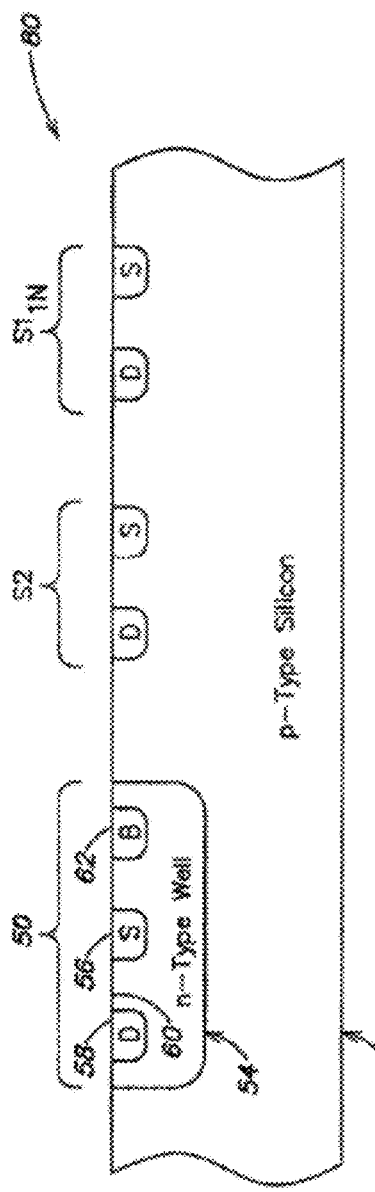
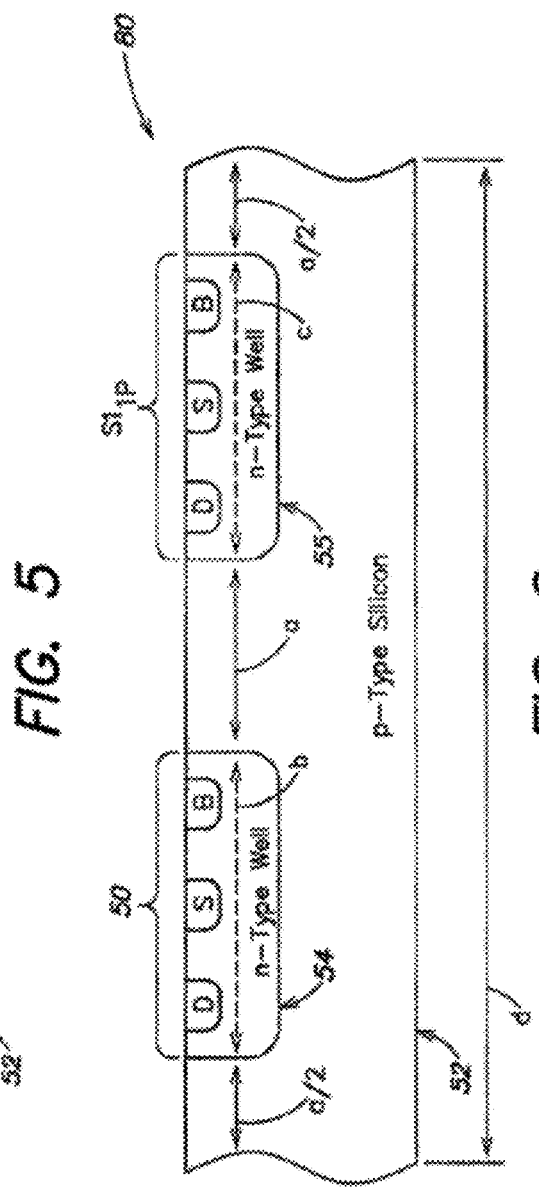
FIG. 5
FIG. 6

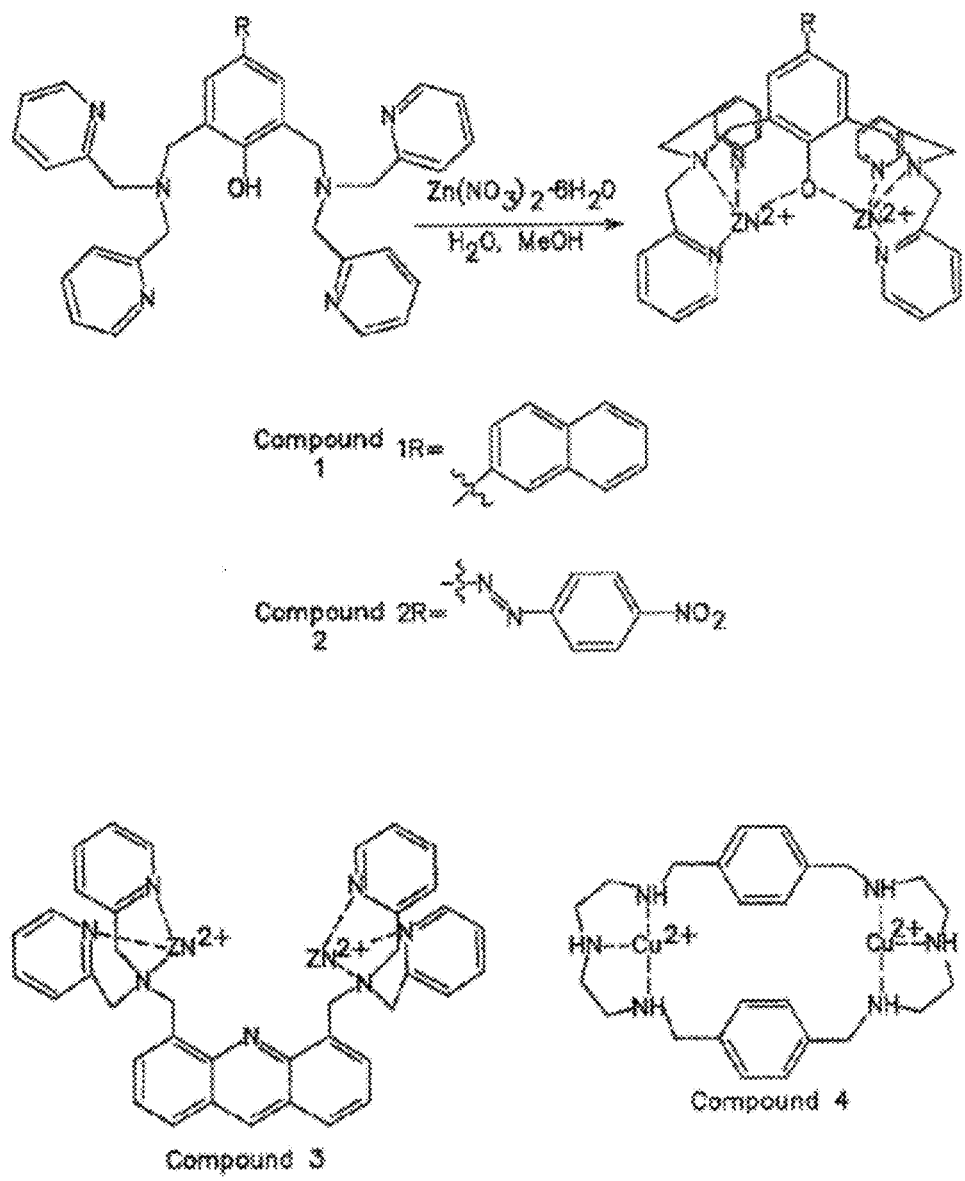
FIG. 11B(1)

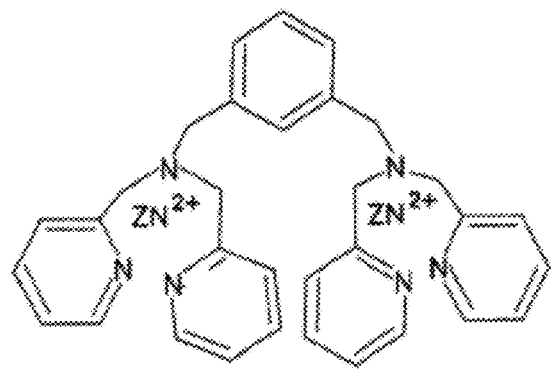
ZN²⁺-dipicolylamine
Compound 5
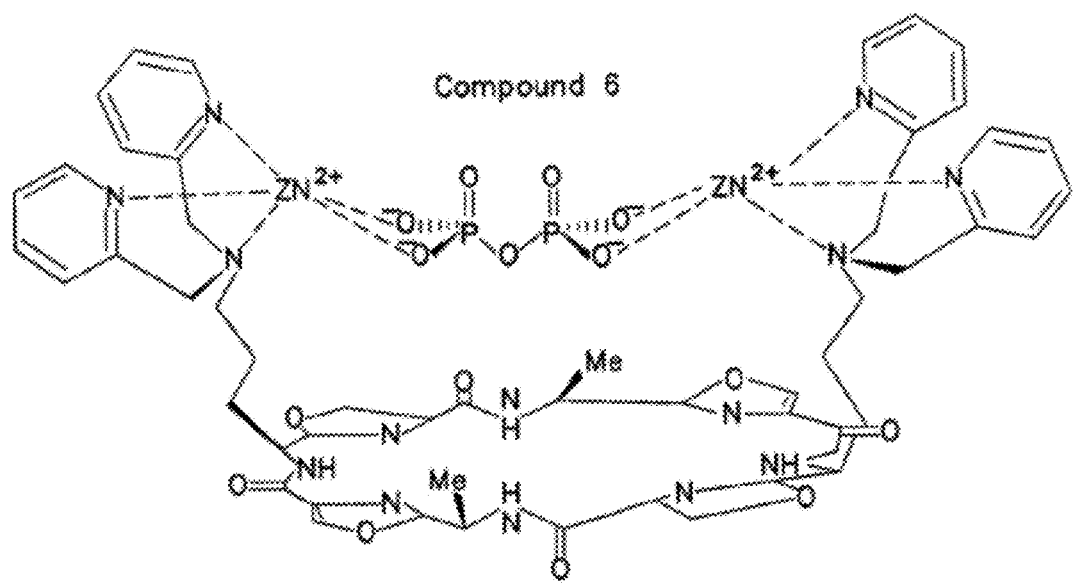
FIG. 11B(2)

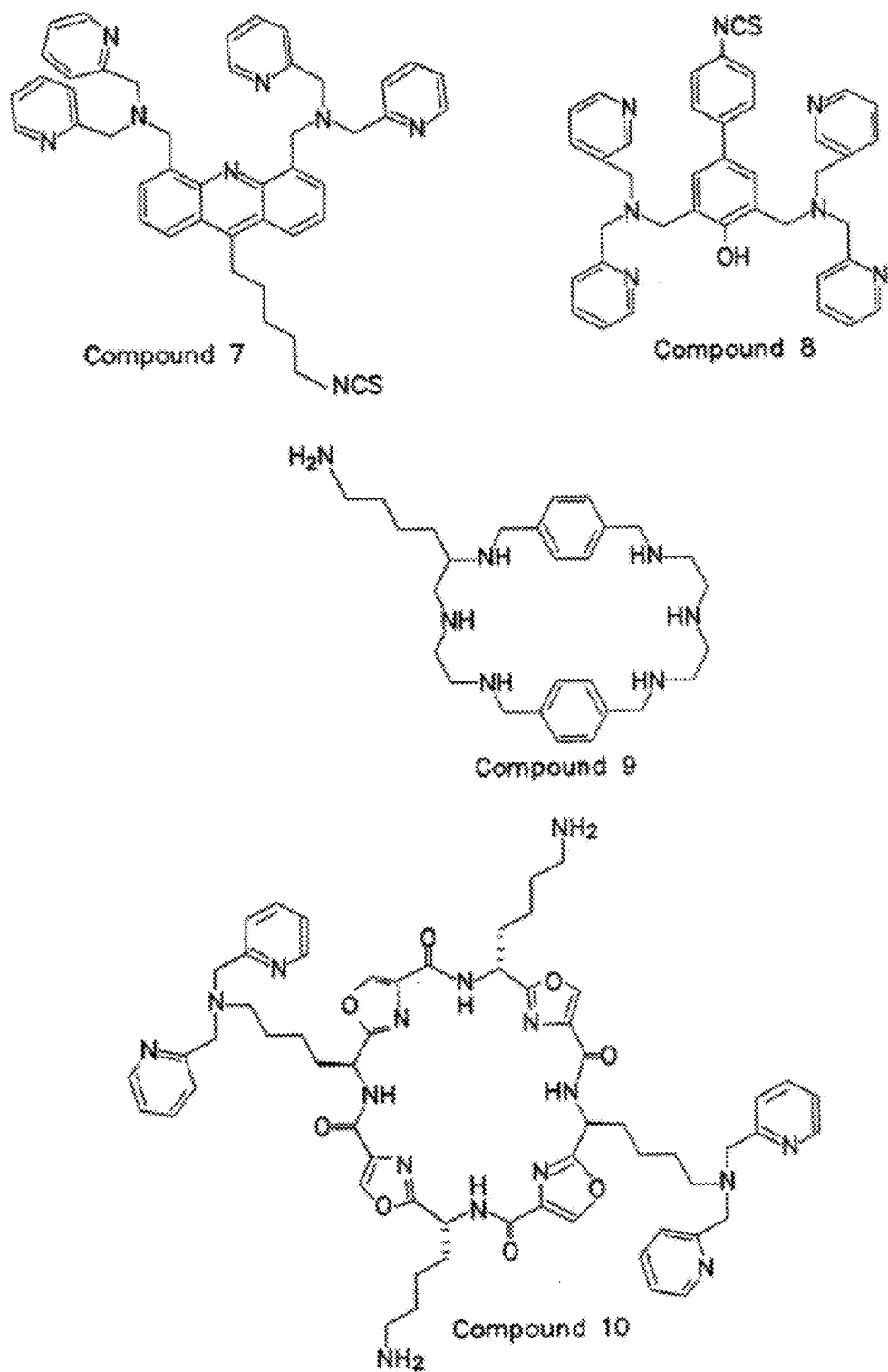
FIG. 11B(3)

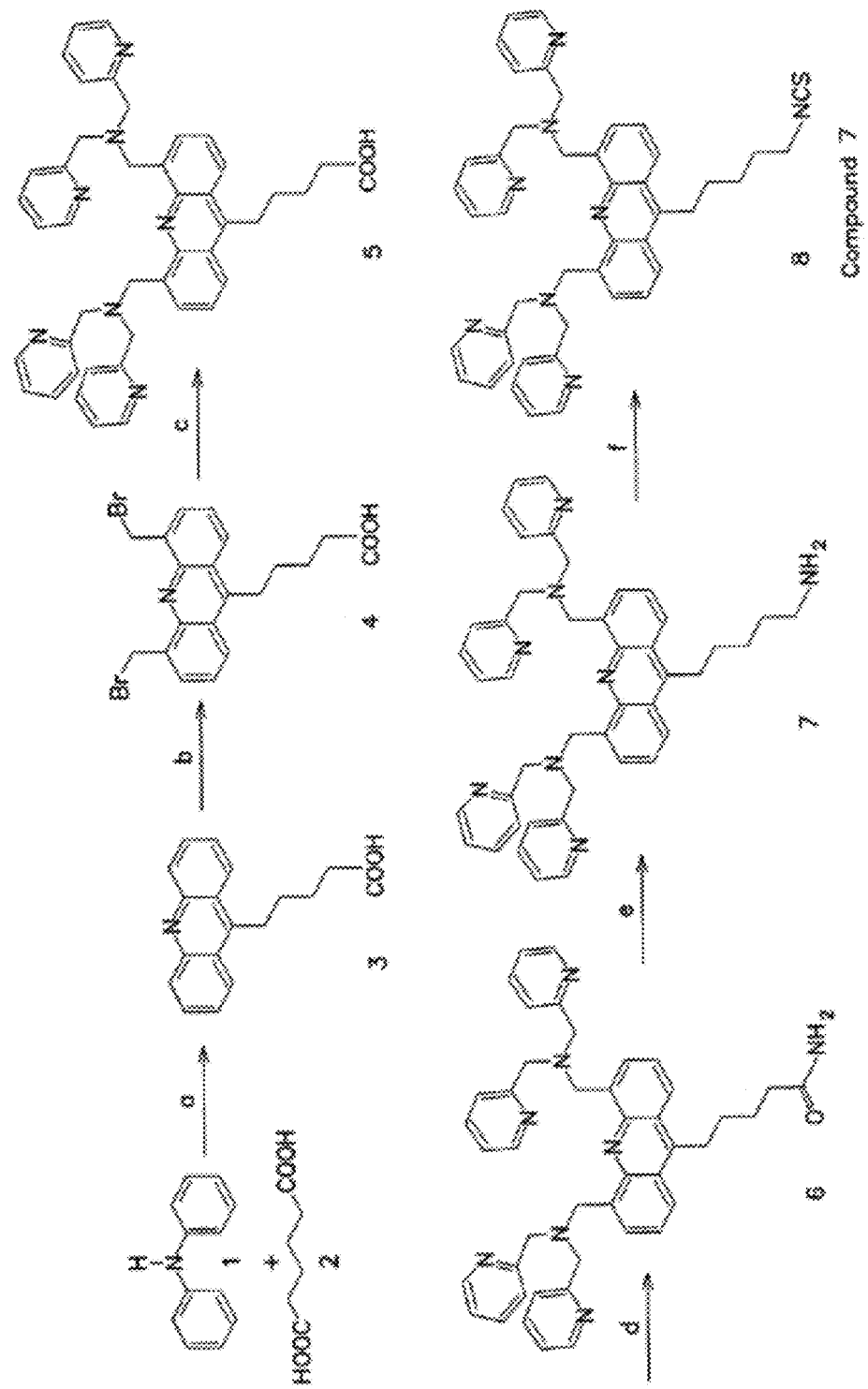
FIG. 11C(1)-1

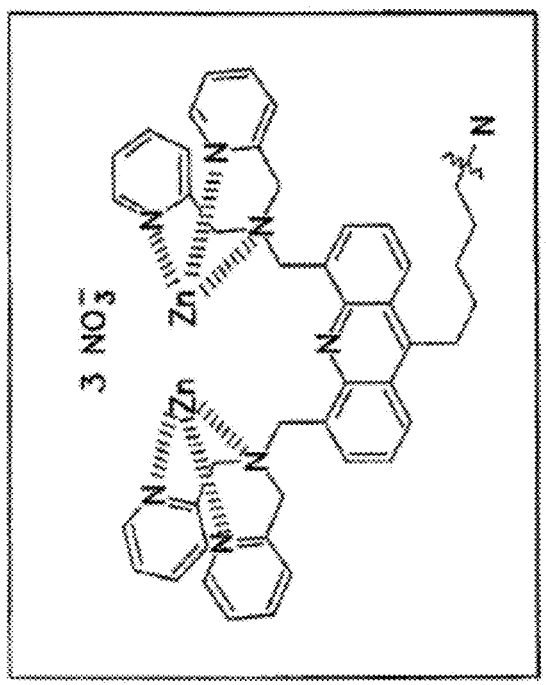
a. $ZnCl_2$; 20% $H_2SO_4$
b. $BrCH_2OCH_3$, $H_2SO_4$, 50°C, 18%
c. dipicorylamine, $K_2CO_3$, $CH_2Cl_2$, 66%
d. $NH_2CONH_2$, heat
e. $LiAlH_4$, $Et_2O$ or $BH_3$
d*i*-2-pyridyl thiocarbonate, $CH_2Cl_2$, 46%
Note: Zn ion are added post covalent linking to surface.
FIG. 11C(1)-2

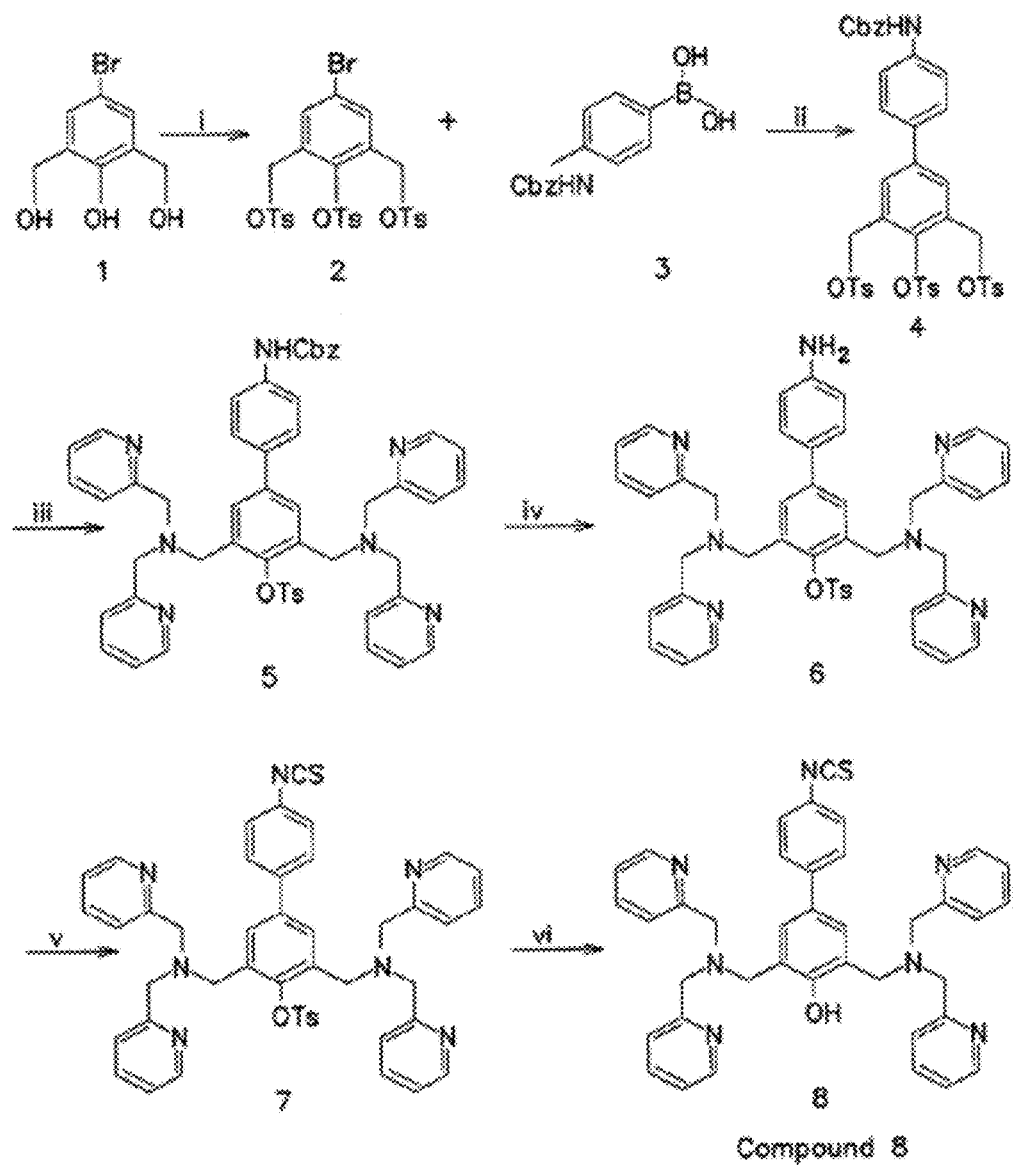
FIG. 11C(2)

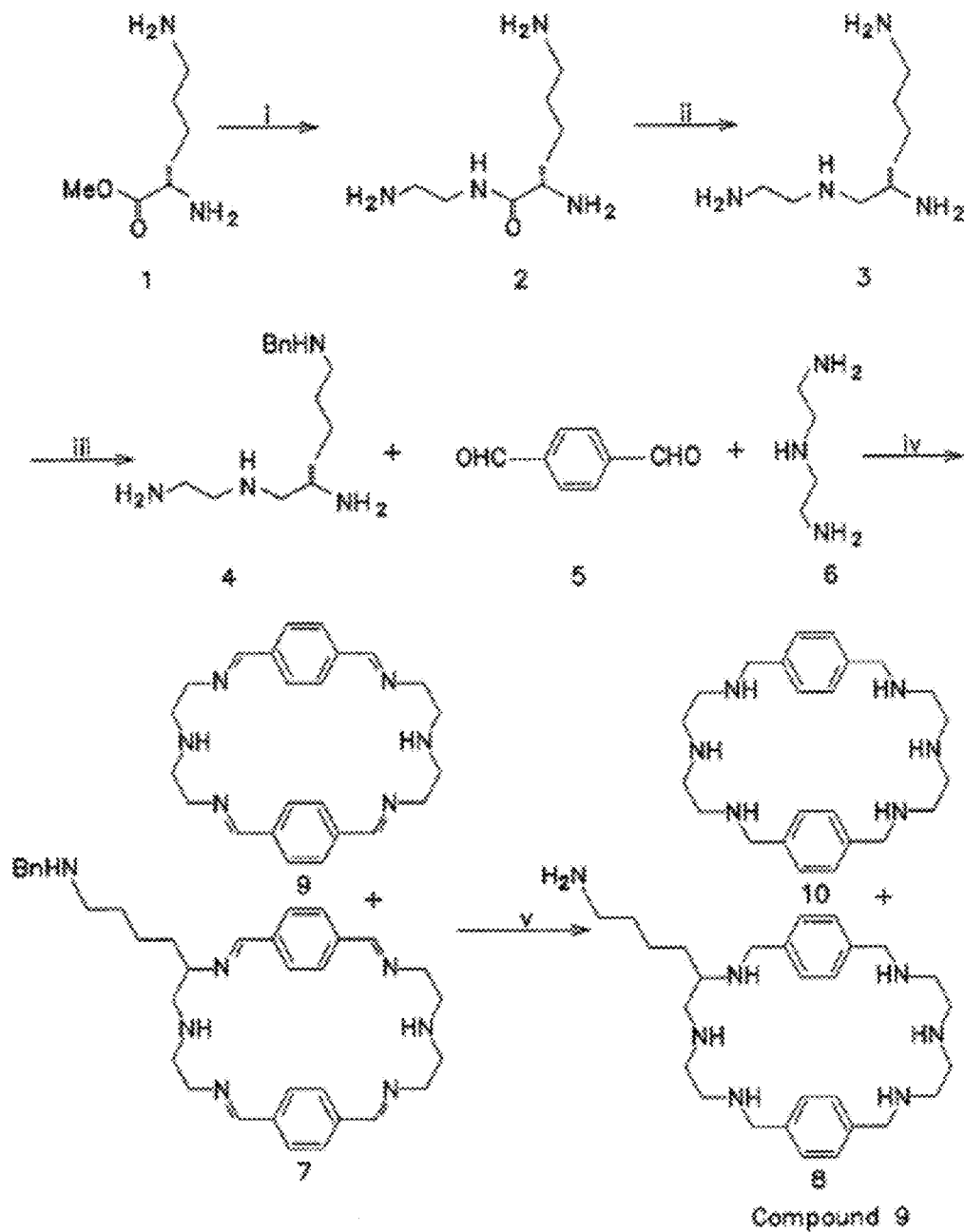
i. ethylenediamine, 90°C
ii. BH₃-THF
iii. KOH, CuCO₃, benzoyl chloride
iv. 1:4 ratio of 4:6, MeCN, r.t.
v. NaBH₄, MeOH; H₂NNH₂ if necessary
*FIG. 11C(3)*

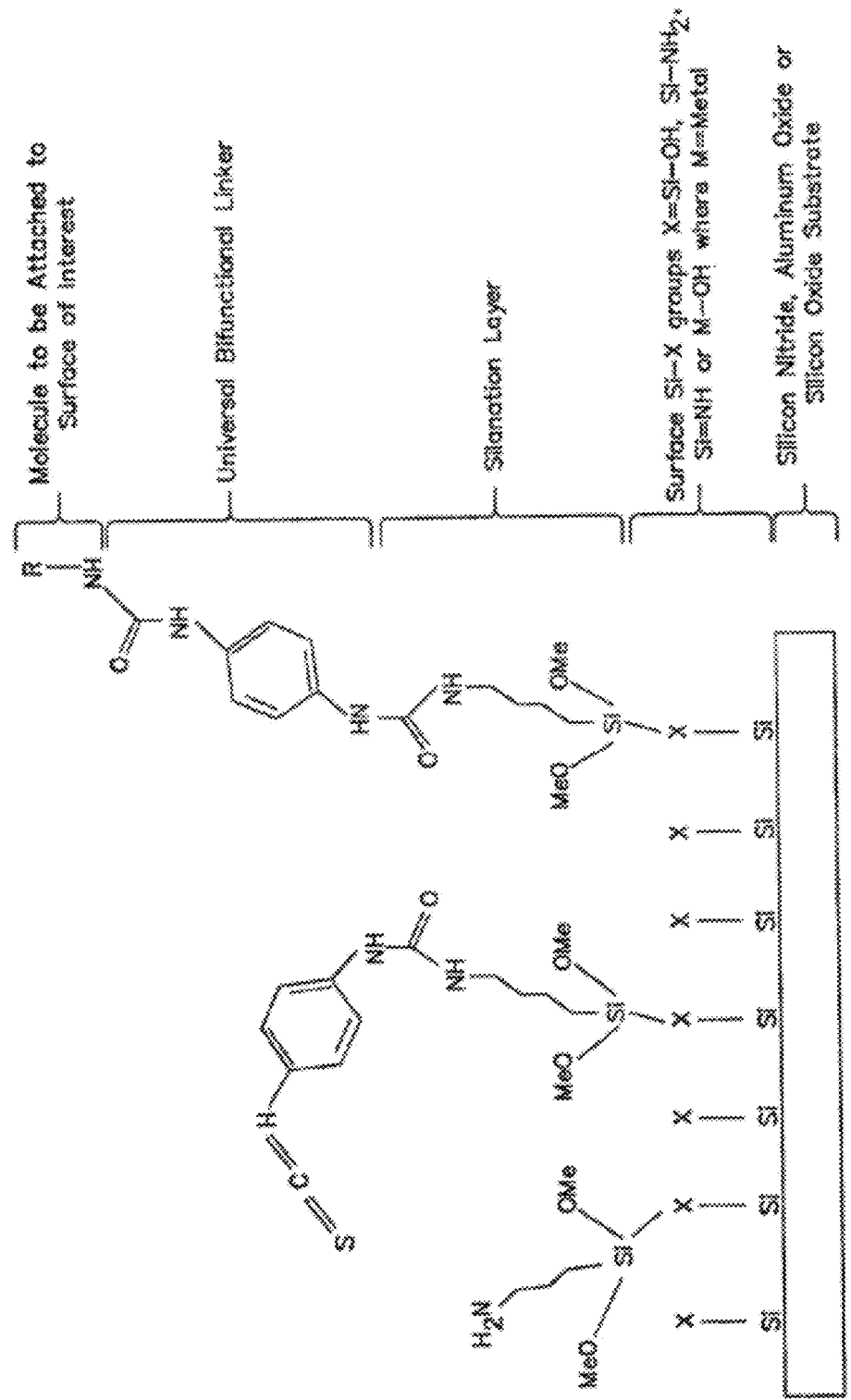
FIG. 11D(1)

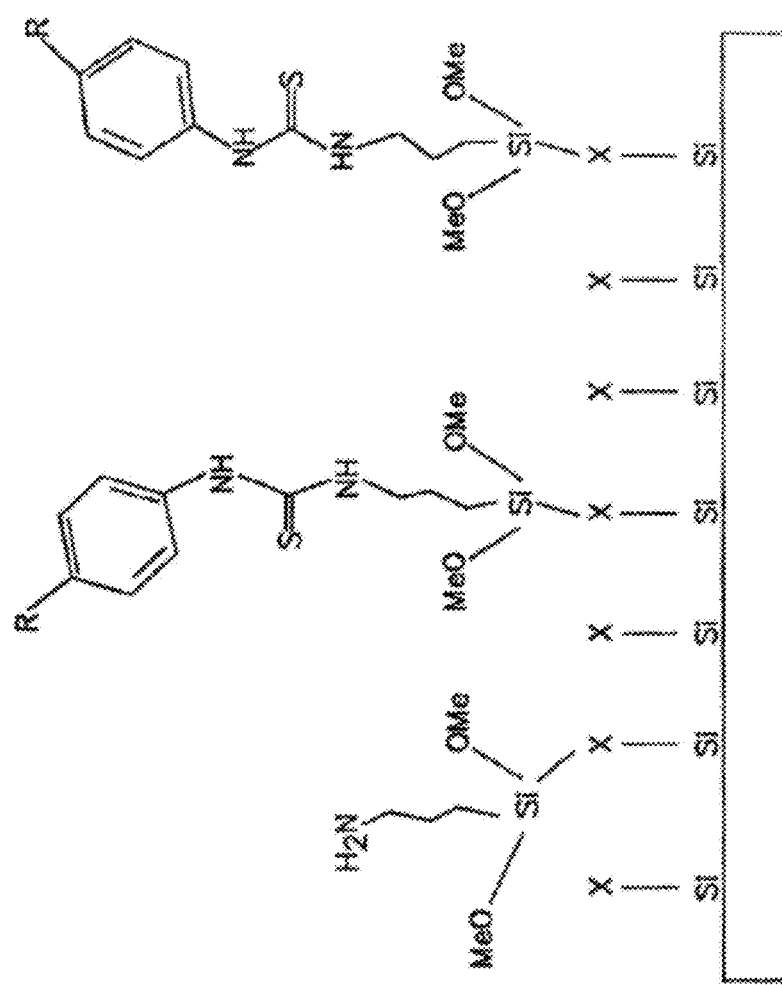
FIG. 11D(2)

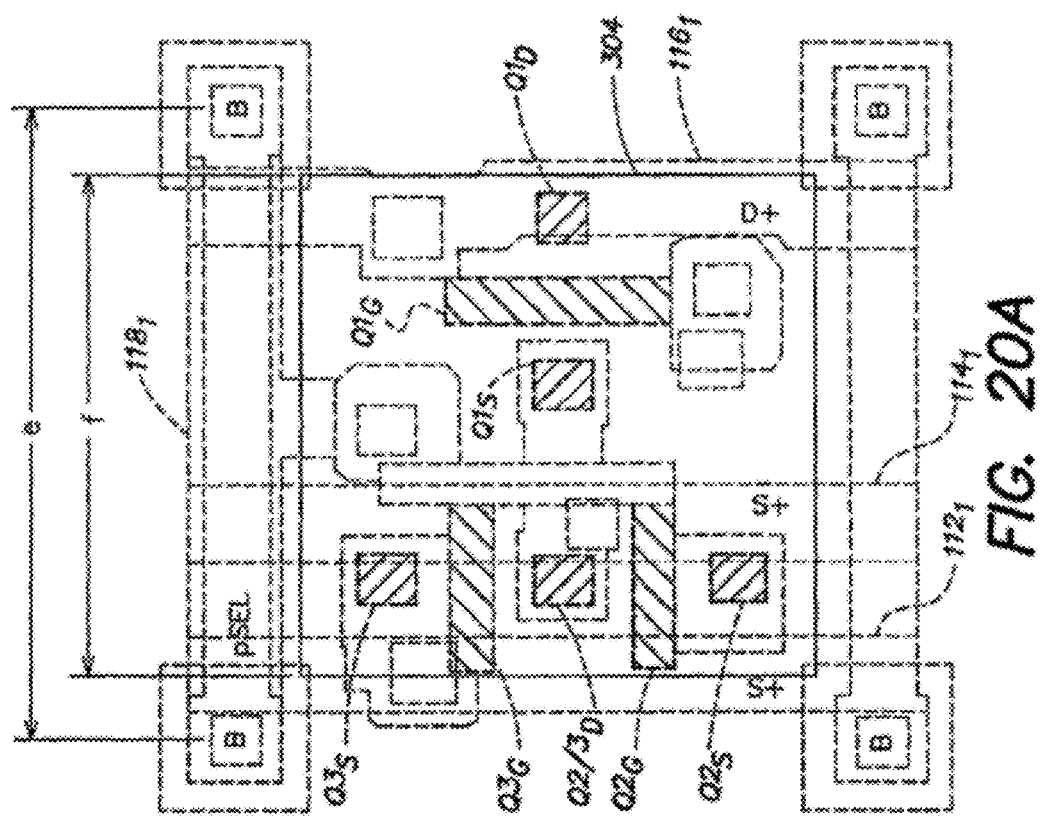

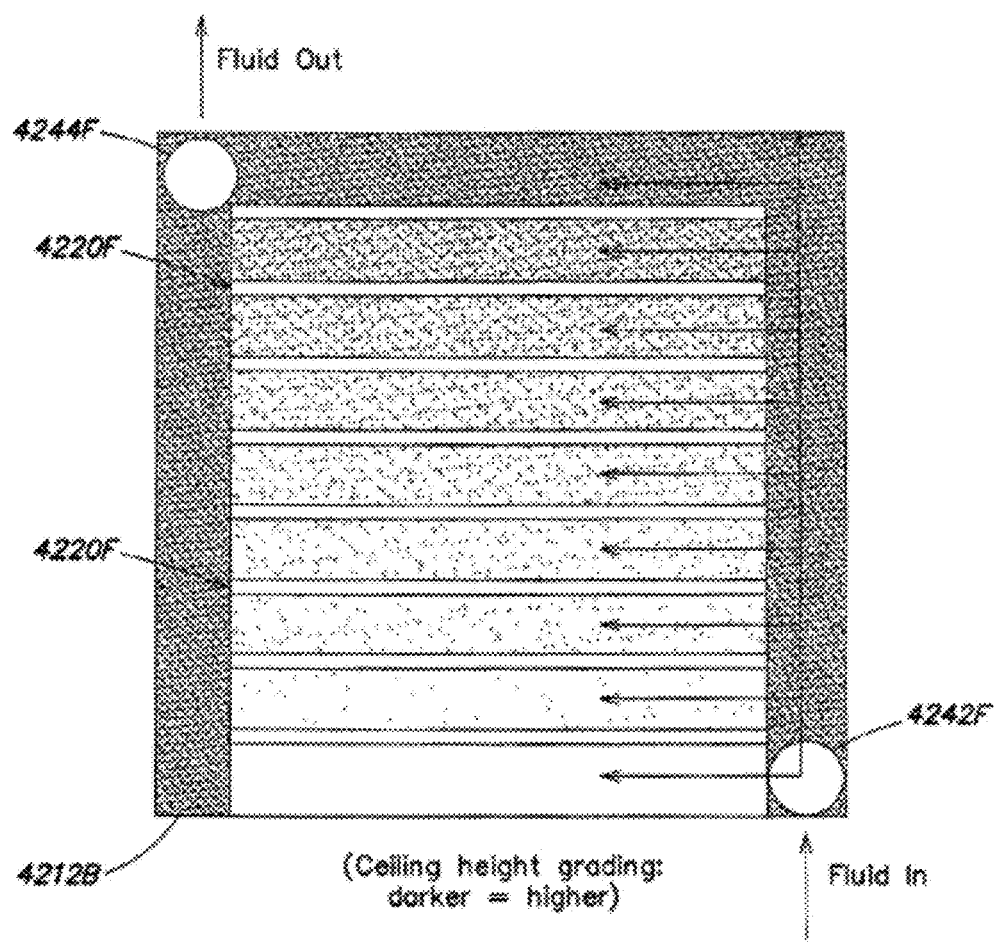
FIG. 42F1

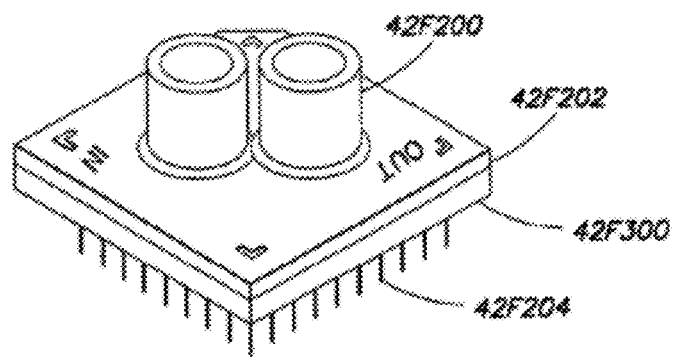
FIG. 42F2
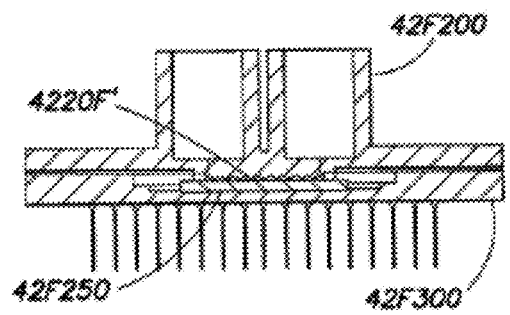
FIG. 42F3
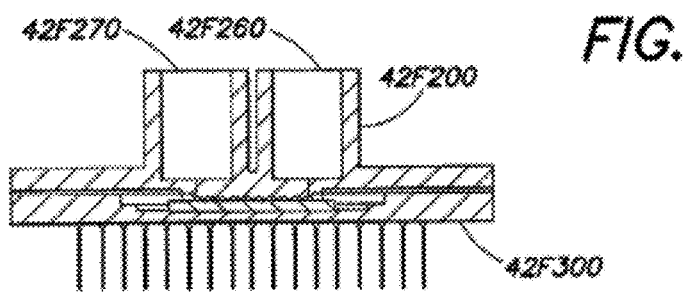
FIG. 42F4
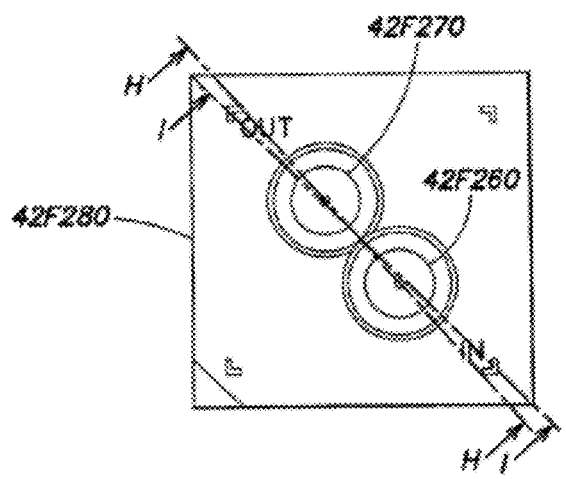
FIG. 42F5

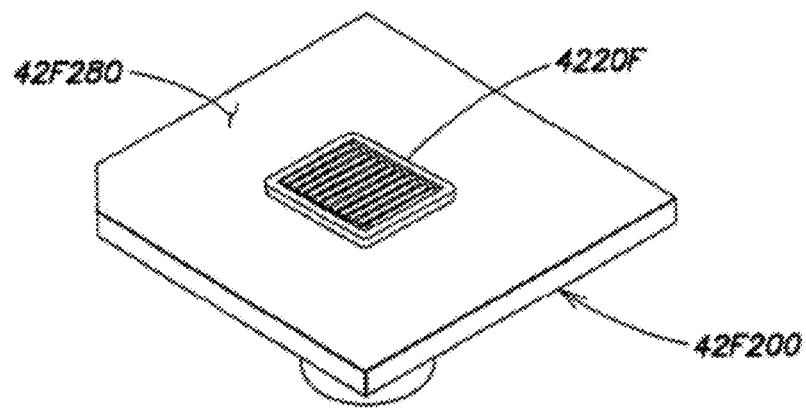
FIG. 42F6
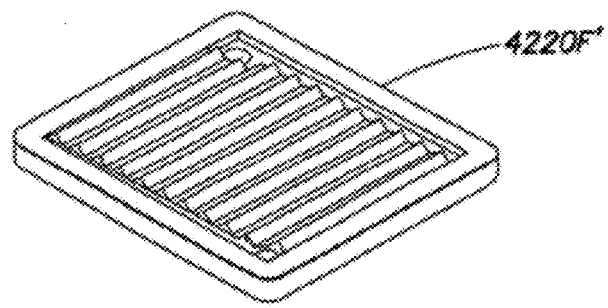
FIG. 42F7
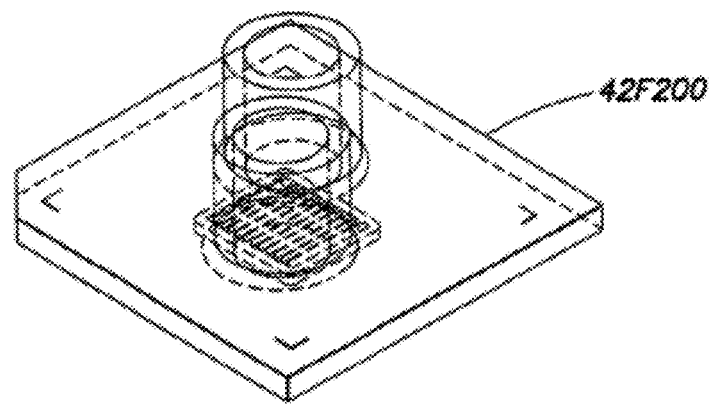
FIG. 42F8

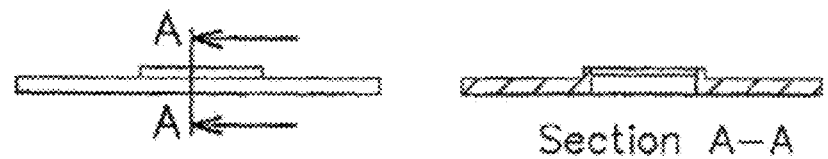
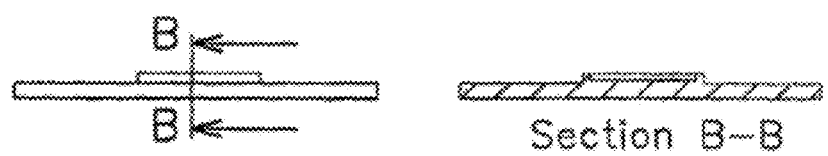
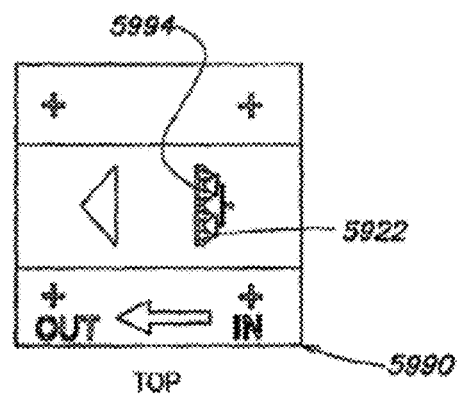
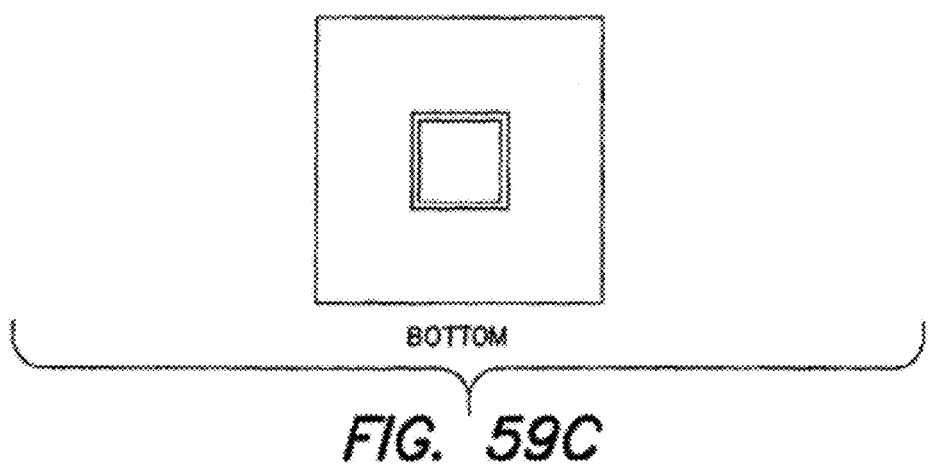
FIG. 59C

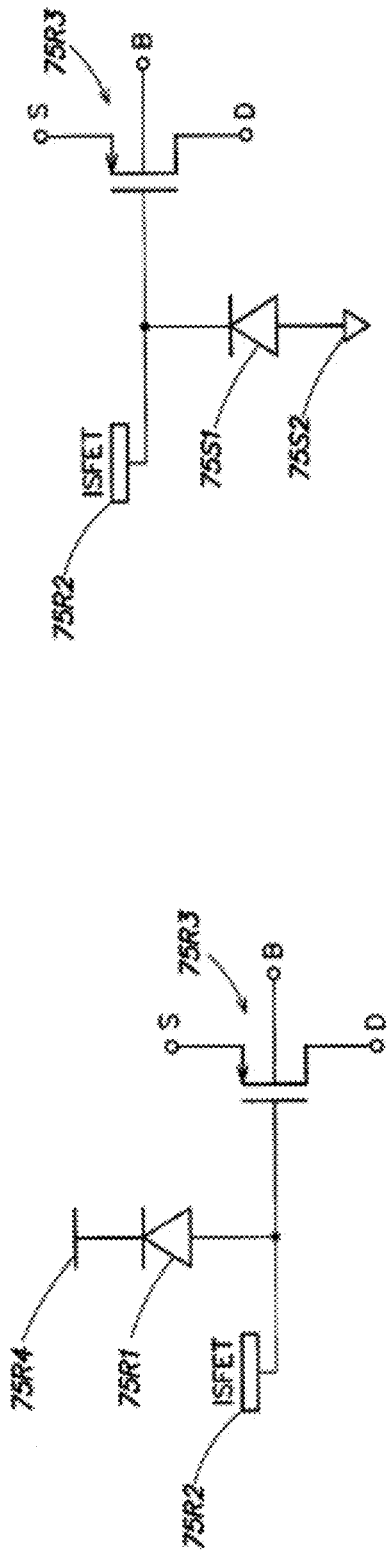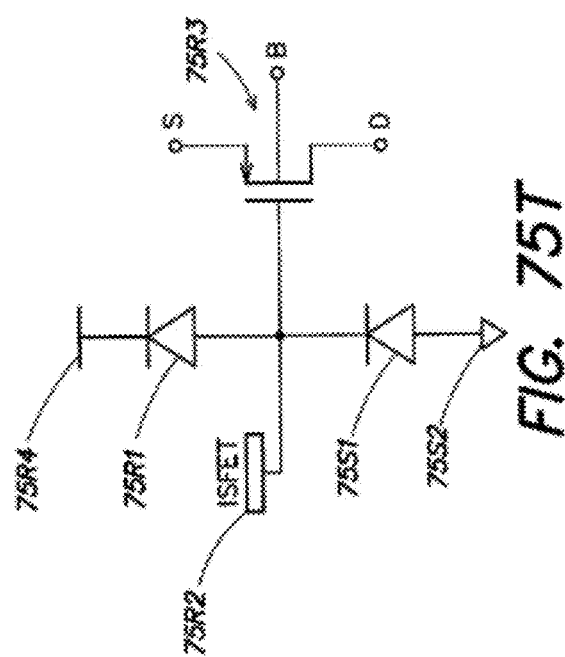
FIG. 75R
FIG. 75S
FIG. 75T

```
                        SEQUENCE LISTING

<160> NUMBER OF SEQ ID NOS: 10

<210> SEQ ID NO 1
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
gcaagtgccc ttaggcttca gttcaaaagt cctaactggg caaggcacac agggatagg      60

<210> SEQ ID NO 2
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
ccatgtcccc ttaagccccc cccattcccc cctgaacccc caaggcacac agggatagg      60

<210> SEQ ID NO 3
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
aagctcaaaa acggtaaaaa aaagccaaaa aactggaaaa caaggcacac agggatagg      60

<210> SEQ ID NO 4
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
ttcgagtttt tgccattttt tttcggtttt ttgaccttttt caaggcacac agggatagg      60

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5 gcccccccccc caaaaaaaaa a                                              21

<210> SEQ ID NO 6
<211> LENGTH: 23
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 6 tttttcttt ttctttctt tcc                                              23

<210> SEQ ID NO 7
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7 ttttttttg cccggttttc tttgc                                           25

<210> SEQ ID NO 8
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
actggtccag cattagccgt acgac                                          25

<210> SEQ ID NO 9
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
gtcgtacggc taa                                                       13

<210> SEQ ID NO 10
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
gtcgtacggc taat                                                      14
```

METHODS AND APPARATUS FOR MEASURING ANALYTES

CROSS-REFERENCE TO RELATED APPLICATIONS

This application is a continuation-in-part of U.S. patent application Ser. No. 12/475,311 filed May 29, 2009, now abandoned titled "Methods and Apparatus for Measuring Analytes". This application also claims priority under 35 U.S.C. §119(e) to U.S. Provisional Application No. 61/428,733, filed Dec. 30, 2010, titled "Apparatus, Methods, and Software for Performing Electrochemical Reactions". The contents of the foregoing applications are incorporated herein by reference in their entireties.

REFERENCE TO BIOLOGICAL SEQUENCE DISCLOSURE

This application contains nucleotide sequence and/or amino acid sequence disclosure in computer readable form and a written sequence listing, the entire contents of both of which are expressly incorporated by reference in their entirety as though fully set forth herein.

FIELD OF THE DISCLOSURE

The present disclosure is directed generally to inventive methods and apparatus relating to detection and measurement of one or more analytes including analytes associated with or resulting from a nucleic acid synthesis reaction.

BACKGROUND

Electronic devices and components have found numerous applications in chemistry and biology (mom generally, "life sciences"), especially for detection and measurement of various chemical and biological reactions and identification, detection and measurement of various compounds. One such electronic device is referred to as an ion-sensitive field effect transistor, often denoted in the relevant literature as ISFET (or pHFET). ISFETs conventionally have been explored, primarily in the academic and research community, to facilitate measurement of the hydrogen ion concentration of a solution (commonly denoted as "pH").

More specifically, an ISFET is an impedance transformation device that operates in a manner similar to that of a MOSFET (Metal Oxide Semiconductor Field Effect Transistor), and is particularly configured to selectively measure ion activity in a solution (e.g., hydrogen ions in the solution are the "analytes"). A detailed theory of operation of an ISFET is given in "Thirty years of ISFETOLOGY: what happened in the past 30 years and what may happen in the next 30 years," P. Bergveld, Sens. Actuators, 88 (2003), pp. 1-20, which publication is hereby incorporated herein by reference (hereinafter referred to as "Bergveld").

FIG. 1 illustrates a cross-section of a p-type (p-channel) ISFET 50 fabricated using a conventional CMOS (Complementary Metal Oxide Semiconductor) process. However, biCMOS (i.e., bipolar and CMOS) processing may also be used, such as a process that would include a PMOS FET array with bipolar structures on the periphery. Alternatively, other technologies may be employed wherein a sensing element can be made with a three-terminal devices in which a sensed ion leads to the development of a signal that controls one of the three terminals; such technologies may also include, for example, GaAs and carbon nanotube technologies. Taking the CMOS example, P-type ISFET fabrication is based on a p-type silicon substrate 52, in which an n-type well 54 forming a transistor "body" is formed. Highly doped p-type (p+) regions S and D, constituting a source 56 and a drain 58 of the ISFET, are formed within the n-type well 54. A highly doped n-type (n+) region B is also formed within the n-type well to provide a conductive body (or "bulk") connection 62 to the n-type well. An oxide layer 65 is disposed above the source, drain and body connection regions, through which openings are made to provide electrical connections (via electrical conductors) to these regions; for example, metal contact 66 serves as a conductor to provide an electrical connection to the drain 58, and metal contact 68 serves as a conductor to provide a common connection to the source 56 and n-type well 54, via the highly conductive body connection 62. A polysilicon gate 64 is formed above the oxide layer at a location above a region 60 of the n-type well 54, between the source 56 and the drain 58. Because it is disposed between the polysilicon gate 64 and the transistor body (i.e., the n-type well), the oxide layer 65 often is referred to as the "gate oxide."

Like a MOSFET, the operation of an ISFET is based on the modulation of charge concentration (and thus channel conductance) caused by a MOS (Metal-Oxide-Semiconductor) capacitance constituted by the polysilicon gate 64, the gate oxide 65 and the region 60 of the n-type well 54 between the source and the drain. When a negative voltage is applied across the gate and source regions ($V_{GS}$<0 Volts), a "p-channel" 63 is created at the interface of the region 60 and the gate oxide 65 by depleting this area of electrons. This p-channel 63 extends between the source and the drain, and electric current is conducted through the p-channel when the gate-source potential $V_{GS}$ is negative enough to attract holes from the source into the channel. The gate-source potential at which the channel 63 begins to conduct current is referred to as the transistor's threshold voltage $V_{TH}$ (the transistor conducts when $V_{GS}$ has an absolute value greater than the threshold voltage $V_{TH}$). The source is so named because it is the source of the charge carriers (holes for a p-channel) that flow through the channel 63; similarly, the drain is where the charge carriers leave the channel 63.

In the ISFET 50 of FIG. 1, the n-type well 54 (transistor body), via the body connection 62, is forced to be biased at a same potential as the source 56 (i.e., $V_{SB}$=0 Volts), as seen by the metal contact 68 connected to both the source 56 and the body connection 62. This connection prevents forward biasing of the p+ source region and the n-type well, and thereby facilitates confinement of charge carriers to the area of the region 60 in which the channel 63 may be formed. Any potential difference between the source 56 and the body/n-type well 54 (a non-zero source-to-body voltage $V_{SB}$) affects the threshold voltage $V_{TH}$ of the ISFET according to a non-linear relationship, and is commonly referred to as the "body effect," which in many applications is undesirable.

As also shown in FIG. 1, the polysilicon gate 64 of the ISFET 50 is coupled to multiple metal layers disposed within one or more additional oxide layers 75 disposed above the gate oxide 65 to form a "floating gate" structure 70. The floating gate structure is so named because it is electrically isolated from other conductors associated with the ISFET; namely, it is sandwiched between the gate oxide 65 and a passivation layer 72. In the ISFET 50, the passivation layer 72 constitutes an ion-sensitive membrane that gives rise to the ion-sensitivity of the device. The presence of analytes such as ions in an "analyte solution" 74 (i.e., a solution containing analytes (including ions) of interest or being tested for the presence of analytes of interest) in contact with the passivation layer 72, particularly in a sensitive area 78 above the floating gate structure 70, alters the electrical characteristics of the ISFET so as to modulate a current flowing through the p-channel 63 between the source 56 and the drain 58. The passivation layer 72 may comprise any one of a variety of different materials to facilitate sensitivity to particular ions; for example, passivation layers comprising silicon nitride or silicon oxynitride, as well as metal oxides such as silicon, aluminum or tantalum oxides, generally provide sensitivity to hydrogen ion concentration (pH) in the analyte solution 74, whereas passivation layers comprising polyvinyl chloride containing valinomycin provide sensitivity to potassium ion concentration in the analyte solution 74, Materials suitable for passivation layers and sensitive to other ions such as sodium, silver, iron, bromine, iodine, calcium, and nitrate, for example, are known.

With respect to ion sensitivity, an electric potential difference, commonly referred to as a "surface potential," arises at the solid/liquid interface of the passivation layer 72 and the analyte solution 74 as a function of the ion concentration in the sensitive area 78 due to a chemical reaction (e.g., usually involving the dissociation of oxide surface groups by the ions in the analyte solution 74 in proximity to the sensitive area 78). This surface potential in turn affects the threshold voltage $V_{TH}$ of the ISFET; thus, it is the threshold voltage $V_{TH}$ of the ISFET that varies with changes in ion concentration in the analyte solution 74 in proximity to the sensitive area 78.

FIG. 2 illustrates an electric circuit representation of the p-channel ISFET 50 shown in FIG. 1. With reference again to FIG. 1, a reference electrode 76 (a conventional Ag/AgCl electrode) in the analyte solution 74 determines the electric potential of the bulk of the analyte solution 74 itself and is analogous to the gate terminal of a conventional MOSFET, as shown in FIG. 2. In a linear or non-saturated operating region of the ISFET, the drain current $I_D$ is given as:

$$I_D = \beta \left( V_{GS} - V_{TH} - \frac{1}{2} V_{DS} \right) V_{DS}, \quad (1)$$

where $V_{DS}$ is the voltage between the drain and the source, and $\beta$ is a transconductance parameter (in units of Amps/Volts²) given by:

$$\beta = \mu C_{ox} \left( \frac{W}{L} \right), \quad (2)$$

where $\mu$ represents the carrier mobility, $C_{ox}$ is the gate oxide capacitance per unit area, and the ratio W/L is the width to length ratio of the channel 63. If the reference electrode 76 provides an electrical reference or ground ($V_G$=0 Volts), and the drain current $I_D$ and the drain-to-source voltage $V_{DS}$ are kept constant, variations of the source voltage $V_S$ of the ISFET directly track variations of the threshold voltage $V_{TH}$, according to Eq. (1); this may be observed by rearranging Eq. (1) as:

$$V_S = -V_{TH} - \left( \frac{I_D}{\beta V_{DS}} + \frac{V_{DS}}{2} \right). \quad (3)$$

Since the threshold voltage $V_{TH}$ of the ISFET is sensitive to ion concentration as discussed above, according to Eq. (3) the source voltage $V_S$ provides a signal that is directly related to the ion concentration in the analyte solution 74 in proximity to the sensitive area 78 of the ISFET. More specifically, the threshold voltage $V_{TH}$ is given by:

$$V_{TH} = V_{FB} - \frac{Q_B}{C_{ox}} + 2\phi_F, \quad (4)$$

where $V_{FB}$ is the flatband voltage, $Q_B$ is the depletion charge in the silicon and $\phi_F$ is the Fermi-potential. The flatband voltage in turn is related to material properties such as workfunctions and charge accumulation. In the case of an ISFET, with reference to FIGS. 1 and 2, the flatband voltage contains terms that reflect interfaces between 1) the reference electrode 76 (acting as the transistor gate G) and the analyte solution 74; and 2) the analyte solution 74 and the passivation layer 72 in the sensitive area 78 (which in turn mimics the interface between the polysilicon gate 64 of the floating gate structure 70 and the gate oxide 65). The flatband voltage $V_{FB}$ is thus given by:

$$V_{FB} = E_{ref} - \Psi_0 + \chi_{sol} - \frac{\Phi_{Si}}{q} - \frac{Q_{ss} + Q_{ox}}{C_{ox}}, \quad (5)$$

where $E_{ref}$ is the reference electrode potential relative to vacuum, $\Psi_0$ is the surface potential that results from chemical reactions at the analyte solution/passivation layer interface (e.g., dissociation of surface groups in the passivation layer), and $\chi_{sol}$ is the surface dipole potential of the analyte solution 74. The fourth term in Eq. (5) relates to the silicon workfunction (q is the electron charge), and the last term relates to charge densities at the silicon surface and in the gate oxide. The only term in Eq. (5) sensitive to ion concentration in the analyte solution 74 is $\Psi_0$, as the ion concentration in the analyte solution 74 controls the chemical reactions (dissociation of surface groups) at the analyte solution/passivation layer interface. Thus, substituting Eq. (5) into Eq. (4), it may be readily observed that it is the surface potential $\Psi_0$ that renders the threshold voltage $V_{TH}$ sensitive to ion concentration in the analyte solution 74.

Regarding the chemical reactions at the analyte solution/passivation layer interface, the surface of a given material employed for the passivation layer 72 may include chemical groups that may donate protons to or accept protons from the analyte solution 74, leaving at any given time negatively charged, positively charged, and neutral sites on the surface of the passivation layer 72 at the interface with the analyte solution 74. A model for this proton donation/acceptance process at the analyte solution/passivation layer interface is referred to in the relevant literature as the "Site-Dissociation Model" or the "Site-Binding Model," and the concepts underlying such a process may be applied generally to characterize surface activity of passivation layers comprising various materials (e.g., metal oxides, metal nitrides, metal oxynitrides).

Using the example of a metal oxide for purposes of illustration, the surface of any metal oxide contains hydroxyl groups that may donate a proton to or accept a proton from the analyte to leave negatively or positively charged sites, respectively, on the surface. The equilibrium reactions at these sites may be described by:

$$AOH \leftrightarrows AO^- + H_S^+ \quad (6)$$

$$AOH_2^+ \leftrightarrows AOH + H_S^+ \quad (7)$$

where A denotes an exemplary metal, $H_S^+$ represents a proton in the analyte solution 74. Eq. (6) describes proton donation by a surface group, and Eq. (7) describes proton acceptance by a surface group. It should be appreciated that the reactions given in Eqs. (6) and (7) also are present and need to be considered in the analysis of a passivation layer comprising metal nitrides, together with the equilibrium reaction:

$$ANH_3^+ \leftrightarrows ANH_2 + H^+, \qquad (7b)$$

wherein Eq. (7b) describes another proton acceptance equilibrium reaction. For purposes of the present discussion however, again only the proton donation and acceptance reactions given in Eqs. (6) and (7) are initially considered to illustrate the relevant concepts.

Based on the respective forward and backward reaction rate constants for each equilibrium reaction, intrinsic dissociation constants $K_a$ (for the reaction of Eq. (6)) and $K_b$ (for the reaction of Eq. (7)) may be calculated that describe the equilibrium reactions. These intrinsic dissociation constants in turn may be used to determine a surface charge density $\sigma_0$ (in units of Coulombs/unit area) of the passivation layer 72 according to:

$$\sigma_0 = -qB, \qquad (8)$$

where the term B denotes the number of negatively charged surface groups minus the number of positively charged surface groups per unit area, which in turn depends on the total number of proton donor/acceptor sites per unit area $N_S$ on the passivation layer surface, multiplied by a factor relating to the intrinsic dissociation constants $K_a$ and $K_b$ of the respective proton donation and acceptance equilibrium reactions and the surface proton activity (or $pH_S$). The effect of a small change in surface proton activity ($pH_S$) on the surface charge density is given by:

$$\frac{\partial \sigma_0}{\partial pH_S} = -q\frac{\partial B}{\partial pH_S} = -q\beta_{int}, \qquad (9)$$

where $\beta_{int}$ is referred to as the "intrinsic buffering capacity" of the surface. It should be appreciated that since the values of $N_S$, $K_a$ and $K_b$ are material dependent, the intrinsic buffering capacity $\beta_{int}$ of the surface similarly is material dependent.

The fact that ionic species in the analyte solution 74 have a finite size and cannot approach the passivation layer surface any closer than the ionic radius results in a phenomenon referred to as a "double layer capacitance" proximate to the analyte solution/passivation layer interface. In the Gouy-Chapinan-Stern model for the double layer capacitance as described in Bergveld, the surface charge density $\sigma_0$ is balanced by an equal but opposite charge density in the analyte solution 74 at some position from the surface of the passivation layer 72. These two parallel opposite charges form a so-called "double layer capacitance" $C_{dl}$ (per unit area), and the potential difference across the capacitance $C_{dl}$ is defined as the surface potential $\Psi_0$, according to:

$$\sigma_0 = C_{dl}\Psi_0 = -\sigma_{dl} \qquad (10)$$

where $\sigma_{dl}$ is the charge density on the analyte solution side of the double layer capacitance. This charge density $\sigma_{dl}$ in turn is a function of the concentration of all ion species or other analyte species (i.e., not just protons) in the bulk analyte solution 74; in particular, the surface charge density can be balanced not only by hydrogen ions but other ion species (e.g., $Na^+$, $K^+$) in the bulk analyte solution.

In the regime of relatively lower ionic strengths (e.g., <1 mole/liter), the Debye theory may be used to describe the double layer capacitance $C_{dl}$ according to:

$$C_{dl} = \frac{k\varepsilon_0}{\lambda} \qquad (11)$$

where k is the dielectric constant $\in/\in_0$ (for relatively lower ionic strengths, the dielectric constant of water may be used), and $\lambda$ is the Debye screening length (i.e., the distance over which significant charge separation can occur). The Debye length $\lambda$ is in turn inversely proportional to the square root of the strength of the ionic species in the analyte solution, and in water at room temperature is given by:

$$\lambda = \frac{0.3 \text{ nm}}{\sqrt{I}}. \qquad (12)$$

The ionic strength I of the bulk analyte is a function of the concentration of all ionic species present, and is given by:

$$I = \frac{1}{2}\sum_s z_s^2 c_s, \qquad (13)$$

where $z_s$ is the charge number of ionic species s and $c_s$ is the molar concentration of ionic species s. Accordingly, from Eqs. (10) through (13), it may be observed that the surface potential is larger for larger Debye screening lengths (i.e., smaller ionic strengths).

The relation between pH values present at the analyte solution/passivation layer interface and in the bulk solution is expressed in the relevant literature by Boltzman statistics with the surface potential $\Psi_0$ as a parameter:

$$(pH_s - pH_B) = \frac{q\Psi_0}{kT}. \qquad (14)$$

From Eqs. (9), (10) and (14), the sensitivity of the surface potential $\Psi_0$ particularly to changes in the bulk pH of the analyte solution (i.e., "pH sensitivity") is given by:

$$\frac{\Delta\Psi_0}{\Delta pH} = -2.3\frac{kT}{q}\alpha, \qquad (15)$$

where the parameter $\alpha$ is a dimensionless sensitivity factor that varies between zero and one and depends on the double layer capacitance $C_{dl}$ and the intrinsic buffering capacity of the surface $\beta_{int}$ as discussed above in connection with Eq. (9). In general, passivation layer materials with a high intrinsic buffering capacity $\beta_{int}$ render the surface potential $\Psi_0$ less sensitive to concentration in the analyte solution 74 of ionic species other than protons (e.g., $\alpha$ is maximized by a large $\beta_{int}$). From Eq. (15), at a temperature T of 298 degrees Kelvin, it may be appreciated that a theoretical maximum pH sensitivity of 59.2 mV/pH may be achieved at $\alpha=1$. From Eqs. (4) and (5), as noted above, changes in the ISFET threshold voltage $V_{TH}$ directly track changes in the surface potential $\Psi_0$; accordingly, the pH sensitivity of an ISFET given by Eq. (15) also may be denoted and referred to herein as $\Delta V_{TH}$ for convenience. In exemplary conventional ISFETs employing a silicon nitride or silicon oxynitride passivation layer 72 for pH-sensitivity, pH sensitivities $\Delta V_{TH}$ (i.e., a change in threshold voltage with change in pH of the analyte solution 74) over a range of approximately 30 mV/pH to 60 mV/pH have been observed experimentally.

Another noteworthy metric in connection with ISFET pH sensitivity relates to the bulk pH of the analyte solution 74 at which there is no net surface charge density $\sigma_0$ and, accordingly, a surface potential $\Psi_0$ of zero volts. This pH is referred to as the "point of zero charge" and denoted as $pH_{pzc}$. With reference again to Eqs. (8) and (9), like the intrinsic buffering capacity $\beta_{int}$, $pH_{pzc}$ is a material dependent parameter. From the foregoing, it may be appreciated that the surface potential at any given bulk $pH_B$; of the analyte solution 74 may be calculated according to:

$$\Psi_0(pH_B) = (pH_B - pH_{pzc}) \frac{\Delta \Psi_0}{\Delta pH}. \tag{16}$$

Table 1 below lists various metal oxides and metal nitrides and their corresponding points of zero charge ($pH_{pzc}$), pH sensitivities ($\Delta V_{TH}$), and theoretical maximum surface potential at a pH of 9:

TABLE 1

| Metal | Oxide/Nitride | $pH_{pzc}$ | $\Delta V_{TH}$ (mV/pH) | Theoretical $\Psi_0$ (mV) @ pH = 9 |
|---|---|---|---|---|
| Al | Al$_2$O$_3$ | 9.2 | 54.5 (35° C.) | −11 |
| Zr | ZrO$_2$ | 5.1 | 50 | 150 |
| Ti | TiO$_2$ | 5.5 | 57.4-62.3 (32° C., pH 3-11) | 201 |
| Ta | Ta$_2$O$_5$ | 2.9, 2.8 | 62.87 (35° C.) | 384 |
| Si | Si$_3$N$_4$ | 4.6, 6-7 | 56.94 (25° C.) | 251 |
| Si | SiO$_2$ | 2.1 | 43 | 297 |
| Mo | MoO$_3$ | 1.8-2.1 | 48-59 | 396 |
| Hf | HfO$_2$ | 7-4-7.6 | 50-58 | 81.2 |
| W | WO$_2$ | 0.3, 0.43, 0.5 | 50 | 435 |

Prior research efforts to fabricate ISFETs for pH measurements based on conventional CMOS processing techniques typically have aimed to achieve high signal linearity over a pH range from 1-14. Using an exemplary threshold sensitivity of approximately 50 mV/pH, and considering Eq. (3) above, this requires a linear operating range of approximately 700 mV for the source voltage $V_s$. As discussed above in connection with FIG. 1, the threshold voltage $V_{TH}$ of ISFETs (as well as MOSFETs) is affected by any voltage $V_{SB}$ between the source and the body (n-type well 54). More specifically, the threshold voltage $V_{TH}$ is a nonlinear function of a nonzero source-to-body voltage $V_{SB}$. Accordingly, so as to avoid compromising linearity due to a difference between the source and body voltage potentials (i.e., to mitigate the "body effect"), as shown in FIG. 1 the source 56 and body connection 62 of the ISFET 50 often are coupled to a common potential via the metal contact 68. This body-source coupling also is shown in the electric circuit representation of the ISFET 50 shown in FIG. 2.

While the foregoing discussion relates primarily to a steady state analysis of ISFET response based on the equilibrium reactions given in Eqs. (6) and (7), the transient or dynamic response of a conventional ISFET to an essentially instantaneous change in ionic strength of the analyte solution 74 (e.g., a stepwise change in proton or other ionic species concentration) has been explored in some research efforts. One exemplary treatment of ISFET transient or dynamic response is found in "ISFET responses on a stepwise change in electrolyte concentration at constant pH," J. C. van Kerkof, J. C. T. Eijkel and P. Bergveld, *Sensors and Actuators B*, 18-19 (1994), pp. 56-59, which is incorporated herein by reference.

For ISFET transient response, a stepwise change in the concentration of one or more ionic species in the analyte solution in turn essentially instantaneously changes the charge density $\sigma_{dl}$ on the analyte solution side of the double layer capacitance $C_{dl}$. Because the instantaneous change in charge density $\sigma_{dl}$ is faster than the reaction kinetics at the surface of the passivation layer 72, the surface charge density $\sigma_0$ initially remains constant, and the change in ion concentration effectively results in a sudden change in the double layer capacitance $C_{dl}$. From Eq. (10), it may be appreciated that such a sudden change in the capacitance $C_{dl}$ at a constant surface charge density $\sigma_0$ results in a corresponding sudden change in the surface potential $\Psi_0$. FIG. 2A illustrates this phenomenon, in which an essentially instantaneous or stepwise increase in ion concentration in the analyte solution, as shown in the top graph, results in a corresponding change in the surface potential $\Psi_0$, as shown in the bottom graph of FIG. 2A. After some time, as the passivation layer surface groups react to the stimulus (i.e., as the surface charge density adjusts), the system returns to some equilibrium point, as illustrated by the decay of the ISFET response "pulse" 79 shown in the bottom graph of FIG. 2A. The foregoing phenomenon is referred to in the relevant literature (and hereafter in this disclosure) as an "ion-step" response.

As indicated in the bottom graph of FIG. 2A, an amplitude $\Delta \Psi_0$ of the ion-step response 79 may be characterized by:

$$\Delta \Psi_0 = \Psi_1 - \Psi_2 = \frac{\sigma_0}{C_{dl,1}} - \frac{\sigma_0}{C_{dl,2}} = \Psi_1 \left(1 - \frac{C_{dl,1}}{C_{dl,2}}\right), \tag{17}$$

where $\Psi_1$ is an equilibrium surface potential at an initial ion concentration in the analyte solution, $C_{dl,1}$ is the double layer capacitance per unit area at the initial ion concentration, $\Psi_2$ is the surface potential corresponding to the ion-step stimulus, and $C_{dl,2}$ is the double layer capacitance per unit area based on the ion-step stimulus. The time decay profile 81 associated with the response 79 is determined at least in part by the kinetics of the equilibrium reactions at the analyte solution/passivation layer interface (e.g., as given by Eqs. (6) and (7) for metal oxides, and also Eq. (7b) for metal nitrides). One instructive treatment in this regard is provided by "Modeling the short-time response of ISFET sensors," P. Woias et al., *Sensors and Actuators B*, 24-25 (1995) 211-217 (hereinafter referred to as "Woias"), which publication is incorporated herein by reference.

In the Woias publication, an exemplary ISFET having a silicon nitride passivation layer is considered. A system of coupled non-linear differential equations based on the equilibrium reactions given by Eqs. (6), (7), and (7a) is formulated to describe the dynamic response of the ISFET to a step (essentially instantaneous) change in pH; more specifically, these equations describe the change in concentration over time of the various surface species involved in the equilibrium reactions, based on the forward and backward rate constants for the involved proton acceptance and proton donation reactions and how changes in analyte pH affect one or more of the reaction rate constants. Exemplary solutions, some of which include multiple exponential functions and associated time constants, are provided for the concentration of each of the surface ion species as a function of time. In one example provided by Woias, it is assumed that the proton donation reaction given by Eq. (6) dominates the transient response of the silicon nitride passivation layer surface for relatively small step changes in pH, thereby facilitating a mono-exponential approximation for the time decay profile 81 of the response 79 according to:

$$\Psi_0(t) = \Delta \Psi_0 e^{-1/t},\qquad(18)$$

where the exponential function essentially represents the change in surface charge density as a function of time. In Eq. (16), the time constant r is both a function of the bulk pH and material parameters of the passivation layer, according to:

$$\tau = \tau_0 \times 10^{pH/2},\qquad(19)$$

where $\tau_0$ denotes a theoretical minimum response time that only depends on material parameters. For silicon nitride, Woias provides exemplary values for $\tau_0$ on the order of 60 microseconds to 200 microseconds. For purposes of providing an illustrative example, using $\tau_0 = 60$ microseconds and a bulk pH of 9, the time constant $\tau$ given by Eq. (19) is 1.9 seconds. Exemplary values for other types of passivation materials may be found in the relevant literature and/or determined empirically.

Previous efforts to fabricate two-dimensional arrays of ISFETs based on the ISFET design of FIG. 1 have resulted in a maximum of 256 ISFET sensor elements (or "pixels") in an array (i.e., a 16 pixel by 16 pixel array). Exemplary research in ISFET array fabrication is reported in the publications "A large transistor-based sensor array chip for direct extracellular imaging," M. J. Milgrew, M. O. Riehle, and D. R. S. Cumming, *Sensors and Actuators, B: Chemical,* 111-112, (2005), pp. 347-353, and "The development of scalable sensor arrays using standard CMOS technology," M. J. Milgrew, P. A. Hammond, and D. R. S. Cumming, *Sensors and Actuators, B: Chemical,* 103, (2004), pp. 37-42, which publications are incorporated herein by reference and collectively referred to hereafter as "Milgrew et al." Other research efforts relating to the realization of ISFET arrays are reported in the publications "A very large integrated pH-ISFET sensor array chip compatible with standard CMOS processes," T. C. W. Yeow, M. R. Haskard, D. E. Mulcahy, H. I. Seo and D. H. Kwon, *Sensors and Actuators B: Chemical,* 44, (1997), pp. 434-440 and "Fabrication of a two-dimensional pH image sensor using a charge transfer technique," Hizawa, T., Sawada, K., Takao, H., Ishida, M., *Sensors and Actuators, B: Chemical* 117 (2), 2006, pp. 509-515, which publications also are incorporated herein by reference.

FIG. 3 illustrates one column 85$_j$ of a two-dimensional ISFET array according to the design of Milgrew et al. The column 85$_j$ includes sixteen (16) pixels 80$_1$ through 80$_{16}$ and, as discussed further below in connection with FIG. 7, a complete two-dimensional array includes sixteen (16) such columns 85$_j$ (j=1, 2, 3, ... 16) arranged side by side. As shown in FIG. 3, a given column 85$_j$ includes a current source $I_{SOURCEj}$ that is shared by all pixels of the column, and ISFET bias/readout circuitry 82$_j$ (including current sink $I_{SINKj}$) that is also shared by all pixels of the column. Each ISFET pixel 80$_1$ through 80$_{16}$ includes a p-channel ISFET 50 having an electrically coupled source and body (as shown in FIGS. 1 and 2), plus two switches S1 and S2 that are responsive to one of sixteen row select signals (RSEL$_1$ through RSEL$_{16}$, and their complements). As discussed below in connection with FIG. 7, a row select signal and its complement are generated simultaneously to "enable" or select a given pixel of the column 85$_j$, and such signal pairs are generated in some sequence to successively enable different pixels of the column one at a time.

As shown in FIG. 3, the switch S2 of each pixel 80 in the design of Milgrew et al, is implemented as a conventional n-channel MOSFET that couples the current source $I_{SOURCEj}$ to the source of the ISFET 50 upon receipt of the corresponding row select signal. The switch S1 of each pixel 80 is implemented as a transmission gate, i.e., a CMOS pair including an n-channel MOSFET and a p-channel MOSFET, that couples the source of the ISFET 50 to the bias/readout circuitry 82$_j$ upon receipt of the corresponding row select signal and its complement. An example of the switch S1$_1$ of the pixel 80$_1$ is shown in FIG. 4, in which the p-channel MOSFET of the transmission gate is indicated as S1$_{1P}$ and the n-channel MOSFET is indicated as S1$_{1N}$. In the design of Milgrew et al., a transmission gate is employed for the switch S1 of each pixel so that, for an enabled pixel, any ISFET source voltage within the power supply range $V_{DD}$ to $V_{SS}$ may be applied to the bias/readout circuitry 82$_j$ and output by the column as the signal $V_{Sj}$. From the foregoing, it should be appreciated that each pixel 80 in the ISFET sensor array design of Milgrew et al. includes four transistors, i.e., a p-channel ISFET, a CMOS-pair transmission gate including an n-channel MOSFET and a p-channel MOSFET for switch S1, and an n-channel MOSFET for switch S2.

As also shown in FIG. 3, the bias/readout circuitry 82$_j$ employs a source-drain follower configuration in the form of a Kelvin bridge to maintain a constant drain-source voltage $V_{DSj}$ and isolate the measurement of the source voltage $V_{Sj}$ from the constant drain current $I_{SOURCEj}$ for the ISFET of an enabled pixel in the column 85$_j$. To this end, the bias/readout circuitry 82$_j$ includes two operational amplifiers A1 and A2, a current sink $I_{SINKj}$, and a resistor $R_{SDj}$. The voltage developed across the resistor $R_{SDj}$ due to the current $I_{SINKj}$ flowing through the resistor is forced by the operational amplifiers to appear across the drain and source of the ISFET of an enabled pixel as a constant drain-source voltage $V_{DSj}$. Thus, with reference again to Eq. (3), due to the constant $V_{DSj}$ and the constant $I_{SOURCEj}$, the source voltage $V_{Sj}$ of the ISFET of the enabled pixel provides a signal corresponding to the ISFETs threshold voltage $V_{TH}$, and hence a measurement of pH in proximity to the ISFETs sensitive area (see FIG. 1). The wide dynamic range for the source voltage $V_{Sj}$ provided by the transmission gate S1 ensures that a full range of pH values front 1-14 may be measured, and the source-body connection of each ISFET ensures sufficient linearity of the ISFETs threshold voltage over the full pH measurement range.

In the column design of Milgrew et al. shown in FIG. 3, it should be appreciated that for the Kelvin bridge configuration of the column bias/readout circuitry 82$_j$ to function properly, a p-channel ISFET 50 as shown in FIG. 1 must be employed in each pixel; more specifically, an alternative implementation based on the Kelvin bridge configuration is not possible using an n-channel ISFET. With reference again to FIG. 1, for an n-channel ISFET based on a conventional CMOS process, the n-type well 54 would not be required, and highly doped n-type regions for the drain and source would be formed directly in the p-type silicon substrate 52 (which would constitute the transistor body). For n-channel FET devices, the transistor body typically is coupled to electrical ground. Given the requirement that the source and body of an ISFET in the design of Milgrew et al. are electrically coupled together to mitigate nonlinear performance due to the body effect, this would result in the source of an n-channel ISFET also being connected to electrical ground (i.e., $V_S = V_B = 0$ Volts), thereby precluding any useful output signal from an enabled pixel. Accordingly, the column design of Milgrew et al. shown in FIG. 3 requires p-channel ISFETs for proper operation.

It should also be appreciated that in the column design of Milgrew et al. shown in FIG. 3, the two n-channel MOSFETs required to implement the switches S1 and S2 in each pixel cannot be formed in the n-type well 54 shown in FIG. 1, in which the p-channel ISFET for the pixel is formed; rather, the n-channel MOSFETs are formed directly in the p-type silicon substrate 52, beyond the confines of the n-type well 54 for the ISFET. FIG. 5 is a diagram similar to FIG. 1, illustrating a wider cross-section of a portion of the p-type silicon substrate 52 corresponding to one pixel 80 of the column 85j shown in FIG. 3, in which the n-type well 54 containing the drain 58, source 56 and body connection 62 of the ISFET 50 is shown alongside a first n-channel MOSFET corresponding to the switch S2 and a second n-channel MOSFET $S1_{IN}$ constituting one of the two transistors of the transmission gate $S1_1$ shown in FIG. 4.

Furthermore, in the design of Milgrew et al., the p-channel MOSFET required to implement the transmission gate S1 in each pixel (e.g., see $S1_{1P}$ in FIG. 4) cannot be formed in the same n-type well in which the p-channel ISFET 50 for the pixel is formed. In particular, because the body and source of the p-channel ISFET are electrically coupled together, implementing the p-channel MOSFET $S1_{1P}$ in the same n-well as the p-channel ISFET 50 would lead to unpredictable operation of the transmission gate, or preclude operation entirely. Accordingly, two separate n-type wells are required to implement each pixel in the design of Milgrew et al. FIG. 6 is a diagram similar to FIG. 5, showing a cross-section of another portion of the p-type silicon substrate 52 corresponding to one pixel 80, in which the n-type well 54 corresponding to the ISFET 50 is shown alongside a second n-type well 55 in which is formed the p-channel MOSFET $S1_{1P}$ constituting one of the two transistors of the transmission gate $S1_1$ shown in FIG. 4. It should be appreciated that the drawings in FIGS. 5 and 6 are not to scale and may not exactly represent the actual layout of a particular pixel in the design of Milgrew et al.; rather these figures are conceptual in nature and are provided primarily to illustrate the requirements of multiple n-wells, and separate n-channel MOSFETs fabricated outside of the n-wells, in the design of Milgrew et al.

The array design of Milgrew et al. was implemented using a 0.35 micrometer (μm) conventional CMOS fabrication process. In this process, various design rules dictate minimum separation distances between features. For example, according to the 0.35 μm CMOS design rules, with reference to FIG. 6, a distance "a" between neighboring n-wells must be at least three (3) micrometers. A distance "a/2" also is indicated in FIG. 6 to the left of the n-well 54 and to the right of the n-well 55 to indicate the minimum distance required to separate the pixel 80 shown in FIG. 6 from neighboring pixels in other columns to the left and right, respectively. Additionally, according to typical 0.35 μm CMOS design rules, a distance "b" shown in FIG. 6 representing the width in cross-section of the n-type well 54 and a distance "c" representing the width in cross-section of the n-type well 55 are each on the order of approximately 3 μm to 4 μm (within the n-type well, an allowance of 1.2 μm is made between the edge of the n-well and each of the source and drain, and the source and drain themselves have a width on the order of 0.7 μm). Accordingly, a total distance "d" shown in FIG. 6 representing the width of the pixel 80 in cross-section is on the order of approximately 12 μm to 14 μm. In one implementation, Milgrew et al. report an array based on the column/pixel design shown in FIG. 3 comprising geometrically square pixels each having a dimension of 12.8 μm by 12.8 μm.

In sum, the ISFET pixel design of Milgrew et al. is aimed at ensuring accurate hydrogen ion concentration measurements over a pH range of 1-14. To ensure measurement linearity, the source and body of each pixel's ISFET are electrically coupled together. To ensure a full range of pH measurements, a transmission gate S1 is employed in each pixel to transmit the source voltage of an enabled pixel. Thus, each pixel of Milgrew's array requires four transistors (p-channel ISFET, p-channel MOSFET, and two n-channel MOSFETs) and two separate n-wells (FIG. 6). Based on a 0.35 micrometer conventional CMOS fabrication process and corresponding design rules, the pixels of such an array have a minimum size appreciably greater than 10 μm, i.e., on the order of approximately 12 μm to 14 μm.

FIG. 7 illustrates a complete two-dimensional pixel array 95 according to the design of Milgrew et al., together with accompanying row and column decoder circuitry and measurement readout circuitry. The array 95 includes sixteen columns $85_1$ through $85_{16}$ of pixels, each column having sixteen pixels as discussed above in connection with FIG. 3 (i.e., a 16 pixel by 16 pixel array). A row decoder 92 provides sixteen pairs of complementary row select signals, wherein each pair of row select signals simultaneously enables one pixel in each column $85_1$ through $85_{16}$ to provide a set of column output signals from the array 95 based on the respective source voltages $V_{S1}$ through $V_{S16}$ of the enabled row of ISFETs. The row decoder 92 is implemented as a conventional four-to-sixteen decoder (i.e., a four-bit binary input $ROW_1$-$ROW_4$ to select one of $2^4$ outputs). The set of column output signals $V_{S1}$ through $V_{S16}$ for an enabled row of the array is applied to switching logic 96, which includes sixteen transmission gates S1 through S16 (one transmission gate for each output signal). As above, each transmission gate of the switching logic 96 is implemented using a p-channel MOSFET and an n-channel MOSFET to ensure a sufficient dynamic range for each of the output signals $V_{S1}$ through $V_{S16}$. The column decoder 94, like the row decoder 92, is implemented as a conventional four-to-sixteen decoder and is controlled via the four-bit binary input $COL_1$-$COL_4$ to enable one of the transmission gates S1 through S16 of the switching logic 96 at any given time, so as to provide a single output signal $V_S$ from the switching logic 96. This output signal $V_S$ is applied to a 10-bit analog to digital converter (ADC) 98 to provide a digital representation $D_1$-$D_{10}$ of the output signal $V_S$ corresponding to a given pixel of the array.

As noted earlier, individual ISFETs and arrays of ISFETs similar to those discussed above have been employed as sensing devices in a variety of chemical and biological applications. In particular, ISFETs have been employed as pH sensors in the monitoring of various processes involving nucleic acids such as DNA. Some examples of employing ISFETs in various life-science related applications are given in the following publications, each of which is incorporated herein by reference: Massimo Barbaro, Annalisa Bonfiglio, Luigi Raffo, Andrea Alessandrini, Paolo Facci and Imrich Barák, "Fully electronic DNA hybridization detection by a standard CMOS biochip," *Sensors and Actuators B: Chemical*, Volume 118, Issues 1-2, 2006, pp. 41-46; Toshinari Sakurai and Yuzuru Husimi, "Real-time monitoring of DNA polymerase reactions by a micro ISFET pH sensor," *Anal. Chem.*, 64(17), 1992, pp 1996-1997; S. Purushothaman, C. Toumazou, J. Georgiou, "Towards fast solid state DNA sequencing," *Circuits and Systems*, vol. 4, 2002, pp. IV-169 to IV-172; S. Purushothaman, C. Toumazou, C. P. Ou, "Protons and single nucleotide polymorphism detection: A simple use for the Ion Sensitive Field Effect Transistor," *Sensors and Actuators B: Chemical*, Vol. 114, no. 2, 2006, pp. 964-968; A. L. Simonian, A. W. Flounders, J. R. Wild, "FET-Based Biosensors for The Direct Detection of Organophosphate Neurotoxins," *Electroanalysis*, Vol. 16, No. 22, 2004, pp. 1896-1906; C. Toumazou, S. Purushothaman, "Sensing Apparatus and Method," United States Patent Application 2004-0134798, published Jul. 15, 2004; and T. W. Koo, S. Chan, X. Su, Z. Jingwu, M. Yamakawa, V. M. Dubin, "Sensor Arrays and Nucleic Acid Sequencing Applications," United States Patent Application 2006-0199193, published Sep. 7, 2006.

In general, the development of rapid and sensitive nucleic acid sequencing methods utilizing automated DNA sequencers has significantly advanced the understanding of biology. The term "sequencing" refers to the determination of a primary structure (or primary sequence) of an unbranched biopolymer, which results in a symbolic linear depiction known as a "sequence" that succinctly summarizes much of the atomic-level structure of the sequenced molecule. Nucleic acid (such as DNA) sequencing particularly refers to the process of determining the nucleotide order of a given nucleic acid fragment. Analysis of entire genomes of viruses, bacteria, fungi, animals and plants is now possible, but such analysis generally is limited due to the cost and time required to sequence such large genomes. Moreover, present conventional sequencing methods are limited in terms of their accuracy, the length of individual templates that can be sequenced, and the rate of sequence determination.

Despite improvements in sample preparation and sequencing technologies, none of the present conventional sequencing strategies, including those to date that may involve ISFETs, has provided the cost reductions required to increase throughput to levels required for analysis of large numbers of individual human genomes. The ability to sequence many human genomes facilitates an analysis of the genetic basis underlying disease (e.g., such as cancer) and aging, for example. Some recent efforts have made significant gains in both the ability to prepare genomes for sequencing and to sequence large numbers of templates simultaneously. However, these and other efforts are still limited by the relatively large size of the reaction volumes, as well as the need for special nucleotide analogues, and complex enzymatic or fluorescent methods to "read out" nucleotide sequence.

SUMMARY

Aspects of the invention relate in part to the use of large arrays of chemically sensitive FETs (chemFETs) or more specifically ISFETs for monitoring reactions, including for example nucleic acid (e.g., DNA) sequencing reactions, based on monitoring analytes present, generated or used during a reaction. More generally, arrays including large arrays of chemFETs may be employed to detect and measure static and/or dynamic amounts or concentrations of a variety of analytes (e.g., hydrogen ions, other ions, non-ionic molecules or compounds, etc.) in a variety of chemical and/or biological processes (e.g., biological or chemical reactions, cell or tissue cultures or monitoring, neural activity, nucleic acid sequencing, etc.) in which valuable information may be obtained based on such analyte measurements. Such chemFET arrays may be employed in methods that detect analytes and/or methods that monitor biological or chemical processes via changes in charge at the chemFET surface. Accordingly, the systems and methods shown herein provide uses for chemFET arrays that involve detection of analytes in solution and/or detection of change in charge bound to the chemFET surface.

Methods am presented for maintaining or increasing signal (and thus signal-to-noise ratio) when using very large chemFET arrays, and in particular when increasing the density of a chemFET array (and concomitantly decreasing the area of any single chemFET within the array). It has been found that as chemFET area decreases in order to accommodate an ever increasing number of sensors on a given array, the signal that can be obtained from a single chemFET may in some instances decrease. The invention provides in some aspects and embodiments methods for overcoming this limitation.

Of particular importance is the ability to increase signal during a nucleic acid synthesis reaction, and more particularly increasing signal attributable to hydrogen ions that are generated during such a reaction.

In this context, some methods of the invention involve increasing the efficiency with which released (or generated) hydrogen ions are detected. It has been determined in the course of our work that released hydrogen ions may be sequestered in a reaction chamber that overlays the chemFET, thereby precluding their detection by the chemFET. This disclosure therefore provides in some aspects methods and compositions for reducing buffering capacity of the solution within which such reactions are carried out or reducing buffering capacity of solid supports that are in contact with such solution. In this way, a greater proportion of the hydrogen ions released during a nucleic acid synthesis reaction (such as one that is part of a sequencing-by-synthesis process) are detected by the chemFET rather than being for example sequestered by buffering components in the reaction solution or chamber.

Additionally or alternatively, aspects of the invention that monitor and/or measure hydrogen ion release (or pH) may be performed in an environment with reduced (i.e., no, low or limited) buffering capacity so as to maximally detect released hydrogen ions. As an example, the invention provides a method for synthesizing a nucleic acid comprising incorporating nucleotides into a nucleic acid in an environment with no or limited buffering capacity. Examples of an environment with reduced buffering capacity (or activity) include one that lacks a buffer, one that includes a buffer (or buffering) inhibitor, and one in which pH changes on the order of 0.01, 0.05, 0.1, 0.2, 0.3, 0.4, 0.5, 0.6. 0.7, 0.8, 0.9. or 1.0 pH units are detectable for example via a chemFET and more particularly an ISFET. The method may be performed in a solution or a reaction chamber that is in contact with or capacitively coupled to a chemFET such as an ISFET. The chemFET (or ISFET) and/or reaction chamber may be in array of chemFETs or reaction chambers, respectively. The reactions are typically carried out at a pH (or a pH range) at which the polymerase is active. An exemplary pH range is 6-9.5, although the invention is not so limited.

In a related aspect, there is shown a method for sequencing a nucleic acid comprising contacting and incorporating known nucleotides into a plurality of identical nucleic acids in a reaction chamber in contact with or capacitively coupled to an ISFET, wherein the nucleic acids are covalently bound to a single bead in the reaction chamber, and detecting hydrogen ions released upon nucleotide incorporation in the presence of no or limited buffering activity. In other embodiments, the single bead is at least 50%, at least 60%, at least 70%, or at least 80% saturated with nucleic acids. In some embodiments, the single bead is at least 90% saturated with nucleic acids. In still other embodiments, the single bead is at least 95% saturated with nucleic acids. The bead may have a diameter of about 1 micron to about 10 microns, or about 1 micron to about 7 microns, or about 1 micron to about 5 microns, including a diameter of about 1 micron, about 2 microns, about 3 microns, about 4 microns, about 5 microns, about 6 microns, about 7 microns, about 8 microns, about 9 microns, or about 10 microns.

In these and in other aspects and embodiments, the chemFET or ISFET arrays may comprise 256 chemFETs or ISFETs, The chemFET or ISFET array may have a center-to-center spacing (between adjacent chemFETs or ISFETs) of 1-10 microns. In some embodiments, the center-to-center spacing is about 9 microns, about 8 microns, about 7 microns, about 6 microns, about 5 microns, about 4 microns, about 3 microns, about 2 microns or about 1 micron. In particular embodiments, the center-to-center spacing is about 5.1 microns or about 2.8 microns. In various embodiments, the chemFET or ISFET comprises a passivation layer that is or is not bound to a nucleic acid.

In these and in other aspects and embodiments, the reaction chamber may comprise a solution having no buffer or low buffer concentration. The methods described herein may be performed in a weak buffer. Alternatively or additionally, the reaction chamber may comprise a solution having a buffering inhibitor. The reaction chamber may or may not comprise packing beads. In some embodiments, the reaction chamber is in contact with a single ISFET. In some embodiments, the reaction chamber has a volume of equal to or less than about 1 picoliter (pL).

In some embodiments, the nucleic acids are sequencing primers. The nucleic acids may be hybridized to template nucleic acids or to concatemers of identical template nucleic acids. In still other embodiments, the nucleic acids are self-priming template nucleic acids. In still other embodiments, the nucleic acids are nicked double-stranded nucleic acids.

In these and in other aspects and embodiments, the nucleotides may be unblocked. In some embodiments, the nucleotides are not extrinsically labeled. In some embodiments, nucleic acids are synthesized or nucleotides are incorporated using a polymerase that is free in solution. In some embodiments, nucleic acids are synthesized or nucleotides are incorporated using a polymerase that is immobilized. In related embodiments, the polymerase is immobilized to the bead, or to a separate bead. The polymerase may be provided in a mixture of polymerases, including a mixture of 2, 3 or more polymerases.

In another aspect, there is provided a method for synthesizing a nucleic acid comprising incorporating nucleotides into a nucleic acid in the presence of a buffering inhibitor. In one embodiment, the method further comprises detecting incorporation of nucleotides by detecting hydrogen ion release.

In another aspect, there is provided a method for determining incorporation of a nucleotide triphosphate into a newly synthesized nucleic acid comprising combining a known nucleotide triphosphate, a template/primer hybrid, a buffering inhibitor and a polymerase, in a solution in contact with or capacitively coupled to a chemFET, and detecting a signal at the chemFET, wherein detection of the signal indicates incorporation of the known nucleotide triphosphate into the newly synthesized nucleic acid. In one embodiment, the signal indicates release of hydrogen ions as a result of nucleotide incorporation. In various embodiments, the nucleic acid is a plurality of identical nucleic acids, the nucleotide triphosphates are a plurality of nucleotide triphosphates, and the hybrids are a plurality of hybrids.

The buffering inhibitor may be a plurality of random sequence oligoribonucleotides such as but not limited to RNA hexamers, or it may be a sulfonic acid surfactant such as but not limited to poly(ethylene glycol) 4-nonylphenyl 3-sulfopropyl ether (PNSE) or a salt thereof, or it may be poly (styrenesulfonic acid), poly(diallydimethylammonium), or tetramethyl ammonium, or a salt thereof.

The buffering inhibitor may also be a phospholipid. The phospholipids may be naturally occurring or non-naturally occurring phospholipids. Examples of phospholipids to be used as buffering inhibitors include but are not limited to phosphatidylcholine, phosphatidylethanolamine, phosphatidylglycerol, and phosphatidylserine. In some embodiments, phospholipids may be coated on the chemFET surface (or reaction chamber surface). Such coating may be covalent or non-covalent. In other embodiments, the phospholipids exist in solution.

Still other methods relate to variations on sequencing-by-synthesis methods that increase the number of released hydrogen ions, again resulting in an increased signal (and signal to noise ratio). In some methods, the number of hydrogen ions released per nucleotide incorporation are increased at least two-fold by combining a nucleotide incorporation event with a nucleotide excision event. An example of such a process is a nick translation reaction in which a nucleotide is incorporated at a first position and another nucleotide is excised from a second, usually adjacent, position along a double stranded region of a nucleic acid. The incorporation and excision each release one hydrogen ion, and thus the coupling of the two events amplifies the number of hydrogen ions per incorporation, thereby increasing signal.

Thus, in one aspect, there is provided a method comprising performing a nick translation reaction along the length of a nicked, double stranded nucleic acid, and detecting hydrogen ions released as a result of the nick translation reaction. In a related aspect, there is provided a method comprising incorporating a first nucleotide at a first position on a nucleic acid and excising a second nucleotide at a second position on the nucleic acid, and detecting hydrogen ions released as a result of nucleotide incorporation and excision. In another aspect, the there is provided a method comprising incorporating a first known nucleotide at a first position on a nucleic acid and excising a second nucleotide at a second adjacent position on the nucleic acid, and detecting hydrogen ions released as a result of nucleotide incorporation and excision. In still another aspect, there is provided a method comprising sequentially excising a nucleotide and incorporating another nucleotide at separate positions along the length of a nicked, double stranded nucleic acid, and detecting hydrogen ions released from a combined nucleotide excision and nucleotide incorporation, wherein released hydrogen ions are indicative of nucleotide incorporation and nucleotide excision. And in yet another aspect, there is provided a method comprising sequentially contacting a nicked, double stranded nucleic acid with each of four nucleotides in the presence of a polymerase, and detecting hydrogen ions released following contact with each of the four nucleotides, wherein released hydrogen ions are indicative of nucleotide incorporation.

In another aspect, there is provided a method comprising detecting excision of a first nucleotide and incorporation of a second known nucleotide in a nicked, double stranded nucleic acid, in a solution in contact with or capacitively coupled to a ISFET. In one embodiment, the nicked, double stranded nucleic acid is a plurality of nicked, double stranded nucleic acids.

In still another aspect, there is provided a method comprising detecting excision of a nucleotide and incorporation of another nucleotide in a plurality of nicked double stranded nucleic acid present in a reaction chamber in contact with or capacitively coupled to an ISFET. In some embodiment, the reaction well is in a reaction chamber array and the ISFET is in a ISFET array. In some embodiments, the ISFET array comprises 256 ISFET.

In another related aspect, a method is disclosed for improving signal from a sequencing-by-synthesis reaction comprising performing a sequencing-by-synthesis reaction using a nick, double stranded template nucleic acid, wherein at least one nucleotide incorporation event is coupled to a nucleotide excision event, and wherein nucleotide incorporation events are detected by generation of a sequencing reaction byproduct. In some embodiments, the sequencing reaction byproduct is hydrogen ions. In some embodiments, the hydrogen ions are detected by an ISFET, which optionally may be present in an ISFET array.

The methods described herein may be performed in order to monitor reactions such as nick translation reactions, nucleotide incorporations events and/or nucleotide excision events. They may also be performed in order to analyze a nucleic acid such as a template nucleic acid (which may be provided as a nicked, double stranded nucleic acid). Such analysis may include sequencing the template nucleic acid.

In some embodiments, released hydrogen ions are detected using an ISFET and/or an ISFET array. The ISFET array may comprise 256 ISFETs (i.e., it may contain 256 or more ISFETs). In some embodiments, the ISFET array is overlayed with a reaction chamber array.

In still other methods, the number of template nucleic acids used per sensor, and optionally per reaction chamber, is increased. Since the sequencing-by-synthesis reactions contemplated by the invention typically occur simultaneously on a plurality of identical template nucleic acids, increasing the number of templates increases the number of sequencing byproduct (such as hydrogen ions) released per simultaneous nucleotide incorporation, thereby increasing signal that can be detected. Similarly, increasing the number of templates immobilized to an ISFET surface, as contemplated by some aspects of the invention, increases the magnitude of the charge change observed following nucleotide incorporation.

In some aspects described herein, increasing the concentration of the nucleic acids to be sequenced also serves to increase signal to noise ratio. Therefore in some instances decreasing the reaction volume (or the reaction chamber volume) does not result in a decreased signal to noise ratio, and can in fact result in an increased signal to noise ratio. In some instances, this may happen even if the total number of nucleic acids being sequenced stays the same or is reduced.

Thus, in another aspect, the invention provides a method for sequencing nucleic acids comprising generating a plurality of template nucleic acids each comprising multiple, tandemly arranged, identical copies of a target nucleic acid fragment, placing single template nucleic acids in reaction chambers of a reaction chamber array, and simultaneously sequencing multiple template nucleic acids in reaction chambers of the reaction chamber array. In a related aspect, two or more template nucleic acids which comprise multiple, tandemly arranged, identical copies of a target nucleic acid (or target nucleic acid fragment) are placed in each reaction chamber. In this aspect, it is to be understood that the target nucleic acids (or target nucleic acid fragments) are identical within a given chamber. The number of copies per template may however vary, although preferably may also be similar or identical. In some embodiments, sequencing multiple target nucleic acid fragments comprises detecting released hydrogen ions.

In some embodiments, the template nucleic acids are generated using rolling circle amplification. In some embodiments, the template nucleic acids are attached to reaction chambers. In some embodiments, the reaction chamber array comprises $10^2$, $10^3$, $10^4$, $10^5$, $10^6$ or $10^7$ reaction chambers. In some embodiments, individual reaction chambers in the reaction chamber array are in contact with or capacitively coupled to an chemFET. In some embodiments, the chemFET is in a chemFET array, and the chemFET array may optionally comprise $10^2$, $10^3$, $10^4$, $10^5$, $10^6$ or $10^7$ chemFETs. The chemFET and chemFET array may be an ISFET and an ISFET array.

In another aspect, a method is provided for sequencing a nucleic acid comprising generating a plurality of template nucleic acids each comprising multiple identical copies of a target nucleic acid (or fragment), placing single template nucleic acids in individual reaction chambers of a reaction chamber array, and sequencing multiple template nucleic acids in reaction chambers of the reaction chamber array, wherein the single template nucleic acid has a cross-sectional area greater than a cross-sectional area of the reaction chamber.

In one embodiment, single template nucleic acids are attached to single reaction chambers in the reaction chamber array (i.e., only one template nucleic acid is attached per reaction chamber). In one embodiment, single template nucleic acids are directly attached to single reaction chambers in the reaction chamber array. In some embodiments, the nucleic acid is not attached to the reaction chamber.

In still another aspect, an apparatus is provided that comprises an array of chemFET each having a surface, and a plurality of template nucleic acids each comprising multiple identical copies of a target nucleic acid (or fragment), wherein single template nucleic acids are present on the surface of an individual chemFET. It is to be understood that the target nucleic acids within a template nucleic acid will be identical but that those between template nucleic acids will typically be different from each other. In other words, each template in this aspect is clonal. In one embodiment, single nucleic acids are attached to the surface of individual chemFET. In one embodiment, the single nucleic acids are directly attached to the surface of individual chemFET. In some embodiments, single nucleic acids are not attached to the surface of individual chemFET.

Thus, it will be appreciated that in some embodiments, nucleic acids are present in a reaction chamber but are not attached to the surface of a bead, although they may be attached or in contact with the chemFET surface or a surface of the reaction chamber. Thus, in some embodiments, the reaction chambers comprise the nucleic acids to be sequenced even in the absence of beads. In these latter embodiments, the nucleic acid within a reaction chamber may comprise multiple (amplified) copies of the same nucleic acid to be sequenced. Single nucleic acids of this type are deposited within single reaction chambers. These nucleic acids need not be attached to the chemFET or reaction chamber surface. Alternatively, a plurality of amplified and physically separate nucleic acids may be present at or near a chemFET surface, and optionally within a reaction chamber.

The methods provided herein contemplate that the nucleic acids may be amplified while in contact with or near the chemFET surface, and optionally within the reaction chamber, or that they may be amplified apart from either the chemFET and/or reaction chamber array and then deposited onto a chemFET surface and/or into a reaction chamber.

Another aspect contemplates increasing the number of template nucleic acids present in or on nucleic acid-bearing beads. Thus, in one aspect the invention provides a bead having a diameter less than 10 microns and having $1-5 \times 10^6$ nucleic acids bound to its surface. In some embodiments, the bead has a diameter of about 1 micron, about 3 microns, about 5 microns, or about 7 microns. In still other embodiments, the bead has a diameter of about 0.5 microns or about 0.1 microns. It will be understood that although such beads are characterized in some instances according to their diameter, they need not be completely spherical in shape. In such instances, the diameter may refer to the diameter averaged over a number of dimensions through the bead. In some embodiments, the bead comprises $1 \times 10^6$ nucleic acids, $2 \times 10^6$ nucleic acids, $3 \times 10^6$ nucleic acids, or $4 \times 10^6$ nucleic acids bound to its surface. In some embodiments, the nucleic acids are 5-50 nucleotides in length, 10-50 nucleotides in length, or 20-50 nucleotides in length. In still other embodiments, the nucleic acids are 50-1000 nucleotides in length or 1000-10000 nucleotides in length. The nucleic acids attached to and/or present in a bead are typically identical.

In some embodiments, the nucleic acids are synthetic nucleic acids (e.g., they have been synthesized using a nucleic acid synthesizer). In some embodiments, the nucleic acids are amplification products.

In some embodiments, the nucleic acids are covalently bound to the surface of the bead.

In some embodiments, the nucleic acids are bound to the surface of the bead with one or more non-nucleic acid polymers. In some embodiments, the non-nucleic acid polymers are polyethylene glycol (PEG) polymers. The PEG polymers may be of varying lengths. In some embodiments, one, some or all of the non-nucleic acid polymers comprises a plurality of functional groups for nucleic acid binding. In some embodiments, the non-nucleic acid polymers are dextran polymers and/or chitosan polymers. In some embodiments, the non-nucleic acid polymers include PEG polymers and dextran polymers. In some embodiments, the non-nucleic acid polymers include PEG polymers and chitosan polymers. The non-nucleic acid polymers may be linear or branched.

In some embodiments, the nucleic acids are bound to a dendrimer that is bound to a bead. In some embodiments, the nucleic acids are bound to a dendrimer that is bound to a PEG polymer.

In some embodiments, the nucleic acids are bound to the bead with self-assembling acrylamide monomers.

In various of these embodiments, the methods used to increase the number of nucleic acids per bead provide no or minimal buffering to the environment.

In some embodiments, the bead is non-paramagnetic. In some embodiments, the bead has a density between 1-3 $g/cm^3$. In some embodiments, the bead has a density of about 2 $g/cm^3$. In some embodiments, the bead is a silica bead. In some embodiments, the bead is a silica bead with an epoxide coat.

In a related aspect, a method is disclosed, comprising simultaneously incorporating known nucleotides into a plurality of the nucleic acids immobilized to and/or in a bead including but not limited to any of the foregoing beads. Immobilized as used herein includes but is not limited to covalent or non-covalent attachment to a bead surface or interior and/or simply physical retention within a porous bead, as described in more detail herein. A plurality of these nucleic acids may be without limitation $2-10^2$, $2-10^3$, $2-10^4$, $2-10^5$, $2-10^6$, $2-2\times10^6$, $2-3\times10^6$, $2-4\times10^6$ or $2-5\times10^6$ nucleic acids. Thus in some embodiments, the nucleotides are incorporated into at least $10^6$ nucleic acids, at least $2\times10^6$ nucleic acids, at least $3\times10^6$ nucleic acids, or at least $4\times10^6$ nucleic acids. It will be understood that the maximum number of nucleic acids into which nucleotides may be incorporated is the maximum number of nucleic acids immobilized to and/or in the bead. In some embodiments, the method further comprises detecting nucleotide incorporation. In some embodiments, nucleotide incorporation is detected non-enzymatically. In some embodiments, nucleotide incorporation is detected by detecting released hydrogen ions.

In some embodiments, the bead is in a reaction chamber, and optionally the only bead in the reaction chamber. In some embodiments, the reaction chamber is in contact with or capacitively coupled to an ISFET. In some embodiments, the ISFET is in an ISFET array. In some embodiments, the ISFET array comprises 10, $10^2$, $10^3$, $10^4$, $10^5$ or $10^6$ ISFET.

In some embodiments, the bead has a diameter of less than 6 microns, less than 3 microns, or about 1 micron. The bead may have a diameter of about 1 micron up to about 7 microns, or about 1 micron up to about 3 microns.

In some embodiments, the nucleic acids are self-priming template nucleic acids.

Thus, it will be understood that the invention contemplates sequencing of nucleic acids that are localized near a sensor such as an ISFET sensor (referred to herein as an ISFET), and optionally in a reaction chamber. The nucleic acids may be localized in a variety of ways including attachment to a solid support such as a bead surface, a bead interior or some combination of bead surface and interior, as discussed above. Typically, the bead is present in a reaction chamber, although the methods may also be carried out in the absence of reaction chambers. The solid support may also be the sensor surface or a wall of a reaction chamber that is capacitively coupled to the sensor.

The localized nucleic acids are typically a plurality of identical nucleic acids. The invention therefore further contemplates amplification of nucleic acids while in contact with the chemFET (e.g., ISFET) array (e.g., in the reaction chamber) followed by sequencing, with or without beads. The invention alternatively contemplates introducing a previously amplified population of nucleic acids to individual sensors of a chemFET array, and optionally into individual reaction chambers, with or without beads.

Nucleic acids present in "porous" beads (or porous microparticles, porous microspheres or porous microcapsules, as the terms are used interchangeably herein) may be amplified and sequenced while individual beads are in contact with individual chemFET sensors, optionally in individual reaction chambers. Bridge amplification is one exemplary method for attaching identical nucleic acids onto a solid support such as a bead surface, a chemFET surface, or a reaction chamber interior surface (e.g., a wall).

The nucleic acid-bearing beads used in various aspects and embodiments of the invention include beads having nucleic acids attached to their surface, beads having nucleic acids in their internal core, or beads having nucleic acids attached to their surface and in their internal core. Beads having nucleic acids in their internal core preferably have a porous surface that allows amplification and/or sequencing reagents to move into and out of the bead but that retains the nucleic acids within the bead. Such beads therefore prevent the nucleic acids of interest from diffusing a significant distance away from the sensor, including for example diffusing out of a reaction chamber. The nucleic acids present in such beads may or may not be physically attached to the beads but they are nevertheless immobilized in the bead.

Accordingly, in another aspect, a disclosed method comprises detecting hydrogen ions as nucleotides are individually contacted with and incorporated into a plurality of identical nucleic acids in a reaction chamber in contact with or capacitively coupled to an ISFET, wherein the nucleic acids are present in a porous microparticle. In a related aspect, the invention provides a method comprising detecting hydrogen ions as unblocked deoxyribonucleotides are individually contacted with and incorporated into a nucleic acid, in a reaction chamber in contact with or capacitively coupled to an ISFET, wherein the nucleic acids are present in a porous microparticle. In some embodiments, the porous microparticle is hollow (i.e., it has a hollow core), while in other embodiments it has a porous core.

Still another aspect of the disclosure provides a method for sequencing nucleic acids comprising generating a porous microparticle comprising a single template nucleic acid (i.e., only a single template nucleic acid in the porous microparticle, initially) and polymerases, amplifying the single template nucleic acid in the porous microparticle, and sequencing amplified template nucleic acids in the porous microparticle.

In some embodiments, the amplified nucleic acids are sequenced in a reaction chamber comprising a single microparticle (i.e., only a single microparticle in the reaction chamber). The reaction chamber may be present in a reaction chamber array, and optionally the reaction chamber and/or the reaction chamber array may be in contact with or capacitively coupled respectively to a single ISFET or an ISFET array. In some embodiments, the reaction chambers in the reaction chamber array and/or the ISFETs in the ISFET array have a center-to-center distance (between adjacent reaction chambers or ISFETs) ranging from about 1 micron to about 10 microns.

In some embodiments, the method further comprises generating the single template nucleic acids by fragmenting a larger nucleic acid (such as a target nucleic acid).

In some embodiments, the amplified nucleic acids are sequenced with unlabeled nucleotide triphosphates and/or unblocked nucleotide triphosphates.

In still another aspect, a disclosed method comprises providing in a reaction chamber a single porous microparticle internally comprising a plurality of identical template nucleic acids, and sequencing the plurality of identical template nucleic acids simultaneously. As used herein, "internally comprising" means that one, some or all of the nucleic acids are partially or completely present in the core of the porous microparticle. The plurality of identical template nucleic acids may be sequenced using a sequencing-by-synthesis method, as described herein. The sequencing may comprise non-enzymatic detection of nucleotide incorporation. The reaction chamber may be in contact with or capacitively coupled to an ISFET, and/or it may be present in a reaction chamber array which is in contact with or capacitively coupled to an ISFET array.

In another aspect, a method is provided for monitoring incorporation of a nucleotide triphosphate into a nucleic acid comprising contacting a plurality of identical primers, a plurality of identical template nucleic acids present in a porous microparticle, and a plurality of identical, known nucleotide triphosphates, in the presence of a polymerase, wherein the microparticle is present in a reaction chamber in contact with or capacitively coupled to a chemFET, and detecting a signal at the chemFET, wherein detection of the signal indicates incorporation of the known nucleotide triphosphates to the primers.

In some embodiments, the signal results from release of a sequencing reaction byproduct such as PPi, Pi and/or hydrogen ions. In some embodiments, the chemFET is an ISFET. In some embodiments, the chemFET is in (or is provided in or as part of) a chemFET array. In some embodiments, the ISFET is in (or is provided in or as part of) an ISFET array. In some embodiments, the chemFET or ISFET array comprises $10^2$, $10^3$, $10^4$, $10^5$, $10^6$ or $10^7$ chemFETs or ISFETs respectively.

In some embodiments, the reaction chamber is in (or is provided in or as part of) a reaction chamber array. In some embodiments, the reaction chamber array comprises $10^2$, $10^3$, $10^4$, $10^5$, $10^6$ or $10^7$ reaction chambers.

In some embodiments, the method further comprises generating the plurality of identical template nucleic acids by amplifying a single template nucleic acid in the porous microparticle prior to contacting with the plurality of identical primers. The plurality of identical template nucleic acids may be present in a concatemer or they may be physically separate from each other.

In still another aspect, there is provided a method for sequencing nucleic acids comprising generating a plurality of template nucleic acids by fragmenting target nucleic acids, placing single template nucleic acids in porous microparticles together with polymerases, amplifying the single template nucleic acids to generate a plurality of identical template nucleic acids in single porous microparticles, placing single porous microparticles in reaction chambers of a reaction chamber array, and simultaneously sequencing identical template nucleic acids in each of a plurality of porous microparticles.

In some embodiments, sequencing identical template nucleic acids comprises detecting sequencing byproducts such as PPi, Pi and/or hydrogen ions released following nucleotide incorporation.

In some embodiments, the reaction chambers have a center-to-center distance of about 1 micron to about 10 microns. In some embodiments, the reaction chamber array comprises $10^2$, $10^3$, $10^4$, $10^5$, $10^6$ or $10^7$ reaction chambers.

In some embodiments, individual reaction chambers are in contact with or capacitively coupled to individual chemFETs in a chemFET array, including individual ISFETs in an ISFET array. The chemFET or ISFET array may comprise $10^2$, $10^3$, $10^4$, $10^5$, $10^6$, $10^7$, or more chemFETs or ISFETs respectively. Adjacent sensors in these arrays may have a center-to-center distance of about 1 micron to about 10 microns. In still another aspect, the invention provides an apparatus comprising an ISFET array and a plurality of porous microparticles each comprising a plurality of identical template nucleic acids, wherein single porous microparticles are in contact with single ISFETS within the array. In one embodiment, the plurality of identical template nucleic acids are tandemly arranged in a single nucleic acid. In one embodiment, single porous microparticles are present in single reaction chambers of a reaction chamber array that is in contact with or capacitively coupled to the ISFET array. (We digress briefly on a definitional fine point. When a reaction chamber sits atop a dielectric that covers the floating metal gate of an ISFET, is that chamber in contact with the ISFET or is it capacitively coupled to the ISFET? This amounts to asking whether the dielectric is or is not part of the ISFET. We answer that it is part of the ISFET; otherwise, a direct electrical connection is being made to a metal gate and the would-be ISFET is simply a FET. However, we recognize that the charge in the reaction chamber builds up on one side of the dielectric and forms one plate of a capacitor and which has as its second plate the floating gate metal layer; thus, we are also comfortable with the terminology stating that the reaction chamber is capacitively coupled to the ISFET. The two alternatives thus are intended to mean the same thing.)

Some aspects of the invention involve detection of charge bound to the chemFET (including an ISFET) surface. Such detection can be used alone or together with detection of soluble analytes (such as hydrogen ions) to detect an event such as for example a nucleotide incorporation event. Thus, as an example, a sequencing-by-synthesis reaction may occur using a template nucleic acid that is immobilized to a chemFET surface. Nucleotide incorporation into the newly synthesized strand results in an addition of negative charge to the nucleic acid and this change can be sensed by the chemFET. Nucleotide incorporation also results in the release of PPi, and subsequently a hydrogen ion, which can also be sensed by the chemFET. Some embodiments involve sequencing such surface immobilized templates in the presence of sufficient buffer to quench (or mask) any released hydrogen ions, thereby tracking a signal that results only from addition of negative charge to the surface as an indicator of nucleotide incorporation. In some embodiments, the method is carried out in the absence of a buffer. Thus, in another aspect, the invention provides a method for sequencing a nucleic acid comprising amplifying a single template nucleic acid in a reaction chamber in contact with or capacitively coupled to an ISFET, wherein amplified template nucleic acids are attached to the reaction chamber, and sequencing amplified template nucleic acids in the reaction chamber.

In some embodiments, the amplified template nucleic acids are attached to the surface of the ISFET. In some embodiments, the single template nucleic acid is attached to a surface of the ISFET prior to amplification. In some embodiments, the single template nucleic acid is amplified in solution and the amplified template nucleic acids are hybridized to primers immobilized on a surface of the ISFET.

In some embodiments, amplifying comprises amplifying by rolling circle amplification, and the amplified template nucleic acids are concatemers of the template nucleic acid.

In some embodiments, sequencing comprises detecting incorporation of a known nucleotide by an increase in negative charge of the amplified template nucleic acids.

In some embodiments, the amplified template nucleic acids are self-priming.

In still another aspect, a method is provided, comprising contacting a known nucleotide to a complex comprising a template nucleic acid and a sequencing primer, wherein the complex is immobilized on a surface of an ISFET, and detecting incorporation of the known nucleotide to the complex by detecting an increase in negative charge of the complex, wherein the ISFET is in an array, and optionally wherein the array comprises 256 ISFETs.

In some embodiments, the template nucleic acid is present in (or provided as) a concatemer of template nucleic acids. In some embodiments, the concatemer comprises 100-1000 copies of the template nucleic acid. In some embodiments, the template nucleic acid is covalently bound to the surface of the ISFET. In some embodiments, the sequencing primer is covalently bound to the surface of the ISFET.

In some embodiments, the ISFET is overlayed with a reaction chamber, and optionally the reaction chamber is in an array. In some embodiments, the reaction chamber contains a buffered solution.

In some embodiments, the complex is a plurality of complexes. In some embodiments, the complexes are identical. In some embodiments, the plurality of complexes is equal to or less than $10^6$ complexes, equal to or less than $10^5$ complexes, equal to or less than $10^4$ complexes, or equal to or less than $10^3$ complexes.

In yet another aspect, a method comprises contacting a known nucleotide to a self-priming template nucleic acid that is immobilized on a surface of an ISFET, and detecting incorporation of the known nucleotide to the self-priming template nucleic acid by detecting an increase in negative charge of the nucleic acid.

In some embodiments, the ISFET is in an ISFET array. The ISFET array may comprise $10^2$, $10^3$, $10^4$, $10^5$, $10^6$ or $10^7$ ISFETs.

In some embodiments, the template nucleic acid is in a reaction chamber in contact with or capacitively coupled to the ISFET. In some embodiments, the reaction chamber is in a reaction chamber array. In some embodiments, the reaction chamber array comprises $10^2$, $10^3$, $10^4$, $10^5$, $10^6$ or $10^7$ reaction chambers.

In some embodiments, the nucleic acid is in a buffer. Thus, in some embodiments, signal at the ISFET results solely from a change in charge of the nucleic acid rather than from released hydrogen ions.

Thus, it is to be understood that various aspects and embodiments of the invention relate generally to large scale FET arrays for measuring one or more analytes or for measuring charge bound to the chemFET surface. It will be appreciated that chemFETs and more particularly ISFETs may be used to detect analytes and/or charge. An ISFET, as discussed above, is a particular type of chemFET that is configured for ion detection such as hydrogen ion (or proton) detection. Other types of chemFETs contemplated by the present disclosure include enzyme FETs (EnFETs) which employ enzymes to detect analytes. It should be appreciated, however, that the present disclosure is not limited to ISFETs and EnFETs, but more generally relates to any FET that is configured for some type of chemical sensitivity. As used herein, chemical sensitivity broadly encompasses sensitivity to any molecule of interest, including without limitation organic, inorganic, naturally occurring, non-naturally occurring, chemical and biological compounds, such as ions, small molecules, polymers such as nucleic acids, proteins, peptides, polysaccharides, and the like.

Various embodiments described herein employ large scale chemFET arrays in the analysis of chemical or biological samples and/or reactions. Chemical or biological samples are typically liquid (or are dissolved in a liquid) and of small volume, to facilitate high-speed, high-density determination of analyte (e.g., ion or other constituent) presence and/or concentration, or other analyte measurements.

For example, some embodiments involve a "very large scale" two-dimensional chemFET sensor array (e.g., greater than 256 sensors), in which one or more chemFET-containing elements or "pixels" constituting the sensors of such an array are configured to monitor one or more independent biological or chemical reactions or events occurring in proximity to the pixels of the array. It will be understood that such arrays may comprise any number of individual sensors and that the invention is not to be limited in this regard. In some exemplary implementations, the array may be coupled to one or more microfluidics structures that form one or more reaction chambers, or "wells" or "microwells," (as the terms are used interchangeably herein) over individual sensors or groups of sensors of the array, and an apparatus that delivers analyte samples (i.e., analyte solutions) to the wells and/or removes them from the wells between measurements. Even when microwells are not employed, the sensor array may be coupled to one or more microfluidics structures for the delivery of one or more samples to the pixels and for removal of sample between measurements. In association with the microfluidics, unique reference electrodes and their coupling to the flow cell are also provided by the invention.

Accordingly, disclosed herein are various microfluidic structures which may be employed to flow analytes and, where appropriate, other agents useful in for example the detection and measurement of analytes to and from the reaction chambers or pixels, the methods of manufacture of the array of reaction chambers, methods and structures for coupling the arrayed reaction chambers with arrayed pixels, and methods and apparatus for loading the reaction chambers with sample to be analyzed, including for example loading the wells with nucleic acids for example when the apparatus is used for nucleic acid (e.g., DNA) sequencing or related analysis, and uses thereof, as will be discussed in greater detail herein. In various aspects of the invention, an analyte that is byproduct of a nucleic acid synthesis reaction is detected. Such a byproduct can be monitored as the readout of a sequencing-by-synthesis method. One particularly important byproduct is hydrogen ions which are released upon addition or incorporation of a deoxynucleotide triphosphate (also referred to herein as a nucleotide or a dNTP) to the 3' end of a nucleic acid (such as a sequencing primer). Nucleotide incorporation releases inorganic pyrophosphate (PPi) which may be hydrolyzed to orthophosphate (Pi) and free hydrogen ion ($H^+$) in the presence of water (and optionally and far more rapidly in the presence of pyrophosphatase). As a result, nucleotide incorporation, and thus a sequencing-by-synthesis reaction, can be monitored by detecting PPi, Pi and/or $H^+$. Conventionally, PPi has not been detected or measured by chemFETs. Instead, optically based sequencing-by-synthesis methods have detected PPi via its sulfurylase-mediated conversion to adenosine triphosphate (ATP), and then luciferase-mediated conversion of luciferin to oxyluciferin in the presence of the previously generated ATP, with concomitant release of light. Such detection is referred to herein as "enzymatic" detection (e.g., of released PPi or of nucleotide incorporation).

As mentioned above, in some aspects the invention provides methods for detecting nucleotide incorporation (optionally in conjunction with nucleotide excision) using non-enzymatic methods. As used herein, non-enzymatic detection of nucleotide incorporation is detection that does not require an enzyme to detect the incorporation event or byproducts thereof. Non-enzymatic detection however does not exclude the use of enzymes to incorporate nucleotides or, in some instances, to excise nucleotides, thereby generating the event that is being detected. An example of non-enzymatic detection of nucleotide incorporation is a detection method that does not require conversion of PPi to ATP. Non-enzymatic detection methods may employ mixtures of polymerases for nucleotide incorporation, or they may employ enzymes that may enhance a signal (e.g., pyrophosphatase in order to enhance conversion of PPi to Pi), enzymes that reduce misincorporations (e.g., apyrase in order to remove unincorporated nucleotides), and/or enzymes that remove nucleotides in conjunction with incorporation of other nucleotides, among others.

Thus, in some aspects the instant invention contemplates and provides methods for monitoring nucleic acid sequencing reactions and thus determining the nucleotide sequence of nucleic acids by detecting H+ (or changes in pH), PPi (or Pi, or changes in either) in the absence or presence of PPi (or Pi) specific receptors, alone or in some combination thereof.

In other aspects, other biological or chemical reactions may be monitored, and the chemFET arrays may be specifically configured to measure hydrogen ions and/or one or more other analytes that provide relevant information relating to the occurrence and/or progress of a particular biological or chemical process of interest.

With respect to analyte detection and measurement, it should be appreciated that in various embodiments discussed in greater detail below, one or more analytes measured by a chemFET array according to the present disclosure may include any of a variety of biological or chemical substances that provide relevant information regarding a biological or chemical process (e.g., binding events such as hybridization of nucleic acids to each other, antigen-antibody binding, receptor-ligand binding, enzyme-inhibitor binding, enzyme-substrate binding, enzyme-agonist binding, enzyme-antagonist binding, and the like). In some aspects, the ability to measure absolute or relative as well as static and/or dynamic levels and/or concentrations of one or more analytes, in addition to merely determining the presence or absence of an analyte, provides valuable information in connection with biological and chemical processes. In other aspects, mere determination of the presence or absence of an analyte or analytes of interest may provide valuable information and may be sufficient.

A chemFET array according to various inventive embodiments of the present disclosure may be configured for sensitivity to any one or more of a variety of analytes. In one embodiment, one or more chemFETs of an array may be particularly configured for sensitivity to one or more analytes, and in other embodiments different chemFETs of a given array may be configured for sensitivity to different analytes. For, example, in one embodiment, one or more sensors (pixels) of the array may include a first type of chemFET configured to be sensitive to a first analyte, and one or more other sensors of the array may include a second type of chemFET configured to be sensitive to a second analyte different from the first analyte. In one embodiment, the first and second analytes may be related to each other. As an example, the first and second analytes may be byproducts of the same biological or chemical reaction/process and therefore they may be detected concurrently to confirm the occurrence of a reaction (or lack thereof). Such redundancy is preferable in some analyte detection methods. Of course, it should be appreciated that more than two different types of chemFETs may be employed in any given array to detect and/or measure different types of analytes, and optionally to monitor biological or chemical processes such as binding events. In general, it should be appreciated in any of the embodiments of sensor arrays discussed herein that a given sensor array may be "homogeneous" and thereby consist of chemFETs of substantially similar or identical type that detect and/or measure the same analyte (e.g., pH or other ion concentration), or a sensor array may be "heterogeneous" and include chemFETs of different types to detect and/or measure different analytes. In another embodiment, the sensors in an array may be configured to detect and/or measure a single type (or class) of analyte even though the species of that type (or class) detected and/or measured may be different between sensors. As an example, all the sensors in an array may be configured to detect and/or measure nucleic acids, but each sensor detects and/or measures a different nucleic acid.

Aspects of the invention provide specific improvements to the ISFET array design of Milgrew et al. discussed above in connection with FIGS. 1-7, as well as other conventional ISFET array designs, so as to significantly reduce pixel size, and thereby increase the number of pixels of a chemFET array for a given semiconductor die size (i.e., increase pixel density). In various embodiments, this increase in pixel density is accomplished while at the same time increasing the signal-to-noise ratio of output signals corresponding to monitored biological and chemical processes, and the speed with which such output signals may be read from the array. In particular, by relaxing requirements for chemFET linearity and focusing on a more limited measurement output signal range (e.g., output signals corresponding to a pH range of from approximately 7 to 9 or smaller, rather than 1 to 14, as well as output signals that do not necessarily relate significantly to pH), individual pixel complexity and size may be significantly reduced, thereby facilitating the realization of very large scale dense chemFET arrays. Alternative less complex approaches to pixel selection in an chemFET array (e.g., alternatives to the row and column decoder approach employed in the design of Milgrew et al. as shown in FIG. 7, whose complexity scales with array size), as well as various data processing techniques involving ISFET response modeling and data extrapolation based on such modeling, facilitate rapid acquisition of data from significantly large and dense arrays.

In various aspects, the chemFET arrays may be fabricated using conventional CMOS (or biCMOS or other suitable) processing technologies, and are particularly configured to facilitate the rapid acquisition of data from the entire array (scanning all of the pixels to obtain corresponding pixel output signals).

Various techniques employed in a conventional CMOS fabrication process, as well as various post-fabrication processing steps (wafer handling, cleaning, dicing, packaging, etc.), may in some instances adversely affect performance of the resulting chemFET array. For example, with reference again to FIG. 1, one potential issue relates to trapped charge that may be induced in the gate oxide 65 during etching of metals associated with the floating gate structure 70, and how such trapped charge may affect chemFET threshold voltage $V_{TH}$. Another potential issue relates to the density/porosity of the chemFET passivation layer (e.g., see ISFET passivation layer 72 in FIG. 1) resulting from low-temperature material deposition processes commonly employed in aluminum metal-based CMOS fabrication. While such low-temperature processes generally provide an adequate passivation layer for conventional CMOS devices, they may result in a somewhat low-density and porous passivation layer which may be potentially problematic for chemFETs in contact with an analyte solution; in particular, a low-density porous passivation layer over time may absorb and become saturated with analytes or other substances in the solution, which may in turn cause an undesirable time-varying drift in the chemFETs threshold voltage $V_{TH}$. This phenomenon may in turn impede accurate measurements of one or more particular analytes of interest. In view of the foregoing, other inventive embodiments disclosed herein relate to methods and apparatuses which mitigate potentially adverse effects on chemFET performance that may arise from various aspects of fabrication and post-fabrication processing/handling of chemFET arrays.

Accordingly, one embodiment is directed to an apparatus, comprising an array of CMOS-fabricated sensors, each sensor comprising one chemically-sensitive field effect transistor (chemFET) and occupying an area on a surface of the array of 10 $\mu m^2$ or less, 9 $\mu m^2$ or less, 8 $\mu m^2$ or less, 7 $\mu m^2$ or less, 6 $\mu m^2$ or less, 5 $\mu m^2$ or less, 4 $\mu m^2$ or less 3 $\mu m^2$ or less, or 2 $\mu m^2$ or less.

Another embodiment is directed to a sensor array, comprising a two-dimensional array of electronic sensors including at least 512 rows and at least 512 columns of the electronic sensors, each sensor comprising one chemically-sensitive field effect transistor (chemFET) configured to provide at least one output signal representing a presence and/or concentration of an analyte proximate to a surface of the two-dimensional array.

Another embodiment is directed to an apparatus, comprising an array of CMOS-fabricated sensors, each sensor comprising one chemically-sensitive field effect transistor (chemFET). The array of CMOS-fabricated sensors includes more than 256 sensors, and a collection of chemFET output signals from all chemFETs of the array constitutes a frame of data.

The apparatus further comprises control circuitry coupled to the array and configured to generate at least one array output signal to provide multiple frames of data from the array at a frame rate of at least 1 frame per second. In one aspect, the frame rate may be at least 10 frames per second. In another aspect, the frame rate may be at least 20 frames per second. In yet other aspects, the frame rate may be at least 30, 40, 50, 70 or up to 100 frames per second.

Another embodiment is directed to an apparatus, comprising an array of CMOS-fabricated sensors, each sensor comprising a chemically-sensitive field effect transistor (chemFET). The chemFET comprises a floating gate structure, and a source and a drain having a first semiconductor type and fabricated in a region having a second semiconductor type, wherein there is no electrical conductor that electrically connects the region having the second semiconductor type to either the source or the drain.

Another embodiment is directed to an apparatus, comprising an array of electronic sensors, each sensor consisting of three field effect transistors (FETs) including one chemically-sensitive field effect transistor (chemFET). Another embodiment is directed to an apparatus, comprising an array of electronic sensors, each sensor comprising three or fewer field effect transistors (FETs), wherein the three or fewer FETs includes one chemically-sensitive field effect transistor (chemFET).

Another embodiment is directed to an apparatus, comprising an array of electronic sensors, each sensor comprising a plurality of field effect transistors (FETs) including one chemically-sensitive field effect transistor (chemFET), and a plurality of electrical conductors electrically connected to the plurality of FETs, wherein the plurality of FETs are arranged such that the plurality of electrical conductors includes no more than four conductors traversing an area occupied by each sensor and interconnecting multiple sensors of the array.

Another embodiment is directed to an apparatus, comprising an array of CMOS-fabricated sensors, each sensor comprising a plurality of field effect transistors (FETs) including one chemically-sensitive field effect transistor (chemFET), wherein all of the FET's in each sensor are of a same channel type and are implemented in a single semiconductor region of an array substrate.

Another embodiment is directed to a sensor array, comprising a plurality of electronic sensors arranged in a plurality of rows and a plurality of columns. Each sensor comprises one chemically-sensitive field effect transistor (chemFET) configured to provide at least one and in some instances at least two output signals representing a presence and/or a concentration of an analyte proximate to a surface of the array. For each column of the plurality of columns, the array further comprises column circuitry configured to provide a constant drain current and a constant drain-to-source voltage to respective chemFETs in the column, the column circuitry including two operational amplifiers and a diode-connected FET arranged in a Kelvin bridge configuration with the respective chemFETs to provide the constant drain-to-source voltage.

Another embodiment is directed to a sensor array, comprising a plurality of electronic sensors arranged in a plurality of rows and a plurality of columns. Each sensor comprises one chemically-sensitive field effect transistor (chemFET) configured to provide at least one output signal and in some instances at least two output signals representing a concentration of ions in a solution proximate to a surface of the array. The array further comprises at least one row select shift register to enable respective rows of the plurality of rows, and at least one column select shift register to acquire chemFET output signals from respective columns of the plurality of columns.

Another embodiment is directed to an apparatus, comprising an array of CMOS-fabricated sensors, each sensor comprising a chemically-sensitive field effect transistor (chemFET). The chemFET comprises a floating gate structure, and a source and a drain having a first semiconductor type and fabricated in a region having a second semiconductor type, wherein there is no electrical conductor that electrically connects the region having the second semiconductor type to either the source or the drain. The array includes a two-dimensional array of at least 512 rows and at least 512 columns of the CMOS-fabricated sensors. Each sensor consists of three field effect transistors (FETs) including the chemFET, and each sensor includes a plurality of electrical conductors electrically connected to the three FETs. The three FETs are arranged such that the plurality of electrical conductors includes no more than four conductors traversing an area occupied by each sensor and interconnecting multiple sensors of the array. All of the FETs in each sensor are of a same channel type and implemented in a single semiconductor region of an array substrate. A collection of chemFET output signals from all chemFETs of the array constitutes a frame of data. The apparatus further comprises control circuitry coupled to the array and configured to generate at least one array output signal to provide multiple frames of data from the array at a frame rate of at least 20 frames per second.

Another embodiment is directed to a method for processing an array of CMOS-fabricated sensors, each sensor comprising a chemically-sensitive field effect transistor (chemFET). The method comprises: A) dicing a semiconductor wafer including the array to form at least one diced portion including the array; and B) performing a forming gas anneal on the at least one diced portion.

Another embodiment is directed to a method for manufacturing an array of chemFETs. The method comprises fabricating an array of chemFETs; depositing on the array a dielectric material; applying a forming gas anneal to the array before a dicing step; dicing the array; and applying a forming gas anneal after the dicing step. The method may further comprise testing the semiconductor wafer between one or more deposition steps.

Another embodiment is directed to a method for processing an array of CMOS-fabricated sensors. Each sensor comprises a chemically-sensitive field effect transistor (chemFET) having a chemically-sensitive passivation layer of silicon nitride and/or silicon oxynitride deposited via plasma enhanced chemical vapor deposition (PECVD). The method comprises depositing at least one additional passivation material on the chemically-sensitive passivation layer so as to reduce a porosity and/or increase a density of the passivation layer.

Various aspects or embodiments of the invention involve an apparatus comprising an array of chemFET sensors overlayed with an array of reaction chambers wherein the bottom of a reaction chamber is in contact with (or capacitively coupled to) a chemFET sensor. In some embodiments, each reaction chamber bottom is in contact with a chemFET sensor, and preferably with a separate chemFET sensor. In some embodiments, less than all reaction chamber bottoms are in contact with a chemFET sensor. In some embodiments, each sensor in the array is in contact with a reaction chamber. In other embodiments, less than all sensors are in contact with a reaction chamber. The sensor (and/or reaction chamber) array may be comprised of 2, 3, 4, 5, 6, 7, 8, 9, 10, 15, 20, 30, 40, 50, 60, 60, 80, 90, 100, 200, 300, 400, 500, 1000, $10^4$, $10^5$, $10^6$, $10^7$, $10^8$, or more chemFET sensors (and/or reaction chambers). As used herein, it is intended that an array that comprises, as an example, 256 sensors or reaction chambers will contain 256 or more (i.e., at least 256) sensors or reaction chambers. It is further intended that aspects and embodiments described herein that "comprise" elements and/or steps also fully support and embrace aspects and embodiments that "consist of" or "consist essentially of" such elements and/or steps.

Various aspects and embodiments of the invention involve sensors (and/or reaction chambers) within an army that are spaced apart from each other at a center-to-center distance or spacing (or "pitch", as the terms are used interchangeably herein) that is in the range of 1-50 microns, 1-40 microns, 1-30 microns, 1-20 microns, 1-10 microns, or 5-10 microns, including equal to or less than about 9 microns, or equal to or less than about 5.1 microns, or 1-5 microns including equal to or less than about 2.8 microns. The center-to-center distance between adjacent reaction chambers in a reaction chamber array may be about 1-9 microns, or about 2-9 microns, or about 1 microns, about 2 microns, about 3 microns, about 4 microns, about 5 microns, about 6 microns, about 7 microns, about 8 microns, or about 9 microns.

In some embodiments, the reaction chamber has a volume of equal to or less than about 1 picoliter (pL), including less than 0.5 pL, less than 0.1 pL, less than 0.05 pL, less than 0.01 pL, less than 0.005 pL.

The reaction chambers may have a square cross section, for example, at their base or bottom. Examples include an 8 µm by 8 µm cross section, a 4 µm by 4 µm cross section, or a 1.5 µm by 1.5 µm cross section. Alternatively, they may have a rectangular cross section, for example, at their base or bottom. Examples include an 8 µm by 12 µm cross section, a 4 µm by 6 µm cross section, or a 1.5 µm by 2.25 µm cross section.

In some embodiments, a reaction chamber comprises a single template nucleic acid or a single bead. In these instances, it is to be understood that such reaction chambers have only one template nucleic acid or only one bead, although they may contain other elements. Such "single nucleic acids" however may be later amplified in order to give rise to a plurality of identical nucleic acids. Similarly, in some embodiments, a single template nucleic acid may be a concatemer and thus may contain multiple copies of a starting nucleic acid such as a starting template nucleic acid or a target nucleic acid fragment. As used herein, a plurality is two or more.

In some embodiments, a reaction chamber comprises a plurality of identical nucleic acids. In some embodiments, the identical nucleic acids are attached (e.g., covalently) to a bead within the well. In other embodiments, the identical nucleic acids are attached (e.g., covalently) to a surface in the reaction chamber such as but not limited to the chemFET surface (or typically at the bottom of the reaction chamber). The plurality of nucleic acids can be 2-10, $2\text{-}10^2$, $2\text{-}10^3$, $2\text{-}10^4$, $2\text{-}10^5$, $2\text{-}10^6$, or more. In some embodiments, the plurality of nucleic acids can be 2 through to 2 million, 2 through to 3 million, 2 through to 4 million, 2 through to 5 million, or more. As used herein, a template nucleic acid may contain a single template or it may contain a plurality of templates (e.g., in the case of a concatemer, whether or not in the context of a DNA "nanoball"). Such concatemers may include 10, 50, 100, 500, 1000, or more copies of the template nucleic acid. When such concatemers are used, they may exist in a reaction well, or otherwise be in close proximity to the chemFET surface, in the absence or presence of a bead. That is, the concatemers may be present independently of beads, and they may or may not be themselves covalently or non-covalently attached to the chemFET surface. Sequencing of such nucleic acids may be via detection of released hydrogen ions and/or detection of addition of negative charge to the chemFET surface following nucleotide incorporations events.

Other aspects of the invention relate to methods for monitoring nucleic acid synthesis reactions, including but not limited to those integral to sequencing-by-synthesis methods. Thus, various aspects of the invention provide methods for monitoring nucleic acid synthesis reactions, methods for determining or monitoring nucleotide incorporation into a nucleic acid, and the like, optionally in the presence of nucleotide excision as may occur for example in a nick translation reaction. These methods are carried out in some important embodiments in a pH sensitive environment (i.e., an environment in which pH and pH changes can be detected).

Various methods provided herein rely on sequencing a nucleic acid by contacting a plurality of the nucleic acids sequentially to a known order of different nucleotides (e.g., dATP, dCTP, dGTP, and dTTP), and detecting an electrical output that results if the nucleotide is incorporated. Some methods employ a primed template nucleic acid and incorporate nucleotides into a sequencing primer based on complementarity with the template nucleic acid.

Thus, some aspects of the invention provide methods for sequencing a nucleic acid comprising sequencing a plurality of identical template nucleic acids in a reaction chamber in contact with a chemFET, in an array which comprises at least 3 (and up to millions) of such assemblies of reaction chambers and chemFETs.

Some methods involve sequencing individually amplified fragmented nucleic acids using a chemFET array, optionally overlayed with a reaction chamber array. In various embodiments, the chemFET array comprises at least 500 chemFETs, at least 100,000 chemFETs, at least 1 million chemFETs, or more. In some embodiments, the plurality of fragmented nucleic acids is individually amplified using a water in oil emulsion amplification method.

Some methods involve disposing (e.g., placing or positioning) a plurality of identical template nucleic acids into a reaction chamber (or well) that is in contact with or capacitively coupled to a chemFET, wherein the template nucleic acids are individually hybridized to sequencing primers or are self-priming (thereby forming a template/primer hybrid), synthesizing a new nucleic acid strand (or extending the sequencing primer) by incorporating one or more known nucleotide triphosphates sequentially at the 3' end of the sequencing primer in the presence of a polymerase, and detecting the incorporation of the one or more known nucleotide triphosphates by a change in voltage and/or current at the chemFET. The chemFET is preferably one sensor in a chemFET array and the reaction chamber is preferably one chamber in a reaction chamber array. The template nucleic acids between reaction chambers may differ but those within a reaction chamber are preferably identical. Thus it will be clear that the invention contemplates performing a plurality of sequencing reactions simultaneously within a reaction chamber and if in the context of an array within the plurality of reaction chambers in the array.

The above-noted methods may be carried out on templates that are immobilized (e.g., covalently) to a bead located within the reaction chamber or on templates that are immobilized (e.g., covalently) to a surface inside the reaction chamber including the chemFET surface. Nucleotide incorporation can then be detected by an increase in the release of hydrogen ions into the solution and ultimately in contact with the chemFET surface and/or by an increase in the negative charge at the chemFET surface.

Various embodiments may be embraced in the various foregoing aspects of the invention and these are recited below once for convenience and brevity.

It is to be understood that although various of the foregoing aspects and embodiments of the invention recite hybridization (or binding) of a sequencing primer to a template, the invention also contemplates the use of template nucleic acids that hybridize to themselves (i.e., intramolecularly) thereby giving rise to free 3' ends onto which nucleotide triphosphates may be incorporated. Such templates, referred to herein as self-priming templates, may be used in any of the foregoing methods.

Similarly, the invention equally contemplates the use of double stranded templates that are engineered to have particular sequences at their free ends that can be acted upon by nicking enzymes such as nickases. In this way, the polymerase incorporates nucleotide triphosphates at the nicked site. In these instances, there is no requirement for a separate sequencing primer. The double stranded template may comprise ribonucleotide (i.e., RNA) bases including for example uracils which are acted upon by different enzymes to create a nick in the template from which sequencing may begin. It is to be understood that such methods are still considered "non-enzymatic" as intended herein since the detection of nucleotide incorporation (via detection of a released product or byproduct of the incorporation reaction or by detection of an increased charge at the chemFET surface) does not rely on an enzyme, even though the nucleotide incorporation event typically does.

In various embodiments, the incorporated nucleotide triphosphate is known. In various embodiments, the nucleotide triphosphate is a plurality of identical nucleotide triphosphates, the template is a plurality of templates, the hybrids are a plurality of hybrids, and the polymerase is a plurality of polymerases. The polymerase may be a plurality of polymerases that are not identical and rather may be comprised of 2, 3, or more types of polymerases. In some instances, a mixture of two polymerases may be used with one having suitable processivity and the other having suitable rate of incorporation. The ratio of the different polymerases can vary. Similarly, the primer, template or hybrid may be a plurality of primers, templates, or hybrids respectively that may not be identical to each other, provided that any primer, template or hybrid in a single reaction chamber, attached to a single capture bead or to another solid support such as a chemFET surface in the same reaction chamber are identical to each other. In some instances, the primers are identical between reaction chambers.

In some embodiments, the incorporation of at least 10, at least 20, at least 30, at least 40, at least 50, at least 60, at least 70, at least 80, at least 90, or at least 100 nucleotide triphosphates is detected. In other embodiments, the incorporation of 100-500 25-750, 500-1000, or 10-1000 nucleotide triphosphates is detected.

In some embodiments, the reaction chamber comprises a plurality of packing beads. In some embodiments, the reaction chamber lacks packing beads.

In some embodiments, the reaction chamber comprises a soluble non-nucleic acid polymer. In some embodiments, the detecting step occurs in the presence of a soluble non-nucleic acid polymer. In some embodiments, the soluble non-nucleic acid polymer is polyethylene glycol, or PEA, or a dextran, or an acrylamide, or a cellulose (e.g., methyl cellulose). In some embodiments, the non-nucleic acid polymer such as polyethylene glycol is attached to the single bead. In some embodiments, the non-nucleic acid polymer is attached to one or more (or all) sides of a reaction chamber, except in some instances the bottom of the reaction chamber which is the PET surface. In some embodiments, the non-nucleic acid polymer is biotinylated such as but not limited to biotinylated polyethylene glycol.

In some embodiments, the method is carried out at a pH of about 6-9.5, or at about 6-9, or at about 7-9, or at about 8.5 to 9.5, or at about 9. The pH range in some instances is dictated by the polymerase (and/or other enzyme) being used in the method.

In some important embodiments, the synthesizing and/or detecting step is carried out in a weak buffer. In some embodiments, the weak buffer comprises Tris-HCl, boric acid or borate buffer, acetate, morpholine, citric acid, carbonic acid, or phosphoric acid as a buffering agent. In some embodiments, the synthesizing and/or detecting step is carried out in an aqueous solution that lacks buffer.

In some embodiments, the synthesizing and/or detecting step is carried out in about 1 mM Tris-HCl. In some embodiments, the synthesizing and/or detecting step is carried out in less than 1 mM Tris-HCl, In some embodiments, the synthesizing and/or detecting step is carried out in about 0.9 mM Tris-HCl, about 0.8 mM Tris-HCl, about 0.7 mM Tris-HCl, about 0.6 mM Tris-HCl, about 0.5 mM Tris-HCl, about 0.4 mM Tris-HCl, about 0.3 mM Tris-HCl, or about 0.2 mM Tris-HCl.

In some embodiments, the synthesizing and/or detecting step is carried out in about 1 mM borate buffer. In some embodiments, the synthesizing and/or detecting step is carried out in less than 1 mM borate buffer. In some embodiments, the synthesizing and/or detecting step is carried out in about 0.9 mM borate buffer, about 0.8 mM borate buffer, about 0.7 mM borate buffer, about 0.6 mM borate buffer, about 0.5 mM borate buffer, about 0.4 mM borate buffer, about 0.3 mM borate buffer, or about 0.2 mM borate buffer.

In various embodiments, the nucleotide triphosphates are unblocked. As used herein, an unblocked nucleotide triphosphate is a nucleotide triphosphate with an unmodified end that can be incorporated into a nucleic acid (at its 3' end) and once it is incorporated can be attached to the following nucleotide triphosphate being incorporated. Blocked dNTP in contrast either cannot be added to a nucleic acid or their incorporation into a nucleic acid prevents any further nucleotide incorporation and any further extension of that nucleic acid. In various embodiments, the nucleotide triphosphates are deoxynucleotide triphosphates (dNTPs).

In various embodiments, the chemFET comprises a silicon nitride passivation layer. The passivation layer may or may not be bound to a nucleic acid such as a template nucleic acid or a concatemer of template nucleic acids.

In some embodiments, the nucleotide triphosphates are pre-soaked in $Mg^{2+}$ (e.g., in the presence of $MgCl_2$) or $Mn^{2+}$ (e.g., in the presence of $MnCl_2$). In some embodiments, the polymerase is pre-soaked in $Mg^{2+}$ (e.g., in the presence of $MgCl_2$) or $Mn^{2+}$ (e.g., in the presence of $MnCl_2$).

In some embodiments, the method is carried out in a reaction chamber comprising a single capture bead, wherein a ratio of reaction chamber width to single capture bead diameter is at least 0.7, at least 0.8, or at least 0.9.

In some embodiments, the polymerase is free in solution. In some embodiments, the polymerase is immobilized to a bead. In some embodiments, the polymerase is immobilized to a capture bead. In some embodiments, the template nucleic acids are attached to capture beads. In some embodiments, the template nucleic acids are attached to the chemFET surface or another wall inside the reaction chamber.

A number of aspects of the disclosed apparatus relate to improving performance by, for example, improving the signal-to-noise ratio of individual ISFET-based pixels as well as arrays of such pixels.

One aspect involves One aspect involves over-coating (i.e., "passivating") the sidewalls (typically formed of TEOS-oxide or another suitable material, as above-described) and sensor surface at the bottom of the microwells with various metal oxide or like materials, to improve their surface chemistry (i.e., make the sidewalls less reactive) and electrical properties.

Another aspect is forming ISFETs with a very thin dielectric coating on the floating gate electrode.

Yet another aspect is forming a combined ISFET and microwell structure wherein the surface area for charge collection at the floating gate is increased by employing a metallization on the microwell sidewalls.

Still a further aspect is employing modified array and pixels designs to reduce noise sources, including charge injection into the electrolyte. In part, these designs include the use of active pixels having current sources configured to reduce ISFET terminal voltage fluctuations.

Yet another aspect is providing a more reliable way to introduce a stable reference potential into a flow cell having a solution flowing therethrough, such that the reference potential will be substantially insensitive to spatial variations in fluid composition and pH.

A further aspect is an improved mechanism for multiplexing fluid flows into the flow cell, whereby switching of fluids is simplified and instead of multiplexing multiple reagents at the location of valves used to control their flow, reagents are multiplexed downstream with a passive micro-fluidic multiplexer circuit that acts as a kind of union. Diffusion-transported effluent is minimized from reagent inputs other than the one currently being used. Laminar flow and/or fluid resistance elements cause diffuse effluent to be discarded to a waste location.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

BRIEF DESCRIPTION OF THE DRAWINGS

In the drawings, like reference characters generally refer to the same parts throughout the different views. Also, the drawings are not necessarily to scale, emphasis instead being placed upon generally illustrating the various concepts discussed herein.

FIG. 5 is a diagram similar to FIG. 1, illustrating a wider cross-section of a portion of a substrate corresponding to one pixel of the array column shown in FIG. 3, in which the ISFET is shown alongside two n-channel MOSFETs also included in the pixel.

FIG. 6 is a diagram similar to FIG. 5, illustrating a cross-section of another portion of the substrate corresponding to one pixel of the array column shown in FIG. 3, in which the ISFET is shown alongside the p-channel MOSFET of the transmission gate shown in FIG. 4.

FIG. 10-1 illustrates a top view of a chip layout design for a cluster of four neighboring pixels of an chemFET array shown in FIG. 9, according to another inventive embodiment of the present disclosure.

FIG. 11A-1 shows a composite cross-sectional view of multiple neighboring pixels, along the line I-I of one of the pixels shown in FIG. 10-1, including additional elements of the pixel between the lines II-II, illustrating a layer-by-layer view of pixel fabrication according to another inventive embodiment of the present disclosure.

FIGS. 11B(1)-(3) provide the chemical structures of ten PPi receptors (compounds 1 through 10).

FIG. 11C(1) is a schematic of a synthesis protocol for compound 7 from FIG. 11B(3).

FIG. 11C(2) is a schematic of a synthesis protocol for compound 8 from FIG. 11B(3).

FIG. 11C(3) is a schematic of a synthesis protocol for compound 9 from FIG. 11B(3).

FIGS. 11D(1) and (2) are schematics illustrating a variety of chemistries that can be applied to the passivation layer in order to bind molecular recognition compounds (such as but not limited to PPi receptors).

FIGS. 12A through 12L provide top views of each of the fabrication layers shown in FIG. 11A, according to one inventive embodiment of the present disclosure.

FIGS. 12-1A through 12-1L provide top views of each of the fabrication layers shown in FIG. 11A-1, according to another inventive embodiment of the present disclosure.

FIG. 20A illustrates a top view of a chip layout design for a pixel of the chemFET array shown in FIG. 20, according to another inventive embodiment of the present disclosure.

FIG. 33B-1 is an image from a scanning electron microscope showing in cross-section a portion of an array architecture as taught herein, with microwells formed in a layer of silicon dioxide over ISFETs.

FIG. 33B-2 is a diagrammatic illustration of a microwell in cross-section, the microwell being produced as taught herein and having sloped sides, and showing how a bead of a correspondingly appropriate diameter larger than that of the well bottom can be spaced from the well bottom by interference with the well sidewalls.

FIG. 33B-3 is another diagrammatic illustration of such a microwell with beads of different diameters shown, and indicating optional use of packing beads below the nucleic acid-carrying bead such as a DNA-carrying bead FIGS. 34-37 diagrammatically illustrate a first example of a suitable experiment apparatus incorporating a fluidic interface with the sensor array, with FIG. 35 providing a cross-section through the FIG. 34 apparatus along section line 35-35' and FIG. 36 expanding part of FIG. 35, in perspective, and FIG. 37 further expanding a portion of the structure to make the fluid flow more visible.

FIG. 42F1 is a diagrammatic illustration of an example of a ceiling baffle arrangement for a flow cell in which fluid is introduced at one corner of the chip and exits at a diagonal corner, the baffle arrangement facilitating a desired fluid flow across the array.

FIGS. 42F2-42F8 comprise a set of illustrations of an exemplary flow cell member that may be manufactured by injection molding and may incorporate baffles to facilitate fluid flow, as well as a metalized surface for serving as a reference electrode, including an illustration of said member mounted to a sensor array package over a sensor array, to form a flow chamber thereover.

FIGS. 59A-59C are illustrations of the pieces for two examples of two-piece injection molded parts for forming a flow cell.

FIG. 61J is an optical microscope image and FIG. 61K is an image captured using the chemFET sensor underlying the microwell array.

FIG. 75O is a partially schematic circuit, partially block diagram of a single pixel, illustrating basically how digital output may be generated at the individual pixel level in an array;

FIGS. 75R-75T are schematic circuit diagrams illustrating alternatives for diode-protecting ISFETs as discussed herein;

DETAILED DESCRIPTION

Figure 1:
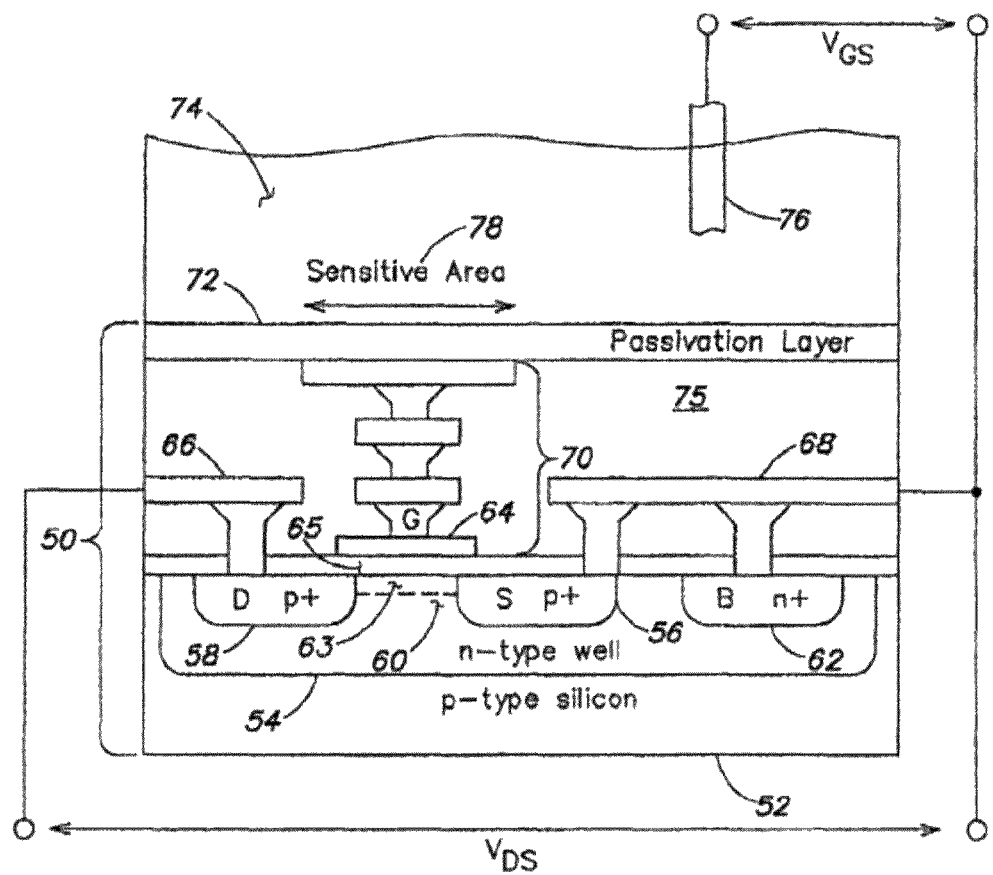
FIG. 1 illustrates a cross-section of a p-type (p-channel) ion-sensitive field effect transistor (ISFET) fabricated using a conventional CMOS process.

Following below are more detailed descriptions of various concepts related to, and embodiments of, inventive methods and apparatus relating to large scale chemFET arrays for analyte detection and/or measurement. It should be appreciated that various concepts introduced above and discussed in greater detail below may be implemented in any of numerous ways, as the disclosed concepts are not limited to any particular manner of implementation. Examples of specific implementations and applications are provided primarily for illustrative purposes.

Various inventive embodiments according to the present disclosure are directed at least in part to a semiconductor-based/microfluidic hybrid system that combines the power of microelectronics with the biocompatibility of a microfluidic system. In some examples below, the microelectronics portion of the hybrid system is implemented in CMOS technology for purposes of illustration. It should be appreciated, however, that the disclosure is not intended to be limiting in this respect, as other semiconductor-based technologies may be utilized to implement various aspects of the microelectronics portion of the systems discussed herein.

One embodiment disclosed herein is directed to a large sensor array (e.g., a two-dimensional array) of chemically-sensitive field effect transistors (chemFETs). In related embodiments, the individual chemFET sensor elements or "pixels" of the array are configured to detect analyte presence (or absence), analyte levels (or amounts), and/or analyte concentration in a sample such as an unmanipulated sample, or as a result of chemical and/or biological processes (e.g., chemical reactions, cell cultures, neural activity, nucleic acid sequencing reactions, etc.) occurring in proximity to the array. Examples of chemFETs contemplated by various embodiments discussed in greater detail below include, but are not limited to, ion-sensitive field effect transistors (IS-FETs) and enzyme-sensitive field effect transistors (En-FETs). In one exemplary implementation, one or more microfluidic structures is/are fabricated above the chemFET sensor array to provide for containment and/or confinement of a biological or chemical reaction in which an analyte of interest may be captured, produced, or consumed, as the case may be. For example, in one implementation, the microfluidic structure(s) may be configured as one or more wells (or microwells, or reaction chambers, or reaction wells as the terms are used interchangeably herein) disposed above one or more sensors of the array, such that the one or more sensors over which a given well is disposed detect and measure analyte presence, level, and/or concentration in the given well. Preferably, there is a 1:1 correspondence of chemFET sensors and reaction wells.

In another exemplary implementation, the invention encompasses a system comprising at least one two-dimensional array of reaction chambers, wherein each reaction chamber is coupled to a chemically-sensitive field effect transistor ("chemFET") and each reaction chamber is no greater than 10 $\mu m^3$ (i.e., 1 pL) in volume. Preferably, each reaction chamber is no greater than 0.34 pL, and more preferably no greater than 0.096 pL or even 0.012 pL in volume. A reaction chamber can optionally be $2^2, 3^2, 4^2, 5^2, 6^2, 7^2, 8^2, 9^2$, or $10^2$ square microns in cross-sectional area at the top. Preferably, the array has at least $10^2, 10^3, 10^4, 10^5, 10^6, 10^7, 10^8, 10^9$, or more reaction chambers. The reaction chambers may be capacitively coupled to the chemFETs, and preferably are capacitively coupled to the chemFETs. Such systems may be used for high-throughput sequencing of nucleic acids.

As used herein, an array is a planar arrangement of elements such as sensors or wells. The array may be one or two dimensional. A one dimensional array is an array having one column (or row) of elements in the first dimension and a plurality of columns (or rows) in the second dimension. An example of a one dimensional array is a 1×5 array. A two dimensional array is an array having a plurality of columns (or rows) in both the first and the second dimensions. The number of columns (or rows) in the first and second dimensions may or may not be the same. An example of a two dimensional array is a 5×10 array.

In some embodiments, such a chemFET array/microfluidics hybrid structure may be used to analyze solution(s)/material(s) of interest containing nucleic acids. For example, such structures may be employed to sequence nucleic acids. Sequencing of nucleic acids may be performed to determine partial or complete nucleotide sequence of a nucleic acid, to detect the presence and in some instances nature of a mutation such as but not limited to a single nucleotide polymorphism in a nucleic acid, to identify source of a cell(s) or nucleic acid for example for forensic purposes, to detect abnormal cells such as cancer cells in the body optionally in the absence of detectable tumor masses, to identify pathogens in a sample such as a bodily sample for example for diagnostic and/or therapeutic purposes, to identify antibiotic resistant strains of pathogens in order to avoid unnecessary (and ineffective) therapeutic regimens, to determine what therapeutic regimen will be most effective to treat a subject having a particular condition as can be determined by the subject's genetic make-up (e.g., personalized medicine), to determine and compare nucleic acid expression profiles of two or more states (e.g., comparing expression profiles of diseased and normal tissue, or comparing expression profiles of untreated tissue and tissue treated with drug, enzymes, radiation or chemical treatment), to haplotype a sample (e.g., comparing genes or variations in genes on each of the two alleles present in a human subject), to karyotype a sample (e.g., analyzing chromosomal make-up of a cell or a tissue such as an embryo, to detect gross chromosomal or other genomic abnormalities), and to genotype (e.g., analyzing one or more genetic loci to determine for example carrier status and/or species-genus relationships).

The systems described herein can be utilized to sequence the nucleic acids of an entire genuine, or any portion thereof, Genomes that can be sequenced include mammalian genomes, and preferably human genomes. Other genomes that can be sequenced include bacterial, viral, fungal and parasitic genomes. Such sequencing may lead to the identification of mutations that give rise to drug resistance, or general evolutionary drift from known species. This latter aspect is useful in determining for example whether a prior therapeutic (such as a vaccine) may be effective against current infecting strains. A specific example is the detection of new influenza strains and a determination of whether a prior year's vaccine cocktail will be effective against a new flu outbreak.

Thus the methods of the invention may be embraced by methods for detecting a nucleic acid in a sample. The nucleic acid may be a marker of its source such as a pathogen including but not limited to a virus, or a cancer or tumor in an individual. In the latter aspect, a sample such as a blood sample may be harvested from a subject and screened for the presence of an occult cancer cell such as one that has extravasated from its original tumor site. In yet another aspect, the methods may be used for forensic purposes in which samples are screened for the presence of a known nucleic acid (e.g., from a suspect or from a law enforcement DNA bank). In related aspects, a sample may be analyzed for nucleic acid heterogeneity in order to determine whether a sample is derived from one source (e.g., a single subject) or more than one source (e.g., a contaminated sample). The methods described herein may also be used to detect the presence of a nucleotide mutation such as but not limited to a single nucleotide polymorphism. Such mutation analysis or screening is typically performed in prenatal or postnatal diagnostics. The nature of the mutation can then be used to determine the most suitable course of therapy, in some instances. Thus the invention intends that any of the methods provided herein can be used in one or more diagnostic, forensic and/or therapeutic methods.

Various aspects of the invention employ a sequencing-by-synthesis approach for sequencing nucleic acids. This approach involves the synthesis of a new nucleic acid strand using a template nucleic acid. The template strand may be primed intermolecularly by hybridizing a sequencing primer to it at one end, or intramolecularly by folding over on itself at one end. The template strand may also be primed by introducing a break or a nick in one strand of a double-stranded nucleic acid, preferably but not exclusively near an end, as described in greater detail herein. In these embodiments, known nucleotides are incorporated into the "primer" based on complementarity with the template. The method requires that nucleotides be contacted with the primer (and thus template) (in the presence of polymerase and any other factors required for incorporation) in a selective manner.

In many embodiments, each nucleotide type is individually contacted with the primer and/or template. In other embodiments, combinations of two or three types of nucleotides may be contacted with the primer and/or template simultaneously. Since the identity of the nucleotides in contact with the primer and/or template at any given time is known, the identity of the incorporated nucleotides (if incorporated) is also known. And based on the necessary complementarity with the template, the sequence of the template can also be deduced. Using different types of nucleotides separately (e.g., using dATP, dCTP, dGTP or dTTP separately from each other), a high resolution sequence can be obtained. Using combinations (or mixtures) of nucleotides (e.g., using dATP, dCTP and dGTP together and separately from dTTP), a lower resolution sequence can be obtained that is nevertheless valuable for certain applications (e.g., ordering and aligning various higher resolution sequences). With regards to the latter embodiment, it will be understood that the invention contemplates using mixtures of any three nucleotides, and in some cases any two nucleotides, and not just the specific combinations recited above.

The nucleotides (or nucleotide triphosphates or deoxyribonucleotides or dNTPs, as they are referred to herein interchangeably) need not be and typically are not extrinsically labeled. Thus, naturally occurring nucleotides (i.e., nucleotides identical to those that exist in vivo naturally) or their synthetic counterparts are suitable for use in the methods of the invention. Such nucleotides may be referred to herein as being "unlabeled".

Preferably, the nucleotides are delivered at substantially the same time to each template. Polymerase(s) are preferably already present, although they also may be introduced along with the nucleotides. The polymerases may be immobilized or may be free flowing. Once the nucleotides are incorporated (if complementarity exists) and any associated signal is detected, an enzyme, such as apyrase, is typically delivered to degrade any unused nucleotides, followed by a washing step to remove substantially an of the enzyme as well as any other remaining and undesirable components. The reaction may occur in a reaction chamber in some embodiments, while in others it may occur in the absence of reaction chambers. In these latter embodiments, the sensor surface may be continuous without any physical divider between sensors.

In important embodiments, the sequencing reaction is performed simultaneously on a plurality of identical templates in a reaction chamber, and optionally in a plurality of reaction chambers. Sequencing a different template in each reaction chamber allows a greater amount of sequence data to be obtained in any given run. Thus, using as many reaction chambers (and sensors) as possible in a given run also maximizes the amount of sequence data that can be obtained in any given run. In important embodiments, the templates in a reaction well are immobilized (e.g., covalently or non-covalently) onto and/or in a bead, referred to herein as a capture bead, or onto a solid support such as the chemFET surface.

It is to be understood that in this and other embodiments and aspects of the invention, a plurality may represent a subset of elements rather than the entirety of all elements. As an example, in the above embodiment, the plurality of templates in the reaction chamber that are sequenced may represent a subset or all of the templates in the reaction chamber. Thus this particular embodiment requires that at least two templates be sequenced, and it does not require that all the templates present in the reaction chamber be sequenced.

As described extensively herein, in some embodiments, nucleotide incorporation is detected through byproducts of the incorporation or by changes in charge to the newly synthesized nucleic acid, especially where it is immobilized on a chemFET surface, rather than by detecting the incorporated nucleotide itself. More specifically, some embodiments exploit the release of inorganic pyrophosphate (PPi), inorganic phosphate (Pi), and hydrogen ions (all of which are considered sequencing reaction byproducts) that occurs following incorporation of a nucleotide into a nucleic acid (such as a primer, for example). In some embodiments of the invention, the method detects the released hydrogen ions as an indication of nucleotide incorporation. The chemFETs (and chemFET arrays) described herein are suited to the detection of these ions as well as other sequencing reaction byproducts. It is to be understood that the aspects and embodiments described herein related to chemFETs equally contemplate and embrace ISFETs unless otherwise stated.

The invention includes methods for improving detection of the hydrogen ions by the chemFET. These methods include generating and/or detecting more hydrogen ions in a given sequencing reaction. This can be done by increasing the number of templates per reaction chamber, increasing the number of templates attached to each capture bead, increasing the number of templates being sequenced per reaction chamber, increasing the number of templates bound to the sensor surface, increasing the stability of the primer/template hybrid, increasing the processivity of the polymerase, and/or combining nucleotide incorporation with nucleotide excision (e.g., performing the sequencing-by-synthesis reaction in the context of a nick translation reaction), among other things. Another alternative or additional approach is to increase the number of released hydrogen ions that are actually detected by the chemFET. This can be done by preventing the released hydrogen ions from interacting with other components in the reaction well including any components with buffering potential. These embodiments include using buffering inhibitors (as described more fully herein) to saturate components that might otherwise sequester released hydrogen ions. Buffering inhibitors may be short RNA oligomers that bind to single stranded regions of the templates, or chemical compounds that interact with the materials comprised in the reaction chambers and/or chemFETs themselves.

Some aspects and embodiments presented herein involve dense chemFET arrays and reaction chamber arrays. It will be apparent that as arrays become more dense, area and/or volume of individual elements (e.g., sensor surfaces and reaction chambers) will typically become smaller in order to accommodate a greater number of sensors or reaction chambers without a concomitant (or significant) increase in total array area. However, it has been determined in accordance with an aspect of the invention that as volume of a reaction chamber decreases, the signal to noise ratio can actually increase due to an increased nucleic acid concentration. For example, it has been determined that a roughly 2.3 fold decrease in reaction chamber volume can yield about a 1.5 fold increase in signal to noise ratio. This increase can occur even if the total number of nucleic acids being sequenced is reduced. Thus, in some instances rather than losing signal by moving to more dense arrays, the invention contemplates a greater signal due to an increased concentration of nucleic acids in the smaller volume reaction chambers.

The invention also contemplates sequencing-by-synthesis methods that detect nucleotide incorporation events based on changes in charge at the chemFET surface due to the a change in charge of a moiety attached to the surface, such as a nucleic acid or a nucleic acid complex (e.g., a template/primer hybrid). Such methods include those that use or extend nucleic acids that are immobilized (e.g., covalently) to the surface of a chemFET. Nucleotide incorporation into a nucleic acid that is bound to a chemFET surface typically results in an increase in the negative charge of the bound nucleic acid or the complex in which it is present (e.g., a template/primer hybrid). In some instances, the primer will be bound to the chemFET surface while in other instances the template will be bound to the chemFET surface. In such instances, a plurality of identical, typically physically separate, nucleic acids are immobilized to individual chemFET surfaces and sequencing-by-synthesis reactions are performed on the plurality simultaneously and synchronously. In some embodiments, the nucleic acids are not concatemers and rather each will include only a single copy of the nucleic acid to be sequenced.

It will be understood that the sequencing methods provided herein can be used to sequence a genome or part thereof. As an example, such a method may include delivering fragmented nucleic acids from the genome or part thereof to a system for high-throughput sequencing comprising at least one array of reaction chambers, wherein each reaction chamber is coupled to a chemFET, and detecting a sequencing reaction in a reaction chamber via a signal from the chemFET coupled with the reaction chamber. Alternatively, the method may include delivering fragmented nucleic acids from the genome or part thereof to a sequencing apparatus comprising an array of reaction chambers, wherein each of the reaction chambers is disposed in a sensing relationship with an individual associated chemFET, and detecting a sequencing reaction a reaction chambers via a signal from its associated chemFET. Typically, all four nucleotides are flowed into the same reaction chamber, either individually (or separately) or as some mixture of less than all four nucleotides, in an ordered and known manner.

The methods provided herein may allow for at least $10^3$, preferably at least $10^4$, more preferably at least $10^5$, and even more preferably at least $10^6$ bases to be determined (or sequenced) per hour. In even more preferred embodiments, at least $10^7$ bases, at least $10^8$ bases, at least $10^9$ bases, or at least $10^{10}$ bases are sequenced per hour using the methods and arrays discussed herein. Thus, the methods may be used to sequence an entire human genome within about 24 hours, more preferably within about 20 hours, even more preferably within about 15 hours, even more preferably within about 10 hours, even more preferably within about 5 hours, and most preferably within about 1 hour.

It should be appreciated, however, that while some illustrative examples of the concepts disclosed herein focus on nucleic acid sequencing, the invention contemplates a broader application of these methods and is not intended to be limited to these examples.

Figure 8:
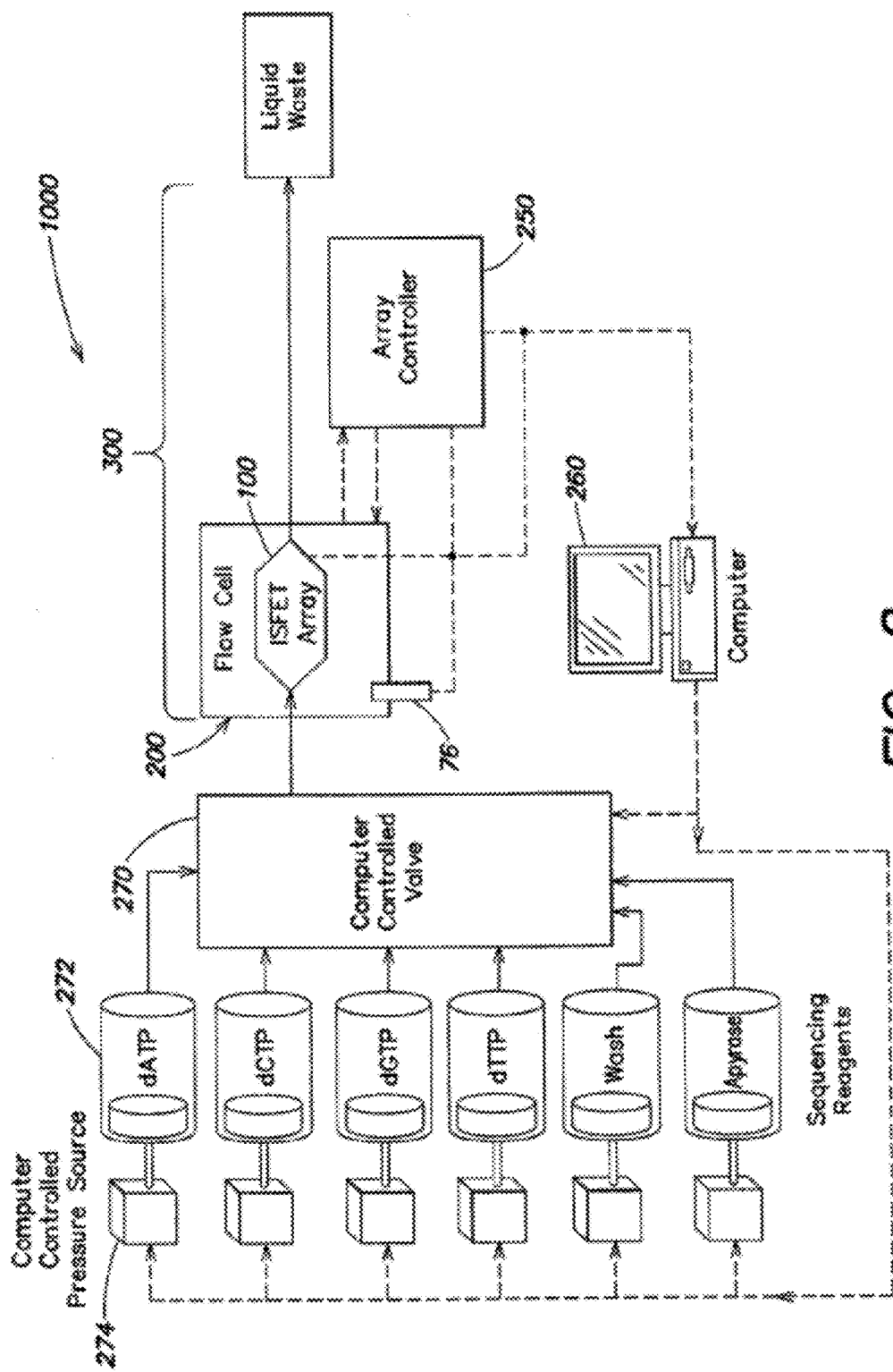
FIG. 8 generally illustrates a nucleic acid processing system comprising a large scale chemFET array, according to one inventive embodiment of the present disclosure.

FIG. 8 generally illustrates a nucleic acid processing system 1000 comprising a large scale chemFET array, according to one inventive embodiment of the present disclosure. An example of a nucleic acid processing system is a nucleic acid sequencing system. In the discussion that follows, the chemFET sensors of the array are described for purposes of illustration as ISFETs configured for sensitivity to static and/or dynamic ion concentration, including but not limited to hydrogen ion concentration. However, it should be appreciated that the present disclosure is not limited in this respect, and that in any of the embodiments discussed herein in which ISFETs are employed as an illustrative example, other types of chemFETs may be similarly employed in alternative embodiments, as discussed in further detail below. Similarly it should be appreciated that various aspects and embodiments of the invention may employ ISFETs as sensors yet detect one or more ionic species that are not hydrogen ions.

The system 1000 includes a semiconductor/microfluidics hybrid structure 300 comprising an ISFET sensor array 100 and a microfluidics flow cell 200. In one aspect, the flow cell 200 may comprise a number of wells (not shown in FIG. 8) disposed above corresponding sensors of the ISFET array 100. In another aspect, the flow cell 200 is configured to facilitate the sequencing of one or more identical template nucleic acids disposed in the flow cell via the controlled and ordered introduction to the flow cell of a number of sequencing reagents 272 (e.g., dATP, dCTP, dGTP, dTTP (generically referred to herein as dNTP), divalent cations such as but not limited to $Mg^{2+}$, wash solutions, and the like).

As illustrated in FIG. 8, the introduction of the sequencing reagents to the flow cell 200 may be accomplished via one or more valves 270 and one or more pumps 274 that are controlled by a computer 260. A number of techniques may be used to admit (i.e., introduce) the various processing materials (i.e., solutions, samples, reaction reagents, wash solutions, and the like) into the wells of such a flow cell. As illustrated in FIG. 8, reagents including dNTP may be admitted to the flow cell (e.g., via the computer controlled valve 270 and pumps 274) from which they diffuse into the wells, or reagents may be added to the flow cell by other means such as an ink jet. In yet another example, the flow cell 200 may not contain any wells, and diffusion properties of the reagents may be exploited to limit cross-talk between respective sensors of the ISFET array 100, or nucleic acids may be immobilized on the surfaces of sensors of the ISFET array 100.

The flow cell 200 in the system of FIG. 8 may be configured in a variety of manners to provide one or more analytes (or one or more reaction solutions) in proximity to the ISFET array 100. For example, a template nucleic acid may be directly attached or applied in suitable proximity to one or more pixels of the sensor array 100, or in or on a support material (e.g., one or more "beads") located above the sensor array but within the reaction chambers, or on the sensor surface itself. Processing reagents (e.g., enzymes such as polymerases) can also be placed on the sensors directly, or on one or more solid supports (e.g., they may be bound to the capture beads or to other beads) in proximity to the sensors, or they may be in solution and free-flowing. It is to be understood that the device may be used without wells or beads.

In the system 1000 of FIG. 8, according to one embodiment the ISFET sensor array 100 monitors ionic species, and in particular, changes in the levels/amounts and/or concentration of ionic species, including hydrogen ions. In important embodiments, the species are those that result from a nucleic acid synthesis or sequencing reaction.

Various embodiments of the present invention may relate to monitoring/measurement techniques that involve the static and/or dynamic responses of an ISFET. It is to be understood that although the particular example of a nucleic acid synthesis or sequencing reaction is provided to illustrate the transient or dynamic response of chemFET such as an ISFET, the transient or dynamic response of a chemFET such as an ISFET as discussed below may be exploited for monitoring/ sensing other types of chemical and/or biological activity beyond the specific example of a nucleic acid synthesis or sequencing reaction.

As noted above, the ISFET may be employed to measure steady state pH values, since in some embodiments pH change is proportional to the number of nucleotides incorporated into the newly synthesized nucleic acid strand. In other embodiments discussed in greater detail below, the FET sensor array may be particularly configured for sensitivity to other analytes that may provide relevant information about the chemical reactions of interest. An example of such a modification or configuration is the use of analyte-specific receptors to bind the analytes of interest, as discussed in greater detail herein.

Via an array controller 250 (also under operation of the computer 260), the ISFET array may be controlled so as to acquire data (e.g., output signals of respective ISFETs of the array) relating to analyte detection and/or measurements, and collected data may be processed by the computer 260 to yield meaningful information associated with the processing (including sequencing) of the template nucleic acid.

With respect to the ISFET array 100 of the system 1000 shown in FIG. 8, in one embodiment the array 100 is implemented as an integrated circuit designed and fabricated using standard CMOS processes (e.g., 0.35 micrometer process, 0.18 micrometer process), comprising all the sensors and electronics needed to monitor/measure one or more analytes and/or reactions. With reference again to FIG. 1, one or more reference electrodes 76 to be employed in connection with the ISFET array 100 may be placed in the flow cell 200 (e.g., disposed in "unused" wells of the flow cell) or otherwise exposed to a reference (e.g., one or more of the sequencing reagents 172) to establish a base line against which changes in analyte concentration proximate to respective ISFETs of the array 100 are compared. The reference electrode(s) 76 may be electrically coupled to the array 100, the array controller 250 or directly to the computer 260 to facilitate analyte measurements based on voltage signals obtained from the array 100; in some implementations, the reference electrode(s) may be coupled to an electric ground or other predetermined potential, or the reference electrode voltage may be measured with respect to ground, to establish an electric reference for ISFET output signal measurements, as discussed further below.

The ISFET array 100 is not limited to any particular size, as one- or two-dimensional arrays, including but not limited to as few as two to 256 pixels (e.g., 16 by 16 pixels in a two-dimensional implementation) or as many as 54 mega-pixels (e.g., 7400 by 7400 pixels in a two-dimensional implementation) or even greater may be fabricated and employed for various chemical/biological analysis purposes pursuant to the concepts disclosed herein. In one embodiment of the exemplary system shown in FIG. 8, the individual ISFET sensors of the array may be configured for sensitivity to hydrogen ions; however, it should also be appreciated that the present disclosure is not limited in this respect, as individual sensors of an ISFET sensor array may be particularly configured for sensitivity to other types of ion concentrations for a variety of applications (materials sensitive to other ions such as sodium, silver, iron, bromine, iodine, calcium, and nitrate, for example, are known).

More generally, a chemFET array according to various embodiments of the present disclosure may be configured for sensitivity to any one or more of a variety of analytes. In one embodiment, one or more chemFETs of an array may be particularly configured for sensitivity to one or more analytes and/or one or more binding events, and in other embodiments different chemFETs of a given array may be configured for sensitivity to different analytes. For example, in one embodiment, one or more sensors (pixels) of the array may include a first type of chemFET configured to be sensitive to a first analyte, and one or more other sensors of the array may include a second type of chemFET configured to be sensitive to a second analyte different from the first analyte. In one exemplary implementation, both a first and a second analyte may indicate a particular reaction such as for example nucleotide incorporation in a sequencing-by-synthesis method. Of course, it should be appreciated that more than two different types of chemFETs may be employed in any given array to detect and/or measure different types of analytes and/or other reactions. In general, it should be appreciated in any of the embodiments of sensor arrays discussed herein that a given sensor array may be "homogeneous" and include chemFETs of substantially similar or identical types to detect and/or measure a same type of analyte (e.g., hydrogen ions), or a sensor array may be "heterogeneous" and include chemFETs of different types to detect and/or measure different analytes.

For simplicity of discussion, again the example of an ISFET is discussed below in various embodiments of sensor arrays, but the present disclosure is not limited in this respect, and several other options for analyte sensitivity are discussed in further detail below (e.g., in connection with FIG. 11A).

The chemFET arrays configured for sensitivity to any one or more of a variety of analytes may be disposed in electronic chips, and each chip may be configured to perform one or more different biological reactions. The electronic chips can be connected to the portions of the above-described system which read the may output by means of pins coded in a manner such that the pins convey information to the system as to characteristics of the array and/or what kind of biological reaction(s) is(are) to be performed on the particular chip.

In one embodiment, the invention encompasses an electronic chip configured for conducting biological reactions thereon, comprising one or more pins for delivering information to a circuitry identifying a characteristic of the chip and/or a type of reaction to be performed on the chip. Such reactions or applications may include, but are not limited to, nucleotide polymorphism detection, short tandem repeat detection, or general sequencing.

In another embodiment, the invention encompasses a system adapted to perform more than one biological reaction on a chip the system comprising a chip receiving module adapted for receiving the chip, and a receiver for detecting information from the electronic chip, wherein the information determines a biological reaction to be performed on the chip. Typically, the system further comprises one or more reagents to perform the selected biological reaction.

In another embodiment, the invention encompasses an apparatus for sequencing a polymer template comprising at least one integrated circuit that is configured to relay information about spatial location of a reaction chamber, the type of monomer added to the spatial location, and the time required to complete reaction of a reagent comprising a plurality of the monomers with an elongating polymer.

In exemplary implementations based on 0.35 micrometer CMOS processing techniques (or CMOS processing techniques capable of smaller feature sizes), each pixel of the ISFET array 100 may include an ISFET and accompanying enable/select components, and may occupy an area on a surface of the array of approximately ten micrometers by ten micrometers (i.e., 100 micrometers$^2$) or less; stated differently, arrays having a pitch (center of pixel-to-center of pixel spacing) on the order of 10 micrometers or less may be realized. An array pitch on the order of 10 micrometers or less using a 0.35 micrometer CMOS processing technique constitutes a significant improvement in terms of size reduction with respect to prior attempts to fabricate ISFET arrays, which resulted in pixel sizes on the order of at least 12 micrometers or greater.

More specifically, in some embodiments discussed further below based on the inventive concepts disclosed herein, an array pitch of approximately nine (9) micrometers allows an ISFET array including over 256,000 pixels (e.g., a 512 by 512 array), together with associated row and column select and bias/readout electronics, to be fabricated on a 7 millimeter by 7 millimeter semiconductor die, and a similar sensor array including over four million pixels (e.g., a 2048 by 2048 array) to be fabricated on a 21 millimeter by 21 millimeter die. In other examples, an array pitch of approximately 5 micrometers allows an ISFET array including approximately 1.55 Mega-pixels (e.g., a 1348 by 1152 array) and associated electronics to be fabricated on a 9 millimeter by 9 millimeter die, and an ISFET sensor array including over 14 Mega-pixels and associated electronics on a 22 millimeter by 20 millimeter die. In yet other implementations, using a CMOS fabrication process in which feature sizes of less than 0.35 micrometers are possible (e.g., 0.18 micrometer CMOS processing techniques), ISFET sensor arrays with a pitch significantly below 5 micrometers may be fabricated (e.g., array pitch of 2.6 micrometers or pixel area of less than 8 or 9 micrometers$^2$), providing for significantly dense ISFET arrays.

As will be understood by those of skill in the art, the ability to miniaturize sequencing reactions reduces the time, cost and labor involved in sequencing of large genomes (such as the human genome). Of course, it should be appreciated that pixel sizes greater than 10 micrometers (e.g., on the order of approximately 20, 50, 100 micrometers or greater) may be implemented in various embodiments of chemFET arrays according to the present disclosure also.

In other aspects of the system shown in FIG. 8, one or more array controllers 250 may be employed to operate the ISFET array 100 (e.g., selecting/enabling respective pixels of the array to obtain output signals representing analyte measurements). In various implementations, one or more components constituting one or more array controllers may be implemented together with pixel elements of the arrays themselves, on the same integrated circuit (IC) chip as the array but in a different portion of the IC chip, or off-chip. In connection with array control, analog-to-digital conversion of ISFET output signals may be performed by circuitry implemented on the same integrated circuit chip as the ISFET array, but located outside of the sensor array region (locating the analog to digital conversion circuitry outside of the sensor array region allows for smaller pitch and hence a larger number of sensors, as well as reduced noise). In various exemplary implementations discussed further below, analog-to-digital conversion can be 4-bit, 8-bit, 12-bit, 16-bit or other bit resolutions depending on the signal dynamic range required.

In general, data may be removed from the array in serial or parallel or some combination thereof. On-chip controllers (or sense amplifiers) can control the entire chip or some portion of the chip. Thus, the chip controllers or signal amplifiers may be replicated as necessary according to the demands of the application. The array may, but need not be, uniform. For instance, if signal processing or some other constraint requires instead of one large array multiple smaller arrays, each with its own sense amplifiers or controller logic, that is quite feasible.

Having provided a general overview of the role of a chemFET (e.g., ISFET) array 100 in an exemplary system 1000 for measuring one or more analytes, following below are more detailed descriptions of exemplary chemFET arrays according to various inventive embodiments of the present disclosure that may be employed in a variety of applications. Again, for purposes of illustration, chemFET arrays according to the present disclosure are discussed below using the particular example of an ISFET array, but other types of chemFETs may be employed in alternative embodiments. Also, again, for purposes of illustration, chemFET arrays are discussed in the context of nucleic acid sequencing applications, however, the invention is not so limited and rather contemplates a variety of applications for the chemFET arrays described herein.

As noted above, various inventive embodiments disclosed herein specifically improve upon the ISFET array design of Milgrew et al. discussed above in connection with FIGS. 1-7, as well as other prior ISFET array designs, so as to significantly reduce pixel size and array pitch, and thereby increase the number of pixels of an ISFET array for a given semiconductor die size (i.e., increase pixel density). In some implementations, an increase in pixel density is accomplished while at the same time increasing the signal-to-noise ratio (SNR) of output signals corresponding to respective measurements relating to one or more analytes and the speed with which such output signals may be read from the array. In particular, by relaxing requirements for ISFET linearity and focusing on a more limited signal output/measurement range (e.g., signal outputs corresponding to a pH range of from approximately 7 to 9 or smaller rather than 1 to 14, as well as output signals that may not necessarily relate significantly to pH changes in sample), individual pixel complexity and size may be significantly reduced, thereby facilitating the realization of very large scale dense ISFET arrays.

Figure 9:
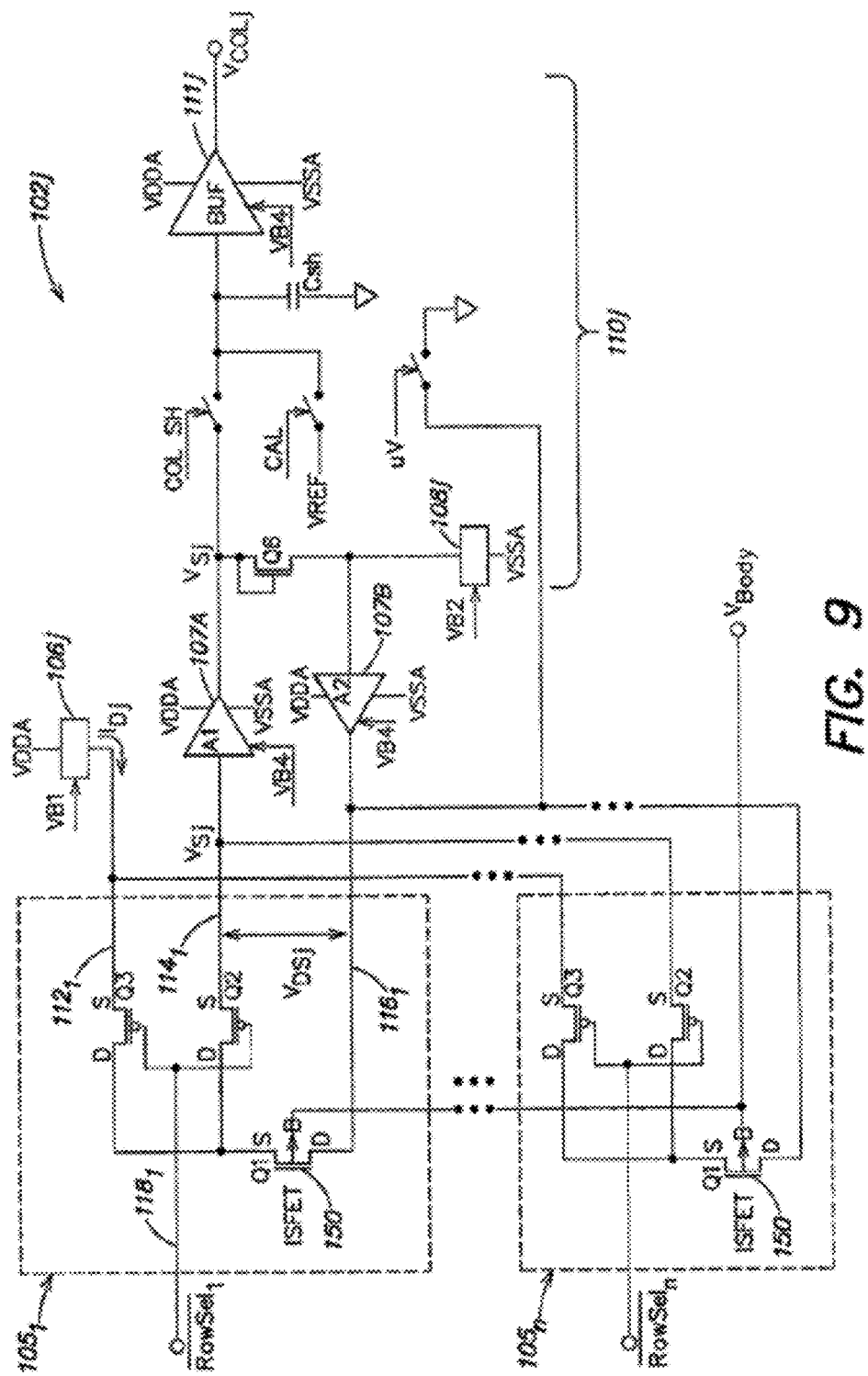
FIG. 9 illustrates one column of an chemFET array similar to that shown in FIG. 8, according to one inventive embodiment of the present disclosure.

To this end, FIG. 9 illustrates one column $102_j$ of an ISFET array 100, according to one inventive embodiment of the present disclosure, in which ISFET pixel design is appreciably simplified to facilitate small pixel size. The column $102_j$ includes n pixels, the first and last of which are shown in FIG. 9 as the pixels $105_1$ and $105_n$. As discussed further below in connection with FIG. 13, a complete two-dimensional ISFET array 100 based on the column design shown in FIG. 9 includes m such columns $102_j$ (j=1, 2, 3, . . . m) with successive columns of pixels generally arranged side by side. Of course, the ISFETs may be arrayed in other than a row-column grid, such as in a honeycomb pattern.

In one aspect of the embodiment shown in FIG. 9, each pixel $105_1$ through $105_n$ of the column $102_j$ includes only three components, namely, an ISFET 150 (also labeled as Q1) and two MOSFET switches Q2 and Q3. The MOSFET switches Q2 and Q3 are both responsive to one of n row select signals ($\overline{RowSel_1}$ through $\overline{RowSel_n}$, logic low active) so as to enable or select a given pixel of the column $102_j$. Using pixel $105_1$ as an example that applies to all pixels of the column, the transistor switch Q3 couples a controllable current source $106_j$ via the line $112_1$ to the source of the ISFET 150 upon receipt of the corresponding row select signal via the line $118_1$. The transistor switch Q2 couples the source of the ISFET 150 to column bias/readout circuitry $110_j$ via the line $114_1$ upon receipt of the corresponding row select signal. The drain of the ISFET 150 is directly coupled via the line $116_1$ to the bias/readout circuitry $110_j$. Thus, only four signal lines per pixel, namely the lines $112_1$, $114_1$, $116_1$ and $118_1$, are required to operate the three components of the pixel $105_1$. In an array of m columns, a given row select signal is applied simultaneously to one pixel of each column (e.g., at same positions in respective columns).

Figure 3:
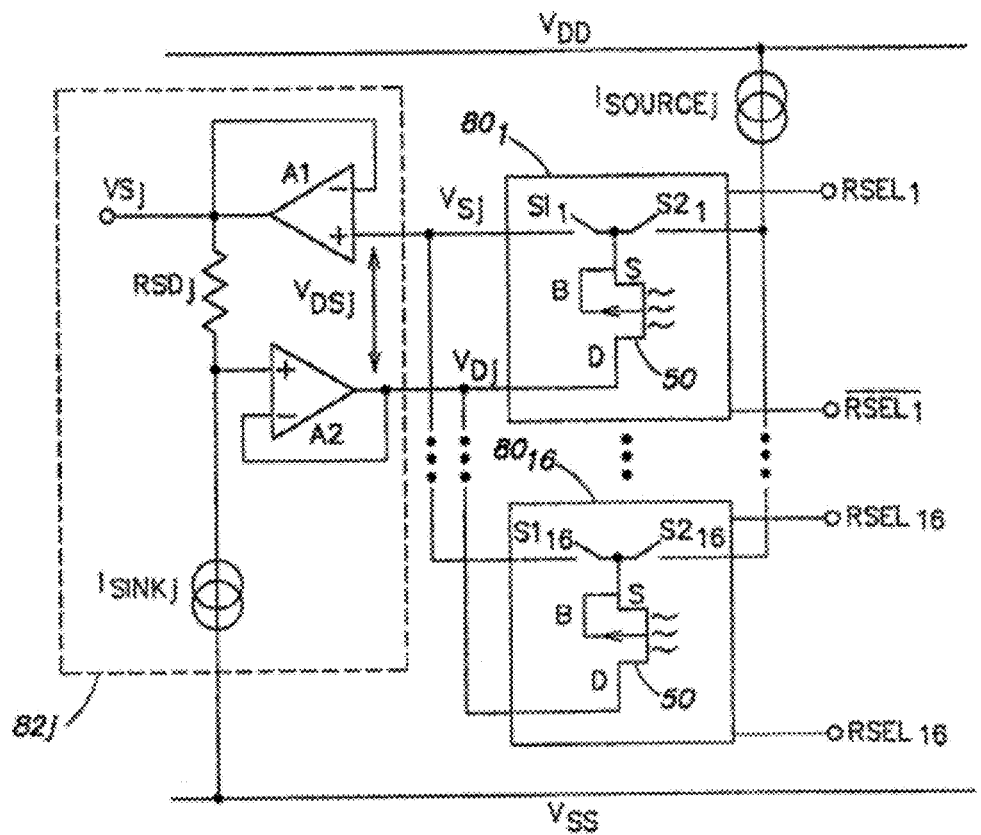
FIG. 3 illustrates one column of a two-dimensional ISFET array based on the ISFET shown in FIG. 1.
Figure 4:
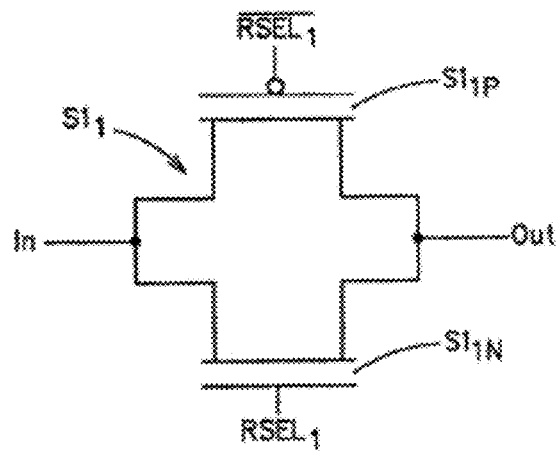
FIG. 4 illustrates a transmission gate including a p-channel MOSFET and an n-channel MOSFET that is employed in each pixel of the array column shown in FIG. 3.

As illustrated in FIG. 9, the design for the column $102_j$ according to one embodiment is based on general principles similar to those discussed above in connection with the column design of Milgrew et al. shown FIG. 3. In particular, the ISFET of each pixel, when enabled, is configured with a constant drain current $I_{Dj}$ and a constant drain-to-source voltage $V_{DSj}$ to obtain an output signal $V_{Sj}$ from an enabled pixel according to Eq. (3) above. To this end, the column $102_j$ includes a controllable current source $106_j$, coupled to an analog circuitry positive supply voltage VDDA and responsive to a bias voltage VB1, that is shared by all pixels of the column to provide a constant drain current $I_{Dj}$ to the ISFET of an enabled pixel. In one aspect, the current source $106_j$ is implemented as a current mirror including two long-channel length and high output impedance MOSFETs. The column also includes bias/readout circuitry $110_j$ that is also shared by all pixels of the column to provide a constant drain-to-source voltage to the ISFET of an enabled pixel. The bias/readout circuitry $110_1$ is based on a Kelvin Bridge configuration and includes two operational amplifiers 107A (A1) and 107B (A2) configured as buffer amplifiers and coupled to analog circuitry positive supply voltage VDDA and the analog supply voltage ground VSSA. The bias/readout circuitry also includes a controllable current sink $108_j$ (similar to the current source $106j$) coupled to the analog ground VSSA and responsive to a bias voltage VB2, and a diode-connected MOSFET Q6. The bias voltages VB1 and VB2 are set/controlled in tandem to provide a complimentary source and sink current. The voltage developed across the diode-connected MOSFET Q6 as a result of the current drawn by the current sink $108_j$ is forced by the operational amplifiers to appear across the drain and source of the ISFET of an enabled pixel as a constant drain-source voltage $V_{DSj}$.

By employing the diode-connected MOSFET Q6 in the bias/readout circuitry $110_j$ of FIG. 9, rather than the resistor $R_{SDj}$ as shown in the design of Milgrew et al. illustrated in FIG. 3, a significant advantage is provided in a CMOS fabrication process; specifically, matching resistors can be fabricated with error tolerances generally on the order of ±20%, whereas MOSFET matching in a CMOS fabrication process is on the order of ±1% or better. The degree to which the component responsible for providing a constant ISFET drain-to-source voltage $V_{Dsj}$ can be matched from column to column significantly affects measurement accuracy (e.g., offset) from column to column. Thus, employing the MOSFET Q6 rather than a resistor appreciably mitigates measurement offsets from column-to-column. Furthermore, whereas the thermal drift characteristics of a resistor and an ISFET may be appreciably different, the thermal drift characteristics of a MOSFET and ISFET are substantially similar, if not virtually identical; hence, any thermal drift in MOSFET Q6 virtually cancels any thermal drift from ISFET Q1, resulting in greater measurement stability with changes in array temperature.

In FIG. 9, the column bias/readout circuitry 110j also includes sample/hold and buffer circuitry to provide an output signal $V_{COLj}$ from the column. In particular, after one of the pixels $105_1$ through $105_n$ is enabled or selected via the transistors Q2 and Q3 in each pixel, the output of the amplifier 107A (A1), i.e., a buffered $V_{Sj}$, is stored on a column sample and hold capacitor $C_{sh}$ via operation of a switch (e.g., a transmission gate) responsive to a column sample and hold signal COL SH. Examples of suitable capacitances for the sample and hold capacitor include, but are not limited to, a range of from approximately 500 fF to 2 pF. The sampled voltage is buffered via a column output buffer amplifier 111j (BUF) and provided as the column output signal $V_{COLj}$. As also shown in FIG. 9, a reference voltage VREF may be applied to the buffer amplifier 111j, via a switch responsive to a control signal CAL, to facilitate characterization of column-to-column non-uniformities due to the buffer amplifier 111j and thus allow post-read data correction.

Figure 9A:
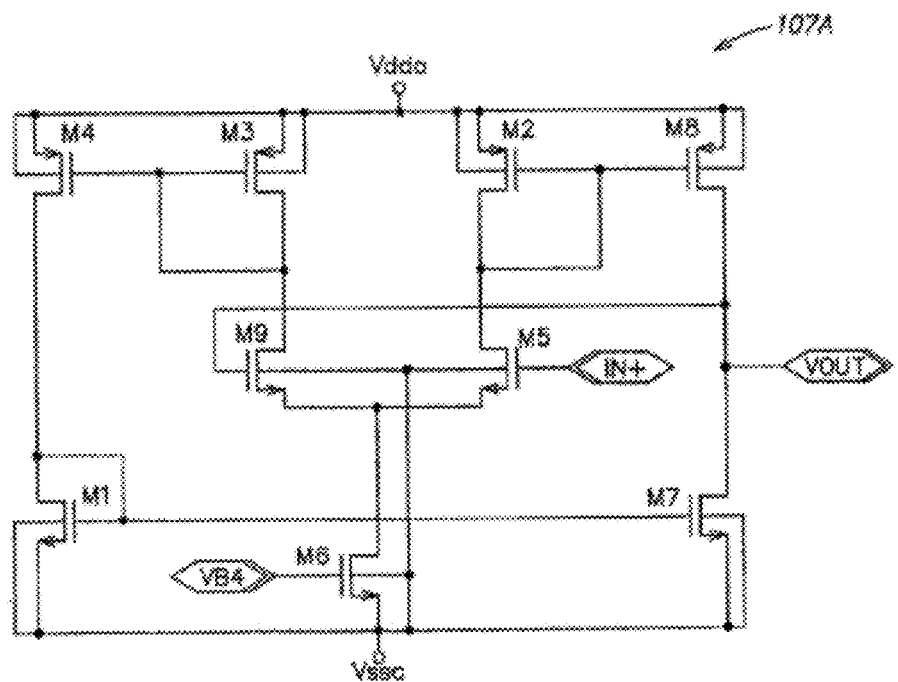
FIG. 9A illustrates a circuit diagram for an exemplary amplifier employed in the array column shown in FIG. 9.
Figure 9B:
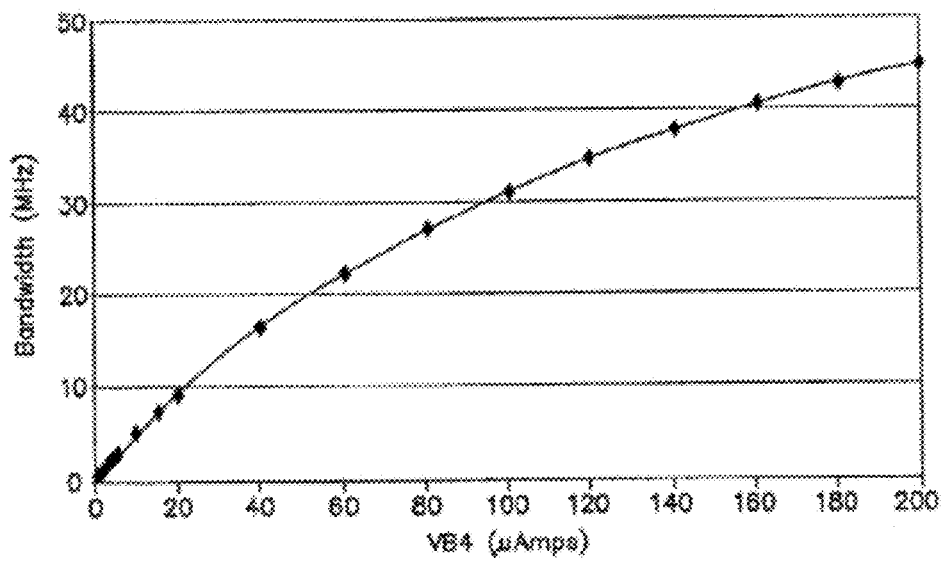
FIG. 9B is a graph of amplifier bias vs. bandwidth, according to one inventive embodiment of the present disclosure.

FIG. 9A illustrates an exemplary circuit diagram for one of the amplifiers 107A of the bias/readout circuitry 110j (the amplifier 107B is implemented identically), and FIG. 9B is a graph of amplifier bias vs. bandwidth for the amplifiers 107A and 107B. As shown in FIG. 9A, the amplifier 107A employs an arrangement of multiple current mirrors based on nine MOSFETs (M1 through M9) and is configured as a unity gain buffer, in which the amplifier's inputs and outputs are labeled for generality as IN+ and VOUT, respectively. The bias voltage VB4 (representing a corresponding bias current) controls the transimpedance of the amplifier and serves as a bandwidth control (i.e., increased bandwidth with increased current). With reference again to FIG. 9, due to the sample and hold capacitor $C_{sh}$, the output of the amplifier 107A essentially drives a filter when the sample and hold switch is closed. Accordingly, to achieve appreciably high data rates, the bias voltage VB4 may be adjusted to provide higher bias currents and amplifier bandwidth. From FIG. 9B, it may be observed that in some exemplary implementations, amplifier bandwidths of at least 40 MHz and significantly greater may be realized. In some implementations, amplifier bandwidths as high as 100 MHz may be appropriate to facilitate high data acquisition rates and relatively lower pixel sample or "dwell" times (e.g., on the order of 10 to 20 microseconds).

In another aspect of the embodiment shown in FIG. 9, unlike the pixel design of Milgrew et al. shown in FIG. 3, the pixels $105_1$ through $105_n$ do not include any transmission gates or other devices that require both n-channel and p-channel FET components; in particular, the pixels $105_1$ through $105_n$ of this embodiment include only FET devices of a same type (i.e., only n-channel or only p-channel). For purposes of illustration, the pixels $105_1$ and $105_n$ illustrated in FIG. 9 are shown as comprising only p-channel components, i.e., two p-channel MOSFETs Q2 and Q3 and a p-channel ISFET 150. By not employing a transmission gate to couple the source of the ISFET to the bias/readout circuitry $110_j$, some dynamic range for the ISFET output signal (i.e., the ISFET source voltage $V_S$) may be sacrificed. However, by potentially foregoing some output signal dynamic range (and thereby potentially limiting measurement range for a given static and/or dynamic chemical property, such as pH), the requirement of different type FET devices (both n-channel and p-channel) in each pixel may be eliminated and the pixel component count reduced. As discussed further below in connection with FIGS. 10-12, this significantly facilitates pixel size reduction. Thus, in one aspect, there is a beneficial tradeoff between reduced dynamic range and smaller pixel size.

In yet another aspect of the embodiment shown in FIG. 9, unlike the pixel design of Milgrew et al., the ISFET 150 of each pixel $105_1$ through $105_n$ does not have its body connection tied to its source (i.e., there is no electrical conductor coupling the body connection and source of the ISFET such that they are forced to be at the same electric potential during operation). Rather, the body connections of all ISFETs of the array are tied to each other and to a body bias voltage $V_{BODY}$. While not shown explicitly in FIG. 9, the body connections for the MOSFETs Q2 and Q3 likewise are not tied to their respective sources, but rather to the body bias voltage $V_{BODY}$. In one exemplary implementation based on pixels having all p-channel components, the body bias voltage $V_{BODY}$ is coupled to the highest voltage potential available to the array (e.g., VDDA), as discussed further below in connection with FIG. 17.

By not tying the body connection of each ISFET to its source, the possibility of some non-zero source-to-body voltage $V_{SB}$ may give rise to the "body effect," as discussed above in connection with FIG. 1, which affects the threshold voltage $V_{TH}$ of the ISFET according to a nonlinear relationship (and thus, according to Eqs. (3), (4) and (5) may affect detection and/or measurement of analyte activity giving rise to surface potential changes at the analyte/passivation layer interface). However, by focusing on a reduced ISFET output signal dynamic range, any body effect that may arise in the ISFET from a non-zero source-to-body voltage may be relatively minimal. Thus, any measurement nonlinearity that may result over the reduced dynamic range may be ignored as insignificant or taken into consideration and compensated (e.g., via array calibration and data processing techniques, as discussed further below in connection with FIG. 17). By not tying each ISFET source to its body connection, all of the FETs constituting the pixel may share a common body connection, thereby further facilitating pixel size reduction, as discussed further below in connection with FIGS. 10-12. Accordingly, in another aspect, there is a beneficial tradeoff between reduced linearity and smaller pixel size.

Figure 10:
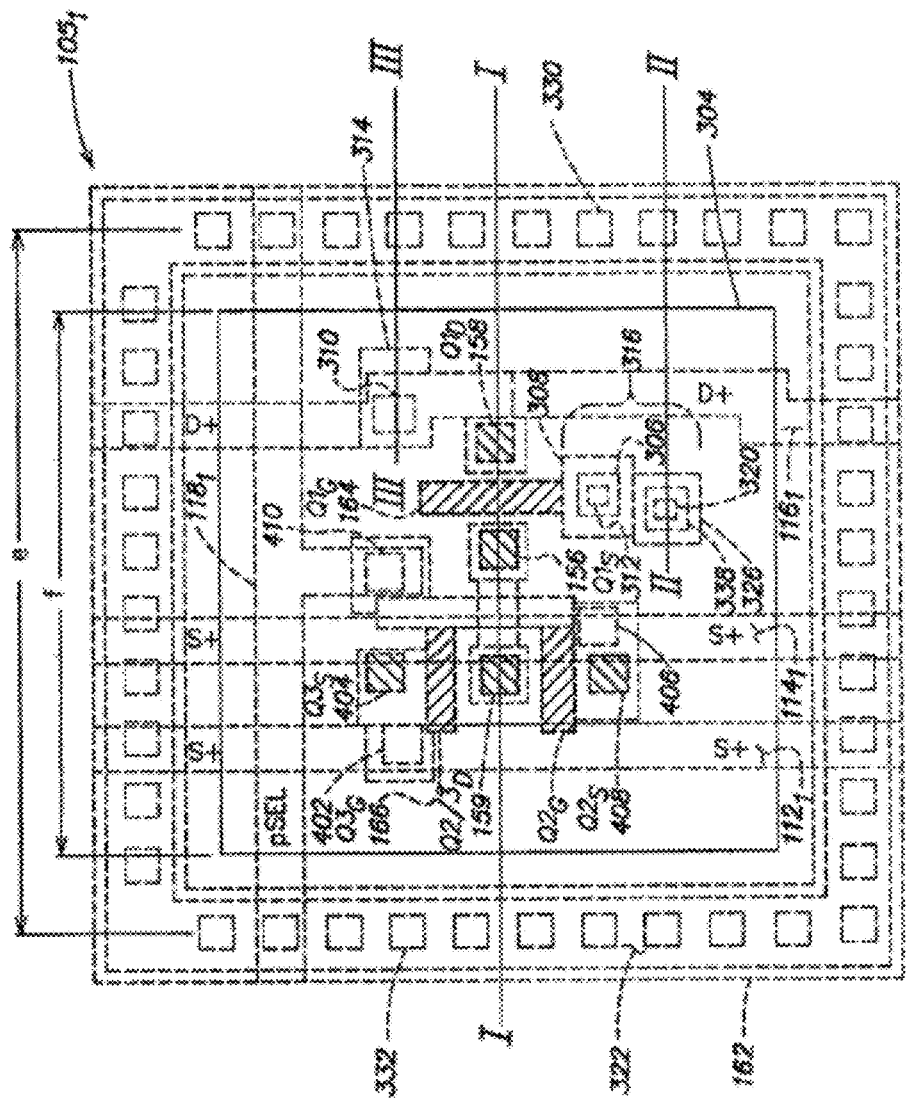
FIG. 10 illustrates a top view of a chip layout design for a pixel of the column of an chemFET array shown in FIG. 9, according to one inventive embodiment of the present disclosure.
Figures 1, 10:
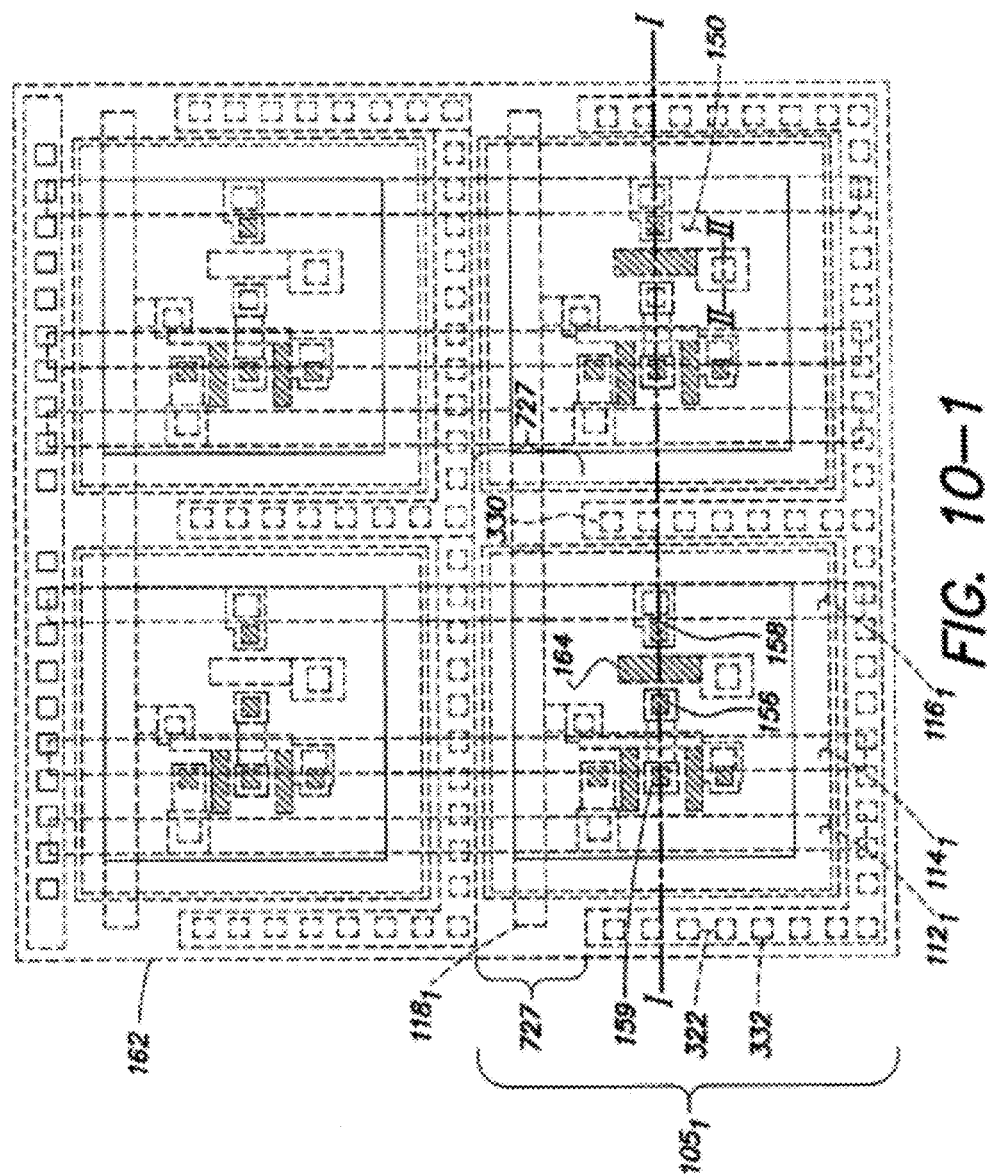

FIG. 10 illustrates a top view of a chip layout design for the pixel $105_1$ shown in FIG. 9, according to one inventive embodiment of the present disclosure. FIG. 11A shows a composite cross-sectional view along the line I-I of the pixel shown in FIG. 10, including additional elements on the right half of FIG. 10 between the lines II-II and illustrating a layer-by-layer view of the pixel fabrication, and FIGS. 12A through 12L provide top views of each of the fabrication layers shown in FIG. 11A (the respective images of FIGS. 12A through 12L are superimposed one on top of another to create the pixel chip layout design shown in FIG. 10). In one exemplary implementation, the pixel design illustrated in FIGS. 10-12 may be realized using a standard 4-metal, 2-poly, 0.35 micrometer CMOS process to provide a geometrically square pixel having a dimension "e" as shown in FIG. 10 of approximately 9 micrometers, and a dimension "1" corresponding to the ISFET sensitive area of approximately 7 micrometers.

In the top view of FIG. 10, the ISFET 150 (labeled as Q1 in FIG. 10) generally occupies the right center portion of the pixel illustration, and the respective locations of the gate, source and drain of the ISFET are indicated as $Q1_G$, $Q1_S$ and $Q1_D$. The MOSFETs Q2 and Q3 generally occupy the left center portion of the pixel illustration; the gate and source of the MOSFET Q2 are indicated as $Q2_G$ and $Q2_S$, and the gate and source of the MOSFET Q3 are indicated as $Q3_G$ and $Q3_S$. In one aspect of the layout shown in FIG. 10, the MOSFETs Q2 and Q3 share a drain, indicated as $Q2/3_D$. In another aspect, it may be observed generally from the top view of FIG. 10 that the ISFET is formed such that its channel lies along a first axis of the pixel (e.g., parallel to the line I-I), while the MOSFETs Q2 and Q3 are formed such that their channels lie along a second axis perpendicular to the first axis. FIG. 10 also shows the four lines required to operate the pixel, namely, the line $112_1$ coupled to the source of Q3, the line $114_1$ coupled to the source of Q2, the line $116_1$ coupled to the drain of the ISFET, and the row select line $118_1$ coupled to the gates of Q2 and Q3. With reference to FIG. 9, it may be appreciated that all pixels in a given column share the lines 112, 114 and 116 (e.g., running vertically across the pixel in FIG. 10), and that all pixels in a given row share the line 118 (e.g., running horizontally across the pixel in FIG. 10); thus, based on the pixel design of FIG. 9 and the layout shown in FIG. 10, only four metal lines need to traverse each pixel.

With reference now to the cross-sectional view of FIG. 11A, highly doped p-type regions 156 and 158 (lying along the line I-I in FIG. 10) in n-well 154 constitute the source (S) and drain (D) of the ISFET, between which lies a region 160 of the n-well in which the ISFETs p-channel is formed below the ISFETs polysilicon gate 164 and a gate oxide 165. According to one aspect of the inventive embodiment shown in FIGS. 10 and 11, all of the FET components of the pixel $105_1$ am fabricated as p-channel FETs in the single n-type well 154 formed in a p-type semiconductor substrate 152. This is possible because, unlike the design of Milgrew et al., 1) there is no requirement for a transmission gate in the pixel; and 2) the ISFETs source is not tied to the n-well's body connection. More specifically, highly doped n-type regions 162 provide a body connection (B) to the n-well 154 and, as shown in FIG. 10, the body connection B is coupled to a metal conductor 322 around the perimeter of the pixel $105_1$. However, the body connection is not directly electrically coupled to the source region 156 of the ISFET (i.e., there is no electrical conductor coupling the body connection and source such that they are forced to be at the same electric potential during operation), nor is the body connection directly electrically coupled to the gate, source or drain of any component in the pixel. Thus, the other p-channel FET components of the pixel, namely Q2 and Q3, may be fabricated in the same n-well 154.

Figure 11A:
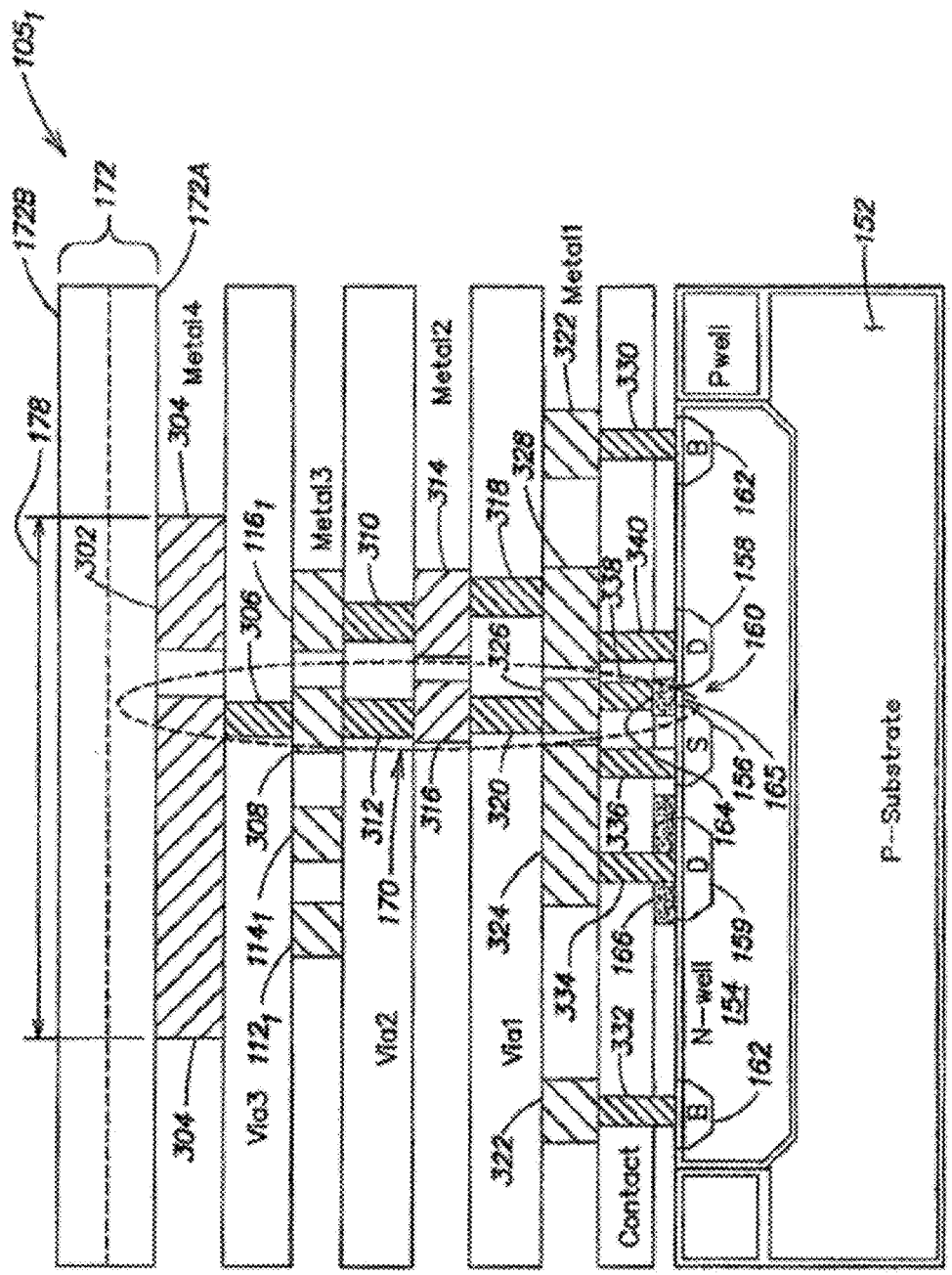
FIG. 11A shows a composite cross-sectional view along the line I-I of the pixel shown in FIG. 10, including additional elements on the right half of FIG. 10 between the lines II-II and III-III, illustrating a layer-by-layer view of the pixel fabrication according to one inventive embodiment of the present disclosure.

In the composite cross-sectional view of FIG. 11A, a highly doped p-type region 159 is also visible (lying along the line I-I in FIG. 10), corresponding to the shared drain (D) of the MOSFETs Q2 and Q3. For purposes of illustration, a polysilicon gate 166 of the MOSFET Q3 also is visible in FIG. 11A, although this gate does not lie along the line I-I in FIG. 10, but rather "behind the plane" of the cross-section along the line I-I. However, for simplicity, the respective sources of the MOSFETs Q2 and Q3 shown in FIG. 10, as well as the gate of Q2, are not visible in FIG. 11A, as they lie along the same axis (i.e., perpendicular to the plane of the figure) as the shared drain (if shown in FIG. 11A, these elements would unduly complicate the composite cross-sectional view of FIG. 11A).

Above the substrate, gate oxide, and polysilicon layers shown in FIG. 11A, a number of additional layers are provided to establish electrical connections to the various pixel components, including alternating metal layers and oxide layers through which conductive vias are formed. Pursuant to the example of a 4-Metal CMOS process, these layers are labeled in FIG. 11A as "Contact," "Metal1," "Via1," "Metal2," "Via2," "Metal3," "Via3," and "Metal4." (Note that more or fewer metal layers may be employed.) To facilitate an understanding particularly of the ISFET electrical connections, the composite cross-sectional view of FIG. 11A shows additional elements of the pixel fabrication on the right side of the top view of FIG. 10 between the lines II-II and With respect to the ISFET electrical connections, the topmost metal layer 304 corresponds to the ISFETs sensitive area 178, above which is disposed an analyte-sensitive passivation layer 172. The topmost metal layer 304, together with the ISFET polysilicon gate 164 and the intervening conductors 306, 308, 312, 316, 320, 326 and 338, form the ISFETs "floating gate" structure 170, in a manner similar to that discussed above in connection with a conventional ISFET design shown in FIG. 1. An electrical connection to the ISFETs drain is provided by the conductors 340, 328, 318, 314 and 310 coupled to the line $116_1$. The ISFETs source is coupled to the shared drain of the MOSFETs Q2 and Q3 via the conductors 334 and 336 and the conductor 324 (which lies along the line in FIG. 10). The body connections 162 to the n-well 154 are electrically coupled to a metal conductor 322 around the perimeter of the pixel on the "Metal1" layer via the conductors 330 and 332.

As indicated above, FIGS. 12A through 12L provide top views of each of the fabrication layers shown in FIG. 11A (the respective images of FIGS. 12A through 12L are superimposed one on top of another to create the pixel chip layout design shown in FIG. 10). In FIG. 12, the correspondence between the lettered top views of respective layers and the cross-sectional view of FIG. 11A is as follows: A) n-type well 154; B) Implant; C) Diffusion; D) polysilicon gates 164 (ISFET) and 166 (MOSFETs Q2 and Q3); E) contacts; F) Metal1; G) Via1; H) Metal2; I) Via2; J) Metal3; K) Via3; L) Metal4 (top electrode contacting ISFET gate). The various reference numerals indicated in FIGS. 12A through 12L correspond to the identical features that are present in the composite cross-sectional view of FIG. 11A.

At least in some applications, pixel capacitance may be a salient parameter for some type of analyte measurements. Accordingly, in another embodiment related to pixel layout and design, various via and metal layers may be reconfigured so as to at least partially mitigate the potential for parasitic capacitances to arise during pixel operation. For example, in one such embodiment, pixels are designed such that there is a greater vertical distance between the signal lines $112_1$, $114_1$, $116_1$ and $118_1$, and the topmost metal layer 304 constituting the floating gate structure 170.

In the embodiment described immediately above, with reference again to FIG. 11A, it may be readily observed that the topmost metal layer 304 is formed in the Metal4 layer (also see FIG. 12L), and the signal lines $112_1$, $114_1$, and $116_1$ are formed in the Metal3 layer (also see FIG. 12J). Also, while not visible in the view of FIG. 11A, it may be observed from FIG. 12H that the signal line $118_1$ is formed in the Metal2 layer. As one or more of these signals may be grounded from time to time during array operation, a parasitic capacitance may arise between any one or more of these signal lines and metal layer 304. By increasing a distance between these signal lines and the metal layer 304, such parasitic capacitance may be reduced.

Figure 12:
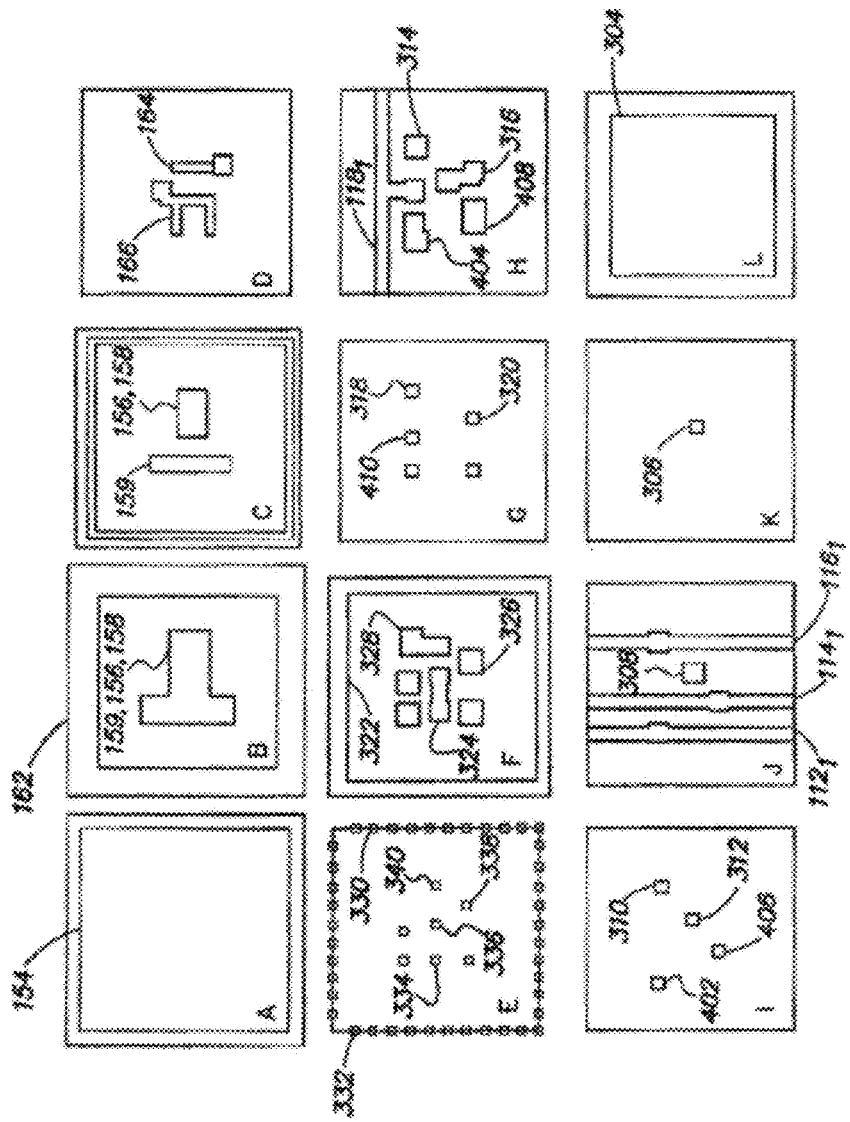
Figures 1, 12:
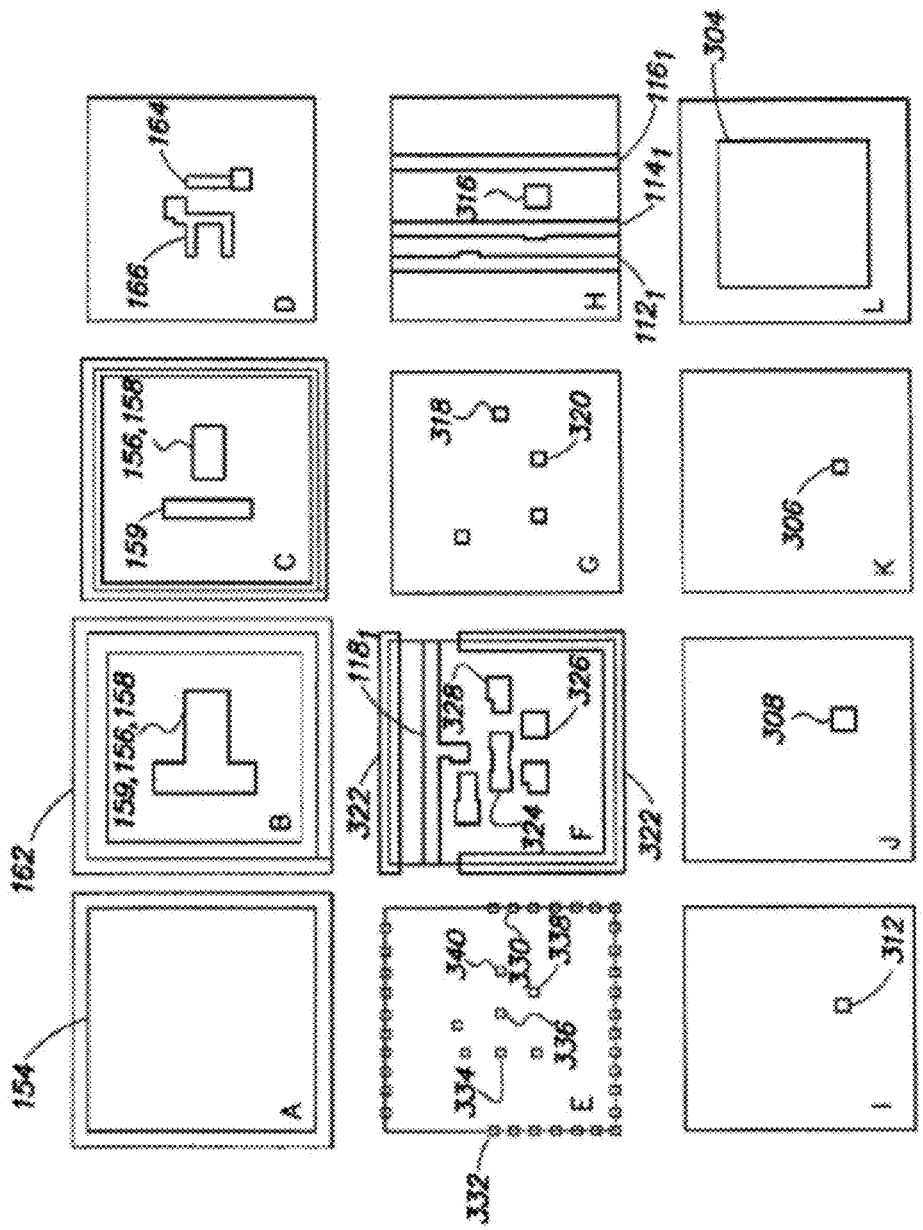

To this end, in another embodiment some via and metal layers are reconfigured such that the signal lines $112_1$, $114_1$, $116_1$ and $118_1$ are implemented in the Metal1 and Metal2 layers, and the Metal3 layer is used only as a jumper between the Metal2 layer component of the floating gate structure 170 and the topmost metal layer 304, thereby ensuring a greater distance between the signal lines and the metal layer 304. FIG. 10-1 illustrates a top view of a such a chip layout design for a cluster of four neighboring pixels of an chemFET array shown in FIG. 9, with one particular pixel $105_1$ identified and labeled. FIG. 11A-1 shows a composite cross-sectional view of neighboring pixels, along the line I-I of the pixel $105_1$, shown in FIG. 10-1, including additional elements between the lines illustrating a layer-by-layer view of the pixel fabrication, and FIGS. 12-1A through 12-1L provide top views of each of the fabrication layers shown in FIG. 11A-1 (the respective images of FIGS. 12-1A through 12-1L are superimposed one on top of another to create the pixel chip layout design shown in FIG. 10-1).

In FIG. 10-1, it may be observed that the pixel top view layout is generally similar to that shown in FIG. 10. For example, in the top view, the ISFET 150 generally occupies the right center portion of each pixel, and the MOSFETs Q2 and Q3 generally occupy the left center portion of the pixel illustration. Many of the component labels included in FIG. 10 are omitted from FIG. 10-1 for clarity, although the ISFET polysilicon gate 164 is indicated in the pixel $105_1$ for orientation. FIG. 10-1 also shows the four lines ($112_1$, $114_1$, $116_1$ and $118_1$) required to operate the pixel. One noteworthy difference between FIG. 10 and FIG. 10-1 relates to the metal conductor 322 (located on the Metal1 layer) which provides an electrical connection to the body region 162; namely, in FIG. 10, the conductor 322 surrounds a perimeter of the pixel, whereas in FIG. 10-1, the conductor 322 does not completely surround a perimeter of the pixel but includes discontinuities 727. These discontinuities 727 permit the line $118_1$ to also be fabricated on the Metal1 layer and traverse the pixel to connect to neighboring pixels of a row.

With reference now to the cross-sectional view of FIG. 11A-1, three adjacent pixels are shown in cross-section, with the center pixel corresponding to the pixel $105_1$ in FIG. 10-1 for purposes of discussion. As in the embodiment of FIG. 11A, all of the FET components of the pixel $105_1$ are fabricated as p-channel FETs in the single n-type well 154. Additionally, as in FIG. 11A, in the composite cross-sectional view of FIG. 11A-1 the highly doped p-type region 159 is also visible (lying along the line I-I in FIG. 10-1), corresponding to the shared drain (D) of the MOSFETs Q2 and Q3. For purposes of illustration, the polysilicon gate 166 of the MOSFET Q3 also is visible in FIG. 11A-1, although this gate does not lie along the line I-I in FIG. 10-1, but rather "behind the plane" of the cross-section along the line I-I. However, for simplicity, the respective sources of the MOSFETs Q2 and Q3 shown in FIG. 10-1, as well as the gate of Q2, are not visible in FIG. 11A-1, as they lie along the same axis (i.e., perpendicular to the plane of the figure) as the shared drain. Furthermore, to facilitate an understanding of the ISFET floating gate electrical connections, the composite cross-sectional view of FIG. 11A-1 shows additional elements of the pixel fabrication between the lines II-II of FIG. 10-1.

More specifically, as in the embodiment of FIG. 11A, the topmost metal layer 304 corresponds to the ISFETs sensitive area 178, above which is disposed an analyte-sensitive passivation layer 172. The topmost metal layer 304, together with the ISFET polysilicon gate 164 and the intervening conductors 306, 308, 312, 316, 320, 326 and 338, form the ISFETs floating gate structure 170. However, unlike the embodiment of FIG. 11A, an electrical connection to the ISFETs drain is provided by the conductors 340, 328, and 318, coupled to the line $116_1$ which is formed in the Metal2 layer rather than the Metal3 layer. Additionally, the lines $112_1$ and $114_1$ also are shown in FIG. 11A-1 as formed in the Metal2 layer rather than the Metal3 layer. The configuration of these lines, as well as the line $118_1$, may be further appreciated from the respective images of FIGS. 12-1A through 12-1L (in which the correspondence between the lettered top views of respective layers and the cross-sectional view of FIG. 11A-1 is the same as that described in connection with FIGS. 12A-12L); in particular, it may be observed in FIG. 12-1F that the line $118_1$, together with the metal conductor 322, is formed in the Metal1 layer, and it may be observed that the lines $112_1$, $114_1$ and $116_1$ are formed in the Metal2 layer, leaving only the jumper 308 of the floating gate structure 170 in the Metal3 layer shown in FIG. 12-1J.

Accordingly, by consolidating the signal lines $112_1$, $114_1$, $116_1$ and $118_1$ to the Metal1 and Metal2 layers and thereby increasing the distance between these signal lines and the topmost layer 304 of the floating gate structure 170 in the Metal4 layer, parasitic capacitances in the ISFET may be at least partially mitigated. It should be appreciated that this general concept (e.g., including one or more intervening metal layers between signal lines and topmost layer of the floating gate structure) may be implemented in other fabrication processes involving greater numbers of metal layers. For example, distance between pixel signal lines and the topmost metal layer may be increased by adding additional metal layers (more than four total metal layers) in which only jumpers to the topmost metal layer are formed in the additional metal layers. In particular, a six-metal-layer fabrication process may be employed, in which the signal lines are fabricated using the Metal1 and Metal2 layers, the topmost metal layer of the floating gate structure is formed in the Metal6 layer, and jumpers to the topmost metal layer are formed in the Metal3, Metal4 and Metal5 layers, respectively (with associated vias between the metal layers). In another exemplary implementation based on a six-metal-layer fabrication process, the general pixel configuration shown in FIGS. 10, 11A, and 12A-12L may be employed (signal lines on Metal2 and Metal 3 layers), in which the topmost metal layer is formed in the Metal6 layer and jumpers are formed in the Metal4 and Metal5 layers, respectively.

In yet another aspect relating to reduced capacitance, a dimension "f" of the topmost metal layer 304 (and thus the ISFET sensitive area 178) may be reduced so as to reduce cross-capacitance between neighboring pixels. As may be observed in FIG. 11A-1 (and as discussed further below in connection with other embodiments directed to well fabrication above an ISFET array), the well 725 may be fabricated so as to have a tapered shape, such that a dimension "g" at the top of the well is smaller than the pixel pitch "e" but yet larger than a dimension "f" at the bottom of the well. Based on such tapering, the topmost metal layer 304 also may be designed with the dimension "f" rather than the dimension "g" so as to provide for additional space between the top metal layers of neighboring pixels. In some illustrative non-limiting implementations, for pixels having a dimension "e" on the order of 9 micrometers the dimension "f" may be on the order of 6 micrometers (as opposed to 7 micrometers, as discussed above), and for pixels having a dimension "e" on the order of 5 micrometers the dimension "f" may be on the order of 3.5 micrometers.

Thus, the pixel chip layout designs respectively shown in FIGS. 10, 11A, and 12A through 12L, and FIGS. 10-1, 11A-1, and 12-1A through 12-1L, illustrate that according to various embodiments FET devices of a same type may be employed for all components of a pixel, and that all components may be implemented in a single well. This dramatically reduces the area required for the pixel, thereby facilitating increased pixel density in a given area.

In one exemplary implementation, the gate oxide 165 for the ISFET may be fabricated to have a thickness on the order of approximately 75 Angstroms, giving rise to a gate oxide capacitance per unit area $C_{ox}$ of 4.5 fF/μm². Additionally, the polysilicon gate 164 may be fabricated with dimensions corresponding to a channel width W of 1.2 μm and a channel length L of from 0.35 to 0.6 μm (i.e., W/L, ranging from approximately 2 to 3.5), and the doping of the region 160 may be selected such that the carrier mobility for the p-channel is 190 μm²/V·s (i.e., 1.9E10 μm²/V·s). From Eq. (2) above, this results in an ISFET transconductance parameter) on the order of approximately 170 to 300 μA/V². In other aspects of this exemplary implementation, the analog supply voltage VDDA is 3.3 Volts, and VB1 and VB2 are biased so as to provide a constant ISFET drain current $I_{Dj}$ on the order of 5 μA (in some implementations, VB1 and VB2 may be adjusted to provide drain currents from approximately 1 μA to 20 μA). Additionally, the MOSFET Q6 (see bias/readout circuitry 110j in FIG. 9) is sized to have a channel width to length ratio (e.g., W/L of approximately 50) such that the voltage across Q6, given $I_{Dj}$ of 5 μA, is 800 mV (i.e., $V_{DSj}$=800 mV). From Eq. (3), based on these exemplary parameters, this provides for pixel output voltages $V_{Sj}$ over a range of approximately 0.5 to 2.5 Volts for ISFET threshold voltage changes over a range of approximately 0 to 2 Volts.

With respect to the analyte-sensitive passivation layer 172 shown in FIG. 11A, in exemplary CMOS implementations the passivation layer may be significantly sensitive to the concentration of various ion species, including hydrogen, and may include silicon nitride ($Si_3N_4$) and/or silicon oxynitride ($Si_2N_2O$). In conventional CMOS processes, a passivation layer may be formed by one or more successive depositions of these materials, and is employed generally to treat or coat devices so as to protect against contamination and increase electrical stability. The material properties of silicon nitride and silicon oxynitride are such that a passivation layer comprising these materials provides scratch protection and serves as a significant barrier to the diffusion of water and sodium, which can cause device metallization to corrode and/or device operation to become unstable. A passivation layer including silicon nitride and/or silicon oxynitride also provides ion-sensitivity in ISFET devices, in that the passivation layer contains surface groups that may donate or accept protons from an analyte solution with which they are in contact, thereby altering the surface potential and the device threshold voltage $V_{TH}$, as discussed above in connection with FIGS. 1 and 2A.

For CMOS processes involving aluminum as the metal (which has a melting point of approximately 650 degrees Celsius), a silicon nitride and/or silicon oxynitride passivation layer generally is formed via plasma-enhanced chemical vapor deposition (PECVD), in which a glow discharge at 250-350 degrees Celsius ionizes the constituent gases that form silicon nitride or silicon oxynitride, creating active species that react at the wafer surface to form a laminate of the respective materials. In one exemplary process, a passivation layer having a thickness on the order of approximately 1.0 to 1.5 μm may be formed by an initial deposition of a thin layer of silicon oxynitride (on the order of 0.2 to 0.4 μm) followed by a slighting thicker deposition of silicon oxynitride (on the order of 0.5 μm) and a final deposition of silicon nitride (on the order of 0.5 μm). Because of the low deposition temperature involved in the PECVD process, the aluminum metallization is not adversely affected.

However, while a low-temperature PECVD process provides adequate passivation for conventional CMOS devices, the low-temperature process results in a generally low-density and somewhat porous passivation layer, which in some cases may adversely affect ISFET threshold voltage stability. In particular, during ISFET device operation, a low-density porous passivation layer over time may absorb and become saturated with ions from the solution, which may in turn cause an undesirable time-varying drift in the ISFETs threshold voltage $V_{TH}$, making accurate measurements challenging.

In view of the foregoing, in one embodiment a CMOS process that uses tungsten metal instead of aluminum may be employed to fabricate ISFET arrays according to the present disclosure. The high melting temperature of Tungsten (above 3400 degrees Celsius) permits the use of a higher temperature low pressure chemical vapor deposition (LPCVD) process (e.g., approximately 700 to 800 degrees Celsius) for a silicon nitride or silicon oxynitride passivation layer. The LPCVD process typically results in significantly more dense and less porous films for the passivation layer, thereby mitigating the potentially adverse effects of ion absorption from the analyte solution leading to ISFET threshold voltage drift.

In yet another embodiment in which an aluminum-based CMOS process is employed to fabricate ISFET arrays according to the present disclosure, the passivation layer 172 shown in FIG. 11A may comprise additional depositions and/or materials beyond those typically employed in a conventional CMOS process. For example, the passivation layer 172 may include initial low-temperature plasma-assisted depositions (PECVD) of silicon nitride and/or silicon oxynitride as discussed above; for purposes of the present discussion, these conventional depositions are illustrated in FIG. 11A as a first portion 172A of the passivation layer 172. In one embodiment, following the first portion 172A, one or more additional passivation materials are disposed to form at least a second portion 172B to increase density and reduce porosity of (and absorption by) the overall passivation layer 172. While one additional portion 172B is shown primarily for purposes of illustration in FIG. 11A, it should be appreciated that the disclosure is not limited in this respect, as the overall passivation layer 172 may comprise two or more constituent portions, in which each portion may comprise one or more layers/depositions of same or different materials, and respective portions may be configured similarly or differently. Regardless of the specific materials, the passivation layer(s) provide chemical isolation between the analyte and the circuitry.

Examples of materials suitable for the second portion 172B (or other additional portions) of the passivation layer 172 include, but are not limited to, silicon nitride, silicon oxynitride, aluminum oxide ($Al_2O_3$), tantalum oxide ($Ta_3O_5$), tin oxide ($SnO_2$) and silicon dioxide ($SiO_2$). In one aspect, the second portion 172B (or other additional portions) may be deposited via a variety of relatively low-temperature processes including, but not limited to, RF sputtering, DC magnetron sputtering, thermal or e-beam evaporation, and ion-assisted depositions. In another aspect, a pre-sputtering etch process may be employed, prior to deposition of the second portion 172B, to remove any native oxide residing on the first portion 172A (alternatively, a reducing environment, such as an elevated temperature hydrogen environment, may be employed to remove native oxide residing on the first portion 172A). In yet another aspect, a thickness of the second portion 172B may be on the order of approximately 0.04 µm to 0.06 µm (400 to 600 Angstroms) and a thickness of the first portion may be on the order of 1.0 to 1.5 µm, as discussed above. In some exemplary implementations, the first portion 172A may include multiple layers of silicon oxynitride and silicon nitride having a combined thickness of 1.0 to 1.5 µm, and the second portion 172B may include a single layer of either aluminum oxide or tantalum oxide having a thickness of approximately 400 to 600 Angstroms. Again, it should be appreciated that the foregoing exemplary thicknesses are provided primarily for purposes of illustration, and that the disclosure is not limited in these respects.

Thus it is to be understood that the chemFET arrays described herein may be used to detect and/or measure various analytes and, by doing so, may monitor a variety of reactions and/or interactions. It is also to be understood that the discussion herein relating to hydrogen ion detection (in the form of a pH change) is for the sake of convenience and brevity and that static or dynamic levels/concentrations of other analytes (including other ions) can be substituted for hydrogen in these descriptions. In particular, sufficiently fast concentration changes of any one or more of various ion species present in the analyte may be detected via the transient or dynamic response of a chemFET, as discussed above in connection with FIG. 2A. As also discussed above in connection with the Site-Dissociation (or Site-Binding) model for the analyte/passivation layer interface, it should be appreciated that various parameters relating to the equilibrium reactions at the analyte/passivation layer interface (e.g., rate constants for forward and backward equilibrium reactions, total number of proton donor/acceptor sires per unit area on the passivation layer surface, intrinsic buffering capacity, pH at point of zero charge) are material dependent properties and thus are affected by the choice of materials employed for the passivation layer.

The chemFETs, including ISFETs, described herein are capable of detecting any analyte that is itself capable of inducing a change in electric field when in contact with or otherwise sensed or detected by the chemFET surface. The analyte need not be charged in order to be detected by the sensor. For example, depending on the embodiment, the analyte may be positively charged (i.e., a cation), negatively charged (i.e., an anion), zwitterionic (i.e., capable of having two equal and opposite charges but being neutral overall), and polar yet neutral. This list is not intended as exhaustive as other analyte classes as well as species within each class will be readily contemplated by those of ordinary skill in the art based on the disclosure provided herein.

In the broadest sense of the invention, the passivation layer may or may not be coated and the analyte may or may not interact directly with the passivation layer.

Passivation Layer Specificity

In some embodiments, the passivation layer and/or the layers and/or molecules coated thereon dictate the analyte specificity of the array readout.

Detection of hydrogen ions, and other analytes as determined by the invention, can be carried out using a passivation layer made of silicon nitride ($Si_3N_4$), silicon oxynitride ($Si_2N_2O$), silicon oxide ($SiO_2$), aluminum oxide ($Al_2O_3$), tantalum pentoxide ($Ta_2O_5$), tin oxide or stannic oxide ($SnO_2$), and the like.

The passivation layer can also detect other ion species directly including but not limited to calcium, potassium, sodium, iodide, magnesium, chloride, lithium, lead, silver, cadmium, nitrate, phosphate, dihydrogen phosphate, and the like.

In some embodiments, the passivation layer is coated with a receptor for the analyte of interest. Preferably, the receptor binds selectively to the analyte of interest or in some instances to a class of agents to which the analyte belongs. As used herein, a receptor that binds selectively to an analyte is a molecule that binds preferentially to that analyte (i.e., its binding affinity for that analyte is greater than its binding affinity for any other analyte). Its binding affinity for the analyte of interest may be 2-fold, 3-fold, 4-fold, 5-fold, 6-fold, 7-fold, 8-fold, 9-fold, 10-fold, 15-fold, 20-fold, 25-fold, 30-fold, 40-fold, 50-fold, 100-fold or more than its binding affinity for any other analyte. In addition to its relative binding affinity, the receptor must also have an absolute binding affinity that is sufficiently high to efficiently bind the analyte of interest (i.e., it must have a sufficient sensitivity). Receptors having binding affinities in the picomolar to micromolar range are suitable. Preferably such interactions are reversible.

The receptor may be of any nature (e.g., chemical, nucleic acid, peptide, lipid, combinations thereof and the like). In such embodiments, the analyte too may be of any nature provided there exists a receptor that binds to it selectively and in some instances specifically. It is to be understood however that the invention further contemplates detection of analytes in the absence of a receptor. An example of this is the detection of PPi and Pi by the passivation layer in the absence of PPi or Pi receptors.

In one aspect, the invention contemplates receptors that are ionophores. As used herein, an ionophore is a molecule that binds selectively to an ionic species, whether anion or cation. In the context of the invention, the ionophore is the receptor and the ion to which it binds is the analyte. Ionophores of the invention include art-recognized carrier ionophores (i.e., small lipid-soluble molecules that bind to a particular ion) derived from microorganisms. Various ionophores are commercially available from sources such as Calbiochem.

Detection of some ions can be accomplished through the use of the passivation layer itself or through the use of receptors coated onto the passivation layer. For example, potassium can be detected selectively using polysiloxane, valinomycin, or salinomycin; sodium can be detected selectively using monensin, nystatin, or SQI-Pr; calcium can be detected selectively using ionomycin, calcimycine (A23187), or CA 1001 (ETH 1001).

Receptors able to bind more than one ion can also be used in some instances. For example, beauvericin can be used to detect calcium and/or barium ions, nigericin can be used to detect potassium, hydrogen and/or lead ions, and gramicidin can be used to detect hydrogen, sodium and/or potassium ions. One of ordinary skill in the art will recognize that these compounds can be used in applications in which single ion specificity is not required or in which it is unlikely (or impossible) that other ions which the compounds bind will be present or generated. Similarly, receptors that bind multiple species of a particular genus may also be useful in some embodiments including those in which only one species within the genus will be present or in which the method does not require distinction between species.

As another example, receptors for neurotoxins are described in Simonian Electroanalysis 2004, 16: 1896-1906.

Passivation Layer and PPi Receptors

Figures 1, 11A:
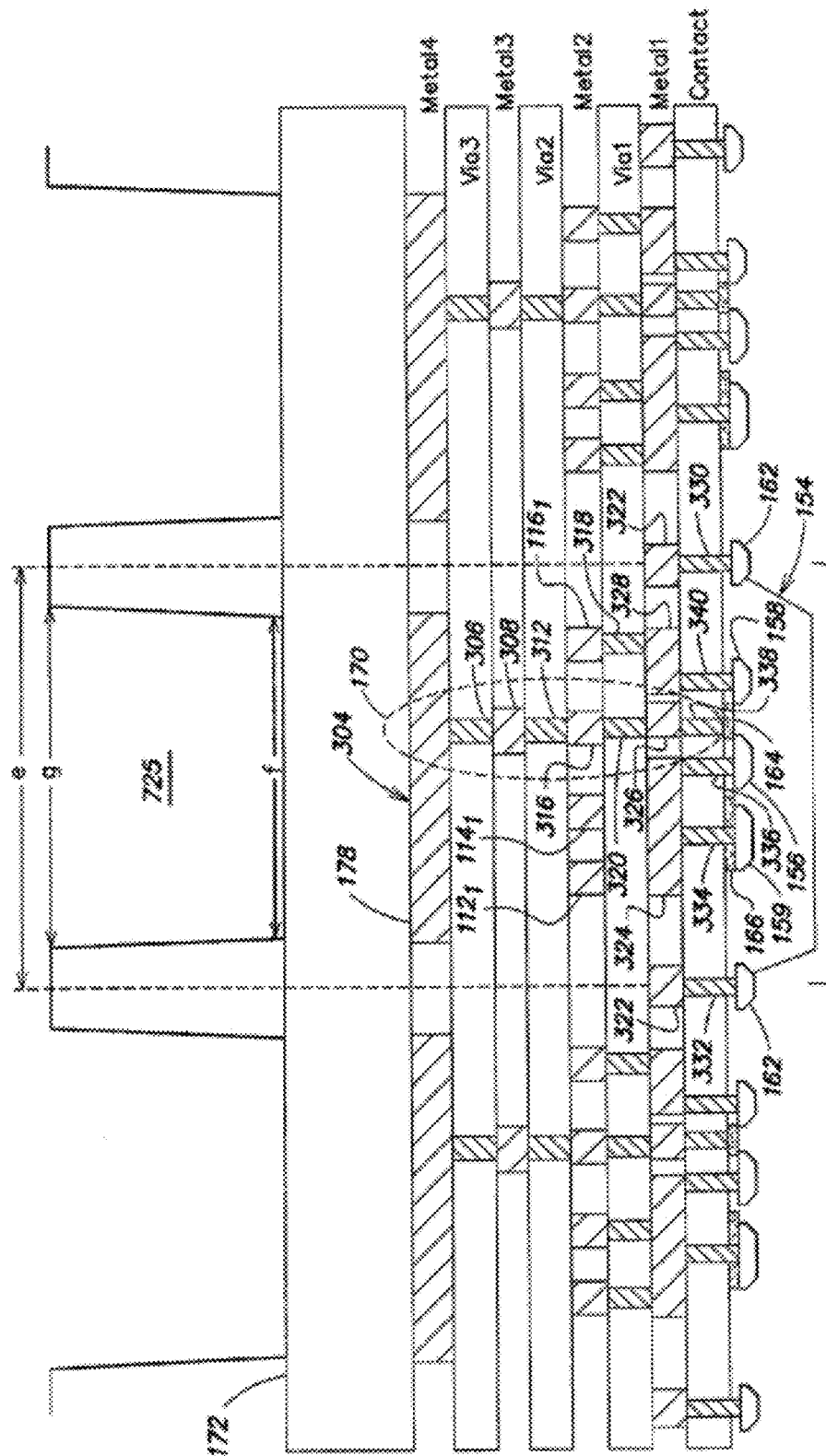
Figure 11E:
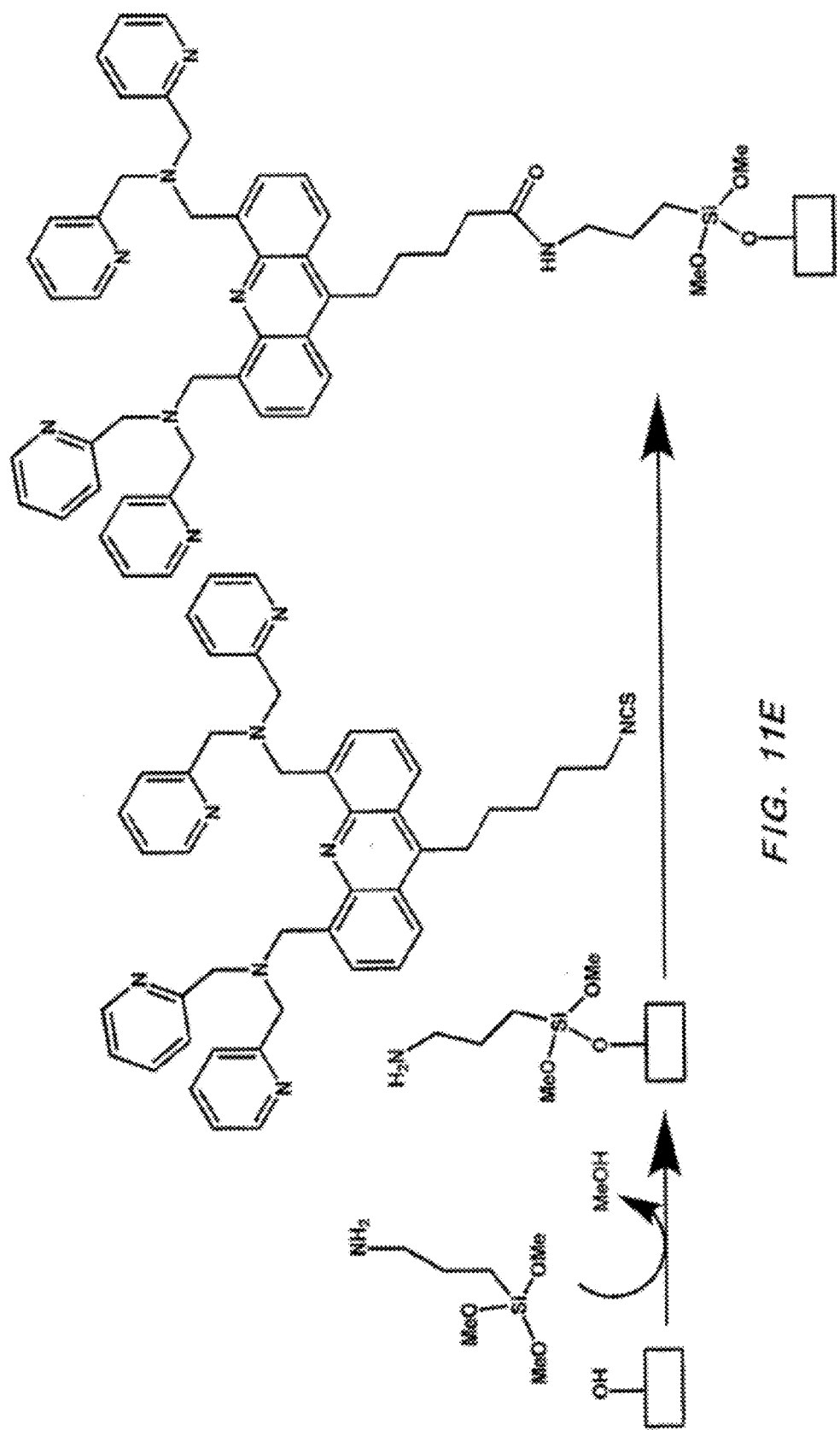
FIG. 11E is a schematic of attachment of compound 7 from FIG. 11B(3) to a metal oxide surface.

In other embodiments, including but not limited to nucleic acid sequencing applications, receptors that bind selectively to PPi can be used, Examples of PPi receptors include those compounds shown in FIGS. 11B(1)-(3) (compounds 1-10). Compound 1 is described in Angew, Chem Int (Ed 2004) 43:4777-4780 and US 2005/0119497 A1 and is referred to as p-naphthyl-bis[(bis(2-pyridylmethyl)amino)methyl]phenol. Compound 2 is described in J Am Chem Soc 2003 125:7752-7753 and US 2005/0119497 A1 and is referred to as p-(p-nitrophenylazo)-bis[(bis(2-pyridylmethyl-1)amino)methyl] phenol (or its dinuclear Zn complex). Synthesis schemes for compounds 1 and 2 are shown provided in US 2005/0119497 A1. Compound 3 is described in by Lee et al. Organic Letters 2007 9(2):243-246, and Sensors and Actuators B 1995 29:324-327. Compound 4 is described in Angew, Chem Int (Ed 2002) 41(20):3811-3814. Exemplary syntheses for compounds 7, 8 and 9 are shown in FIGS. 11C(1)-(3). Compound 5 is described in WO 2007/002204 and is referred to therein as bis-$Zn^{2+}$-dipicolylamine ($Zn^{2+}$-DPA). Compound 6 is illustrated in FIG. 11B(3) bound to PPi. (McDonough et al. Chem. Commun. 2006 2971-2973.) Attachment of compound 7 to a metal oxide surface is shown in FIG. 11E.

Passivation Layer—Receptor Binding

Receptors may be attached to the passivation layer covalently or non-covalently. Covalent attachment of a receptor to the passivation layer may be direct or indirect (e.g., through a linker). FIGS. 11D(1) and (2) illustrate the use of silanol chemistry to covalently bind receptors to the passivation layer. Receptors may be immobilized on the passivation layer using for example aliphatic primary amines (bottom left panel) or aryl isothiocyanates (bottom right panel). In these and other embodiments, the passivation layer which itself may be comprised of silicon nitride, aluminum oxide, silicon oxide, tantalum pentoxide, or the like, is bonded to a silanation layer via its reactive surface groups. For greater detail on silanol chemistry for covalent attachment to the FET surface, reference can be made to at least the following publications: for silicon nitride, see Sensors and Actuators B 1995 29:324-327, Jpn J Appl Phys 1999 38:3912-3917 and Langmuir 2005 21:395-402; for silicon oxide, see Protein Sci 1995 4:2532-2544 and Am Biotechnol Lab 2002 20(7):16-18; and for aluminum oxide, see Colloids and Surfaces 1992 63:1-9, Sensors and Actuators B 2003 89:40-47, and Bioconjugate Chem 1997 8:424-433. The receptor is then conjugated to the silanation layer reactive groups. This latter binding can occur directly or indirectly through the use of a bifunctional linker, as illustrated in FIGS. 11D(1) and (2).

A bifunctional linker is a compound having at least two reactive groups to which two entities may be bound. In some instances, the reactive groups are located at opposite ends of the linker. In some embodiments, the bifunctional linker is a universal bifunctional linker such as that shown in FIGS. 11D(1) and (2). A universal linker is a linker that can be used to link a variety of entities. It should be understood that the chemistries shown in FIGS. 11D(1) and (2) are meant to be illustrative and not limiting.

The bifunctional linker may be a homo-bifunctional linker or a hetero-bifunctional linker, depending upon the nature of the molecules to be conjugated. Homo-bifunctional linkers have two identical reactive groups. Hetero-bifunctional linkers are have two different reactive groups. Various types of commercially available linkers are reactive with one or more of the following groups: primary amines, secondary amines, sulphydryls, carboxyls, carbonyls and carbohydrates. Examples of amine-specific linkers are bis(sulfosuccinimidyl) suberate, bis[2-(succinimidooxycarbonyloxy)ethyl]sulfone, disuccinimidyl suberate, disuccinimidyl tartarate, dimethyl adipimate.2HCl, dimethyl pimelimidate.2HCl, dimethyl suberimidate.2HCl, and ethylene glycolbis-[succinimidyl-[succinate]]. Linkers reactive with sulfhydryl groups include bismaleimidohexane, 1,4-di-[3'-(2'-pyridyldithio)-propionamido)]butane, 1-[p-azidosalicylamido]-4-[iodoacetamido]butane, and N-[4-(p-azidosalicylamido) butyl]-3'-[2'-pyridyldithio]propionamide. Linkers preferentially reactive with carbohydrates include azidobenzoyl hydrazine. Linkers preferentially reactive with carboxyl groups include 4[p-azidosalicylamido]butylamine.

Heterobifunctional linkers that react with amines and sulfhydryls include N-succinimidyl-3-[2-pyridyldithio]propionate, succinimidyl [4-iodoacetyl]aminobenzoate, succinimidyl 4-[N-maleimidomethyl]cyclohexane-1-carboxylate, m-maleimidobenzoyl-N-hydroxysuccinimide ester, sulfosuccinimidyl 6-[3-[2-pyridyldithio]propionamido]hexanoate, and sulfosuccinimidyl 4-[N-maleimidomethyl]cyclohexane-1-carboxylate. Heterobifunctional linkers that react with carboxyl and amine groups include 1-ethyl-3-[3-dimethylaminopropyl]-carbodiimide hydrochloride. Heterobifunctional linkers that react with carbohydrates and sulfhydryls include 4-[N-maleimidomethyl]-cyclohexane-1-carboxylhydrazide.2 4-(4-N-maleimidophenyl)-butyric acid hydrazide.2HCl, and 3-[2-pyridyldithio]propionyl hydrazide.

Alternatively, receptors may be non-covalently coated onto the passivation layer. Non-covalent deposition of the receptor onto the passivation layer may involve the use of a polymer matrix. The polymer may be naturally occurring or non-naturally occurring and may be of any type including but not limited to nucleic acid (e.g., DNA, RNA, PNA, LNA, and the like, or mimics, derivatives, or combinations thereof), amino acid (e.g., peptides, proteins (native or denatured), and the like, or mimics, derivatives, or combinations thereof, lipids, polysaccharides, and functionalized block copolymers. The receptor may be adsorbed onto and/or entrapped within the polymer matrix. The nature of the polymer will depend on the nature of the receptor being used and/or analyte being detected.

Alternatively, the receptor may be covalently conjugated or crosslinked to the polymer (e.g., it may be "grafted" onto a functionalized polymer).

An example of a suitable peptide polymer is poly-lysine (e.g., poly-L-lysine). Examples of other polymers include block copolymers that comprise polyethylene glycol (PEG), polyamides, polycarbonates, polyalkylenes, polyalkylene glycols, polyalkylene oxides, polyalkylene terepthalates, polyvinyl alcohols, polyvinyl ethers, polyvinyl esters, polyvinyl halides, polyvinylpyrrolidone, polyglycolides, polysiloxanes, polyurethanes, alkyl cellulose, hydroxyalkyl celluloses, cellulose ethers, cellulose esters, nitrocelluloses, polymers of acrylic and methacrylic esters, methyl cellulose, ethyl cellulose, hydroxypropyl cellulose, hydroxypropyl methyl cellulose, hydroxybutyl methyl cellulose, cellulose acetate, cellulose propionate, cellulose acetate butyrate, cellulose acetate phthalate, carboxylethyl cellulose, cellulose triacetate, cellulose sulphate sodium salt, poly(methyl methacrylate), poly(ethyl methacrylate), poly(butylmethacrylate), poly(isobutyl methacrylate), poly(hexylmethacrylate), poly (isodecyl methacrylate), poly(lauryl methacrylate), poly (phenyl methacrylate), poly(methyl acrylate), poly(isopropyl acrylate), poly(isobutyl acrylate), poly(octadecyl acrylate), polyethylene, polypropylene, poly(ethylene glycol), polyethylene oxide), poly(ethylene terephthalate), poly(vinyl alcohols), polyvinyl acetate, polyvinyl chloride, polystyrene, polyhyaluronic acids, casein, gelatin, glutin, polyanhydrides, polyacrylic acid, alginate, chitosan, poly(methyl methacrylates), poly(ethyl methacrylates), poly(butylmethacrylate), poly(isobutyl methacrylate), poly(hexylmethacrylate), poly (isodecyl methacrylate), poly(lauryl methacrylate), poly (phenyl methacrylate), poly(methyl acrylate), poly(isopropyl acrylate), poly(isobutyl acrylate), and poly(octadecyl acrylate), poly(lactide-glycolide), copolyoxalates, polycaprolactones, polyesteramides, polyorthoesters, polyhydroxybutyric acid, polyanhydrides, poly (styrene-b-isobutylene-b-styrene) (SIBS) block copolymer, ethylene vinyl acetate, poly(meth) acrylic acid, polymers of lactic acid and glycolic acid, polyanhydrides, poly(ortho)esters, polyurethanes, poly(butic acid), poly(valeric acid), and poly(lactide-cocaprolactone), and natural polymers such as alginate and other polysaccharides including dextran and cellulose, collagen, albumin and other hydrophilic proteins, zein and other prolamines and hydrophobic proteins, copolymers and mixtures thereof, and chemical derivatives thereof including substitutions and/or additions of chemical groups, for example, alkyl, alkylene, hydroxylations, oxidations, and other modifications routinely made by those skilled in the art.

Trapped Charge

Another issue that relates to ISFET threshold voltage stability and/or predictability involves trapped charge that may accumulate (especially) on metal layers of CMOS-fabricated devices as a result of various processing activities during or following array fabrication (e.g., back-end-of-line processing such as plasma metal etching, wafer cleaning, dicing, packaging, handling, etc.). In particular, with reference to FIG. 11A, trapped charge may in some instances accumulate on one or more of the various conductors 304, 306, 308, 312, 316, 320, 326, 338, and 164 constituting the ISFETs floating gate structure 170. This phenomenon also is referred to in the relevant literature as the "antenna effect."

One opportunity for trapped charge to accumulate includes plasma etching of the topmost metal layer 304. Other opportunities for charge to accumulate on one or more conductors of the floating gate structure or other portions of the FETs includes wafer dicing, during which the abrasive process of a dicing saw cutting through a wafer generates static electricity, and/or various post-processing wafer handling/packaging steps, such as die-to-package wire bonding, where in some cases automated machinery that handles/transports wafers may be sources of electrostatic discharge (ESD) to conductors of the floating gate structure. If there is no connection to the silicon substrate (or other semi-conductor substrate) to provide an electrical path to bleed off such charge accumulation, charge may build up to the point of causing undesirable changes or damage to the gate oxide 165 (e.g., charge injection into the oxide, or low-level oxide breakdown to the underlying substrate). Trapped charge in the gate oxide or at the gate oxide-semiconductor interface in turn can cause undesirable and/or unpredictable variations in ISFET operation and performance, such as fluctuations in threshold voltage.

In view of the foregoing, other inventive embodiments of the present disclosure are directed to methods and apparatus for improving ISFET performance by reducing trapped charge or mitigating the antenna effect. In one embodiment, trapped charge may be reduced after a sensor array has been fabricated, while in other embodiments the fabrication process itself may be modified to reduce trapped charge that could be induced by some conventional process steps. In yet other embodiments, both "during fabrication" and "post fabrication" techniques may be employed in combination to reduce trapped charge and thereby improve ISFET performance.

With respect to alterations to the fabrication process itself to reduce trapped charge, in one embodiment the thickness of the gate oxide 165 shown in FIG. 11A may be particularly selected so as to facilitate bleeding of accumulated charge to the substrate; in particular, a thinner gate oxide may allow a sufficient amount of built-up charge to pass through the gate oxide to the substrate below without becoming trapped. In another embodiment based on this concept, a pixel may be designed to include an additional "sacrificial" device, i.e., another transistor having a thinner gate oxide than the gate oxide 165 of the ISFET. The floating gate structure of the ISFET may then be coupled to the gate of the sacrificial device such that it serves as a "charge bleed-off transistor." Of course, it should be appreciated that some trade-offs for including such a sacrificial device include an increase in pixel size and complexity.

In another embodiment, the topmost metal layer 304 of the ISFETs floating gate structure 170 shown in FIG. 11A may be capped with a dielectric prior to plasma etching to mitigate trapped charge. As discussed above, charge accumulated on the floating gate structure may in some cases be coupled from the plasma being used for metal etching. Typically, a photoresist is applied over the metal to be etched and then patterned based on the desired geometry for the underlying metal. In one exemplary implementation, a capping dielectric layer (e.g., an oxide) may be deposited over the metal to be etched, prior to the application of the photoresist, to provide an additional barrier on the metal surface against charge from the plasma etching process. In one aspect, the capping dielectric layer may remain behind and form a portion of the passivation layer 172.

In yet another embodiment, the metal etch process for the topmost metal layer 304 may be modified to include wet chemistry or ion-beam milling rather than plasma etching. For example, the metal layer 304 could be etched using an aqueous chemistry selective to the underlying dielectric (e.g., see website for Transene relating to aluminum, which is hereby incorporated herein by reference). Another alternative approach employs ion-milling rather than plasma etching for the metal layer 304. Ion-milling is commonly used to etch materials that cannot be readily removed using conventional plasma or wet chemistries. The ion-milling process does not employ an oscillating electric field as does a plasma, so that charge build-up does not occur in the metal layer(s). Yet another metal etch alternative involves optimizing the plasma conditions so as to reduce the etch rate (i.e. less power density).

In yet another embodiment, architecture changes may be made to the metal layer to facilitate complete electrical isolation during definition of the floating gate. In one aspect, designing the metal stack-up so that the large area ISFET floating gate is not connected to anything during its final definition may require a subsequent metal layer serving as a "jumper" to realize the electrical connection to the floating gate of the transistor. This "jumper" connection scheme prevents charge flow from the large floating gate to the transistor. This method may be implemented as follows (M=metal layer): i) M1 contacting Poly gate electrode; ii) M2 contacting M1; iii) M3 defines floating gate and separately connects to M2 with isolated island; iv) M4 jumper, having very small area being etched over the isolated islands and connections to floating gate M3, connects the M3 floating gate to the M1/M2/M3 stack connected to the Poly gate immediately over the transistor active area; and v) M3 to M4 interlayer dielectric is removed only over the floating gate so as to expose the bare M3 floating gate. In the method outlined immediately above, step v) need not be done, as the ISFET architecture according to some embodiments discussed above leaves the M4 passivation in place over the M4 floating gate. In one aspect, removal may nonetheless improve ISFET performance in other ways (i.e. sensitivity). In any case, the final sensitive passivation layer may be a thin sputter-deposited ion-sensitive metal-oxide layer. It should be appreciated that the over-layer jumpered architecture discussed above may be implemented in the standard CMOS fabrication flow to allow any of the first three metal layers to be used as the floating gates (i.e. M1, M2 or M3).

With respect to post-fabrication processes to reduce trapped charge, in one embodiment a "forming gas anneal" may be employed as a post-fabrication process to mitigate potentially adverse effects of trapped charge. In a forming gas anneal, CMOS-fabricated ISFET devices are heated in a hydrogen and nitrogen gas mixture. The hydrogen gas in the mixture diffuses into the gate oxide 165 and neutralizes certain forms of trapped charges. In one aspect, the forming gas anneal need not necessarily remove all gate oxide damage that may result from trapped charges; rather, in some cases, a partial neutralization of some trapped charge is sufficient to significantly improve ISFET performance. In exemplary annealing processes according to the present disclosure, ISFETs may be heated for approximately 30 to 60 minutes at approximately 400 to 425 degrees Celsius in a hydrogen/nitrogen mixture that includes 10% to 15% hydrogen. In one particular implementation, annealing at 425 degrees Celsius at 30 minutes in a hydrogen/nitrogen mixture that includes 10% hydrogen is observed to be particularly effective at improving ISFET performance. For aluminum CMOS processes, the temperature of the anneal should be kept at or below 450 degrees Celsius to avoid damaging the aluminum metallurgy. In another aspect of an annealing process according to the present disclosure, the forming gas anneal is performed after wafers of fabricated ISFET arrays are diced, so as to ensure that damage due to trapped charge induced by the dicing process itself, and/or other pre-dicing processing steps (e.g., plasma etching of metals) may be effectively ameliorated. In yet another aspect, the forming gas anneal may be performed after die-to-package wirebonding to similarly ameliorate damage due to trapped charge. At this point in the assembly process, a diced array chip is typically in a heat and chemical resistant ceramic package, and low-tolerance wire-bonding procedures as well as heat-resistant die-to-package adhesives may be employed to withstand the annealing procedure. Thus, in one exemplary embodiment, the invention encompasses a method for manufacturing an array of FETs, each having or coupled to a floating gate having a trapped charge of zero or substantially zero comprising: fabricating a plurality of FETs in a common semiconductor substrate, each of a plurality of which is coupled to a floating gate; applying a forming gas anneal to the semiconductor prior to a dicing step; dicing the semiconductor; and applying a forming gas anneal to the semiconductor after the dicing step. Preferably, the semiconductor substrate comprises at least 100,000 FETs. Preferably, the plurality of FETs are chemFETs. The method may further comprise depositing a passivation layer on the semiconductor, depositing a polymeric, glass, ion-reactively etchable or photodefineable material layer on the passivation layer and etching the polymeric, glass ion-reactively etchable or photodefineable material to form an array of reaction chambers in the glass layer.

In yet other processes for mitigating potentially adverse effects of trapped charge according to embodiments of the present disclosure, a variety of "electrostatic discharge (ESD)-sensitive protocols" may be adopted during any of a variety of wafer post-fabrication handling/packaging steps. For example, in one exemplary process, anti-static dicing tape may be employed to hold wafer substrates in place (e.g., during the dicing process). Also, although high-resistivity (e.g., 10 MΩ) deionized water conventionally is employed in connection with cooling of dicing saws, according to one embodiment of the present disclosure less resistive/more conductive water may be employed for this purpose to facilitate charge conduction via the water; for example, deionized water may be treated with carbon dioxide to lower resistivity and improve conduction of charge arising from the dicing process. Furthermore, conductive and grounded die-ejection tools may be used during various wafer dicing/handling/packaging steps, again to provide effective conduction paths for charge generated during any of these steps, and thereby reduce opportunities for charge to accumulate on one or more conductors of the floating gate structure of respective ISFETs of an array.

In yet another embodiment involving a post-fabrication process to reduce trapped charge, the gate oxide region of an ISFET may be irradiated with UV radiation. With reference again to FIG. 11A, in one exemplary implementation based on this embodiment, an optional hole or window 302 is included during fabrication of an ISFET array in the top metal layer 304 of each pixel of the array, proximate to the ISFET floating gate structure. This window is intended to allow UV radiation, when generated, to enter the ISFETs gate region; in particular, the various layers of the pixel $105_1$, as shown in FIGS. 11 and 12 A-L, are configured such that UV radiation entering the window 302 may impinge in an essentially unobstructed manner upon the area proximate to the polysilicon gate 164 and the gate oxide 165.

To facilitate a UV irradiation process to reduce trapped charge, materials other than silicon nitride and silicon oxynitride generally need to be employed in the passivation layer 172 shown in FIG. 11A, as silicon nitride and silicon oxynitride significantly absorb UV radiation. In view of the foregoing, these materials need to be substituted with others that are appreciably transparent to UV radiation, examples of which include, but are not limited to, phososilicate glass (PSG) and boron-doped phososilicate glass (BPSG). PSG and BPSG, however, are not impervious to hydrogen and hydroxyl ions; accordingly, to be employed in a passivation layer of an ISFET designed for pH sensitivity, PSG and BPSG may be used together with an ion-impervious material that is also significantly transparent to UV radiation, such as aluminum oxide ($Al_2O_3$), to form the passivation layer. For example, with reference again to FIG. 11A, PSG or BPSG may be employed as a substitute for silicon nitride or silicon oxynitride in the first portion 172A of the passivation layer 172, and a thin layer (e.g., 400 to 600 Angstroms) of aluminum oxide may be employed in the second portion 172B of the passivation layer 172 (e.g., the aluminum oxide may be deposited using a post-CMOS lift-off lithography process).

In another aspect of an embodiment involving UV irradiation, each ISFET of a sensor array must be appropriately biased during a UV irradiation process to facilitate reduction of trapped charge. In particular, high energy photons from the UV irradiation, impinging upon the bulk silicon region 160 in which the ISFET conducting channel is formed, create electron-hole pairs which facilitate neutralization of trapped charge in the gate oxide as current flows through the ISFETs conducting channel. To this end, an array controller, discussed further below in connection with FIG. 17, generates appropriate signals for biasing the ISFETs of the array during a UV irradiation process. In particular, with reference again to FIG. 9, each of the signals $\overline{RowSel_1}$ through $\overline{RowSel_n}$ is generated so as to enable/select (i.e., turn on) all rows of the sensor array at the same time and thereby couple all of the ISFETs of the array to respective controllable current sources $106_j$ in each column. With all pixels of each column simultaneously selected, the current from the current source $106_j$ of a given column is shared by all pixels of the column. The column amplifiers 107A and 107B are disabled by removing the bias voltage VB4, and at the same time the output of the amplifier 107B, connected to the drain of each ISFET in a given column, is grounded via a switch responsive to a control signal "UV." Also, the common body voltage $V_{BODY}$ for all ISFETs of the array is coupled to electrical ground (i.e., $V_{BODY}$=0 Volts) (as discussed above, during normal operation of the array, the body bias voltage $V_{BODY}$ is coupled to the highest voltage potential available to the array, e.g., VDDA). In one exemplary procedure, the bias voltage VB1 for all of the controllable current sources $106_j$ is set such that each pixel's ISFET conducts approximately 1 μA of current. With the ISFET array thusly biased, the array then is irradiated with a sufficient dose of UV radiation (e.g., from an EPROM eraser generating approximately 20 milliWatts/cm$^2$ of radiation at a distance of approximately one inch from the array for approximately 1 hour). After irradiation, the array may be allowed to rest and stabilize over several hours before use for measurements of chemical properties such as ion concentration.

Utilizing at least one of the above-described techniques for reducing trapped charge, we have been able to fabricate FETs floating gates having a trapped charge of zero or substantially zero. Thus, in some embodiments, an aspect of the invention encompasses a floating gate having a surface area of about 4 μm$^2$ to about 50 μm$^2$ having baseline threshold voltage and preferably a trapped charge of zero or substantially zero. Preferably the FETs are chemFETs. The trapped charge should be kept to a level that does not cause appreciable variations from FET to FET across the array, as that would limit the dynamic range of the devices, consistency of measurements, and otherwise adversely affect performance.

Array and Chip Design

Figure 13:
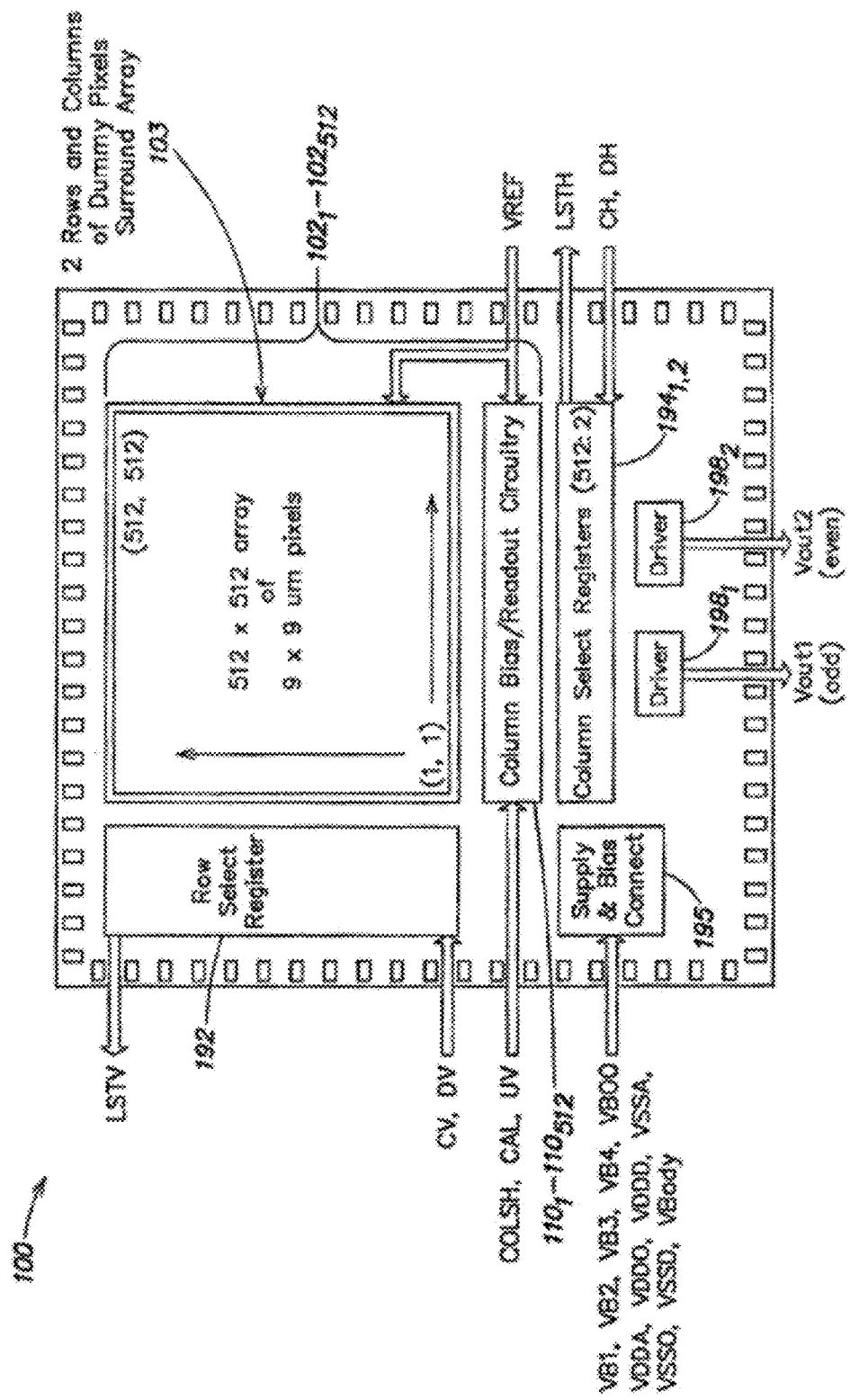
FIG. 13 illustrates a block diagram of an exemplary CMOS IC chip implementation of an chemFET sensor array similar to that shown in FIG. 8, based on the column and pixel designs shown in FIGS. 9-12, according to one inventive embodiment of the present disclosure.

FIG. 13 illustrates a block diagram of an exemplary CMOS IC chip implementation of an ISFET sensor array 100 based on the column and pixel designs discussed above in connection with FIGS. 9-12, according to one embodiment of the present disclosure. In one aspect of this embodiment, the array 100 includes 512 columns $102_1$ through $102_{512}$ with corresponding column bias/readout circuitry $110_1$ through $110_{512}$ (one for each column, as shown in FIG. 9), wherein each column includes 512 geometrically square pixels $105_1$ through $105_{512}$, each having a size of approximately 9 micrometers by 9 micrometers (i.e., the array is 512 columns by 512 rows). In another aspect, the entire array (including pixels together with associated row and column select circuitry and column bias/readout circuitry) may be fabricated on a semiconductor die as an application specific integrated circuit (ASIC) having dimensions of approximately 7 millimeters by 7 millimeters. While an array of 512 by 512 pixels is shown in the embodiment of FIG. 13, it should be appreciated that arrays may be implemented with different numbers of rows and columns and different pixel sizes according to other embodiments, as discussed further below in connection with FIGS. 19-23.

Also, as discussed above, it should be appreciated that arrays according to various embodiments of the present invention may be fabricated according to conventional CMOS fabrications techniques, as well as modified CMOS fabrication techniques (e.g., to facilitate realization of various functional aspects of the chemFET arrays discussed herein, such as additional deposition of passivation materials, process steps to mitigate trapped charge, etc.) and other semiconductor fabrication techniques beyond those conventionally employed in CMOS fabrication. Additionally, various lithography techniques may be employed as part of an array fabrication process. For example, in one exemplary implementation, a lithography technique may be employed in which appropriately designed blocks are "stitched" together by overlapping the edges of a step and repeat lithography exposures on a wafer substrate by approximately 0.2 micrometers. In a single exposure, the maximum die size typically is approximately 21 millimeters by 21 millimeters. By selectively exposing different blocks (sides, top & bottoms, core, etc.) very large chips can be defined on a wafer (up to a maximum, in the extreme, of one chip per wafer, commonly referred to as "wafer scale integration").

In one aspect of the array 100 shown in FIG. 13, the first and last two columns $102_1$, $102_2$, $102_{511}$ and $102_{512}$, as well as the first two pixels $105_1$ and $105_2$ and the last two pixels $105_{511}$ and $105_{512}$ of each of the columns $102_3$ through $102_{510}$ (e.g., two rows and columns of pixels around a perimeter of the array) may be configured as "reference" or "dummy" pixels 103. With reference to FIG. 11A, for the dummy pixels of an array, the topmost metal layer 304 of each dummy pixel's ISFET (coupled ultimately to the ISFETs polysilicon gate 164) is tied to the same metal layer of other dummy pixels and is made accessible as a terminal of the chip, which in turn may be coupled to a reference voltage VREF. As discussed above in connection with FIG. 9, the reference voltage VREF also may be applied to the bias/readout circuitry of respective columns of the array. In some exemplary implementations discussed further below, preliminary test/evaluation data may be acquired from the array based on applying the reference voltage VREF and selecting and reading out dummy pixels, and/or reading out columns based on the direct application of VREF to respective column buffers (e.g., via the CAL signal), to facilitate offset determination (e.g., pixel-to-pixel and column-to-column variances) and array calibration.

In yet another implementation of an array similar to that shown in FIG. 13, rather than reserving the first and last two columns of 512 columns and the first and last two pixels of each column of 512 pixels as reference pixels, the array may be fabricated to include an additional two rows/columns of reference pixels surrounding a perimeter of a 512 by 512 region of active pixels, such that the total size of the array in terms of actual pixels is 516 by 516 pixels. As arrays of various sizes and configurations are contemplated by the present disclosure, it should be appreciated that the foregoing concept may be applied to any of the other array embodiments discussed herein. For purposes of the discussion immediately below regarding the exemplary array 100 shown in FIG. 13, a total pixel count for the array of 512 by 512 pixels is considered.

In FIG. 13, various power supply and bias voltages required for array operation (as discussed above in connection with FIG. 9) are provided to the array via electrical connections (e.g., pins, metal pads) and labeled for simplicity in block 195 as "supply and bias connections." The array 100 of FIG. 13 also includes a row select shift register 192, two sets of column select shift registers 194$_{1,2}$ and two output drivers 198$_1$ and 198$_2$ to provide two parallel array output signals, Vout1 and Vout2, representing sensor measurements (i.e., collections of individual output signals generated by respective ISFETs of the array). The various power supply and bias voltages, control signals for the row and column shift registers, and control signals for the column bias/readout circuitry shown in FIG. 13 are provided by an array controller, as discussed further below in connection with FIG. 17, which also reads the array output signals Vout1 and Vout2 (and other optional status/diagnostic signals) from the array 100. In another aspect of the array embodiment shown in FIG. 13, configuring the array such that multiple regions (e.g., multiple columns) of the array may be read at the same time via multiple parallel array output signals (e.g., Vout1 and Vout2) facilitates increased data acquisition rates, as discussed further below in connection with FIGS. 17 and 18. While FIG. 13 illustrates an array having two column select registers and parallel array output signals Vout1 and Vout2 to acquire data simultaneously from two columns at a time, it should be appreciated that, in other embodiments, arrays according to the present disclosure may be configured to have only one measurement signal output, or more than two measurement signal outputs; in particular, as discussed further below in connection with FIGS. 19-23, more dense arrays according to other inventive embodiments may be configured to have four our more parallel measurement signal outputs and simultaneously enable different regions of the array to provide data via the four or more outputs.

Figure 14:
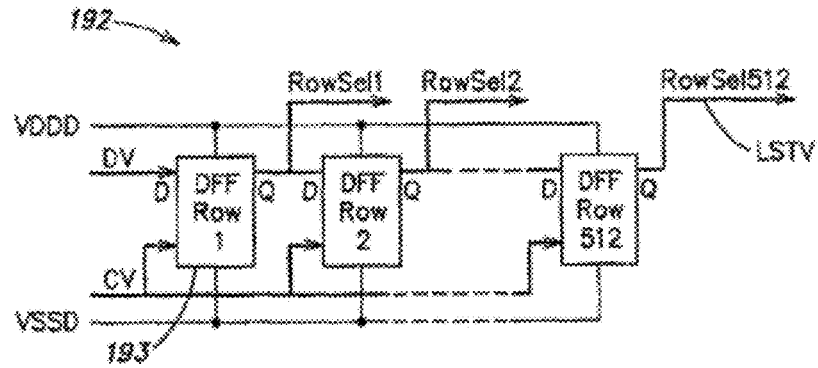
FIG. 14 illustrates a row select shift register of the array shown in FIG. 13, according to one inventive embodiment of the present disclosure.
Figure 15:
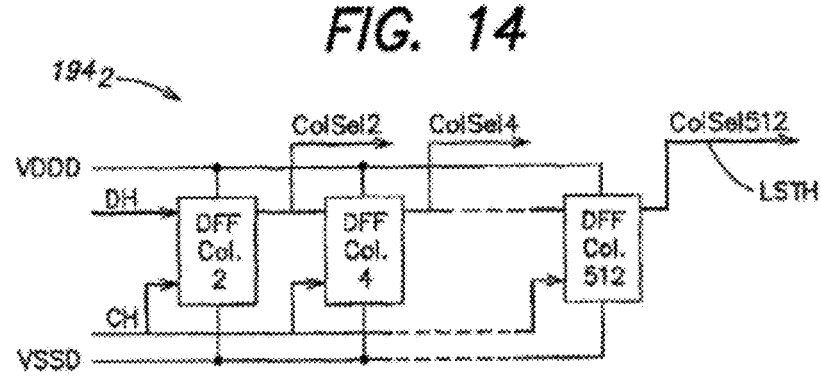
FIG. 15 illustrates one of two column select shift registers of the array shown in FIG. 13, according to one inventive embodiment of the present disclosure.
Figure 16:
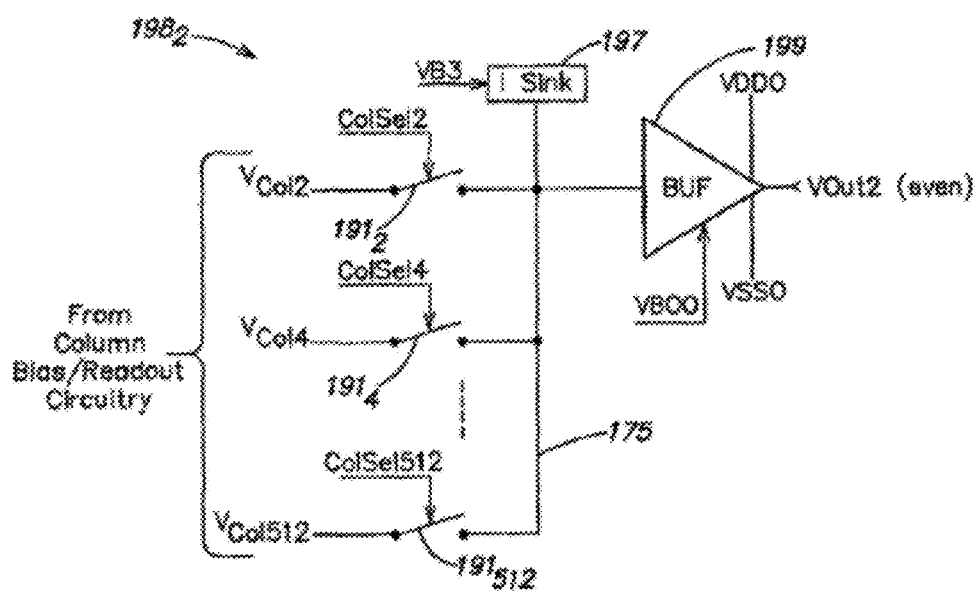
FIG. 16 illustrates one of two output drivers of the array shown in FIG. 13, according to one inventive embodiment of the present disclosure.

FIG. 14 illustrates the row select shift register 192, FIG. 15 illustrates one of the column select shift registers 194$_2$ and FIG. 16 illustrates one of the output drivers 198$_2$ of the array 100 shown in FIG. 13, according to one exemplary implementation. As shown in FIGS. 14 and 15, the row and column select shift registers are implemented as a series of D-type flip-flops coupled to a digital circuitry positive supply voltage VDDD and a digital supply ground VSSD. In the row and column shift registers, a data signal is applied to a D-input of first flip-flop in each series and a clock signal is applied simultaneously to a clock input of all of the flip-flops in the series. For each flip-flop, a "Q" output reproduces the state of the D-input upon a transition (e.g., falling edge) of the clock signal. With reference to FIG. 14, the row select shift register 192 includes 512 D-type flip-flops, in which a first flip-flop 193 receives a vertical data signal DV and all flip-flops receive a vertical clock signal CV. A "Q" output of the first flip-flop 193 provides the first row select signal RowSel$_1$ and is coupled to the D-input of the next flip-flop in the series. The Q outputs of successive flip-flops are coupled to the D-inputs of the next flip-flop in the series and provide the row select signals RowSel$_2$ through RowSel$_{512}$ with successive falling edge transitions of the vertical clock signal CV, as discussed further below in connection with FIG. 18. The last row select signal RowSel$_{512}$ also may be taken as an optional output of the array 100 as the signal LSTV (Last STage Vertical), which provides an indication (e.g., for diagnostic purposes) that the last row of the array has been selected. While not shown explicitly in FIG. 14, each of the row select signals RowSel$_1$ through RowSel$_{512}$ is applied to a corresponding inverter, the output of which is used to enable a given pixel in each column (as illustrated in FIG. 9 by the signals $\overline{\text{RowSel}_1}$ through $\overline{\text{RowSel}_n}$).

Regarding the column select shift registers 194$_1$ and 194$_2$, these are implemented in a manner similar to that of the row select shift registers, with each column select shift register comprising 256 series-connected flip-flops and responsible for enabling readout from either the odd columns of the array or the even columns of the array. For example, FIG. 15 illustrates the column select shift register 194$_2$, which is configured to enable readout from all of the even numbered columns of the array in succession via the column select signals ColSel$_2$, ColSel$_4$, . . . ColSel$_{512}$, whereas another column select shift register 194$_1$ is configured to enable readout from all of the odd numbered columns of the array in succession (via column select signals ColSel$_1$, ColSel$_3$, . . . ColSel$_{511}$). Both column select shift registers are controlled simultaneously by the horizontal data signal DH and the horizontal clock signal CH to provide the respective column select signals, as discussed further below in connection with FIG. 18. As shown in FIG. 15, the last column select signal ColSel$_{512}$ also may be taken as an optional output of the array 100 as the signal LSTH (Last STage Horizontal), which provides an indication (e.g., for diagnostic purposes) that the last column of the array has been selected.

With reference again for the moment to FIG. 7, an implementation for array row and column selection based on shift registers, as discussed above in connection with FIGS. 13-15, is a significant improvement to the row and column decoder approach employed in various prior art ISFET array designs, including the design of Milgrew et al. shown in FIG. 7. In particular, regarding the row decoder 92 and the column decoder 94 shown in FIG. 7, the complexity of implementing these components in an integrated circuit array design increases dramatically as the size of the array is increased, as additional inputs to both decoders are required. For example, an array having 512 rows and columns as discussed above in connection with FIG. 13 would require nine inputs ($2^9$=512) per row and column decoder if such a scheme were employed for row and column selection; similarly, arrays having 7400 rows and 7400 columns, as discussed below in connection with other embodiments, would require 13 inputs ($2^{13}$=8192) per row and column decoder. In contrast, the row and column select shift registers shown in FIGS. 14 and 15 require no additional input signals as array size is increased, but rather additional D-type flip-flops (which are routinely implemented in a CMOS process). Thus, the shift register implementations shown in FIGS. 14 and 15 provide an easily scalable solution to array row and column selection.

In the embodiment of FIG. 13, the "odd" column select shift register 194$_1$ provides odd column select signals to an "odd" output driver 198$_1$ and the even column select shift register 194$_2$ provides even column select signals to an "even" output driver 198$_2$. Both output drivers are configured similarly, and an example of the even output driver 198$_2$ is shown in FIG. 16. In particular, FIG. 16 shows that respective even column output signals $V_{COL2}$, $V_{COL4}$, ... $V_{COL512}$ (refer to FIG. 9 for the generic column signal output $V_{COLj}$) are applied to corresponding switches 191$_2$, 191$_4$, ... 191$_{512}$, responsive to the even column select signals ColSel$_2$, ColSel$_4$, ... ColSel$_{512}$ provided by the column select register 194$_2$, to successively couple the even column output signals to the input of a buffer amplifier 199 (BUF) via a bus 175. In FIG. 16, the buffer amplifier 199 receives power from an output buffer positive supply voltage VDDO and an output buffer supply ground VSSO, and is responsive to an output buffer bias voltage VBO0 to set a corresponding bias current for the buffer output. Given the high impedance input of the buffer amplifier 199, a current sink 197 responsive to a bias voltage VB3 is coupled to the bus 175 to provide an appropriate drive current (e.g., on the order of approximately 100 μA) for the output of the column output buffer (see the buffer amplifier 111*j* of FIG. 9) of a selected column. The buffer amplifier 199 provides the output signal Vout2 based on the selected even column or the array; at the same time, with reference to FIG. 13, a corresponding buffer amplifier of the "odd" output driver 198$_1$ provides the output signal Vout1 based on a selected odd column of the array.

In one exemplary implementation, the switches of both the even and odd output drivers 198$_1$ and 198$_2$ (e.g., the switches 191$_2$, 191$_4$, ... 191$_{512}$ shown in FIG. 16) may be implemented as CMOS-pair transmission gates (including an n-channel MOSFET and a p-channel MOSFET; see FIG. 4), and inverters may be employed so that each column select signal and its complement may be applied to a given transmission gate switch 191 to enable switching. Each switch 191 has a series resistance when enabled or "on" to couple a corresponding column output signal to the bus 175; likewise, each switch adds a capacitance to the bus 175 when the switch is off. A larger switch reduces series resistance and allows a higher drive current for the bus 175, which generally allows the bus 175 to settle more quickly; on the other hand, a larger switch increases capacitance of the bus 175 when the switch is off, which in turn increases the settling time of the bus 175. Hence, them is a trade-off between switch series resistance and capacitance in connection with switch size.

The ability of the bus 175 to settle quickly following enabling of successive switches in turn facilitates rapid data acquisition from the array. To this end, in some embodiments the switches 191 of the output drivers 198$_1$ and 198$_2$ are particularly configured to significantly reduce the settling time of the bus 175. Both the n-channel and the p-channel MOSFETs of a given switch add to the capacitance of the bus 175; however, n-channel MOSFETs generally have better frequency response and current drive capabilities than their p-channel counterparts. In view of the foregoing, some of the superior characteristics of n-channel MOSFETs may be exploited to improve settling time of the bus 175 by implementing "asymmetric" switches in which respective sizes for the n-channel MOSFET and p-channel MOSFET of a given switch are different.

For example, in one embodiment, with reference to FIG. 16, the current sink 197 may be configured such that the bus 175 is normally "pulled down" when all switches 191$_2$, 191$_4$, ... 191$_{512}$ are open or off (not conducting). Given a somewhat limited expected signal dynamic range for the column output signals based on ISFET measurements, when a given switch is enabled or on (conducting), in many instances most of the conduction is done by the n-channel MOSFET of the CMOS-pair constituting the switch. Accordingly, in one aspect of this embodiment, the n-channel MOSFET and the p-channel MOSFET of each switch 191 are sized differently; namely, in one exemplary implementation, the n-channel MOSFET is sized to be significantly larger than the p-channel MOSFET. More specifically, considering equally-sized n-channel and p-channel MOSFETs as a point of reference, in one implementation the n-channel MOSFET may be increased to be about 2 to 2.5 times larger, and the p-channel MOSFET may be decreased in size to be about 8 to 10 times smaller, such that the n-channel MOSFET is approximately 20 times larger than the p-channel MOSFET. Due to the significant decrease in size of the p-channel MOSFET and the relatively modest increase in size of the n-channel MOSFET, the overall capacitance of the switch in the off state is notably reduced, and there is a corresponding notable reduction in capacitance for the bus 175; at the same time, due to the larger n-channel MOSFET, there is a significant increase in current drive capability, frequency response and transconductance of the switch, which in turn results in a significant reduction in settling time of the bus 175.

While the example above describes asymmetric switches 191 for the output drivers 198$_1$ and 198$_2$ in which the n-channel MOSFET is larger than the p-channel MOSFET, it should be appreciated that in another embodiment, the converse may be implemented, namely, asymmetric switches in which the p-channel MOSFET is larger than the n-channel MOSFET. In one aspect of this embodiment, with reference again to FIG. 16, the current sink 197 may alternatively serve as a source of current to appropriately drive the output of the column output buffer (see the buffer amplifier 111*j* of FIG. 9) of a selected column, and be configured such that the bus 175 is normally "pulled up" when all switches 191$_2$, 191$_4$, ... 191$_{512}$ are open or off (not conducting). In this situation, most of the switch conduction may be accomplished by the p-channel MOSFET of the CMOS-pair constituting the switch. Benefits of reduced switch capacitance (and hence reduced bus capacitance) may be realized in this embodiment, although the overall beneficial effect of reduced settling time for the bus 175 may be somewhat less than that described previously above, due to the lower frequency response of p-channel MOSFETs as compared to n-channel MOSFETs. Nevertheless, asymmetric switches based on larger p-channel MOSFETs may still facilitate a notable reduction in bus settling time, and may also provide for circuit implementations in which the column output buffer amplifier (111*j* of FIG. 9) may be a body-tied source follower with appreciably increased gain.

In yet another embodiment directed to facilitating rapid settling of the bus 175 shown in FIG. 16, it may be appreciated that fewer switches 191 coupled to the bus 175 results in a smaller bus capacitance. With this in mind, and with reference again to FIG. 13, in yet another embodiment, more than two output drivers 198$_1$ and 198$_2$ may be employed in the ISFET array 100 such that each output driver handles a smaller number of columns of the array. For example, rather than having all even columns handled by one driver and all odd columns handled by another driver, the array may include four column select registers 194$_{1,2,3,4}$ and four corresponding output drivers 198$_{1,2,3,4}$ such that each output driver handles one-fourth of the total columns of the array, rather than one-half of the columns. In such an implementation, each output driver would accordingly have half the number of switches 191 as compared with the embodiment discussed above in connection with FIG. 16, and the bus 175 of each output driver would have a corresponding lower capacitance, thereby improving bus settling time. While four output drivers are discussed for purposes of illustration in this example, it should be appreciated that the present disclosure is not limited in this respect, and virtually any number of output drivers greater than two may be employed to improve bus settling time in the scenario described above. Other array embodiments in which more than two output drivers are employed to facilitate rapid data acquisition from the array are discussed in greater detail below (e.g., in connection with FIGS. 19-23).

For purposes of illustration, the bus 175 may have a capacitance in the range of approximately 5 pF to 20 pF in any of the embodiments discussed immediately above (e.g. symmetric switches, asymmetric switches, greater numbers of output drivers, etc.). Of course, it should be appreciated that the capacitance of the bus 175 is not limited to these exemplary values, and that other capacitance values are possible in different implementations of an array according to the present disclosure.

In one aspect of the array design discussed above in connection with FIGS. 13-16, separate analog supply voltage connections (for VDDA, VSSA), digital supply voltage connections (for VDDD, VSSD) and output buffer supply voltage connections (for VDDO, VSSO) are provided on the array to facilitate noise isolation and reduce signal cross-talk amongst various array components, thereby increasing the signal-to-noise ratio (SNR) of the output signals Vout1 and Vout2. In one exemplary implementation, the positive supply voltages VDDA, VDDD and VDDO each may be approximately 3.3 Volts. In another aspect, these voltages respectively may be provided "off chip" by one or more programmable voltage sources, as discussed further below in connection with FIG. 17.

Figure 17:
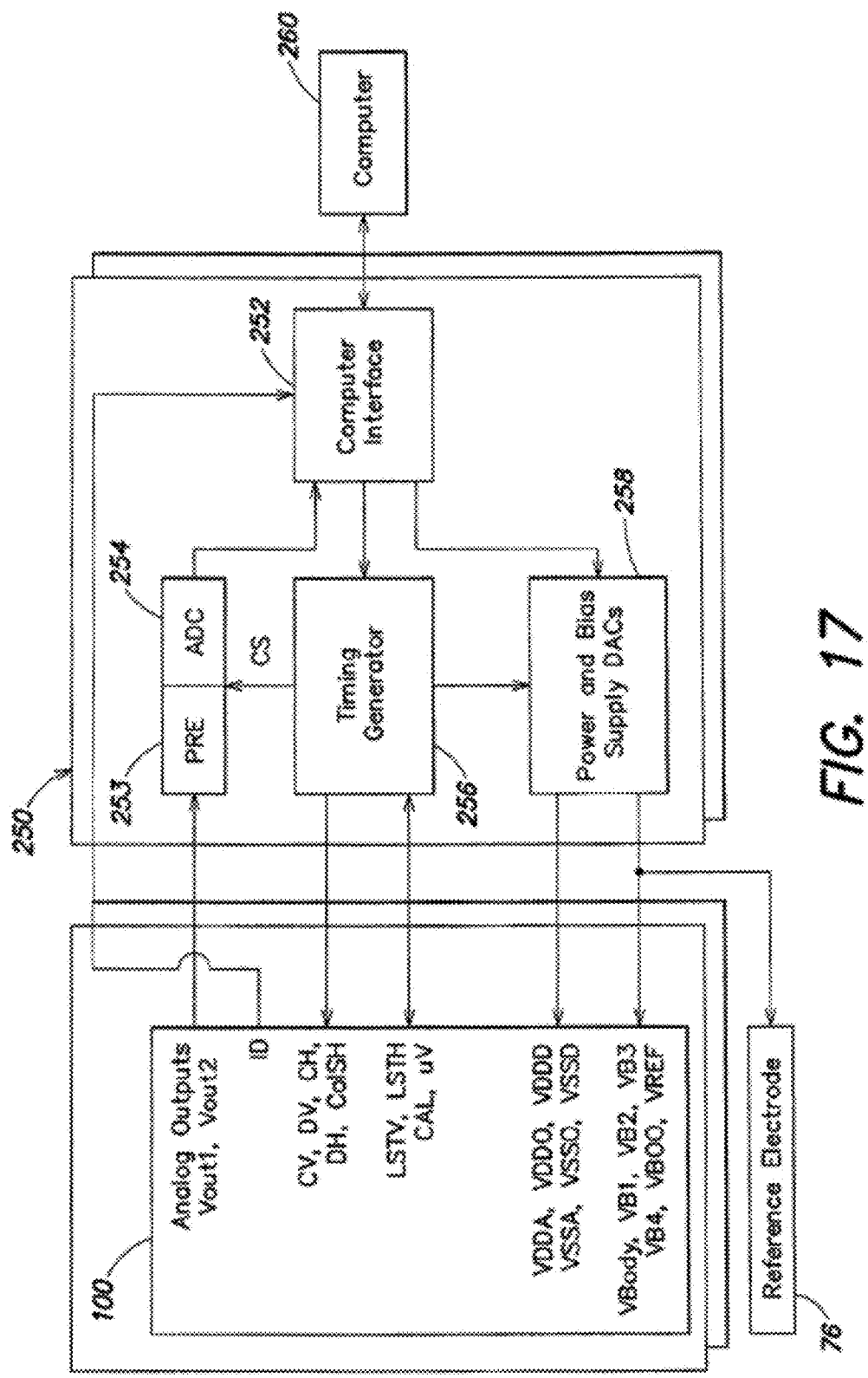
FIG. 17 illustrates a block diagram of the chemFET sensor array of FIG. 13 coupled to an array controller, according to one inventive embodiment of the present disclosure.

FIG. 17 illustrates a block diagram of the sensor array 100 of FIG. 13 coupled to an array controller 250, according to one inventive embodiment of the present disclosure. In various exemplary implementations, the array controller 250 may be fabricated as a "stand alone" controller, or as one or more computer compatible "cards" forming part of a computer 260, as discussed above in connection with FIG. 8. In one aspect, the functions of the array controller 250 may be controlled by the computer 260 through an interface block 252 (e.g., serial interface, via USB port or PCI bus, Ethernet connection, etc.), as shown in FIG. 17. In one embodiment, all or a portion of the array controller 250 is fabricated as one or more printed circuit boards, and the array 100 is configured to plug into one of the printed circuit boards, similar to a conventional IC chip (e.g., the array 100 is configured as an ASIC that plugs into a chip socket, such as a zero-insertion-force or "ZIP" socket, of a printed circuit board). In one aspect of such an embodiment, an array 100 configured as an ASIC may include one or more pins/terminal connections dedicated to providing an identification code, indicated as "ID" in FIG. 17, that may be accessed/read by the array controller 250 and/or passed on to the computer 260. Such an identification code may represent various attributes of the array 100 (e.g., size, number of pixels, number of output signals, various operating parameters such as supply and/or bias voltages, etc.) and may be processed to determine corresponding operating modes, parameters and or signals provided by the array controller 250 to ensure appropriate operation with any of a number of different types of arrays 100. In one exemplary implementation, an array 100 configured as an ASIC may be provided with three pins dedicated to an identification code, and during the manufacturing process the ASIC may be encoded to provide one of three possible voltage states at each of these three pins (i.e., a tri-state pin coding scheme) to be read by the array controller 250, thereby providing for 27 unique array identification codes. In another aspect of this embodiment, all or portions of the array controller 250 may be implemented as a field programmable gate array (FPGA) configured to perform various array controller functions described in further detail below.

Generally, the array controller 250 provides various supply voltages and bias voltages to the array 100, as well as various signals relating to row and column selection, sampling of pixel outputs and data acquisition. In particular, the array controller 250 reads one or more analog output signals (e.g., Vout1 and Vout2) including multiplexed respective pixel voltage signals from the array 100 and then digitizes these respective pixel signals to provide measurement data to the computer 260, which in turn may store and/or process the data. In some implementations, the array controller 250 also may be configured to perform or facilitate various array calibration and diagnostic functions, and an optional array UV irradiation treatment as discussed above in connection with FIG. 11A.

As illustrated in FIG. 17, the array controller 250 generally provides to the array 100 the analog supply voltage and ground (VDDA, VSSA), the digital supply voltage and ground (VDDD, VSSD), and the buffer output supply voltage and ground (VDDO, VSSO). In one exemplary implementation, each of the supply voltages VDDA, VDDD and VDDO is approximately 3.3 Volts. In another implementation, the supply voltages VDDA, VDDD and VDDO may be as low as approximately 1.8 Volts. As discussed above, in one aspect each of these power supply voltages is provided to the array 100 via separate conducting paths to facilitate noise isolation. In another aspect, these supply voltages may originate from respective power supplies/regulators, or one or more of these supply voltages may originate from a common source in a power supply 258 of the array controller 250. The power supply 258 also may provide the various bias voltages required for array operation (e.g., VB1, VB2, VB3, VB4, VBO0, $V_{BODY}$) and the reference voltage VREF used for array diagnostics and calibration.

In another aspect, the power supply 258 includes one or more digital-to-analog converters (DACs) that may be controlled by the computer 260 to allow any or all of the bias voltages, reference voltage, and supply voltages to be changed under software control (i.e., programmable bias settings). For example, a power supply 258 responsive to computer control (e.g., via software execution) may facilitate adjustment of one or more of the supply voltages (e.g., switching between 3.3 Volts and 1.8 Volts depending on chip type as represented by an identification code), and or adjustment of one or more of the bias voltages VB1 and VB2 for pixel drain current, VB3 for column bus drive, VB4 for column amplifier bandwidth, and VBO0 for column output buffer current drive. In some aspects, one or more bias voltages may be adjusted to optimize settling times of signals from enabled pixels. Additionally, the common body voltage $V_{BODY}$ for all ISFETs of the array may be grounded during an optional post-fabrication UV irradiation treatment to reduce trapped charge, and then coupled to a higher voltage (e.g., VDDA) during diagnostic analysis, calibration, and normal operation of the array for measurement/data acquisition. Likewise, the reference voltage VREF may be varied to facilitate a variety of diagnostic and calibration functions.

As also shown in FIG. 17, the reference electrode 76 which is typically employed in connection with an analyte solution to be measured by the array 100 (as discussed above in connection with FIG. 1), may be coupled to the power supply 258 to provide a reference potential for the pixel output voltages. For example, in one implementation the reference electrode 76 may be coupled to a supply ground (e.g., the analog ground VSSA) to provide a reference for the pixel output voltages based on Eq. (3) above. In other exemplary implementations, the reference electrode voltage may be set by placing a solution/sample of interest having a known pH level in proximity to the sensor array 100 and adjusting the reference electrode voltage until the array output signals Vout1 and Vout2 provide pixel voltages at a desired reference level, from which subsequent changes in pixel voltages reflect local changes in pH with respect to the known reference pH level. In general, it should be appreciated that a voltage associated with the reference electrode 76 need not necessarily be identical to the reference voltage VREF discussed above (which may be employed for a variety of array diagnostic and calibration functions), although in some implementations the reference voltage VREF provided by the power supply 258 may be used to set the voltage of the reference electrode 76.

Regarding data acquisition from the array 100, in one embodiment the array controller 250 of FIG. 17 may include one or more preamplifiers 253 to further buffer one or more output signals (e.g., Vout1 and Vout2) from the sensor array and provide selectable gain. In one aspect, the array controller 250 may include one preamplifier for each output signal (e.g., two preamplifiers for two analog output signals). In other aspects, the preamplifiers may be configured to accept input voltages from 0.0 to 1.8 Volts or 0.0 to 3.3 Volts, may have programmable/computer selectable gains (e.g., 1, 2, 5, 10 and 20) and low noise outputs (e.g., <10 nV/sqrtHz), and may provide low pass filtering (e.g., bandwidths of 5 MHz and 25 MHz). With respect to noise reduction and increasing signal-to-noise ratio, in one implementation in which the array 100 is configured as an ASIC placed in a chip socket of a printed circuit board containing all or a portion of the array controller 250, filtering capacitors may be employed in proximity to the chip socket (e.g., the underside of a ZIP socket) to facilitate noise reduction. In yet another aspect, the preamplifiers may have a programmable/computer selectable offset for input and/or output voltage signals to set a nominal level for either to a desired range.

The array controller 250 of FIG. 17 also comprises one or more analog-to-digital converters 254 (ADCs) to convert the sensor array output signals Vout1 and Vout2 to digital outputs (e.g., 10-bit or 12-bit) so as to provide data to the computer 260. In one aspect, one ADC may be employed for each analog output of the sensor array, and each ADC may be coupled to the output of a corresponding preamplifier (if preamplifiers are employed in a given implementation). In another aspect, the ADC(s) may have a computer-selectable input range (e.g., 50 mV, 200 mV, 500 mV, 1V) to facilitate compatibility with different ranges of array output signals and/or preamplifier parameters. In yet other aspects, the bandwidth of the ADC(s) may be greater than 60 MHz, and the data acquisition/conversion rate greater than 25 MHz (e.g., as high as 100 MHz or greater).

In the embodiment of FIG. 17, ADC acquisition timing and array row and column selection may be controlled by a timing generator 256. In particular, the timing generator provides the digital vertical data and clock signals (DH, CV) to control row selection, the digital horizontal data and clock signals (DH, CH) to control column selection, and the column sample and hold signal COL SH to sample respective pixel voltages for an enabled row, as discussed above in connection with FIG. 9. The timing generator 256 also provides a sampling clock signal CS to the ADC(s) 254 so as to appropriately sample and digitize consecutive pixel values in the data stream of a given array analog output signal (e.g., Vout1 and Vout2), as discussed further below in connection with FIG. 18. In some implementations, the timing generator 256 may be implemented by a microprocessor executing code and configured as a multi-channel digital pattern generator to provide appropriately timed control signals. In one exemplary implementation, the timing generator 256 may be implemented as a field-programmable gate array (FPGA).

Figure 18:
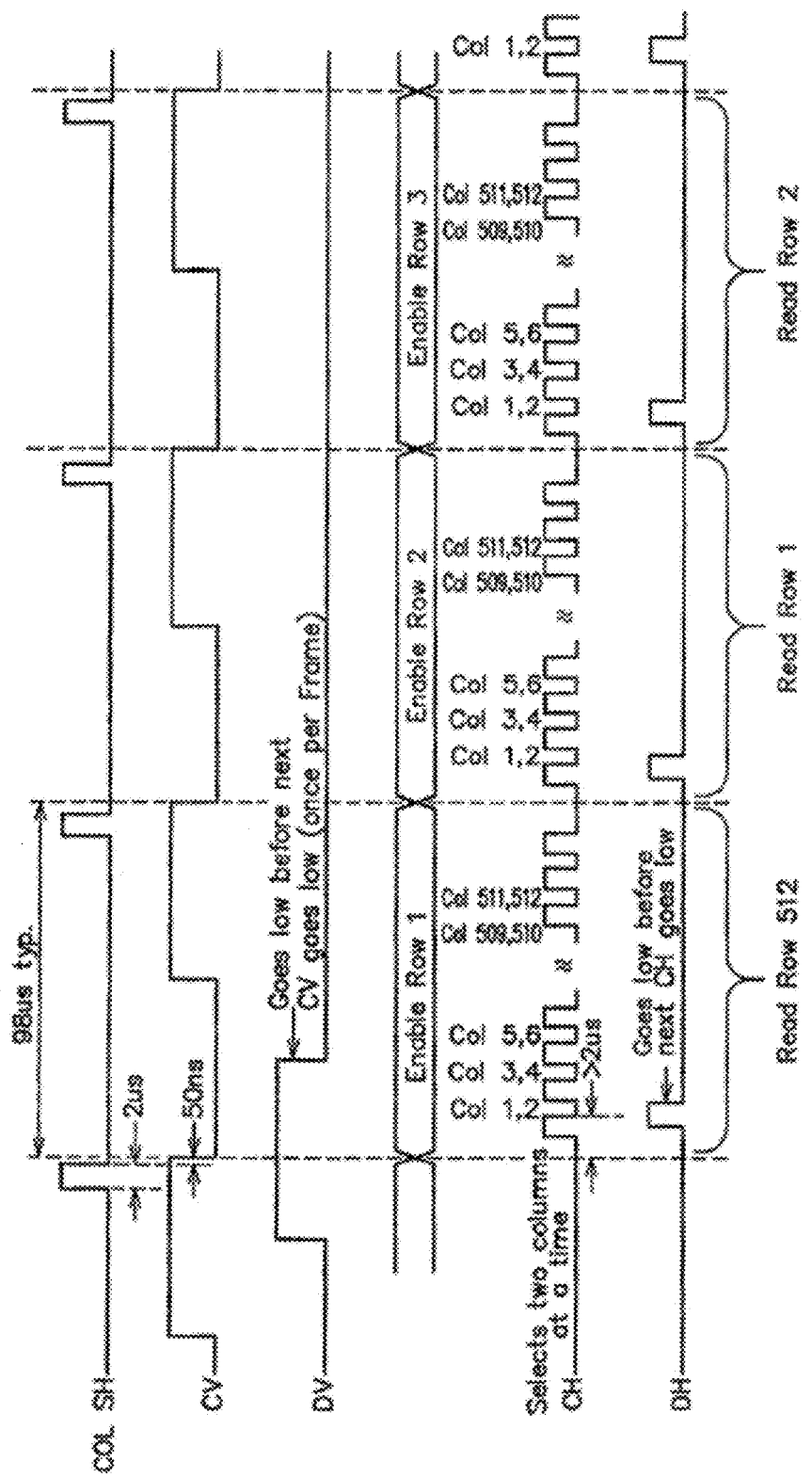
FIG. 18 illustrates an exemplary timing diagram for various signals provided by the array controller of FIG. 17, according to one inventive embodiment of the present disclosure.

FIG. 18 illustrates an exemplary timing diagram for various array control signals, as provided by the timing generator 256, to acquire pixel data from the sensor array 100. For purposes of the following discussion, a "frame" is defined as a data set that includes a value (e.g., pixel output signal or voltage $V_S$) for each pixel in the array, and a "frame rate" is defined as the rate at which successive frames may be acquired from the array. Thus, the frame rate corresponds essentially to a "pixel sampling rate" for each pixel of the array, as data from any given pixel is obtained at the frame rate.

In the example of FIG. 18, an exemplary frame rate of 20 frames/sec is chosen to illustrate operation of the array (i.e., row and column selection and signal acquisition); however, it should be appreciated that arrays and array controllers according to the present disclosure are not limited in this respect, as different frame rates, including lower frame rates (e.g., 1 to 10 frames/second) or higher frame rates (e.g., 25, 30, 40, 50, 60, 70 to 100 frames/sec., etc.), with arrays having the same or higher numbers of pixels, are possible. In some exemplary applications, a data set may be acquired that includes many frames over several seconds to conduct an experiment on a given analyte or analytes. Several such experiments may be performed in succession, in some cases with pauses in between to allow for data transfer/processing and/or washing of the sensor array ASIC and reagent preparation for a subsequent experiment.

For example, with respect to the method for detecting nucleotide incorporation, appropriate frame rates may be chosen to sufficiently sample the ISFET's output signal. In some exemplary implementations, a hydrogen ion signal may have a full-width at half-maximum (FWHM) on the order of approximately 1 second to approximately 2.5 seconds, depending on the number of nucleotide incorporation events. Given these exemplary values, a frame rate (or pixel sampling rate) of 20 Hz is sufficient to reliably resolve the signals in a given pixel's output signal. Again, the frame rates given in this example are provided primarily for purposes of illustration, and different frame rates may be involved in other implementations.

In one implementation, the array controller 250 controls the array 100 to enable rows successively, one at a time. For example, with reference again for the moment to FIG. 9, a first row of pixels is enabled via the row select signal $\overline{RowSel_1}$. The enabled pixels are allowed to settle for some time period, after which the COL SH signal is asserted briefly to close the sample/hold switch in each column and store on the column's sample/hold capacitor $C_{sh}$ the voltage value output by the first pixel in the column. This voltage is then available as the column output voltage $V_{COLj}$ applied to one of the two (odd and even column) array output drivers $198_1$ and $198_2$ (e.g., see FIG. 16). The COL SH signal is then de-asserted, thereby opening the sample/hold switches in each column and decoupling the column output buffer 111j from the column amplifiers 107A and 107B. Shortly thereafter, the second row of pixels is enabled via the row select signal $\overline{RowSel_2}$. During the time period in which the second row of pixels is allowed to settle, the column select signals are generated two at a time (one odd and one even; odd column select signals am applied in succession to the odd output driver, even column select signals are applied in succession to the even output driver) to read the column output voltages associated with the first row. Thus, while a given row in the array is enabled and settling, the previous row is being read out, two columns at a time. By staggering row selection and sampling/readout (e.g., via different vertical and horizontal clock signals and column sample/hold), and by reading multiple columns at a time for a given row, a frame of data may be acquired from the array in a significantly streamlined manner.

FIG. 18 illustrates the timing details of the foregoing process for an exemplary frame rate of 20 frames/sec. Given this frame rate and 512 rows in the array, each row must be read out in approximately 98 microseconds, as indicated by the vertical delineations in FIG. 18. Accordingly, the vertical clock signal CV has a period of 98 microseconds (i.e., a clock frequency of over 10 kHz), with a new row being enabled on a trailing edge (negative transition) of the CV signal. The left side of FIG. 18 reflects the beginning of a new frame cycle, at which point the vertical data signal DV is asserted before a first trailing edge of the CV signal and de-asserted before the next trailing edge of the CV signal (for data acquisition from successive frames, the vertical data signal is reasserted again only after row 512 is enabled). Also, immediately before each trailing edge of the CV signal (i.e., new row enabled), the COL SH signal is asserted for 2 microseconds, leaving approximately 50 nanoseconds before the trailing edge of the CV signal.

In FIG. 18, the first occurrence of the COL SH signal is actually sampling the pixel values of row 512 of the array. Thus, upon the first trailing edge of the CV signal, the first row is enabled and allowed to settle (for approximately 96 microseconds) until the second occurrence of the COL SH signal. During this settling time for the first row, the pixel values of row 512 are read out via the column select signals. Because two column select signals are generated simultaneously to read 512 columns, the horizontal clock signal CH must generate 256 cycles within this period, each trailing edge of the CH signal generating one odd and one even column select signal. As shown in FIG. 18, the first trailing edge of the CH signal in a given row is timed to occur two microseconds after the selection of the row (after deactivation of the COL SH signal) to allow for settling of the voltage values stored on the sample/hold capacitors $C_{sh}$ and provided by the column output buffers. It should be appreciated however that in other implementations (e.g., as discussed below in connection with FIG. 18A), the time period between the first trailing edge of the CH signal and a trailing edge (i.e., deactivation) of the COL SH signal may be significantly less than two microseconds, and in some cases as small as just over 50 nanoseconds. Also for each row, the horizontal data signal DH is asserted before the first trailing edge of the CH signal and de-asserted before the next trailing edge of the CFI signal. The last two columns (e.g., 511 and 512) are selected before the occurrence of the COL SH signal which, as discussed above, occurs approximately two microseconds before the next row is enabled. Thus, 512 columns are read, two at a time, within a time period of approximately 94 microseconds (i.e., 98 microseconds per row, minus two microseconds at the beginning and end of each row). This results in a data rate for each of the array output signals Vout1 and Vout2 of approximately 2.7 MHz.

Figure 18A:
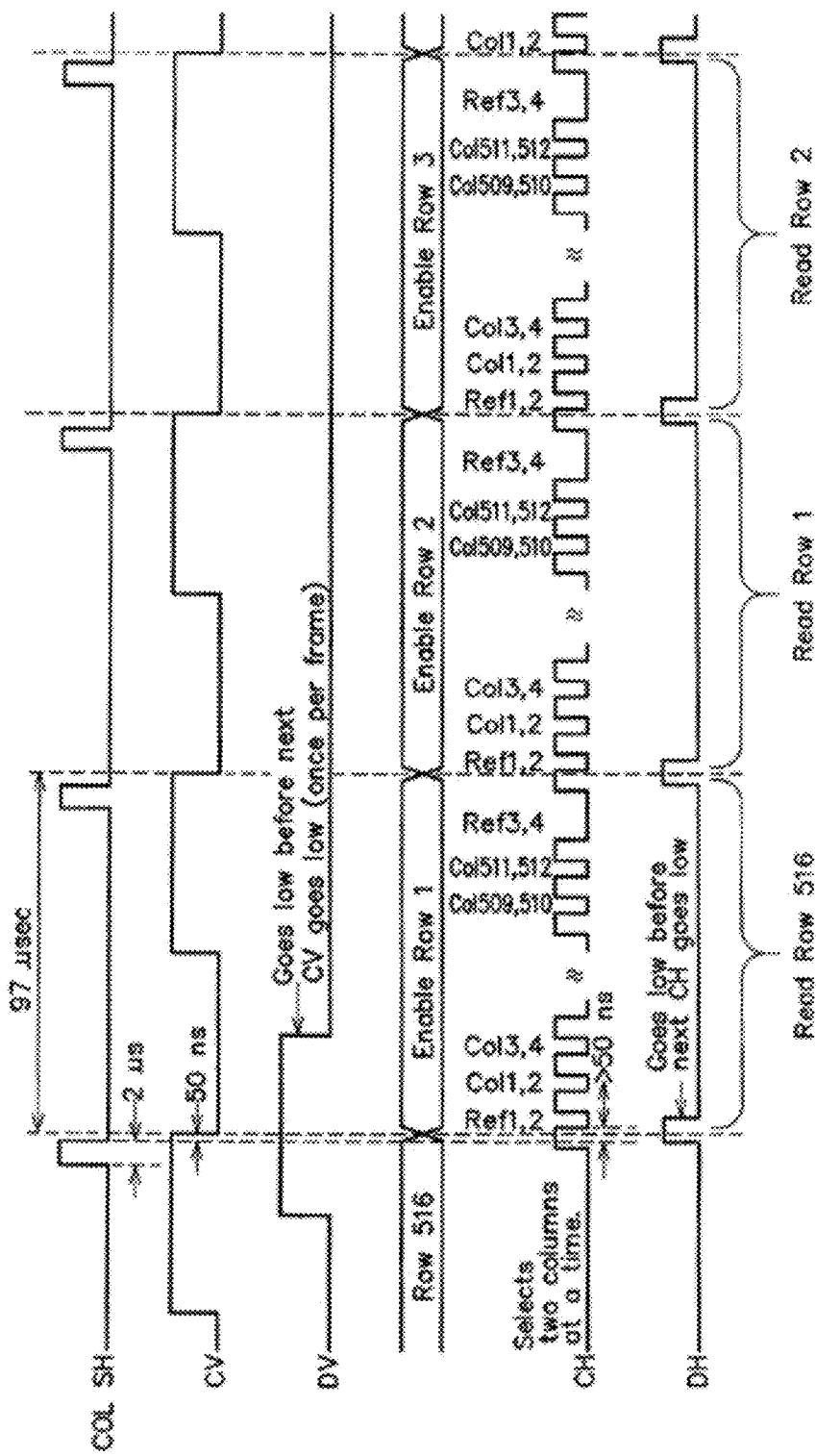
FIG. 18A illustrates another exemplary timing diagram for various signals provided by the array controller of FIG. 17, according to one inventive embodiment of the present disclosure.

FIG. 18A illustrates another timing diagram of a data acquisition process from an array 100 that is slightly modified from the timing diagram of FIG. 18. As discussed above in connection with FIG. 13, in some implementations an array similar to that shown in FIG. 13 may be configured to include a region of 512 by 512 "active" pixels that are surrounded by a perimeter of reference pixels (i.e., the first and last two rows and columns of the array), resulting in an array having a total pixel count of 516 by 516 pixels. Accordingly, given the exemplary frame rate of 20 frames/sec and 516 rows in the array, each row must be read out in approximately 97 microseconds, as indicated by the vertical delineations in FIG. 18A. Accordingly, the vertical clock signal CV has a slightly smaller period of 97 microseconds. Because two column select signals are generated simultaneously to read 516 columns, the horizontal clock signal CH must generate 258 cycles within this period, as opposed to the 256 cycles referenced in connection with FIG. 18. Accordingly, in one aspect illustrated in FIG. 18A, the first trailing edge of the CH signal in a given row is tinted to occur just over 50 nanoseconds from the trailing edge (i.e., deactivation) of the COL SH signal, so as to "squeeze" additional horizontal clock cycles into a slightly smaller period of the vertical clock signal CV. As in FIG. 18, the horizontal data signal DH is asserted before the first trailing edge of the CH signal, and as such also occurs slightly earlier in the timing diagram of FIG. 18A as compared to FIG. 18. The last two columns (i.e., columns 515 and 516, labeled as "Ref3,4 in FIG. 18A) are selected before the occurrence of the COL SH signal which, as discussed above, occurs approximately two microseconds before the next row is enabled. Thus, 516 columns are read, two at a time, within a time period of approximately 95 microseconds (i.e., 97 microseconds per row, minus two microseconds at the end of each row and negligible time at the beginning of each row). This results in essentially the same data rate for each of the array output signals Vout1 and Vout2 provided by the timing diagram of FIG. 18, namely, approximately 2.7 MHz.

As discussed above in connection with FIG. 17, the timing generator 256 also generates the sampling clock signal CS to the ADC(s) 254 so as to appropriately sample and digitize consecutive pixel values in the data stream of a given array output signal. In one aspect, the sampling clock signal CS provides for sampling a given pixel value in the data stream at least once. Although the sampling clock signal CS is not shown in the timing diagrams of FIGS. 18 and 18A, it may be appreciated that in exemplary implementations the signal CS may essentially track the timing of the horizontal clock signal CH; in particular, the sampling clock signal CS may be coordinated with the horizontal clock signal CH so as to cause the ADC(s) to sample a pixel value immediately prior to a next pixel value in the data stream being enabled by CH, thereby allowing for as much signal settling time as possible prior to sampling a given pixel value. For example, the ADC(s) may be configured to sample an input pixel value upon a positive transition of CS, and respective positive transitions of CS may be timed by the timing generator 256 to occur immediately prior to, or in some cases essentially coincident with, respective negative transitions of CH, so as to sample a given pixel just prior to the next pixel in the data stream being enabled. In another exemplary implementation, the ADC(s) 254 may be controlled by the timing generator 256 via the sampling clock signal CS to sample the output signals Vout1 and Vout2 at a significantly higher rate to provide multiple digitized samples for each pixel measurement, which may then be averaged (e.g., the ADC data acquisition rate may be approximately 100 MHz to sample the 2.7 MHz array output signals, thereby providing as many as approximately 35-40 samples per pixel measurement).

Figure 18B:
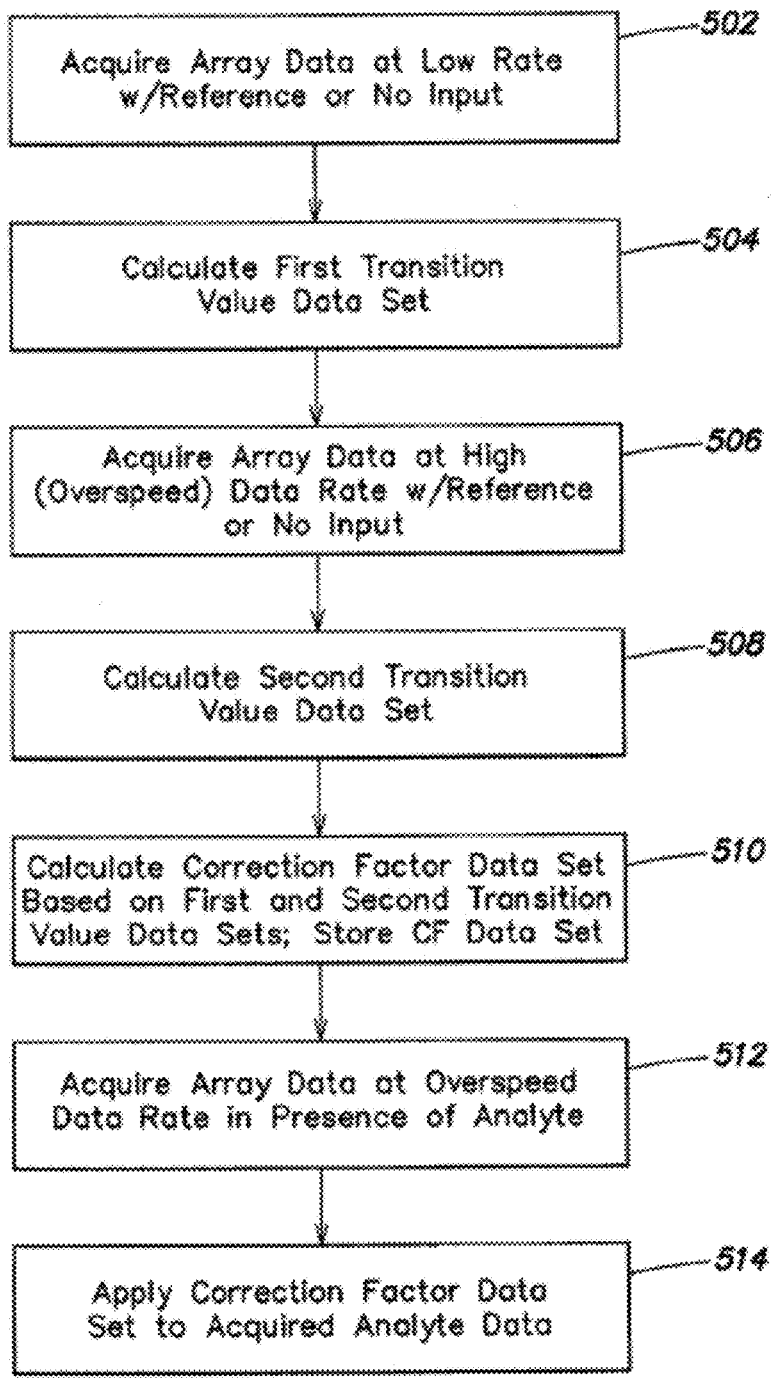
FIG. 18B shows a flow chart illustrating an exemplary method for processing and correction of array data acquired at high acquisition rates, according to one inventive embodiment of the present disclosure.

In one embodiment, once pixel values are sampled and digitized by the ADC(s) 254, the computer 260 may be programmed to process pixel data obtained from the array 100 and the array controller 250 so as to facilitate high data acquisition rates that in some cases may exceed a sufficient settling time for pixel voltages represented in a given array output signal. A flow chart illustrating an exemplary method according to one embodiment of the present invention that may be implemented by the computer 260 for processing and correction of array data acquired at high acquisition rates is illustrated in FIG. 18B. In various aspects of this embodiment, the computer 260 is programmed to first characterize a sufficient settling time for pixel voltages in a given array output signal, as well as array response at appreciably high operating frequencies, using a reference or "dry" input to the array (e.g., no analyte present). This characterization forms the basis for deriving correction factors that are subsequently applied to data obtained from the array at the high operating frequencies and in the presence of an analyte to be measured.

Figure 18C:
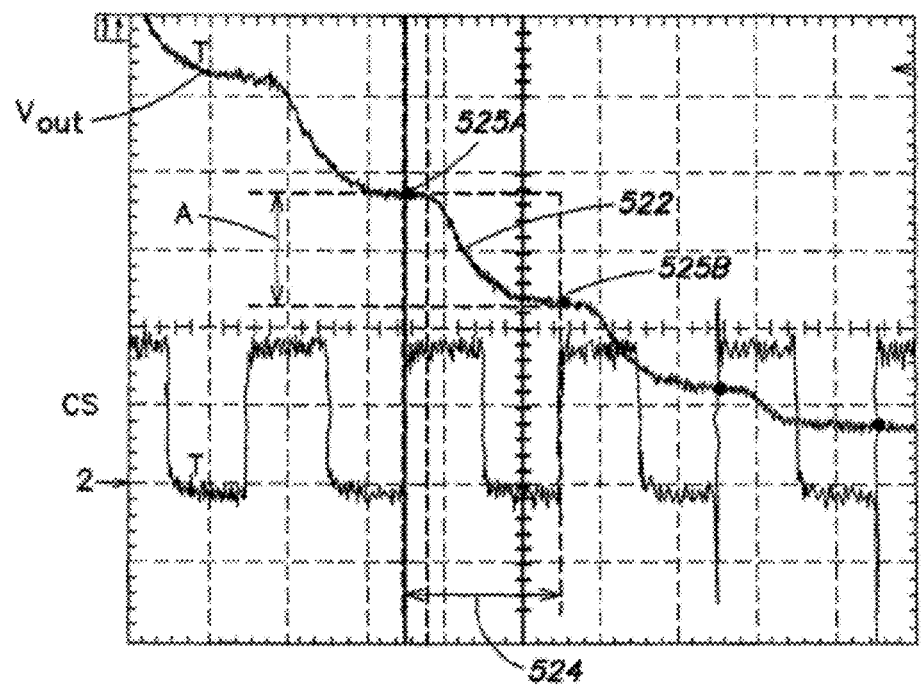
FIGS. 18C and 18D illustrate exemplary pixel voltages showing pixel-to-pixel transitions in a given array output signal, according to one embodiment of the present disclosure.
Figure 18D:
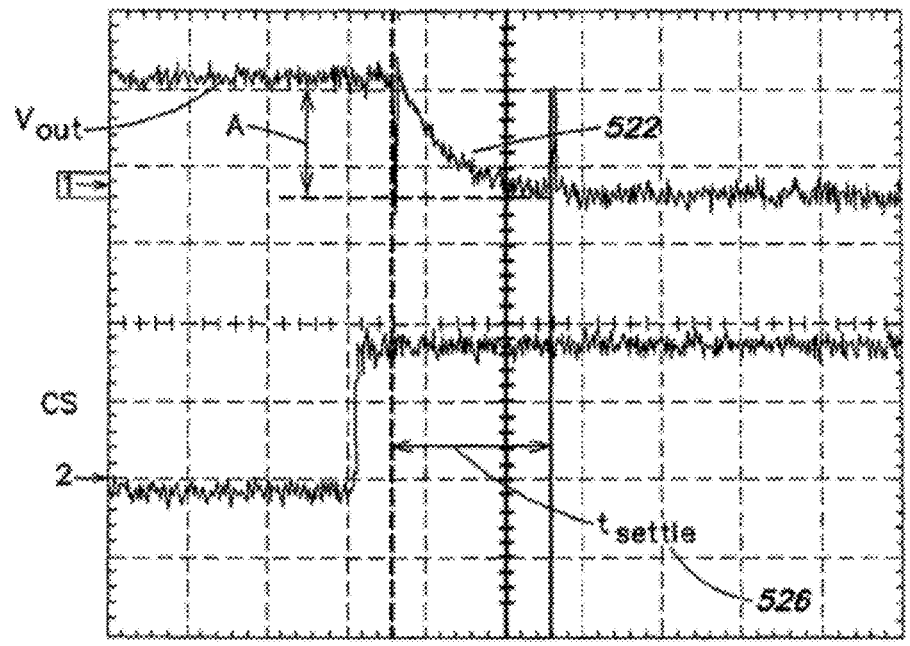

Regarding pixel settling time, with reference again to FIG. 16, as discussed above a given array output signal (e.g., Vout2 in FIG. 16) includes a series of pixel voltage values resulting from the sequential operation of the column select switches 191 to apply respective column voltages $V_{COLj}$ via the bus 175 to the buffer amplifier 199 (the respective column voltages $V_{COLj}$ in turn represent buffered versions of ISFET source voltages $V_{Sj}$). In some implementations, it is observed that voltage changes $\Delta V_{PIX}$ in the array output signal between two consecutive pixel reads is characterized as an exponential process given by $$\Delta V_{PIX}(t) = A(1 - e^{-kt}), \quad \text{(PP)}$$

where A is the difference ($V_{COLj} - V_{COLj-1}$) between two pixel voltage values and k is a time constant associated with a capacitance of the bus 175. FIGS. 18C and 18D illustrate exemplary pixel voltages in a given array output signal Vout (e.g., one of Vout1 and Vout2) showing pixel-to-pixel transitions in the output signal as a function of time, plotted against exemplary sampling clock signals CS. In FIG. 18C, the sampling clock signal CS has a period 524, and an ADC controlled by CS samples a pixel voltage upon a positive transition of CS (as discussed above, in one implementation CS and CH have essentially a same period). FIG. 18C indicates two samples 525A and 525B, between which an exponential voltage transition 522 corresponding to $\Delta V_{PIX}(t)$, between a voltage difference A, may be readily observed.

For purposes of the present discussion, pixel "settling time" $t_{settle}$ is defined as the time t at which $\Delta V_{PIX}(t)$ attains a value that differs from it's final value by an amount that is equal to the peak noise level of the array output signal. If the peak noise level of the array output signal is denoted as $n_p$, then the voltage at the settling time $t_{settle}$ is given by $\Delta V_{PIX}(t_{settle}) = A[1 - (n_p/A)]$. Substituting in Eq. (PP) and solving for $t_{settle}$ yields $$t_{settle} = -k \ln\left(\frac{n_p}{A}\right). \quad \text{(QQ)}$$

FIG. 18D conceptually illustrates a pixel settling time $t_{settle}$ (reference numeral 526) for a single voltage transition 522 between two pixel voltages having a difference A, using a sampling clock signal CS having a sufficiently long period so as to allow for full settling. To provide some exemplary parameters for purposes of illustration, in one implementation a maximum value for A, representing a maximum range for pixel voltage transitions (e.g., consecutive pixels at minimum and maximum values), is on the order of approximately 250 mV. Additionally, a peak noise level $n_p$ of the array output signal is taken as approximately 100 μV, and the time constant k is taken as 5 nanoseconds. These values provide an exemplary settling time $t_{settle}$ of approximately 40 nanoseconds. If a maximum data rate of an array output signal is taken as the inverse of the settling time $t_{settle}$, a settling time of 40 nanoseconds corresponds to maximum data rate of 25 MHz. In other implementations, A may be on the order of 20 mV and the time constant k may be on the order of 15 nanoseconds, resulting in a settling time $t_{settle}$ of approximately 80 nanoseconds and a maximum data rate of 12.5 MHz. The values of k indicated above generally correspond to capacitances for the bus 175 in a range of approximately 5 pF to 20 pF. It should be appreciated that the foregoing values are provided primarily for purposes of illustration, and that various embodiments of the present invention are not limited to these exemplary values; in particular, arrays according to various embodiment of the present invention may have different pixel settling times $t_{settle}$ (e.g., in some cases less than 40 nanoseconds).

As indicated above, in one embodiment pixel data may be acquired from the array at data rates that exceed those dictated by the pixel settling time. FIG. 18B illustrates a flow chart for such a method according to one inventive embodiment of the present disclosure. In the method of FIG. 18B, sufficiently slow clock frequencies initially are chosen for the signals CV, CH and CS such that the resulting data rate per array output signal is equal to or lower than the reciprocal of the pixel settling time $t_{settle}$ to allow for fully settled pixel voltage values from pixel to pixel in a given output signal. With these clock frequencies, as indicated in block 502 of FIG. 18B, settled pixel voltage values are then acquired for the entire array in the absence of an analyte (or in the presence of a reference analyte) to provide a first "dry" or reference data image for the array. In block 504 of FIG. 18B, for each pixel voltage constituting the first data image, a transition value between the pixel's final voltage and the final voltage of the immediately preceding pixel in the corresponding output signal data stream (i.e., the voltage difference A) is collected and stored. The collection of these transition values for all pixels of the array provides a first transition value data set.

Subsequently, in block 506 of FIG. 18B, the clock frequencies for the signals CV, CH and CS are increased such that the resulting data rate per array output signal exceeds a rate at which pixel voltage values are fully settled (i.e., a data rate higher than the reciprocal of the settling time $t_{settle}$). For purposes of the present discussion, the data rate per array output signal resulting from the selection of such increased clock frequencies for the signals CV, CH and CS is referred to as an "overspeed data rate." Using the clock frequencies corresponding to the overspeed data rate, pixel voltage values are again obtained for the entire array in the absence of an analyte (or in the presence of the same reference analyte) to provide a second "dry" or reference data image for the array. In block 508 of FIG. 18B, a second transition value data set based on the second data image obtained at the overspeed data rate is calculated and stored, as described above for the first data image.

In block 510 of FIG. 18B, a correction factor for each pixel of the array is calculated based on the values stored in the first and second transition value data sets. For example, a correction factor for each pixel may be calculated as a ratio of its transition value from the first transition value data set and its corresponding transition value from the second transition value data set (e.g., the transition value from the first data set may be divided by the transition value from the second data set, or vice versa) to provide a correction factor data set which is then stored. As noted in blocks 512 and 514 of FIG. 18B, this correction factor data set may then be employed to process pixel data obtained from the array operated at clock frequencies corresponding to the overspeed data rate, in the presence of an actual analyte to be measured; in particular, data obtained from the array at the overspeed data rate in the presence of an analyte may be multiplied or divided as appropriate by the correction factor data set (e.g., each pixel multiplied or divided by a corresponding correction factor) to obtain corrected data representative of the desired analyte property to be measured (e.g., ion concentration). It should be appreciated that once the correction factor data set is calculated and stored, it may be used repeatedly to correct multiple frames of data acquired from the array at the overspeed data rate.

In addition to controlling the sensor array and ADCs, the timing generator 256 may be configured to facilitate various array calibration and diagnostic functions, as well as an optional UV irradiation treatment. To this end, the timing generator may utilize the signal LSTV indicating the selection of the last row of the array and the signal LSTH to indicate the selection of the last column of the array. The timing generator 256 also may be responsible for generating the CAL signal which applies the reference voltage VREF to the column buffer amplifiers, and generating the UV signal which grounds the drains of all ISFETs in the array during a UV irradiation process (see FIG. 9). The timing generator also may provide some control function over the power supply 258 during various calibration and diagnostic functions, or UV irradiation, to appropriately control supply or bias voltages; for example, during UV irradiation, the timing generator may control the power supply to couple the body voltage $V_{BODY}$ to ground while the UV signal is activated to ground the ISFET drains. With respect to array calibration and diagnostics, as well as UV irradiation, in some implementations the timing generator may receive specialized programs from the computer 260 to provide appropriate control signals. In one aspect, the computer 260 may use various data obtained from reference and/or dummy pixels of the array, as well as column information based on the application of the CAL signal and the reference voltage VREF, to determine various calibration parameters associated with a given array and/or generate specialized programs for calibration and diagnostic functions.

Having discussed several aspects of an exemplary ISFET array, FIGS. 19-23 illustrate block diagrams of alternative CMOS IC chip implementations of ISFET sensor arrays having greater numbers of pixels, according to yet other inventive embodiments. In one aspect, each of the ISFET arrays discussed further below in connection with FIGS. 19-23 may be controlled by an array controller similar to that shown in FIG. 17, in some cases with minor modifications to accommodate higher numbers of pixels (e.g., additional preamplifiers 253 and analog-to-digital converters 254).

Figure 19:
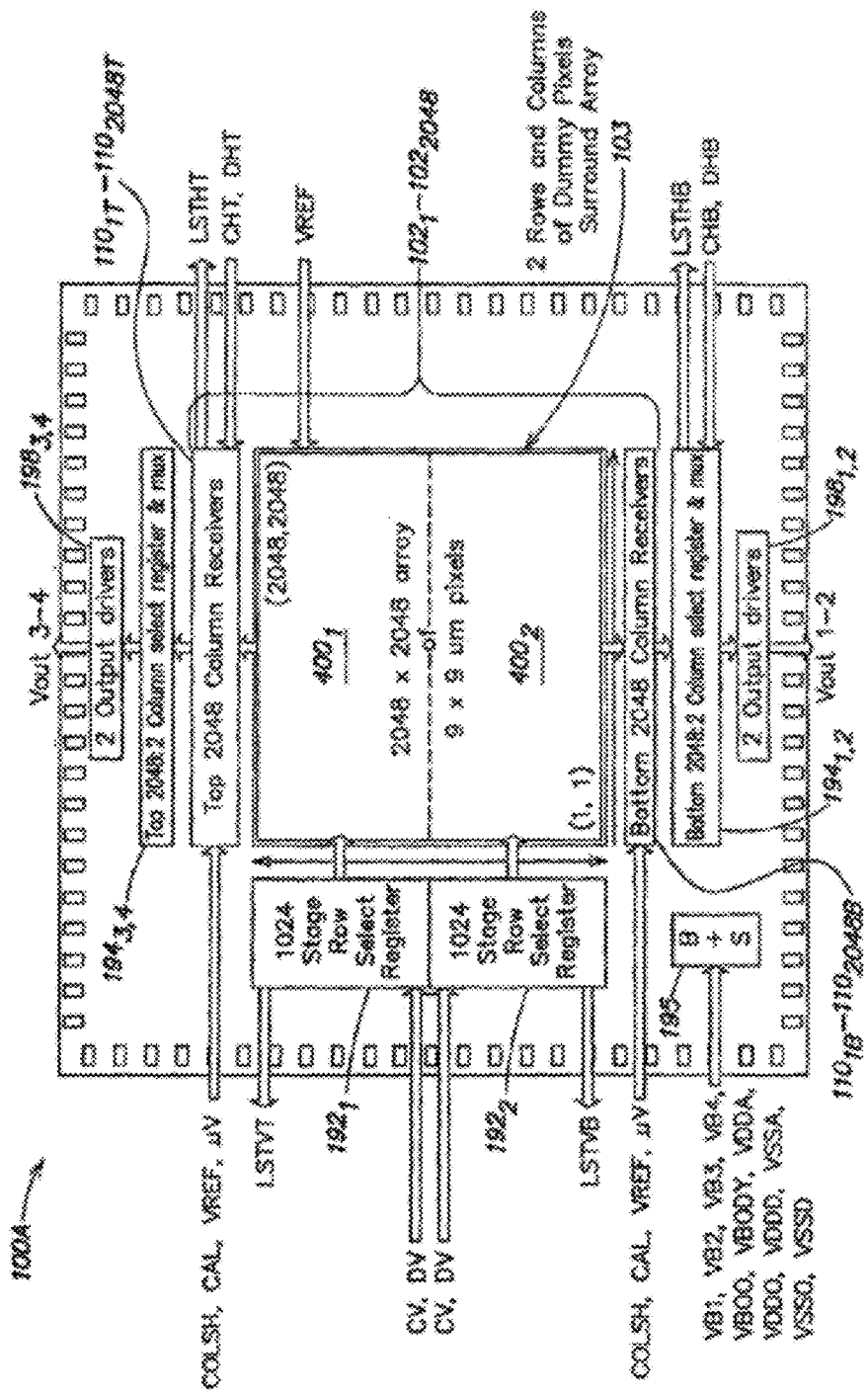
FIGS. 19-20 illustrate block diagrams of alternative CMOS IC chip implementations of chemFET sensor arrays, according to other inventive embodiments of the present disclosure.

FIG. 19 illustrates a block diagram of an ISFET sensor array 100A based on the column and pixel designs discussed above in connection with FIGS. 9-12 and a 0.35 micrometer CMOS fabrication process, according to one inventive embodiment. The array 100A includes 2048 columns $102_1$ through $102_{2048}$, wherein each column includes 2048 geometrically square pixels $105_1$ through $105_{2048}$, each having a size of approximately 9 micrometers by 9 micrometers. Thus, the array includes over four million pixels (>4 Mega-pixels) and, in one exemplary implementation, the complete array (ISFET pixels and associated circuitry) may be fabricated as an integrated circuit chip having dimensions of approximately 20.5 millimeters by 20.5 millimeters.

In one aspect of the embodiment shown in FIG. 19, the array 100A may be configured, at least in part, as multiple groups of pixels that may be respectively controlled. For example, each column of pixels may be divided into top and bottom halves, and the collection of pixels in respective top halves of columns form a first group $400_1$ of rows (e.g., a top group, rows 1-1024) and the collection of pixels in respective bottom halves of columns form a second group $400_2$ of rows (e.g., a bottom group, rows 1025-2048). In turn, each of the first and second (e.g., top and bottom) groups of rows is associated with corresponding row select registers, column bias/readout circuitry, column select registers, and output drivers. In this manner, pixel selection and data acquisition from each of the first and second groups of rows $400_1$ and $400_2$ is substantially similar to pixel selection and data acquisition from the entire array 100 shown in FIG. 13; stated differently, in one aspect, the array 100A of FIG. 19 substantially comprises two simultaneously controlled "sub-arrays" of different pixel groups to provide for significantly streamlined data acquisition from higher numbers of pixels.

In particular, FIG. 19 shows that row selection of the first group $400_1$ of rows may be controlled by a first row select register $192_1$, and row selection of the second group $400_2$ of rows may be controlled by a second row select register $192_2$. In one aspect, each of the row select registers $192_1$ and $192_2$ may be configured as discussed above in connection with FIG. 14 to receive vertical clock (CV) and vertical data (DV) signals and generate row select signals in response; for example the first row select register $192_1$ may generate the signals $\overline{RowSel}_1$ through $\overline{RowSel}_{1024}$ and the second row select register $192_2$ may generate the signals $\overline{RowSel}_{1025}$ through $\overline{RowSel}_{2048}$. In another aspect, both row select registers $192_1$ and $192_2$ may simultaneously receive common vertical clock and data signals, such that two rows of the array are enabled at any given time, one from the top group and another from the bottom group.

For each of the first and second groups of rows, the array 100A of FIG. 19 further comprises column bias/readout circuitry $110_{1T}$-$110_{2048T}$ (for the first row group $400_1$) and $110_{1B}$-$110_{2048B}$ (for the second row group $400_2$), such that each column includes two instances of the bias/readout circuitry $110j$ shown in FIG. 9. The array 100A also comprises two column select registers $192_{1,2}$ (odd and even) and two output drivers $198_{1,2}$ (odd and even) for the second row group $400_2$, and two column select registers $192_{3,4}$ (odd and even) and two output drivers $198_{3,4}$ (odd and even) for the first row group $400_1$ (i.e., a total of four column select registers and four output drivers). The column select registers receive horizontal clock signals (CHT and CHB for the first row group and second row group, respectively) and horizontal data signals (DHT and DHB for the first row group and second row group, respectively) to control odd and even column selection. In one implementation, the CHT and CHB signals may be provided as common signals, and the DHT and DHB may be provided as common signals, to simultaneously read out four columns at a time from the array (i.e., one odd and one even column from each row group); in particular, as discussed above in connection with FIGS. 13-18, two columns may be simultaneously read for each enabled row and the corresponding pixel voltages provided as two output signals. Thus, via the enablement of two rows at any given time, and reading of two columns per row at any given time, the array 100A may provide four simultaneous output signals Vout1, Vout2, Vout3 and Vout4.

In one exemplary implementation of the array 100A of FIG. 19, in which complete data frames (all pixels from both the first and second row groups $400_1$ and $400_2$) are acquired at a frame rate of 20 frames/sec, 1024 pairs of rows are successively enabled for periods of approximately 49 microseconds each. For each enabled row, 1024 pixels are read out by each column select register/output driver during approximately 45 microseconds (allowing 2 microseconds at the beginning and end of each row, as discussed above in connection with FIG. 18). Thus, in this example, each of the array output signals Vout1, Vout2, Vout3 and Vout4 has a data rate of approximately 23 MHz. Again, it should be appreciated that in other implementations, data may be acquired from the array 100A of FIG. 19 at frame rates other than 20 frames/sec (e.g., 50-100 frames/sec).

Like the array 100 of FIG. 13, in yet other aspects the array 100A of FIG. 19 may include multiple rows and columns of dummy or reference pixels 103 around a perimeter of the array to facilitate preliminary test/evaluation data, offset determination an/or array calibration. Additionally, various power supply and bias voltages required for array operation (as discussed above in connection with FIG. 9) are provided to the array 100A in block 195, in a manner similar to that discussed above in connection with FIG. 13.

Figure 20:
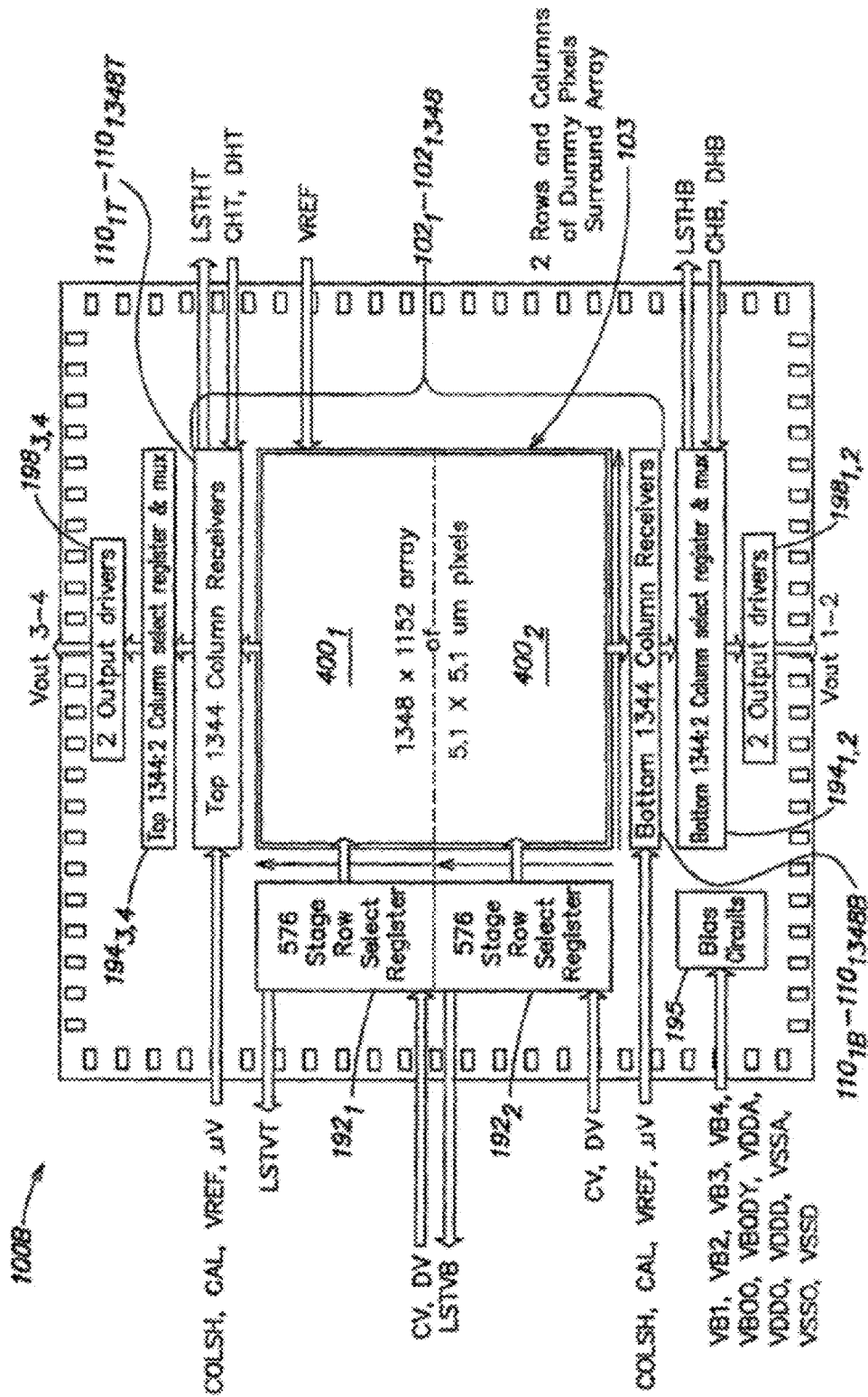

FIG. 20 illustrates a block diagram of an ISFET sensor array 100B based on a 0.35 micrometer CMOS fabrication process and having a configuration substantially similar to the array 100A discussed above in FIG. 19, according to yet another inventive embodiment. While the array 100E also is based generally on the column and pixel designs discussed above in connection with FIGS. 9-12, the pixel size/pitch in the array 100B is smaller than that of the pixel shown in FIG. 10. In particular, with reference again to FIGS. 10 and 11, the dimension "e" shown in FIG. 10 is substantially reduced in the embodiment of FIG. 20, without affecting the integrity of the active pixel components disposed in the central region of the pixel, from approximately 9 micrometers to approximately 5 micrometers; similarly, the dimension "f" shown in FIG. 10 is reduced from approximately 7 micrometers to approximately 4 micrometers. Stated differently, some of the peripheral area of the pixel surrounding the active components is substantially reduced with respect to the dimensions given in connection with FIG. 10, without disturbing the top-view and cross-sectional layout and design of the pixel's active components as shown in FIGS. 10 and 11. A top view of such a pixel 105A is shown in FIG. 20A, in which the dimension "e" is 5.1 micrometers and the dimension "f" is 4.1 micrometers. In one aspect of this pixel design, to facilitate size reduction, fewer body connections B are included in the pixel 105A (e.g., one at each corner of the pixel) as compared to the pixel shown in FIG. 10, which includes several body connections B around the entire perimeter of the pixel.

As noted in FIG. 20, the array 100B includes 1348 columns $102_1$ through $102_{1348}$, wherein each column includes 1152 geometrically square pixels $105A_1$ through $105A_{1152}$, each having a size of approximately 5 micrometers by 5 micrometers. Thus, the array includes over 1.5 million pixels (>1.5 Mega-pixels) and, in one exemplary implementation, the complete array (ISFET pixels and associated circuitry) may be fabricated as an integrated circuit chip having dimensions of approximately 9 millimeters by 9 millimeters. Like the array 100A of FIG. 19, in one aspect the array 100B of FIG. 20 is divided into two groups of rows $400_1$ and $400_2$, as discussed above in connection with FIG. 19. In one exemplary implementation, complete data frames (all pixels from both the first and second row groups $400_1$ and $400_2$) are acquired at a frame rate of 50 frames/sec, thereby requiring 576 pairs of rows to be successively enabled for periods of approximately 35 microseconds each. For each enabled row, 674 pixels are read out by each column select register/output driver during approximately 31 microseconds (allowing 2 microseconds at the beginning and end of each row, as discussed above in connection with FIG. 18). Thus, in this example, each of the array output signals Vout1, Vout2, Vout3 and Vout4 has a data rate of approximately 22 MHz. Again, it should be appreciated that in other implementations, data may be acquired from the array 100B of FIG. 20 at frame rates other than 50 frames/sec.

Figure 21:
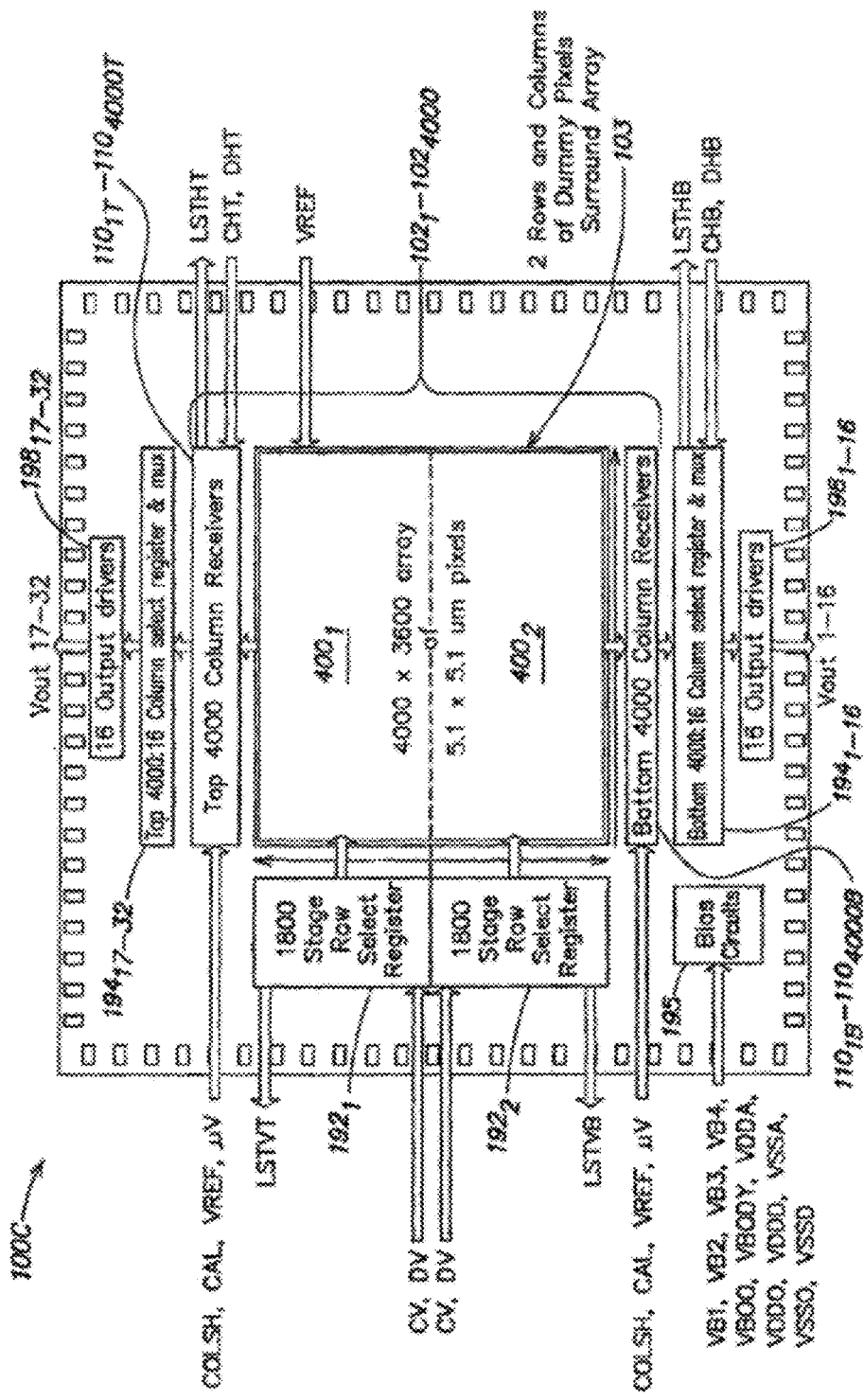
FIGS. 21-23 illustrate block diagrams of additional alternative CMOS IC chip implementations of chemFET sensor arrays, according to other inventive embodiments of the present disclosure.

FIG. 21 illustrates a block diagram of an ISFET sensor array 100C based on a 0.35 micrometer CMOS fabrication process and incorporating the smaller pixel size discussed above in connection with FIGS. 20 and 20A (5.1 micrometer square pixels), according to yet another embodiment. As noted in FIG. 21, the array 100C includes 4000 columns $102_1$ through $102_{4000}$, wherein each column includes 3600 geometrically square pixels $105A_1$ through $105A_{3600}$, each having a size of approximately 5 micrometers by 5 micrometers. Thus, the array includes over 14 million pixels (>14 Mega-pixels) and, in one exemplary implementation, the complete array (ISFET pixels and associated circuitry) may be fabricated as an integrated circuit chip having dimensions of approximately 22 millimeters by 22 millimeters. Like the arrays 100A and 100B of FIGS. 19 and 20, in one aspect the array 1000 of FIG. 21 is divided into two groups of rows $400_1$ and $400_2$. However, unlike the arrays 100A and 100B, for each row group the array 100C includes sixteen column select registers and sixteen output drivers to simultaneously read sixteen pixels at a time in an enabled row, such that thirty-two output signals Vout1-Vout32 may be provided from the array 100C. In one exemplary implementation, complete data frames (all pixels from both the first and second row groups $400_1$ and $400_2$) may be acquired at a frame rate of 50 frames/sec, thereby requiring 1800 pairs of rows to be successively enabled for periods of approximately 11 microseconds each. For each enabled row, 250 pixels (4000/16) are read out by each column select register/output driver during approximately 7 microseconds (allowing 2 microseconds at the beginning and end of each row). Thus, in this example, each of the array output signals Vout1-Vout32 has a data rate of approximately 35 MHz. As with the previous embodiments, it should be appreciated that in other implementations, data may be acquired from the array 100C at frame rates other than 50 frames/sec.

Figure 22:
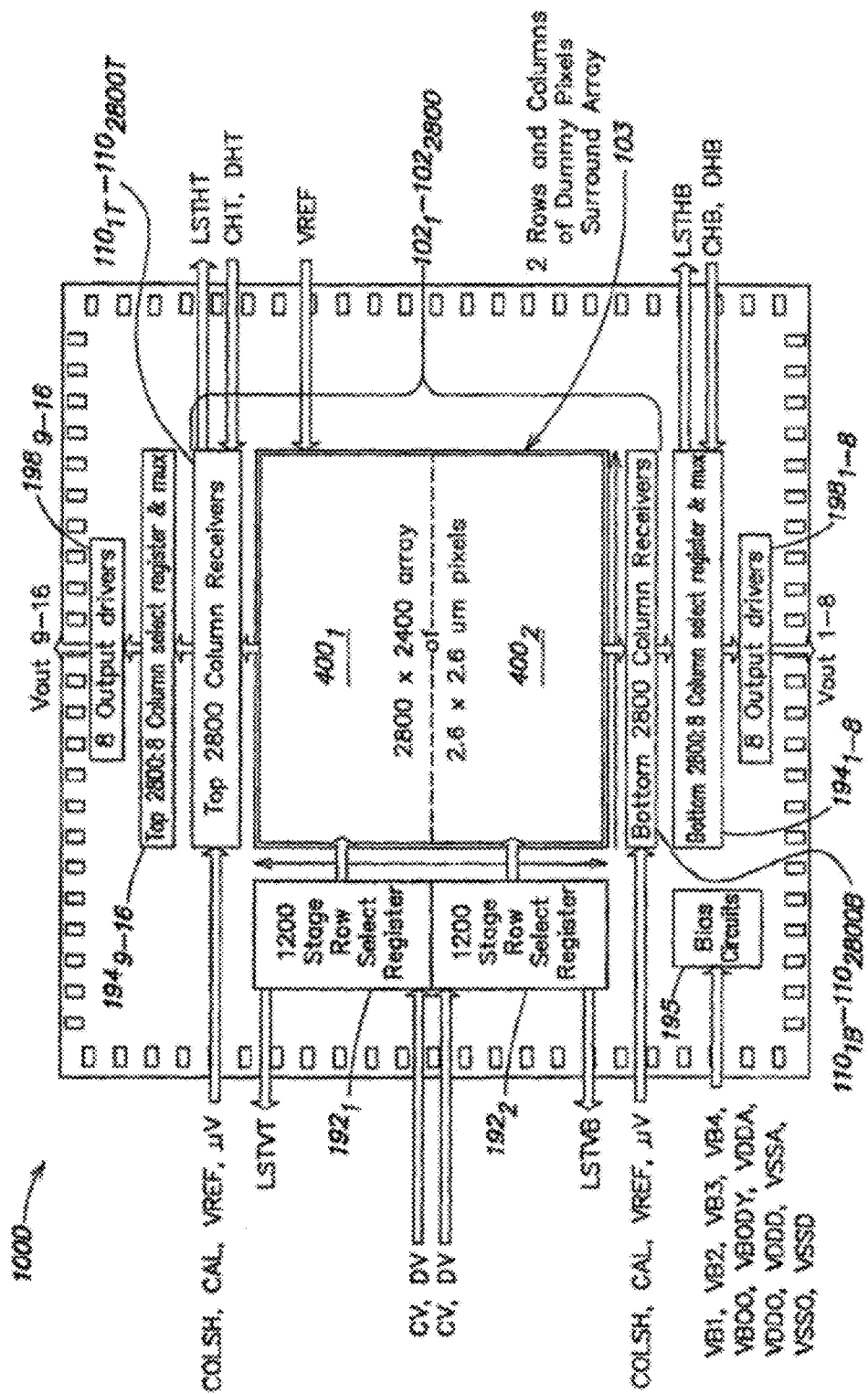
Figure 23:
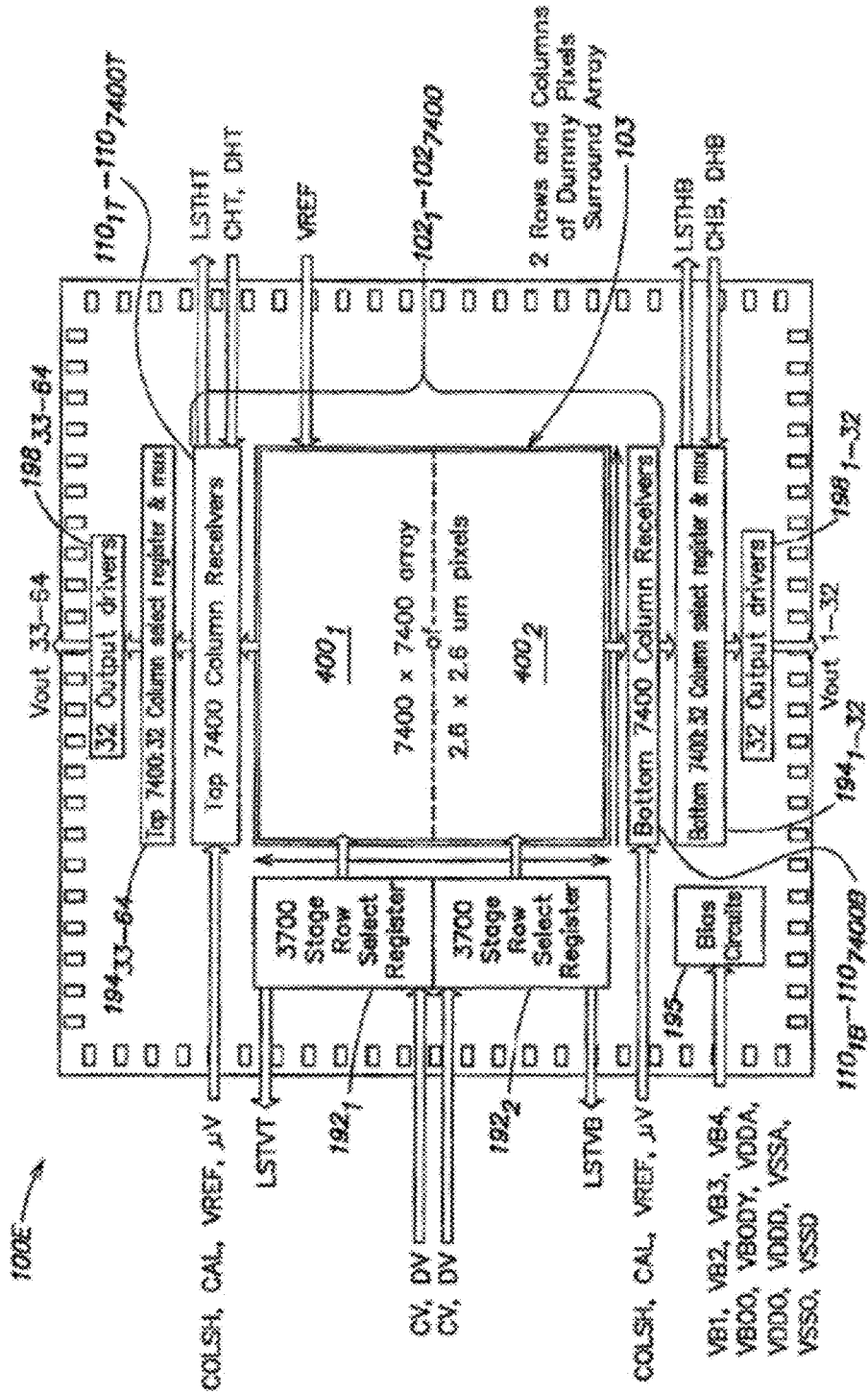

While the exemplary arrays discussed above in connection with FIGS. 13-21 are based on a 0.35 micrometer conventional CMOS fabrication process, it should be appreciated that arrays according to the present disclosure are not limited in this respect, as CMOS fabrication processes having feature sizes of less than 0.35 micrometers may be employed (e.g., 0.18 micrometer CMOS processing techniques) to fabricate such arrays. Accordingly, ISFET sensor arrays with a pixel size/pitch significantly below 5 micrometers may be fabricated, providing for significantly denser ISFET arrays. For example, FIGS. 22 and 23 illustrate respective block diagrams of ISFET sensor arrays 100D and 100E according to yet other embodiments based on a 0.18 micrometer CMOS fabrication process, in which a pixel size of 2.6 micrometers is achieved. The pixel design itself is based substantially on the pixel 105A shown in FIG. 20A, albeit on a smaller scale due to the 0.18 micrometer CMOS process.

The array 100D of FIG. 22 includes 2800 columns $102_1$ through $102_{2800}$, wherein each column includes 2400 geometrically square pixels each having a size of approximately 2.6 micrometers by 2.6 micrometers. Thus, the array includes over 6.5 million pixels (>6.5 Mega-pixels) and, in one exemplary implementation, the complete array (ISFET pixels and associated circuitry) may be fabricated as an integrated circuit chip having dimensions of approximately 9 millimeters by 9 millimeters. Like the arrays 100A, 100E and 1000 of FIGS. 19-21, in one aspect the array 100D of FIG. 22 is divided into two groups of rows $400_1$ and $400_2$. However, unlike the arrays 100A, 100B, and 100C, for each row group the array 100D includes eight column select registers and eight output drivers to simultaneously read eight pixels at a time in an enabled row, such that sixteen output signals Vout1-Vout16 may be provided from the array 100D. In one exemplary implementation, complete data frames (all pixels from both the first and second row groups $400_1$ and $400_2$) may be acquired at a frame rate of 50 frames/sec, thereby requiring 1200 pairs of rows to be successively enabled for periods of approximately 16-17 microseconds each. For each enabled row, 350 pixels (2800/8) are read out by each column select register/output driver during approximately 14 microseconds (allowing 1 to 2 microseconds at the beginning and end of each row). Thus, in this example, each of the array output signals Vout1-Vout16 has a data rate of approximately 25 MHz. As with the previous embodiments, it should be appreciated that in other implementations, data may be acquired from the array 100D at frame rates other than 50 frames/sec.

The array 100E of FIG. 23 includes 7400 columns $102_1$ through $102_{7400}$, wherein each column includes 7400 geometrically square pixels each having a size of approximately 2.6 micrometers by 2.6 micrometers. Thus, the array includes over 54 million pixels (>54 Mega-pixels) and, in one exemplary implementation, the complete array (MET pixels and associated circuitry) may be fabricated as an integrated circuit chip having dimensions of approximately 21 millimeters by 21 millimeters. Like the arrays 100A-100D of FIGS. 19-22, in one aspect the array 100E of FIG. 23 is divided into two groups of rows $400_1$ and $400_2$. However, unlike the arrays 100A-100D, for each row group the array 100E includes thirty-two column select registers and thirty-two output drivers to simultaneously read thirty-two pixels at a time in an enabled row, such that sixty-four output signals Vout1-Vout64 may be provided from the array 100E. In one exemplary implementation, complete data frames (all pixels from both the first and second row groups $400_1$ and $400_2$) may be acquired at a frame rate of 100 frames/sec, thereby requiring 3700 pairs of rows to be successively enabled for periods of approximately 3 microseconds each. For each enabled row, 230 pixels (7400/32) are read out by each column select register/output driver during approximately 700 nanoseconds. Thus, in this example, each of the array output signals Vout1-Vout64 has a data rate of approximately 328 MHz. As with the previous embodiments, it should be appreciated that in other implementations, data may be acquired from the array 100D at frame rates other than 100 frames/sec.

Thus, in various examples of ISFET arrays based on the inventive concepts disclosed herein, an array pitch of approximately nine (9) micrometers (e.g., a sensor surface area of less than ten micrometers by ten micrometers) allows an ISFET array including over 256,000 pixels (i.e., a 512 by 512 array), together with associated row and column select and bias/readout electronics, to be fabricated on a 7 millimeter by 7 millimeter semiconductor die, and a similar sensor array including over four million pixels (i.e., a 2048 by 2048 array, over 4 Mega-pixels) to be fabricated on a 21 millimeter by 21 millimeter die. In other examples, an array pitch of approximately 5 micrometers allows an ISFET array including approximately 1.55 Mega-pixels (i.e., a 1348 by 1152 array) and associated electronics to be fabricated on a 9 millimeter by 9 millimeter die, and an ISFET sensor array including over 14 Mega-pixels and associated electronics on a 22 millimeter by 20 millimeter die. In yet other implementations, using a CMOS fabrication process in which feature sizes of less than 0.35 micrometers are possible (e.g., 0.18 micrometer CMOS processing techniques), ISFET sensor arrays with a pixel size/pitch significantly below 5 micrometers may be fabricated (e.g., array pitch of 2.6 micrometers or pixel/sensor area of less than 8 or 9 micrometers$^2$), providing for significantly dense ISFET arrays.

In the embodiments of ISFET arrays discussed above, array pixels employ a p-channel ISFET, as discussed above in connection with FIG. 9. It should be appreciated, however, that ISFET arrays according to the present disclosure are not limited in this respect, and that in other embodiments pixel designs for ISFET arrays may be based on an n-channel ISFET. In particular, any of the arrays discussed above in connection with FIGS. 13 and 19-23 may be implemented with pixels based on n-channel ISFETs.

Figure 24:
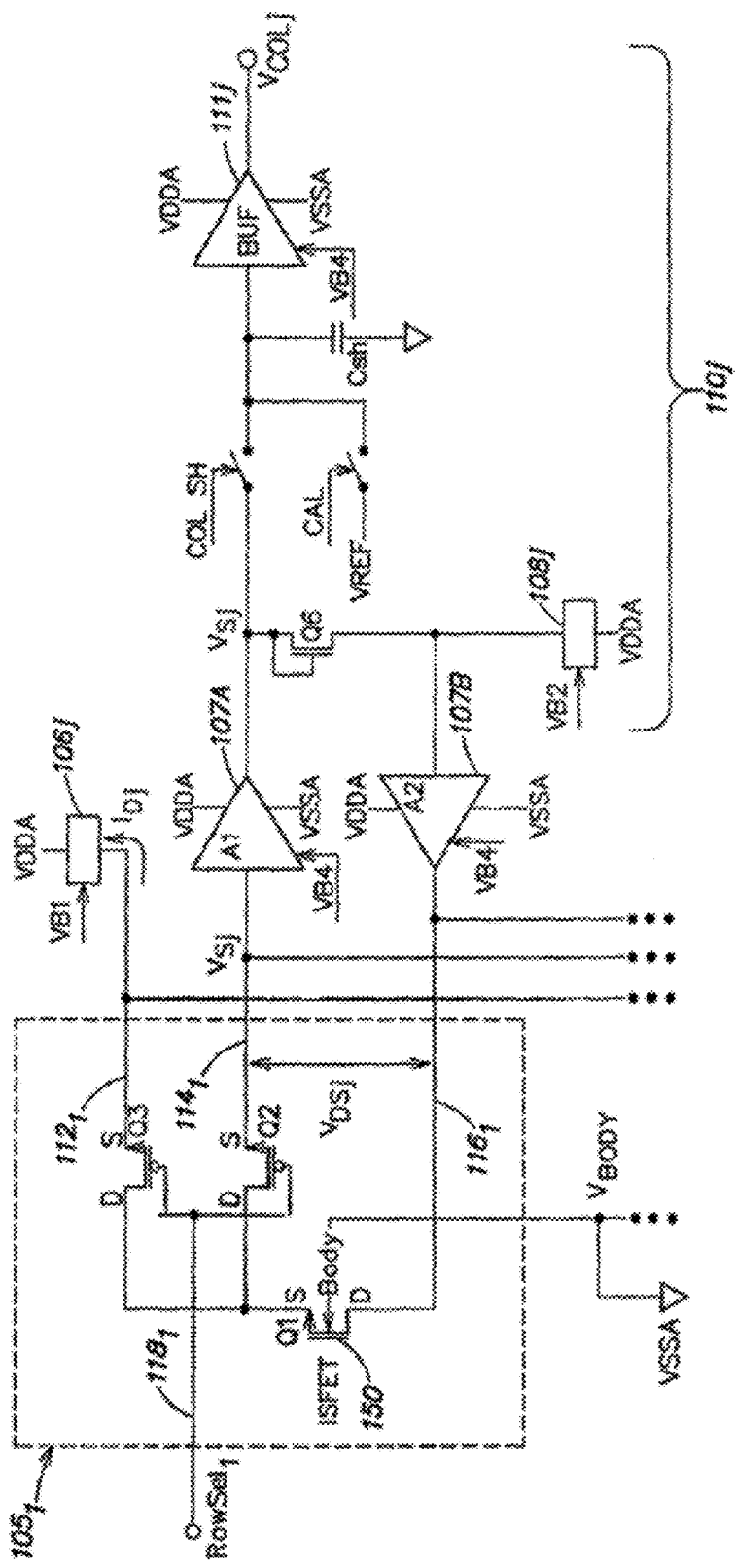
FIG. 24 illustrates the pixel design of FIG. 9 implemented with an n-channel channel chemFET and accompanying n-channel MOSFETs, according to another inventive embodiment of the present disclosure.

For example, FIG. 24 illustrates the pixel design of FIG. 9 implemented with an n-channel ISFET and accompanying n-channel MOSFETs, according to another inventive embodiment of the present disclosure. More specifically, FIG. 24 illustrates one exemplary pixel $105_1$ of an array column (i.e., the first pixel of the column), together with column bias/readout circuitry $110j$, in which the ISFET 150 (Q1) is an n-channel ISFET. Like the pixel design of FIG. 9, the pixel design of FIG. 24 includes only three components, namely, the ISFET 150 and two n-channel MOSFET switches Q2 and Q3, responsive to one of n row select signals (RowSel$_1$ through RowSel$_n$, logic high active). No transmission gates are required in the pixel of FIG. 24, and all devices of the pixel are of a "same type," i.e., n-channel devices. Also like the pixel design of FIG. 9, only four signal lines per pixel, namely the lines $112_1$, $114_1$, $116_1$ and $118_1$, are required to operate the three components of the pixel $105_1$ shown in FIG. 24. In other respects, the pixel designs of FIG. 9 and FIG. 24 are similar, in that they am both configured with a constant drain current $I_{Dj}$ and a constant drain-to-source voltage $V_{DSj}$ to obtain an output signal $V_{Sj}$ from an enabled pixel.

One of the primary differences between the n-channel ISFET pixel design of FIG. 24 and the p-channel ISFET design of FIG. 9 is the opposite direction of current flow through the pixel. To this end, in FIG. 24, the element $106_j$ is a controllable current sink coupled to the analog circuitry supply voltage ground VSSA, and the element $108_j$ of the bias/readout circuitry $110j$ is a controllable current source coupled to the analog positive supply voltage VDDA. Additionally, the body connection of the ISFET 150 is not tied to its source, but rather to the body connections of other ISFETs of the array, which in turn is coupled to the analog ground VSSA, as indicated in FIG. 24.

Figure 25:
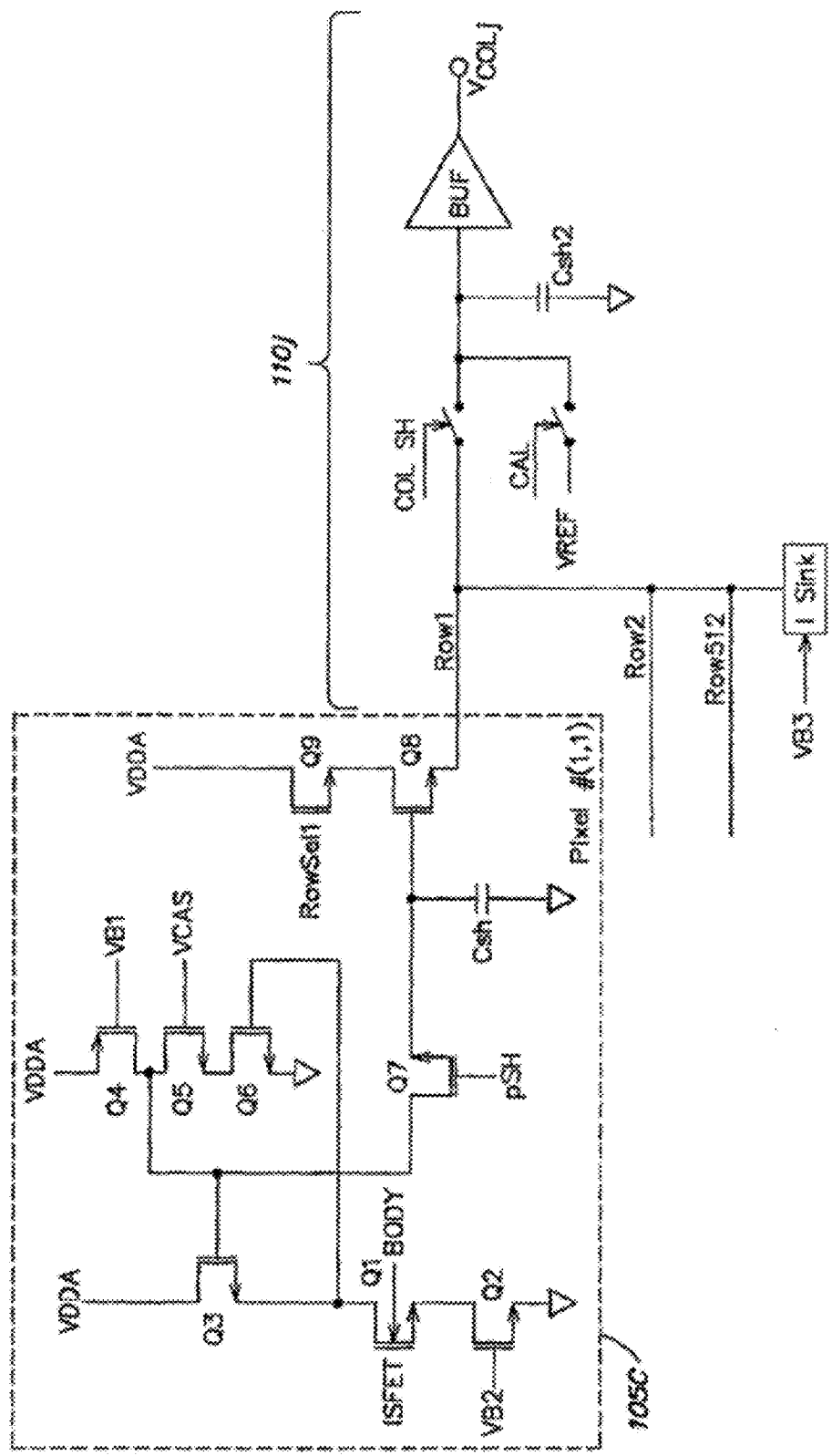
FIGS. 25-27 illustrate alternative pixel designs and associated column circuitry for chemFET arrays according to other inventive embodiments of the present disclosure.
Figure 26:
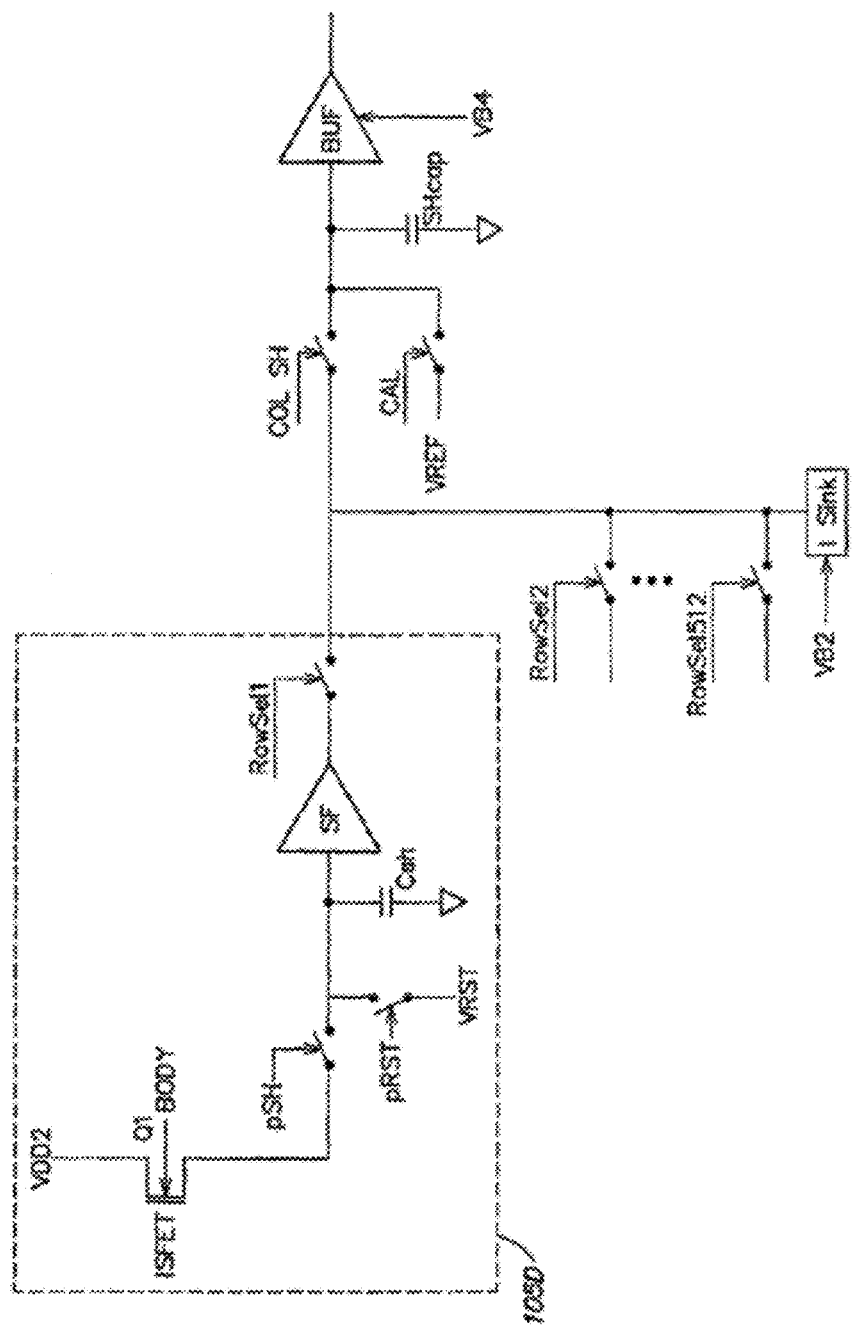
Figure 27:
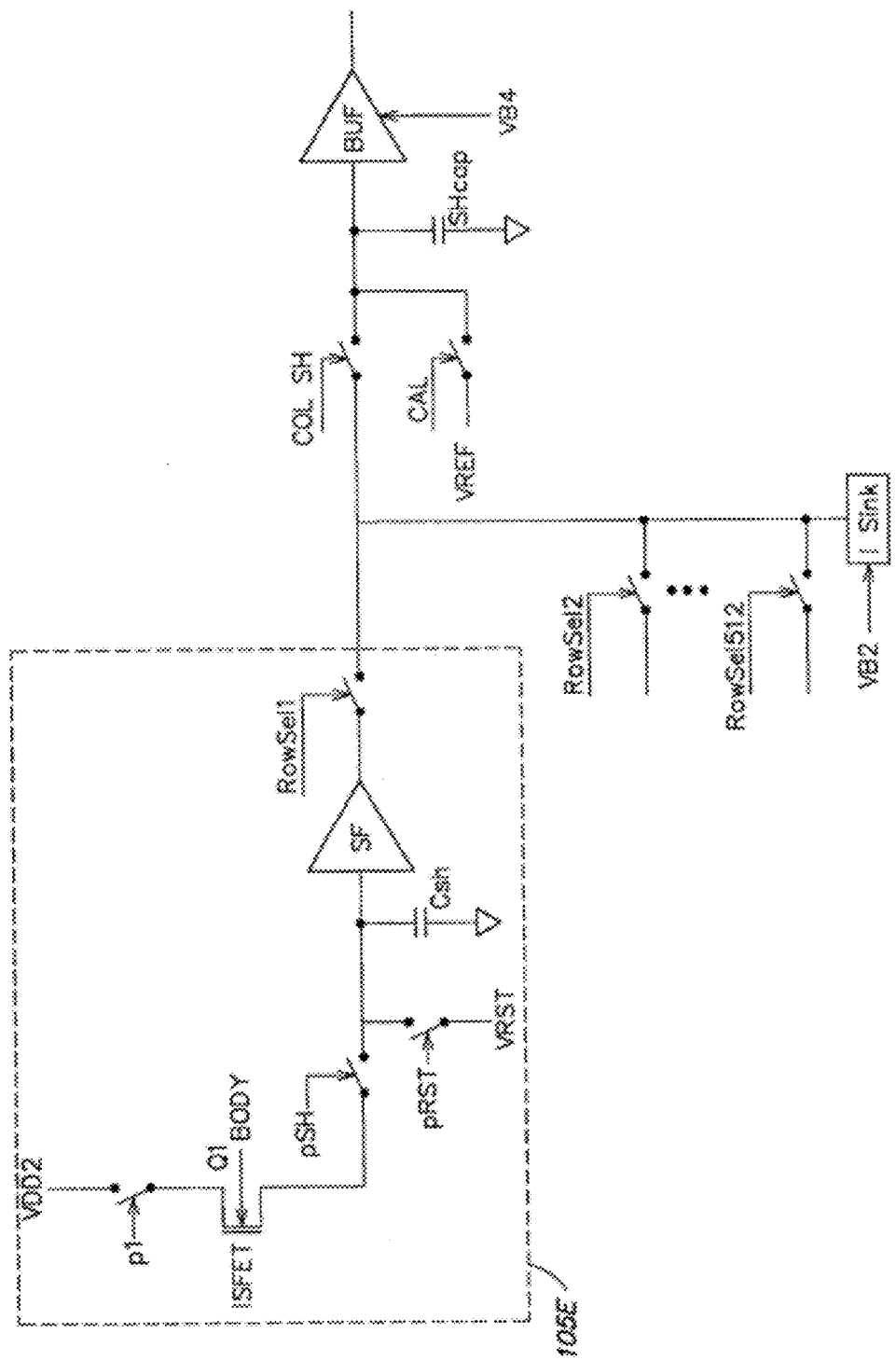

In addition to the pixel designs shown in FIGS. 9 and 24 (based on a constant ISFET drain current and constant ISFET drain-source voltage), alternative pixel designs are contemplated for ISFET arrays, based on both p-channel ISFETs and n-channel ISFETs, according to yet other inventive embodiments of the present disclosure, as illustrated in FIGS. 25-27. As discussed below, some alternative pixel designs may require additional and/or modified signals from the array controller 250 to facilitate data acquisition. In particular, a common feature of the pixel designs shown in FIGS. 25-27 includes a sample and hold capacitor within each pixel itself, in addition to a sample and hold capacitor for each column of the array. While the alternative pixel designs of FIGS. 25-27 generally include a greater number of components than the pixel designs of FIGS. 9 and 24, the feature of a pixel sample and hold capacitor enables "snapshot" types of arrays, in which all pixels of an array may be enabled simultaneously to sample a complete frame and acquire signals representing measurements of one or more analytes in proximity to respective ISFETs of the array. In some applications, this may provide for higher data acquisition speeds and/or improved signal sensitivity (e.g., higher signal-to-noise ratio).

FIG. 25 illustrates one such alternative design for a single pixel 105C and associated column circuitry $110j$. The pixel 105C employs an n-channel ISFET and is based generally on the premise of providing a constant voltage across the ISFET Q1 based on a feedback amplifier (Q4, Q5 and Q6). In particular, transistor Q4 constitutes the feedback amplifier load, and the amplifier current is set by the bias voltage VB1 (provided by the array controller), Transistor Q5 is a common gate amplifier and transistor Q6 is a common source amplifier. Again, the purpose of feedback amplifier is to hold the voltage across the ISFET Q1 constant by adjusting the current supplied by transistor Q3. Transistor Q2 limits the maximum current the ISFET Q1 can draw (e.g., so as to prevent damage from overheating a very large array of pixels). This maximum current is set by the bias voltage VB2 (also provided by the array controller). In one aspect of the pixel design shown in FIG. 25, power to the pixel 105C may be turned off by setting the bias voltage VB2 to 0 Volts and the bias voltage VB1 to 3.3 Volts. In this manner, the power supplied to large arrays of such pixels may be modulated (turned on for a short time period and then off by the array controller) to obtain ion concentration measurements while at the same time reducing overall power consumption of the array. Modulating power to the pixels also reduces heat dissipation of the array and potential heating of the analyte solution, thereby also reducing any potentially deleterious effects from sample heating.

In FIG. 25, the output of the feedback amplifier (the gate of transistor Q3) is sampled by MOS switch Q7 and stored on a pixel sample and hold capacitor Csh within the pixel itself. The switch Q7 is controlled by a pixel sample and hold signal pSH (provided to the array chip by the array controller), which is applied simultaneously to all pixels of the array so as to simultaneously store the readings of all the pixels on their respective sample and hold capacitors. In this manner, arrays based on the pixel design of FIG. 25 may be considered as "snapshot" arrays, in that a full frame of data is sampled at any given time, rather than sampling successive rows of the array. After each pixel value is stored on the corresponding pixel sample and hold capacitor Csh, each pixel 105C (ISFET and feedback amplifier) is free to acquire another pH reading or it can by turned off to conserve power.

In FIG. 25, the pixel values stored on all of the pixel sample and hold capacitors Csh are applied to the column circuitry 110$j$ one row at a time through source follower Q8, which is enabled via the transistor Q9 in response to a row select signal (e.g., RowSel1). In particular, after a row is selected and has settled out, the values stored in the pixel sample and hold capacitors are then in turn stored on the column sample and hold capacitors Csh2, as enabled by the column sample and hold signal COL_SH, and provided as the column output signal $V_{COLj}$.

FIG. 26 illustrates another alternative design for a single pixel 105D and associated column circuitry 110$j$, according to one embodiment of the present disclosure. In this embodiment, the ISFET is shown as a p-channel device. At the start of a data acquisition cycle, CMOS switches controlled by the signals pSH (pixel sample/hold) and pRST (pixel reset) are closed (these signals are supplied by the array controller). This pulls the source of ISFET (Q1) to the voltage VRST. Subsequently, the switch controlled by the signal pRST is opened, and the source of ISFET Q1 pulls the pixel sample and hold capacitor Csh to a threshold below the level set by pH. The switch controlled by the signal pSH is then opened, and the pixel output value is coupled, via operation of a switch responsive to the row select signal RowSel1, to the column circuitry 110$j$ to provide the column output signal $V_{COLj}$. Like the pixel design in the embodiment illustrated in FIG. 25, arrays based on the pixel 105D are "snapshot" type arrays in that all pixels of the array may be operated simultaneously. In one aspect, this design allows a long simultaneous integration time on all pixels followed by a high-speed read out of an entire frame of data.

FIG. 27 illustrates yet another alternative design for a single pixel 105E and associated column circuitry 110$j$, according to one embodiment of the present disclosure. In this embodiment, again the ISFET is shown as a p-channel device. At the start of a data acquisition cycle, the switches operated by the control signals p1 and pRST are briefly closed. This clears the value stored on the sampling capacitor Csh and allows a charge to be stored on ISFET (Q1), Subsequently, the switch controlled by the signal pSH is closed, allowing the charge stored on the ISFET Q1 to be stored on the pixel sample and hold capacitor Csh. The switch controlled by the signal pSH is then opened, and the pixel output value is coupled, via operation of a switch responsive to the row select signal RowSel1, to the column circuitry 110$j$ to provide the column output signal $V_{COLj}$. Gain may be provided in the pixel 105E via the ratio of the ISFET capacitance to the Csh cap, i.e., gain=$C_{Q1}/C_{sh}$ or by enabling the pixel multiple times (i.e., taking multiple samples of the analyte measurement) and accumulating the ISFET output on the pixel sample and hold capacitor Csh without rescuing the capacitor (i.e., gain is a function of the number of accumulations). Like the embodiments of FIGS. 25 and 26, arrays based on the pixel 105D are "snapshot" type arrays in that all pixels of the array may be operated simultaneously.

Computer Hardware and Software

With respect to the computer interface 252 of the array controller 250, in one exemplary implementation the interface is configured to facilitate a data rate of approximately 200 MB/sec to the computer 260, and may include local storage of up to 400 MB or greater. The computer 260 is configured to accept data at a rate of 200 MB/sec, and process the data so as to reconstruct an image of the pixels (e.g., which may be displayed in false-color on a monitor). For example, the computer may be configured to execute a general-purpose program with routines written in C++ or Visual Basic to manipulate the data and display is as desired.

The systems described herein, when used for sequencing, typically involve a chemFET array supporting reaction chambers, the chemFETs being coupled to an interface capable of executing logic that converts the signals from the chemFETs into sequencing information.

The sequencing information obtained from the system may be delivered to a handheld computing device, such as a personal digital assistant. Thus, in one embodiment, the invention encompasses logic for displaying a complete genome of an organism on a handheld computing device. The invention also encompasses logic adapted for sending data from a chemFET array to a handheld computing device. Any of such logic may be computer-implemented.

Microfluidics and Microwell Arrays

Figure 28A:
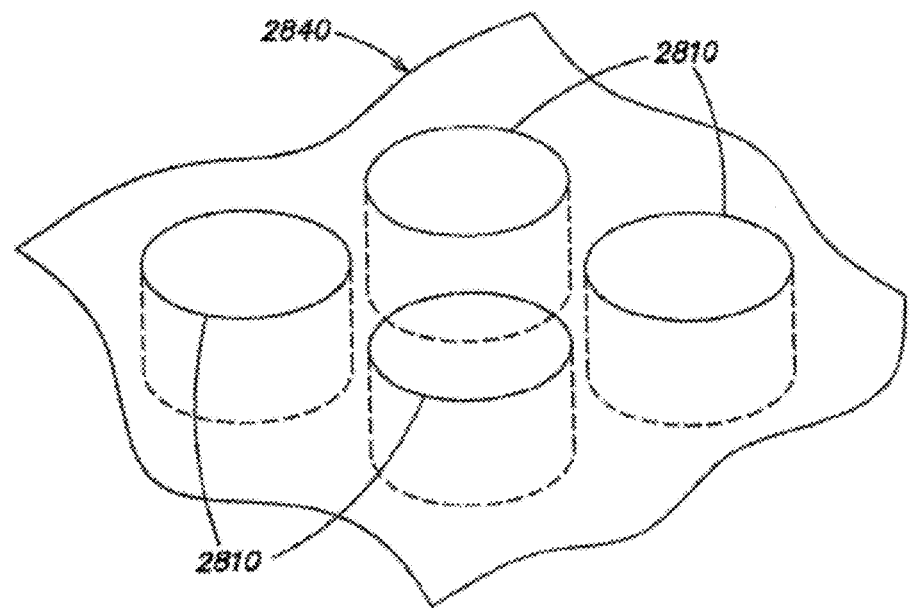
FIGS. 28A and 28B are isometric illustrations of portions of microwell arrays as employed herein, showing round wells and rectangular wells, to assist three-dimensional visualization of the array structures.
Figure 28B:
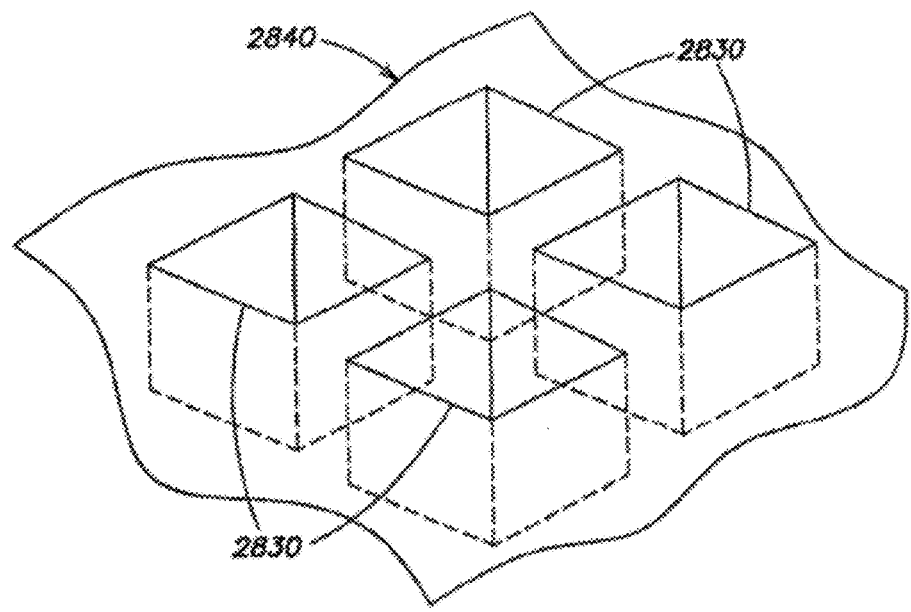

Turning from the sensor discussion, we will now be addressing the combining of the ISFET array with a microwell array and the attendant fluidics. As most of the drawings of the microwell array structure are presented only in cross-section or showing that array as only a block in a simplified diagram, FIGS. 28A and 28B are provided to assist the reader in beginning to visualize the resulting apparatus in three-dimensions. FIG. 28A shows a group of round cylindrical wells 2810 arranged in an array, while FIG. 28B shows a group of rectangular cross-section wells 2830 arranged in an array. It will be seen that the wells are separated (isolated) from each other by the material 2840 forming the well walls. While it is certainly possible to fabricate wells of other cross-sections, in some embodiments it may not be advantageous to do so. Such an array of microwells sits over the above-discussed ISFET array, with one or more ISFETs per well. In the subsequent drawings, when the microwell array is identified, one may picture one of these arrays.

Fluidic System: Apparatus and Method for Use with High Density Electronic Sensor Arrays For many uses, to complete a system for sensing chemical reactions or chemical agents using the above-explained high density electronic arrays, techniques and apparatus are required for delivery to the array elements (called "pixels") fluids containing chemical or biochemical components for sensing. In this section, exemplary techniques and methods will be illustrated, which are useful for such purposes, with desirable characteristics.

As high speed operation of the system may be desired, it is preferred that the fluid delivery system, insofar as possible, not limit the speed of operation of the overall system.

Accordingly, needs exist not only for high-speed, high-density arrays of ISFETs or other elements sensitive to ion concentrations or other chemical attributes, or changes in chemical attributes, but also for related mechanisms and techniques for supplying to the array elements the samples to be evaluated, in sufficiently small reaction volumes as to substantially advance the speed and quality of detection of the variable to be sensed.

There are two and sometimes three components or subsystems, and related methods, involved in delivery of the subject chemical samples to the array elements: (1) macrofluidic system of reagent and wash fluid supplies and appropriate valving and ancillary apparatus, (2) a flow cell and (3) in many applications, a microwell array. Each of these subsystems will be discussed, though in reverse order.

Microwell Array

As discussed elsewhere, for many uses, such as in DNA sequencing, it is desirable to provide over the array of semiconductor sensors a corresponding array of microwells, each microwell being small enough preferably to receive only one DNA-loaded bead, in connection with which an underlying pixel in the array will provide a corresponding output signal.

The use of such a microwell array involves three stages of fabrication and preparation, each of which is discussed separately: (1) creating the array of microwells to result in a chip having a coat comprising a microwell array layer; (2) mounting of the coated chip to a fluidic interface; and in the case of DNA sequencing, (3) loading DNA-loaded bead or beads into the wells. It will be understood, of course, that in other applications, beads may be unnecessary or beads having different characteristics may be employed.

The systems described herein can include an array of microfluidic reaction chambers integrated with a semiconductor comprising an array of chemFETs. In some embodiments, the invention encompasses such an array. The reaction chambers may, for example, be formed in a glass, dielectric, photodefineable or etchable material. The glass material may be silicon dioxide.

Preferably, the array comprises at least 100,000 chambers. Preferably, each reaction chamber has a horizontal width and a vertical depth that has an aspect ratio of about 1:1 or less. Preferably, the pitch between the reaction chambers is no more than about 10 microns.

The above-described array can also be provided in a kit for sequencing. Thus, in some embodiments, the invention encompasses a kit comprising an array of microfluidic reaction chambers integrated with an array of chemFETs, and one or more amplification reagents.

In some embodiments, the invention encompasses a sequencing apparatus comprising a dielectric layer overlying a chemFET, the dielectric layer having a recess laterally centered atop the chemFET. Preferably, the dielectric layer is formed of silicon dioxide.

Microwell Array Fabrication

Microwell fabrication may be accomplished in a number of ways. The actual details of fabrication may require some experimentation and vary with the processing capabilities that are available.

In general, fabrication of a high density array of microwells involves photo-lithographically patterning the well may configuration on a layer or layers of material such as photoresist (organic or inorganic), a dielectric, using an etching process. The patterning may be done with the material on the sensor array or it may be done separately and then transferred onto the sensor array chip, of some combination of the two. However, techniques other than photolithography are not to be excluded if they provide acceptable results.

Figure 29:
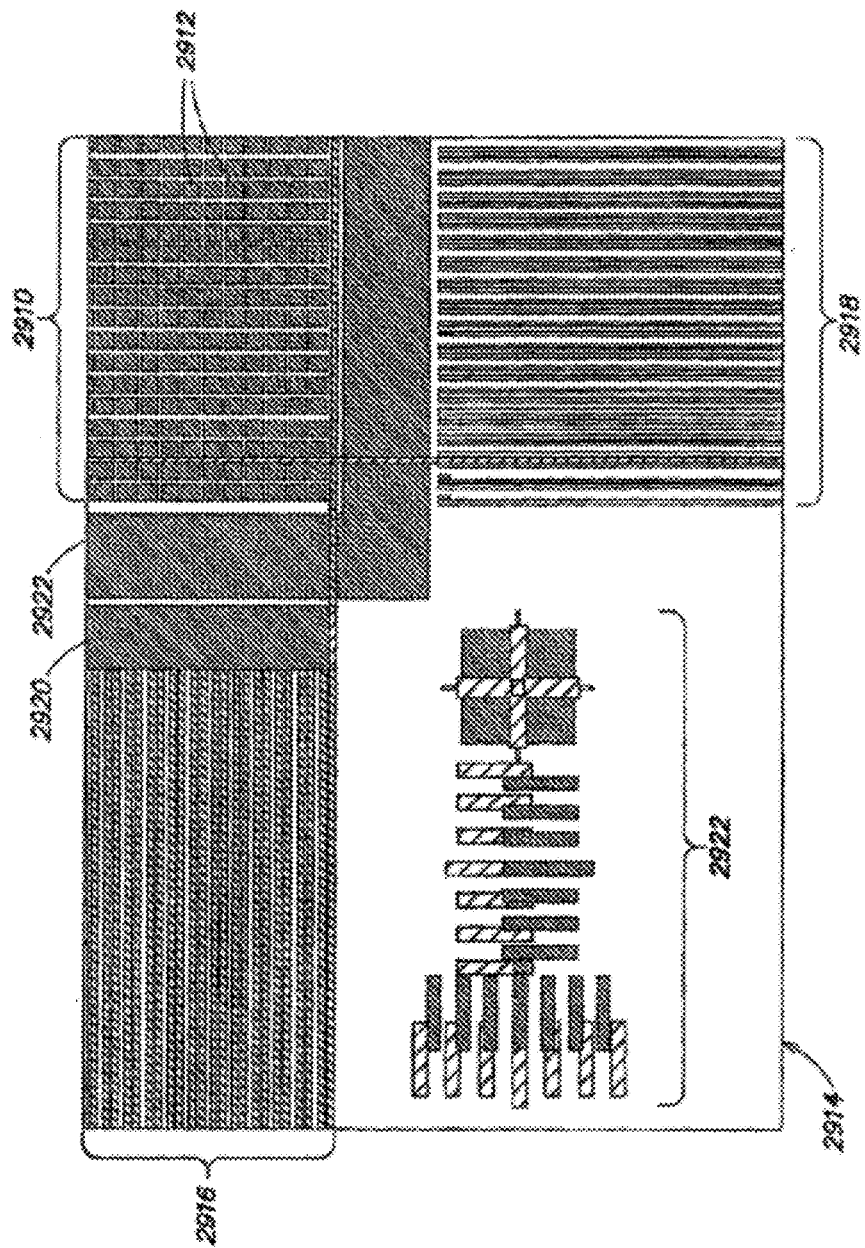
FIG. 29 is a diagrammatic depiction of a top view of one corner (i.e., the lower left corner) of the layout of a chip showing an array of individual ISFET sensors on a CMOS die.

One example of a method for forming a microwell array is now discussed, starting with reference to FIG. 29. That figure diagrammatically depicts a top view of one corner (i.e., the lower left collier) of the layout of a chip showing an array 2910 of the individual ISFET sensors 2912 on the CMOS die 2914. Signal lines 2916 and 2918 are used for addressing the array and reading its output. Block 2920 represents some of the electronics for the array, as discussed above, and layer 2922 represents a portion of a wall which becomes part of a microfluidics structure, the flow cell, as more fully explained below; the flow cell is that structure which provides a fluid flow over the microwell array or over the sensor surface directly, if there is no microwell structure. On the surface of the die, a pattern such as pattern 2922 at the bottom left of FIG. 29 may be formed during the semiconductor processing to form the ISFETs and associated circuitry, for use as alignment marks for locating the wells over the sensor pixels when the dielectric has covered the die's surface.

After the semiconductor structures, as shown, are formed, the microwell structure is applied to the die. That is, the microwell structure can be formed right on the die or it may be formed separately and then mounted onto the die, either approach being acceptable. To form the microwell structure on the die, various processes may be used. For example, the entire die may be spin-coated with, for example, a negative photoresist such as Microchem's SU-8 2015 or a positive resist/polyimide such as HD Microsystems HD8820, to the desired height of the microwells. The desired height of the wells (e.g., about 4-12 µm in the example of one pixel per well, though not so limited as a general matter) in the photoresist layer(s) can be achieved by spinning the appropriate resist at predetermined rates (which can be found by reference to the literature and manufacturer specifications, or empirically), in one or more layers. (Well height typically may be selected in correspondence with the lateral dimension of the sensor pixel, preferably for a nominal 1:1-1.5:1 aspect ratio, height:width or diameter. Based on signal-to-noise considerations, there is a relationship between dimensions and the required data sampling rates to achieve a desired level of performance. Thus there are a number of factors that will go into selecting optimum parameters for a given application.) Alternatively, multiple layers of different photoresists may be applied or another form of dielectric material may be deposited. Various types of chemical vapor deposition may also be used to build up a layer of materials suitable for microwell formation therein.

Once the photoresist layer (the singular form "layer" is used to encompass multiple layers in the aggregate, as well) is in place, the individual wells (typically mapped to have either one or four ISFET sensors per well) may be generated by placing a mask (e.g., of chromium) over the resist-coated die and exposing the resist to cross-linking (typically UV) radiation. All resist exposed to the radiation (i.e., where the mask does not block the radiation) becomes cross-linked and as a result will form a permanent plastic layer bonded to the surface of the chip (die). Unreacted resist (i.e., resist in areas which are not exposed, due to the mask blocking the light from reaching the resist and preventing cross-linking) is removed by washing the chip in a suitable solvent (i.e., developer) such as propyleneglycolmethylethylacetate (PGMEA) or other appropriate solvent. The resultant structure defines the walls of the microwell array.

Figure 30:
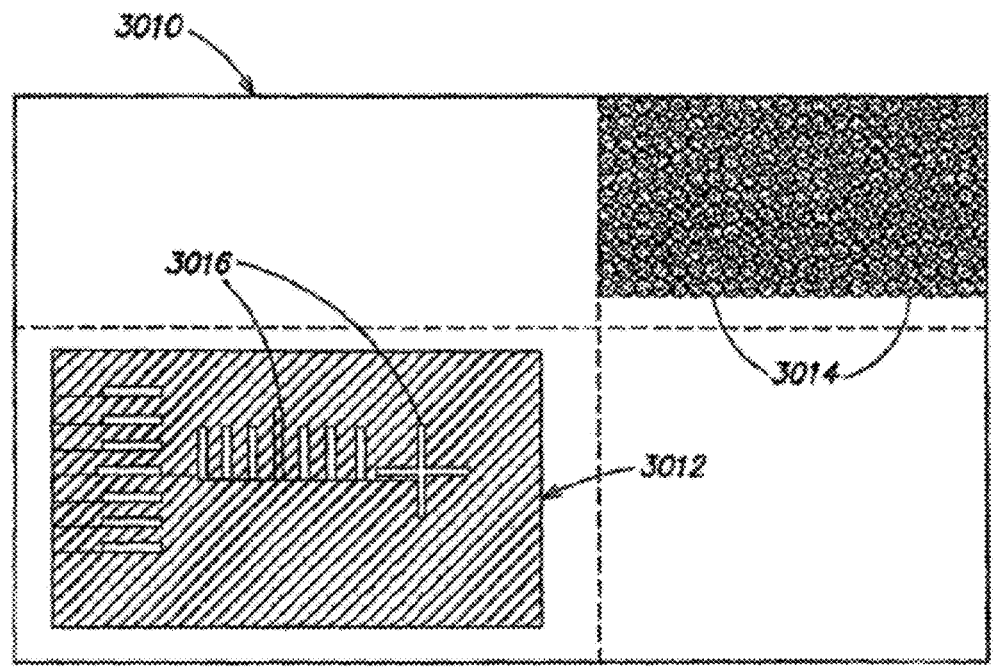
FIG. 30 is an illustration of an example of a layout for a portion of a (typically chromium) mask for a one-sensor-per-well embodiment of the above-described sensor array, corresponding to the portion of the die shown in FIG. 29.

FIG. 30 shows an example of a layout for a portion of a chromium mask 3010 for a one-sensor-per-well embodiment, corresponding to the portion of the die shown in FIG. 29. The grayed areas 3012, 3014 are those that block the UV radiation. The alignment marks in the white portions 3016 on the bottom left quadrant of FIG. 30, within gray area 3012, are used to align the layout of the wells with the ISFET sensors on the chip surface. The array of circles 3014 in the upper right quadrant of the mask block radiation from reaching the well areas, to leave unreacted resist which can be dissolved in forming the wells.

Figure 31:
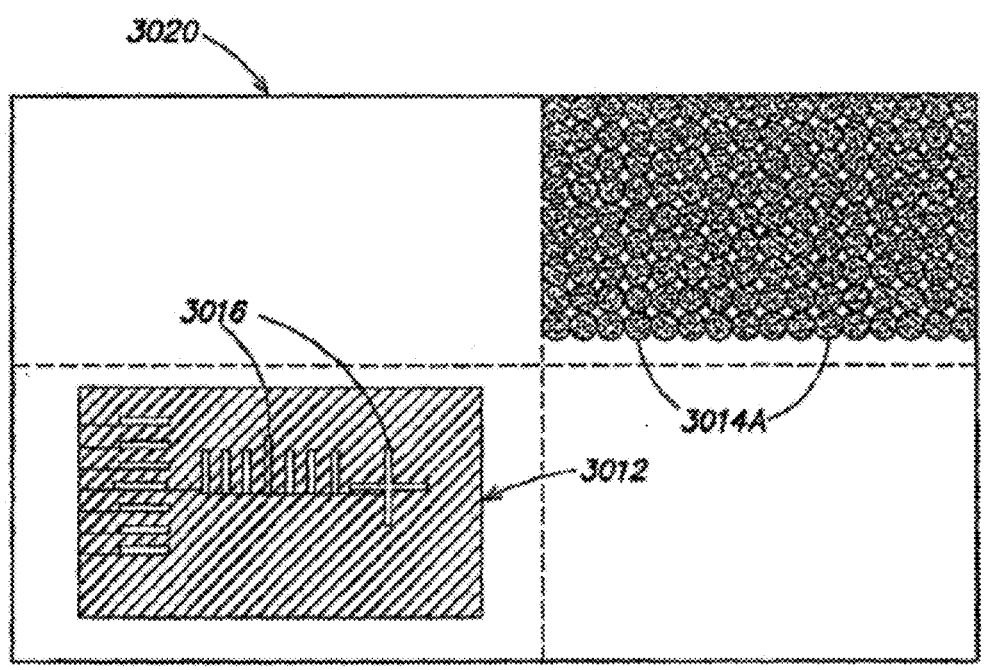
FIG. 31 is a corresponding layout for a mask for a 4-sensors-per-well embodiment.

FIG. 31 shows a corresponding layout for the mask 3020 for a 4-sensors-per-well embodiment. Note that the alignment pattern 3016 is still used and that the individual well-masking circles 3014A in the array 2910 now have twice the diameter as the wells 3014 in FIG. 30, for accommodating four sensors per well instead of one sensor-per-well.

Figure 32:
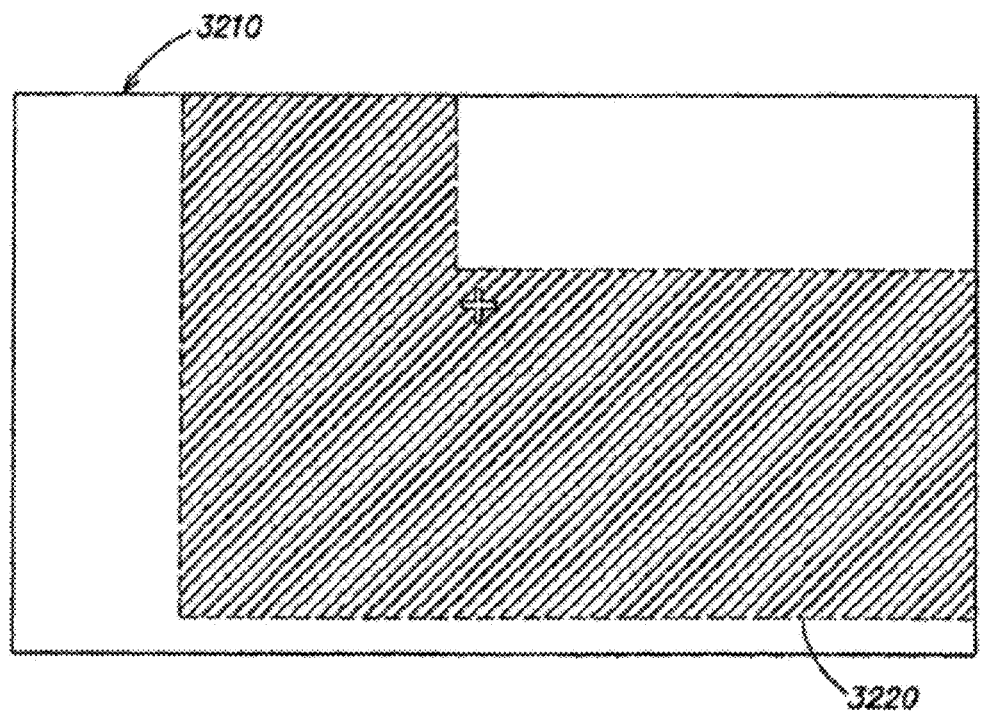
FIG. 32 is an illustration of a second mask used to mask an area which surrounds the array, to build a collar or wall (or basin, using that term in the geological sense) of resist which surrounds the active array of sensors on a substrate, as shown in FIG. 33A.
Figure 33:
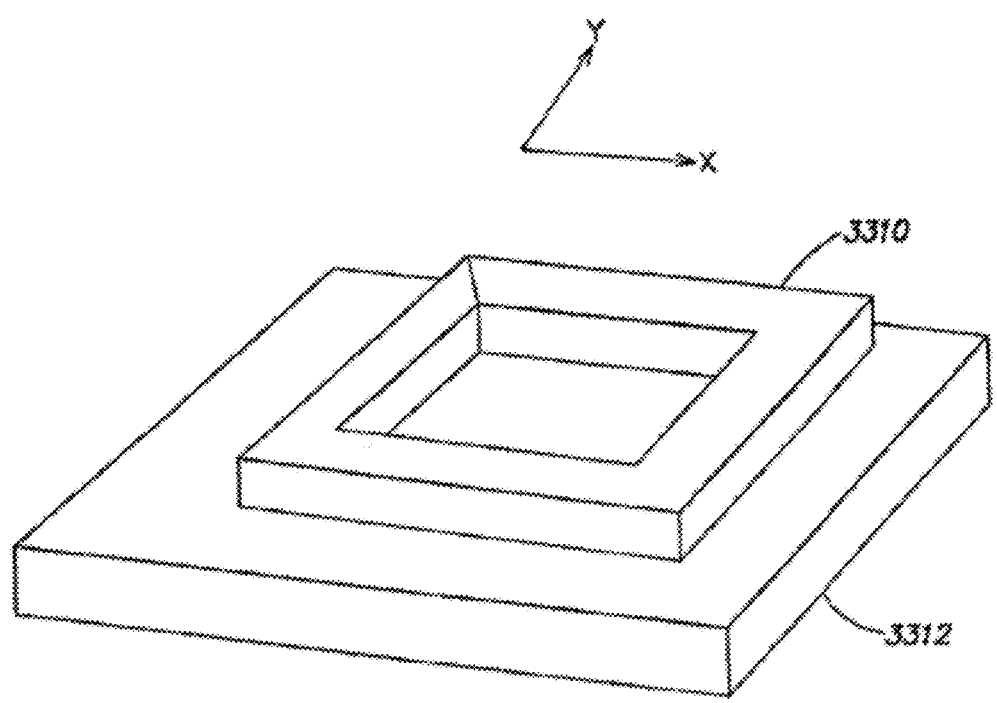
FIG. 33 is an illustration of the resulting basin.

After exposure of the die/resist to the UV radiation, a second layer of resist may be coated on the surface of the chip. This layer of resist may be relatively thick, such as about 400-450 μm thick, typically. A second mask 3210 (FIG. 32), which also may be of chromium, is used to mask an area 3220 which surrounds the array, to build a collar or wall (or basin, using that term in the geological sense) 3310 of resist which surrounds the active array of sensors on substrate 3312, as shown in FIG. 33. In the particular example being described, the collar is 150 μm wider than the sensor array, on each side of the array, in the x direction, and 9 μm wider on each side than the sensor array, in the y direction. Alignment marks on mask 3210 (most not shown) are matched up with the alignment marks on the first layer and the CMOS chip itself.

Other photolithographic approaches may be used for formation of the microwell array, of course, the foregoing being only one example.

For example, contact lithography of various resolutions and with various etchants and developers may be employed. Both organic and inorganic materials may be used for the layer(s) in which the microwells are formed. The layer(s) may be etched on a chip having a dielectric layer over the pixel structures in the sensor array, such as a passivation layer, or the layer(s) may be formed separately and then applied over the sensor array. The specific choice or processes will depend on factors such as array size, well size, the fabrication facility that is available, acceptable costs, and the like.

Among the various organic materials which may be used in some embodiments to form the microwell layer(s) are the above-mentioned SU-8 type of negative-acting photoresist, a conventional positive-acting photoresist and a positive-acting photodefineable polyimide. Each has its virtues and its drawbacks, well known to those familiar with the photolithographic art.

Naturally, in a production environment, modifications will be appropriate.

Contact lithography has its limitations and it may not be the production method of choice to produce the highest densities of wells—i.e., it may impose a higher than desired minimum pitch limit in the lateral directions. Other techniques, such as a deep UV step-and-repeat process, are capable of providing higher resolution lithography and can be used to produce small pitches and possibly smaller well diameters. Of course, for different desired specifications (e.g., numbers of sensors and wells per chip), different techniques may prove optimal. And pragmatic factors, such as the fabrication processes available to a manufacturer, may motivate the use of a specific fabrication method. While novel methods are discussed, various aspects of the invention are limited to use of these novel methods.

Preferably the CMOS wafer with the ISFET array will be planarized after the final metallization process. A chemical mechanical dielectric planarization prior to the silicon nitride passivation is suitable. This will allow subsequent lithographic steps to be done on very flat surfaces which are free of back-end CMOS topography.

By utilizing deep-UV step-and-repeat lithography systems, it is possible to resolve small features with superior resolution, registration, and repeatability. However, the high resolution and large numerical aperture (NA) of these systems precludes their having a large depth of focus. As such, it may be necessary, when using such a fabrication system, to use thinner photodefinable spin-on layers (i.e., resists on the order of 1-2 μm rather than the thicker layers used in contact lithography) to pattern transfer and then etch microwell features to underlying layer or layers. High resolution lithography can then be used to pattern the microwell features and conventional $SiO_2$ etch chemistries can be used—one each for the bondpad areas and then the microwell areas—having selective etch stops; the etch stops then can be on aluminum bondpads and silicon nitride passivation (or the like), respectively. Alternatively, other suitable substitute pattern transfer and etch processes can be employed to render microwells of inorganic materials.

Another approach is to form the microwell structure in an organic material. For example, a dual-resist "soft-mask" process may be employed, whereby a thin high-resolution deep-UV resist is used on top of a thicker organic material (e.g., cured polyimide or opposite-acting resist). The top resist layer is patterned. The pattern can be transferred using an oxygen plasma reactive ion etch process. This process sequence is sometimes referred to as the "portable conformable mask" (PCM) technique. See B. J. Lin et al., "Practicing the Novolac deep-UV portable conformable masking technique", Journal of Vacuum Science and Technology 19, No. 4, 1313-1319 (1981); and A. Cooper et al, "Optimization of a photosensitive spin-on dielectric process for copper inductor coil and interconnect protection in RF SoC devices."

Alternatively a "drill-focusing" technique may be employed, whereby several sequential step-and-repeat exposures are done at different focal depths to compensate for the limited depth of focus (DOF) of high-resolution steppers when patterning thick resist layers. This technique depends on the stepper NA and DOF as well as the contrast properties of the resist material.

Figure 33A:
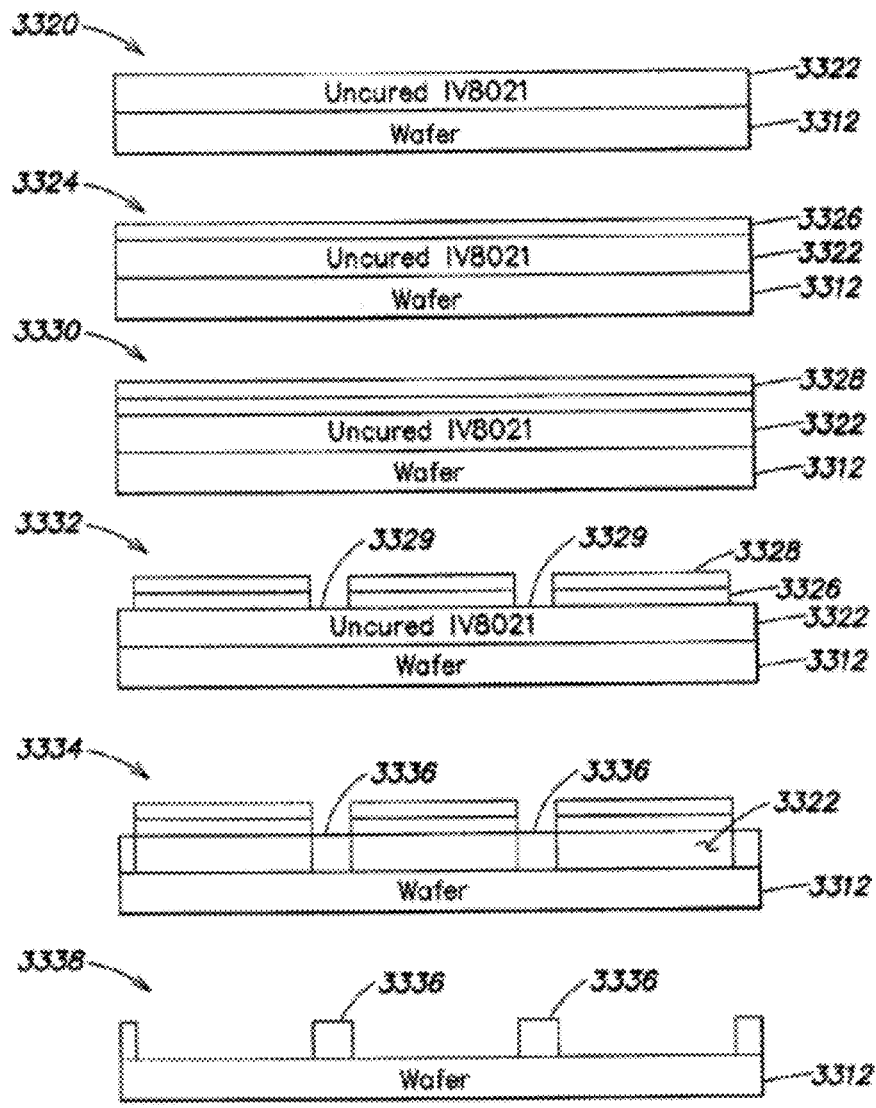
FIG. 33A is an illustration of a three-layer PCM process for making the microwell array.

Another PCM technique may be adapted to these purposes, such as that shown in U.S. patent application publication no. 2006/0073422 by Edwards et al. This is a three-layer PCM process and it is illustrated in FIG. 33A. As shown there, basically six major steps are required to produce the microwell array and the result is quite similar to what contact lithography would yield.

In a first step, 3320, a layer of high contrast negative-acting photoresist such as type Shipley InterVia Photodielectric Material 8021 (IV8021) 3322 is spun on the surface of a wafer, which we shall assume to be the wafer providing the substrate 3312 of FIG. 33 (in which the sensor array is fabricated), and a soft bake operation is performed, Next, in step 3324, a blocking anti-reflective coating (BARC) layer 3326, is applied and soft baked. On top of this structure, a thin resist layer 3328 is spun on and soft baked, step 3330, the thin layer of resist being suitable for fine feature definition. The resist layer 3328 is then patterned, exposed and developed, and the BARC in the exposed regions 3329, not protected any longer by the resist 3328, is removed, Step 3332. This opens up regions 3329 down to the uncured IV8021 layer. The BARC layer can now act like a conformal contact mask A blanket exposure with a flooding exposure tool, Step 3334, crosslinks the exposed IV8021, which is now shown as distinct from the uncured IV8021 at 3322. One or more developer steps 3338 are then performed, removing everything but the cross-linked IV8021 in regions 3336. Regions 3336 now constitute the walls of the microwells.

Although as shown above, the wells bottom out (i.e. terminate) on the top passivation layer of the ISFETs, it is believed that an improvement in ISFET sensor performance (i.e. such as signal-to-noise ratio) can be obtained if the active bead(s) is(are) kept slightly elevated from the ISFET passivation layer. One way to do so is to place a spacer "bump" within the boundary of the pixel microwell. An example of how this could be rendered would be not etching away a portion of the layer-or-layers used to form the microwell structure (i.e. two lithographic steps to form the microwells—one to etch part way done, the other to pattern the bump and finish the etch to bottom out), by depositing and lithographically defining and etching a separate layer to form the "bump", by using a permanent photo-definable material for the bump once the microwells are complete, or by forming the bump prior to forming the microwell. The bump feature is shown as 3350 in FIG. 33B. An alternative (or additional) non-integrated approach is to load the wells with a layer or two of very small packing beads before loading the DNA-bearing beads.

Figure 33B:
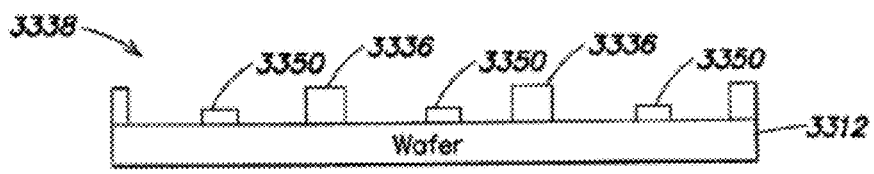
FIG. 33B is a diagrammatic cross-section of a microwell with a "bump" feature etched into the bottom.
Figures 1, 33B:
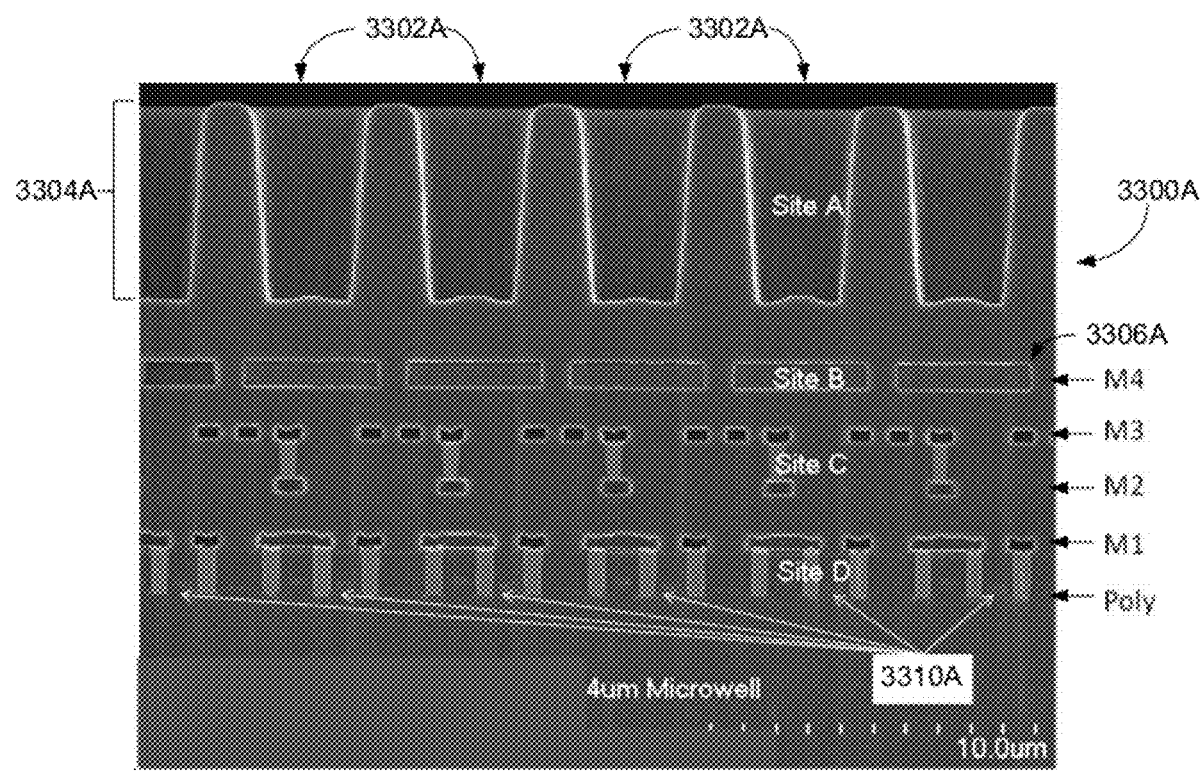
Figures 2, 33B:
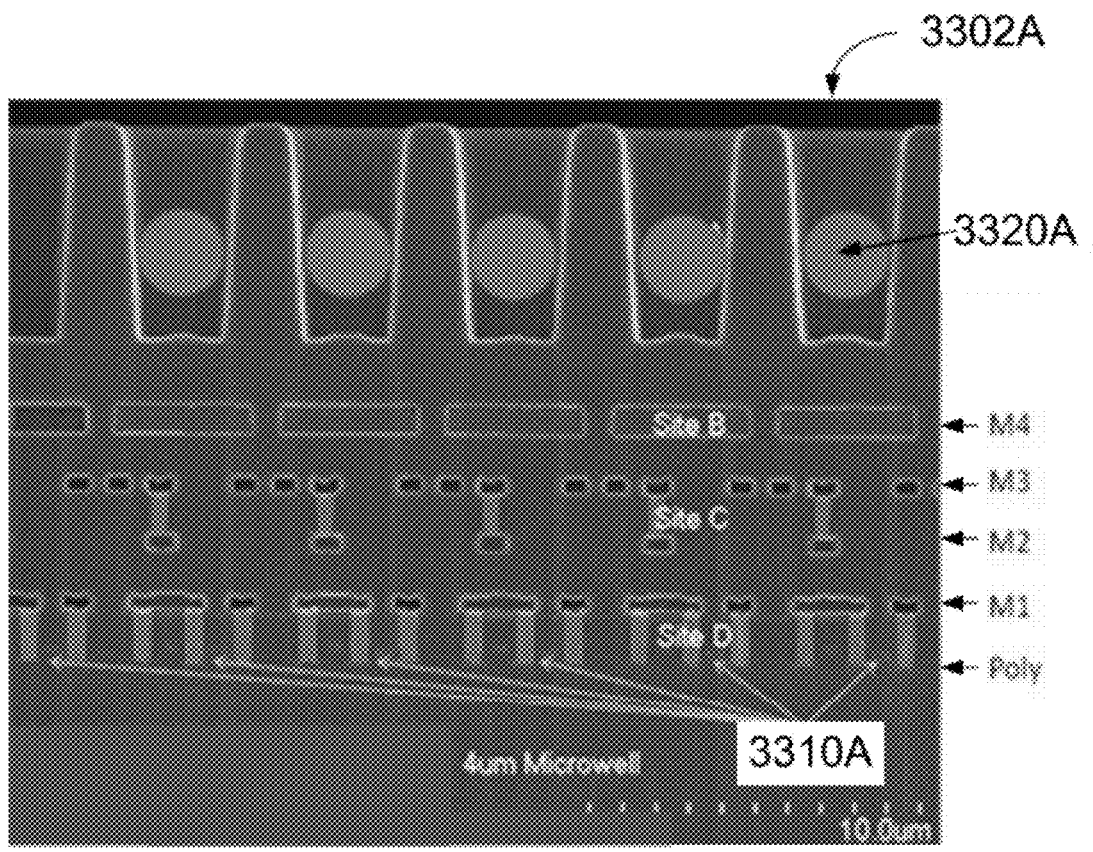
Figures 3, 33B:
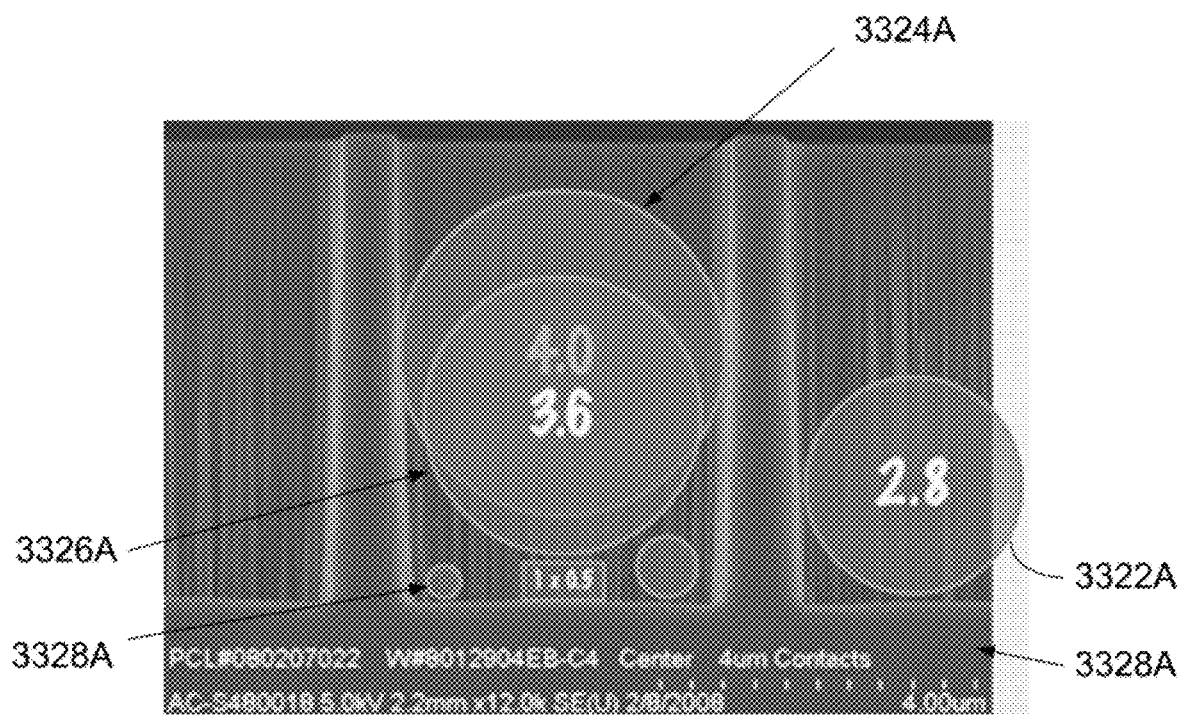

Using a 6 micron thick layer of tetra-methyl-ortho-silicate (TEOS) as a $SiO_2$-like layer for microwell formation, FIG. 33B-1 shows a scanning electron microscope (SEM) image of a cross-section of a portion 3300A of an array architecture as taught herein. Microwells 3302A are formed in the TEOS layer 3304A. The wells extend about 4 µm into the 6 µm thick layer. Typically, the etched well bottoms are an etch-stop material which may be, for example, an oxide, an organic material or other suitable material known in semiconductor processing for etch-stopping use. A thin layer of etch stop material may be formed on top of a thicker layer of polyimide or other suitable dielectric, such that there is about 2 µm of etch stop-1-polyimide between the well bottom and the Metal4 (M4) layer of the chip in which the extended gate electrode 3308A is formed for each underlying ISFET in the array. As labeled on the side, the CMOS metallization layers M3, M2 and M1, which form lower level interconnects and structures, are shown, with the ISFET channels being formed in the areas indicated by arrows 3310A.

In the orthogonal cross-sectional view (i.e., looking down from the top), the wells may be formed in either round or square shape. Round wells may improve bead capture and may obviate the need for packing beads at the bottom or top of the wells.

Figure 2:
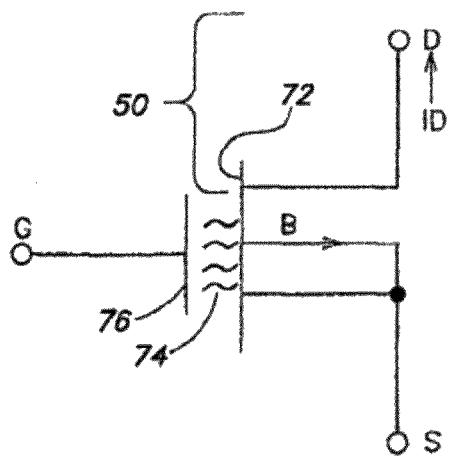
FIG. 2 illustrates an electric circuit representation of the p-channel ISFET shown in FIG. 1.
Figure 2A:
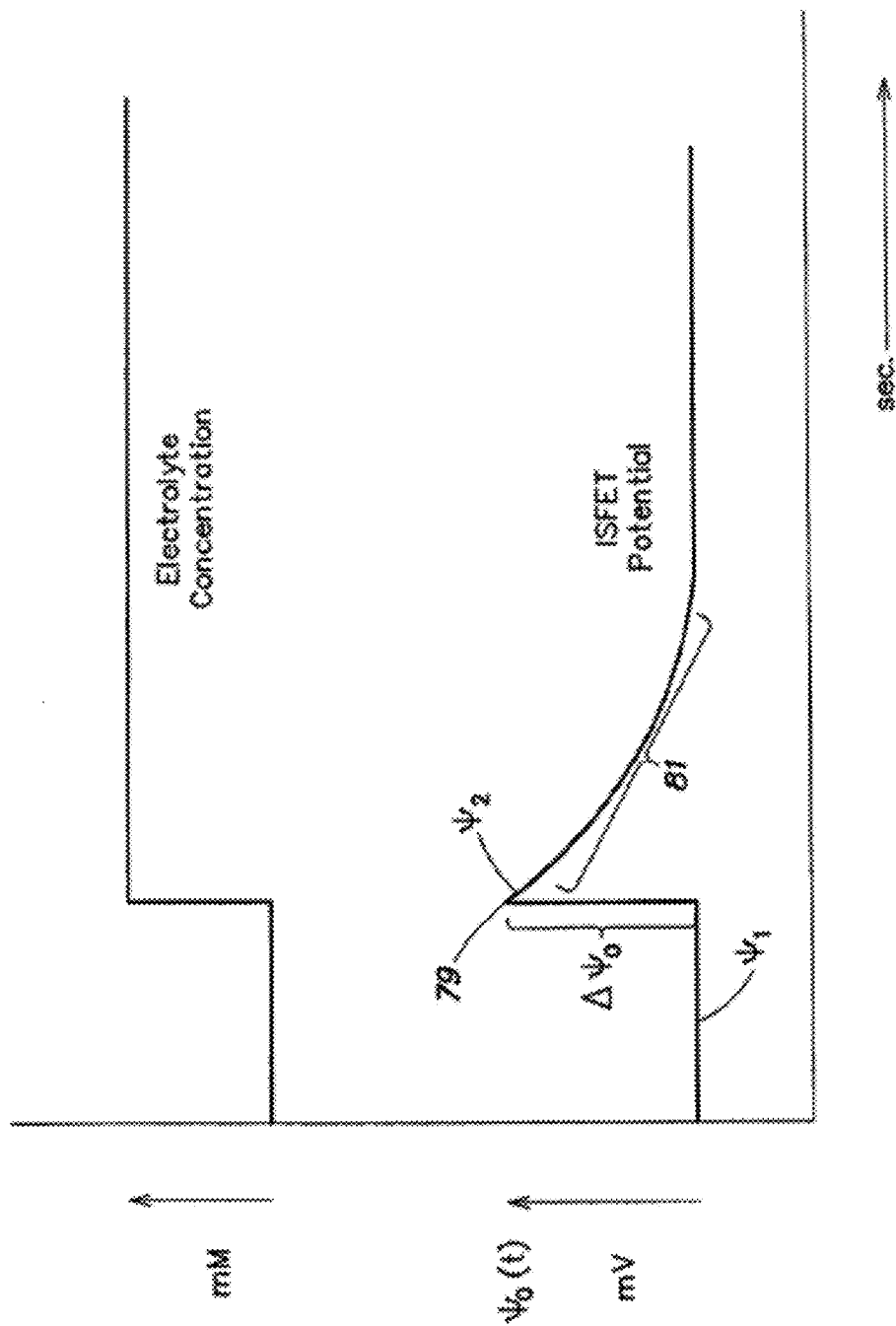
FIG. 2A illustrates an exemplary ISFET transient response to a step-change in ion concentration of an analyte.

The tapered slopes to the sides of the microwells also may be used to advantage. Referring to FIG. 33B-2, if the beads 3320A have a diameter larger than the bottom span across the wells, but small enough to fit into the mouths of the wells, the beads will be spaced of the bottom of the wells due to the geometric constraints. For example, FIG. 33B-2 illustrates the example of microwells that are square in cross-section as viewed from the top, 4 µm on a side, with 3.8 µm diameter beads 3320A loaded. Experimentally and with some calculation, one may determine suitable bead size and well dimension combinations. FIG. 33B-3 shows a portion of one 4 µm well loaded with a 2.8 µm diameter bead 3322A, which obviously is relatively small and falls all the way to the bottom of the well; a 4.0 µm diameter bead 3324A which is stopped from reaching the bottom by the sidewall taper of the well; and an intermediate-sized bead 3326A of 3.6 µm diameter which is spaced from the well bottom by packing beads 3328A. Clearly, bead size has to be carefully matched to the microwell etch taper.

Thus, microwells can be fabricated by any high aspect ratio photo-definable or etchable thin-film process, that can provide requisite thickness (e.g., about 4-10 um). Among the materials believed to be suitable are photosensitive polymers, deposited silicon dioxide, non-photosensitive polymer which can be etched using, for example, plasma etching processes, etc. In the silicon dioxide family, TEOS and silane nitrous oxide (SILOX) appear suitable. The final structures are similar but the various materials present differing surface compositions that may cause the target biology or chemistry to react differently.

When the microwell layer is formed, it may be necessary to provide an etch stop layer so that the etching process does not proceed further than desired. For example, there may be an underlying layer to be preserved, such as a low-K dielectric. The etch stop material should be selected according to the application. SiC and SiN materials may be suitable, but that is not meant to indicate that other materials may not be employed, instead. These etch-stop materials can also serve to enhance the surface chemistry which drives the ISFET sensor sensitivity, by choosing the etch-stop material to have an appropriate point of zero charge (PZC). Various metal oxides may be suitable addition to silicon dioxide and silicon nitride.

The PZCs for various metal oxides may be found in various texts, such as "Metal Oxides—Chemistry and Applications" by J. Fierro. We have learned that $Ta_2O_5$ may be preferred as an etch stop over $Al_2O_3$ because the PZC of $Al_2O_3$ is right at the pH being used (i.e., about 8.8) and, hence, right at the point of zero charge. In addition $Ta_2O_5$ has a higher sensitivity to pH (i.e., mV/pH), another important factor in the sensor performance. Optimizing these parameters may require judicious selection of passivation surface materials.

Using thin metal oxide materials for this purpose (i.e., as an etch stop layer) is difficult due to the fact of their being so thinly deposited (typically 200-500 A). A post-microwell fabrication metal oxide deposition technique may allow placement of appropriate PZC metal oxide films at the bottom of the high aspect ratio microwells.

Electron-beam depositions of (a) reactively sputtered tantalum oxide, (b) non-reactive stoichiometric tantalum oxide, (c) tungsten oxide, or (d) Vanadium oxide may prove to have superior "clown-in-well" coverage due to the superior directionality of the deposition process.

The array typically comprises at least 100 microfluidic wells, each of which is coupled to one or more chemFET sensors. Preferably, the wells are formed in at least one of a glass (e.g., $SiO_2$), a polymeric material, a photodefinable material or a reactively ion etchable thin film material. Preferably, the wells have a width to height ratio less than about 1:1. Preferably the sensor is a field effect transistor, and more preferably a chemFET. The chemFET may optionally be coupled to a PPi receptor. Preferably, each of the chemFETs occupies an area of the array that is $10^2$ microns or less.

In some embodiments, the invention encompasses a sequencing device comprising a semiconductor wafer device coupled to a dielectric layer such as a glass (e.g., $SiO_2$), polymeric, photodefinable or reactive ion etchable material in which reaction chambers are formed. Typically, the glass, dielectric, polymeric, photodefinable or reactive ion etchable material is integrated with the semiconductor wafer layer. In some instances, the glass, polymeric, photodefinable or reactive ion etchable layer is non-crystalline. In some instances, the glass may be $SiO_2$. The device can optionally further comprise a fluid delivery module of a suitable material such as a polymeric material, preferably an injection moldable material. More preferably, the polymeric layer is polycarbonate.

In some embodiments, the invention encompasses a method for manufacturing a sequencing device comprising: using photolithography, generating wells in a glass, dielectric, photodefinable or reactively ion etchable material on top of an array of transistors.

Yet another alternative when a CMOS or similar fabrication process is used for array fabrication is to form the microwells directly using the CMOS materials. That is, the CMOS top metallization layer forming the floating gates of the ISFET array usually is coated with a passivation layer that is about 1.3 µm thick. Microwells 1.3 µm deep can be formed by etching away the passivation material. For example, microwells having a 1:1 aspect ratio may be formed, 1.3 µm deep and 1.3 µm across at their tops. Modeling indicates that as the well size is reduced, in fact, the DNA concentration, and hence the SNR, increases. So, other factors being equal, such small wells may prove desirable.

Mounting the Flow Cell (Fluidic Interface) to the Sensor Chip

The process of using the assembly of an array of sensors on a chip combined with an array of microwells to sequence the DNA in a sample is referred to as an "experiment." Executing an experiment requires loading the wells with the DNA-bound beads and the flowing of several different fluid solutions (i.e., reagents and washes) across the wells. A fluid delivery system (e.g., valves, conduits, pressure source(s), etc.) coupled with a fluidic interface is needed which flows the various solutions across the wells in a controlled even flow with acceptably small dead volumes and small cross contamination between sequential solutions, Ideally, the fluidic interface to the chip (sometimes referred to as a "flow cell") would cause the fluid to reach all microwells at the same time. To maximize array speed, it is necessary that the array outputs be available at as close to the same time as possible. The ideal clearly is not possible, but it is desirable to minimize the differentials, or skews, of the arrival times of an introduced fluid, at the various wells, in order to maximize the overall speed of acquisition of all the signals from the array.

Flow cell designs of many configurations are possible; thus the system and methods presented herein are not dependent on use of a specific flow cell configuration. It is desirable, though, that a suitable flow cell substantially conform to the following set of objectives:

- have connections suitable for interconnecting with a fluidics delivery system—e.g., via appropriately-sized tubing;
- have appropriate head space above wells;
- minimize dead volumes encountered by fluids;
- minimize small spaces in contact with liquid but not quickly swept clean by flow of a wash fluid through the flow cell (to minimize cross contamination);
- configured to achieve uniform transit time of the flow over the array;
- generate or propagate minimal bubbles in the flow over the wells;
- be adaptable to placement of a removable reference electrode inside or as close to the flow chamber as possible;
- facilitate easy loading of beads;
- be manufacturable at acceptable cost; and
- be easily assembled and attached to the chip package.

Satisfaction of these criteria so far as possible will contribute to system performance positively. For example, minimization of bubbles is important so that signals from the array truly indicate the reaction in a well rather than being spurious noise.

Each of several example designs will be discussed, meeting these criteria in differing ways and degrees. In each instance, one typically may choose to implement the design in one of two ways: either by attaching the flow cell to a frame and gluing the frame (or otherwise attaching it) to the chip or by integrating the frame into the flow cell structure and attaching this unified assembly to the chip. Further, designs may be categorized by the way the reference electrode is integrated into the arrangement. Depending on the design, the reference electrode may be integrated into the flow cell (e.g., form part of the ceiling of the flow chamber) or be in the flow path (typically to the outlet or downstream side of the flow path, after the sensor array).

A first example of a suitable experiment apparatus 3410 incorporating such a fluidic interface is shown in FIGS. 34-37, the manufacture and construction of which will be discussed in greater detail below.

The apparatus comprises a semiconductor chip 3412 (indicated generally, though hidden) on or in which the arrays of wells and sensors are formed, and a fluidics assembly 3414 on top of the chip and delivering the sample to the chip for reading. The fluidics assembly includes a portion 3416 for introducing fluid containing the sample, a portion 3418 for allowing the fluid to be piped out, and a flow chamber portion 3420 for allowing the fluid to flow front inlet to outlet and along the way interact with the material in the wells, Those three portions are unified by an interface comprising a glass slide 3422 (e.g., Erie Microarray Cat #C22-5128-M20 from Erie Scientific Company, Portsmouth, N.H., cut in thirds, each to be of size about 25 mm×25 mm).

Mounted on the top face of the glass slide are two fittings, 3424 and 3426, such as nanoport fittings Part #N-333 from Upchurch Scientific of Oak Harbor, Wash. One port (e.g., 3424) serves as an inlet delivering liquids from the pumping/valving system described below but not shown here. The second port (e.g., 3426) is the outlet which pipes the liquids to waste. Each port connects to a conduit 3428, 3432 such as flexible tubing of appropriate inner diameter. The nanoports are mounted such that the tubing can penetrate corresponding holes in the glass slide. The tube apertures should be flush with the bottom surface of the slide.

On the bottom of the glass slide, flow chamber 3420 may comprise various structures for promoting a substantially laminar flow across the microwell array. For example, a series of microfluidic channels fanning out from the inlet pipe to the edge of the flow chamber may be patterned by contact lithography using positive photoresists such as SU-8 photoresist from MicroChem Corp. of Newton, Mass. Other structures will be discussed below.

The chip 3412 will in turn be mounted to a carrier 3430, for packaging and connection to connector pins 3432.

Figure 36:
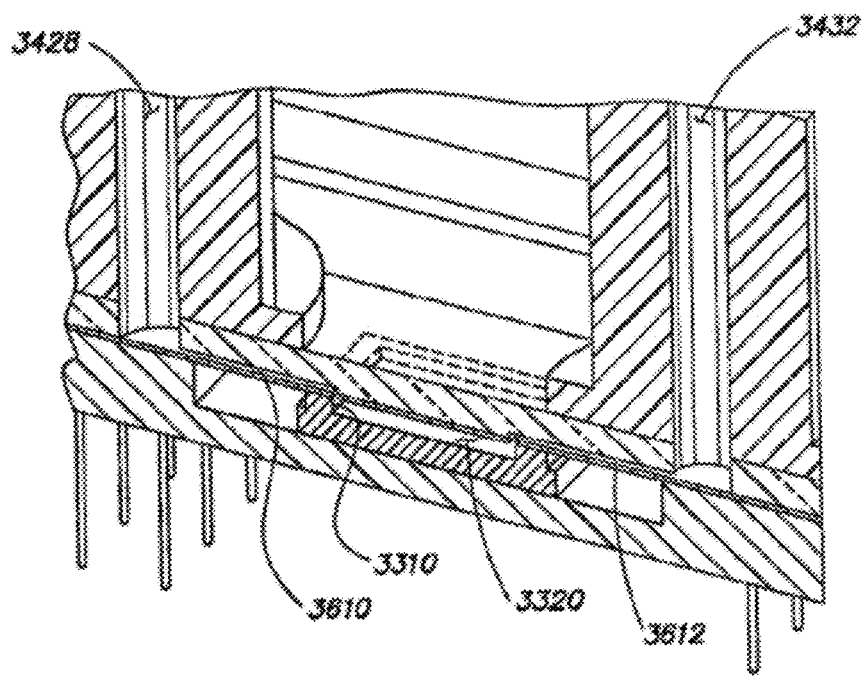
Figure 37:
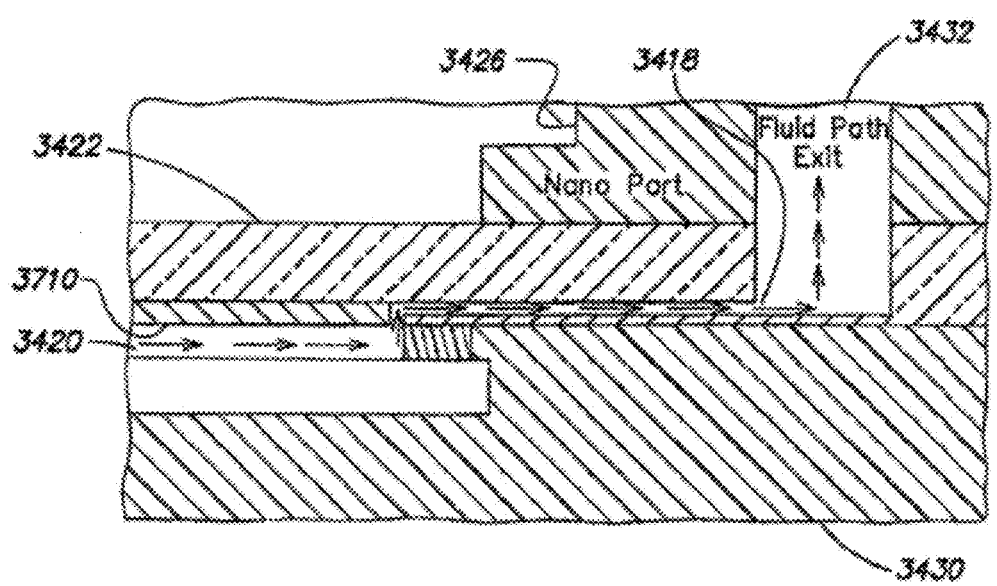
Figure 38:
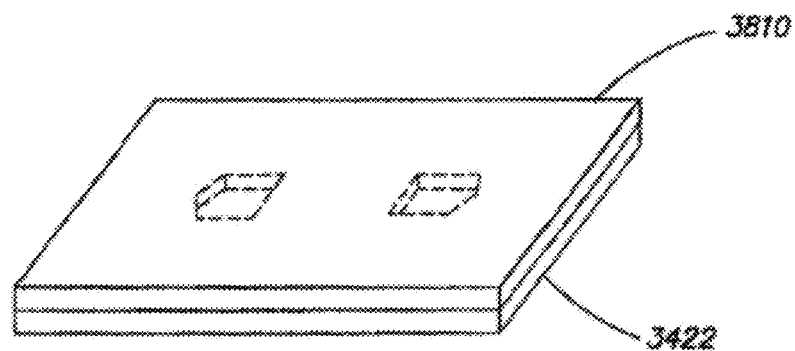
FIG. 38 is a diagrammatic illustration of a substrate with an etched photoresist layer beginning the formation of an example flow cell of a certain configuration.

For ease of description, to discuss fabrication starting with FIG. 38 we shall now consider the glass slide 3422 to be turned upside down relative to the orientation it has in FIGS. 34-37.

Figure 39:
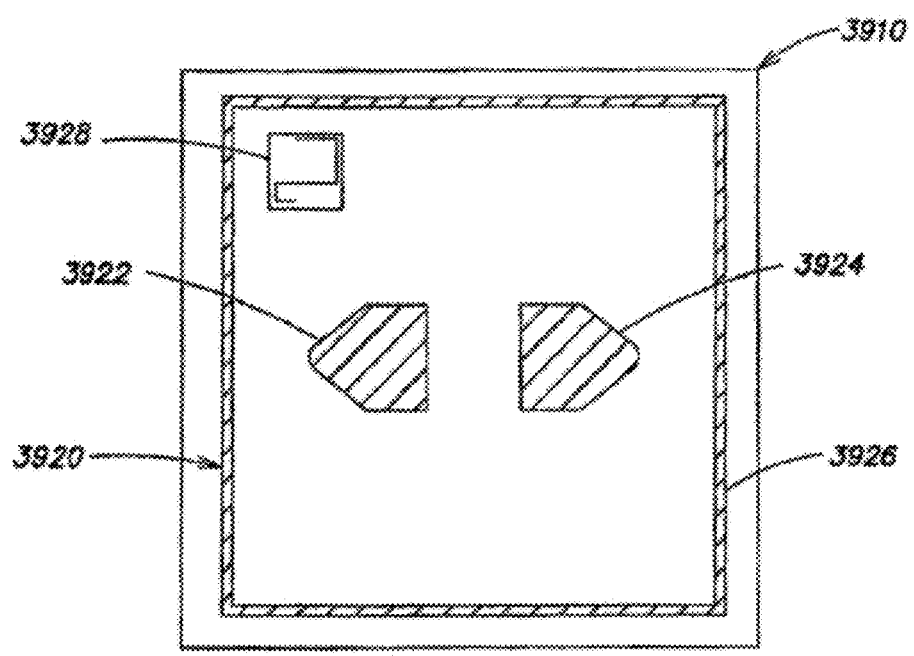
FIGS. 39-41 are diagrams of masks suitable for producing a first configuration of flow cell consistent with FIG. 38.

A layer of photoresist 3810 is applied to the "top" of the slide (which will become the "bottom" side when the slide and its additional layers is turned over and mounted to the sensor assembly of ISFET array with microwell array on it). Layer 3810 may be about 150 µm thick in this example, and it will form the primary fluid carrying layer from the end of the tubing in the nanoports to the edge of the sensor array chip. Layer 3810 is patterned using a mask such as the mask 3910 of FIG. 39 ("patterned' meaning that a radiation source is used to expose the resist through the mask and then the non-plasticized resist is removed). The mask 3910 has radiation-transparent regions which are shown as white and radiation-blocking regions 3920, which are shown in shading. The radiation-blocking regions are at 3922-3928. The region 3926 will form a channel around the sensor assembly; it is formed about 0.5 mm inside the outer boundary of the mask 3920, to avoid the edge bead that is typical. The regions 3922 and 3924 will block radiation so that corresponding portions of the resist are removed to form voids shaped as shown. Each of regions 3922, 3924 has a rounded end dimensioned to receive an end of a corresponding one of the tubes 3428, 3432 passing through a corresponding nanoport 3424, 3426. From the rounded end, the regions 3922, 3924 fan out in the direction of the sensor array to allow the liquid to spread so that the flow across the array will be substantially laminar. The region 3928 is simply an alignment pattern and may be any suitable alignment pattern or be replaced by a suitable substitute alignment mechanism. Dashed lines on FIG. 38 have been provided to illustrate the formation of the voids 3822 and 3824 under mask regions 3922 and 3924.

Figure 40:
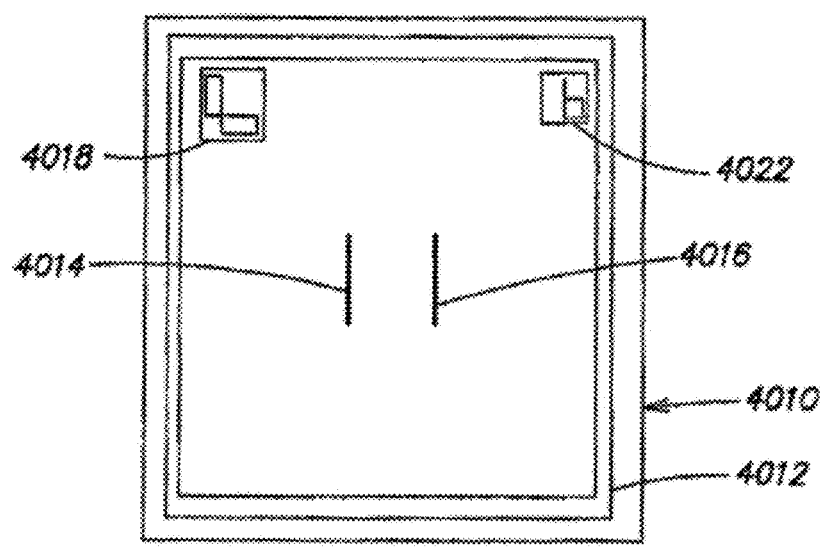

A second layer of photoresist is formed quite separately, not on the resist 3810 or slide 3422. Preferably it is formed on a flat, flexible surface (not shown), to create a peel-off, patterned plastic layer. As shown in FIG. 40, this second layer of photoresist may be formed using a mask such as mask 4010, which will leave on the flexible substrate, after patterning, the border under region 4012, two slits under regions 4014, 4016, whose use will be discussed below, and alignment marks produced by patterned regions 4018 and 4022. The second layer of photoresist is then applied to the first layer of photoresist using one alignment mark or set of alignment marks, let's say produced by pattern 4018, for alignment of these layers. Then the second layer is peeled from its flexible substrate and the latter is removed.

The other alignment mark or set of marks produced by pattern 4022 is used for alignment with a subsequent layer to be discussed.

The second layer is preferably about 150 μm deep and it will cover the fluid-carrying channel with the exception of a slit about 150 μm long at each respective edge of the sensor array chip, under slit-forming regions 4014 and 4016.

Figure 41:
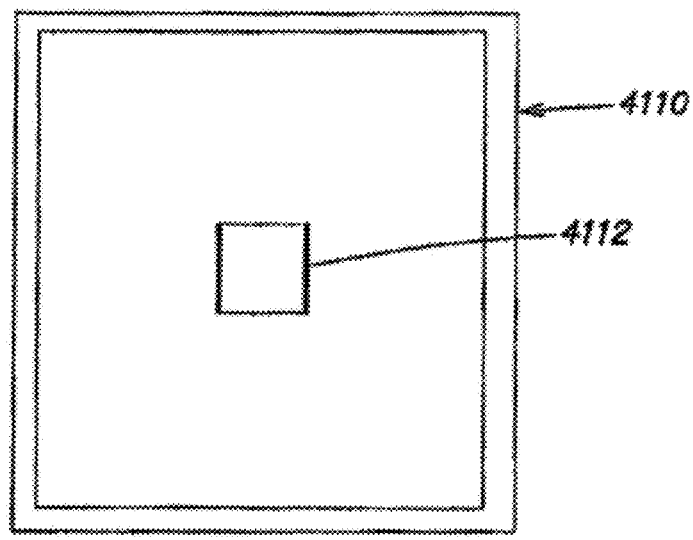

Once the second layer of photoresist is disposed on the first layer, a third patterned layer of photoresist is formed over the second layer, using a mask such as mask 4110, shown in FIG. 41. The third layer provides a baffle member under region 4112 which is as wide as the collar 3310 on the sensor chip array (see FIG. 33) but about 300 μm narrower to allow overlap with the fluid-carrying channel of the first layer. The third layer may be about 150 μm thick and will penetrate the chip collar 3310, toward the floor of the basin formed thereby, by 150 μm. This configuration will leave a headspace of about 300 μm above the wells on the sensor array chip. The liquids are flowed across the wells along the entire width of the sensor array through the 150 μm slits under 4014, 4016.

Figure 34:
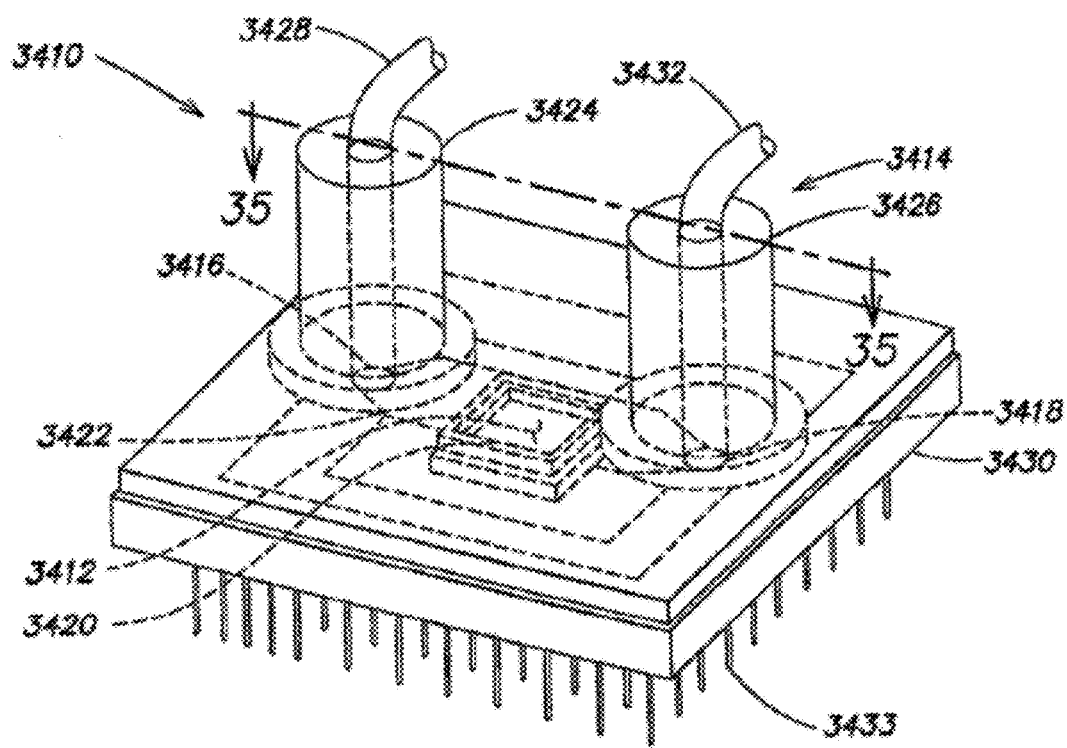
Figure 35:
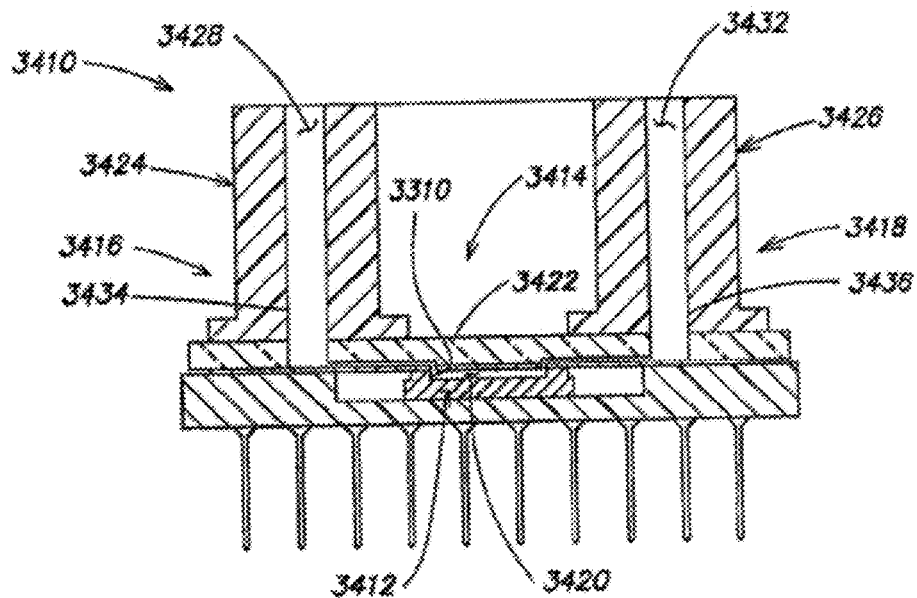

FIG. 36 shows a partial sectional view, in perspective, of the above-described example embodiment of a microfluidics and sensor assembly, also depicted in FIGS. 34 and 35, enlarged to make more visible the fluid flow path. (A further enlarged schematic of half of the flow path is shown in FIG. 37.) Here, it will be seen that fluid enters via the inlet pipe 3428 in inlet port 3424. At the bottom of pipe 3428, the fluid flows through the flow expansion chamber 3610 formed by mask area 3922, that the fluid flows over the collar 3310 and then down into the bottom 3320 of the basin, and across the die 3412 with its microwell array. After passing over the array, the fluid then takes a vertical turn at the far wall of the collar 3310 and flows over the top of the collar to and across the flow concentration chamber 3612 formed by mask area 3924, exiting via outlet pipe 3432 in outlet port 3426. Part of this flow, from the middle of the array to the outlet, may be seen also in the enlarged diagrammatic illustration of FIG. 37, wherein the arrows indicate the flow of the fluid.

The fluidics assembly may be secured to the sensor array chip assembly by applying an adhesive to parts of mating surfaces of those two assemblies, and pressing them together, in alignment.

Though not illustrated in FIGS. 34-36, the reference electrode may be understood to be a metallization 3710, as shown in FIG. 37, at the ceiling of the flow chamber.

Figure 42:
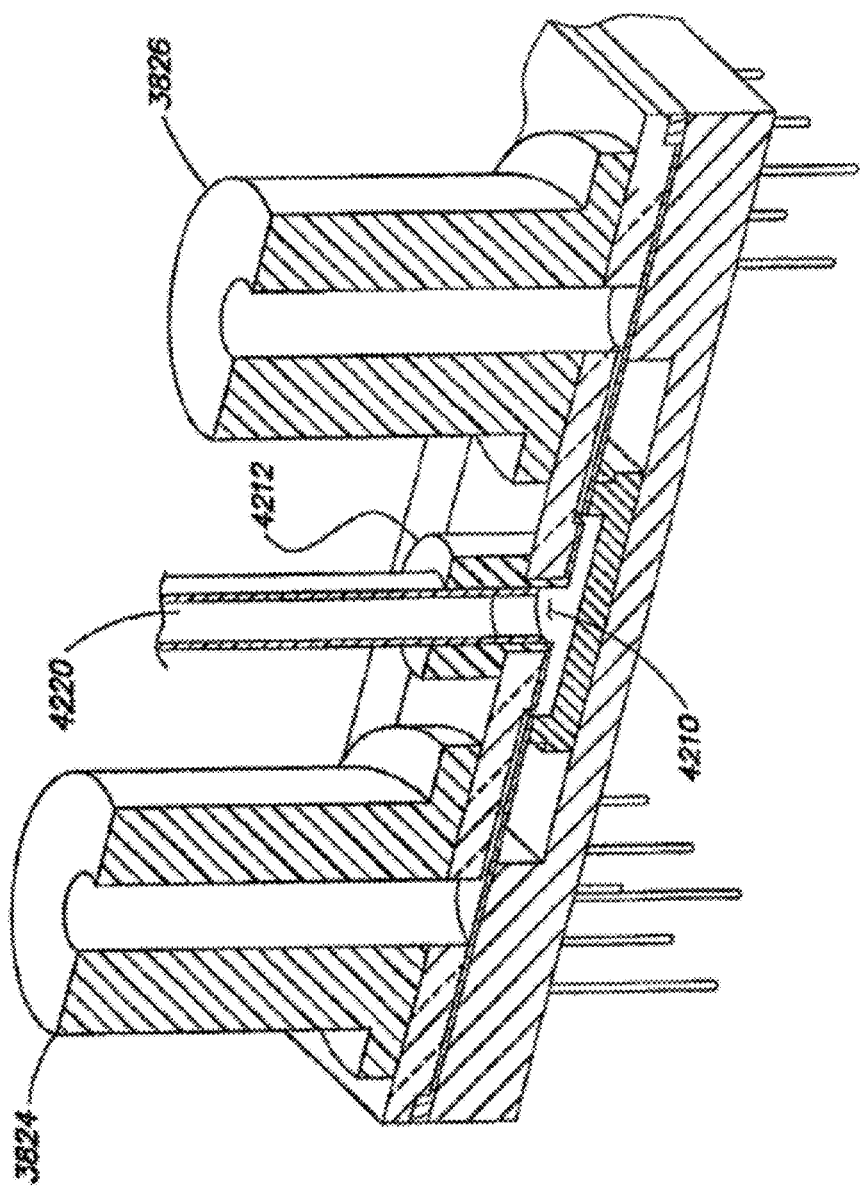
FIGS. 42-54 (but not including FIGS. 42A-42L) and 57-58 are pairs of partly isometric, sectional views of example apparatus and enlargements, showing ways of introducing a reference electrode into, and forming, a flow cell and flow chamber, using materials such as plastic and PDMS.
Figure 42A:
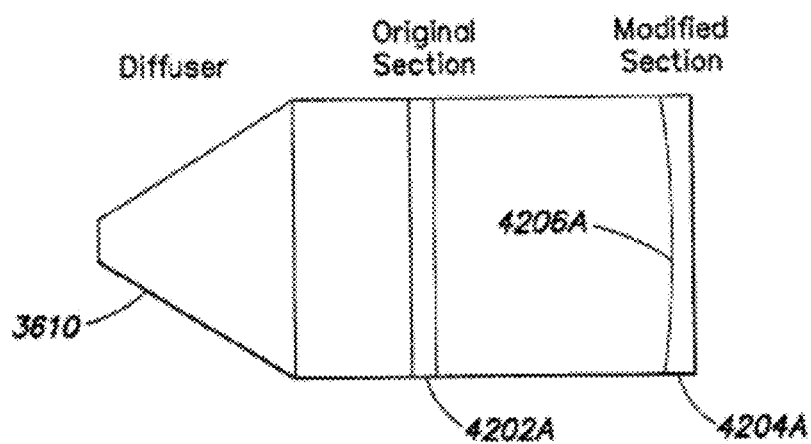
FIG. 42A is an illustration of a possible cross-sectional configuration of a non-rectangular flow chamber antechamber (diffuser section) for use to promote laminar flow into a flow cell as used in the arrangements shown herein.

Another way to introduce the reference electrode is shown in FIG. 42. There, a hole 4210 is provided in the ceiling of the flow chamber and a grommet 4212 (e.g., of silicone) is fitted into that hole, providing a central passage or bore through which a reference electrode 4220 may be inserted. Baffles or other microfeatures (not shown in FIG. 42 but discussed below in connection with FIG. 42A) may be patterned into the flow channel to promote laminar flow over the microwell array.

Achieving a uniform flow front and eliminating problematic flow path areas is desirable for a number of reasons. One reason is that very fast transition of fluid interfaces within the system's flow cell is desired for many applications, particularly gene sequencing. In other words, an incoming fluid must completely displace the previous fluid in a short period of time. Uneven fluid velocities and diffusion within the flow cell, as well as problematic flow paths, can compete with this requirement. Simple flow through a conduit of rectangular cross section can exhibit considerable disparity of fluid velocity from regions near the center of the flow volume to those adjacent the sidewalls, one sidewall being the top surface of the microwell layer and the fluid in the wells. Such disparity leads to spatially and temporally large concentration gradients between the two traveling fluids. Further, bubbles are likely to be trapped or created in stagnant areas like sharp corners interior the flow cell. (The surface energy (hydrophilic vs. hydrophobic) can significantly affect bubble retention. Avoidance of surface contamination during processing and use of a surface treatment to create a more hydrophilic surface should be considered if the as-molded surface is too hydrophobic.) Of course, the physical arrangement of the flow chamber is probably the factor which most influences the degree of uniformity achievable for the flow front.

Figure 42E:
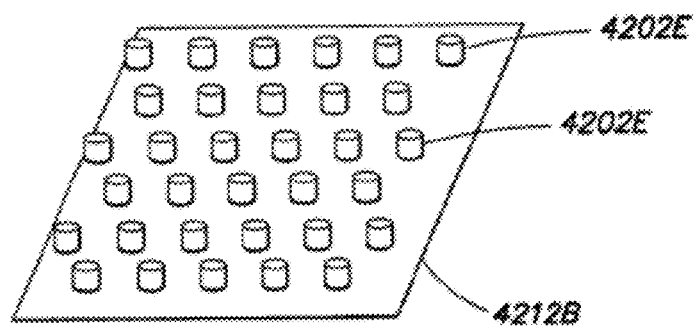
FIGS. 42B-42F are diagrammatic illustrations of examples of flow cell structures for unifying fluid flow.

One approach is to configure the flow cross section of the flow chamber to achieve flow rates that vary across the array width so that the transit times are uniform across the array. For example, the cross section of the diffuser (i.e., flow expansion chamber) section 3416, 3610 may be made as shown at 4204A in FIG. 42A, instead of simply being rectangular, as at 4204A. That is, it may have a curved (e.g., concave) wall. The non-flat wall 4206A of the diffuser can be the top or the bottom. Another approach is to configure the effective path lengths into the array so that the total path lengths from entrance to exit over the array are essentially the same. This may be achieved, for example, by placing flow-disrupting features such as cylinders or other structures oriented normal to the flow direction, in the path of the flow. If the flow chamber has as a floor the top of the microwell array and as a ceiling an opposing wall, these flow-disrupting structures may be provided either on the top of the microwell layer or on (or in) the ceiling wall. The structures must project sufficiently into the flow to have the desired effect, but even small flow disturbances can have significant impact. Turning to FIGS. 42B-42F, there are shown diagrammatically some examples of such structures. In FIG. 42B, on the surface of microwell layer 4210B there are formed a series of cylindrical flow disruptors 4214B extending vertically toward the flow chamber ceiling wall 4212B, and serving to disturb laminar flow for the fluid moving in the direction of arrow A. FIG. 42C depicts a similar arrangement except that the flow disruptors 4216C have rounded tops and appear more like bumps, perhaps hemispheres or cylinders with spherical tops. By contrast, in FIG. 42D, the flow disruptors 4218D protrude, or depend, from the ceiling wall 4212B of the flow chamber.

Only one column of flow disruptors is shown but it will be appreciated that a plurality of more or less parallel columns typically would be required. For example, FIG. 42E shows several columns 4202E of such flow disruptors (projecting outwardly from ceiling wall 4212B (though the orientation is upside down relative to FIGS. 42B-42D). The spacing between the disruptors and their heights may be selected to influence the distance over which the flow profile becomes parabolic, so that transit time equilibrates.

Figure 42F:
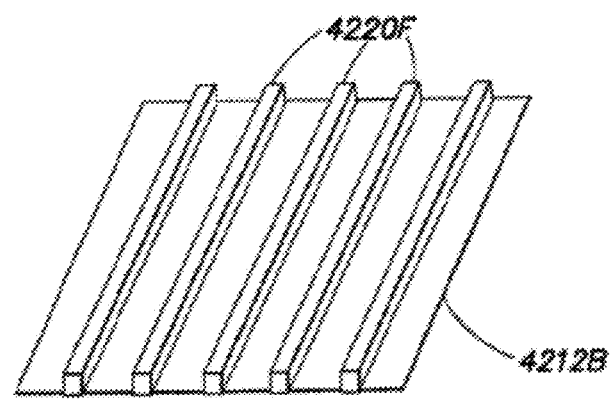
Figure 42B:
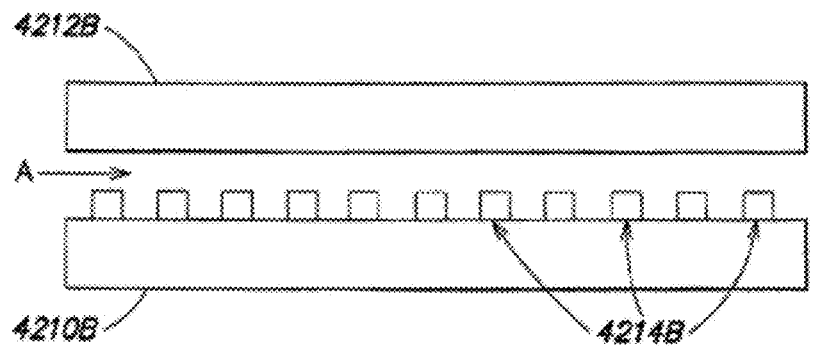
Figure 42C:
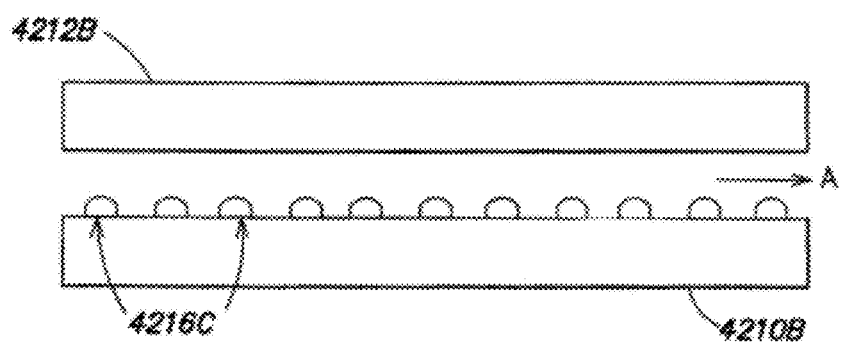
Figure 42D:
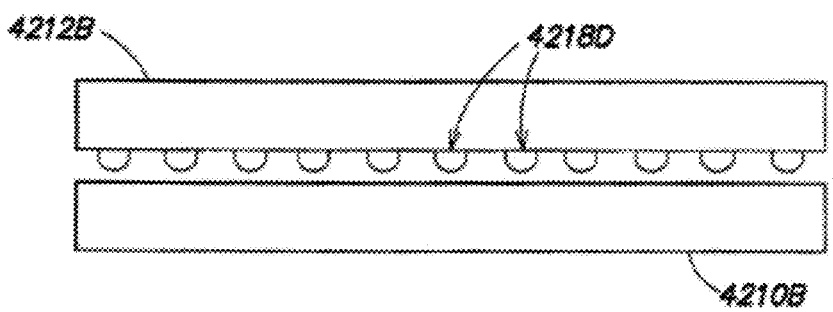

Another configuration, shown in FIGS. 42F and 42F1, involves the use of solid, beam-like projections or baffles 4220F as disruptors. This concept may be used to form a ceiling member for the flow chamber. Such an arrangement encourages more even fluid flow and significantly reduces fluid displacement times as compared with a simple rectangular cross-section without disruptor structure. Further, instead of fluid entry to the array occurring along one edge, fluid may be introduced at one corner 4242F, through a small port, and may exit from the opposite corner, 4244F, via a port in fluid communication with that corner area. The series of parallel baffles 4220F separates the flow volume between input and outlet corners into a series of channels. The lowest fluid resistant path is along the edge of the chip, perpendicular to the baffles. As incoming liquid fills this channel, the fluid is then directed between the baffles to the opposite side of the chip. The channel depth between each baffle pair preferably is graded across the chip, such that the flow is encouraged to travel toward the exit port through the farthest channel, thereby evening the flow front between the baffles. The baffles extend downwardly nearly to the chip (i.e., microwell layer) surface, but because they are quite thin, fluid can diffuse under them quickly and expose the associated area of the array assembly.

Figure 7:
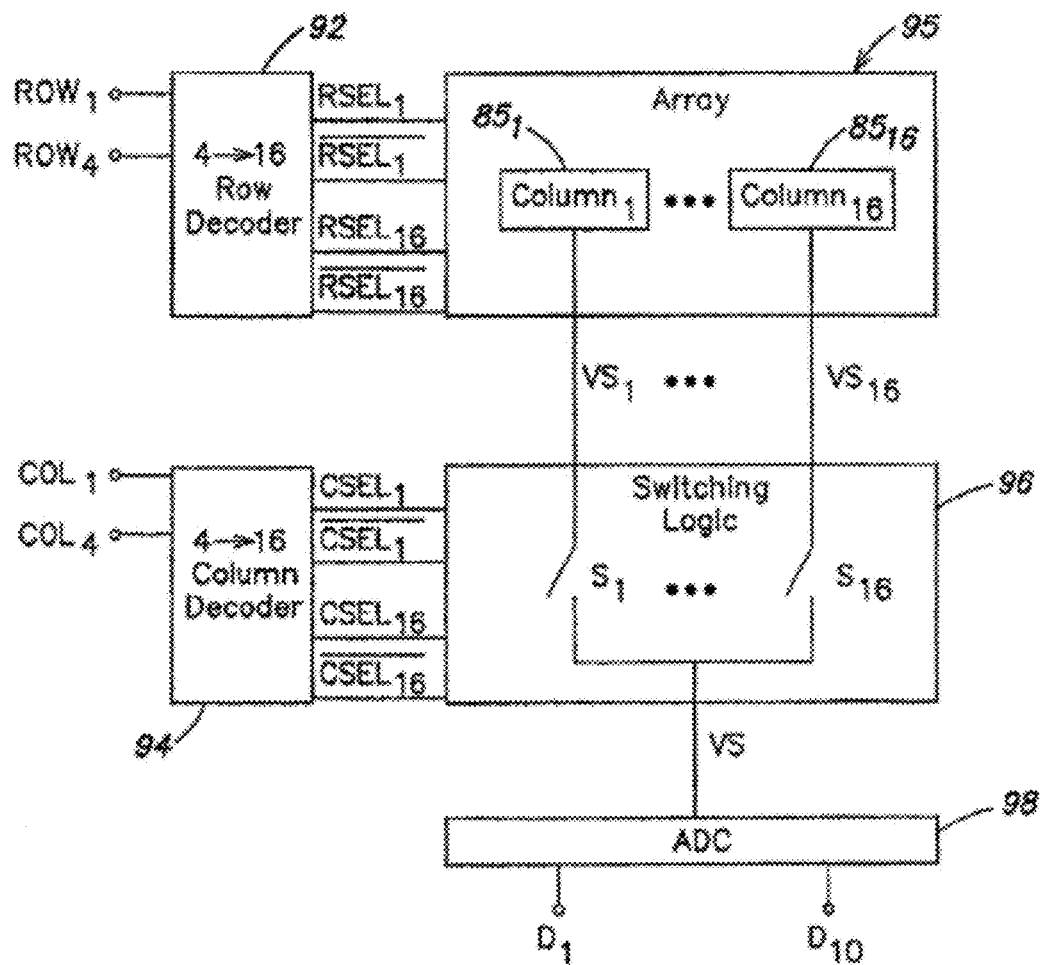
FIG. 7 illustrates an example of a complete two-dimensional ISFET pixel array based on the column design of FIG. 3, together with accompanying row and column decoder circuitry and measurement readout circuitry.

FIGS. 42F2-42F8 illustrate an example of a single-piece, injection-molded (preferably of polycarbonate) flow cell member 42F200 which may be used to provide baffles 4220F, a ceiling to the flow chamber, fluid inlet and outlet ports and even the reference electrode. FIG. 42F7 shows an enlarged view of the baffles on the bottom of member 42F200 and the baffles are shown as part of the underside of member 42F200 in FIG. 42F6. As it is difficult to forum rectangular features in small dimensions by injection molding, the particular instance of these baffles, shown as 4220F', are triangular in cross section.

In FIG. 42F2, there is a top, isometric view of member 42F200 mounted onto a sensor array package 42F300, with a seal 42F202 formed between them and contact pins 42F204 depending from the sensor array chip package. FIGS. 42F3 and 421F4 show sections, respectively, through section lines H-H and I-I of FIG. 42F5, permitting one to see in relationship the sensor array chip 42P250, the baffles 4220F' and fluid flow paths via inlet 42F260 and outlet 42F270 ports.

By applying a metallization to bottom 42F280 of member 42F200, the reference electrode may be formed.

Various other locations and approaches may be used for introducing fluid flow into the flow chamber, as well. In addition to embodiments in which fluid may be introduced across the width of an edge of the chip assembly 42F1, as in FIGS. 57-58, for example, or fluid may be introduced at one corner of the chip assembly, as in FIG. 42F1. Fluid also may be introduced, for example, as in FIGS. 42G and 42H, where fluid is flowed through an inlet conduit 4252G to be discharged adjacent and toward the center of the chip, as at 4254G, and flowed radially outwardly from the introduction point.

Figure 42G:
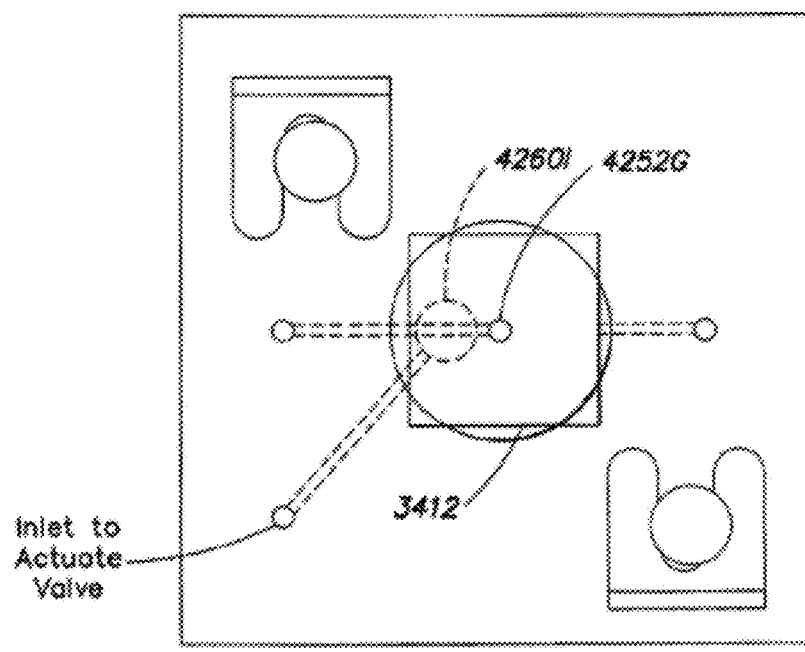
FIGS. 42G and 42H are diagrammatic illustrations of alternative embodiments of flow cells in which fluid flow is introduced to the middle of the chip assembly.
Figure 42H:
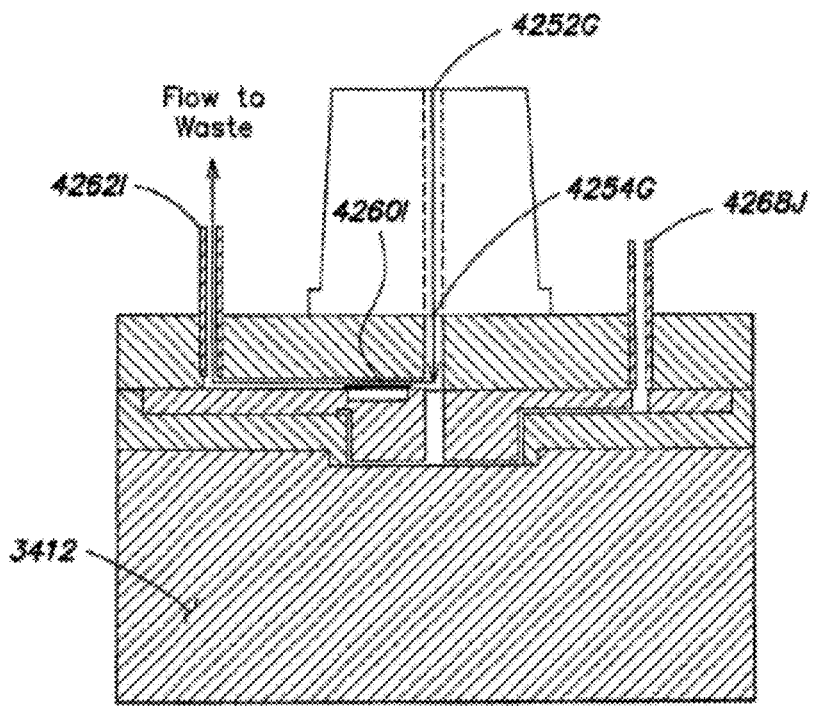
Figure 42I:
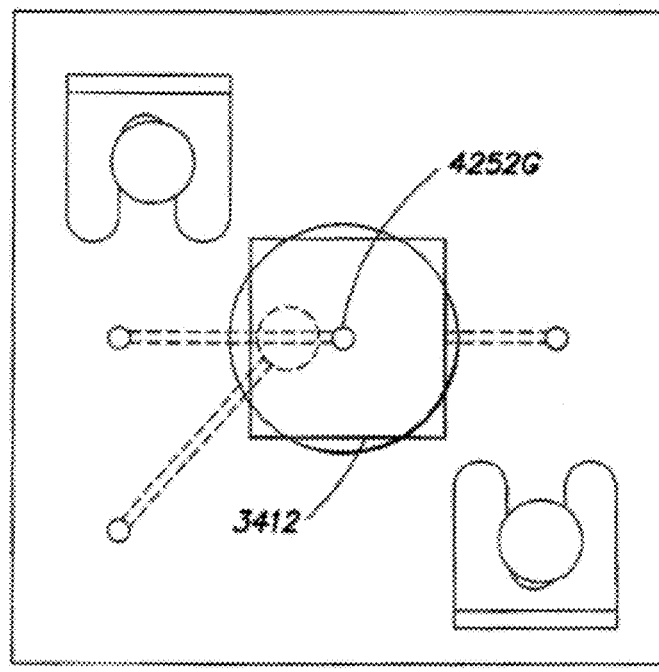
FIGS. 42I and 42J are cross-sectional illustrations of the type of flow cell embodiments shown in FIGS. 42G and 42H, mounted on a chip assembly.
Figure 42J:
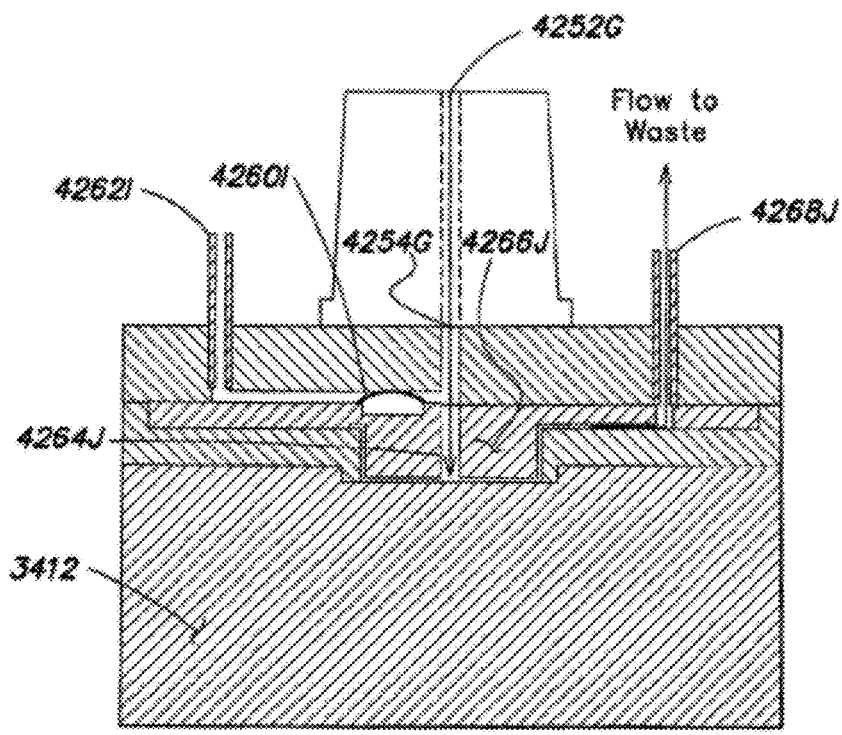

FIGS. 42I and 42J in conjunction with FIGS. 42G and 42H depict in cross-section an example of such a structure and its operation. In contrast with earlier examples, this embodiment contains an additional element, a diaphragm valve, 4260I. Initially, as shown in FIG. 42H, the valve 4260I is open, providing a path via conduit 4262I to a waste reservoir (not shown). The open valve provides a low impedance flow to the waste reservoir or outlet, Air pressure is then applied to the diaphragm valve, as in FIG. 42J, closing the low impedance path and causing the fluid flow to continue downwardly through central bore 4264J in member 4266J which forms the ceiling of the flow chamber, and across the chip (sensor) assembly. The flow is collected by the channels at the edges of the sensor, as described above, and exits to the waste output via conduit 4268J.

Figure 42K:
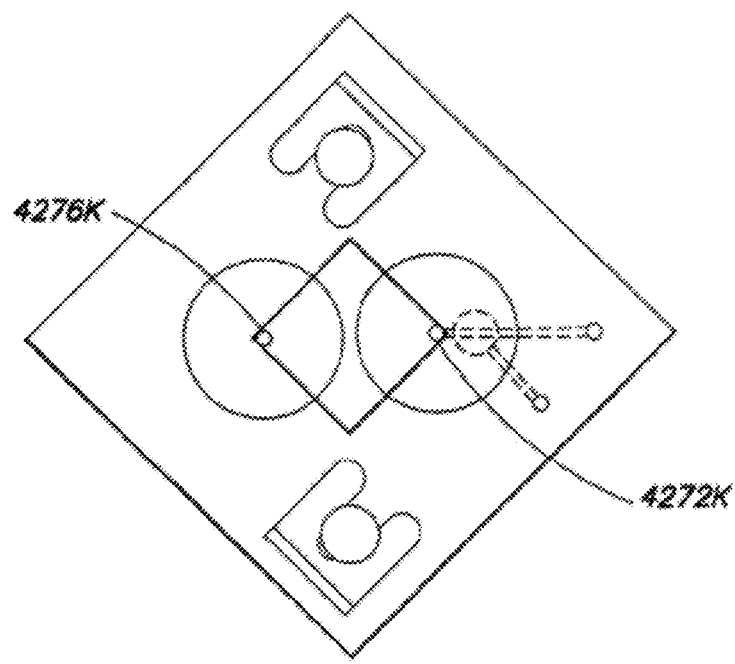
FIGS. 42K and 42L are diagrammatic illustrations of flow cells in which the fluid is introduced at a corner of the chip assembly.
Figure 42L:
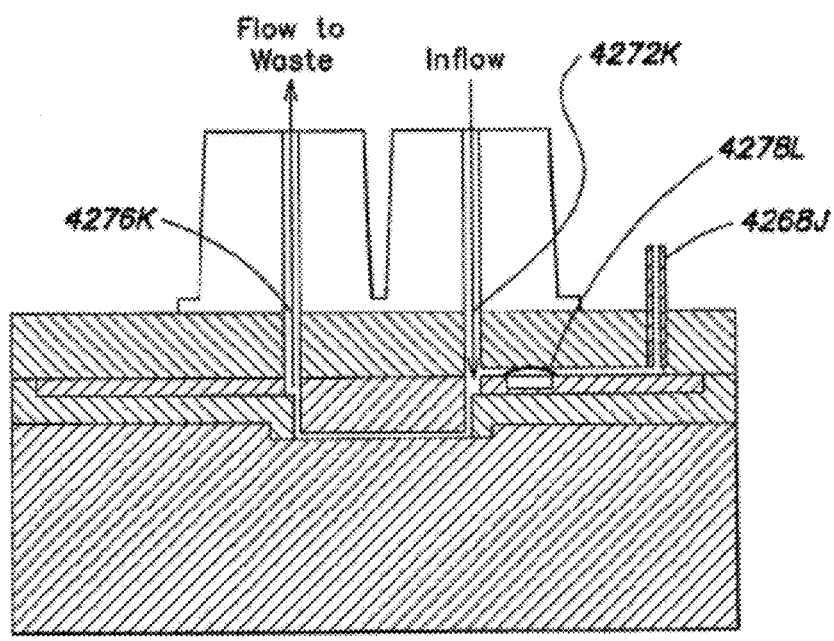
Figure 42M:
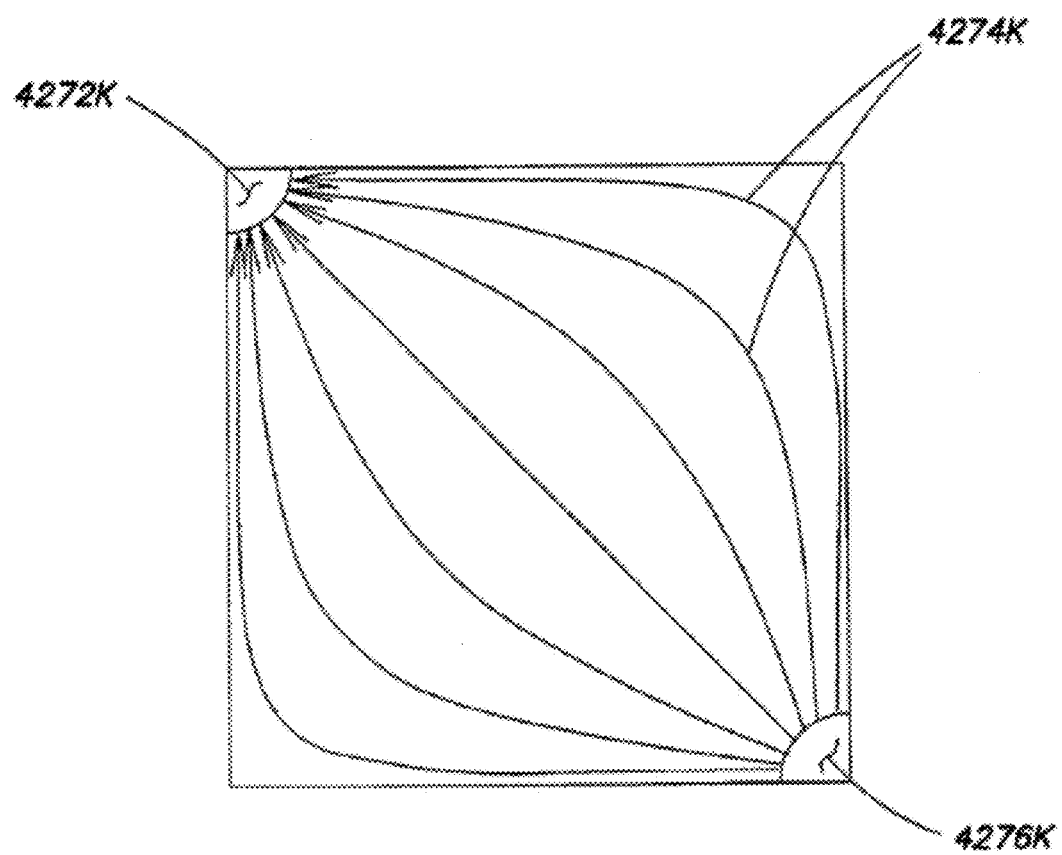
FIG. 42M is a diagrammatic illustration of fluid flow from one corner of an array on a chip assembly to an opposite corner, in apparatus such as that depicted in FIGS. 42K and 42L.

A variation on this idea is depicted in FIGS. 42K-42M, which show fluid being introduced not at the center of the chip assembly, but at one corner, 4272K, instead. It flows across the chip 3412 as symbolically indicated by lines 4274K and is removed at the diagonally opposing corner, 4276K. The advantage of this concept is that it all but eliminates any stagnation points. It also has the advantage that the sensor array can be positioned vertically so that the flow is introduced at the bottom and removed at the top to aid in the clearance of bubbles. This type of embodiment, by the way, may be considered as one quadrant of the embodiments with the flow introduced in the center of the array. An example of an implementation with a valve 4278L closed and shunting flow to the waste outlet or reservoir is shown in FIG. 42L. The main difference with respect to the embodiment of FIGS. 42I and 42J is that the fluid flow is introduced at a corner of the array rather than at its center.

In all cases, attention should be given to assuring a thorough washing of the entire flow chamber, along with the microwells, between reagent cycles, Flow disturbances may exacerbate the challenge of fully cleaning out the flow chamber.

Flow disturbances may also induce or multiply bubbles in the fluid. A bubble may prevent the fluid from reaching a microwell, or delay its introduction to the microwell, introducing error into the microwell reading or making the output from that microwell useless in the processing of outputs from the array. Thus, care should be taken in selecting configurations and dimensions for the flow disruptor elements to manage these potential adverse factors. For example, a tradeoff may be made between the heights of the disruptor elements and the velocity profile change that is desired.

Figure 43:
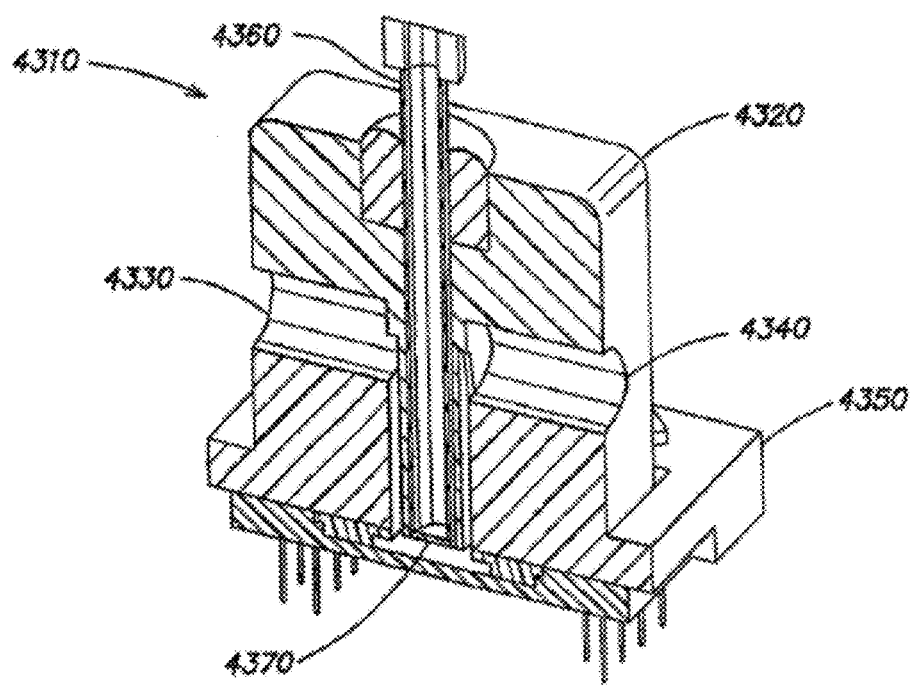
Figure 44:
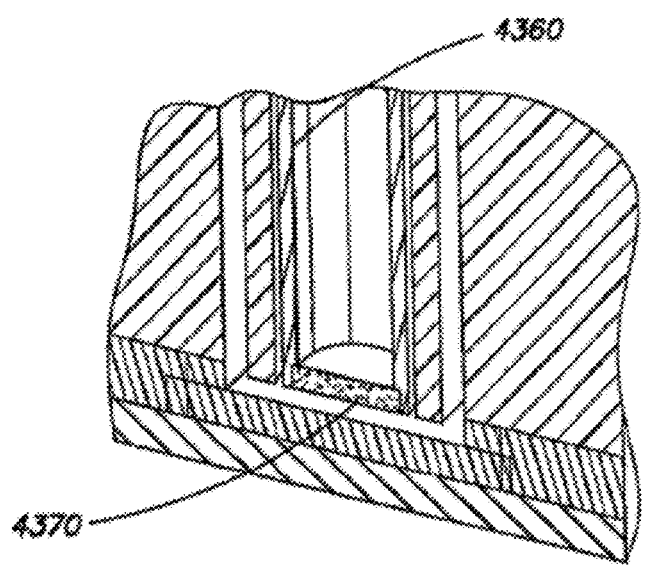

FIGS. 43-44 show another alternative flow cell design, 4310. This design relies on the molding of a single plastic piece or member 4320 to be attached to the chip to complete the flow cell. The connection to the fluidic system is made via threaded connections tapped into appropriate holes in the plastic piece at 4330 and 4340. Or, if the member 4320 is made of a material such as polydimethylsiloxane (PDMS), the connections may be made by simply inserting the tubing into an appropriately sized hole in the member 4320. A vertical cross section of this design is shown in FIGS. 43-44. This design may use an overhanging plastic collar 4350 (which may be a solid wall as shown or a series of depending, spaced apart legs forming a downwardly extending fence-like wall) to enclose the chip package and align the plastic piece with the chip package, or other suitable structure, and thereby to alignment the chip frame with the flow cell forming member 4320. Liquid is directed into the flow cell via one of apertures 4330, 4340, thence downwardly towards the flow chamber.

In the illustrated embodiment, the reference electrode is introduced to the top of the flow chamber via a bore 4325 in the member 4320. The placement of the removable reference electrode is facilitated by a silicone sleeve 4360 and an epoxy stop ring 4370 (see the blow-up of FIG. 44). The silicone sleeve provides a tight seal and the epoxy stop ring prevent the electrode from being inserted too far into the flow cell. Of course, other mechanisms may be employed for the same purposes, and it may not be necessary to employ structure to stop the electrode. And if a material such as PDMS is used for member 4320, the material itself may form a watertight seal when the electrode is inserted, obviating need for the silicone sleeve.

Figure 45:
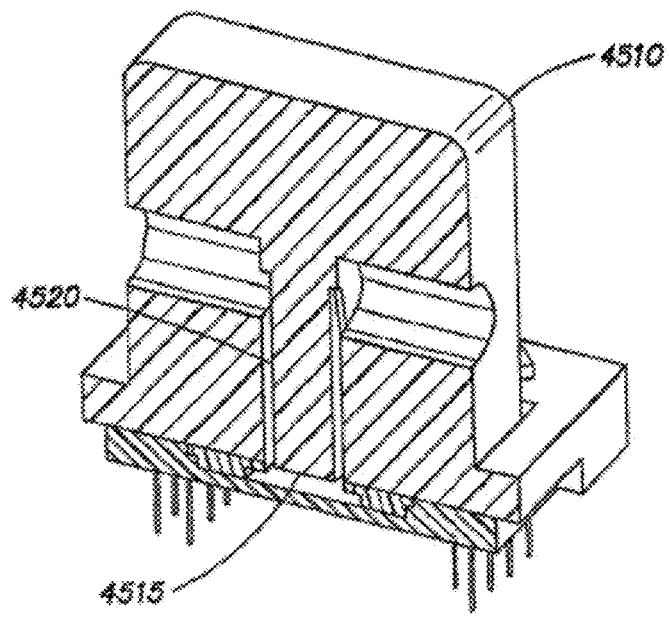
Figure 46:
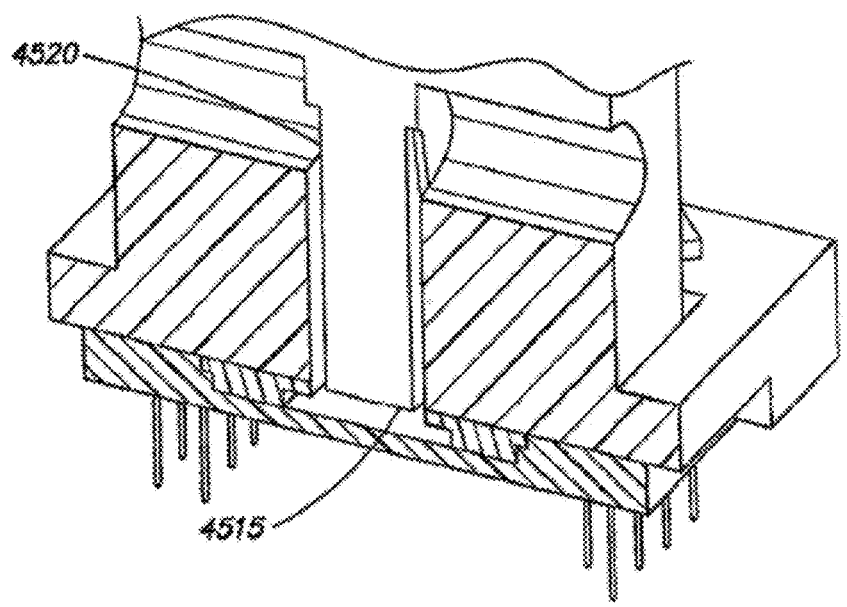

FIGS. 45 and 46 show a similar arrangement except that member 4510 lacks a bore for receiving a reference electrode. Instead, the reference electrode 4515 is formed on or affixed to the bottom of central portion 4520 and forms at least part of the flow chamber ceiling. For example, a metallization layer may be applied onto the bottom of central portion 4520 before member 4510 is mounted onto the chip package.

Figure 47:
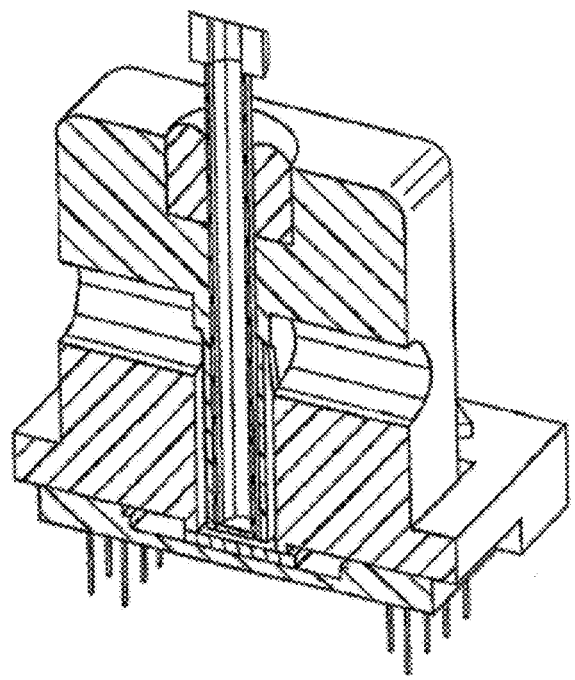
Figure 48:
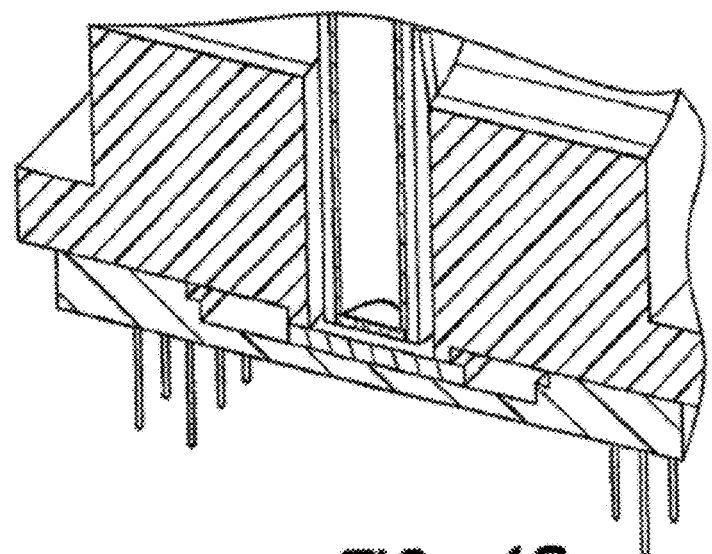
Figure 49:
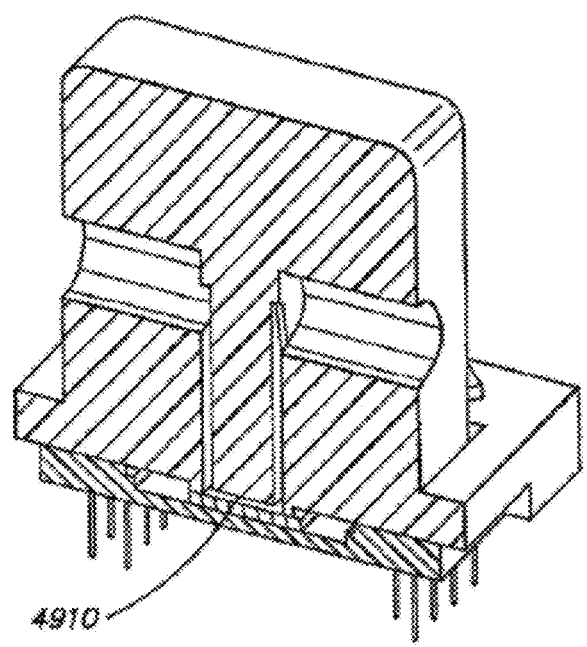
Figure 50:
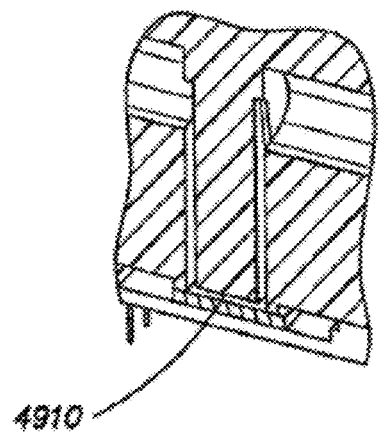

FIGS. 47-48 show another example, which is a variant of the embodiment shown in FIGS. 43-44, but wherein the frame is manufactured as part of the flow cell rather attaching a flow port structure to a frame previously attached to the chip surface. In designs of this type, assembly is somewhat more delicate since the wirebonds to the chip are not protected by the epoxy encapsulating the chip. The success of this design is dependent on the accurate placement and secure gluing of the integrated "frame" to the surface of the chip. A counterpart embodiment to that of FIGS. 45-46, with the reference electrode 4910 on the ceiling of the flow chamber, and with the frame manufactured as part of the flow cell, is shown in FIGS. 49-50.

Figure 51:
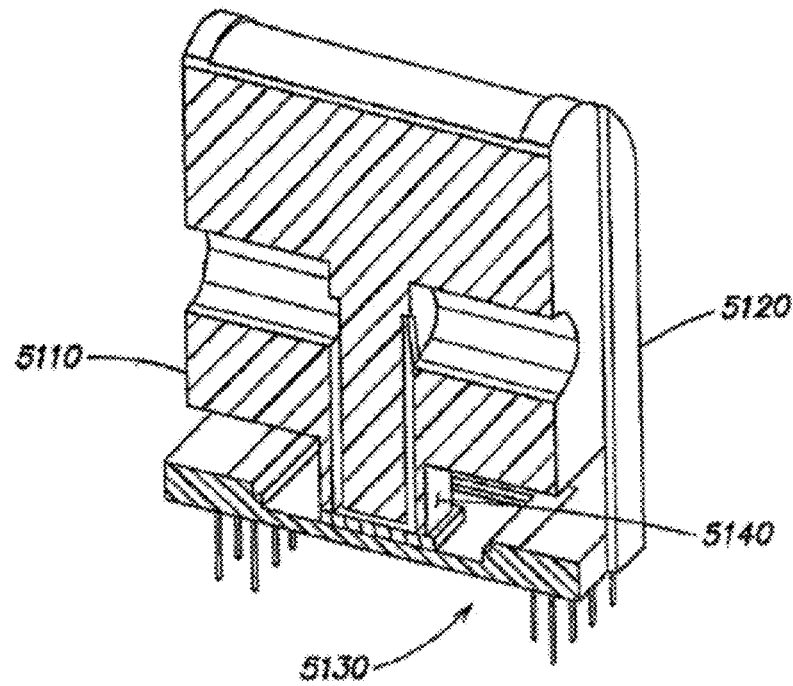
Figure 52:
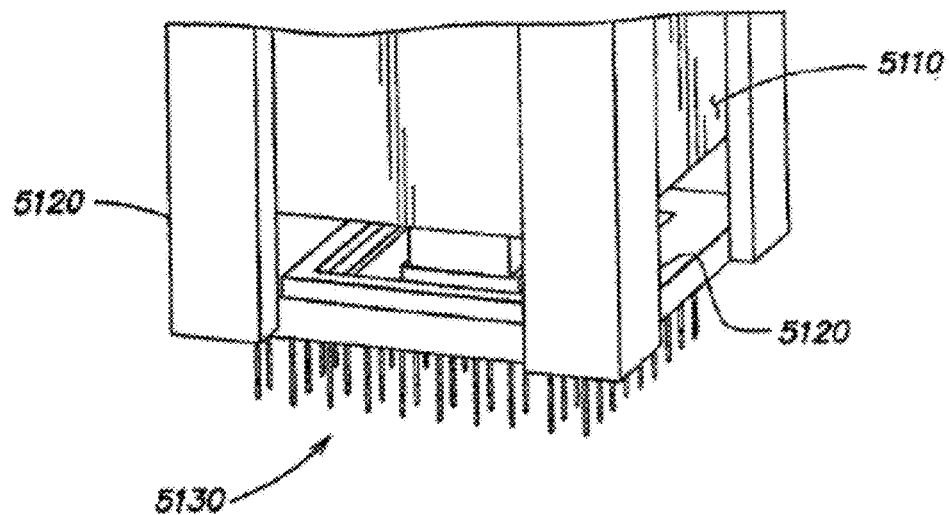

Yet another alternative for a fluidics assembly, as shown in FIGS. 51-52, has a fluidics member 5110 raised by about 5.5 mm on stand-offs 5120 from the top of the chip package 5130. This allows for an operator to visually inspect the quality of the bonding between plastic piece 5140 and chip surface and reinforce the bonding externally if necessary.

Figure 53:
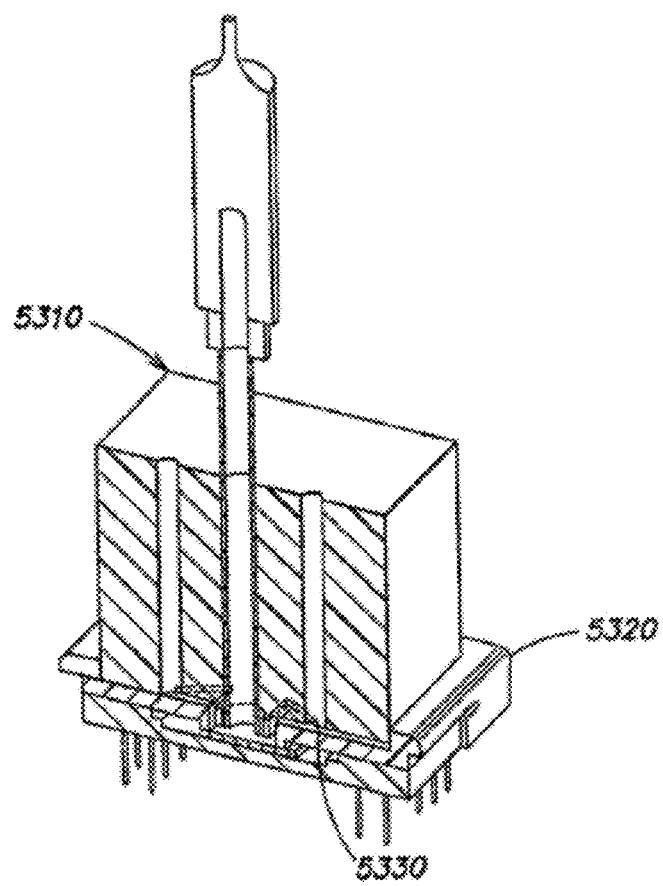
Figure 54:
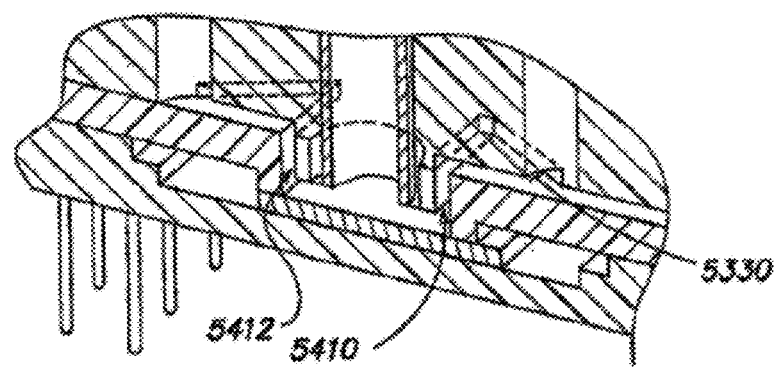

Some of the foregoing alternative embodiments also may be implemented in a hybrid plastic/PDMS configuration. For example, as shown in FIGS. 53-54, a plastic part 5310 may make up the frame and flow chamber, resting on a PDMS "base" portion 5320. The plastic part 5310 may also provides a region 5330 to the array, for expansion of the fluid flow from the inlet port; and the PDMS part may then include communicating slits 5410, 5412 through which liquids are passed from the PDMS part to and from the flow chamber below.

The fluidic structure may also be made from glass as discussed above, such as photo-definable (PD) glass. Such a glass may have an enhanced etch rate in hydrofluoric acid once selectively exposed to UV light and features may thereby be micromachined on the top-side and back-side, which when glued together can form a three-dimensional low aspect ratio fluidic cell.

Figure 55:
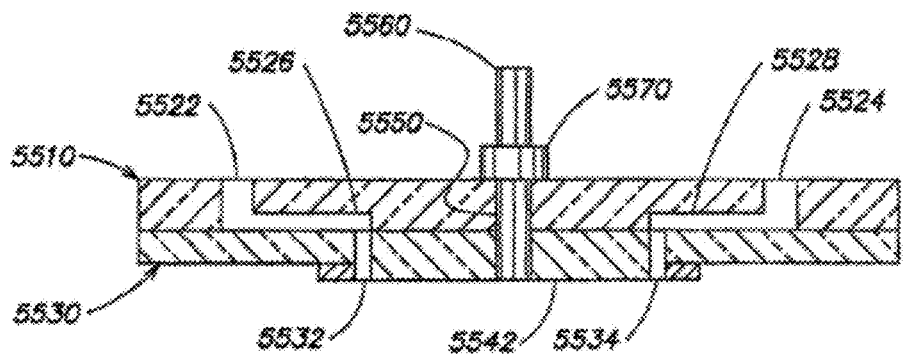
FIGS. 55 and 56 are schematic, cross-sectional views of two-layer glass (or plastic) arrangements for manufacturing fluidic apparatus for mounting onto a chip for use as taught herein.

An example is shown in FIG. 55. A first glass layer or sheet 5510 has been patterned and etched to create nanoport fluidic holes 5522 and 5524 on the top-side and fluid expansion channels 5526 and 5528 on the back-side. A second glass layer or sheet 5530 has been patterned and etched to provide downward fluid input/output channels 5532 and 5534, of about 300 μm height (the thickness of the layer). The bottom surface of layer 5530 is thinned to the outside of channels 5532 and 5534, to allow the layer 5530 to rest on the chip frame and protrusion area 5542 to be at an appropriate height to form the top of the flow channel. Two glass layers, or wafers, and four lithography steps required. Both wafers should be aligned and bonded (e.g., with an appropriate glue, not shown) such that the downward fluid input/output ports are aligned properly with the fluid expansion channels. Alignment targets may be etched into the glass to facilitate the alignment process.

Nanoports may be secured over the nanoport fluidic holes to facilitate connection of input and output tubing.

A central bore 5550 may be etched through the glass layers for receiving a reference electrode, 5560. The electrode may be secured and sealed in place with a silicone collar 5570 or like structure; or the electrode may be equipped integrally with a suitable washer for effecting the same purpose.

Figure 56:
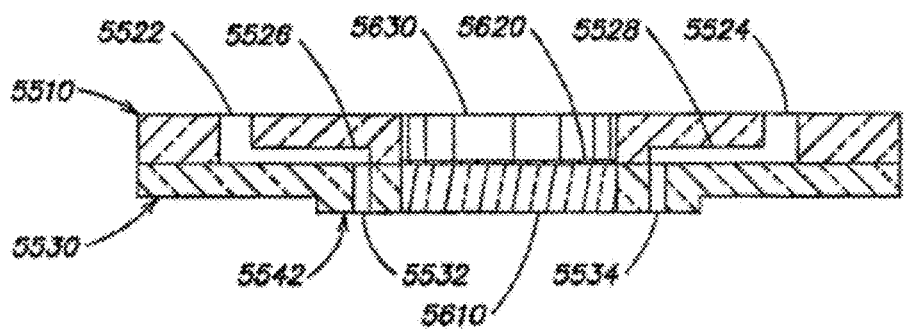

By using glass materials for the two-layer fluidic cell, the reference electrode may also be a conductive layer or pattern deposited on the bottom surface of the second glass layer (not shown). Or, as shown in FIG. 56, the protrusion region may be etched to form a permeable glass membrane 5610 on the top of which is coated a silver (or other material) thin-film 5620 to form an integrated reference electrode. A hole 5630 may be etched into the upper layer for accessing the electrode and if that hole is large enough, it can also serve as a reservoir for a silver chloride solution. Electrical connection to the thin-film silver electrode may be made in any suitable way, such as by using a clip-on pushpin connector or alternatively wirebonded to the ceramic ISFET package.

Another alternative is to integrate the reference electrode to the sequencing chip/flow cell by using a metalized surface on the ceiling of the flow chamber—i.e., on the underside of the member forming the ceiling of the fluidic cell. An electrical connection to the metalized surface may be made in any of a variety of ways, including, but not limited to, by means of applying a conductive epoxy to the ceramic package seal ring that, in turn, may be electrically connected through a via in the ceramic substrate to a spare pin at the bottom of the chip package. Doing this would allow system-level control of the reference potential in the fluid cell by means of inputs through the chip socket mount to the chip's control electronics.

By contrast, an externally inserted electrode requires extra fluid tubing to the inlet port, which requires additional fluid flow between cycles.

Ceramic pin grid array (PGA) packaging may be used for the ISFET array, allowing customized electrical connections between various surfaces on the front face with pins on the back.

The flow cell can be thought of as a "lid" to the ISFET chip and its PGA. The flow cell, as stated elsewhere, may be fabricated of many different materials. Injection molded polycarbonate appears to be quite suitable. A conductive metal (e.g., gold) may be deposited using an adhesion layer (e.g., chrome) to the underside of the glow cell roof (the ceiling of the flow chamber). Appropriate low-temperature thin-film deposition techniques preferably are employed in the deposition of the metal reference electrode due to the materials (e.g., polycarbonate) and large step coverage topography at the bottom-side of the fluidic cell (i.e., the frame surround of ISFET array). One possible approach would be to use electron-beam evaporation in a planetary system.

The active electrode area is confined to the central flow chamber inside the frame surround of the ISFET array, as that is the only metalized surface that would be in contact with the ionic fluid during sequencing.

Once assembly is complete—conductive epoxy (e.g., Epo-Tek H20E or similar) may be dispensed on the seal ring with the flow cell aligned, placed, pressed and cured—the ISFET flow cell is ready for operation with the reference potential being applied to the assigned pin of the package.

The resulting fluidic system connections to the ISFET device thus incorporate shortened input and output fluidic lines, which is desirable.

Figure 57:
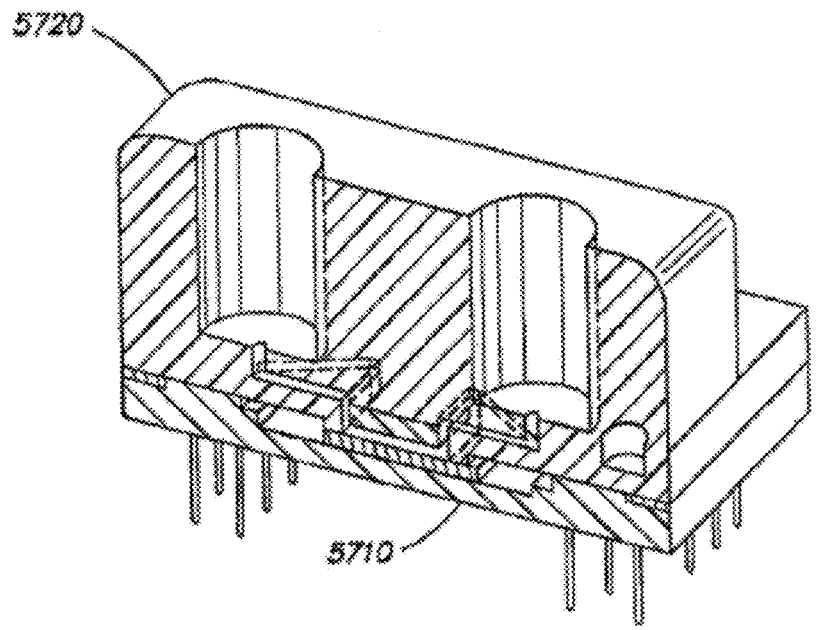
FIGS. 57 and 58 are schematic embodiments of a fluidic assembly.
Figure 58:
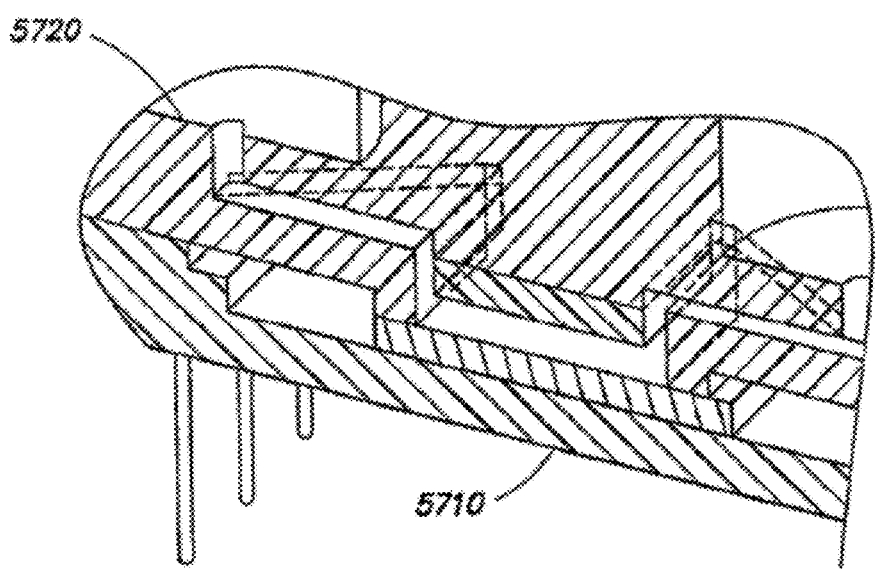

Still another example embodiment for a fluidic assembly is shown in FIGS. 57-58. This design is limited to a plastic piece 5710 which incorporates the frame and is attached directly to the chip surface, and to a second piece 5720 which is used to connect tubing from the fluidic system and similarly to the PDMS piece discussed above, distributes the liquids from the small bore tube to a wide flat slit. The two pieces are glued together and multiple (e.g., three) alignment markers (not shown) may be used to precisely align the two pieces during the gluing process. A hole may be provided in the bottom plate and the hole used to fill the cavity with an epoxy (for example) to protect the wirebonds to the chip and to fill in any potential gaps in the frame/chip contact. In the illustrated example, the reference electrode is external to the flow cell (downstream in the exhaust stream, through the outlet port— see below), though other configurations of reference electrode may, of course, be used.

Figure 59A:
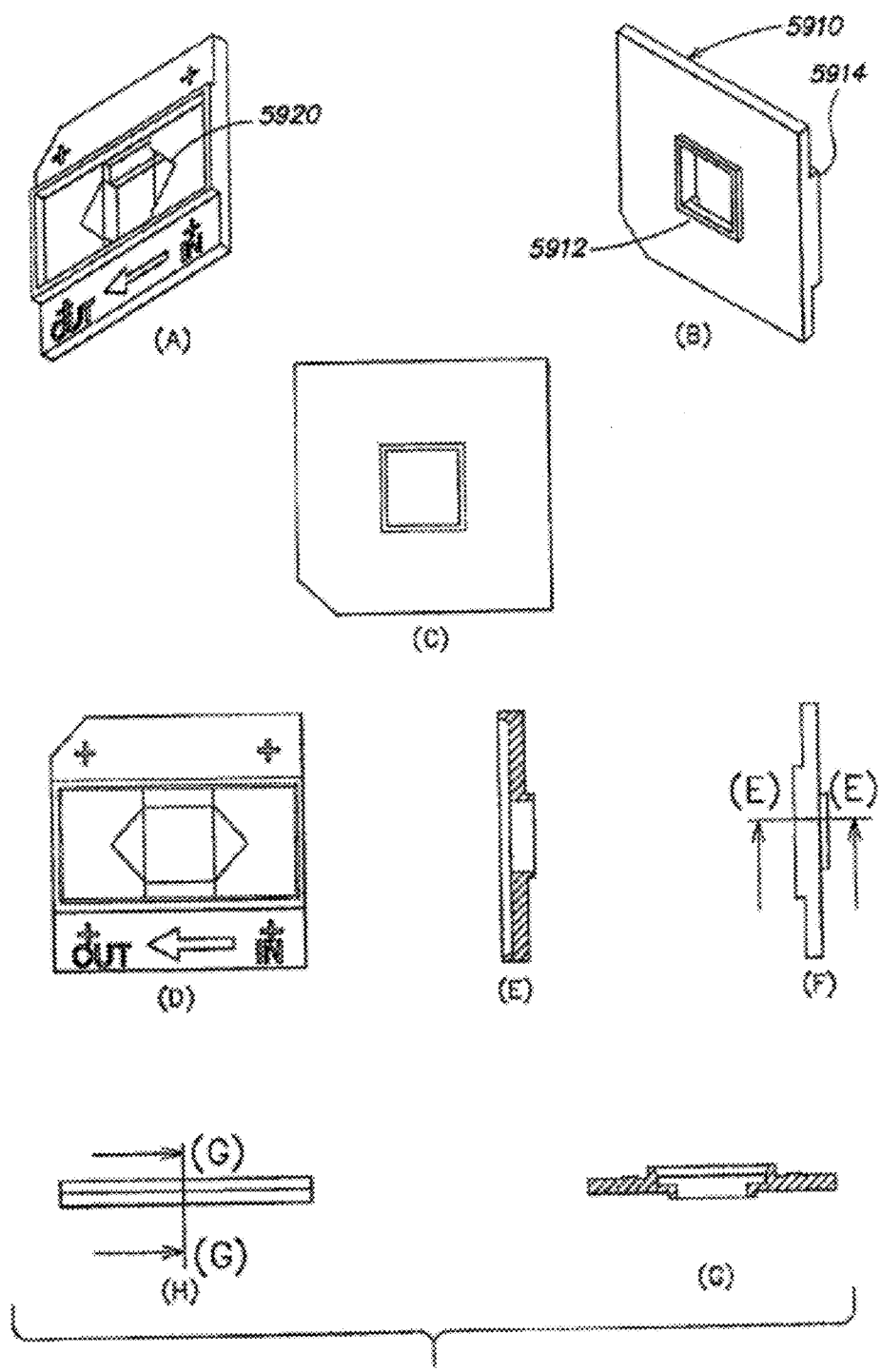
Figure 59B:
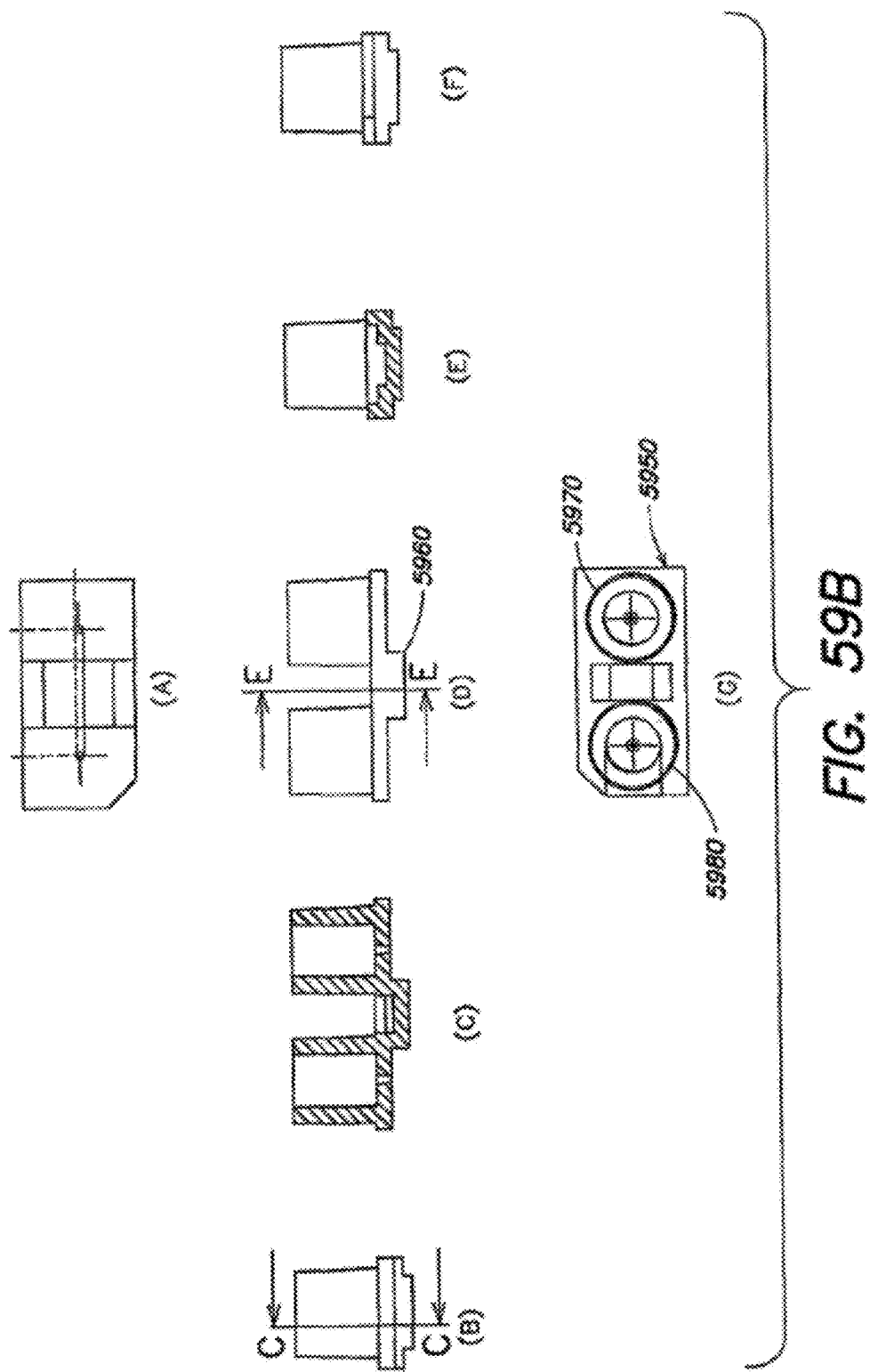
Figure 60:
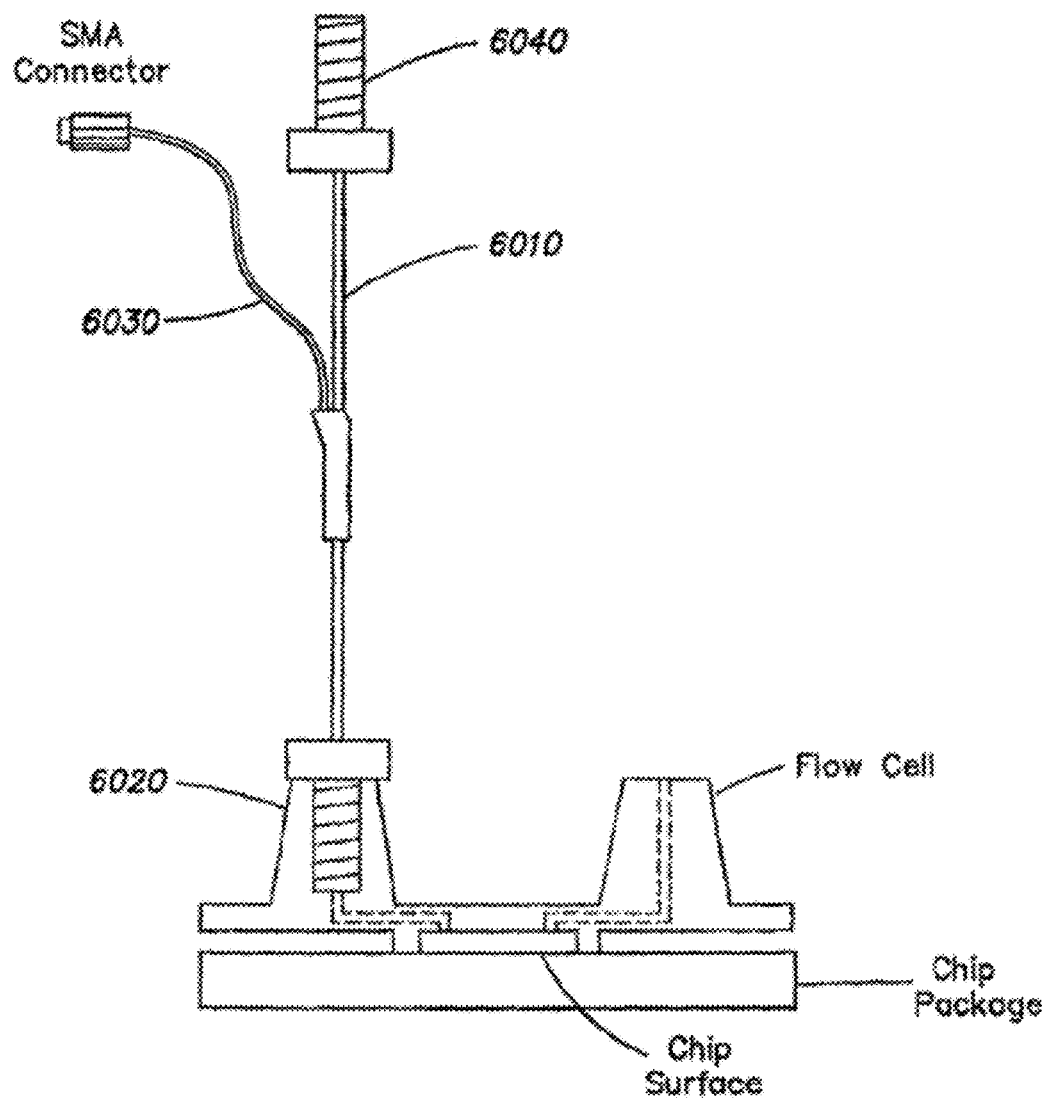
FIG. 60 is a schematic illustration, in cross-section, for introducing a stainless steel capillary tube as an electrode, into a downstream port of a flow cell such as the flow cells of FIGS. 59A-59C, or other flow cells.

Still further examples of flow cell structures are shown in FIGS. 59-60. FIG. 59A comprises eight views (A-H) of an injection molded bottom layer, or plate, 5910, for a flow cell fluidics interface, while FIG. 59B comprises seven views (A-G) of a mating, injection molded top plate, or layer, 5950. The bottom of plate 5910 has a downwardly depending rim 5912 configured and arranged to enclose the sensor chip and an upwardly extending rim 5914 for mating with the top plate 5610 along its outer edge. To form two fluid chambers (an inlet chamber and an outlet chamber) between them. A stepped, downwardly depending portion 5960 of top plate 5950, separates the input chamber from the output chamber. An inlet tube 5970 and an outlet tube 5980 are integrally molded with the rest of top plate 5950. From inlet tube 5970, which empties at the small end of the inlet chamber formed by a depression 5920 in the top of plate 5910, to the outlet edge of inlet chamber fans out to direct fluid across the whole array.

Whether glass or plastic or other material is used to form the flow cell, it may be desirable, especially with larger arrays, to include in the inlet chamber of the flow cell, between the inlet conduit and the front edge of the array, not just a gradually expanding (fanning out) space, but also some structure to facilitate the flow across the array being suitably laminar. Using the bottom layer 5990 of an injection molded flow cell as an example, one example type of structure for this purpose, shown in FIG. 59C, is a tree structure 5992 of channels from the inlet location of the flow cell to the front edge of the microwell array or sensor array, which should be understood to be under the outlet side of the structure, at 5994.

The above-described systems typically utilize a laminar fluid flow system. In part, the fluid flow system preferably includes a flow chamber formed by the sensor chip and a single piece, injection molded member comprising inlet and outlet ports and mountable over the chip to establish the flow chamber. The surface of such member interior to the chamber is preferably formed to facilitate a desired expedient fluid flow, as described herein.

In some embodiments, the invention encompasses an apparatus for detection of pH comprising a laminar fluid flow system. Preferably, the apparatus is used for sequencing a plurality of nucleic acid templates present in an array.

The apparatus typically includes a fluidics assembly comprising a member comprising one or more apertures for non-mechanically directing a fluid to flow to an array of at least 100K (100 thousand), 500K (500 thousand), or 1M (1 million) microfluidic reaction chambers such that the fluid reaches all of the microfluidic reaction chambers at the same time or substantially the same time. Typically, the fluid flow is parallel to the sensor surface. Typically, the assembly has a Reynolds number of less than 1000, 500, 200, 100, 50, 20, or 10. Preferably, the member further comprises a first aperture for directing fluid towards the sensor array and a second aperture for directing fluid away from the sensor array.

In some embodiments, the invention encompasses a method for directing a fluid to a sensor array comprising: providing a fluidics assembly comprising an aperture fluidly coupling a fluid source to the sensor array; and non-mechanically directing a fluid to the sensor array. By "non-mechanically" it is meant that the fluid is moved under pressure from a gaseous pressure source, as opposed to a mechanical pump.

In some embodiments, the invention encompasses an array of wells, each of which is coupled to a lid having an inlet port and an outlet port and a fluid delivery system for delivering and removing fluid from said inlet and outlet ports non-mechanically.

In some embodiments, the invention encompasses a method for sequencing a biological polymer such as a nucleic acid utilizing the above-described apparatus, comprising: directing a fluid comprising a monomer to an array of reaction chambers wherein the fluid has a fluid flow Reynolds number of at most 2000, 1000, 200, 100, 50, or 20. The method may optionally further comprise detecting a pH or a change in pH from each said reaction chamber. This is typically detected by ion diffusion to the sensor surface. There are various other ways of providing a fluidics assembly for delivering an appropriate fluid flow across the microwell and sensor array assembly, and the forgoing examples are thus not intended to be exhaustive.

Reference Electrode

Commercial flow-type fluidic electrodes, such as silver chloride proton-permeable electrodes, may be inserted in series in a fluidic line and are generally designed to provide a stable electrical potential along the fluidic line for various electrochemical purposes. In the above-discussed system, however, such a potential must be maintained at the fluidic volume in contact with the microwell ISFET chip. With conventional silver chloride electrodes, it has been found difficult, due to an electrically long fluidic path between the chip surface and the electrode (through small channels in the flow cell), to achieve a stable potential. This led to reception of noise in the chip's electronics. Additionally, the large volume within the flow cavity of the electrode tended to trap and accumulate gas bubbles that degraded the electrical connection to the fluid. With reference to FIG. 60, a solution to this problem has been found in the use of a stainless steel capillary tube electrode 6010, directly connected to the chip's flow cell outlet port 6020 and connected to a voltage source (not shown) through a shielded cable 6030. The metal capillary tube 6010 has a small inner diameter (e.g., on the order of 0.01") that does not trap gas to any appreciable degree and effectively transports fluid and gas like other microfluidic tubing. Also, because the capillary tube can be directly inserted into the flow cell port 6020, it close to the chip surface, reducing possible electrical losses through the fluid. The large inner surface area of the capillary tube (typically about 2" long) may also contribute to its high performance. The stainless steel construction is highly chemically resistant, and should not be subject to electrochemical effects due to the very low electrical current use in the system (<1 $\mu$A). A fluidic fitting 6040 is attached to the end of the capillary that is not in the flow cell port, for connection to tubing to the fluid delivery and removal subsystem.

Fluidics System

A complete system for using the sensor array will include suitable fluid sources, valving and a controller for operating the valving to low reagents and washes over the microarray or sensor array, depending on the application. These elements are readily assembled from off-the-shelf components, with and the controller may readily be programmed to perform a desired experiment.

It should be understood that the readout at the chemFET may be current or voltage (and change thereof) and that any particular reference to either readout is intended for simplicity and not to the exclusion of the other readout. Therefore any reference in the following text to either current or voltage detection at the chemFET should be understood to contemplate and apply equally to the other readout as well. In important embodiments, the readout reflects a rapid, transient change in concentration of an analyte. The concentration of more than one analyte may be detected at different times. In some instances, such measurements are to be contrasted with methods that focus on steady state concentration measurements.

Biological and Chemical Reactions

As already discussed, the apparatus, systems and methods of the invention can be used to detect and/or monitor interactions between various entities. These interactions include biological and chemical reactions and may involve enzymatic reactions and/or non-enzymatic interactions such as but not limited to binding events. As an example, the invention contemplates monitoring reactions in which substrates and/or reagents are consumed and/or reaction intermediates, byproducts and/or products are generated. An example of a reaction that can be monitored according to the invention is a nucleic acid synthesis method such as one that provides information regarding nucleic acid sequence. This reaction will be discussed in greater detail herein.

Nucleic Acid Sequencing

In the context of a sequencing reaction, the apparatus and system provided herein is able to detect nucleotide incorporation based on changes in the chemFET current and/or voltage, as those latter parameters are interrelated. Current changes may be the result of one or more of the following events either singly or some combination thereof: generation of hydrogen (and concomitant changes in pH for example in the presence of low strength buffer or no buffer), generation of PPi, generation of Pi (e.g., in the presence of pyrophosphatase), increased charge of nucleic acids attached to the chemFET surface, and the like.

As discussed herein, the invention contemplates methods for determining the nucleotide sequence of a nucleic acid. Such methods involve the synthesis of a new nucleic acid (e.g., using a primer that is hybridized to a template nucleic acid or a self-priming template, as will be appreciated by those of ordinary skill), based on the sequence of a template nucleic acid. That is, the sequence of the newly synthesized nucleic acid is complimentary to the sequence of the template nucleic acid and therefore knowledge of sequence of the newly synthesized nucleic acid yields information about the sequence of the template nucleic acid.

More specifically, knowledge of the sequence of the newly synthesized nucleic acid is obtained by determining whether a known nucleotide has been incorporated into the newly synthesized nucleic acid and, if so, how many of such known nucleotides have been incorporated. Importantly, the order in which the known nucleotides are added to the reaction mixture is known and thus the order of incorporated nucleotides (if any) is also known. In an illustrative embodiment, a template hybridized to a primer is contacted with a first pool of identical known nucleotides (e.g., dATP) in the presence of polymerase. If the next available position on the template is a thymidine residue, then the dATP is incorporated into the primed nucleic acid strand and a signal is detected for example based on hydrogen release. If the next available position is not a thymidine residue, then the dATP will not incorporate and no signal will be detected because no hydrogen will be released. If the next available position and one or more contiguous positions thereafter are thymidine residues, then a corresponding number of dATP will be incorporated and a signal commensurate with the number of nucleotides incorporated will be detected. The reaction well or chamber is then washed to remove unincorporated nucleotides and released hydrogen, following which another pool of identical known nucleotides (e.g., dCTP) is added. The process is repeated until all four nucleotides are separately added to the reaction well (i.e., one cycle), and then the cycles are repeated. The cycles may be repeated for 50 times, 100 times, 200 times, 300 times, 400 times, 500 times, 750 times, or more, depending on the length of sequence information desired.

Figure 61A:
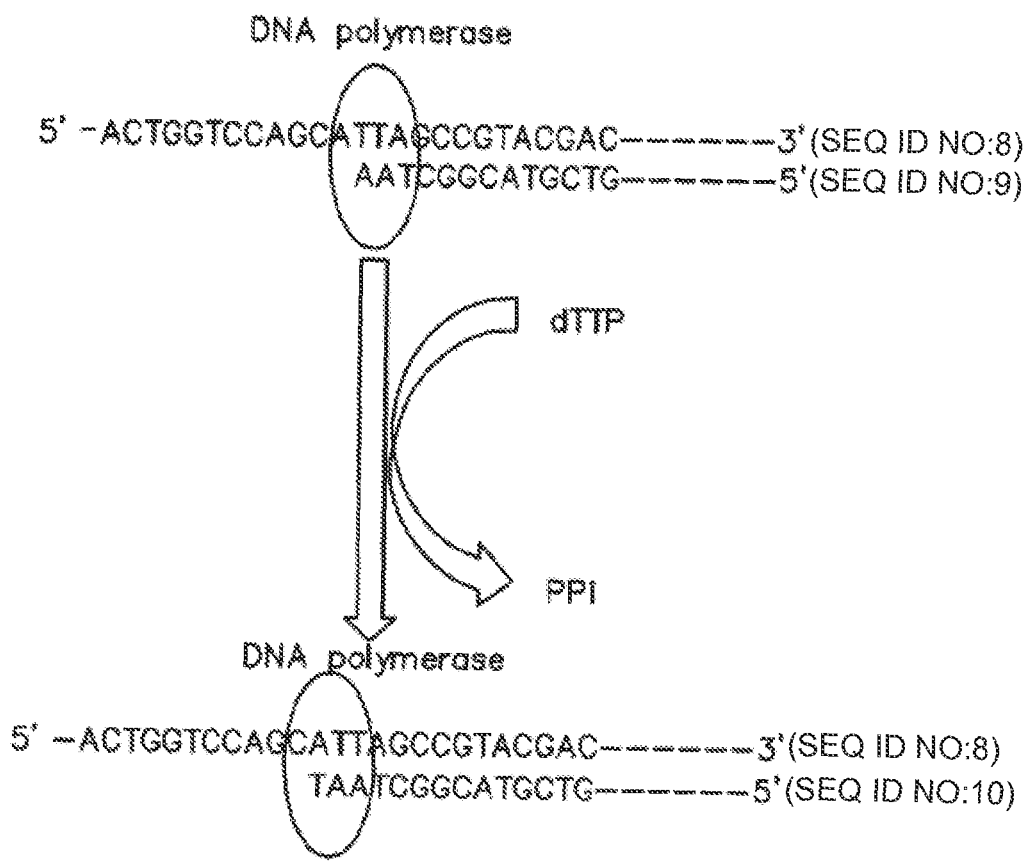
FIG. 61A is a schematic illustrating the incorporation of a dNTP into a synthesized nucleic acid strand with concomitant release of inorganic pyrophosphate (PPi).

Nucleotide incorporation can be monitored in a number of ways, including the production of products such as PPi, Pi and/or $H^+$. The incorporation of a dNTP into the nucleic acid strand releases PPi which can then be hydrolyzed to two orthophosphates (Pi) and one hydrogen ion (FIG. 61A), The generation of the hydrogen ion therefore can be detected as an indicator of nucleotide incorporation. Alternatively, Pi may be detected directly or indirectly.

Alternatively, when templates or primers are attached to the sensor surface, nucleotide incorporation is detected based on an increase in charge (typically, negative charge) of the template, primer or template/primer complex. Templates may be bound to the chemFET surface or they may be hybridized to primers that am bound to the chemFET surface, Primers hybridized to the templates can be extended in the presence of polymerase and one or a combination of known nucleotides, Nucleotide incorporation is detected by increases in charge at the chemFET surface that result from the addition of phosphodiester backbone linkages that carry negative charges. Thus, with each successive addition of a nucleotide, the negative charge of the immobilized nucleic acid increases, and this increase can be detected by the chemFET. The number of nucleotide incorporations that can be detected in this manner may be at least 10, at least 20, at least 30, at least 40, at least 50, at least 60, at least 70, at least 80, at least 90, at least 100, or more. The invention contemplates that in this instance nucleotide incorporation can be detected by measuring change in charge at the chemFET surface as well as released hydrogen ions that come into contact with the chemFET.

Any and all of these events (and more as described herein) may be detected at the chemFET thereby causing a current change that correlates with nucleotide incorporation.

The systems described herein can be used for sequencing nucleic acids without optical detection. Preferably, at least $10^6$ base pairs are sequenced per hour, more preferably at least $10^7$ base pairs are sequenced per hour, and most preferably at least $10^8$ base pairs are sequenced per hour using the above-described method. Thus, the method may be used to sequence an entire human genome within about 24 hours, more preferably within about 20 hours, even more preferably within about 15 hours, even more preferably within about 10 hours, even more preferably within about 5 hours, and most preferably within about 1 hour. These rates may be achieved using multiple ISFET arrays as shown herein, and processing their outputs in parallel.

pH Based Nucleic Acid Sequencing

Reduced Buffering

Certain aspects of the invention therefore relate to detecting hydrogen ions released as a function of nucleotide incorporation and in some embodiments as a function of nucleotide excision. It is important in these and various other aspects to detect as many released hydrogen ions as possible in order to achieve as high a signal (and/or a signal to noise ratio) as possible. Strategies for increasing the number of released protons that are ultimately detected by the chemFET surface include without limitation limiting interaction of released protons with reactive groups in the well, choosing a material from which to manufacture the well in the first instance that is relatively inert to protons, preventing released protons from exiting the well prior to detection at the chemFET, and increasing the copy number of templates per well (in order to amplify the signal from each nucleotide incorporation), among others.

Some instances of the invention employ an environment, including a reaction solution, that is minimally buffered, if at all. Buffering can be contributed by the components of the solution or by the solid supports in contact with such solution. A solution having no or low buffering capacity (or activity) is one in which changes in hydrogen ion concentration on the order of at least about +/−0.005 pH units, at least about +/−0.01, at least about +/−0.015, at least about +/−0.02, at least about +/−0.03, at least about +/−0.04, at least about +/−0.05, at least about +/−0.10, at least about +/−0.15, at least about +/−0.20, at least about +/−0.25, at least about +/−0.30, at least about +/−0.35, at least about +/−0.45, at least about +/−0.50, or more are detectable (e.g., using the chemFET sensors described herein). In some embodiments, the pH change per nucleotide incorporation is on the order of about 0.005. In some embodiments, the pH change per nucleotide incorporation is a decrease in pH. Reaction solutions that have no or low buffering capacity may contain no or very low concentrations of buffer, or may use weak buffers.

A buffer is an ionic molecule (or a solution comprising an ionic molecule) that resists, to varying extents, changes in pH. Buffers include without limitation Tris, tricine, phosphate, boric acid, borate, acetate, morpholine, citric acid, carbonic acid, and phosphoric acid. The strength of a buffer is a relative term since it depends on the nature, strength and concentration of the acid or base added to or generated in the solution of interest. A weak buffer is a buffer that allows detection (and therefore is not able to control or mask) pH changes on the order of those listed above.

The reaction solution may have a buffer concentration equal to or less than 1 mM, equal to or less than 0.9 mM, equal to or less than 0.8 mM, equal to or less than 0.7 mM, equal to or less than 0.6 mM, equal to or less than 0.5 mM, equal to or less than 0.4 mM, equal to or less than 0.3 mM, equal to or less than 0.2 mM, equal to or less than 0.1 mM, or less including zero. The buffer concentration may be 50-100 µM. A non-limiting example of a weak buffer suitable for the sequencing reactions described herein wherein pH change is the readout is 0.1 mM Tris or Tricine.

In some aspects, in addition to or instead of using reduced buffering solutions, nucleotide incorporation (and optionally excision) is carried out in the presence of additional agents which serve to shield potential buffering events that may occur in solution. These agents are referred to herein as buffering inhibitors since they inhibit the ability of components within a solution or a solid support in contact with the solution to sequester and/or otherwise interfere with released hydrogen ions prior to their detection by the chemFET surface. In the absence of such inhibitors, released hydrogen ions may interact with or be sequestered by reactive groups in the solution or on solid supports in contact with the solution. These hydrogen ions are less likely to reach and be detected by the chemFET surface, leading to a weaker signal than is otherwise possible. In the presence of such inhibitors however there will be fewer reactive groups available for interaction with or sequestration of hydrogen ions. As a result, a greater proportion of released hydrogen ions will reach and be detected by the chemFET surface, leading to stronger signals. Reactive groups that can interfere with released hydrogen ions include without limitation reactive groups such as free bases on single stranded nucleic acids and Si—OH groups that may be present in the passivation layer. Some suitable buffering inhibitors demonstrate little or no buffering capacity in the pH range of 5-9, meaning that pH changes on the order of 0.005, 0.01, 0.02, 0.03, 0.04, 0.05, 0.1, 0.2, 0.3, 0.4, 0.5 or more pH units are detectable (e.g., by using an ISFET) in the presence of such inhibitors.

Figure 61B:
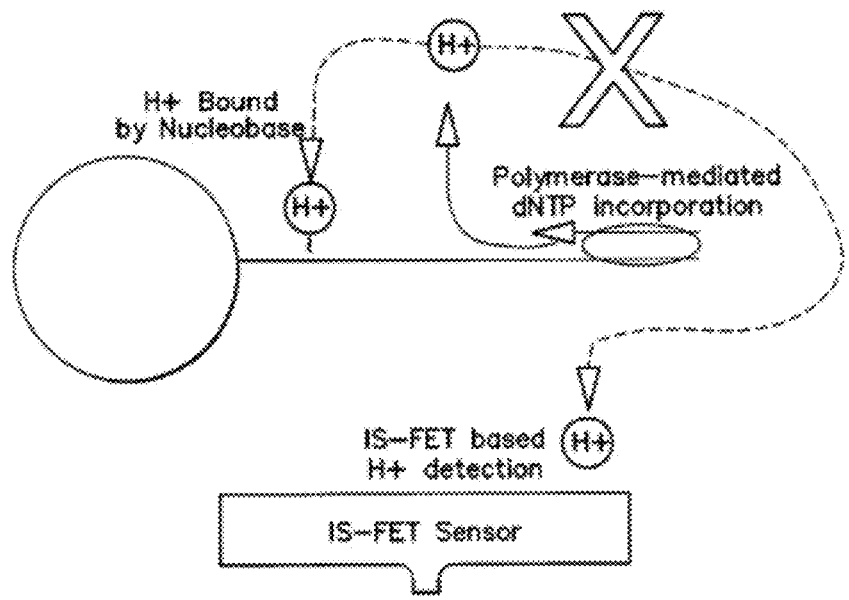
FIG. 61B is a schematic illustrating an embodiment of the invention in which the single stranded region of the template is not hybridized to RNA oligomers. Hydrogen ion that is released as a result of nucleotide incorporation is able to interact with and possibly be sequestered by free bases on the single stranded region of the template. Such hydrogen ions are then unable to flow to the ISFET surface and be detected. The free bases in the single stranded regions are proton acceptors at pH below 7.5.
Figure 61C:
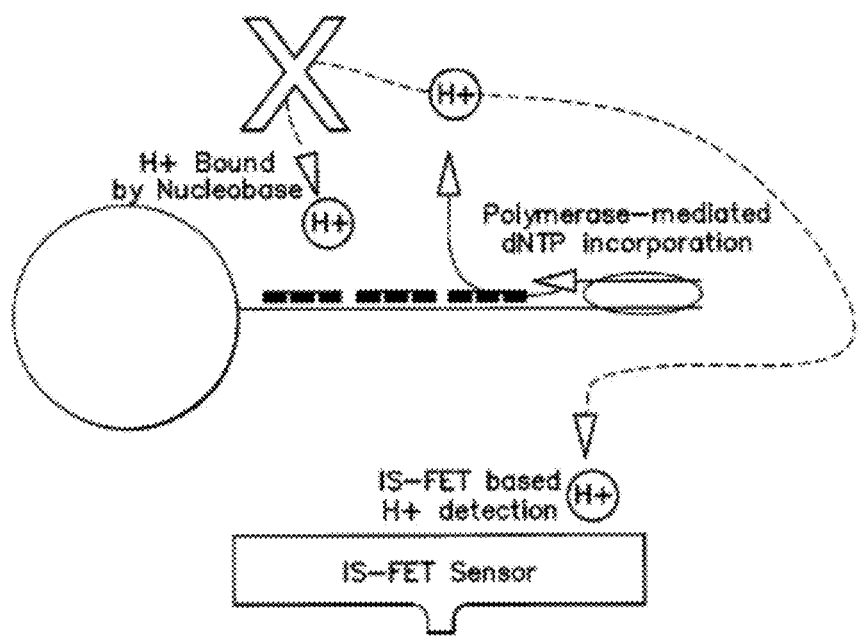
FIG. 61C is a schematic illustrating an embodiment of the invention in which the single stranded region of the template is hybridized to RNA oligomers. Hydrogen ion that is released as a result of nucleotide incorporation is not able to interact with the template which is hybridized to the RNA oligomers. These hydrogen ions are therefore able to flow to the ISFET surface and be detected.

There are various types of buffering inhibitors. One example of a buffering agent is an agent that binds to single stranded nucleic acids (or single stranded nucleic acid regions, as may occur in a template nucleic acid) thereby shielding reactive groups such as free bases. These agents may be RNA oligonucleotides (or RNA oligomers, or oligoribonucleotides, as they are referred to herein interchangeably) having complementary sequences to the afore-mentioned single stranded regions of template nucleic acids. RNA oligonucleotides are useful because they are not able to serve as primers for a sequencing reaction as compared to DNA oligonucleotides. In order to bind to (or shield the effects of) as much of a single stranded nucleic acid as possible, a plurality (or set, or mixture) of RNA oligonucleotides can be used. As an example, a set of RNA oligonucleotides that are 2, 3, 4, 5, 6, or more nucleotides in length can be used together with single stranded templates. The short length of these RNA oligonucleotides allows them to be displaced by the polymerase as it progresses along with the length of the nucleic acid template. Such displacement does not require exonuclease activity from the polymerase. Typically, the RNA oligonucleotides are of random sequence. In some embodiments, this is preferred as no prior knowledge of the sequence of the single stranded region of the template is required. FIGS. 61B and 61C illustrate the difference in ion detection at an ISFET in the presence or absence of a RNA hexamer hound to a single stranded template.

Another example of a class of buffering inhibitors is phospholipids. The phospholipids may be naturally occurring or non-naturally occurring phospholipids. Examples of phospholipids that may be used as buffering inhibitors include but are not limited to phosphatidylcholine, phosphatidylethanolamine, phosphatidylglycerol, and phosphatidylserine.

Figure 61D:
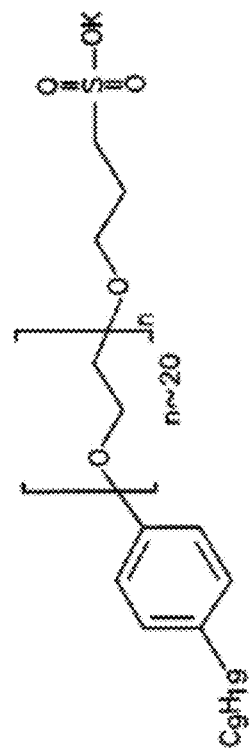
FIG. 61D is the structure of the potassium salt of PNSE.

Another example of a buffering inhibitor is sulfonic acid based surfactants such as poly(ethylene glycol)4-nonylphenyl 3-sulfopropyl ether (PNSE), the potassium salt of which is shown in FIG. 61D. In addition to shielding reactive groups that would otherwise interfere with released protons, PNSE has also been reported to enhance polymerase activity.

Figure 61E:
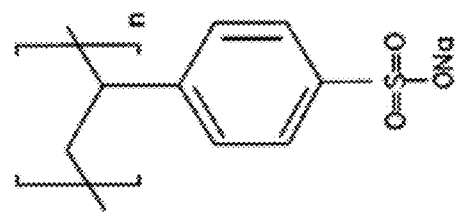
FIG. 61E is the structure of the sodium salt of poly(styrene sulfonic acid).

Another example of a buffering inhibitor is polyanionic electrolytes such as poly(styrenesulfonic acid), the sodium salt of which is shown in FIG. 61E.

Figure 61F:
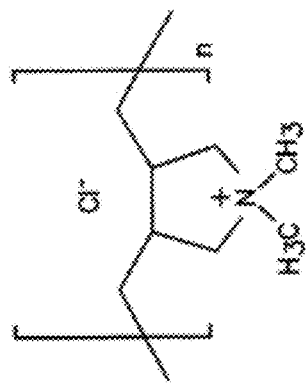
FIG. 61F is the structure of the chloride salt of poly(diallydimethylammonium).

Another example of a buffering inhibitor is polycationic electrolytes such as poly(diallydimethylammonium), the chloride salt of which is shown in FIG. 61F. These compounds are known to bind to DNA.

Figure 61G:
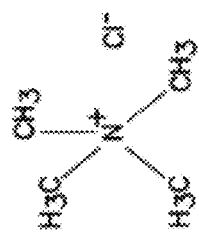
FIG. 61G is the structure of the chloride salt of tetramethyl ammonium.

Another example of a buffering inhibitor is tetramethyl ammonium, the chloride salt of which is shown in FIG. 61G.

These various inhibitors may be present throughout a reaction by being included in nucleotide solutions, wash solutions, and the like. Alternatively, they may be flowed through the chamber at set times relative to the flow through of nucleotides and/or other reaction reagents. In still other embodiments, they may be coated on the chemFET surface (or reaction chamber surface). Such coating may be covalent or non-covalent.

Another way of reducing the buffering capacity in the reaction well is to covalently attach nucleic acids to capture beads, in embodiments in which capture beads are used. Such covalent attachment is in contrast to non-covalent methods described herein that include for example biotin, streptavidin interactions. In these latter embodiments, biotinylated primers can be attached to streptavidin coated beads, followed by hybridization to template. However, streptavidin, like other proteins, is capable of buffering, and therefore its presence would interfere with the detection of hydrogen ions released as a consequence of nucleotide incorporation. Thus, the invention also contemplates in some instances approaches that do not rely on streptavidin in the attachment mechanism. One such alternative involves covalently coupling primers to beads (and/or other solid supports such as the chemFET surface). Covalently coupling primers to such solid supports serves at least two purposes. First, it eliminates the need for proteins, such as streptavidin, that comprise functional side groups (such as primary, secondary or tertiary amines and carboxylic acids) that can buffer pH changes in the range of pH 5-9. Second, it serves to increase the number of templates that can be conjugated to the solid support, such as a single bead, by reducing steric hindrance effects that may exist when using bulky proteins such as streptavidin. In still other embodiments, templates may be directly conjugated covalently to solid supports such as beads.

Figures 61H, 61I:
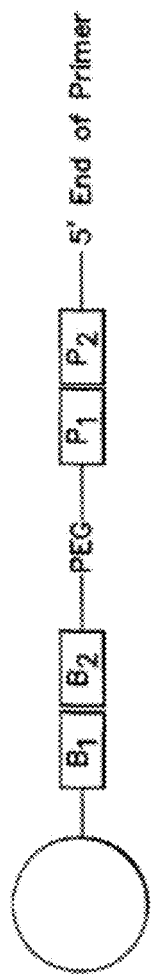
FIG. 61H is a schematic showing the chemistry for covalently conjugating a primer to a bead.
FIG. 61I is a table showing the possible reactive groups that can be used in combination at positions B1, B2, P1 and P2 in order to covalently conjugate a primer to a bead.

Primers can be covalently coupled to beads in any number of ways, several of which are shown in FIGS. 61H and 61I or described in Steinberg et al. Biopolymers 73:597-605, 2004, as an example. Reactive groups that can be used to conjugate primers to beads include epoxide, tosyl, amino and carboxyl groups. In addition, beads having a silica surface, as discussed below, can be used with chlorophyl, azide, and alkyne reactive groups. In some embodiments, the preferred combination is a polymer core bead with a polymer surface using tosyl reactive groups.

Increasing the number of templates or primers (i.e., copy number) results in a greater number of nucleotide incorporations per sensor and/or per reaction chamber, thereby leading to a higher signal and thus signal to noise ratio. Copy number can be increased for example by using templates that are concatemers (i.e., nucleic acids comprising multiple, tandemly arranged, copies of the nucleic acid to be sequenced), by increasing the number of nucleic acids on or in beads up to and including saturating such beads, and by attaching templates or primers to beads or to the sensor surface in ways that reduce steric hindrance and/or ensure template attachment (e.g., by covalently attaching templates), among other things. Concatemer templates may be immobilized on or in beads or on other solid supports such as the sensor surface, although in some embodiments concatemers templates may be present in a reaction chamber without immobilization. For example, the templates (or complexes comprising templates and primers) may be covalently or non-covalently attached to the chemFET surface and their sequencing may involve detection of released hydrogen ions and/or addition of negative charge to the chemFET surface upon a nucleotide incorporation event. The latter detection scheme may be performed in a buffered environment or solution (i.e., any changes in pH will not be detected by the chemFET and thus such changes will not interfere with detection of negative charge addition to the chemFET surface).

For some aspects described herein, it is important that buffering capacity not be affected in the process of increasing copy number. Thus, various methods are provided for increasing copy number using strategies and/or linkers that do not impact the buffering capacity of the environment. In some instances, the functional groups, linkers and/or polymers themselves have no or limited buffering capacity, and their use does not obscure the detection of hydrogen ions released as a result of nucleotide incorporation or excision, as the case may be.

Increasing copy number may also be accomplished by increasing the number of attachment points for primers (or templates). Some of these methodologies are described below.

In one embodiment, the solid support is coated with a polymer such as polyethylene glycol (PEG) which does not comprise functional groups that interact with the primer and its functional groups, except as provided below for initially attaching primer. PEG linkers of varying lengths can be used so that primers can be attached at varying distances from the solid support surface, thereby decreasing the amount of steric hindrance that may otherwise exist between primers and the complexes they ultimately form primer/template hybrids). The solid supports can be coated one or more times with a mixture of 2, 3, 4, or more PEG linkers of differing lengths. The end result is an increased distance between ends of PEG linkers attached to the solid support. Attachment of primers to the PEG linkers can be accomplished using any reactive groups known in the art. As an example, click chemistry can be used between azide groups on the ends of PEG linkers and alkyde groups on the primers.

In another embodiment, polymers having preferably more than one functional (or reactive) group are used. Each of the functional groups is available for conjugation with a separate primer. Useful polymers in this regard include those having hydroxyl groups, amine groups, thiol groups, and the like. Examples of suitable polymers include dextran and chitosan. Linear or branched forms of these polymers may be used. An example of a branched polymer with multiple functionalities is branched dextran. It will be apparent to those of ordinary skill in the art than any chimeric polymer or copolymer may also be used provided it has a sufficient number of functional groups for primer attachment.

Yet another embodiment involves the use of dendrimers and preferably higher order dendrimers to bind primer. Dendrimers are three-dimensional complexes that can be made having any functional group. Examples of dendrimers include the PAMAM dendrimers, an example of which is CAS No. 163442-69-1 which has 256 amine groups. Dendrimers are commercially available from sources such as Sigma-Aldrich and Dendritic Nanotechnologies Inc. It will be understood that dendrimers with other functional groups also can be used.

The invention further contemplates the use of any combination of the above embodiments for maximizing the number of primers attached to a solid support. Thus for example the solid support surface may be coated one or more times (e.g., once or twice) with the PEG linkers of varying lengths, and to such linkers may be attached multifunctionality polymers such as dextran or chitosan (in either linear or branched form), followed by attachment of primers. As another example, dendrimers may be attached to the PEG linkers, followed by primer attachment to the dendrimers.

In still another embodiment, the invention contemplates coating the solid support surface with a population of self-assembling monomers some proportion of which are bound to primers. As an example, the monomers may be acrylamide monomers some of which are attached to primers. The end result is a solid support having a polyacrylamide coating with interspersed primers. The density of primers bound to the solid support can be manipulated by changing the ratio of monomers that have primers and monomers that lack primers. This strategy has been reported by Rehman et al. Nucleic Acids Research, 1999, 27(2):649-655.

Still other methods for attaching nucleic acids to beads are taught by Lund et al., Nucleic Acids Research, 1988, 16(22): 10861-10880, Joos et al. Anal Biochem, 1997, 247:96-101, Steinberg et al. Biopolymers, 2004, 73:597-605, and Steinberg-Tatman et al. Bioconjugate Chem 2006 17:841-848.

Beads can be made of any material including but not limited to cellulose, cellulose derivatives, gelatin, acrylic resins, glass, silica gels, polyvinyl pyrrolidine (PVP), co-polymers of vinyl and acrylamide, polystyrene, polystyrene cross-linked with divinylbenzene or the like (see, Merrifield Biochemistry 1964, 3, 1385-1390), polyacrylamides, latex gels, dextran, crosslinked dextrans (e.g., Sephadex™), rubber, silicon, plastics, nitrocellulose, natural sponges, metal, and agarose gel (Sepharose™). In one embodiment, the beads are streptavidin-coated beads.

Beads suitable for covalent attachment may be magnetic or non-magnetic in nature. They may have a polymer core with a polymer surface, a polymer core with a silica surface, and a silica core with a silica surface. The bead core may be hollow, porous, or solid, as described below.

The bead diameter will depend on the density of the chemFET and microwell arrays used, with larger arrays (and thus smaller sized wells) requiring smaller beads. Generally the bead size may be about 1-10 microns, and more preferably 2-6 microns. In some embodiments, the beads are about 5.9 microns while in other embodiments the beads are about 2.8 microns. In still other embodiments, the beads are about 1.5 microns, or about 1 micron in diameter. In some embodiments, beads having a diameter that ranges from about 3.3 to 3.5 microns may be used for reaction well arrays having a pitch on the order of about 5.1 microns. In other embodiments, beads having a diameter that ranges from about 5 to 6.5 microns may be used for reaction well arrays having a pitch on the order to about 9 microns. It is to be understood that the beads may or may not be perfectly spherical in shape. It is also to be understood that other beads may be used and other mechanisms for attaching the nucleic acid to the beads may be used. In some instances the capture beads (i.e., the beads on which the sequencing reaction occurs) are the same as the template preparation beads including the amplification beads. In some instances, even where non-covalent attachment is contemplated, a spacer is used to distance the template nucleic acid (and in particular the target nucleic acid sequence comprised therein) from a solid support such as a bead. This facilitates sequencing of the end of the target closest to the bead, for instance. Examples of suitable linkers are known in the art (see Diehl et al, Nature Methods, 2006, 3(7):551-559) and include but are not limited to carbon-carbon linkers such as but not limited to iSp18. Beads can be purchased from commercial suppliers such as Bangs, Dynal and Micromod. Additional spacers and nucleic acid attachment mechanisms are discussed above.

As stated above, some beads may be solid while others may be porous or hollow. These beads will have a porous surface such that reagents from the reaction solution may move into and out of the bead These may have empty channels or hollow cores that comprise at least 10%, at least 20%, at least 30%, at least 40%, at least 50%, at least 60%, at least 70%, at least 80%, at least 90% of the bead volume. These beads will be referred to herein as porous beads, porous microparticles, or capsules in view of their non-solid cores, and these terms are intended to embrace porous as well as hollow beads regardless of diameter or volume. They may or may not be spherical.

The invention contemplates the use of such porous beads in the various sequencing methods described herein. More specifically, the invention contemplates sequencing nucleic acids that are present in porous beads. Porous beads may be generated by methods known in the art. See for example Mak et al. Adv. Funct. Mater. 2008 18:2930-2937; Morimoto et al, MEMS 2008 Tucson Ariz. USA Jan. 13-17, 2008 Poster Abstract 304-307; Lee et al. Adv. Mater. 2008 20:3498-3503; Martin-Banderas et al. Small, 2005 1(7):688-92; and published PCT application WO03/078659.

Porous microparticles may be initially generated to contain a single template nucleic acid which is later amplified with all amplified copies of the nucleic acid being retained in the microparticle. Amplification may occur before or while the bead is in contact with a chemFET array, and/or optionally in a reaction chamber. If performed before contact with the chemFET array, beads that have successfully undergone amplification can be selected and thereby enriched. As an example, beads having amplified nucleic acids can be separated from other beads based on density. Amplification may be isothermal or PCR amplification, or other means of amplification, as the invention is not to be limited in this regard. The beads may contain at least two types of enzymes such as two types of polymerases. For example, the beads may contain one type of polymerase that is suitable for amplification of the nucleic acid and a second type of polymerase that is suitable for sequencing the amplified nucleic acids. The beads preferably contain a plurality of both types of polymerases and preferably the number of each polymerase will be in excess of a saturating amount so as not to create a polymerase-limited environment. Once amplification is completed, the amplification polymerase may be inactivated, while maintaining the activity of the sequencing polymerase. Typically, the enzymes and nucleic acids will be retained in the bead while smaller compounds, such as dNTPs and other nucleic acid synthesis reagents and cofactors, are allowed to diffuse into and out of the bead. Importantly for the invention, synthesis byproducts such as PPi and hydrogen ions will also diffuse out of the beads, in order to be detected by the chemFET.

Nick Translation

The invention provides, in various other aspects, other modes for analyzing, including for example sequencing, nucleic acids using reactions that involve interdependent nucleotide incorporation and nucleotide excision. As used herein, interdependent nucleotide incorporation and nucleotide excision means that both reactions occur on the same nucleic molecule at contiguous sites on the nucleic acid, and one reaction facilitates the other.

An example of such a reaction is a nick translation reaction. A nick translation reaction, as used herein, refers to a reaction catalyzed by a polymerase enzyme having 5' to 3' exonuclease activity, that involves incorporation of a nucleotide onto the free 3' end of a nicked region of double stranded DNA and excision of a nucleotide located at the free 5' end of the nicked region of the double stranded DNA. Nick translation therefore refers to the movement of the nicked site along the length of the nicked strand of DNA in a 5' to 3' direction. As will be recognized by those of ordinary skill in the art, the nick translation reaction includes a sequencing-by-synthesis reaction based on the intact strand of the double stranded DNA. This strand acts as the template from which the new strand is synthesized. The method does not require the use of a primer because the double stranded DNA can prime the reaction independently. These aspects of the invention will refer specifically to nick translation for the sake of brevity, but it is to be understood that any other combined reaction of nucleotide excision and incorporation will be equally and fully intended in the following discussion.

The nick translation approach has two features that make it well suited to the detection methods provided herein. First, the nick translation reaction results in the release of two hydrogen ions for each combined excision/incorporation step, thereby providing a more robust signal at the chemFET each time a nucleotide is incorporated into a newly synthesized strand. A sequencing-by-synthesis method, in the absence of nucleotide excision, releases one hydrogen ion per nucleotide incorporation. In contrast, nick translation releases a first hydrogen ion upon incorporation of a nucleotide and a second hydrogen ion upon excision of another nucleotide. This increases the signal that can be sensed at the chemFET, thereby increasing signal to noise ratio and providing a more definitive readout of nucleotide incorporation.

Second, the use of a double stranded DNA template (rather than a single stranded DNA template) results in less interference of the template with released ions and a better signal at the chemFET. A single stranded DNA has exposed groups that are able to interfere with (for example, sequester) hydrogen ions. These reactive groups are shielded in a double stranded DNA where they are hydrogen bonded to complementary groups. By being so shielded, these groups do not substantially impact hydrogen ion level or concentration. As a result, signal resulting from hydrogen ion release is greater in the presence of double stranded as compared to single stranded templates, as will be signal to noise ratio, thereby further contributing to a more definitive readout of nucleotide incorporation.

Templates suitable for nick translation typically are completely or partially double stranded. Such templates comprise an opening (or a nick) which acts as an entry point for a polymerase. Such openings can be introduced into the template in a controlled manner as described below and known in the art.

As will be appreciated by one of ordinary skill in the art, it is preferable that these openings be present in each of the plurality of identical templates at the same location in the template sequence. Typical molecular biology techniques involving nick translation use randomly created nicks along the double stranded DNA because their aim is to produce a detectably labeled nucleic acid. These prior art methods generate nicks through the use of sequence-independent nicking enzymes such as DNase I. In the methods of the invention however the nick location must be known, non-random and uniform for all templates of identical sequence. There are various ways of achieving this, and some of these are discussed below.

One way of achieving this is to create a population of identical double stranded nucleic acid templates that comprise a uracil residue in a defined location on one strand. The uracil may be present in a primer that is used to generate the double stranded nucleic acid or a probe that is hybridized to a single stranded region of a predominantly double stranded nucleic acid. The population of identical template nucleic acids can be generated by an amplification reaction, for example a PCR reaction. The PCR reaction can be performed using a primer pair, one of which comprises a uracil residue. Alternatively, the PCR reaction can be performed with non-uracil containing primers, followed by denaturation of the double stranded amplified products, and hybridization of one strand to a uracil-containing primer. This latter embodiment requires that the single stranded, primed templates be made double stranded prior to the nick translation reaction. These reactions may be carried out while the nucleic acids are bound to a solid support such as a bead. Alternatively, the double stranded nucleic acid templates may be first generated and then attached to a solid support.

The uracil-containing double stranded nucleic acids are then contacted with uracil DNA glycosylase (UDG). UDG is an enzyme that removes uracil from DNA by cleaving the N-glycosylic bond. In some instances, the nucleic acid is contacted with a second enzyme that removes uracil. The second enzyme may be an AP endonuclease, or a lyase or another enzyme having similar nuclease activity. The nucleic acids may be in the reaction chamber (or well) discussed herein during exposure to these enzymes, or they may be added to the reaction chamber (or well) following enzyme contact. Following contact with one (in some instances) or both enzymes, the double stranded nucleic acid comprises a nick at a specific location. More importantly, all nucleic acids of the same sequence and treated in an identical manner will be nicked at the same location. These nicked nucleic acids can then be used as templates for nucleic acid sequencing or other analysis.

Another way in which double stranded nucleic acids can be uniformly nicked is similar to the method just described with the exception that a nucleotide sequence recognized by a nickase or nicking enzyme is incorporated into the nucleic acid. The nickase cuts on only one strand of the double stranded DNA. Some nickases cut their recognition sequence while others cut at a distance from their recognition sequence (e.g., type II nickases). Nickases with longer recognition sites are preferred because such sites are more infrequent and thus less likely to be present in the target nucleic acid (e.g., the genomic fragment) included in the template nucleic acid. Examples of single stranded sequence specific nucleases (and their respective sequences) include without limitation Nb.BbvCI (CCTCA↓GC), Nt.BbvCI (CC↓TCAGC), Nb.BsmI (GAATG↓C), Nt.SapI (GCTCTTCN↓), Nb.BsrDI (GCAATG↓), and Nb.BtsI (GCAGTG↓), wherein the arrow indicates the site of nicking. Nickases are commercially available from a number of suppliers including NEB. Accordingly, the nucleic acids are prepared having a copy of the nickase recognition sequence in a region of known sequence (e.g., a primer or other artificial sequence in the template nucleic acid). These nucleic acids are then contacted with the corresponding nickase to nick the nucleic acid. As with the uracil embodiment, contact with the nickase can occur before or after the nucleic acids are attached to solid support such as beads, and before or after the nucleic acids are loaded in reaction wells.

Still another way in which double stranded nucleic acids may be uniformly nicked is by incorporating ribonucleotides (rather than deoxyribonucleotides) into one strand of the double stranded nucleic acids. This can be accomplished in a manner similar to that described for the generation of uracil-containing nucleic acids. In other words, a double stranded nucleic acid can be generated using primers that contain one or more ribonucleotides at predetermined and thus known positions. The resultant nucleic acids are then contacted with RNase H or other enzyme that degrades the RNA portion of DNA-RNA hybrids. RNase H in particular hydrolyses phosphodiester bonds of RNA in RNA:DNA heteroduplexes, thereby producing 3' OH groups and 5' phosphate groups. If the double stranded nucleic acid is generated with only a single ribonucleotide then only a single abasic site will result, whereas if the double stranded nucleic acid is generated with multiple ribonucleotides then multiple abasic sites will result. In either case, identical nucleic acids can still be analyzed using a nick translation reaction once all but one of the abasic sites are filled by the polymerase. Taq polymerase is preferred in some embodiments involving these RNA-DNA hybrids, Again, as with the other methods described above, contact with RNase H or other similar enzyme can occur before or after the nucleic acids are attached to a solid support such as beads, and before or after the nucleic acids are loaded in reaction wells.

Still another way to prepare double stranded nucleic acids suitable as templates for nucleotide incorporation and excision events is to generate a double stranded nucleic acid having a 3' overhang on one end, and then subsequently hybridize to the 3' overhang a nucleic acid that is shorter than the overhang by at least one nucleotide. Preferably, after hybridization of the two nucleic acids to each other, there will be one unpaired internal nucleotide in the overhang and this will be the site from which nick translation will begin. Again, the sequence of the 3' overhang and the hybridizing nucleic acid will be known and therefore the location of the abasic site will also be known and will be identical for all template nucleic acids. The hybridization can occur before or after the nucleic acids are attached to a solid support such as beads, and before or after the nucleic acids are loaded into reaction wells.

Another example of a suitable nick translation template is a self-priming nucleic acid. The self priming nucleic acid may comprise a double stranded and a single stranded region that is capable of self-annealing in order to prime a nucleic acid synthesis reaction. The single stranded region is typically a known synthetic sequence ligated to a nucleic acid of interest. Its length can be predetermined and engineered to create an opening following self-annealing, and such opening can act as an entry point for a polymerase.

It is to be understood that, as the term is used herein, a nicked nucleic acid, such as a nicked double stranded nucleic acid, is a nucleic acid having an opening (e.g., a break in its backbone, or having abasic sites, etc.) from which a polymerase can incorporate and optionally excise nucleotides. The term is not limited to nucleic acids that have been acted upon by an enzyme such as a nicking enzyme, nor is it limited simply to breaks in a nucleic acid backbone, as will be clear based on the exemplary methods described herein for creating such nucleic acids.

Once the nicked double stranded nucleic acids are generated, they are then subjected to a nick translation reaction. If the nick translation reaction is performed to sequence the template nucleic acid, the nick translation can be carried out in a manner that parallels the sequencing-by-synthesis methods described herein. More specifically, in some embodiments each of the four nucleotides is separately contacted with the nicked templates in the presence of a polymerase having 5' to 3' exonuclease activity. In other embodiments, known combinations of nucleotides are used. Examples of suitable enzymes include DNA polymerase I from *E. coli*, Bst DNA polymerase, and Taq DNA polymerase, The order of the nucleotides is not important as long as it is known and preferably remains the same throughout a run. After each nucleotide is contacted with the nicked templates, it is washed out followed by the introduction of another nucleotide, just as described herein. In the nick translation embodiments, the wash will also carry the excised nucleotide away from the chemFET.

It should be appreciated that just as with other aspects and embodiments described herein the nucleotides that are incorporated into the nicked region need not be extrinsically labeled since it is a byproduct of their incorporation that is detected as a readout rather than the incorporated nucleotide itself. Thus, the nick translation methods may be referred to as label-free methods, or fluorescence-free methods, since incorporation detection is not dependent on an extrinsic label on the incorporated nucleotide. The nucleotides are typically naturally occurring nucleotides. It should also be recognized that since the methods benefit from the consecutive incorporation of as many nucleotides as possible, the nucleotides are not for example modified versions that lead to premature main termination, such as those used in some sequencing methods.

Target and Template Nucleic Acids

The nucleic acid being sequenced is referred to herein as the target nucleic acid. Target nucleic acids include but are not limited to DNA such as but not limited to genomic DNA, mitochondrial DNA, cDNA and the like, and RNA such as but not limited to mRNA, miRNA, and other interfering RNA species, and the like. The nucleic acids may be naturally or non-naturally occurring. They may be obtained from any source including naturally occurring sources such as any bodily fluid or tissue that contains DNA, including, but not limited to, blood, saliva, cerebrospinal fluid ("CSF"), skin, hair, urine, stool, and mucus, or synthetic sources. The nucleic acids may be PCR products, cosmids, plasmids, naturally occurring or synthetic libraries, and the like. The invention is not intended to be limited in this regard. It should therefore be understood that the invention contemplates analysis, including sequencing, of DNA as well as RNA.

With respect to RNA, amplification methods such as the SMART system and NASBA are known in the art and have been reported by van Gelder et al. PNAS, 1990, 87:1663-1667, Chadwick et al. BioTechniques, 1998, 25:818-822, Brink et al. J Clin Microbiol, 1998, 36(11):3164-3169, Voisset et al. BioTechniques, 2000, 29:236-240, and Zhu et al. BioTechniques, 2001, 30:892-897. The amplification methods described in these references are incorporated by reference herein.

The starting amounts of nucleic acids to be sequenced determine the minimum sample requirements. Considering the following bead sizes, with an average of 450 bases in the single stranded region of a template, with an average molecular weight of 325 g/mol per base, Table 2 shows the following:

TABLE 2

| Bead Size (um) | femto gram of DNA |
|---|---|
| 0.2 | 0.124 |
| 0.3 | 0.279 |
| 0.7 | 1.52 |
| 1.05 | 3.42 |
| 2.8 | 24.3 |
| 5.9 | 108 |

Given the number of beads and microwells contemplated for use in an array, in some embodiments of the invention, it will be apparent that a sample taken from a subject to be tested need only be on the order of 3 µg. Thus, the systems and methods described herein can be utilized to sequence an entire genome of an organism from about 3 µg of DNA or less. As discussed herein, such sequences can be obtained without the use of optics or extrinsic labels.

Target nucleic acids are prepared using any manner known in the art. As an example, genomic DNA may be harvested from a sample according to techniques known in the art (see for example Sambrook et al. "Maniatis"). Following harvest, the DNA may be fragmented to yield nucleic acids of smaller length. The resulting fragments may be on the order of hundreds, thousands, or tens of thousands nucleotides in length. In some embodiments, the fragments are 200-1000 base pairs in size, or 300-800 base pairs in size, about 200, about 300, about 400, about 500, about 600, about 700, about 800, about 900, or about 1000 base pairs in length, although they are not so limited.

Nucleic acids may be fragmented by any means including but not limited to mechanical, enzymatic or chemical means. Examples include shearing, sonication, nebulization, endonuclease (e.g., DNase I) digestion, amplification such as PCR amplification, or any other technique known in the art to produce nucleic acid fragments, preferably of a desired length. As used herein, fragmentation also embraces the use of amplification to generate a population of smaller sized fragments of the target nucleic acid. That is, the target nucleic acids may be melted and then annealed to two (and preferably more) amplification primers and then amplified using for example a thermostable polymerase (such as Taq). An example is a massively parallel PCR-based amplification. Fragmentation can be followed by size selection techniques to enrich or isolate fragments of a particular length or size. Such techniques are also known in the art and include but are not limited to gel electrophoresis or SPRI.

Alternatively, target nucleic acids that are already of sufficiently small size (or length) may be used. Such target nucleic acids include those derived from an exon enrichment process. Thus, rather than fragmenting (randomly or non-randomly) longer target nucleic acids, the targets may be nucleic acids that naturally exist or can be isolated in shorter, useable lengths such as mRNAs, cDNAs, exons, PCR products (as described above), and the like. See Albert et al. Nature Methods 2007 4(11):903-905 (microarray hybridization of exons and locus-specific regions), Porreca et al. Nature Methods 2007 4(11):931-936, and Okou et al. Nature Methods 2007 4(11):907-909 for methods of isolating and/or enriching sequences such as exons prior to sequencing.

The target nucleic acids are typically ligated to adaptor sequences on both the 5' and 3' ends. The resulting nucleic acid is referred to herein as a template nucleic acid. The template nucleic acid therefore comprises at least the target nucleic acid and usually comprises nucleotide sequences in addition to the target at both the 5' and 3' ends. The template nucleic acids may be engineered such that different templates have identical 5' ends and identical 3' ends. The 5' and 3' ends in each individual template are preferably different in sequence.

Adaptor sequences may comprise sequences complementary to amplification primer sequences, to be used in amplifying the target nucleic acids. One adaptor sequence may also comprise a sequence complementary to the sequencing primer (i.e., the primer from which sequencing occurs). The opposite adaptor sequence may comprise a moiety that facilitates binding of the nucleic acid to a solid support such as but not limited to a bead. An example of such a moiety is a biotin molecule (or a double biotin moiety, as described by Diehl et al. Nature Methods, 2006, 3(7):551-559) and such a labeled nucleic acid can therefore be bound to a solid support having avidin or streptavidin groups. Another moiety that can be used is the NHS-ester and amine affinity pair. It is to be understood that the invention is not limited in this regard and one of ordinary skill is able to substitute these affinity pairs with other binding pairs. In some embodiments, the solid support is a bead and in others it is a wall of the reaction chamber (or well) such as a bottom wall or a side wall, or both.

In some embodiments, the invention contemplates the use of a plurality of template populations, wherein each member of a given plurality shares the same 3' end but different template populations differ from each other based on their 3' end sequences. As an example, the invention contemplates in some instances sequencing nucleic acids from more than one subject or source. Nucleic acids from a first source may have a first 3' sequence, nucleic acids from a second source may have a second 3' sequence, and so on, provided that the first, second, and any additional 3' sequences are different from each other. In this respect, the 3' end, which is typically a unique sequence, can be used as a barcode or identifier to label (or identify) the source of the particular nucleic acid in a given well. Reference can be made to Meyer et al. Nucleic Acids Research 2007 35(15):e97 for a discussion of labeling nucleic acid with barcodes followed by sequencing.

Templates disposed onto a chemFET array (and thus over more than one sensor in the array) may share identical primer binding sequences. This facilitates the use of an identical primer across microwells and also ensures that a similar (or identical) degree of primer hybridization occurs across microwells. Once annealed to complementary primers such as sequencing primers, the templates are in a complex referred to herein as a template/primer hybrid. In this hybrid, at least one region of the template is double stranded (i.e., where it is bound to its complementary primer) and in some instances the remaining region of the template is single stranded. It is this single stranded region that acts as the template for the incorporation of nucleotides to the end of the primer and thus it is also this single stranded region which is ultimately sequenced according to the invention. As discussed herein, this single stranded region may be bound by short RNA oligomers, of known or unknown (i.e., random) sequence, and still capable of being sequenced.

In some embodiments, the template nucleic acid is able to self-anneal thereby creating a 3' end from which to incorporate nucleotide triphosphates. Thus in such instances, there is no need for a separate sequencing primer since the template acts as both template and primer. See Eriksson et al. Electrophoresis 25:20-27, 2004 for a discussion of the use of self-annealing template in a pyrosequencing reaction. In other instances, sequencing primers are hybridized (or annealed, as the terms are used interchangeably herein) to the templates prior to introduction or contact with the chemFET or reaction chamber.

The plurality of templates in each microwell may be introduced into the microwells (e.g., via a nucleic acid loaded bead), or it may be generated in the microwell itself. A plurality is defined herein as at least two, and in the context of template nucleic acids in a microwell or on a nucleic acid loaded bead includes tens, hundreds, thousands, ten thousands, hundred thousands, millions, or more copies of the template nucleic acid. The limit on the number of copies will depend on a number of variables including the number of binding sites for template nucleic acids (e.g., on the beads or on the walls of the microwells), the size of the beads, the length of the template nucleic acid, the extent of the amplification reaction used to generate the plurality, and the like. It is generally preferred to have as many copies of a given template per well in order to increase signal to noise ratio as much as possible, as discussed herein. In some embodiments, the amplification is a representative amplification. A representative amplification is an amplification that does not alter the relative representation of any nucleic acid species.

Thus, the template nucleic acid may be amplified prior to or after placement in the well and/or contact with the sensor. Amplification and conjugation of nucleic acids to solid supports such as beads may be accomplished in a number of ways. For example, in one aspect once a template nucleic acid is loaded into a well of the flow cell 200, amplification may be performed in the well, the resulting amplified product denatured, and sequencing-by-synthesis then performed. In one embodiment, the template is amplified in solution and then hybridized to a single primer that is immobilized on the chemFET surface. The use of only one primer type on the surface ensures that only one of the amplified strands is eventually bound to the surface, and the other strand is removed through wash.

Amplification methods include but are not limited to emulsion PCR (i.e., water in oil emulsion amplification) as described by Margulies et al. Nature 2005 437(15):376-380 and accompanying supplemental materials, bridge amplification, rolling circle amplification (RCA), concatemer chain reaction (CCR), or other strategies using isothermal or non-isothermal amplification techniques.

Bridge amplification can be used to produce a solid support (such as a reaction chamber wall or a bead) having amplified copies of the same template. The method involves contacting template nucleic acids with the chemFET/reaction chamber array at a limiting dilution in order to ensure that reaction chambers contain only a single template. The chemFET surface will typically be coated with two populations of primers. In one embodiment, the chemFET surface is coated with both forward and reverse primers that are complementary to the engineered 5' and 3' sequences of the template. The template is bound to the chemFET surface directly and then allowed to hybridize at its free end with a complementary primer on the surface. The primer is extended using unlabeled nucleotides, and the resultant double stranded nucleic acid is then denatured. This results in immobilized copies of the template nucleic acid and its complement in close proximity on the surface. This process is repeated by allowing the template and its complement to hybridize at their free ends to other primers on the surface. The net result is a population of immobilized template and a population of immobilized complement that are interspersed amongst each other. The sequencing-by-synthesis reaction is then carried out using a sequencing primer that binds to one but not both immobilized strands. This effectively selects for one of the strands and ensures that only one strand is sequenced, Either strand can be sequenced since they are complements of each other.

In a related embodiment, the solid support is a bead and the bead is coated with the two primer populations and only a single stranded template nucleic acid, at least initially. This amplification method is described in U.S. Pat. No. 5,641,658 to Adams et al.

In still another embodiment, each solid support surface (whether bead or reaction chamber wall) has bound thereto a specific and unique primer pair that may be but is not limited to a gene specific primer pair. One or both of the primers in the pair select for templates in a library that is applied to the solid support. Due to the unique sequence of the primers, it is expected that only the desired template will hybridize and then be amplified and sequenced, as described above.

RCA or CCR amplification methods generate concatemers of template nucleic acids that comprise tens, hundreds, thousands or more tandemly arranged copies of the template. Such concatemers may still be referred to herein as template nucleic acids, although they may contain multiple copies of starting template nucleic acids. In some embodiments, they may also be referred to as amplified template nucleic acids. Alternatively, they may be referred to herein as comprising multiple copies of target nucleic acid fragment. Concatemers may contain 2, 3, 4, 5, 6, 7, 8, 9, 10, 20, 30, 40, 50, 60, 70, 80, 90, 100, 500, 1000, or more copies of the starting nucleic acid. They may contain $10$-$10^2$, $10^2$-$10^3$, $10^3$-$10^4$, $10^3$-$10^5$, or more copies of the starting nucleic acid. Concatemers generated using these or other methods (such as for example DNA nanoballs) can be used in the sequencing-by-synthesis methods described herein. The concatemers may be generated in vitro apart from the array and then placed into reaction chambers of the array or they may be generated in the reaction chambers. One or more inside walls of the reaction chamber may be treated to enhance attachment and retention of the concatemers, although this is not required. In some embodiments of the invention, if the concatemers are attached to an inside wall of the reaction chamber, such as the chemFET surface, then nucleotide incorporation at least in the context of a sequencing-by-synthesis reaction may be detected by a change in charge at the chemFET surface, as an alternative to or in addition to the detection of released hydrogen ions as discussed herein. If the concatemers are deposited onto a chemFET surface and/or into a reaction chamber, sequencing-by-synthesis can occur through detection of released hydrogen ions as discussed herein. The invention embraces the use of other approaches for generating concatemerized templates. One such approach is a PCR described by Stemmer et al. in U.S. Pat. No. 5,834,252, and the description of this approach is incorporated by reference herein.

The ability to use template nucleic acids independently of beads and that can be deposited into reaction chambers or onto chemFET surfaces facilitates the use of dense chemFET arrays. As will be understood, denser arrays will typically incorporate more chemFETs and optionally more reaction chambers (where they are used) per array (or chip). In order to accommodate the increased number of chemFETs and optionally reaction chambers, the size of the chemFETs and optionally reaction chambers is reduced. Accordingly, in some instances, it may be preferable to use nucleic acids that are concatemers of the nucleic acid to be sequenced, independently of beads. Such nucleic acids may be allowed to self-assemble onto a treated chemFET surface, or they may settle into the well (for example, by gravity), or they may be pulled in by magnetic or other force. Thus, the invention contemplates the use of such concatemerized template nucleic acids in the pH based sequencing-by-synthesis methods described herein.

As discussed herein, one approach for generating nucleic acids that comprise multiple copies of a nucleic acid to be sequenced involves amplification of a circular template. The resultant amplified product forms a three dimensional structure that may occupy a spherical volume or other three dimensional volume and shape. The occupied volume may vary, depending on the size of the resultant nucleic acid. For example, in some instances the spherical volume may have an average diameter on the order of about 100-300 nm. The generation of these three dimensional structures is described further in published US patent applications US20070072208A1 and US20070099208A1, both to Drmanac et al.

Such nucleic acids may be generated in solution (i.e., amplification occurs in solution) and therefore emulsion based techniques or reaction chambers or wells are not necessary in some instances. As each resultant nucleic acid consists of a clonal amplified population of a starting nucleic acid, there will be no cross contamination of nucleic acids and nor does there have to be any physical separation between individual amplification reactions. Thus, in some aspects, it is contemplated that nucleic acids such as "DNA nanoballs" or "amplicons") are generated in solution and then deposited onto chemFET surfaces and/or into reaction chambers. Further references that describe amplifications methods suitable for the synthesis of these nucleic acids include U.S. Pat. Nos. 4,683,195, 4,965,188, 4,683,202, 4,800,159, 5,210,015, 6,174,670, 5,399,491, 6,287,824, 5,854,033 and published U.S. patent application US20060024711, Linear rolling circle amplification, multiple displacement amplification, and padlock probe rolling circle amplification can all be used to generate clonal amplicons without the need for limiting dilution in order to avoid cross-contamination of nucleic acid templates by each other.

The chemFET surfaces may be treated (or patterned) or untreated (or unpatterned). In some instances, treated (or patterned) surfaces are preferred in order to maximize nucleic acid deposition and/or retention onto a surface. It is further known in the art that these nucleic acids may self-assemble onto the chemFET surface provided the chemFET array surface comprises regions to which the nucleic acids bind and optionally regions to which they do not bind. Additionally, the binding of a nucleic acid to one region on the surface will repel the binding of another nucleic acid, thereby precluding the possibility that two or more nucleic acids of different sequence could co-exist at the same chemFET surface. The chemFET array may have an occupancy on the order of greater than 50%, greater than 60%, greater than 70%, greater than 80%, or 90% or greater (i.e., the number of individual chemFET surfaces onto which a single nucleic acid is deposited). It will be understood that, as used herein, the term deposited refers simply to the placement of the nucleic acid in close proximity and potentially in contact with a chemFET surface (and optionally reaction chamber), but it does not require any particular interaction, whether covalent or non-covalent, between the nucleic acid and the chemFET surface.

The amplified nucleic acids discussed herein may be attached to the chemFET surface through functionalities incorporated into (e.g., during amplification) or added post-synthesis to the nucleic acid. Such functionalities may be located at adaptor regions within the nucleic acid which are not intended for sequencing according to the methods provided herein. For example, a concatemer may be generated from a circular template having two or more adaptor sequences (or nucleic acids) located upstream and downstream of the nucleic acids being sequenced. Alternatively, the starting (or initial) nucleic acid may consist of a single adaptor sequence and a single nucleic acid to be sequenced and in the process of amplification (such as, for example, RCA) the adaptor sequence is used to separate the copies of the nucleic acid to be sequenced from each other. Whether in this embodiment or others described herein, functionalities present in the adaptor sequences may be used to attach and/or retain the resultant amplified nucleic acids on a chemFET surface and optionally a reaction chamber. Exemplary functionalities include but are not limited to amino groups, sulfhydryl groups, carbonyl groups, biotin, streptavidin, avidin, amine allyl labeled nucleotides, NHS-ester interaction, thioether linkages, and the like.

Attachment may be via non-covalent bonds between capture nucleic acids present on the chemFET surface and complementary sequences in the adapter regions, or adsorption to the surface via Van der Waals forces, hydrogen bonding, static charge interactions, ionic and hydrophobic interactions, and the like. Techniques used to attach DNAs to microarrays may also be used to attach the amplified products to the chemFET surface. These techniques include but are not limited to those described by Smirnov, Genes, Chrom & Cancer 40:72-77, 2004 and Beaucage Curr Med Chem 8:1213-1244, 2001.

Deposition and/or retention may also be accomplished using magnetic forces. In these embodiments, magnetic particles may be incorporated into and/or attached post-synthesis to the amplified nucleic acids (e.g., at regions not intended for sequencing). Once the nucleic acids are distributed on a chemFET array and optionally a reaction chamber array, the array is placed in proximity to a magnet in order to move the nucleic acids towards the chemFET surface and optionally into a reaction chamber.

It should also be understood that the methods described herein contemplate the synthesis of the amplified nucleic acids on or in proximity to the chemFET and optionally in a reaction chamber in addition to synthesis in solution followed by deposition onto the chemFET surface. It is expected however that the latter approach will result in a greater degree of occupancy of chemFET surfaces in the array.

Accordingly, provided herein is an array of nucleic acids comprising a plurality of chemFETs each having a surface, and a plurality of nucleic acids, each nucleic acid deposited onto (or attached to) individual chemFET surfaces, wherein each nucleic acid comprises multiple identical copies of an initial nucleic acid to be sequenced. In some instances, the nucleic acid has a random coil state.

Also provided herein is a method for sequencing a nucleic acid present in a reaction chamber of a reaction chamber array, comprising synthesizing a concatemer of a starting nucleic acid, wherein the concatemer has a cross-sectional diameter greater than the diameter of the reaction well, optionally immobilizing (whether covalently or non-covalently) the concatemer in the reaction chamber, and sequencing the concatemer, preferably by sequencing-by-synthesis methods provided herein (e.g., pH based sequencing-by-synthesis methods). It will be understood that if the reaction chamber has a non-circular cross-section then one or more or an average of cross-sectional dimensions can be used (as can a cross-sectional area) in comparing the concatemer and the reaction chamber sizes or dimensions. It should also be understood that the size of the concatemer relative to the reaction chamber will preclude the presence of more than one concatemer per reaction chamber.

Solid Supports and Capture Beads

The solid support to which the template nucleic acids or primers are bound is referred to herein as the "capture solid support". The solid support may be a wall of the reaction chamber (or well) including the surface of the chemFET, or a bottom or side wall of the reaction chamber provided such wall is capacitively coupled to the chemFET. If the solid support is a bead, then such bead may be referred to herein as a "capture bead". Such beads are generally referred to herein as "loaded" with or "bearing" nucleic acid if they have nucleic acids attached to their surface (whether covalently or non-covalently) and/or present in their interior core. Some capture beads comprise a porous surface that allows entry and exit of small compounds such as amplification or sequencing reagents (e.g., dNTPs, co-factors, etc.). This class of beads typically will comprise nucleic acids internally and in this way they function to localize the nucleic acids, optionally without the need to attach the nucleic acids to a solid support. In embodiments in which capture beads are used, preferably each reaction well comprises only a single capture bead.

The degree of saturation of any capture (i.e., sequencing) bead with template nucleic acid to be sequenced may not be 100%. In some embodiments, a saturation level of 10%-100% exists. As used herein, the degree of saturation of a capture bead with a template refers to the proportion of sites on the bead that are conjugated to template. In some instances this may be at least 5%, 10%, 15%, 20%, 25%, 30%, 35%, 40%, 45%, 50%, 55%, 60%, 65%, 70%, 75%, 80%, 85%, 90%, 95%, or it may be 100%.

Microwell Arrays

Important aspects of the invention contemplate sequencing a plurality of different template nucleic acids simultaneously. This may be accomplished using the sensor arrays described herein. In one embodiment, the sensor arrays are overlayed (and/or integral with) an array of microwells (or reaction chambers or wells, as those terms are used interchangeably herein), with the proviso that there be at least one sensor per microwell. Present in a plurality of microwells is a population of identical copies of a template nucleic acid. There is no requirement that any two microwells carry identical template nucleic acids, although in some instances such templates may share overlapping sequence. Thus, each microwell comprises a plurality of identical copies of a template nucleic acid, and the templates between microwells may be different.

The microwells may vary in size between arrays. The size of these microwells may be described in terms of a width (or diameter) to height ratio. In some embodiments, this ratio is 1:1 to 1:1.5, The bead to well size (e.g., the bead diameter to well width, diameter, or height) is preferably in the range of 0.6-0.8.

The microwell size may be described in terms of cross section. The cross section may refer to a "slice" parallel to the depth (or height) of the well, or it may be a slice perpendicular to the depth (or height) of the well. The microwells may be square in cross-section, but they are not so limited. The dimensions at the bottom of a microwell (i.e., in a cross section that is perpendicular to the depth of the well) may be 1.5 µm by 1.5 µm, or it may be 1.5 µm by 2 µm, Suitable diameters include but are not limited to at or about 100 µm, 95 µm, 90 µm, 85 µm, 80 µm, 75 µm, 70 µm, 65 µm, 60 µm, 55 µm, 50 µm, 45 µm, 40 µm, 35 µm, 30 µm, 25 µm, 20 µm, 15 µm, 10 µm, 9 µm, 8 µm, 7 µm, 6 µm, 5 µm, 4 µm, 3 µm, 2 µm, 1 µm or less. In some particular embodiments, the diameters may be at or about 44 µm, 32 µm, 8 µm, 4 µm, or 1.5 µm. Suitable heights include but are not limited to at or about 100 µm, 95 µm, 90 µm, 85 µm, 80 µm, 75 µm, 70 µm, 65 µm, 60 µm, 55 µm, 50 µm, 45 µm, 40 µm, 35 µm, 30 µm, 25 µm, 20 µm, 15 µm, 10 µm, 9 µm, 8 µm, 7 µm, 6 µm, 5 µm, 4 µm, 3 µm, 2 µm, 1 µm or less. In some particular embodiments, the heights may be at or about 55 µm, 48 µm, 32 µm, 12 µm, 8 µm, 6 µm, 4 µm, 2.25 µm, 1.5 µm, or less. Various embodiments of the invention contemplate the combination of any of these diameters with any of these heights. In still other embodiments, the reaction well dimensions may be (diameter in µm by height in µm) 44 by 55, 32 by 32, 32 by 48, 8 by 8, 8 by 12, 4 by 4, 4 by 6, 1.5 by 1.5, or 1.5 by 2.25.

The reaction well volume may range (between arrays, and preferably not within a single array) based on the well dimensions. This volume may be at or about 100 picoliter (pL), 90, 80, 70, 60, 50, 40, 30, 20, 10, or fewer pL. In important embodiments, the well volume is less than 1 pL, including equal to or less than 0.5 pL, equal to or less than 0.1 pL, equal to or less than 0.05 pL, equal to or less than 0.01 pL, equal to or less than 0.005 pL, or equal to or less than 0.001 pL. The volume may be 0.001 to 0.9 pL, 0.001 to 0.5 pL, 0.001 to 0.1 pL, 0.001 to 0.05 pL, or 0.005 to 0.05 pL. In particular embodiments, the well volume is 75 pL, 34 pL, 23 pL, 0.54 pL, 0.36 pL, 0.07 pL, 0.045 pL, 0.0024 pL, or 0.004 pL. In some embodiments, each reaction chamber is no greater than about 0.39 pL in volume and about 49 µm² surface aperture, and more preferably has an aperture no greater than about 16 µm² and volume no greater than about 0.064 pL.

It is to be understood therefore that the invention contemplates a sequencing apparatus for sequencing unlabeled nucleic acids, optionally using unlabeled nucleotides, without optical detection and comprising an array of at least 100 reaction chambers. In some embodiments, the array comprises $10^3$, $10^4$, $10^5$, $10^6$, $10^7$ or more reaction chambers. The pitch (or center-to-center distance between adjacent reaction chambers) is on the order of about 1-10 microns, including 1-9 microns, 1-8 microns, 1-7 microns, 1-6 microns, 1-5 microns, 1-4 microns, 1-3 microns, or 1-2 microns.

In various aspects and embodiments of the invention, the nucleic acid loaded beads, of which there may be tens, hundreds, thousands, or more, first enter the flow cell and then individual beads enter individual wells. The beads may enter the wells passively or otherwise. For example, the beads may enter the wells through gravity without any applied external force. The beads may enter the wells through an applied external force including but not limited to a magnetic force or a centrifugal force. In some embodiments, if an external force is applied, it is applied in a direction that is parallel to the well height/depth rather than transverse to the well height/depth, with the aim being to "capture" as many beads as possible. Preferably, the wells (or well arrays) are not agitated, as for example may occur through an applied external force that is perpendicular to the well height/depth. Moreover, once the wells are so loaded, they are not subjected to any other force that could dislodge the beads from the wells.

The Examples provide a brief description of an exemplary bead loading protocol in the context of magnetic beads. It is to be understood that a similar approach could be used to load other bead types. The protocol has been demonstrated to reduce the likelihood and incidence of trapped air in the wells of the flow chamber, uniformly distribute nucleic acid loaded beads in the totality of wells of the flow chamber, and avoid the presence and/or accumulation of excess beads in the flow chamber.

In various instances, the invention contemplates that each well in the flow chamber contain only one nucleic acid loaded bead. This is because the presence of two beads per well will yield unusable sequencing information derived from two different template nucleic acids.

Figure 61J:
FIGS. 61J and K are data capture images of microwell arrays following bead deposition. The white spots are beads.
Figure 61K:
Figure 62:
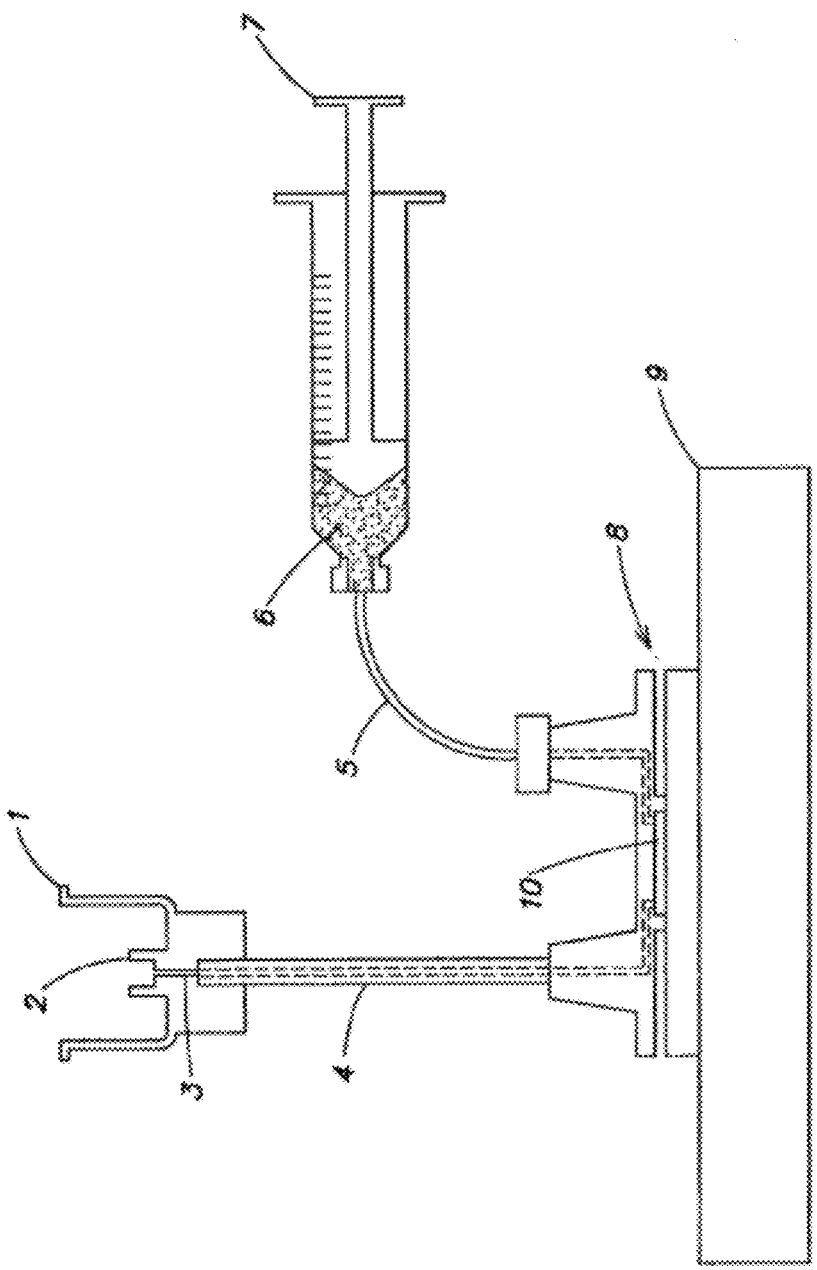
FIGS. 62-70 illustrate bead loading into the microfluidic arrays of the invention.
Figure 63:
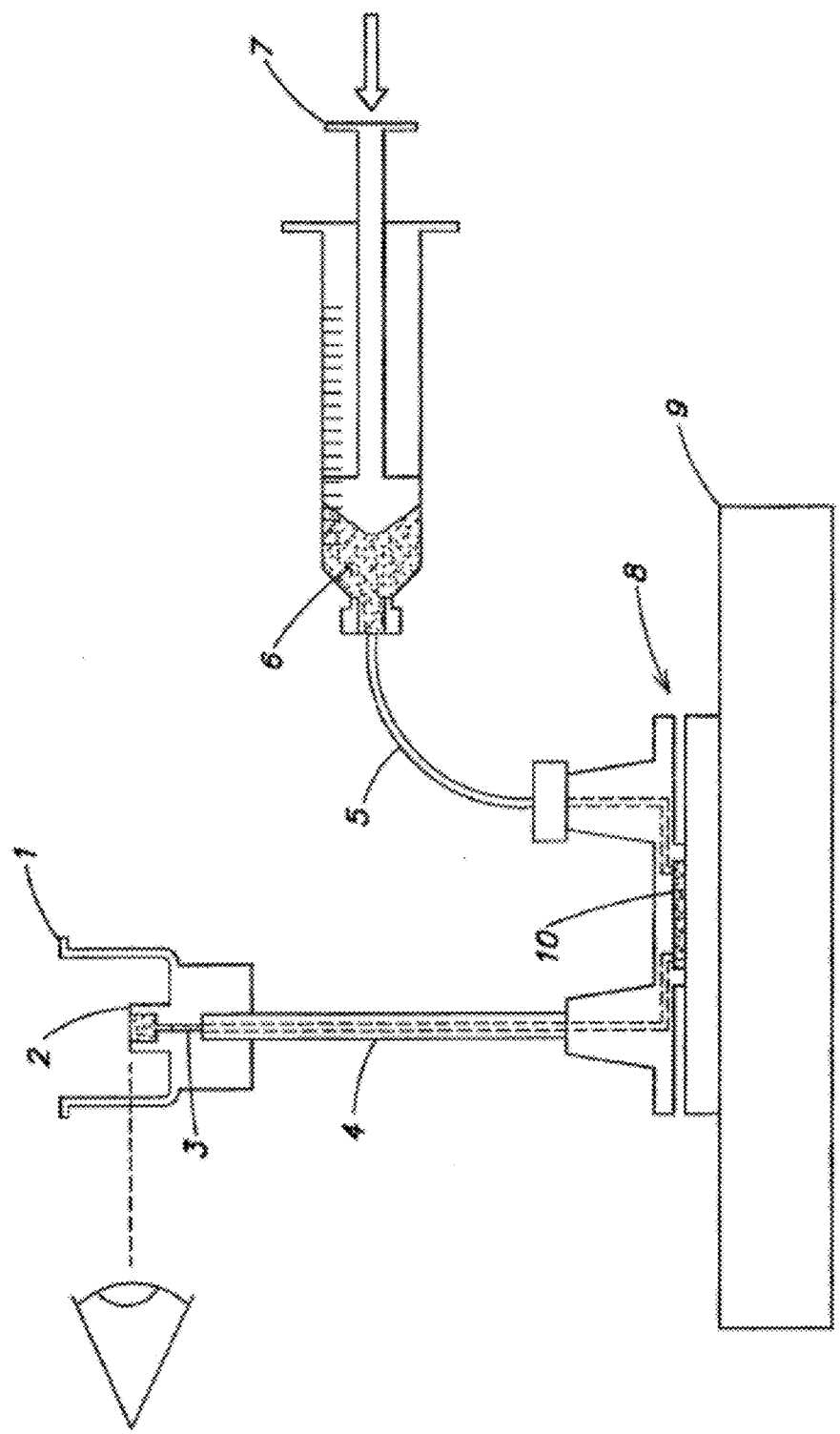
Figure 64:
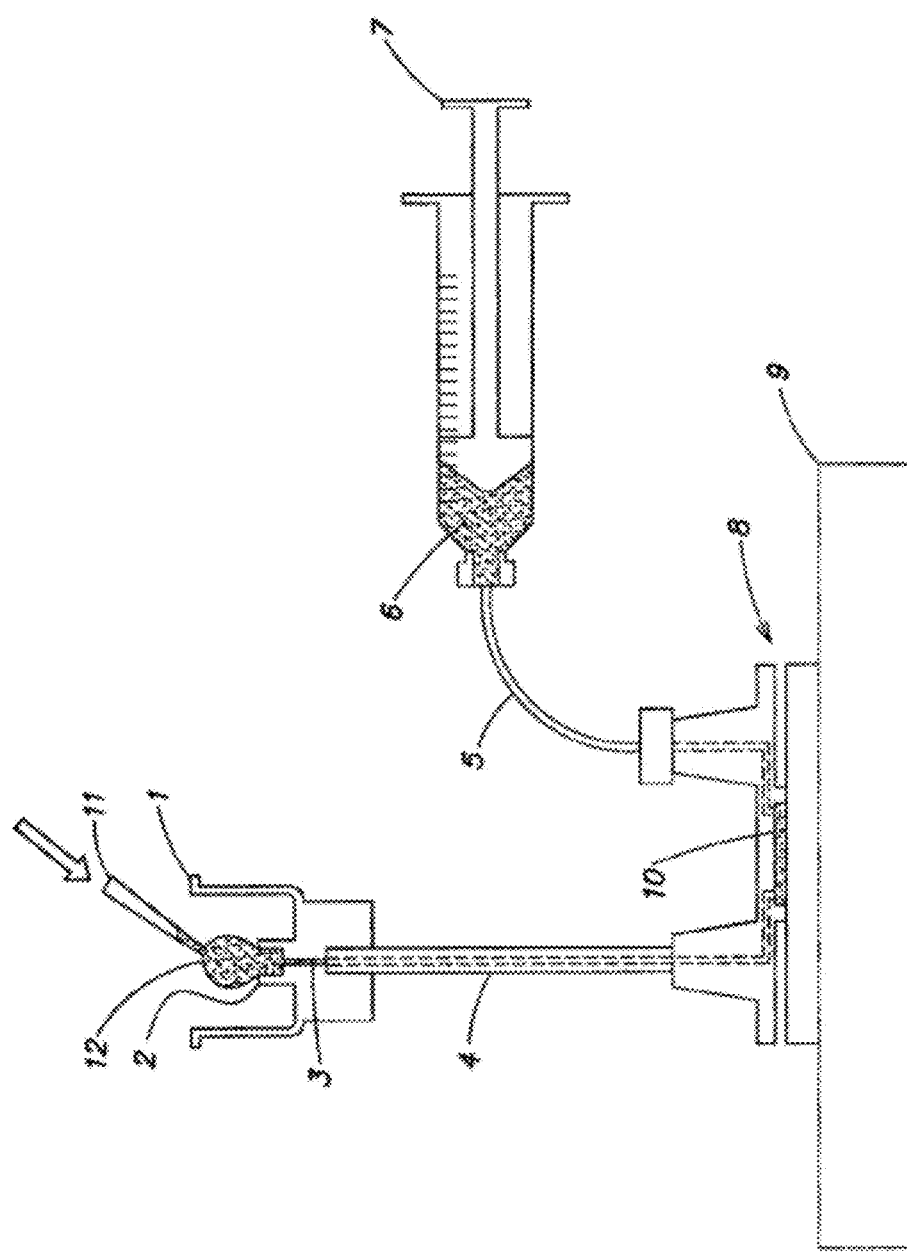
Figure 65:
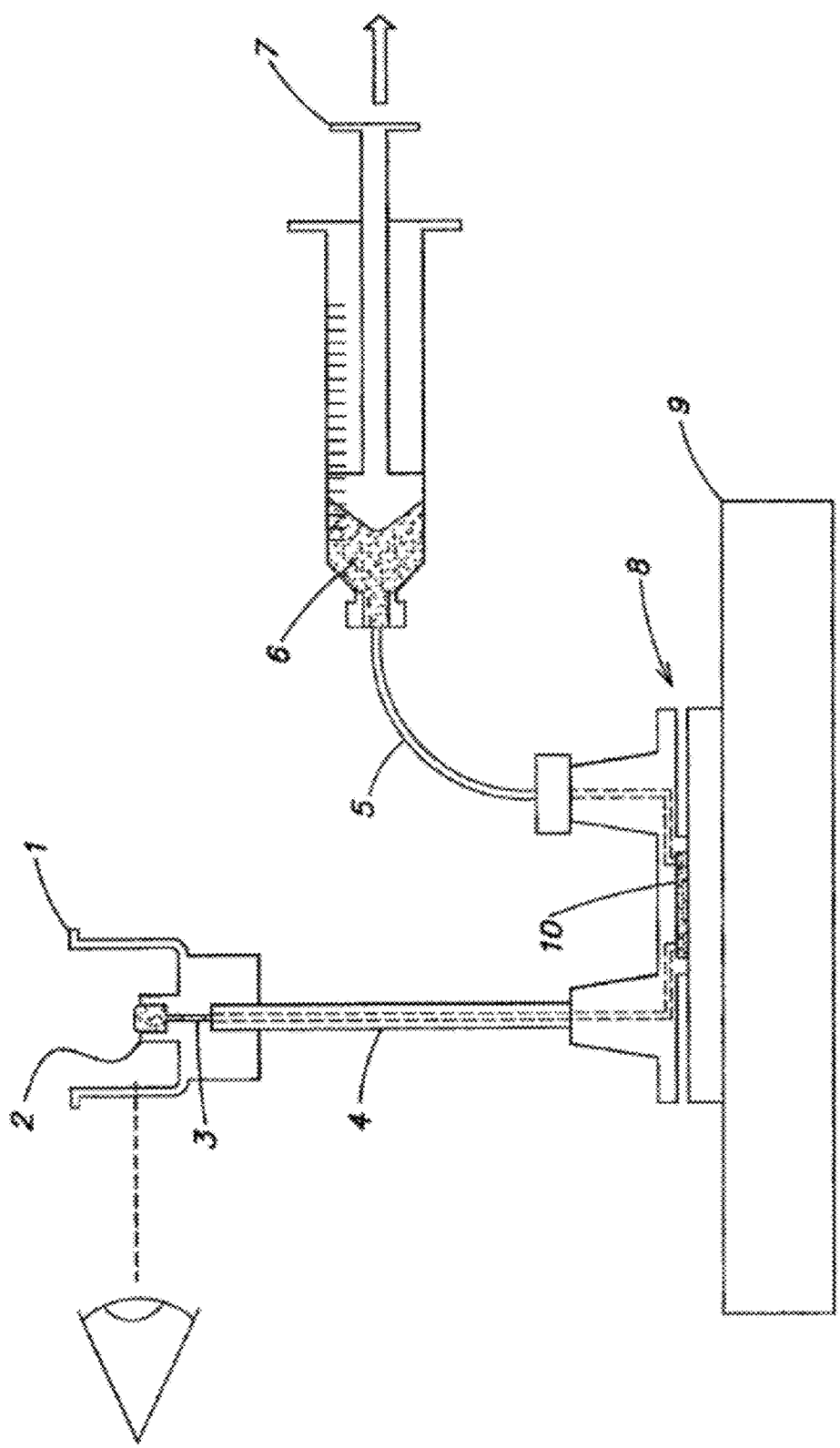
Figure 66:
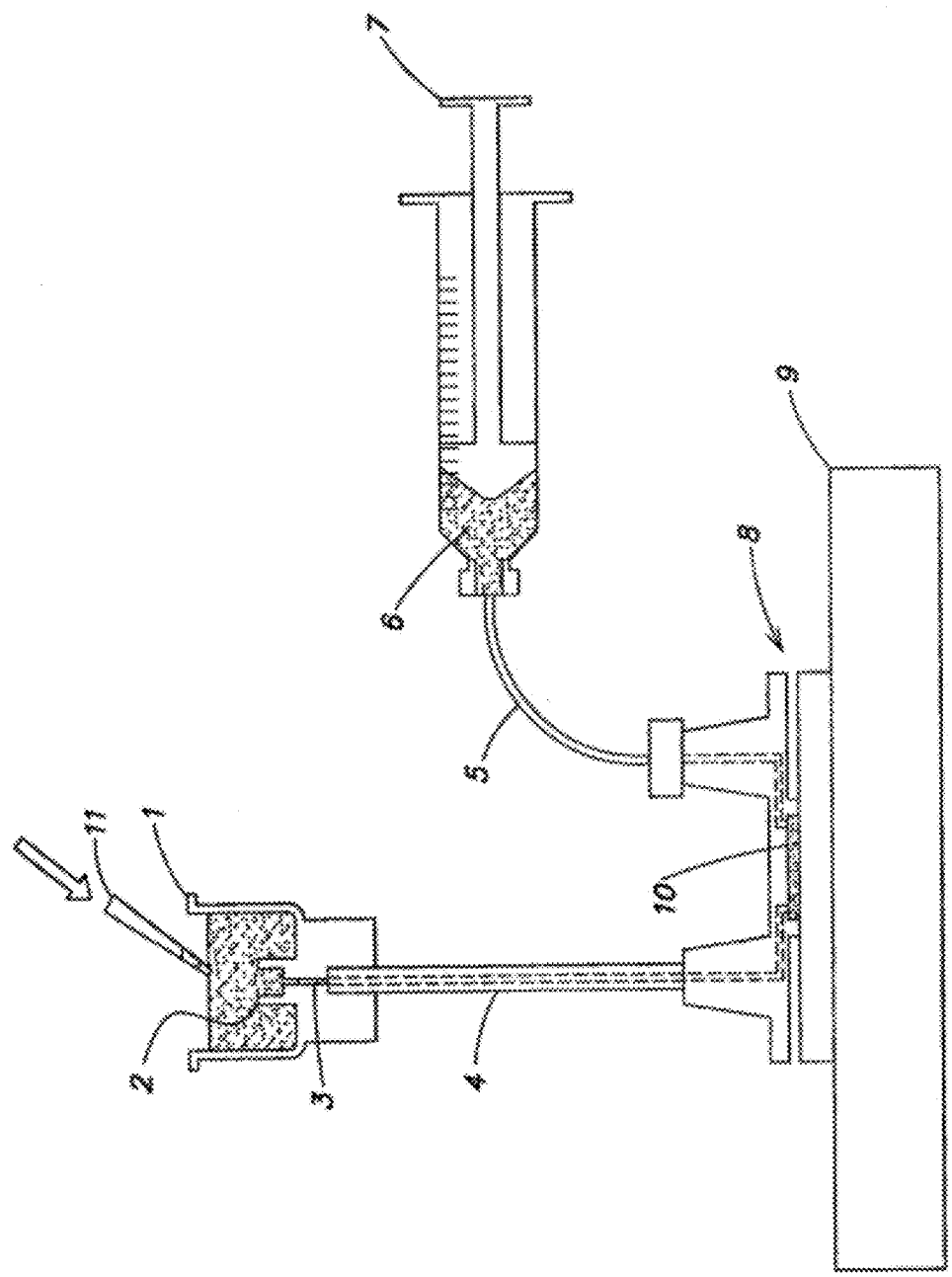
Figure 67:
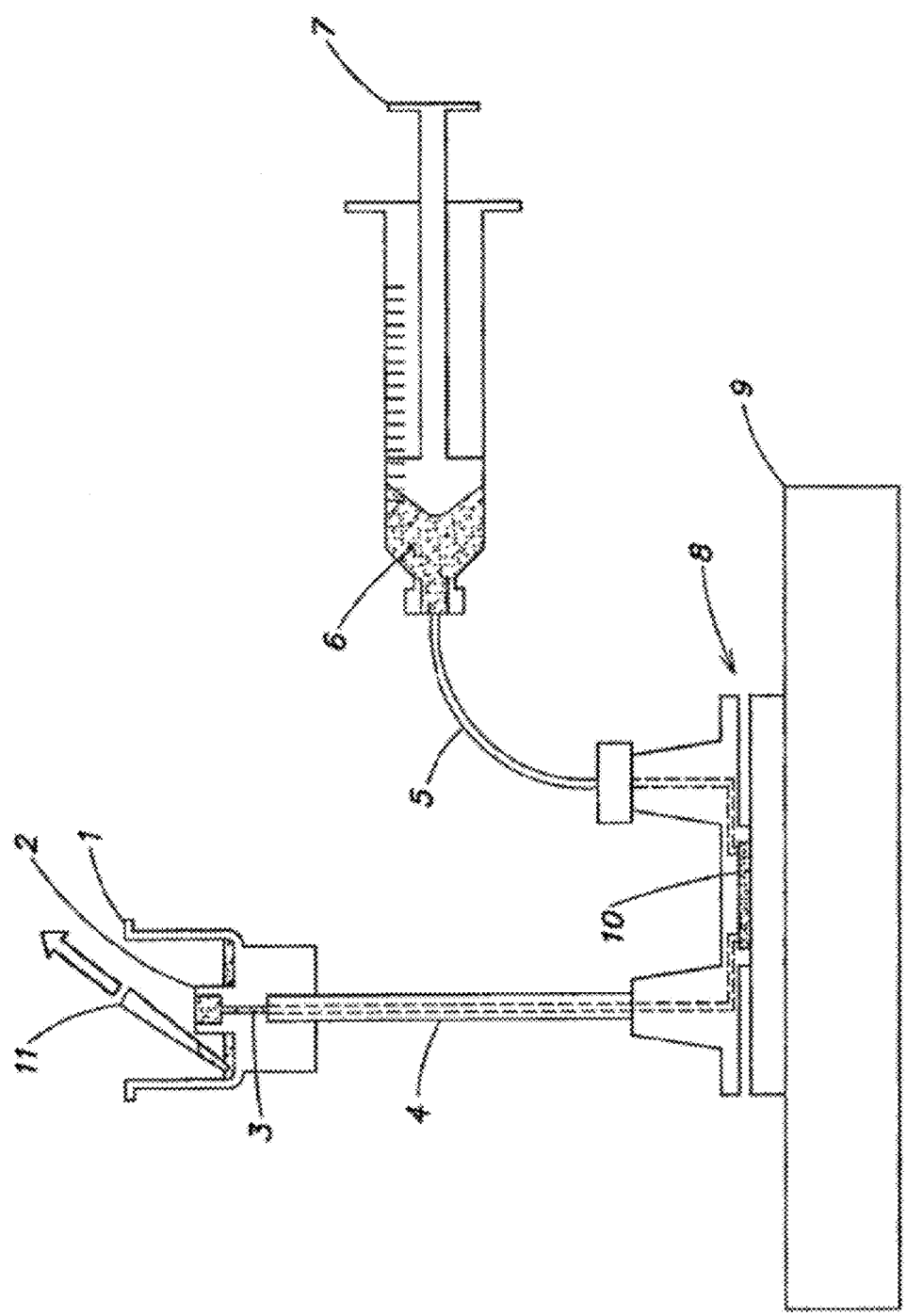
Figure 68:
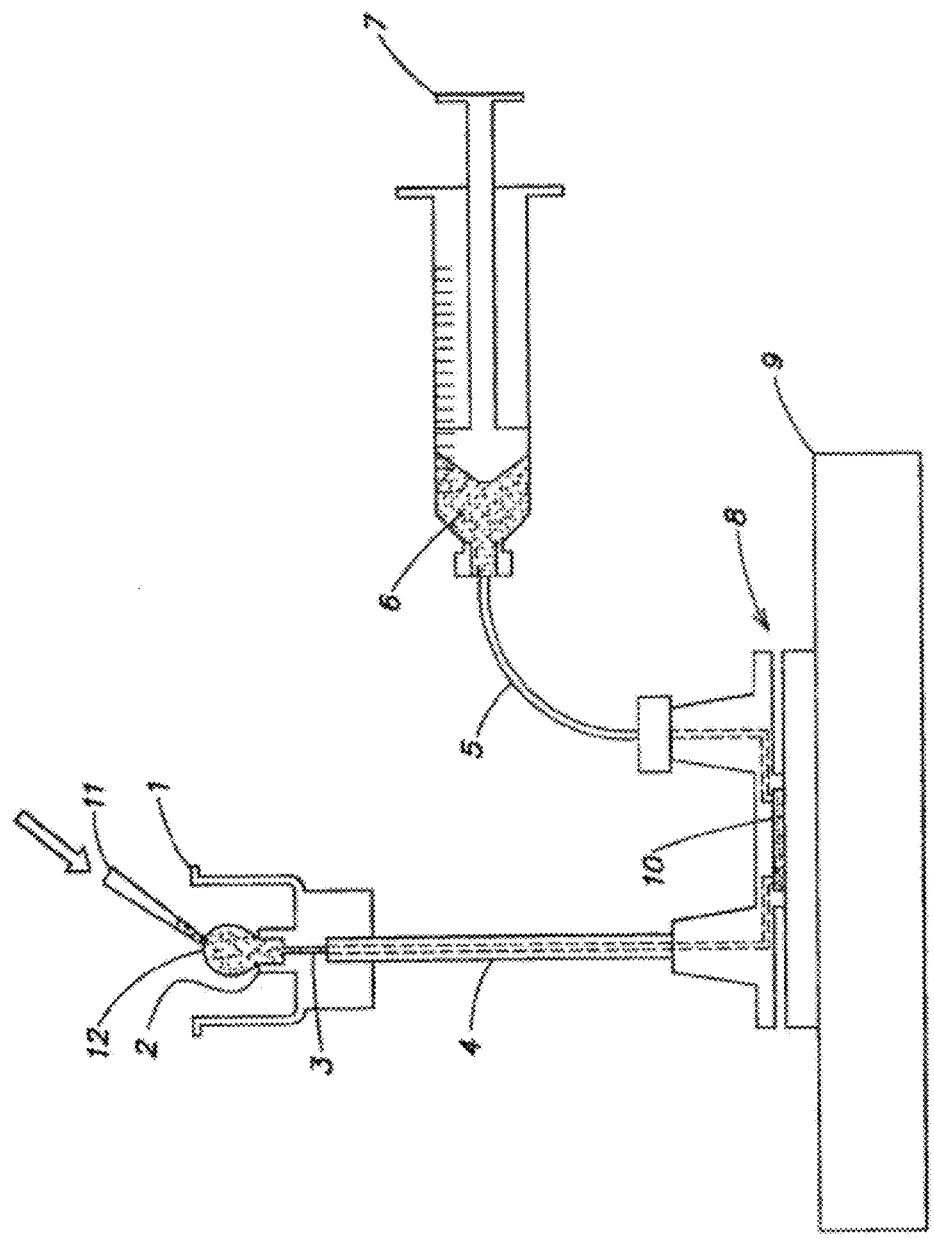
Figure 69:
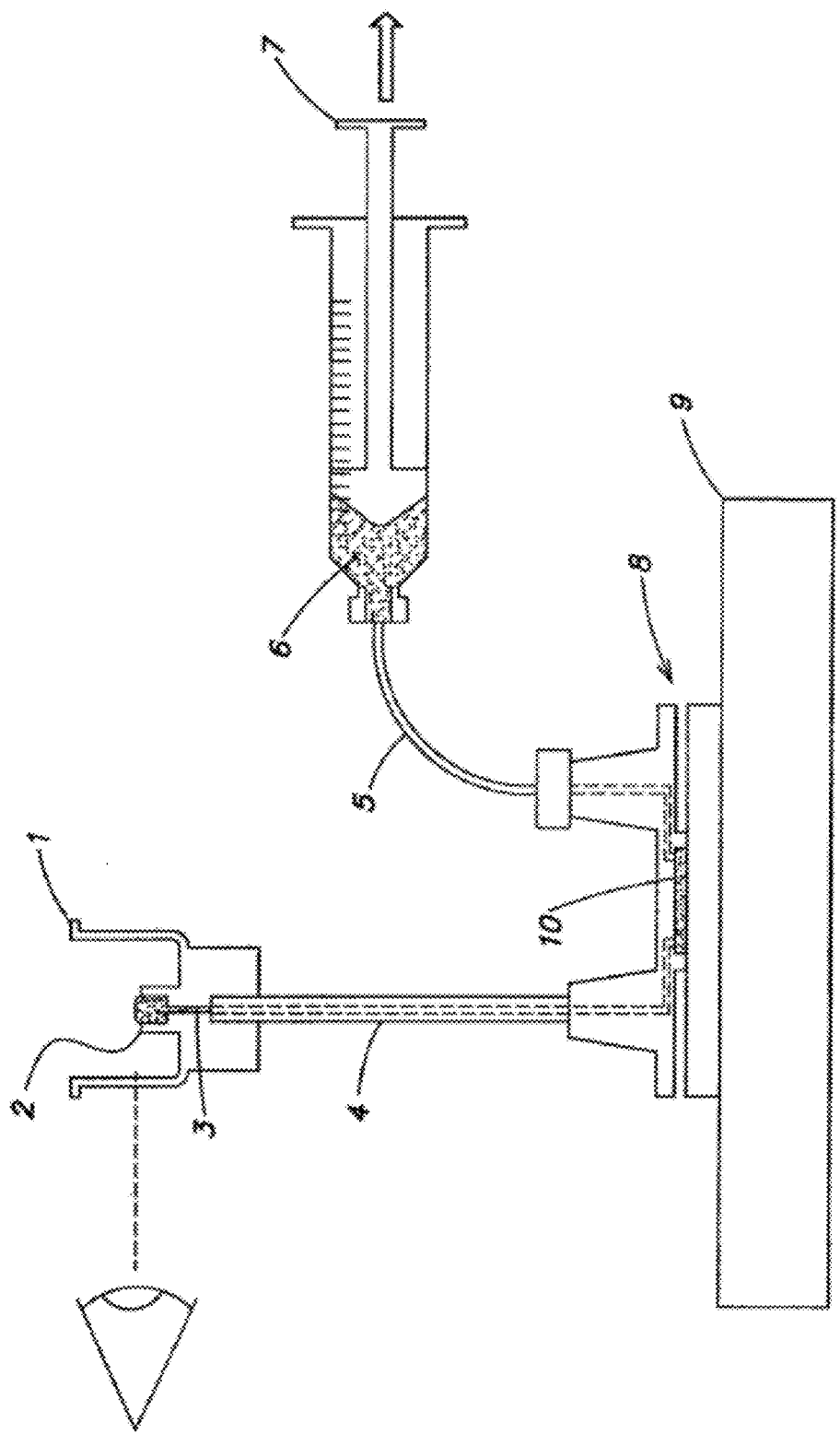
Figure 70:
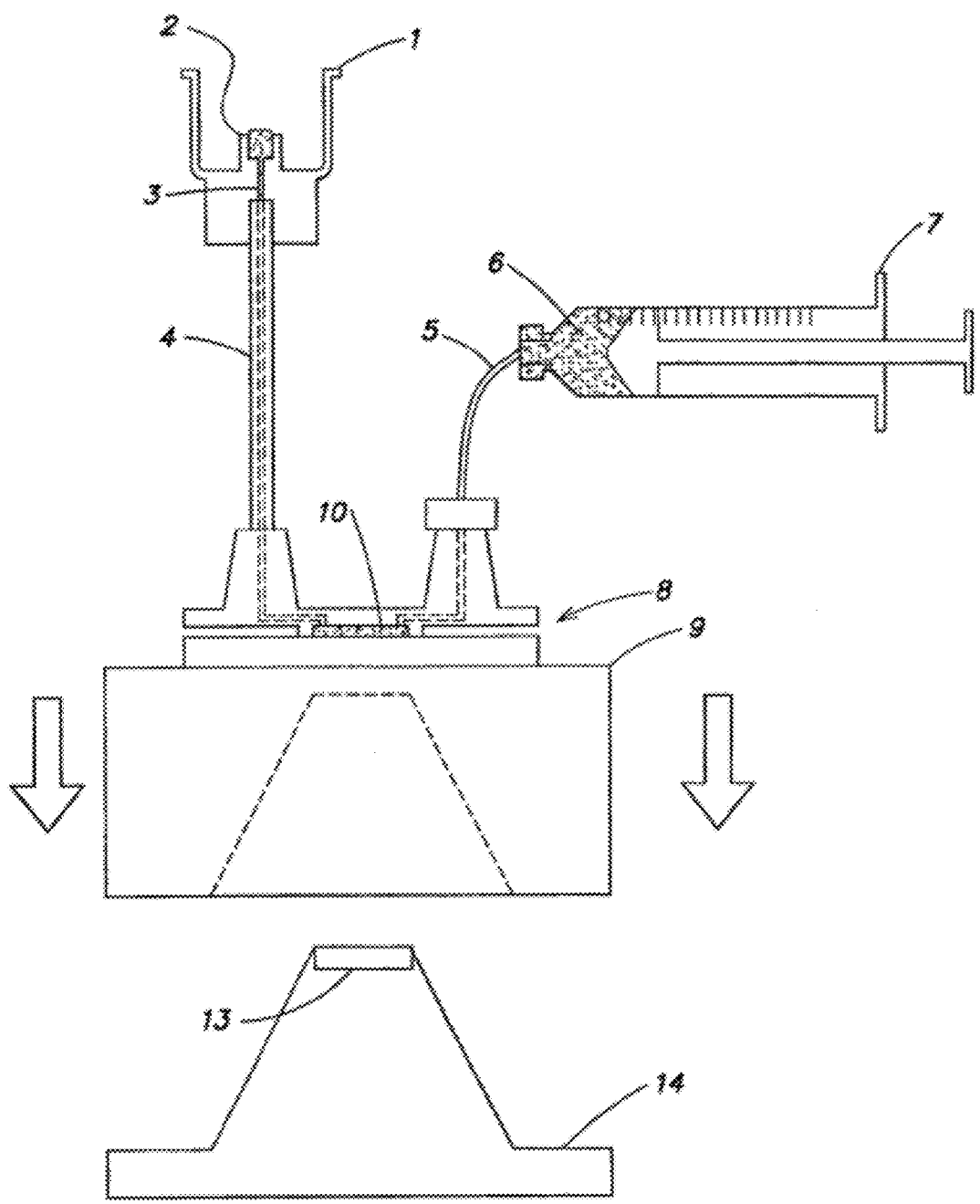

In some embodiments, the microwell array may be analyzed to determine the degree of loading of beads into the microwells, and in some instances to identify those microwells having beads and those lacking beads. The ability to know which microwells lack heads provides another internal control for the sequencing reaction. The presence or absence of a bead in a well can be determined by standard microscopy or by the sensor itself. FIGS. 61J and K are images captured from an optical microscope inspection of a microwell array (J) and from the sensor array underlying the microwell array (K). The white spots in both images each represent a bead in a well. Such microwell observation usually is only made once per run particularly since the beads once disposed in a microwell are unlikely to move to another well.

It has also been found that in the absence of flow the background signal (i.e., noise) is less than or equal to about 0.25 mV, but that in the presence of DNA-loaded capture beads that signal increases to about 1.0 mV=/−0.5 mV. This increase is sufficient to allow one to determine wells with beads.

The percentage of occupied wells in the well array may vary depending on the methods being performed. If the method is aimed at extracting maximum sequence data in the shortest time possible, then higher occupancy is desirable. If speed and throughout is not as critical, then lower occupancy may be tolerated. Therefore depending on the embodiment, suitable occupancy percentages may be at least 10%, at least 20%, at least 30%, at least 40%, at least 50%, at least 60%, at least 70%, at least 80%, at least 90%, at least 91%, at least 92%, at least 93%, at least 94%, at least 95%, at least 96%, at least 97%, at least 98%, at least 99%, or 100% of the wells. As used herein, occupancy refers to the presence of one nucleic acid loaded bead in a well and the percentage occupancy refers to the proportion of total wells in an array that are occupied by a single bead. Wells that are occupied by more than one bead typically cannot be used in the analyses contemplated by the invention.

Simultaneous Sequencing Reactions

The invention therefore contemplates performing a plurality of different sequencing reactions simultaneously. A plurality of identical sequencing reactions is occurring in each occupied well simultaneously. It is this simultaneous and identical incorporation of dNTP within each well that increases the signal to noise ratio. By performing sequencing reactions in a plurality of wells simultaneously, a plurality of different nucleic acids are simultaneously sequenced. The methods aim to maximize complete incorporation across all microwells for any given dNTP, reduce or decrease the number of unincorporated dNTPs that remain in the wells after signal detection is complete, and achieve as a high a signal to noise ratio as possible.

Before and/or while in the wells, the template nucleic acids are incubated with a sequencing primer that binds to its complementary sequence located on the 3' end of the template nucleic acid (i.e., either in the amplification primer sequence or in another adaptor sequence ligated to the 3' end of the target nucleic acid) and with a polymerase for a time and under conditions that promote hybridization of the primer to its complementary sequence and that promote binding of the polymerase to the template nucleic acid. The primer can be of virtually any sequence provided it is long enough to be unique. The hybridization conditions are such that the primer will hybridize to only its true complement on the 3' end of the template. Suitable conditions are disclosed in Margulies et al. Nature 2005 437(15):376-380 and accompanying supplemental materials.

It will be understood that the amount of sequencing primers and polymerases may be saturating, above saturating level, or in some instances below saturating levels. As used herein, a saturating level of a sequencing primer or a polymerase is a level at which every template nucleic acid is hybridized to a sequencing primer or bound by a polymerase, respectively. Thus the saturating amount is the number of polymerases or primers that is equal to the number of templates on a single bead. In some embodiments, the level is greater than this, including at least 2 fold, 3 fold, 4 fold, 5 fold, 10 fold, or more than the level of the template nucleic acid. In other embodiments, the number of polymerases and/or primers may be 10%, 20%, 30%, 40%, 50%, 60%, 70%, 80%, 90%, or up to 100% of the number of templates on a single bead in a single well.

Suitable polymerases include but are not limited to DNA polymerase, RNA polymerase, or a subunit thereof, provided it is capable of synthesizing a new nucleic acid strand based on the template and starting from the hybridized primer. An example of a suitable polymerase subunit for some but not all embodiments of the invention is the exo-minus (exo⁻) version of the Klenow fragment of *E. coli* DNA polymerase I which lacks 3' to 5' exonuclease activity. Other polymerases include T4 exo⁻, Therminator, and Bst polymerases. In still other embodiments that require excision of nucleotides (e.g., in the process of a nick translation reaction), polymerases with exonuclease activity are preferred. The polymerase may be free in solution (and may be present in wash and dNTP solutions) or it may be bound for example to the beads (or corresponding solid support) or to the walls of the chemFET but preferably not to the ISFET surface itself. The polymerase may be one that is modified to comprise accessory factors including without limitation single or double stranded DNA binding proteins.

Some embodiments of the invention require that the polymerase have sufficient processivity. As used herein, processivity is the ability of a polymerase to remain bound to a single primer/template hybrid. As used herein, it is measured by the number of nucleotides that a polymerase incorporates into a nucleic acid (such as a sequencing primer) prior to dissociation of the polymerase from the primer/template hybrid. In some embodiments, the polymerase has a processivity of at least 100 nucleotides, although in other embodiments it has a processivity of at least 200 nucleotides, at least 300 nucleotides, at least 400 nucleotides, or at least 500 nucleotides. It will be understood by those of ordinary skill in the art that the higher the processivity of the polymerase, the more nucleotides that can be incorporated prior to dissociation, and therefore the longer the sequence that can be obtained. In other words, polymerases having low processivity will provide shorter read-lengths than will polymerases having higher processivity. As an example, a polymerase that dissociates from the hybrid after five incorporations will only provide a sequence of 5 nucleotides in length, while a polymerase that dissociates on average from the hybrid after 500 incorporations will provide sequence of about 500 nucleotides.

The rate at which a polymerase incorporates nucleotides will vary depending on the particular application, although generally faster rates of incorporation are preferable. The rate of "sequencing" will depend on the number of arrays on chip, the size of the wells, the temperature and conditions at which the reactions are run, etc.

In some embodiments of the invention, the time for a 4 nucleotide cycle may be 50-100 seconds, 60-90 seconds, or about 70 seconds. In other embodiments, this cycle time can be equal to or less than 70 seconds, including equal to or less than 60 seconds, equal to or less than 50 seconds, equal to or less than 40 seconds, or equal to or less than 30 seconds. A read length of about 400 bases may take on the order of 30 minutes, 60 minutes, 1.5 hours, 2 hours, 2.5 hours, 3 hours, 3.5 hours, 4 hours, 4.5 hours, or in some instance 5 or more hours. These times are sufficient for the sequencing of megabases, and more preferably gigabases of sequence, with greater amounts of sequence being attainable through the use of denser arrays (i.e., arrays with greater numbers of reaction wells and FETs) and/or the simultaneous use of multiple arrays.

Table 3 provides estimates for the rates of sequencing based on various array, chip and system configurations contemplated herein. It is to be understood that the invention contemplates even denser arrays than those shown in Table 3. These denser arrays can be characterized as 90 nm CMOS with a pitch of 1.4 μm and a well size of 1 μm which may be used with 0.7 μm beads, or 65 nm CMOS with a pitch of 1 μm and a well size of 0.5 μm which may be used with 0.3 μm beads, or 45 μm CMOS with a pitch of 0.7 μm and a well size of 0.3 μm which can be used with 0.2 μm beads.

TABLE 3

Reaction Parameters and Read Rates.

| chip type | A | B | C | D | E |
|---|---|---|---|---|---|
| pixel/CMOS | 2.8 μm/0.18 μm | 5.1 μm/0.35 μm | 5.1 μm/0.35 μm | 9 μm/3.5 μm | 9 μm/0.35 μm |
| chip size | 17.5 × 17.5 | 17.5 × 17.5 | 12 × 12 | 17.5 × 17.5 | 12 × 12 |
| # possible reads | 27,800,000 | 7,220,000 | 2,950,000 | 2,320,000 | 1,060,000 |
| read length (assumption) | 400 | 400 | 400 | 400 | 400 |
| # chips/board | 4 | 4 | 4 | 4 | 4 |
| bead load efficiency | 0.80 | 0.80 | 0.80 | 0.80 | 0.80 |
| # yielded Gbp* per run | 35.6 | 9.2 | 3.8 | 3.0 | 1.4 |
| # times HG** (3 Gbp/HG) | 11.86 | 3.08 | 1.26 | 0.99 | 0.45 |

*Gbp is gigabases
**HG is human genome

The template nucleic acid is also contacted with other reagents and/or cofactors including but not limited to buffer, detergent, reducing agents such as dithiothrietol (DTT, Cleland's reagent), single stranded binding proteins, and the like before and/or while in the well. In one embodiment, the polymerase comprises one or more single stranded binding proteins (e.g., the polymerase may be one that is engineered to include one or more single stranded binding proteins). In one embodiment, the template nucleic acid is contacted with the minter and the polymerase prior to its introduction into the flow chamber and wells thereof.

The primers may be DNA in nature or they may be modified moieties such as PNA or LNA, or they may comprise some other modification such as those described herein, or some combination of the foregoing. It has been found according to the invention that LNA-containing primers bind efficiently to DNA templates under stringent conditions and are still able to mediate a polymerase-mediated extension.

Some reactions may be carried out at a pH equal to or greater than 7.5, equal to or greater than 8, equal to or greater than 8.5, equal to or greater than 9, equal to or greater than 9.5, equal to or greater than 10, or equal to or greater than 11. The polymerase may be one that incorporates nucleotides into a nucleic acid at a pH of 7-11, 7.5-10.5, 8-10, 8.5-9.5, or at about 9.

In some embodiments, the enzyme has high activity in low concentrations of dNTPs. In some embodiments, the dNTP concentration is 50 μM, 40 μM, 30 μM, 20 μM, 10 μM, 5 μM, and preferably 20 μM or less.

Apyrase is an enzyme that degrades residual unincorporated nucleotides converting them into monophosphate and releasing inorganic phosphate in the process. It is useful for degrading dNTPs that are not incorporated and/or that are in excess. It is important that excess and/or unincorporated dNTP be washed away from all wells after measurements are complete and before introduction of the subsequent dNTP. Accordingly, addition of apyrase between the introduction of different dNTPs is useful to remove unincorporated dNTPs that would otherwise obscure the sequencing data.

Thus, according to some aspects of the invention, a homogeneous population of (or a plurality of identical) template nucleic acids is placed into each of a plurality of wells, each well situated over and thus corresponding to at least one sensor. As discussed above, preferably the well contains at least 10, at least 100, at least 1000, at least $10^4$, at least $10^5$, at least $10^6$, or more copies of an identical template nucleic acid. Identical template nucleic acids means that the templates are identical in sequence. Most and preferably all the template nucleic acids within a well are uniformly hybridized to a primer. Uniform hybridization of the template nucleic acids to the primers means that the primer hybridizes to the template at the same location (i.e., the sequence along the template that is complementary to the primer) as every other template/primer hybrid in the well. The uniform positioning of the primer on every template allows the co-ordinated synthesis of all new nucleic acid strands within a well, thereby resulting in a greater signal-to-noise ratio.

In some embodiments, nucleotides are then added in flow, or by any other suitable method, in sequential order to the flow chamber and thus the wells. The nucleotides can be added in any order provided it is known and for the sake of simplicity kept constant throughout a run.

In some embodiments, the method involves adding ATP to the wash buffer so that dNTPs flowing into a well displace ATP from the well. The ATP matches the ionic strength of the dNTPs entering the wells and it also has a similar diffusion profile as dNTPs. In this way, influx and efflux of dNTPs during the sequencing reaction do not interfere with measurements at the chemFET. The concentration of ATP used is on the order of the concentration of dNTP used.

In some embodiments, the dNTP and/or the polymerase may be pre-incubated with divalent cation such as but not limited to $Mg^{2+}$ (for example in the form of $MgCl_2$) or $Mn^{2+}$ (for example in the form of $MnCl_2$). Other divalent cations can also be used including but not limited to $Ca^{2+}$, $Co^{2+}$. This pre-incubation (and thus "pre-loading" of the dNTP and/or the polymerase can ensure that the polymerase is exposed to a sufficient amount of divalent cation for proper and necessary functioning even if it is present in a low ionic strength environment. Pre-incubation may occur for 1-60 minutes, 5-45 minutes, or 10-30 minutes, depending on the embodiment, although the invention is not limited to these time ranges.

A sequencing cycle may therefore proceed as follows washing of the flow chamber (and wells) with wash buffer (optionally containing ATP), introduction of a first dNTP species (e.g., dATP) into the flow chamber (and wells), release and detection of PPi and then unincorporated nucleotides (if incorporation occurred) or detection of solely unincorporated nucleotides (if incorporation did not occur) (by any of the mechanisms described herein), washing of the flow chamber (and wells) with wash buffer, washing of the flow chamber (and wells) with wash buffer containing apyrase (to remove as many of the unincorporated nucleotides as possible prior to the flow through of the next dNTP, washing of the flow chamber (and wells) with wash buffer, and introduction of a second dNTP species. This process is continued until all 4 dNTP (i.e., dATP, dCTP, dGTP and dTTP) have been flowed through the chamber and allowed to incorporate into the newly synthesized strands. This 4-nucleotide cycle may be repeated any number of times including but not limited to 10, 25, 50, 100, 200 or more times. The number of cycles will be governed by the length of the template being sequenced and the need to replenish reaction reagents, in particular the dNTP stocks and wash buffers.

As part of the sequencing reaction, a dNTP will be ligated to (or "incorporated into" as used herein) the 3' of the newly synthesized strand (or the 3' end of the sequencing primer in the case of the first incorporated dNTP) if its complementary nucleotide is present at that same location on the template nucleic acid. Incorporation of the introduced dNTP (and concomitant release of PPi) therefore indicates the identity of the corresponding nucleotide in the template nucleic acid. If no dNTP has been incorporated, no hydrogens are released and no signal is detected at the chemFET surface. One can therefore conclude that the complementary nucleotide was not present in the template at that location. If the introduced dNTP has been incorporated into the newly synthesized strand, then the chemFET will detect a signal. The signal intensity and/or area under the curve is a function of the number of nucleotides incorporated (for example, as may occur in a homopolymer stretch in the template. The result is that no sequence information is lost through the sequencing of a homopolymer stretch (e.g., poly A, poly T, poly C, or poly G) in the template.

The sequencing reaction can be run at a range of temperatures. Typically, the reaction is run in the range of 30° C. to 70° C., 30° C. to 65° C., 30-60° C., 35-55° C., 40-50° C., or 40-45° C. It is preferable to run the reaction at temperatures that prevent formation of secondary structure in the nucleic acid. However this must be balanced with the binding of the primer (and the newly synthesized strand) to the template nucleic acid and the reduced half-life of apyrase at higher temperatures. The optimum temperature for the polymerase is also important as the closer the reaction is run to that temperature, the higher the nucleotide incorporation rate will be. Bst polymerase has a optimum temperature of about 65° C., while T4 polymerase has an optimum temperature of about 37° C. Thus, the optimum temperature will depend upon the polymerase being used. Some embodiments use a temperature of about 41° C. Other embodiments use a temperature that is higher including for example about 45° C., about 50° C. or about 65° C. The solutions, including the wash buffers and the dNTP solutions, are generally warmed to these temperatures in order not to alter the temperature in the wells. The wash buffer containing apyrase however is preferably maintained at a lower temperature in order to extend the half-life of the enzyme. Typically, this solution is maintained at about 4-15° C., and more preferably 4-10° C.

Figure 71:
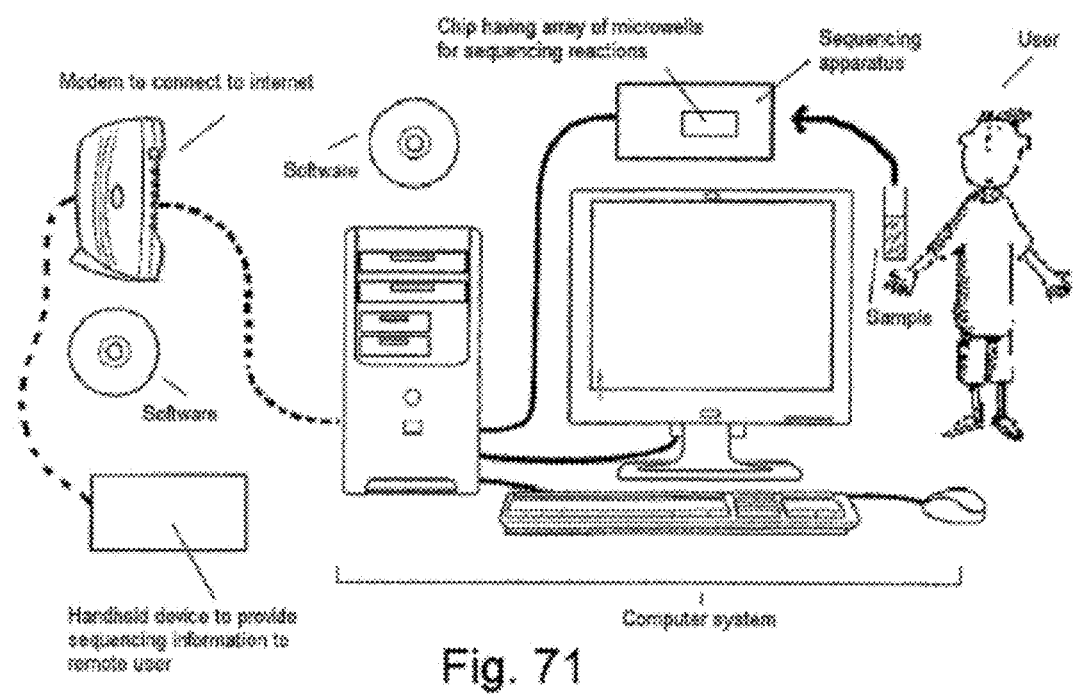
FIG. 71 illustrates an exemplary sequencing process.

As will be appreciated all of the foregoing methods may be automated such that the various biological and/or chemical reactions are performed via robotics. In addition, the information obtained via the signal from the chemFET (or chemFET array) may be provided to a personal computer, a personal digital assistant, a cellular phone, a video game system, or a television so that a user can monitor the progress of the sequencing reactions remotely. This process is illustrated, for example, in FIG. 71.

Diffusion Control

The nucleotide incorporation reaction can occur very rapidly. As a result, it may be desirable in some instances to slow the reaction down or to slow the diffusion of analytes in the well in order to ensure maximal data capture during the reaction. The diffusion of reagents and/or byproducts can be slowed down in a number of ways including but not limited to addition of packing beads in the wells, and/or the use of polymers such as polyethylene glycol in the wells (e.g., PEG attached to the capture beads and/or to packing beads). The packing beads also tend to increase the concentration of reagents and/or byproducts at the chemFET surface, thereby increasing the potential for signal. The presence of packing beads generally allows a greater time to sample (e.g., by 2- or 4-fold).

Data capture rates can vary and be for example anywhere from 10-100 frames per second and the choice of which rate to use will be dictated at least in part by the well size and the presence of packing beads or other diffusion limiting techniques. Smaller well sizes generally require faster data capture rates.

In some aspects of the invention that are flow-based and where the top face of the well is open and in communication with fluid over the entirety of the chip, it is important to detect the released hydrogen ion prior to its diffusion out of the well. Diffusion of reaction byproducts out of the well will lead to false negatives (because the byproduct is not detected in that well) and potential false positives in adjacent or downstream wells (where the byproduct may be detected), and thus should be avoided. Packing beads and/or polymers such as PEG may also help reduce the degree of diffusion and/or cross-talk between wells.

In addition to the nucleic acid loaded beads, each well may also comprise a plurality of smaller beads, referred to herein as "packing beads". The packing beads may be composed of any inert material that does not interact or interfere with analytes, reagents, reaction parameters, and the like, present in the wells. The packing beads may be magnetic (including superparamagnetic) but they are not so limited. In some embodiments the packing beads and the capture beads are made of the same material (e.g., both are magnetic, both are polystyrene, etc.), while in other embodiments they are made of different materials (e.g., the packing beads are polystyrene and the capture beads are magnetic).

The packing beads are generally smaller than the capture beads. The difference in size may vary and may be 5-fold, 10-fold, 15-fold, 20-fold or more. As an example, 0.35 µm diameter packing beads can be used with 5.91 µm capture beads. Such packing beads are commercially available from sources such as Bang Labs.

The placement of the packing beads relative to the capture bead may vary. Packing beads may be positioned between the chemFET surface and the nucleic acid loaded bead, in which case they may be introduced into the wells before the nucleic acid loaded beads. In this way, the packing beads prevent contact and thus interference of the chemFET surface with the template nucleic acids bound to the capture beads. A layer of packing beads that is 0.1-0.5 µm in depth or height would preclude this interaction. The presence of packing beads between the capture bead and the chemFET surface may also slow the diffusion of the sequencing byproducts such as hydrogen ions, thereby facilitating data capture in some embodiments. Alternatively, the packing beads may be positioned all around the nucleic acid loaded beads, in which case they may be added to the wells before, during and/or after the nucleic acid loaded beads. In still other embodiments, the majority of the packing beads may be positioned on top of the nucleic acid loaded beads, in which case they may be added to the wells after the nucleic acid loaded beads. If placed above the nucleic acid loaded beads, the packing beads may act to minimize or prevent altogether dislodgement of nucleic acid loaded beads from wells. In still other embodiments, the reaction wells may comprise packing beads even if nucleic acid loaded beads are not used. It is to be understood that in other embodiments however packing beads are not required as there is no need to slow the diffusion of reaction byproducts such as hydrogen ions.

In some embodiments, diffusion may also be impacted by including in the reaction chambers viscosity increasing agents. An example of such an agent is a polymer that is not a nucleic acid (i.e., a non-nucleic acid polymer). The polymer may be naturally or non-naturally occurring, and it may be of any nature provided it does not interfere with nucleotide incorporation and/or excision and detection thereof except for slowing the diffusion of polymerase, released hydrogen ions, PPi, unincorporated nucleotides, and/or other reaction byproducts or reagents. An example of a suitable polymer is polyethylene glycol (PEG). Other examples include PEO, PEA, dextrans, acrylamides, celluloses (e.g. methyl cellulose), and the like. The polymer may be free in solution (e.g., PEG, DMSO, glycerol, and the like) or it may be immobilized (covalently or non-covalently) to one or more sides of the reaction chamber, to the capture bead (e.g., PEG, PEO, dextrans, and the like), and/or to any packing beads that may be present. Non-covalent attachment may be accomplished via a biotin-avidin interaction.

The invention further contemplates in some embodiments the use of soluble counterions that bind to released hydrogen ions and prevent their exit from the well. Counterions having a pKa that is close to the pH of the reaction are preferred. Examples of counterions with diffusion rates that are slower than that of protons (at both 25° C. and 37° C.) include without limitation $Cl^-$, $H_2PO_4^-$, $HCO_3^-$, acetate, butyrate, histidyl, formate, lactate, and the like. In some embodiments, the counterions are free in solution while in others they are immobilized on a solid support including without limitation reaction chamber walls. One of ordinary skill in the art will be able to select the most appropriate counterion and concentration based on its pKa and the pH at which the reaction is conducted, and the mobility of the counterion. It will be understood that various embodiments of the invention do not require the use of counterions.

Kits

The invention further contemplates kits comprising the various reagents necessary to perform a sequencing reaction and instructions of use according to the methods set forth herein.

One preferred kit comprises one or more containers housing wash buffer, one or more containers each containing one of the following reagents: dATP buffer, dCTP buffer, dGTP buffer or dTTP buffer, dATP, dCTP, dGTP and dTTP stocks, apyrase, SSB, polymerase, packing beads, and optionally pyrophosphatase. Importantly the kits may comprise only naturally occurring dNTPs. The kits may also comprise one or more wash buffers comprising components as described in the Examples, but are not so limited. The kits may also comprise instructions for use including diagrams that demonstrate the methods of the invention.

The following Examples are included for purposes of illustration and are not intended to limit the scope of the invention.

EXAMPLES

The Examples provide a proof of principle demonstration of the sequencing of four templates of known sequence. This artificial model is intended to show that embodiments of the apparatuses and systems described herein are able to readout nucleotide incorporation that correlates to the known sequence of the templates. This is not intended to represent typical use of the method or system in the field. The following is a brief description of these methods.

Example 1

Bead Preparation

Binding of Single-Stranded Oligonucleotides to Streptavidin-Coated Magnetic Beads.

Single-stranded DNA oligonucleotide templates with a 5' Dual Biotin tag (HPLC purified), and a 20-base universal primer were ordered from IDT (Integrated DNA Technologies, Coralville, Ind.). Templates were 60 bases in length, and were designed to include 20 bases at the 3' end that were complementary to the 20-base primer (Table 4, italics). The lyophilized and biotinylated templates and primer were re-suspended in TE buffer (10 mM Tris-HCl, 1 mM EDTA, pH 8) as 40 µM stock solutions and as a 400 µM stock solution, respectively, and stored at −20° C. until use.

For each template, 60 µl of magnetic 5.91 µm (Bangs Laboratories, Inc. Fishers, Ind.) streptavidin-coated beads, stored as an aqueous, buffered suspension ($8.57 \times 10^4$ beads/µL), at 4° C., were prepared by washing with 120 µl bead wash buffer three times and then incubating with templates 1, 2, 3 and 4 (T1, T2, T3, T4: Table 4) with biotin on the 5' end, respectively.

Due to the strong covalent binding affinity of streptavidin for biotin (Kd~10-15), these magnetic beads are used to immobilize the templates on a solid support, as described below. The reported binding capacity of these beads for free biotin is 0.650 pmol/µL of bead stock solution. For a small (<100 bases) biotinylated ssDNA template, it was conservatively calculated that $9.1 \times 10^5$ templates could be bound per bead. The beads are easily concentrated using simple magnets, as with the Dynal Magnetic Particle Concentrator or MPC-s (Invitrogen, Carlsbad, Calif.). The MPC-s was used in the described experiments.

An MPC-s was used to concentrate the beads for 1 minute between each wash, buffer was then added and the beads were resuspended. Following the third wash the beads were resuspended in 120 µL bead wash buffer plus 1 µl of each template (40 µM). Beads were incubated for 30 minutes with rotation (Labquake Tube Rotator, Barnstead, Dubuque, Iowa). Following the incubation, beads were then washed three times in 120 µL Annealing Buffer (20 mM Tris-HCl, 5 mM magnesium acetate, pH 7.5), and re-suspended in 60 µL of the same buffer.

TABLE 4

Sequences for Templates 1, 2, 3, and 4

T1: 5'/52Bio/GCA AGT GCC CTT AGG CTT CAG TTC AAA AGT CCT AAC TGG GCA *AGG CAC ACA GGG GAT AGG*-3' (SEQ ID NO: 1)

T2: 5'/52Bio/CCA TGT CCC CTT AAG CCC CCC CCA TTC CCC CCT GAA CCC CCA *AGG CAC ACA GGG GAT AGG*-3' (SEQ ID NO: 2)

T3: 5'/52Bio/AAG CTC AAA AAC GGT AAA AAA AAG CCA AAA AAC TGG AAA ACA *AGG CAC ACA GGG GAT AGG*-3' (SEQ ID NO: 3)

TABLE 4 -continued

Sequences for Templates 1, 2, 3, and 4

T4: 5'/52Bio/TTC GAG TTT TTG CCA TTT TTT TTC GGT TTT TTG ACC
TTT TCA AGG CAC ACA GGG GAT AGG-3' (SEQ ID NO: 4)

Annealing of Sequencing Primer.

The immobilized templates, bound at the 5' end to 5.91 µm magnetic beads, are then annealed to a 20-base primer complementary to the 3' end of the templates (Table 4). A 1.0 µL aliquot of the 400 µM primer stock solution, representing a 20-fold excess of primer to immobilized template, is then added and then the beads plus template are incubated with primer for 15 minutes at 95° C. and the temperature was then slowly lowered to room temperature. The beads were then washed 3 times in 120 µL of 25 mM Tricine buffer (25 mM Tricine, 0.4 mg/ml PVP, 0.1% Tween 20, 8.8 mM Magnesium Acetate; pH 7.8) as described above using the MPC-s. Beads were resuspended in 25 mM Tricine buffer.

Incubation of Hybridized Templates/Primer with DNA Polymerase.

Template and primer hybrids are incubated with polymerase essentially as described by Margulies et al. Nature 2005 437(15); 376-380 and accompanying supplemental materials.

Loading of Prepared Test Samples onto the ISFET Sensor Array.

The dimensions and density of the ISFET array and the microfluidics positioned thereon may vary depending on the application. A non-limiting example is a 512×512 array. Each grid of such an array (of which there would be 262144) has a single ISFET. Each grid also has a well (or as they may be interchangeably referred to herein as a "microwell") positioned above it. The well (or microwell) may have any shape including columnar, conical, square, rectangular, and the like. In one exemplary conformation, the wells are square wells having dimensions of 7×7×10 µm. The center-to-center distance between wells is referred to herein as the "pitch". The pitch may be any distance although it is preferably to have shorter pitches in order to accommodate as large of an array as possible. The pitch may be less than 50 µm, less than 40 µm, less than 30 µm, less than 20 µm, or less than 10 µm. In one embodiment, the pitch is about 9 µm. The entire chamber above the array (within which the wells are situated) may have a volume of equal to or less than about 30 µL, equal to or less than about 20 µL, equal to or less than about 15 µL, or equal to or less than 10 µL. These volumes therefore correspond to the volume of solution within the chamber as well.

Loading of Beads in an 'Open' System.

Beads with templates 1-4 were loaded on the chip (10 µL of each template). Briefly, an aliquot of each template was added onto the chip using an Eppendorf pipette. A magnet was then used to pull the beads into the wells.

Loading of Beads in a 'Closed' System.

Both the capture beads the packing beads are loaded using flow. Microliter precision of bead solution volume, as well as positioning of the bead solution through the fluidics connections, is achieved as shown in FIGS. 62-70 using the bead loading fitting, which includes a major reservoir (approx. 1 mL in volume), minor reservoir (approx. 10 µL in volume), and a microfluidic channel for handling small volumes of bead solution. This method also leverages the microliter precision of fluid application allowed by precision pipettes.

The chip comprising the ISFET array and flow cell is seated in the ZIP (zero insertion force) socket of the loading fixture, then attaching a stainless steel capillary to one port of the flow cell and flexible nylon tubing on the other port. Both materials are microfluidic-type fluid paths (e.g., on the order of <0.01" inner diameter). The bead loading fitting, consisting of the major and minor reservoirs, it attached to the end of the capillary. A common plastic syringe is filled with buffer solution, then connected to the free end of the nylon tubing. The electrical leads protruding from the bottom of the chip are inserted into a socket on the top of a fixture unit (not shown).

The chip comprising the ISFET array and flow cell is seated in a socket such as a ZIF (zero insertion force) socket of the loading fixture, then a stainless steel capillary may be attached to one port of the flow cell and flexible nylon tubing on the other port. Both materials are microfluidic-type fluid paths (e.g., on the order of <0.01" inner diameter). The bead loading fitting, consisting of the major and minor reservoirs, it attached to the end of the capillary. A common plastic syringe is filled with buffer solution, then connected to the free end of the nylon tubing. The electrical leads protruding from the bottom of the chip are inserted into a socket on the top of a fixture unit (not shown).

It will be appreciated that there will be other ways of drawing the beads into the wells of the flow chamber, including centrifugation or gravity. The invention is not limited in this respect.

DNA Sequencing using the ISFET Sensor Array in an Open System.

A illustrative sequencing reaction can be performed in an 'open' system (i.e., the ISFET chip is placed on the platform of the ISFET apparatus and then each nucleotide (5 µL resulting in 6.5 µM each) is manually added in the following order: dATP, dCTP, dGTP and dTT (100 mM stock solutions, Pierce, Milwaukee, Wis.), by pipetting the given nucleotide into the liquid already on the surface of the chip and collecting data from the chip at a rate of 2.5 MHz. This can result in data collection over 7.5 seconds at approximately 18 frames/second, Data may then analyzed using LabView.

Given the sequences of the templates, it is expected that addition of dATP will result in a 4 base extension for template 4. Addition of dCTP will result in a 4 base extension in template 1. Addition of dGTP will cause template 1, 2 and 4 to extend as indicated in Table 5 and addition of dTTP will result in a run-off (extension of all templates as indicated).

Preferably when the method is performed in a non-automated manner (i.e., in the absence of automated flow and reagent introduction), each well contains apyrase in order to degrade the unincorporated dNTPs, or alternatively apyrase is added into each well following the addition and incorporation of each dNTP (e.g., dATP) and prior to the addition of another dNTP (e.g., dTTP). It is to be understood that apyrase can be substituted, in this embodiment or in any other embodiment discussed herein, with another compound (or enzyme) capable of degrading dNTPs.

TABLE 5

Set-up of experiment and order of nucleotide addition.

|    | dATP | dCTP       | dGTP | dTTP         |
|----|------|------------|------|--------------|
| T1 | 0    | (3:C; 1:A)4 | 1    | Run-off (25) |
| T2 | 0    | 0          | 4    | Run-off (26) |
| T3 | 0    | 0          | 0    | Run-off (30) |
| T4 | 4    | 0          | 2    | Run-off (24) |

DNA Sequencing Using Microfluidics on Sensor Chip.

Sequencing in the flow regime is an extension of open application of nucleotide reagents for incorporation into DNA. Rather than add the reagents into a bulk solution on the ISFET chip, the reagents are flowed in a sequential manner across the chip surface, extending a single DNA base(s) at a time. The dNTPs are flowed sequentially, beginning with dTTP, then dATP, dCTP, and dGTP. Due to the laminar flow nature of the fluid movement over the chip, diffusion of the nucleotide into the microwells and finally around the nucleic acid loaded bead is the main mechanism for delivery. The flow regime also ensures that the vast majority of nucleotide solution is washed away between applications. This involves rinsing the chip with buffer solution and apyrase solution following every nucleotide flow. The nucleotides and wash solutions are stored in chemical bottles in the system, and are flowed over the chip using a system of fluidic tubing and automated valves. The ISFET chip is activated for sensing chemical products of the DNA extension during nucleotide flow.

Example 2

On-Chip Polymerase Extension Detected by pH Shift on an ISFET Array

Figure 72A:
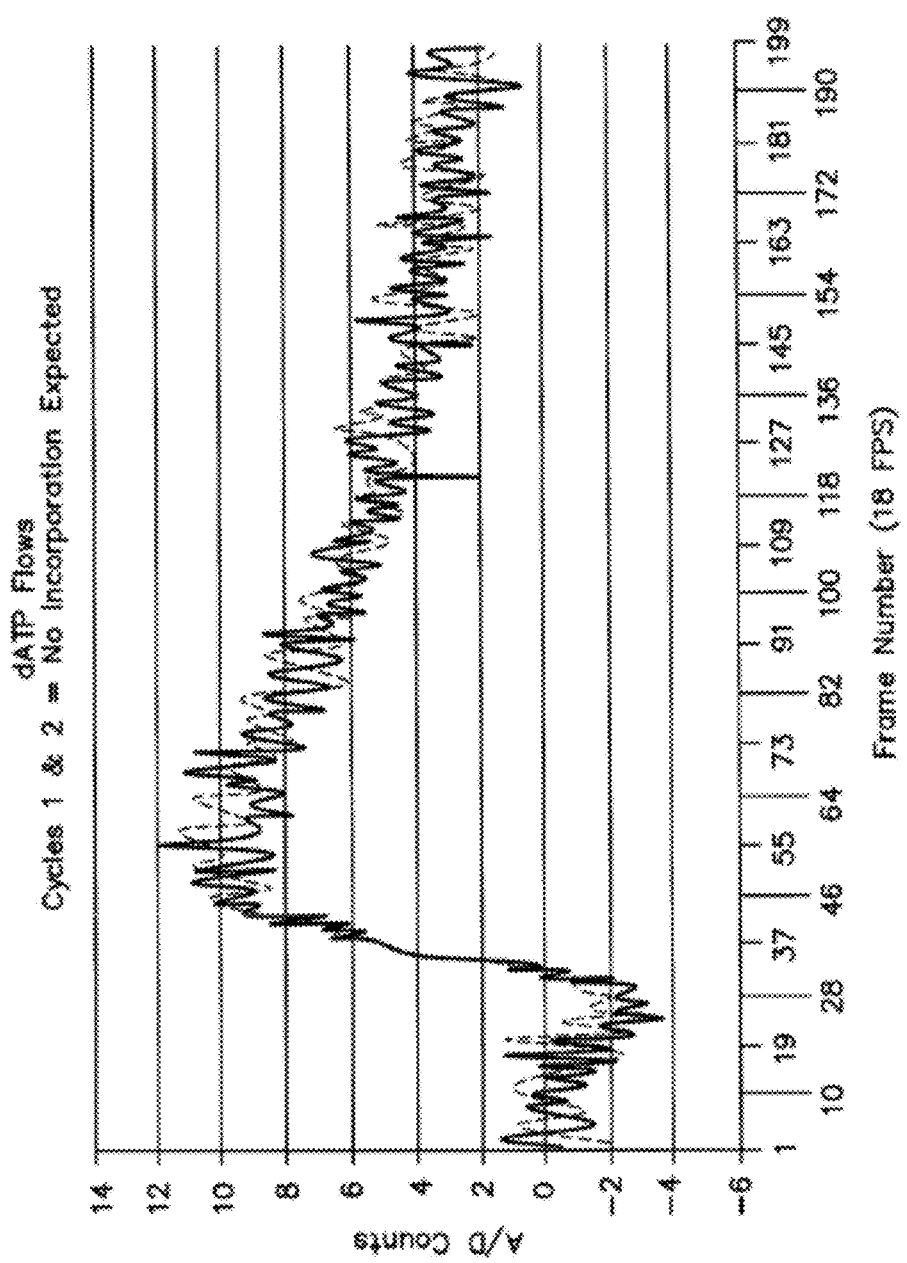
FIGS. 72A-D are graphs showing on-chip detection of nucleotide incorporation using a template of known sequence.
Figure 72B:
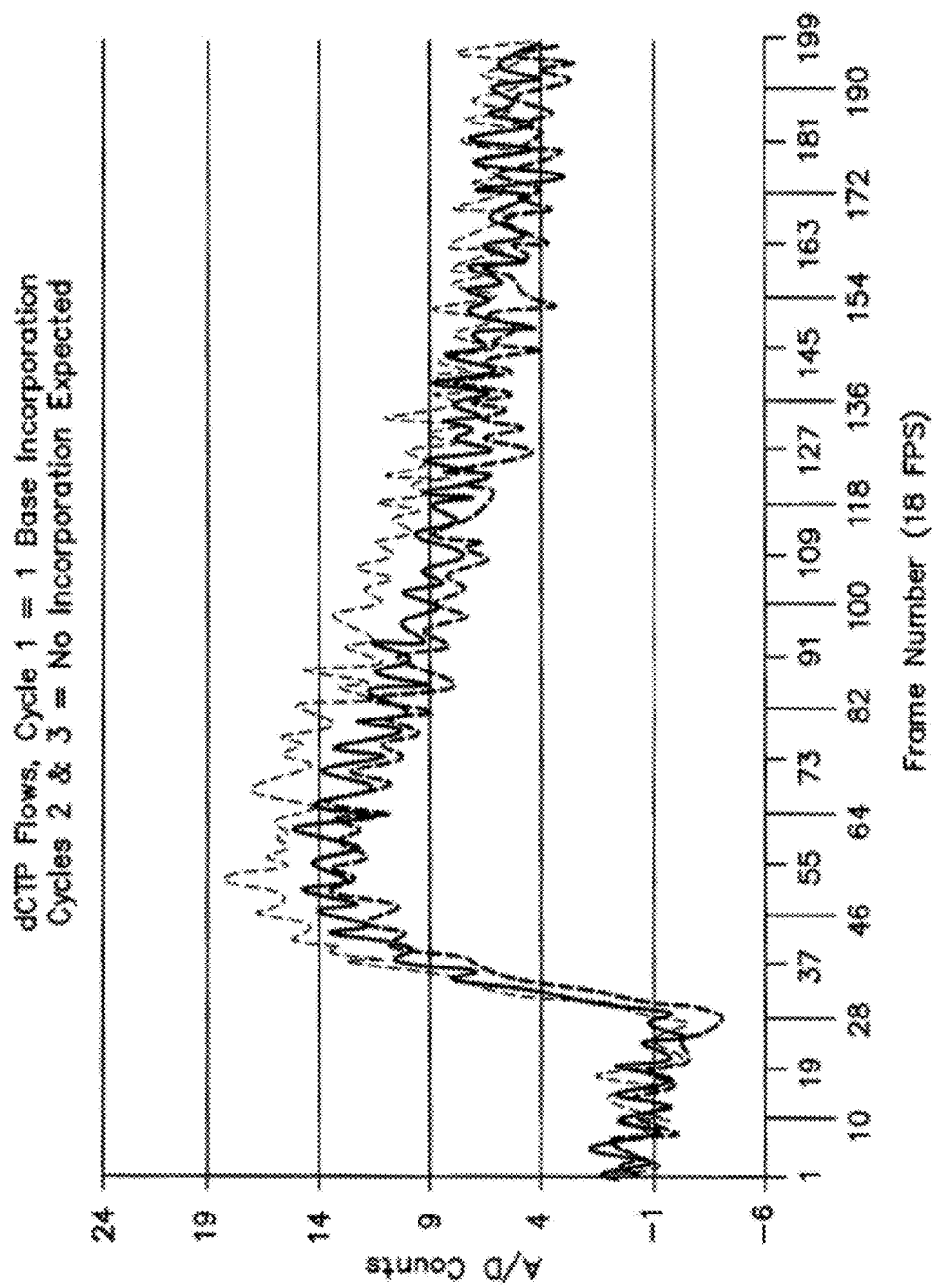
Figure 72C:
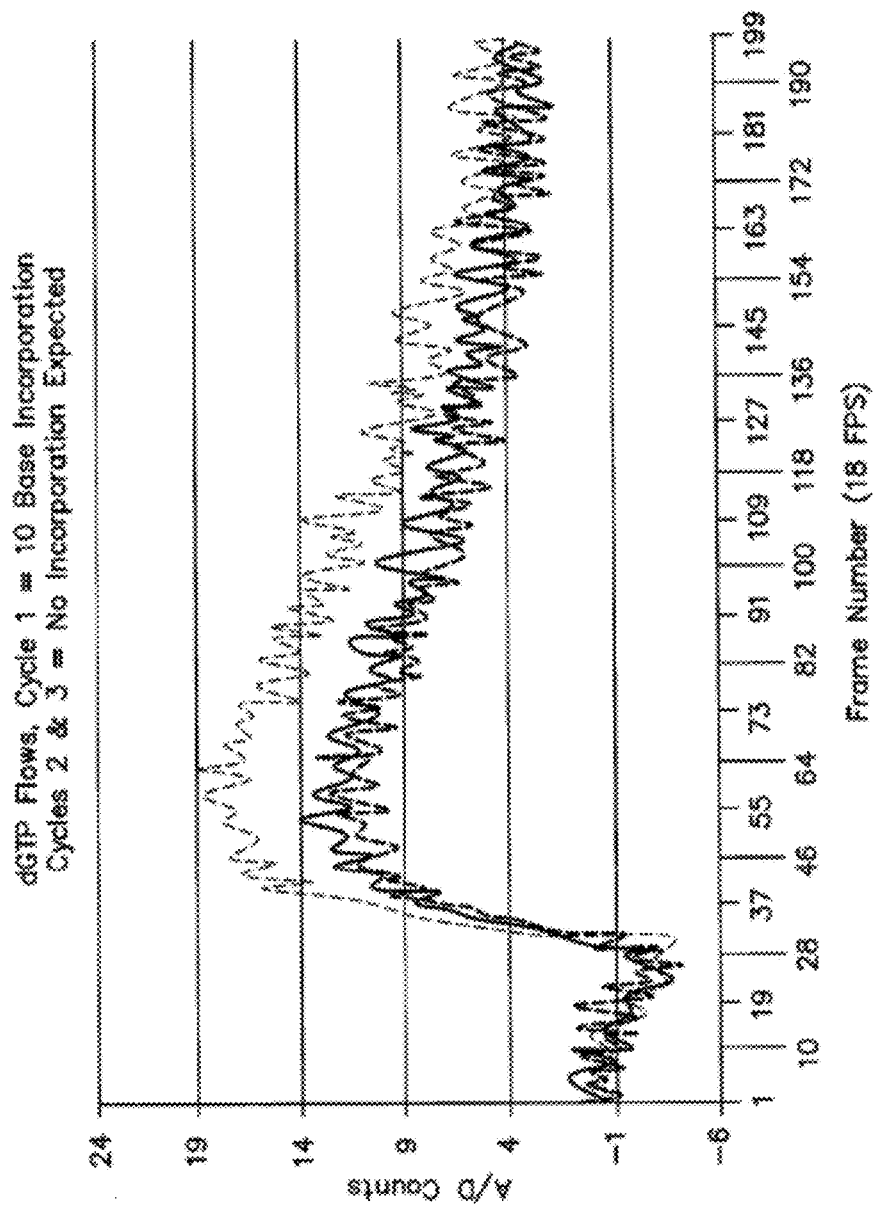
Figure 72D:
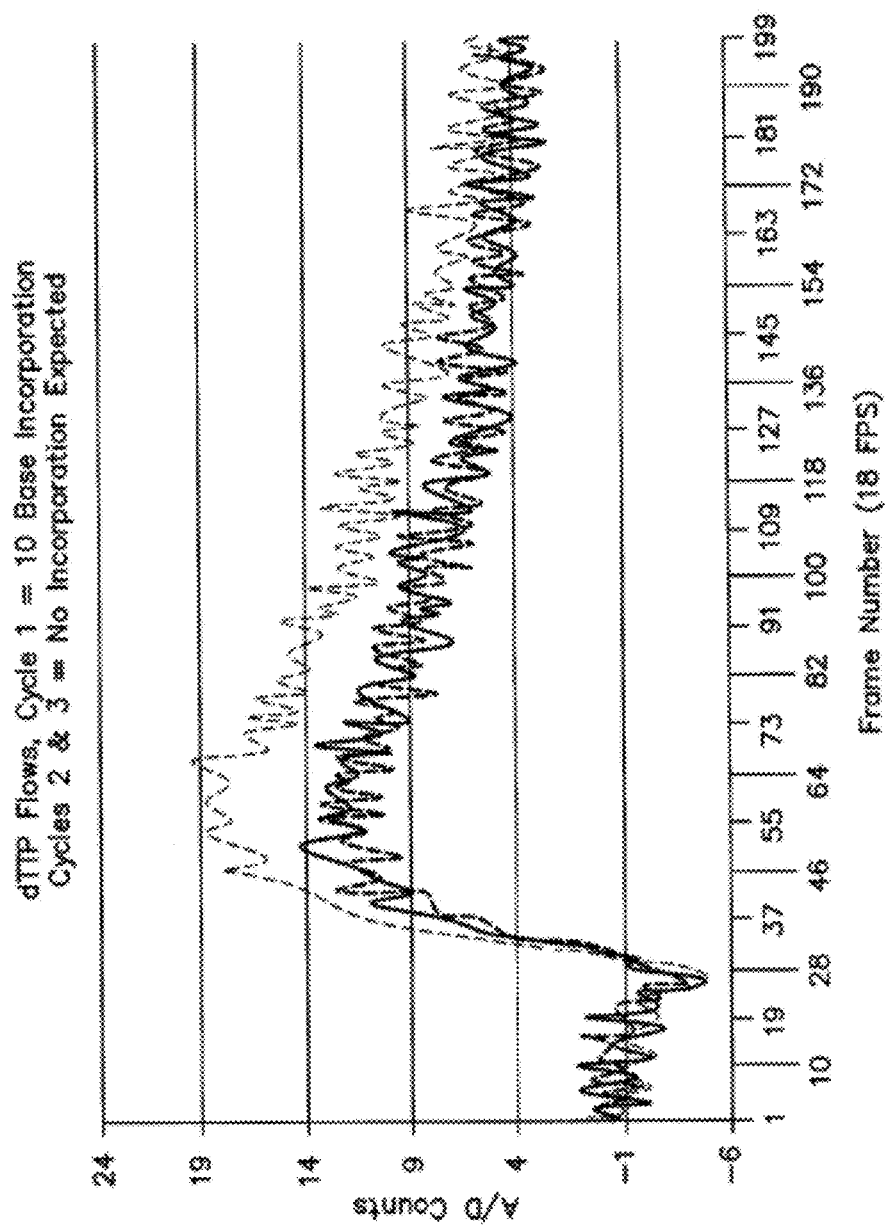

Streptavidin-coated 2.8 micron beads carrying biotinylated synthetic template to which sequencing primers and T4 DNA polymerase are bound were subjected to three sequential flows of each of the four nucleotides. The template sequence downstream of the sequencing primer was a $G(C)_{10}(A)_{10}$ (SEQ ID NO:5). Each nucleotide cycle consisted of flows of dATP, dCTP, dGTP and dTTP, each interspersed with a wash flow of buffer only. Flows from the first cycle are shown in blue, flows from the second cycle in red, and the third cycle in yellow. As shown in FIG. 72A, signal generated for both of the two dATP flows were very similar. FIG. 72B shows that the first (blue) trace of dCTP is higher than the dCTP flows from subsequent cycles, corresponding to the flow in which the polymerase should incorporate a single nucleotide per template molecule. FIG. 72C shows that the first (blue) trace of dGTP is approximately 6 counts higher (peak-to-peak) than the dGTP flows from subsequent cycles, corresponding to the flow in which the polymerase should incorporate a string of 10 nucleotides per template molecule. FIG. 72D shows that the first (blue) trace of dTTP is also approximately 6 counts higher (peak-to-peak) than the dTTP flows from subsequent cycles, corresponding to the flow in which the polymerase should incorporate 10 nucleotides per template molecule.

Example 3

Sequencing in a Closed System and Data Manipulation

Sequence has been obtained from a 23-mer synthetic oligonucleotide and a 25-mer PCR product oligonucleotide. The oligonucleotides were attached to beads which were then loaded into individual wells on a chip having 1.55 million sensors in a 1348×1152 array having a 5.1 micron pitch (38400 sensors per $mm^2$). About 1 million copies of the synthetic oligonucleotide were loaded per bead, and about 300000 to 600000 copies of the PCR product were loaded per bead. A cycle of 4 nucleotides through and over the array was 2 minutes long. Nucleotides were used at a concentration of 50 micromolar each. Polymerase was the only enzyme used in the process. Data were collected at 32 frames per second.

Figure 73A:
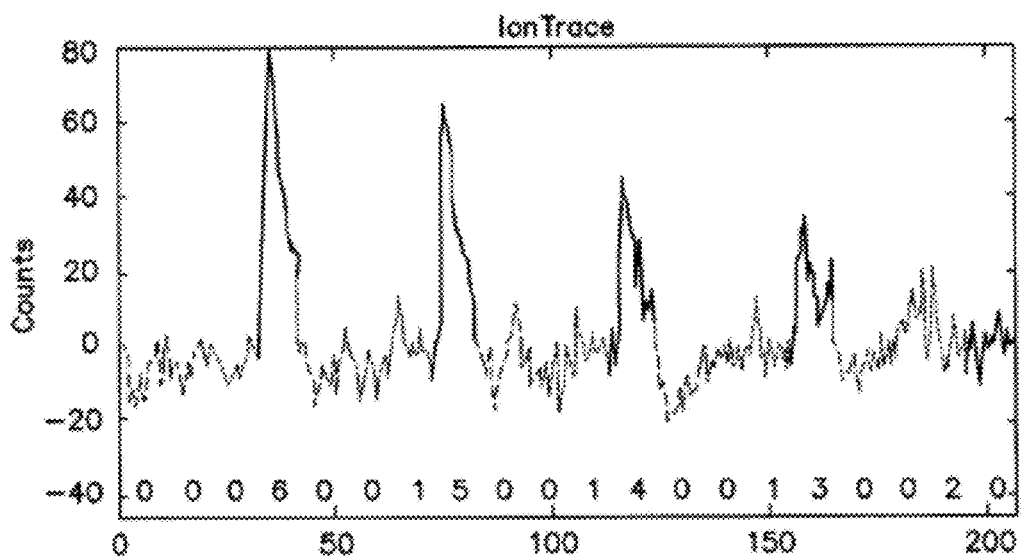
FIGS. 73A and B are graphs showing a trace from an ISFET device (A) and a nucleotide readout (B) from a sequencing reaction of a 23-mer synthetic oligonucleotide.

FIG. 73A depicts the raw data measured directly from an ISFET for the synthetic oligonucleotide (SE ID NO:6). One millivolt is equivalent to 68 counts. The data are sampled at each sensor on the chip (1550200 sensors on a 314 chip) many times per second, The Figure is color-coded for each nucleotide flow. With each nucleotide flow, several seconds of imaging occur. The graph depicts the concatenation of those individual measurements taken during each flow. The Y axis is in raw counts, and the X axis is in seconds, Superimposed just above the X axis are the expected incorporations at each flow.

Figure 73B:
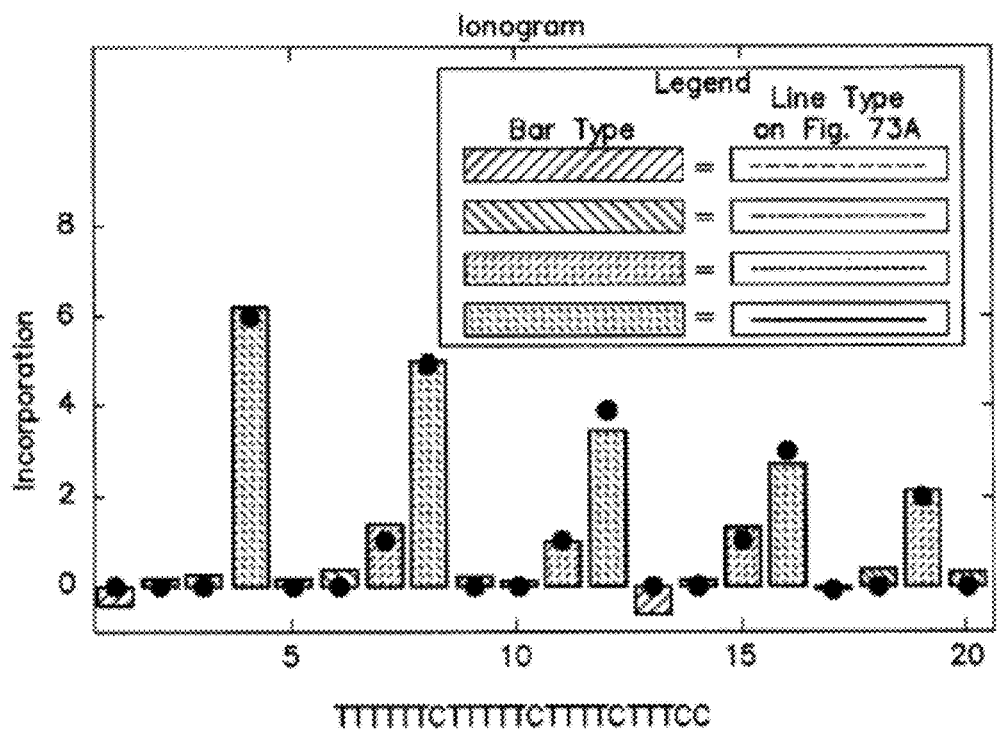

FIG. 73B depicts the integrated value for each nucleotide flow, normalized to the template being sequenced. The integrated value is taken from the raw trace measurements shown in FIG. 73A, and the integral bounds have been chosen to maximize signal to noise ratio. The results have been normalized to the signal per base incorporation, and graphed per nucleotide flow. The Y axis is incorporation count, and the X axis is nucleotide flow number, alternating through TACG.

Figure 74A:
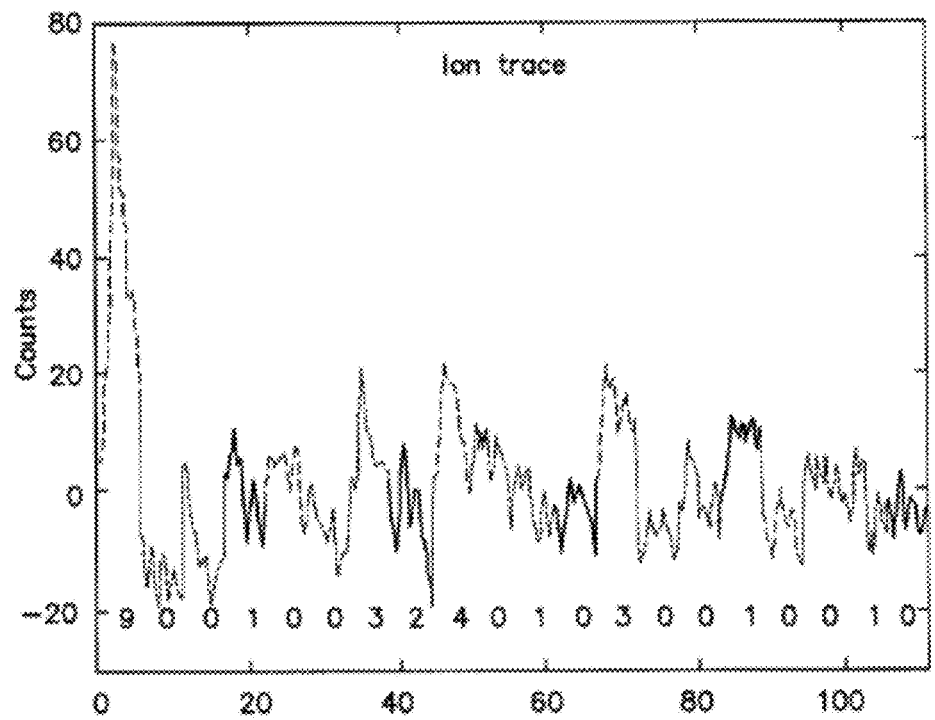
FIGS. 74A and B are graphs showing a trace from an ISFET device (A) and a nucleotide readout (B) from a sequencing reaction of a 25-mer PCR product.
Figure 74B:
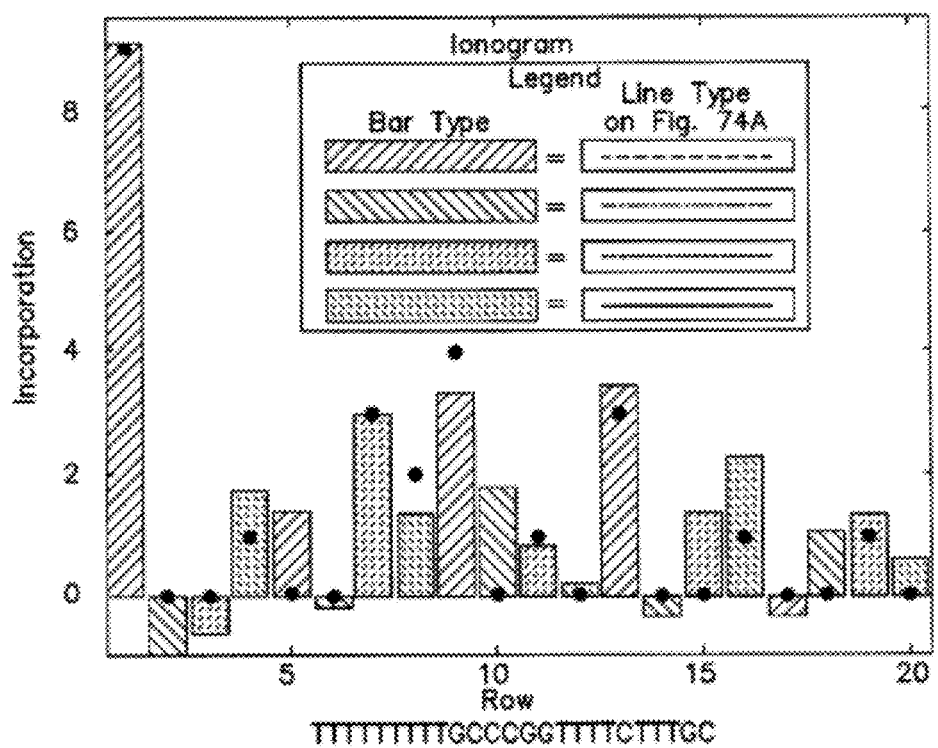

FIGS. 74A and 74B represent the same type of measurements taken and shown in FIGS. 73A and 73B, with the exception that the signal being detected here is from a PCR product (the 25-mer oligonucleotide, SEQ ID NO:7), rather than a synthetic oligonucleotide.

Improving Pixel and Array Signal-to-Noise Ratio

The reliability of signal decoding from each ISFET and from the ISFET array as a whole is dependent on the amplitude of the signal output by each ISFET, and its respective signal-to-noise ratio. Some changes to the foregoing fabrication methods, judicious materials selection, and changes to pixel and array design can be employed to increase considerably the output of the ISFETs in the array and decrease various noise sources. That is, these changes result in a more sensitive and more accurate sensor array. The improvements can be implemented individually or in various combinations, and can result in significant performance gains to the signal-to-noise ratio (SNR).

As more fully discussed below, the improvements involve: (1) over-coating (i.e., "passivating") the sidewalls (typically formed of TEOS-oxide or another suitable material, as above-described) and sensor surface at the bottom of the microwells with various metal oxide or like materials, to improve their surface chemistry (i.e., make the sidewalls less reactive) and electrical properties; (2) thinning out the coating (deposition material) on the floating gate; (3) increasing the surface area for charge collection at the floating gate; (4) and modified array and pixels designs to reduce charge injection into the electrolyte and other noise sources.

Floating Gate Deposition Layer Material and Thickness

Figure 75A:
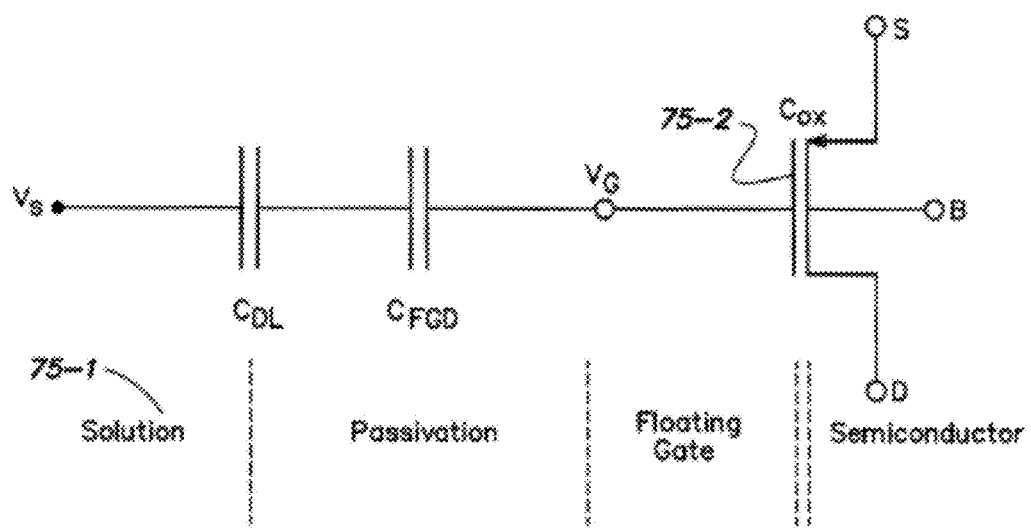
FIG. 75A is a modeling circuit diagram for use in analyzing the factors influencing ISFET gate gain.

As illustrated in FIG. 75A, it is now appreciated that if a dielectric layer is added over the floating gate structure of the ISFET sensor arrangement, the path from the analyte to the ISFET gate may be modeled as a series connection of three capacitances: (1) the capacitance attributable to the above-described charge double layer at the analyte-dielectric layer interface (labeled $C_{DL}$), (2) the capacitance due to the floating gate dielectric layer ($C_{FGD}$), and (3) the gate oxide capacitance ($C_{OX}$). (Note that in the text above, the floating gate dielectric layer is sometimes referred to as a "passivation" layer. Here, we refer more specifically to the layer as a floating gate dielectric layer in order to avoid any suggestion that the material composition of the layer is necessarily related to the so-called passivation material(s) often used in CMOS processing (e.g., PECVD silicon nitride) to coat and protect circuit elements.) The series capacitance string extends between the liquid analyte 75-1 in the wells and the ISFET gate 75-2.

It is well known that capacitances in series form a capacitive voltage divider. Consequently, only a fraction of the signal voltage, $V_S$, generated by or in the analyte, is applied to the gate oxide as the voltage $V_G$ that drives the ISFET. If we define the gate gain as $V_G/V_S$, one would ideally like to have unity gain—i.e., no signal loss across any of the three capacitances. Of course, unity gain is not achievable, but the actual gate gain can be optimized. The value of $C_{DL}$ is a function of material properties and is typically on the order of about 10-40 μF/cm². The gate oxide capacitance is typically a very small value by comparison. Thus, by making $C_{FGD}$ much greater than the series combination of $C_{OX}$ and $C_{DL}$ (for short, $C_{FGD} \gg C_{OX}$), the gate gain can be made to approach unity as closely as is practical.

To achieve the relationship $C_{FGD} \gg C_{OX}$, one can minimize $C_{OX}$, maximize $C_{FGD}$, or both. There is not a lot that can be done to alter the gate oxide capacitance much when using standard CMOS foundry techniques to fabricate the ISFETs. That is, for practical reasons one must typically accept the gate oxide capacitance value as a "given." Thus, emphasis may be placed on maximizing $C_{FGD}$. Such maximization can be achieved by using a thin layer of high dielectric constant material, or by increasing the area of the floating gate metallization. Since increasing floating gate area conflicts with a goal of having a high density sensor array, attention has been focused on the dielectric layer.

Materials exist and may be used that have higher dielectric constants than the customary CMOS gate oxide material, silicon dioxide. So, if in the course of fabrication such a gate oxide material has been deposited onto the floating gate metallization, one may etch away that material, essentially eliminating it, and deposit a suitable high dielectric constant floating gate dielectric layer directly onto the floating gate metallization. Or, one may simply deposit such a floating gate dielectric layer directly onto the floating gate metallization without having to etch first. In either situation, there are then only two series capacitances that matter between the analyte and the ISFET gate, $C_{DL}$ and $C_{FGD}$. Gate gain can then be maximized by making $C_{FGD} \gg C_{DL}$. Thus, achieving a large value for $C_{FGD}$ is desirable, while also satisfying other requirements (e.g., reliable manufacture).

The capacitance $C_{FGD}$ is essentially formed by a parallel plate capacitor having the floating gate dielectric layer as its dielectric, Consequently, for a given plate (i.e., floating gate metallization) area, the parameters principally available for increasing the value of $C_{FGD}$ are (1) the thickness of the dielectric layer and (2) the selection of the dielectric material and, hence, its dielectric constant. The capacitance of the floating gate dielectric layer varies directly with its dielectric constant and inversely with its thickness. Thus, a thin, high-dielectric-constant layer would be preferred, to satisfy the objective of obtaining maximum gate gain.

One candidate for the floating gate dielectric layer material is the passivation material used by standard CMOS foundry processes. The standard (typically, PECVD nitride or, to be more precise, silicon nitride over silicon oxynitride) passivation layer is relatively thick when formed (e.g., about 1.3 μm), and typical passivation materials have a limited dielectric constant. A first improvement can be achieved by thinning the passivation layer after formation. This can be accomplished by etching back the CMOS passivation layer, such as by using an over-etch step during microwell formation, to etch into and consume much of the nitride passivation layer, leaving a thinner layer, such as a layer only about 200-600 Angstroms thick. While simple, this approach is prone to wafer-to-wafer etch variations, resulting in variability in the final passivation layer thickness and capacitance.

Two approaches have been at least partially evaluated for etching a standard CMOS passivation layer of silicon nitride deposited over silicon oxynitride. We call the first approach the "partial etch" technique. It involves etching away the silicon nitride layer plus approximately half of the silicon oxynitride layer before depositing the thin-film metal oxide sensing layer. The second approach we call the "etch-to-metal" technique. It involves etching away all of the silicon nitride and silicon oxynitride layers before depositing the thin-film metal oxide sensing layer. Theoretical modeling indicates that the partial etch approach should lead to an ISFET gate gain of about 0.42. This corresponds to an increase of signal level by about 50% compared with a non-etched passivation layer. With an ALD $Ta_2O_5$ thin-film sensing layer deposited over a "partial etch," ISFET gains from about 0.37 to about 0.43 have been obtained empirically, with sensor sensitivities of about 15.02-17.08 mV/pH.

Theoretical modeling indicates that in the "etch-to-metal" approach with the same sensing layer, an ISFET gate gain of about 0.94 should be possible. This would correspond to a greater than three-fold increase in signal. With an imperfect etch process that does not produce a uniform etch across the surface of the floating gate, the empirically obtained gain has only been about 0.6, corresponding to a little more than doubling of the signal. With improved etch chemistry/process to obtain a more uniform and flat surface at the bottom of the well, a gain close to the model 0.94 gain should be possible.

One promising approach for improving the uniformity and flatness of the etch process is to perform two or more separate etches in series—i.e., use a multi-step etch process. A first etch step may be performed and the progress of that etch step may be monitored optically, at one or multiple wavelengths. When it is detected that the first step etch has exposed a part of the underlying metal surface, the first etch process can be stopped and a second process or step may be begun, using conditions that will remove the dielectric material without removing (much of) the metal.

An alternative to use of the foregoing etch processes is to simply deposit a thinner layer of dielectric (passivation) material in the first place, such as the indicated 200-600 Angstroms instead of the 1.3 μm of the conventional CMOS passivation process. Even better performance can be achieved with the use of other materials and deposition techniques to form a thin dielectric layer, preferably one of relatively higher dielectric constant. Among the materials believed useful for the floating gate dielectric layer are metal oxides such as tantalum oxide, tungsten oxide, aluminum oxide, and hafnium oxide, though other materials of dielectric constant greater than that of the usual silicon nitride passivation material may be substituted, provided that such material is sensitive to the ion of interest. The etch-to-metal approach is preferred, with the CMOS process' passivation oxide on the floating gate being etched completely away prior to depositing the floating gate dielectric material layer. That dielectric layer may be applied directly on the metal extended ISFET floating gate electrode. This will help maximize the value of the capacitance $C_{FGD}$.

The etch-to-metal approach is preferred, with the CMOS process' passivation oxide on the floating gate being etched completely away prior to depositing the floating gate dielectric material layer. That dielectric layer may be applied directly on the metal extended ISFET floating gate electrode. This will help maximize the value of the capacitance $C_{FGD}$.

Among the processes which may be used for depositing a thin layer of floating gate dielectric material are reactive or non-reactive sputtering, electron cyclotron resonance (ECR), e-beam evaporation, and atomic layer deposition (ALD), though any suitable technique may be employed. Each of the foregoing processes has well known characteristics. Importantly, however, these processes differ in their abilities to provide conformal and uniform films, which are qualities that may be important for some applications. Thus, all are usable, but they are not necessarily equally desirable. Of the four enumerated techniques, ALD appears to be superior with respect to the particular desired qualities. It is good for depositing layers whose thickness can be controlled precisely so that wafer-to-wafer repeatability is not a problem. Also, it is a low-temperature process that does not threaten the aluminum interconnects that typically already will have been formed on the wafer by the time the floating gate dielectric material layer is applied. ALD, moreover, promises to enable conformal, pinhole-free and crack-free film coverage on the well bottom, which is required; and it is compatible with extending the deposition from the well bottoms onto the high aspect ratio (i.e., steep) well sidewalls. Covering the sidewalls with a passivation or buffering layer will render them more inert to the analyte.

To create such structures, a layer of microwells should be formed on top of the ISFETs wherein the microwells are open at their bottoms. If the structure is to be formed without a floating gate dielectric layer other than a conventional passivation material over the floating gate, then the passivation material preferably should be partially etched down to the desired thinness. This alone increases the floating gate dielectric capacitance $C_{FGD}$ relative to $C_{DL}$, improving gate gain. Optionally, a thin, higher-dielectric-constant layer may be deposited or otherwise formed over such passivation material.

The deposited layer should preferably be relatively thin—e.g., only about 200-600 Angstroms thick, possibly even less. As the thin layer of floating gate dielectric material is deposited over the well bottom onto the floating gate or its immediate coating layer, it also may be allowed to deposit conformally over the well sidewalls using, for example, the aforementioned ALD process.

The potential for improvement is considerable. As a starting point, consider one standard CMOS foundry passivation material, silicon nitride, $Si_3N_4$. This particular material has a sub-Nernstian response to pH. Consequently, the best response we have been able to measure is about 40 mV/pH for an ISFET sensor with a silicon nitride floating gate deposition layer (though some improvement might be obtainable with improved nitride deposition). This is considerably less than the ideal Nernstian response of 59 mV/pH at 25° C. Thus, about one-third of the signal voltage at the interface between the analyte and the floating gate deposition layer is lost due to use of materials with so great a sub-Nernstian response. Indeed, in one example, simulations indicated that a three-fold improvement in gate gain is possible with changes in both floating gate deposition material and floating gate deposition layer thickness, for the gate geometries studied. This was then corroborated empirically with electrical test results on a 400 Angstrom aluminum oxide ($Al_2O_3$) floating gate deposition material.

From available literature or experimentation, one can determine that in addition to $Al_2O_3$, there are other metal oxides that can be substituted for silicon nitride at the well bottom, to obtain a closer to Nernstian response. For example, Table 6 compares the pH response of ISFETs with various floating gate deposition oxides (specifically, SiO2, $Si_3N_4$, $Al_2O_3$ and $Ta_2O_5$, using published data.

TABLE 6

| Characteristic | SiO$_2$ | Si$_3$N$_4$ | Al$_2$O$_3$ | Ta$_2$O$_5$ |
|---|---|---|---|---|
| pH range | 4-10 | 1-13 | 1-13 | 1-13 |
| Sensitivity (mV/pH) | 23-35 (pH > 7) 37-48 (pH < 7) | 46-56 | 53-57 | 56-57 |
| Sensitivity (mV/pX) | | | | |
| Na+ | 30-50 | 5-20 | 2 | <1 |
| K+ | 20-30 | 5-25 | 2 | <1 |
| Response time | | | | |
| (95%) (s) | 1 | <0.1 | <0.1 | <0.1 |
| (98%) (min) | Undefined | 4-10 | 2 | 1 |
| Drift (mV/hr, pH 1-7) | Unstable | 1.0 | 0.1-0.2 | 0.1-0.2 |

Of the four materials compared in Table 6, $SiO_2$ had the lowest sensitivity to pH and no linear dependence on pH. The literature indicated that $Si_3N_4$ had higher sensitivities (46-56 mV/pH) but experiments have shown its performance to be dependent on the type of deposition technique and oxygen content. The best reported materials were $Al_2O_3$ and $Ta_2O_5$, which exhibited higher sensitivity in the ranges of 53-57 and 56-57 mV/pH, respectively. One other study has indicated that tungsten oxide, $WO_3$, a material with a high dielectric constant (about 300), has a sensitivity of 50 mV/pH.

Consequently, the data indicates that using a floating gate deposition material such as $Ta_2O_5$, $Al_2O_3$, $HfO_3$ or $WO_3$ will result in a larger signal in response to pH changes. In other words, if it is assumed that the sensitivity of $Ta_2O_5$ is 56 mV/pH and that the Nernstian gain is defined as the material sensitivity divided by the ideal Nernstian response of 59 mV/pH at 25° C., then the Nernstian gain increases from 0.67 for $Si_3N_4$ to about 0.95-0.96 for $Ta_2O_5$. Thus, with $Ta_2O_5$, only about 4-5% of the signal voltage is lost across the floating gate deposition layer.

The deposition of a thin film floating gate deposition layer over the side walls of the microwells provides a further benefit. By coating the walls with a material whose pKa value is more conducive to analyte pH conditions than the TEOS oxide sidewall above mentioned, the floating gate deposition material buffers the sidewalls so that surface reactions there capture fewer of the protons that otherwise would be available as signal generators once they reach the gate region.

Thus, the above-taught thin-film floating gate deposition layers provide a three-fold benefit: First, they enhance sensor performance at the sensor surface by providing a more reactive interface between the analyte and the ISFET gate (or, in other words, they are more Nernstian). Second, they serve as a replacement, thinner dielectric between the analyte and the metal ISFET gate (if directly applied to the metal) or between the analyte and the gate oxide (if applied over a gate oxide layer), thereby increasing the coupling capacitance and gate gain. Third, if also used to cover the microwell sidewalls, as would be typical for most deposition processes, they provide buffering by coating the TEOS-oxide sidewalls with a material whose pKa differs more substantially from the analyte pH than that of the sidewall material itself.

There are also materials such as Iridium oxide which provide super-Nernstian responses, which can provide a still further improvement in SNR if used as the thin film floating gate deposition layer. See, e.g., D. O. Wipf et al, "Microscopic Measurement of pH with Iridium Oxide Microelectrodes," *Anal. Chem.* 2000, 72, 4921-4927, and Y. J. Kim et al, "Configuration for Micro pH Sensor," *Electronics Letters*, Vol. 39, No. 21 (Oct. 16, 2003).

Figure 75B:
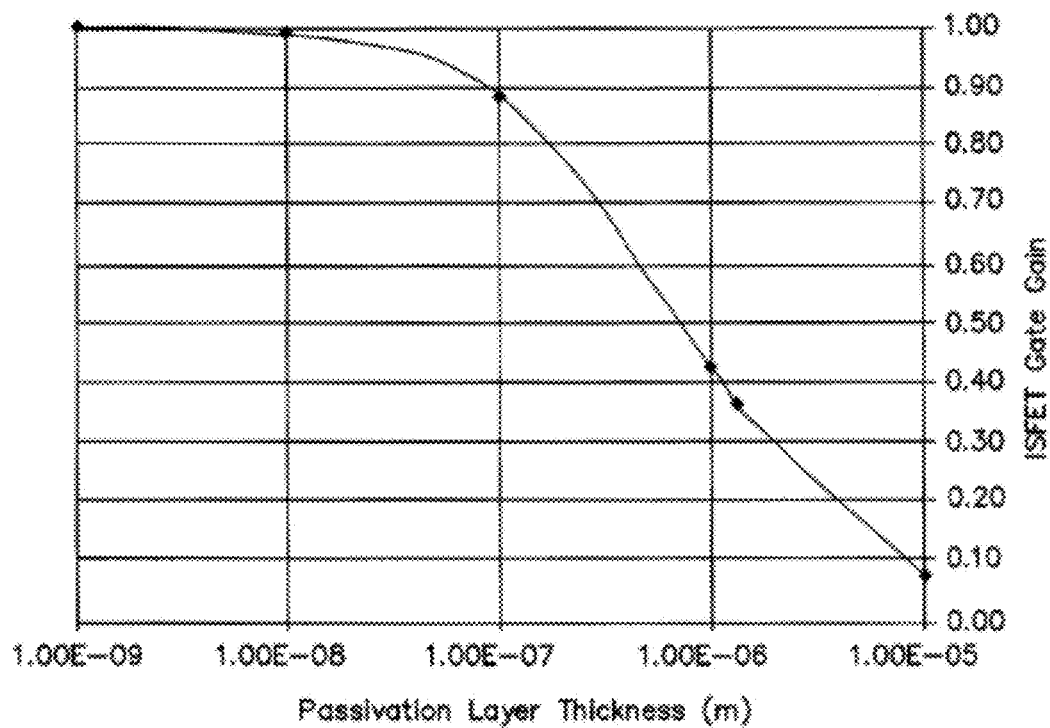
FIG. 75B is a graph of simulated ISFET gate gain dependence on passivation layer thickness for a first set of parameters set forth in the specification.
Figure 75C:
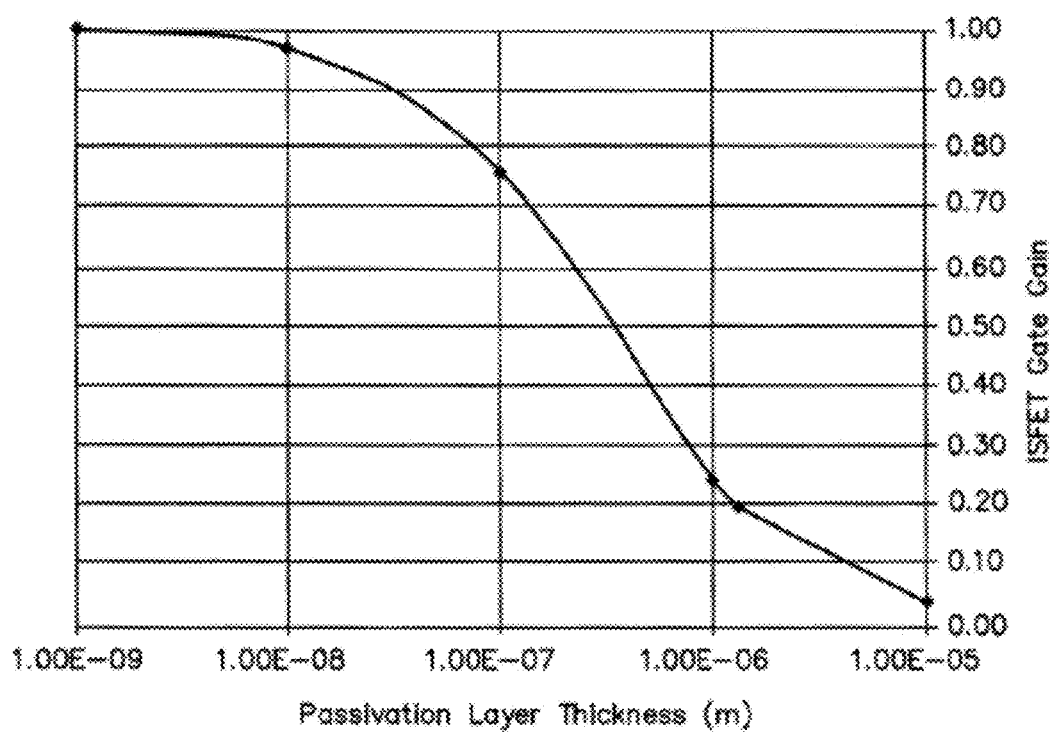
FIG. 75C is a graph of simulated ISFET gate gain dependence on passivation layer thickness for a second set of parameters set forth in the specification.
Figure 75D:
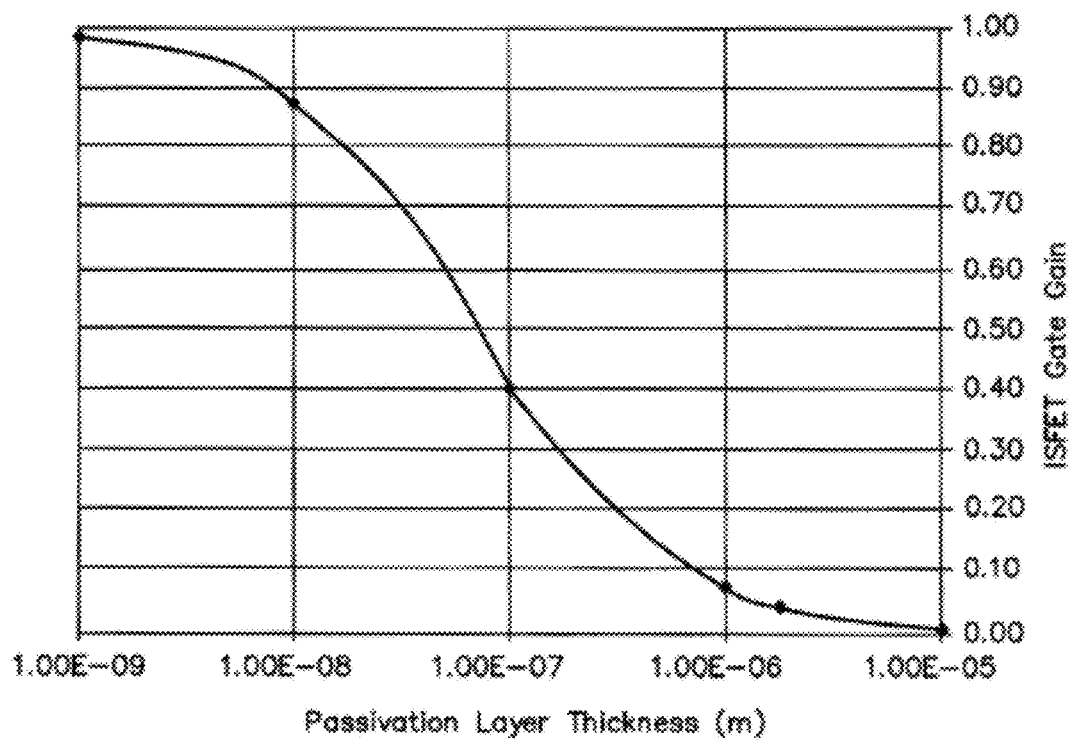
FIG. 75D is a graph of simulated ISFET gate gain dependence on passivation layer thickness for a third set of parameters set forth in the specification.

FIGS. 75B-D model the dependence of gate gain on floating gate deposition layer thickness and material, assuming use of a conventional gate oxide, under differing conditions. The conditions for FIG. 75B are given in Table 7, below:

TABLE 7

| Gate oxide thickness (m) | 7.70E−09, typ. |
| --- | --- |
| ISFET gate length (m) | 6.00E−07 |
| ISFET gate width (m) | 1.20E−06 |
| ISFET gate area (m2) | 7.20E−13 |
| ISFET gate capacitance (F) | 3.23E−15 |
| ISFET sensor plate side length (m) | 6.00E−06 |
| ISFET sensor plate area (m2) | 3.60E−11 |
| ISFET sensor plate capacitance (F) | 1.84E−15 |

The conditions for FIG. 75C are given in Table 8, below:

TABLE 8

| Gate oxide thickness (m) | 7.70E−09, typ. |
| --- | --- |
| ISFET gate length (m) | 5.00E−07 |
| ISFET gate width (m) | 1.20E−06 |
| ISFET gate area (m2) | 6.00E−13 |
| ISFET gate capacitance (F) | 2.69E−15 |
| ISFET sensor plate side length (m) | 3.50E−06 |
| ISFET sensor plate area (m2) | 1.23E−11 |
| ISFET sensor plate capacitance (F) | 6.25E−16 |

The conditions for FIG. 75D are given in Table 9, below:

TABLE 9

| Gate oxide thickness (m) | 3.80E−09 |
| --- | --- |
| ISFET gate length (m) | 4.00E−07 |
| ISFET gate width (m) | 7.00E−07 |
| ISFET gate area (m2) | 2.80E−13 |
| ISFET gate capacitance (F) | 2.54E−15 |
| ISFET sensor plate side length (m) | 1.60E−06 |
| ISFET sensor plate area (m2) | 2.56E−12 |
| ISFET sensor plate capacitance (F) | 9.71E−17 |

The deposited ALD thin film layers discussed above, like all deposited thin-films, have an intrinsic stress and stress gradient resulting from material properties and/or deposition conditions. These properties can affect the adhesion of the deposited film to the underlying substrate (the floating gate metallization and microwell sidewalls). In the fabrication examples above, various metal-oxide ceramic materials are to be deposited onto silicon dioxide (i.e., the TEOS material of the microwells), silicon nitride (i.e., the remaining CMOS passivation material that has been etched through but which is still present on the bottom of the sidewalls) and aluminum (i.e., the metal ISFET floating gate electrode).

Some ALD processes involve depositing materials at temperatures below 400° C.; others, at temperatures above 400° C. As described above, an end-of-line forming gas anneal above 400° C. may be employed as part of the CMOS trapped charge neutralization process. The ALD layers deposited at temperatures less than this tend to delaminate or spall off the silicon dioxide sidewalls. It has been found empirically that $Ta_2O_5$ (deposited at 325° C.) spalls off the well sidewalls and $Al_2O_3$ (deposited at 460° C.) does not.

Two methods are proposed to correct this problem, as applied to fabricating an optimum microwell passivation/floating gate dielectric (protection) material into a microwell and onto an ISFET sensor gate. In a first method, a laminated film may be used to relieve the stress in the as-deposited metal oxide ceramic. In a second method, a glue layer is first deposited, having superior adhesion onto which a microwell passivation/floating gate dielectric (protection) material of optimum surface chemistry is deposited.

As an example, the laminate layer may be an approximately 400 Angstrom thick structure of alternating layers of $Ta_2O_5$, and $Al_2O_3$, (for instance, but not limited to, each about 10-20 Angstroms thick, or of different thicknesses). It is believed to be preferable to start with $Al_2O_3$ (as it exhibits better adhesion to oxide) and terminate with $Ta_2O_5$, (for its superior surface chemistry). The ALD process is ideally suited to this as film thicknesses can be controlled down to the atomic layer (i.e., a few Angstroms) and can be switched easily from one material to another simply by switching the precursor gasses introduced into the reactor system.

The overall stress of such a laminate layer would be a combination of the intrinsic stresses—compressive and tensile—of the individual layers. More than two materials could be used if, say, a tertiary laminate were required.

The "glue layer" idea is a more straight-forward implantation. First, a very thin (e.g., 50 Angstrom) layer of good adherent material (e.g., high temperature$_{Al2O3}$) may be deposited and then immediately following that, a thicker (e.g., 400 Angstrom) layer of $Ta_2O_5$.

Increasing Floating Gate Surface Area

The various metal oxide materials discussed above for improving the surface properties both of the well surface and/or of the sensor surface at the bottom of the well are not electrically conductive. However, one can create an extended floating gate electrode underneath such material, extending the electrically conductive properties of the ISFET gate electrode, by first depositing and planarize-etching a thin conformal metal coating prior to the "passivation" layer deposition. The removal via CMP (chemical-mechanical polishing) or other etch techniques of the thin-metal from the tops of the microwells would realize discrete electrically isolated wells having passivated gates consisting of substantially the entire interior surface area of the microwell sidewalls. This would increase the available surface area of the ISFET gate several fold. Doing so would virtually eliminate "lost protons at microwell walls" (i.e., those protons emanating from the sequencing reaction on the bead and otherwise hitting the non-sensing microwell wall).

The extended floating gate dielectric capacitor would be formed (by, e.g., ALD) after microwell etch, Adjustments to the microwell lateral dimensions could be necessary, depending on the thickness of the thin-metal plus passivation layers being deposited, and the bead size.

Figure 75E:
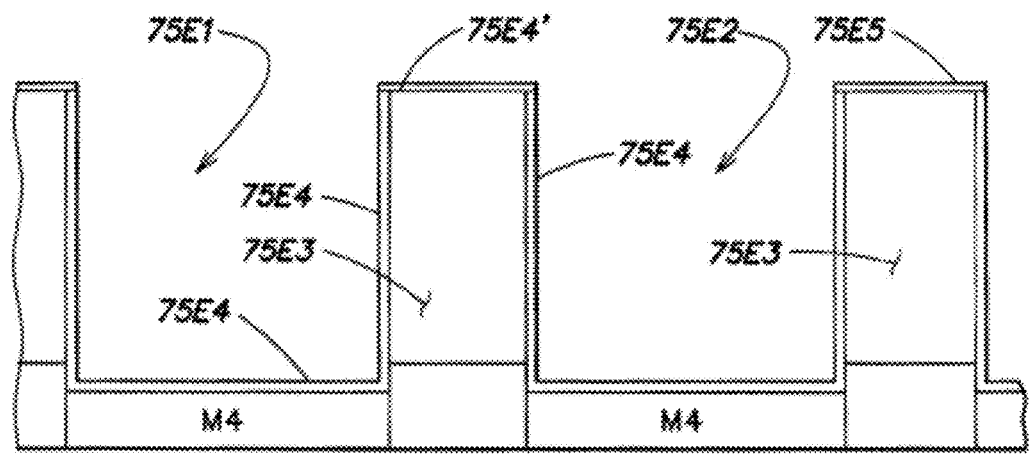
FIG. 75E is a diagrammatic illustration of two microwells formed over ISFETs having extended floating gate electrodes lining the walls of the microwells.

FIG. 75E depicts diagrammatically two microwells 75E1 and 75E2 being formed with such an extended floating gate structure. As will become clear in a moment, the structures of FIG. 75E are in a partial state of completion. With reference to FIG. 75E, one possible sequence for fabricating the microwell structure with an extended gate electrode could be as follow: After forming the layer 75E3 of material (e.g., TEOS) which will provide the microwell walls, on top of a CMOS wafer wherein the ISFET structures have been formed, the areas that will become the wells are etched down to the metal layer, labeled M4, constituting the floating gate of the ISFETs. (Or, alternatively, if as stated above the microwells are formed directly in the CMOS passivation layer, layer 75E3 can be omitted and this and other passages referring to such a layer can be understood to refer instead to the passivation layer and formation of the microwells in the passivation layer, instead.) Next, using a process such as sputtering or ALD, a thin layer of metal (e.g., about 0.25-0.50 μm of aluminum, titanium, tantalum or other suitable material) is deposited to form a layer 74E4 in contact with the M4 layer, running over the bottom of the well and up the sidewalls. The thin metal layer will also cover the tops of the (e.g., TEOS) material between the microwells, forming an electrical short circuit between the wells, which will have to be removed. Next, one may optionally fill the wells with a suitable material such as various organic fill materials that are readily available, to prevent the next step from leaving unwanted debris in the microwells. The next step is to employ CMP or another suitable technique to planarize the top of the structure down to a level that exposes the tops of the microwells and the material layer 75E4 on the top of the sidewalls. Having thus exposed the metal layer 75E4, that metal is removed from the tops of the microwell array (especially the tops of the sidewalls and TEOS between the sidewalls) in any satisfactory way). For example, the metal 75E4' at the top of the microwell structure on the exterior top of the sidewalls) may be etched away or removed using metal CMP to further planarize the tops of the wells. Having removed the short circuit between the wells, the filler material, if used, is then removed. The extended gate metallization is then covered by application of the thin dielectric layer discussed above, 75E5, such as a tantalum pentoxide ($Ta_2O_5$) ALD passivation, using ALD, for example. The dielectric/passivation must cover all edges of layer 75E5 to avoid electrically short-circuiting wells via the analyte fluid.

As an alternate fabrication process, the removal of material 75E4' could be done by patterning an inverse of the microwell pattern as a mask (i.e., opening the areas between the wells) and then using a standard metal etch.

The collection of all charge that reaches the microwell sidewalls, as well as its bottom, renders the pixels more sensitive to the reaction in the wells.

Another way to improve charge collection and sensitivity is to employ for the surfaces contacting the electrolyte a material that has a point of zero charge that matches the operating pH of the analyte.

Improved On-Chip Electronics

There are two key areas where the on-chip electronics can potentially be improved to increase the voltage signal gain and to reduce noise: the pixel circuit and the readout circuit.

Pixel Circuit

In a basic pixel circuit such as is illustrated above in FIG. 9, for example, the bulk potential of the ISFET 150 is taken to the highest circuit potential. Unfortunately, the threshold voltage $V_T$ of the device is affected by the potential difference between the source and bulk, VSB. This phenomenon is known as the body effect and is modeled as:

$$V_T = V_{T0} + \gamma(\sqrt{(2|\phi_F| + V_{SB})} - \sqrt{2|\phi_F|})$$

where $V_{T0}$ is the threshold voltage when the source voltage is equal to the bulk potential, 2 is the surface potential at threshold, and γ is the body effect coefficient. Consequently, the threshold voltage will vary due to the body effect; and the ISFET source gain, defined as the ratio VS/VG, will be less than the ideal value of unity. Although it cannot be measured directly, it is thought that the ISFET source gain is in the neighborhood of 0.9. In other words, up to 10% of the maximum voltage signal that could be measured may be lost due to the body effect.

If each ISFET is placed in its own n-well, and the source and bulk terminals are connected together, then the body effect can be eliminated and an ISFET source gain of unity can be realized. Furthermore, if each ISFET is isolated from the rest of the chip by a reverse-biased diode between the n-well and the substrate, then the device will be less susceptible to substrate noise. In other words, the total ISFET noise should be lower if the device is located in its own n-well.

Reducing Injection of Noise into Electrolyte

A second aspect to improving the SNR is that of reducing noise. A major component of such noise is noise that is coupled into the analyte fluid by the pixels in every column of the array, due to the circuit dynamics. Two noise injection mechanisms have been identified: the drain side column buffer injects noise through each pixel and each row selection pumps charge into the fluid. These mechanisms are focused on the ISFET drain and on the ISFET source.

The ISFET Drain Problem

When a row is selected in the array, the drain terminal voltage shared between all of the ISFETs in a column moves up or down (as a necessary requirement of the source-and-drain follower). This changes the gate-to-drain capacitances of all of the unselected ISFETs in the column. In turn, this change in capacitance couples from the gate of every unselected ISFET into the fluid, ultimately manifesting itself as noise in the fluid (i.e., an incorrect charge, one not due to the chemical reaction being monitored). That is, any change in the shared drain terminal voltage can be regarded as injecting noise into the fluid by each and every unselected ISFET in the column. Hence, if the shared drain terminal voltage of the unselected ISFETs can be kept constant when selecting a row in the array, this mechanism of coupling noise into the fluid can be reduced or even effectively eliminated.

The ISFET Source Problem

When a row is selected in the array, the source terminal voltage of all of the unselected ISFETs in the column also changes. In turn, that changes the gate-to-source capacitance of all of these ISFETs in the column. This change in capacitance couples from the gate of every unselected ISFET into the fluid, again ultimately manifesting itself as noise in the fluid. That is, any change in the source terminal voltage of an unselected ISFET in the column can be regarded as an injection of noise into the fluid. Hence, if the source terminal voltage of the unselected ISFETs can be kept when selecting a row in the array, this mechanism of coupling noise into the fluid via can be reduced or even effectively eliminated.

A column buffer may be used with some passive pixel designs to alleviate the ISFET drain problem but not the ISFET source problem. Thus, a column buffer most likely is preferable to the above-illustrated source-and-drain follower. With the illustrated three-transistor passive pixels employing a source-and-drain follower arrangement, there are essentially two sense nodes, the ISFET source and drain terminals. By connecting the pixel to a column buffer and grounding the drain terminal of the ISFET, there will be only one sense node: the ISFET source terminal. So the drain problem is eliminated.

Active Pixel Design

All of the above-discussed passive pixels circuits present noise and scalability challenges. That is, increasing the size of the array typically leads to increased bus capacitance and a non-linear increase in power needs. Increasing readout speed conies at the expense of increased readout noise, Replacing passive ISFET pixels with active pixels, each having an active amplifier transistor as an integral element, can reduce noise coupled into the fluid, along with reducing readout noise, low frequency noise and fixed pattern noise. This approach, moreover, appears to provide a low-noise ISFET pixel that successfully eliminates both the ISFET drain problem and the ISFET source problem, the latter because the sense node (i.e., ISFET source terminal) is decoupled from the column bus.

Note that, to make a measurement, the sense node has to be connected to a current source, with current flowing. However, switching the current source off and on introduces a disturbance at its own to the sense node, and thus couples noise into the fluid. To avoid this problem and further improve the signal-to-noise ratio, a single transistor current source can be introduced into each active ISFET pixel. Current then would be flowing through every pixel in every column of the array all of the time. Of course, there are obvious implications for power consumption and it would be advisable to operate this current source transistor in sub-threshold mode to minimize power consumption.

Figure 75F:
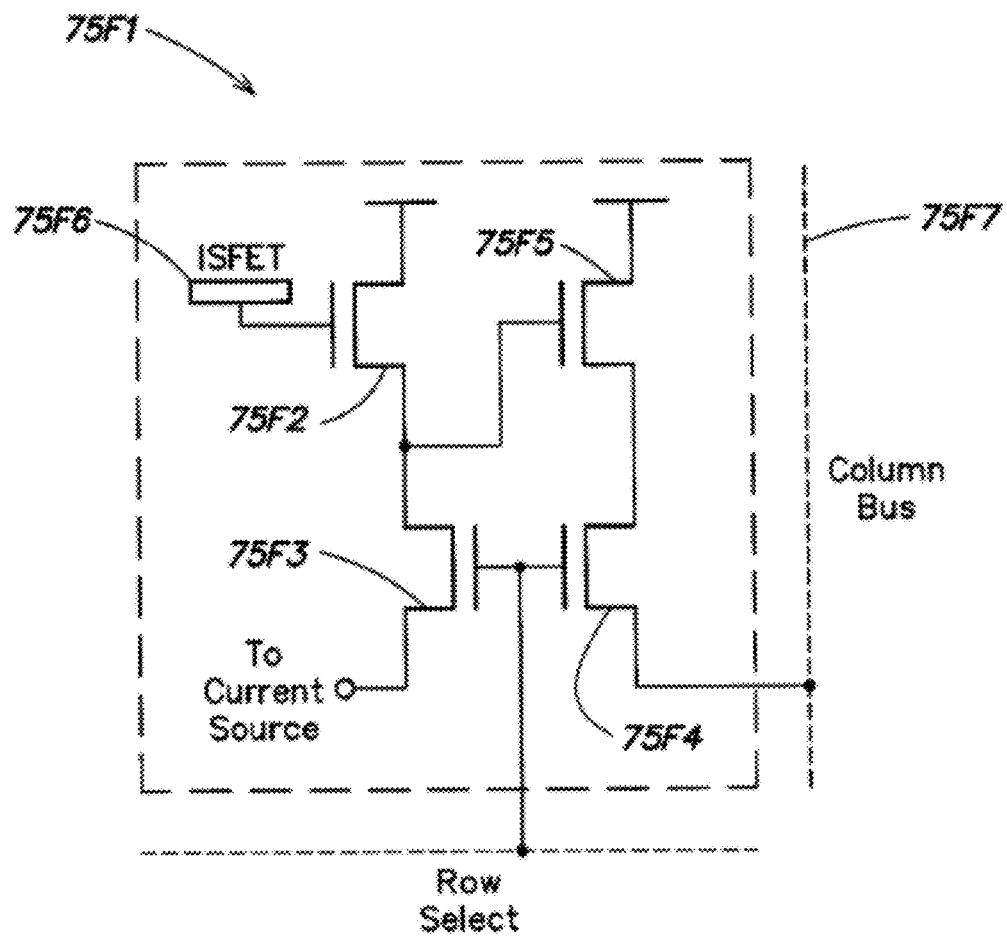
FIG. 75F is a partially-circuit, partially diagrammatic illustration of an example embodiment of a four-transistor pixel (sensor) employing an active circuit design.

Turning to FIG. 75F, there is shown a first example 75F1 of such an active pixel. The active pixel 75F1 has four transistors, 75F2-75F5, of which 75F2 is the ISFET, its floating gate being shown diagrammatically at 75F6. While the column bus 75F7 is decoupled from the sense node by source follower transistors 75F4 and 75F5 to reduce readout noise, switching the current source (not shown) on and off with transistor 75F3 introduces a disturbance at the sense node (the source of ISFET 75F2) which couples noise into the fluid.

Figure 75G:
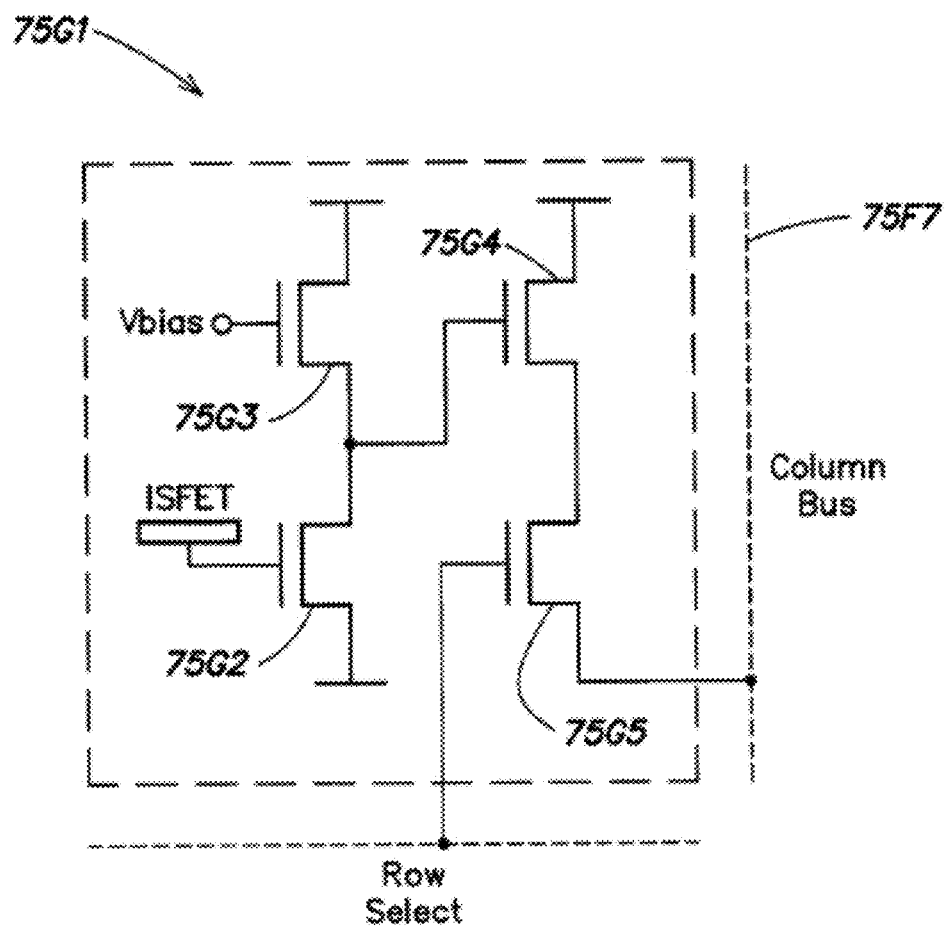
FIG. 75G is a diagram of a second example of a four-transistor active pixel, employing a single-MOSFET current source to avoid (or at least minimize) introducing a disturbance at the sense node.

A second example of a four-transistor active pixel 7501 is shown in FIG. 75G. This pixel uses a single-MOSFET current source 75G3 to avoid introducing a disturbance at the sense node. The current source transistor can be operated as a reverse-biased diode (cutoff) or in sub-threshold mode to minimize power consumption.

Figure 75H:
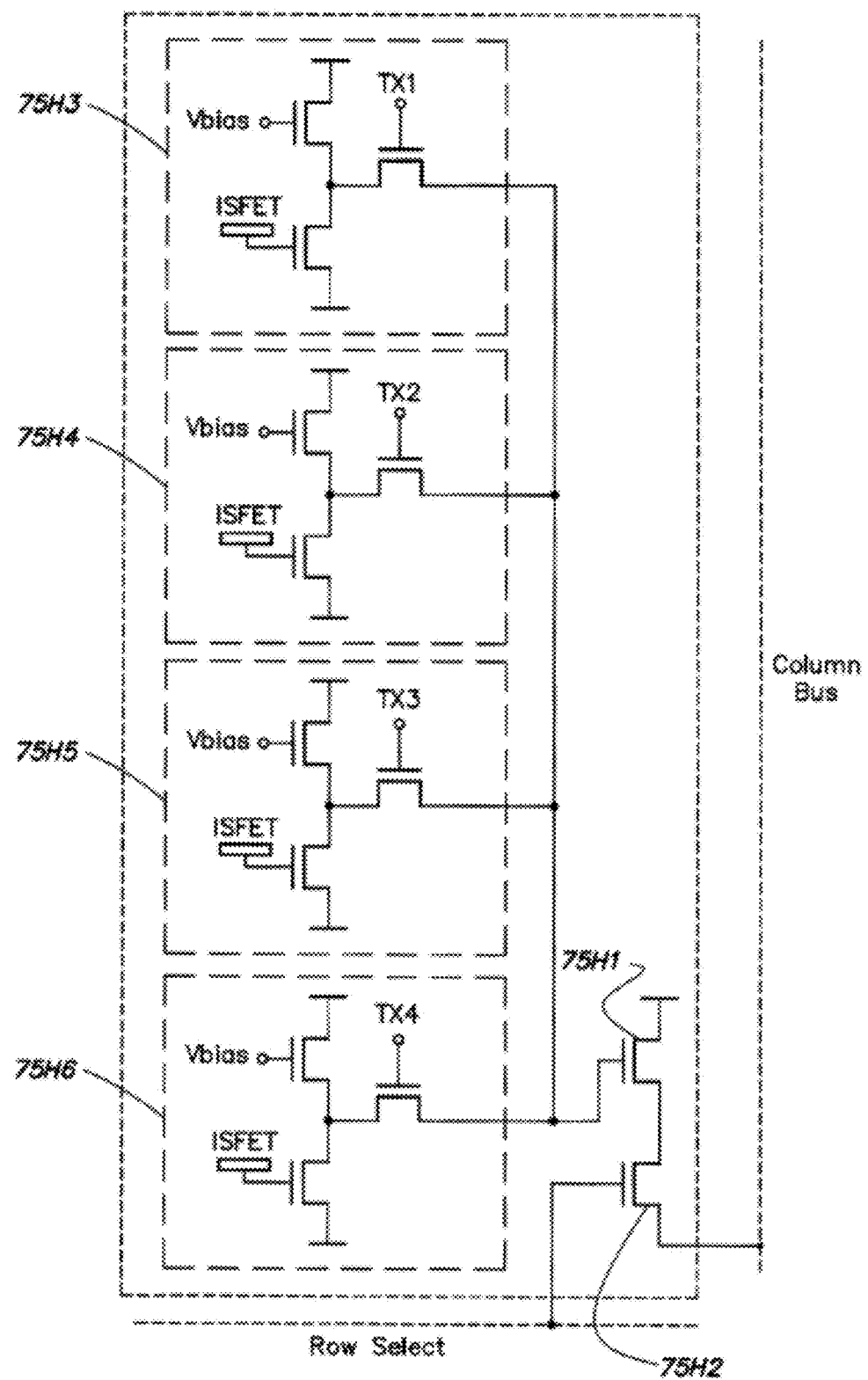
FIG. 75H is a diagram of a group of four pixels, each similar to that of FIG. 75G, sharing certain components to reduce chip area requirements.

By sharing some transistors between pixels, the average number of transistors per pixel, and hence pixel size, can be reduced. For example, see the arrangement of FIG. 75H, wherein transistors 75H1 and 75H2 are shared between four pixels 75H3-74H6, resulting in an average of 3.5 transistors per pixel.

Figure 75I:
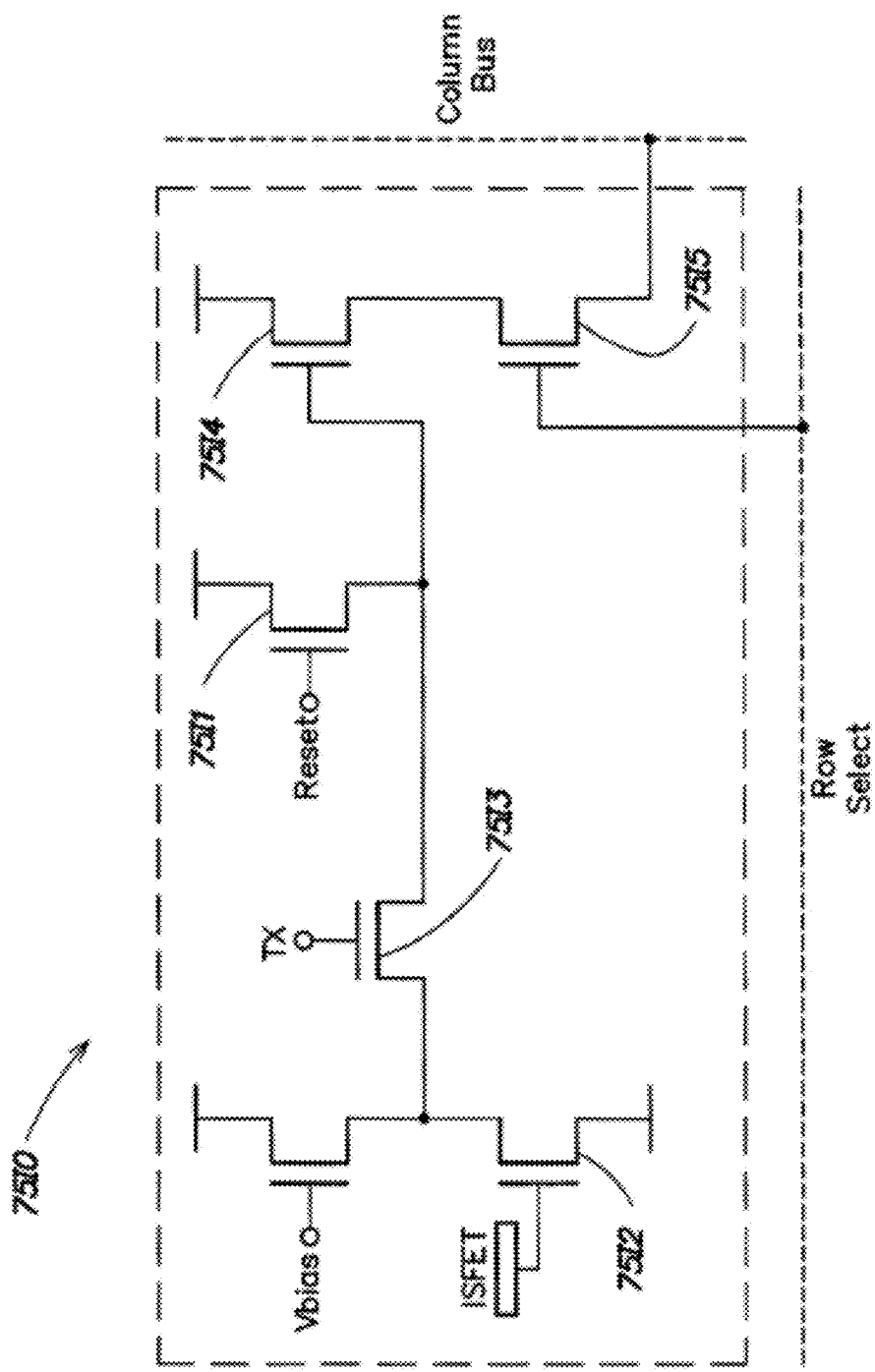
FIG. 75I is a diagram of an active pixel employing six transistors.

An example of a six-transistor active pixel 75I0 is shown in FIG. 75I. In operation, the reset input 75I1 is enabled, transistor 75I3 is turned on and the resultant voltage from ISFET 75I2 is measured by the source follower transistors 75I4-75I5. The difference between the reset level and the signal level from ISFET 75I2 is the output of the sensor.

By taking two samples per pixel (i.e., using correlated double sampling (CDS), the six transistor pixel 75I0 can suppress 1/f noise, and fixed pattern noise due to threshold voltage variations.

Figure 75J:
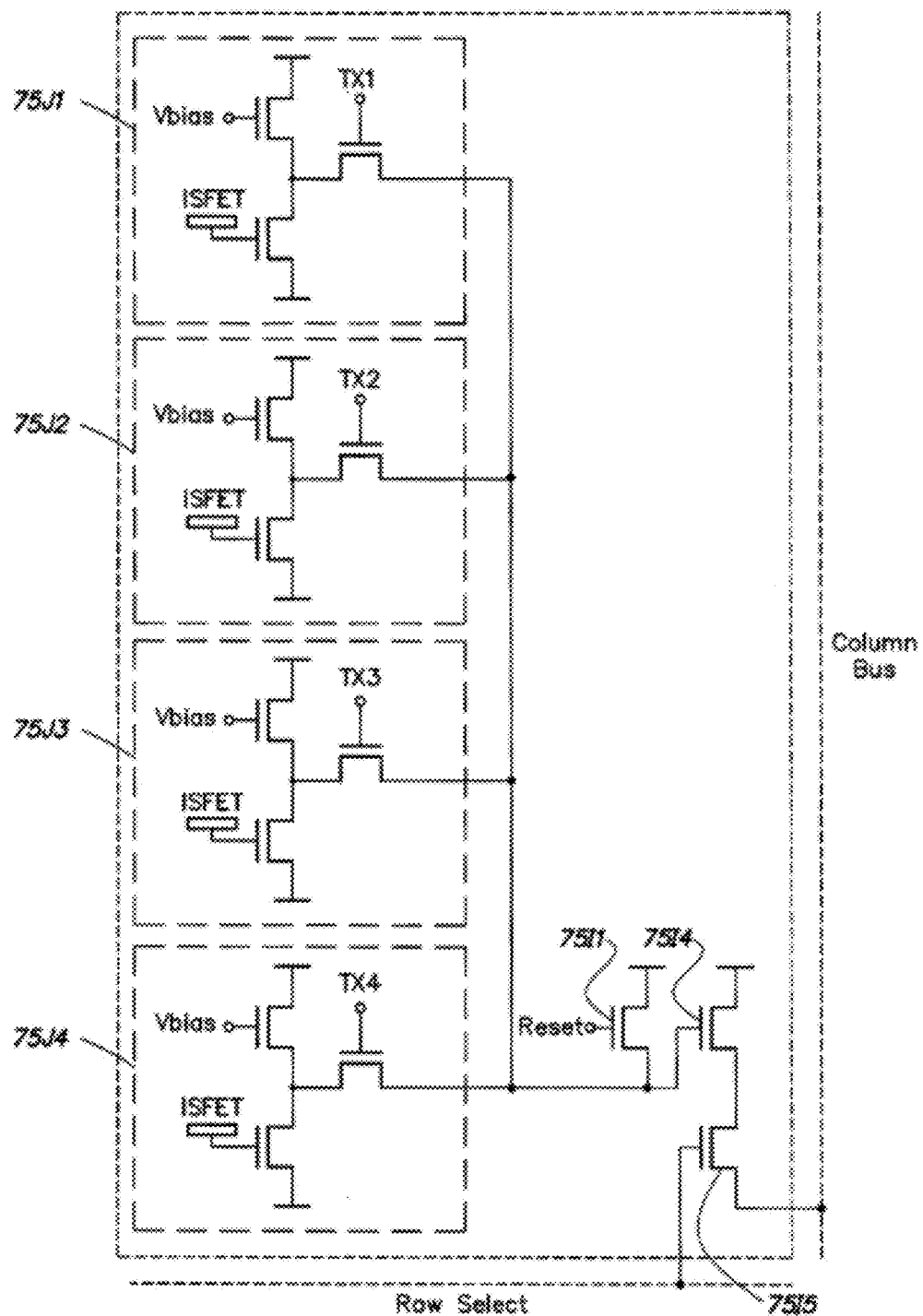
FIG. 75J is a diagram of a group of four pixels, each similar to that of FIG. 75I, sharing certain components to reduce chip area requirements.

As shown in FIG. 75J, the concept of sharing transistors among a group of pixels also can be applied to the six-transistor pixel example of FIG. 75I. By sharing three transistors 75I1, 75I4 and 75I5, four pixels 75J1-75J4 can have an average of 3.75 transistors each. The two sharing examples use four pixels but there is no reason transistors cannot be shared among a different number of pixels.

Moving from a passive pixel design to an active amplified pixel design thus improves the scalability of the design and reduces the readout noise. A single-MOSFET current source is required in each ISFET pixel to avoid coupling noise into the fluid. By increasing the number of transistors per pixel, correlated double sampling can be used at the pixel level to reduce flicker noise and fixed pattern noise. Further, the "shared pixel" concept can be used to reduce the effective number of transistors per pixel to achieve a smaller pixel size.

To reduce power consumption, the FETs (or selected ones of them) can be operated in the so-called "weak inversion" or "sub-threshold" mode.

Readout Circuit

The above-described readout circuit, which comprises both sample-and-hold and multiplexer blocks, also has a gain that is less than the ideal value of unity. Furthermore, the sample-and-hold block contributes a significant percentage of the overall chip noise, perhaps more than 25%. From switched-capacitor theory, the sample-and-hold "kT/C" noise is inversely proportional to capacitance. Hence, by choosing a larger capacitor, the sample-and-hold noise can be reduced. Another approach to reducing noise is to employ Correlated Double Sampling (CDS), where a second sample-and-hold and difference circuit is used to cancel out correlated noise. This approach is discussed at greater length, below.

Correlated Double Sampling

Correlated Double Sampling (CDS) is a known technique for measuring electrical values such as voltages or currents that allows for removal of an undesired offset. The output of the sensor is measured twice: once in a known condition and once in an unknown condition. The value measured from the known condition is then subtracted from the unknown condition to generate a value with a known relation to the physical quantity being measured. The challenge here is how to be efficient in implementing CDS and how to address both correlated noise and the minimization of noise injection into the analyte fluid.

Figure 77A:
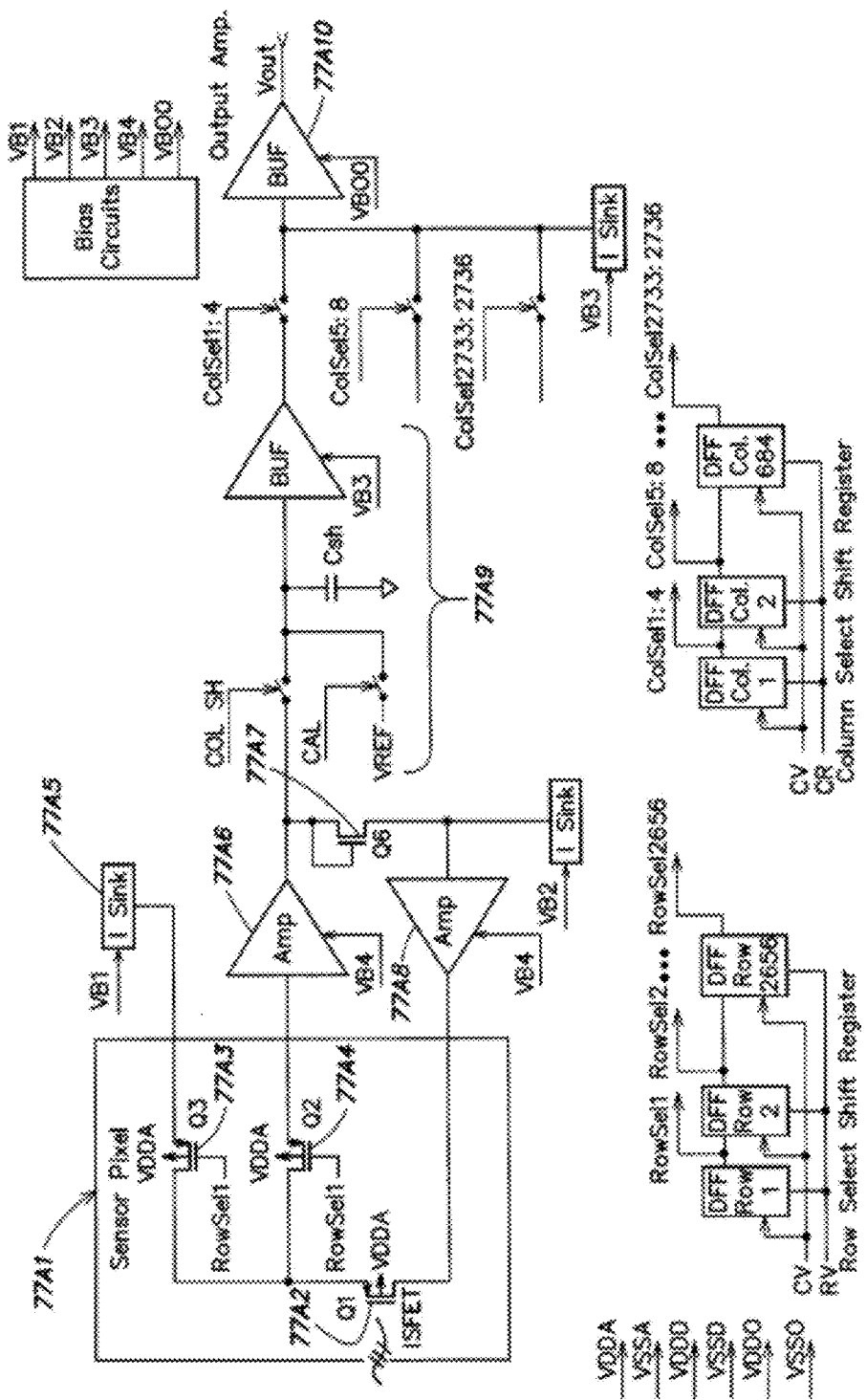
FIG. 77A is a high-level, partially block, partially circuit diagram showing a basic passive sensor pixel in which the voltage changes on the ISFET source and drain inject noise into the analyte, causing errors in the sensed values.

A starting point is the sensor pixel and its readout configuration as expressed in earlier parts of this application. Referring to FIG. 77A, the basic passive sensor pixel 77A1 is a three-transistor arrangement of an ISFET 77A2 and a pair of row select transistors, 77A3 and 77A4 connected to the ISFET source. Transistor 77A3 is connected in turn to a current source or sink 77A5. A readout is obtained via transistor 77A4 which is connected to the input of sense amplifier 77A6. A diode-connected transistor 77A7 in series with another amplifier, 77A8, connects in a feedback loop from the output of the sense amplifier to the drain of the ISFET. The sense amplifier output is captured by a sample-and-hold circuit 77A9, which feeds an output amplifier 77A10.

Figure 77B:
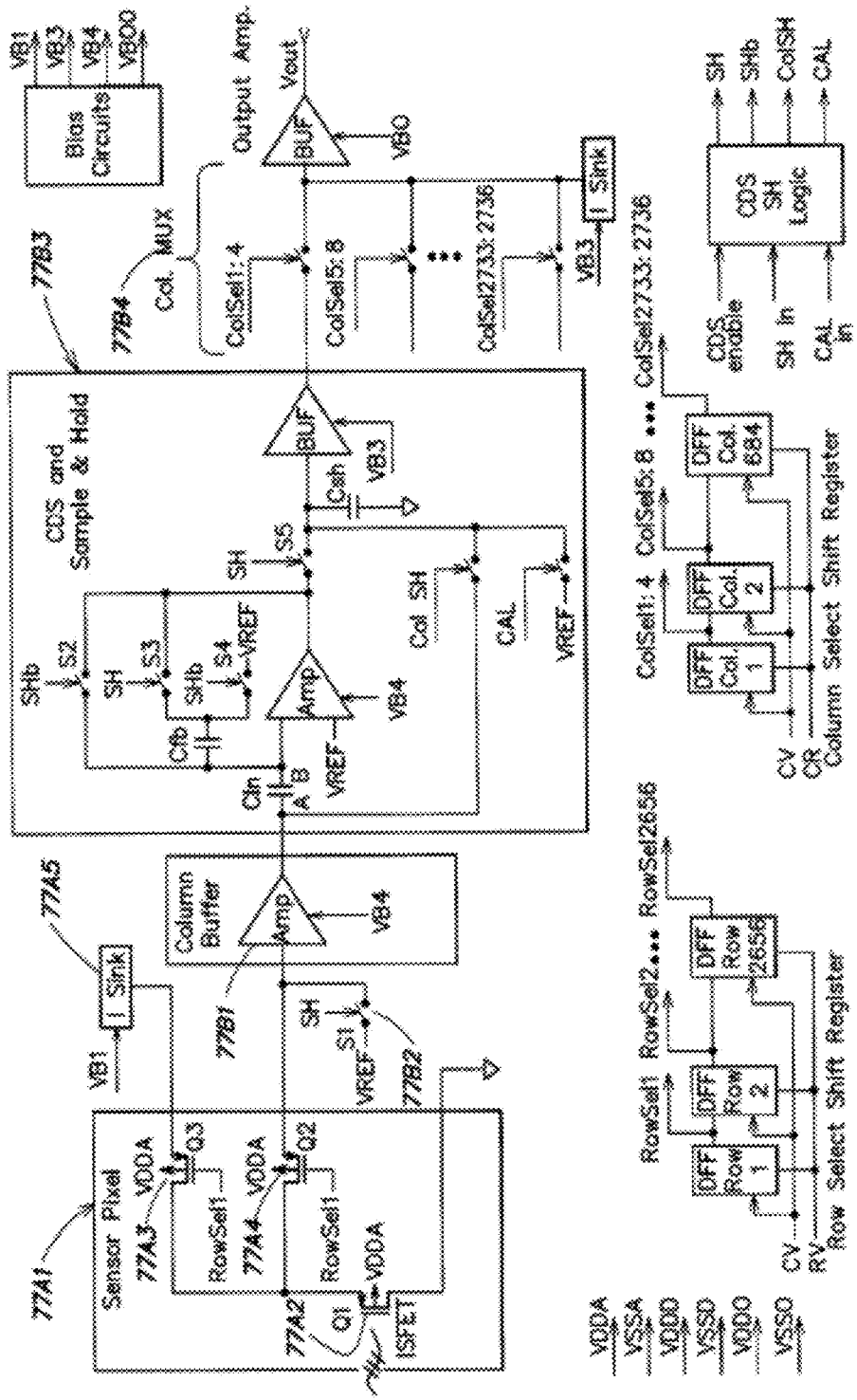
FIG. 77B is a high-level partially block, partially circuit diagram showing a basic passive sensor pixel in which the voltage changes on the ISFET drain are eliminated by tying it to ground, the pixel output is obtained via a column buffer, and CDS is employed on the output of the column buffer to reduce correlated noise.

As discussed above, the voltage changes on the ISFET source and drain inject noise into the analyte, causing errors in the sensed values. Two constructive modifications can reduce the noise level appreciably, as shown in FIG. 77B.

The first change is to alter the signals on the ISFET. The feedback loop to the drain of the ISFET is eliminated and the drain is connected to a stable voltage, such as ground. A column buffer 77B is connected to the emitter of transistor.

The second change is to include a circuit to perform CDS on the output of the column buffer. As mentioned above, CDS requires a first, reference value. This is obtained by connecting the input of column buffer 77B1 to a reference voltage via switch 77B2, during a first, or reference phase of a clock, indicated as the "SH" phase. A combined CDS and sample-and-hold circuit then double samples the output of the column buffer, obtaining a reference sample and a sensed value, performs a subtraction, and supplies a resulting noise-reduced output value, since the same correlated noise appears in the reference sample and in the sensor output.

The operation of the CDS and sample-and-hold circuit is straightforward. The circuit operates on a two-phase clock, the first phase being the SH phase and the second phase being the SHb phase. Typically, the phases will be symmetrical and thus inverted values of each other. The reference sample is obtained in the SH phase and places a charge (and thus a voltage) on capacitor Cin, which is subtracted from the output of the column buffer when the clock phase changes.

Figure 77C:
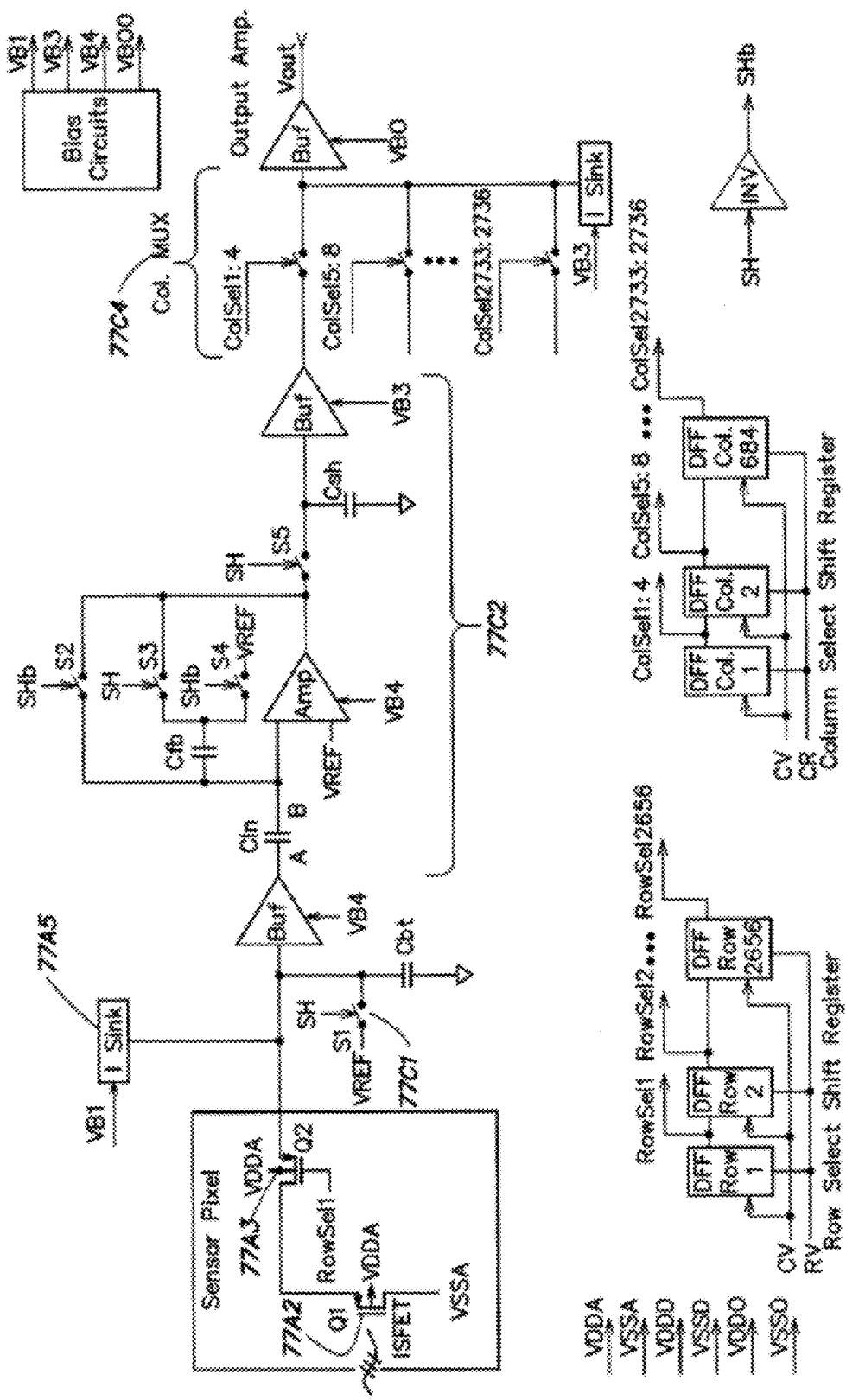
FIG. 77C is a high-level partially block, partially circuit diagram showing a two-transistor passive sensor pixel in which the voltage changes on the ISFET drain and source are substantially eliminated, the pixel output is obtained via a buffer, and CDS is employed on the output of the column buffer to reduce correlated noise.

An alternative embodiment, still with a passive sensor pixel, is shown in FIG. 77C. The sensor pixel in this embodiment is a two-transistor circuit comprising ISFET whose drain is connected to a fixed supply voltage, VSSA. There is no transistor comparable to 77A4, and the pixel output is taken from the emitter of transistor 77A3, instead. The CDS and sample-and-hold circuit has been simplified slightly, by the elimination of a feedback loop, but it serves the same function, in conjunction with the charge (voltage) stored on capacitor Cb1, of subtracting a reference value on capacitor Cin from the signal supplied by the sensor pixel.

Digital Pixels and Readouts

As signal-to-noise ratios often can be improved by moving from the analog domain into the digital domain, we have also begun to explore the possibilities for creating digital ISFRT pixels and digital pixel readouts.

Figure 75K:
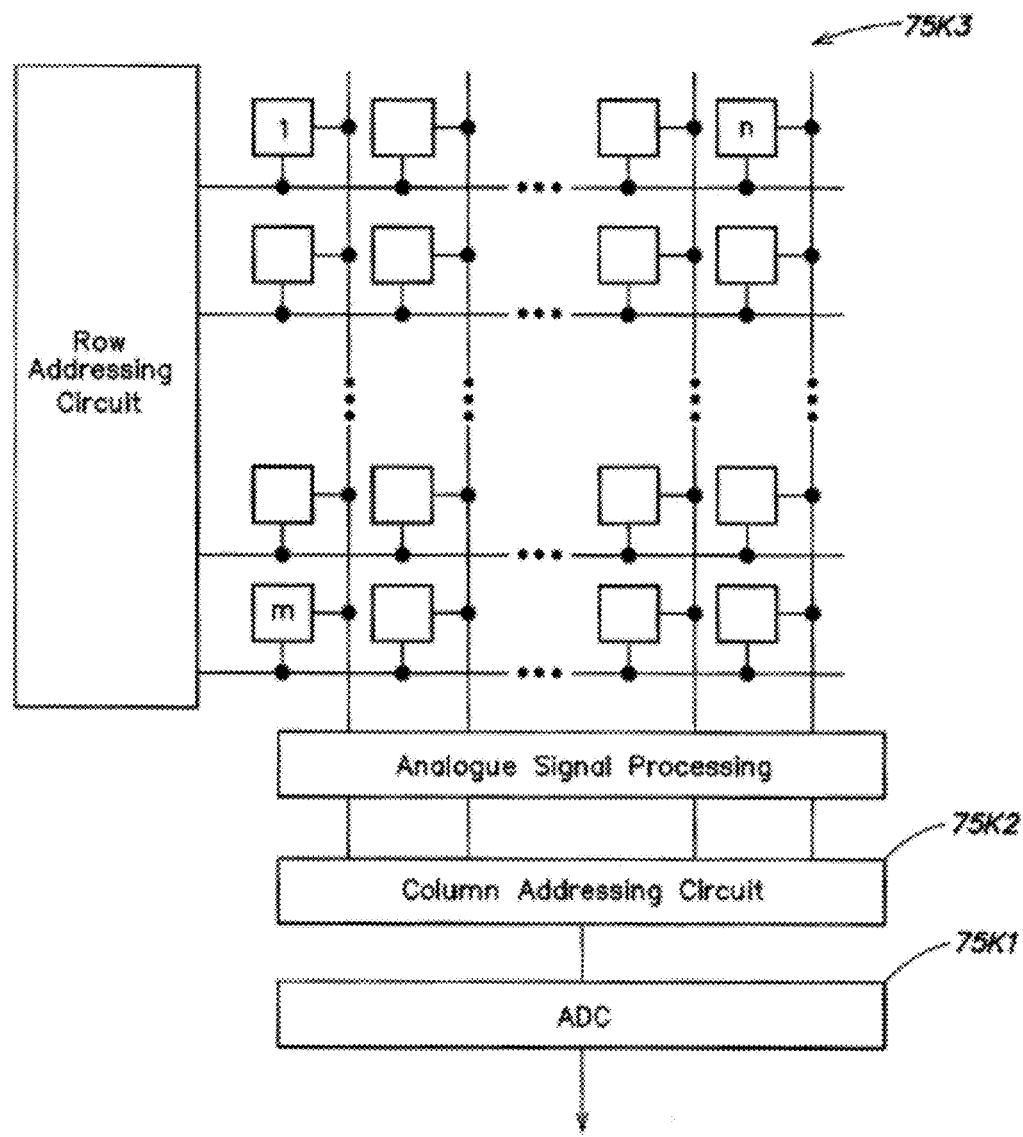
FIG. 75K is a diagrammatic illustration of an example of an array of ISFET sensors (pixels) as taught herein, sharing a common analog-to-digital converter (ADC) for producing digital pixel values.

Consider first the architecture shown in FIG. 75K. There, a single analog-to-digital converter (ADC) 75K1 converts the analog output of a column addressing circuit 75K2, supplying output from pixel array 75K3, to digital form. Low fixed pattern noise is achievable but the operation of this architecture is low, the single ADC being a bottleneck. The frame rate is limited by the number of pixels and the time required for the ADC to complete one conversion. Thus, this architecture is not suitable for high resolutions.

Figure 75L:
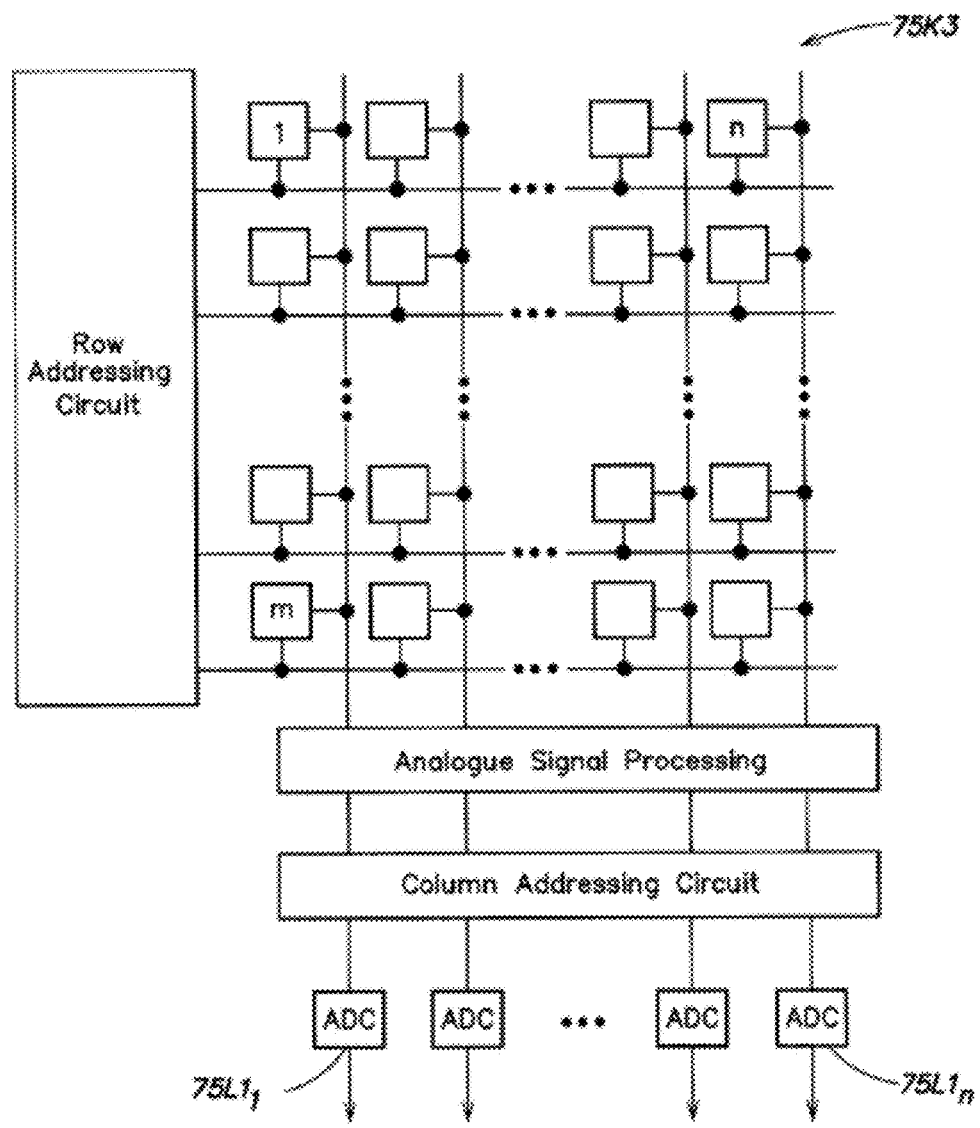
FIG. 75L is a diagrammatic illustration of another example of an ISFET array in which one ADC is provided per column (or group of columns) to speed up digital readout.

To achieve higher throughput (i.e., frame rate), one ADC 75L11-75L1n may be used for each column of the array 75K3, as illustrated in FIG. 75L. Indeed, the frame rate can be nearly n times faster. Instead of the ADC being a speed-limiting factor, frame rate can be limited by the output transfer capabilities of the array. The down-side, of course, is that power consumption is increased.

Figure 75M:
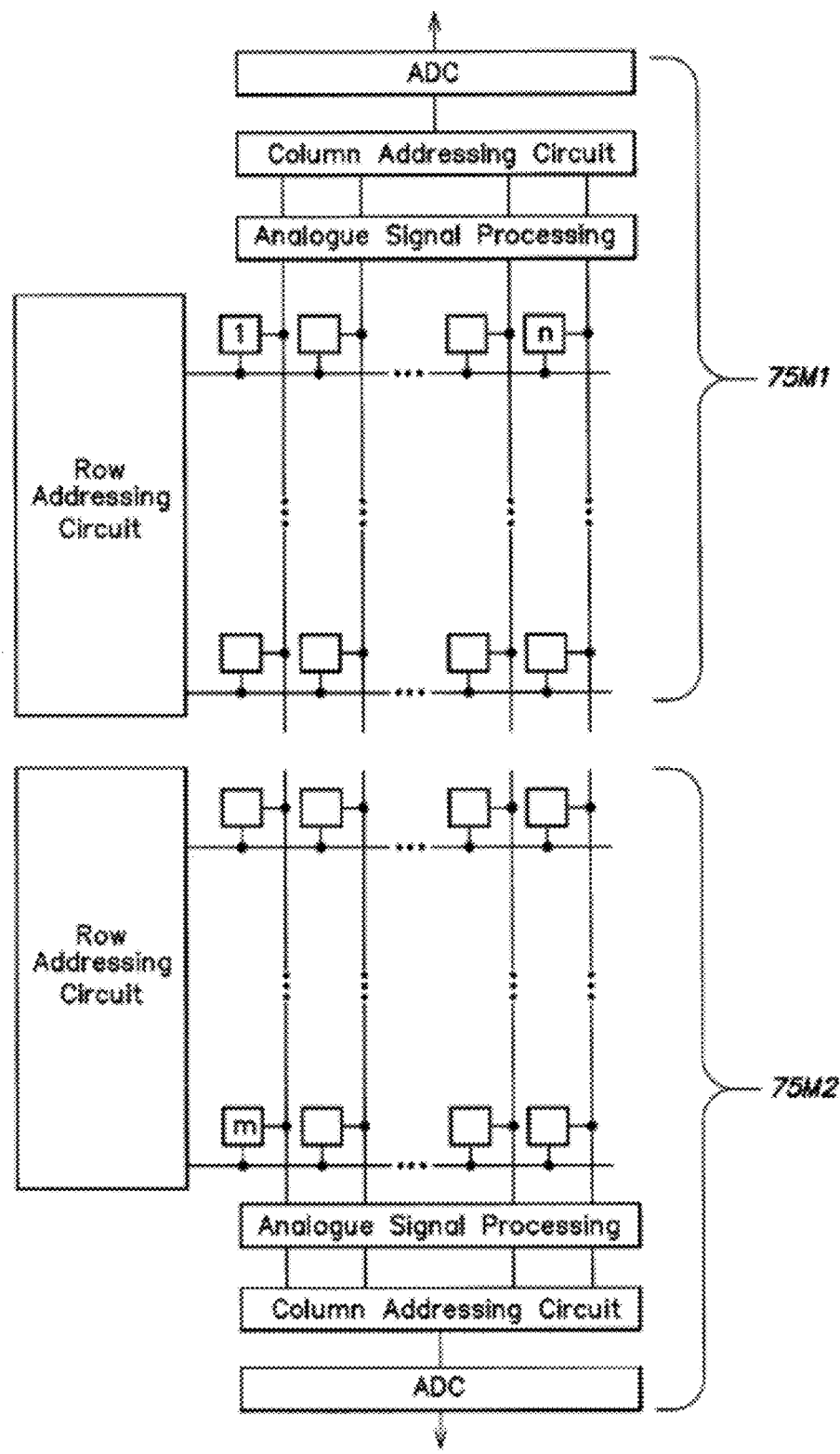
FIGS. 75M and 75N are illustrations showing how the arrays of FIGS. 75K and 75L may be segmented to form sub-arrays, for example to speed operation or to treat differently different portions of the overall array.
Figure 75N:
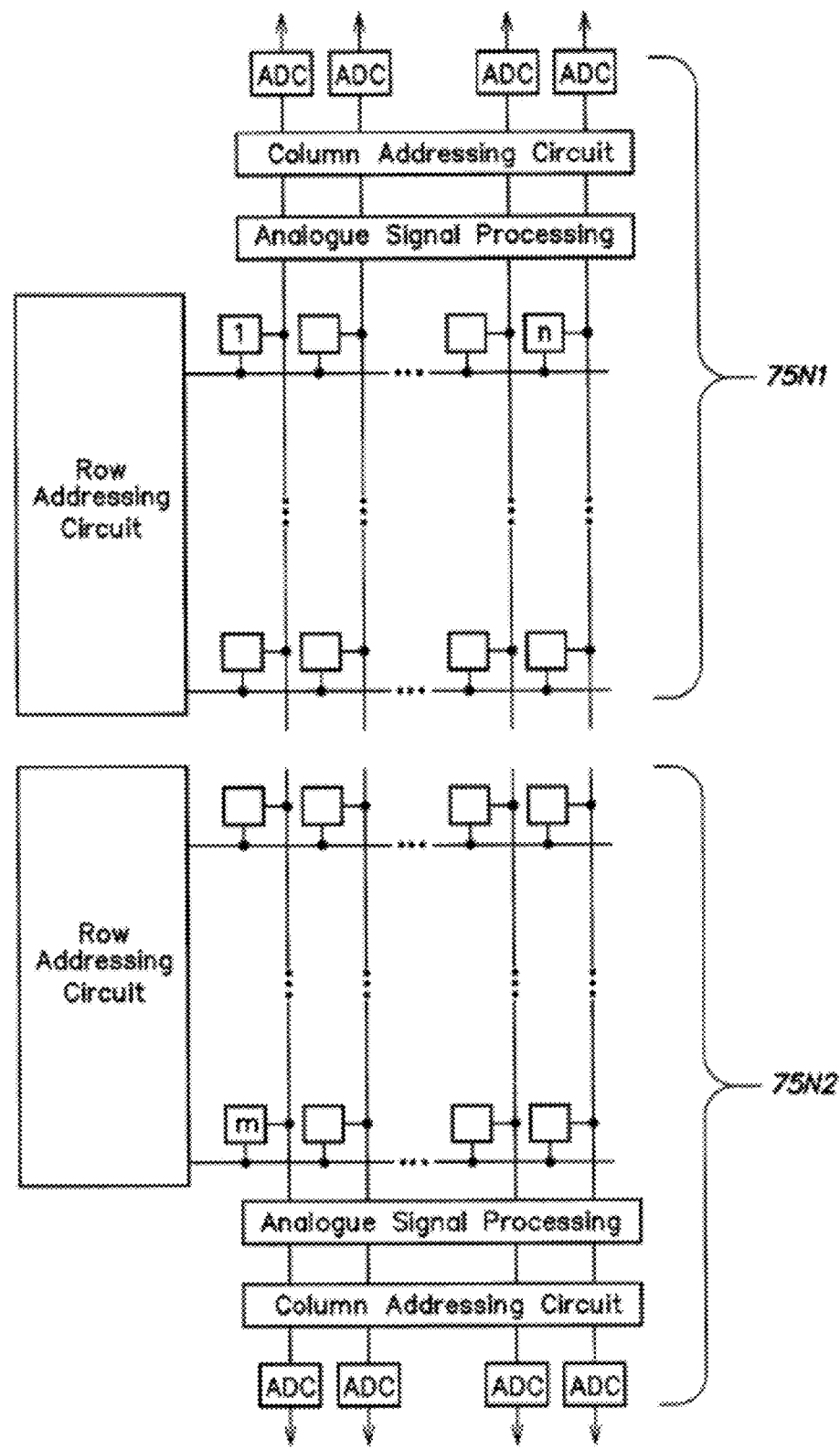
Figure 750:
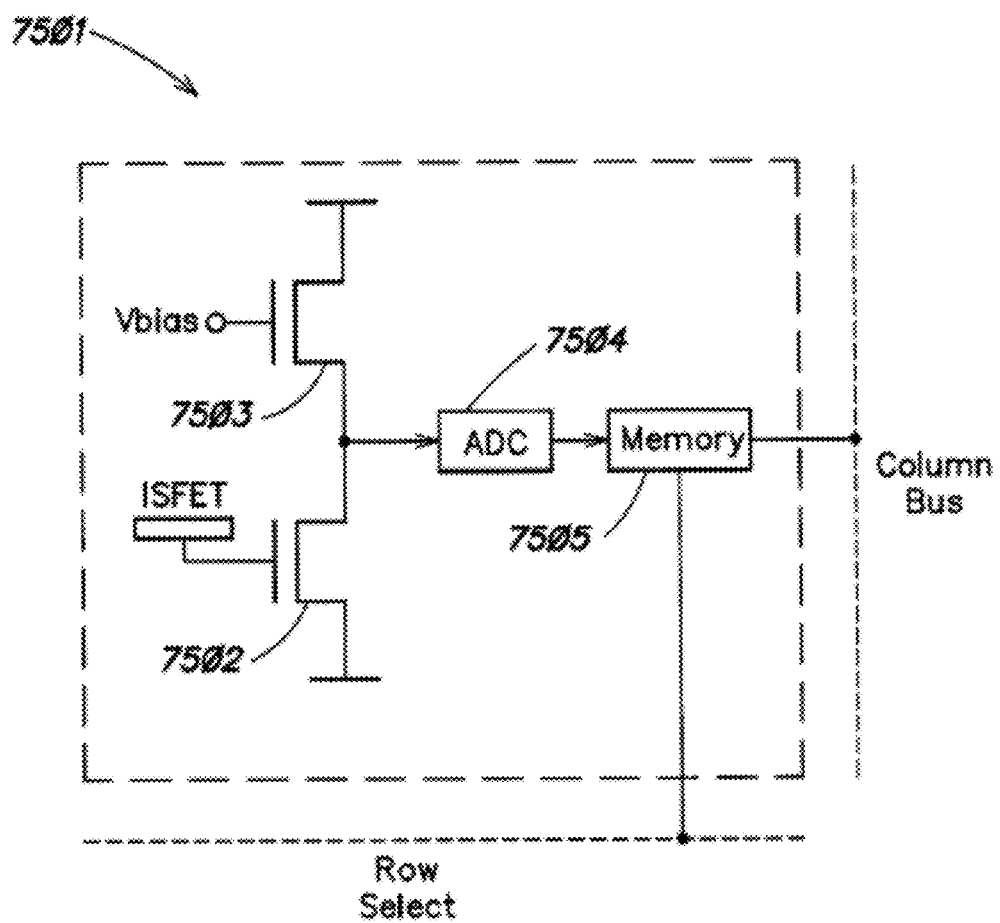

In either of these two cases, parallelism and frame rate can be increased by dividing the array into two groups (75M1, 75M2 in FIGS. 75M and 75N1, 75N2 in FIG. 75N), and reading out each group separately. Again, however, there is a power consumption penalty to be paid. Not illustrated in FIGS. 75M and 75N is a multiplexer which may be used, if desired to provide a single output stream (e.g., interleaving outputs of the first, or top, group with outputs of the second, or bottom, group).

To go more directly into the digital domain, one has to move from converting an analog array output into generating a digital output directly at each pixel. In general, this requires providing at each pixel some form of analog-to-digital conversion, and memory (at least 1-bit, for each). Converting the analog sensor signal to digital on an "in-pixel" basis creates an opportunity to achieve the largest possible signal-to-noise ration (SNR). It also is inherently scalable, allowing high speed, massively parallel readout of digital sensor data, with the frame rate limitations being dominated by array input/output (I/O) transfer speed, owing to the fact that all pixels are converting sensed values to digital form in parallel.

A basic digital pixel architecture 75O1 is as shown in FIG. 75O. It includes an ISFET 75O2, a current source 75O3, an ADC 75O4 and memory 75O5, whose operation is as discussed above. As with the above-discussed active ISFET pixels, the circuitry around the sense node (not shown in detail hem, for clarity) preferably is chosen to avoid coupling noise into the fluid.

Figure 75P:
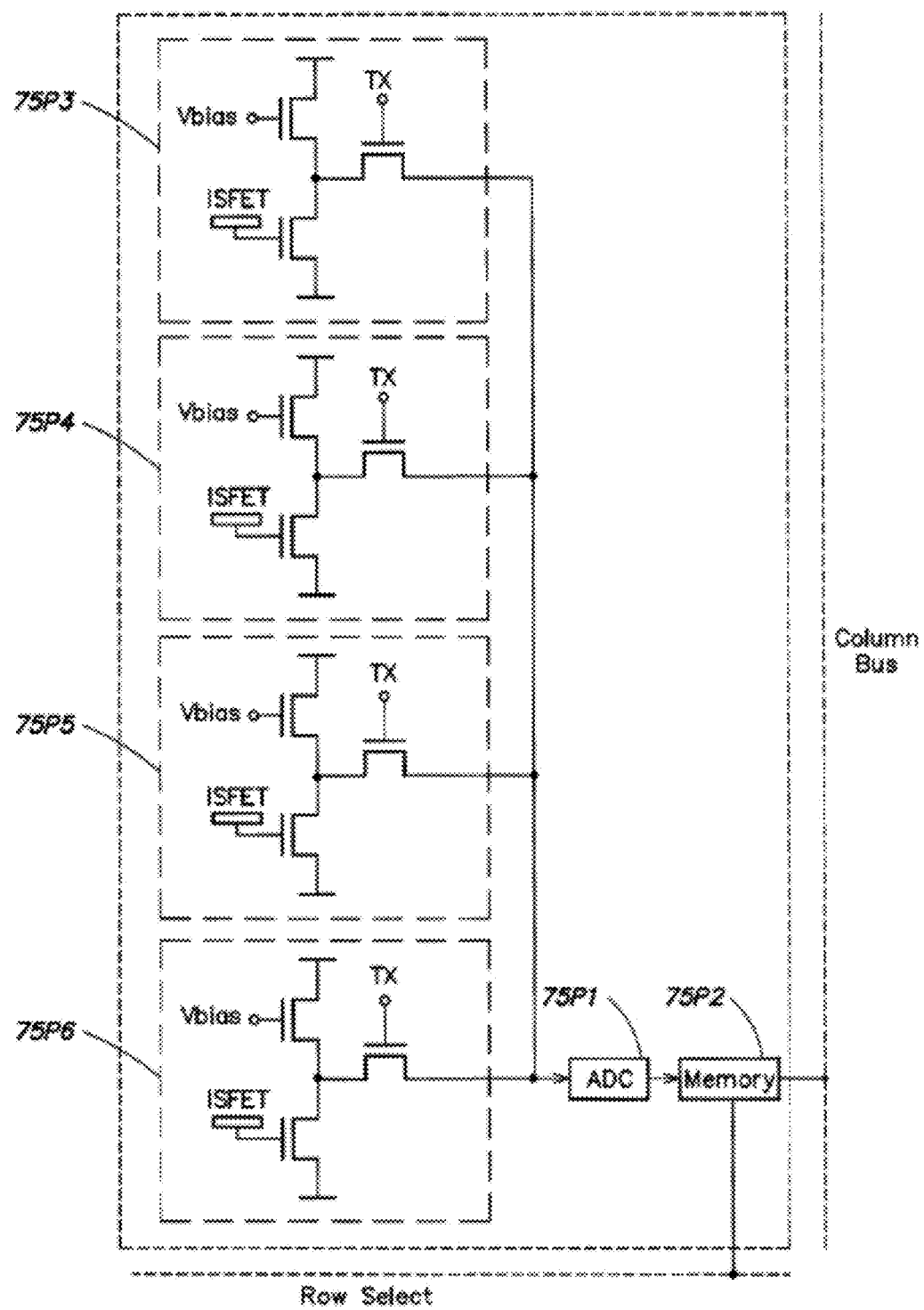
FIG. 75P is a diagram of a group of four pixels, each similar to that of FIG. 75P, sharing an ADC and memory to provide per-pixel digital output.

The concept of sharing circuitry between multiple pixels, to reduce the average chip area per pixel and to reduce the average and total power consumption, can be extended to digital pixel architectures, as well. For example, FIG. 75P depicts an ADC 75P1 and memory 75P2 being shared by four ISFET cells 75P3-75P6 or pixels (here using that term even though the ADC and memory are shared and not part of the cells within the dotted lines).

Figure 75Q:
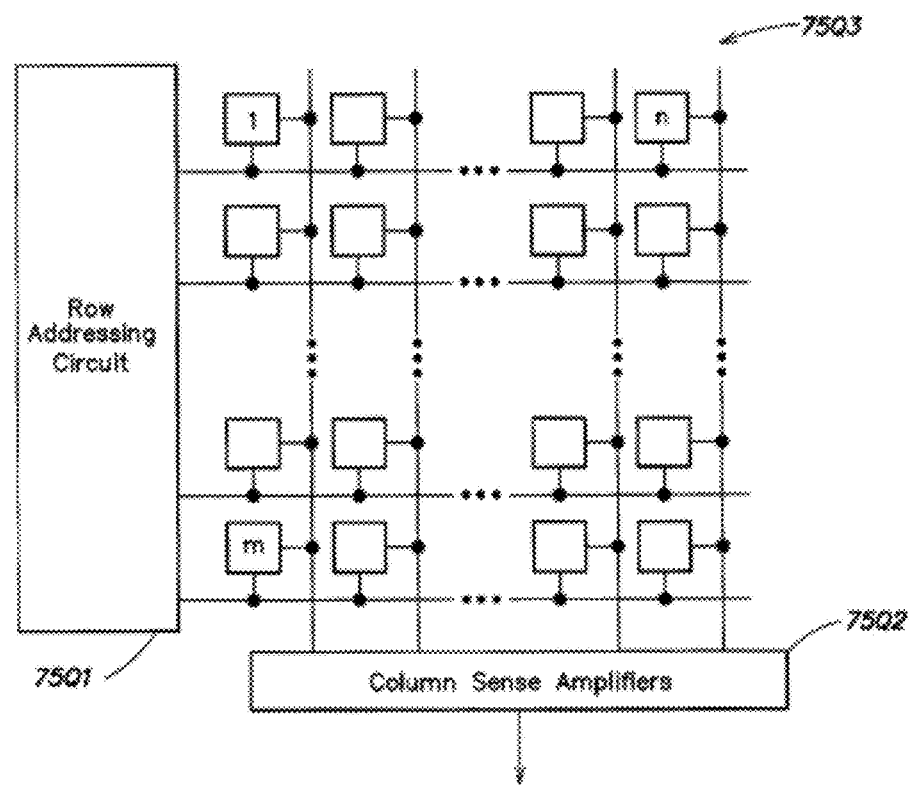
FIG. 75Q is a diagram of row addressing circuitry and column sense amplifiers providing readout functionality from a pixel array in which the pixels provide digital outputs.

With such digital pixels formed into an array, from a read-out perspective the array resembles a memory array. Thus, as shown in FIG. 75Q, when the individual pixels provide digital output values, row addressing circuitry 75Q1 and column sense amplifiers 75Q2 can provide the readout functionality from pixel array 75Q3, as they would in a memory array.

The approaches of FIGS. 75M and 75N—i.e., subdividing or segmenting the array and processing separately the subdivisions/segments—may be implemented with any suitable pixel architecture, such as those of FIGS. 77B and 77C, with digital or analog pixel output. For example, the output of the column mux 77B4 or 77C4 of each segment can be an input to a further multiplexer, not shown for selecting between segments to supply a common output.

Thus, a row and column addressing scheme allows selection of a variably sized sub-region within the array. This facilitates a trade-off of the size of the array being interrogated with the readout speed (i.e. frames per second). A faster sample rate can have a number of potential advantages:

1.) A faster sample rate when combined with a digital filter can produce better signal-to-noise measurements for the pixels within the sub-region. For example, selecting a sub-region of one-fourth the array size would allow sample rates approximately four times higher for the pixels within the sub-region. A simple filter that averages four consecutive samples together would reduce the final sample rate back down to the nominal whole-array frame rate, but each measurement would only have approximately half the noise content.

2.) The faster sample rate can be used to examine higher-frequency signals than would otherwise be possible at the nominal whole-array frame rate of the device. For example, selecting a sub-region of one-fourth the array size would allow sample rates approximately four times higher and the bandwidth limit for measured signals would be increased by a factor of four.

3.) Both cases can be combined to provide both high-frequency response and higher SNR. For example, selecting a sub-region one-sixteenth the whole-array size would allow for both a two-fold increase in SNR and a four-fold increase in bandwidth.

In some applications, sensitivity and/or signal bandwidth may be more important than the number of active pixels. The availability of variable frame size (which might also be called flexible bandwidth allocation, or perhaps dynamic bandwidth allocation) is valuable in these situations.

With an appropriately segmented array, it would also be possible to perform a 'rolling' sequencing reaction across a large array. One would *slowly* flow dNTP across a large chip. As the wave of dNTP flows across the chip slowly, the sequencing reaction would only be occurring in a small region along the 'front' of the dNTP flow. In theory, it would be possible to synchronize sub-region oversampling with the dNTP front to get very accurate measurements of the entire array

Protection Diodes

To reduce possible gate oxide degradation during plasma processing (e.g., plasma etch, sputtering, PECVD, etc.), a well diode and/or a substrate diode may be employed, as illustrated in FIGS. 75R-75T.

In FIG. 75R, diode 75R1 between the gate 75R2 of ISFET 75R3 and the well 75R4 limits the voltage that can build up on the gate relative to the well. The "overhead" added in the form of real estate occupied is quite small. A typical ISFET, for example, might be 1.2×0.5 µm, and the diode might have a perimeter of about 2.8 µm and occupy only 0.49 $\mu m^2$.

In FIG. 75S, diode 75S1 between the gate 75R1 of ISFET 75R3 and the substrate 75S2 limits the voltage that can build up on the gate relative to the substrate. The "overhead" added in the form of real estate occupied is quite small. A typical ISFET, for example, night be 1.2×0.5 µm, and the diode might have a perimeter of about 2.8 µm and occupy only 0.49 $pm^2$.

As shown in FIG. 75T, both diodes can be used together and their total area might typically be only about 0.98 $pm^2$.

Reference Electrode Alternatives: the Fluid-Fluid Interface

Performance of the instrument, over all, also can be enhanced with further attention to the reference electrode. With the above-described "simple" electrodes involving a metal tube, wire, etc. inserted into the flow cell, it has been observed that the reference potential introduced into the flow cell by such electrodes is not stable. It is sensitive to variations in fluid composition and pH. Accordingly, attention also has been given to devising an improved electrode arrangement, which can introduce a more stable reference potential.

With the simple electrode designs discussed above, the fluid-electrode interface influences the way the reference potential is transmitted into the fluid. That is, the interface potential between the fluid and the electrode fluctuates with the composition of the fluid (which may be somewhat turbulent and inhomogeneous), introducing a voltage offset to the potential of the bulk fluid which varies with time and possibly location, as well.

Considerably greater reference potential stability may be achieved by moving the location of the reference electrode so that it is substantially isolated from changes in fluid composition. This may be accomplished by introducing a conductive solution of a consistent composition over at least part of the surface of the electrode (hereafter the "electrode solution"), arranging the electrode to avoid it coming into direct contact with the fluid in the flow cell and, instead, arranging the electrode solution (not the electrode) to come into electrical contact with the fluid in the flow cell. The result is a transfer of the reference potential to the flow cell solution (be it a reagent or wash or other solution) that is considerably more stable than is obtained by direct insertion of an electrode into the flow cell solution. We refer to this arrangement as a liquid-liquid or fluid-fluid reference electrode interface.

The fluid-fluid interface may be created downstream from the flow cell, upstream from the flow cell, or in the flow cell. Examples of such alternative embodiments are shown in FIGS. 76A-76D.

Figure 76A:
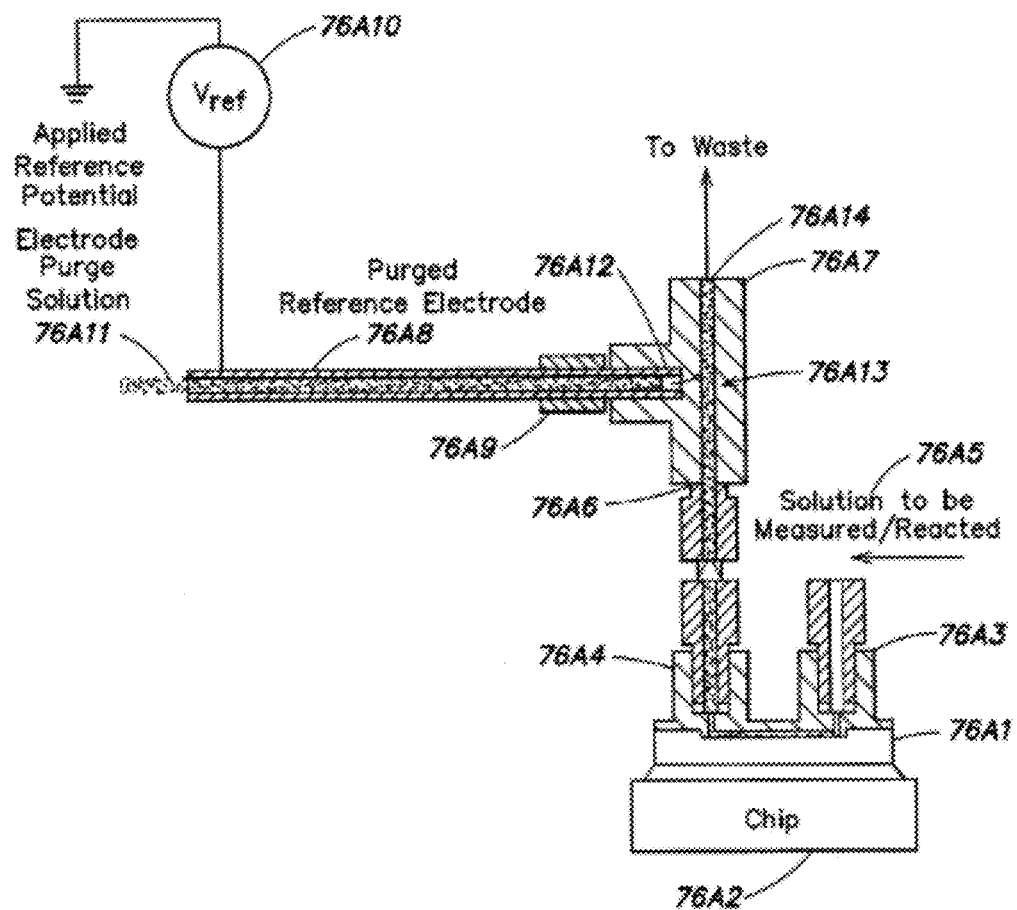
FIG. 76A is a diagrammatic illustration of a cross-section of a first example of a fluid-fluid reference electrode interface in which the reference electrode is introduced downstream in the reagent path from the flow cell.

Turning first to FIG. 76A, there is shown a diagrammatic illustration of an embodiment in which the fluid-fluid interface is created downstream from the flow cell. In this example, the flow cell apparatus 76A1 is, as above, mounted on a chip 76A2 which contains the sensor array (not shown). The flow cell apparatus includes an inlet port 76A3 and an outlet port 76A4. That is, the reagent fluids are introduced into port 76A3 via conduit 76A4 and they exit via port 76A4.

A first port 76A6 of a fluid "Tee" connector 76A7 is coupled onto flow cell outlet port 76A4 via conventional couplings to receive the fluid exiting from the flow cell. A reference electrode such as a hollow electrically conductive tube 76A8 is fed into another port of the Tee connector via a fluid-tight coupling 79A9. The reference electrode is connected to a reference potential source 76A10 and a suitable electrode solution 76A11 is flowed into the center bore of the electrode tube.

Two modes of operation are possible. According to a first mode, the electrode solution may be flowed at a rate that is high enough to avoid backflow or diffusion from the fluid flowing out of the flow cell. According to a second mode, once the electrode solution has filled the electrode and come into contact with the outlet flow from the flow cell, a valve (not shown) may be closed to block further flow of the electrode solution into the electrode and, as the electrode solution is an incompressible liquid, there will be substantially no flow into or out of the electrode, yet the fluid-fluid interface will remain intact. This presumes, of course an absence of bubbles and other compressible components. For a fluid-fluid interface to take the place of a metal-fluid interface, the tip 76A12 of the electrode 76A8 is positioned to stop within the Tee connector short of the fluid flow out of the flow cell, so that it is the "electrode solution," not the electrode itself, that meets the outlet flow from the flow cell, indicated at 76A13, and carries the reference potential from the electrode to the reagent solution exiting the flow cell. The two fluid streams interact in the Tee connector at 76A13 and if the electrode solution is flowing, it flows out the third port 76A14 of the Tee connector with the reagent flow, as a waste fluid flow, for disposal.

This approach eliminates interfacial potential changes at the electrode surface.

Using a fluid-fluid interface to convey a stable reference potential from a reference electrode to a flow cell, various alternative embodiments are possible.

Figure 76B:
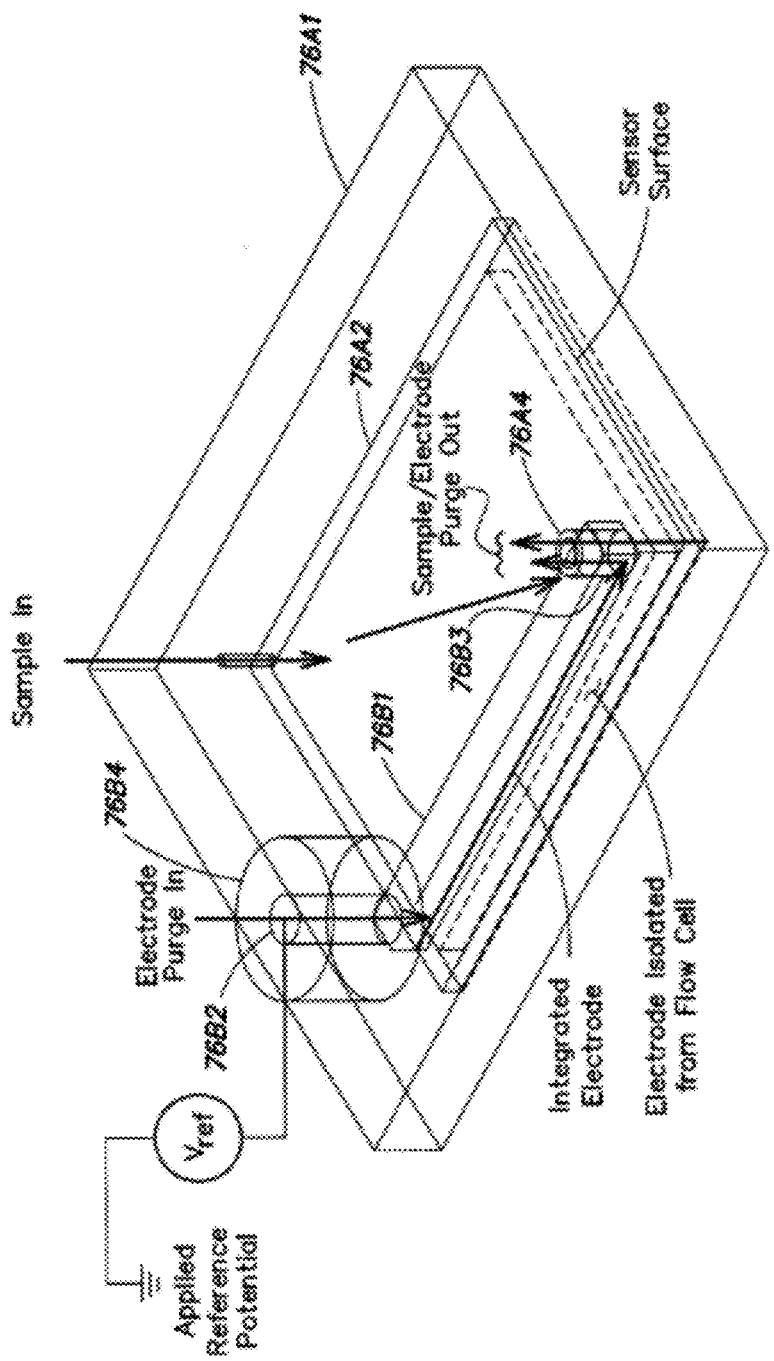
FIGS. 76B and 76C are diagrammatic illustrations of two alternative examples of ways to construct apparatus to achieve the fluid-fluid interface of FIG. 76A.

In one alternative, illustrated in FIG. 76B, the referencing junction (i.e., the fluid-fluid interface) can be moved into the structure of the members forming the flow cell or even into the sensor chip itself, but with the electrode solution never entering the flow cell. For example, a manifold 76B 1 may be formed in the flow cell assembly outside the flow chamber itself, having an inlet 76B2 for receiving electrode solution and an outlet 76B3 in fluid communication with the flow cell's outlet conduit 76A4. The electrode may be a separate element disposed in the manifold or it may be a metallization applied to an interior surface of the manifold.

Alternatively, the manifold can be formed in the substrate of the chip itself by fabricating in the substrate a hollow region which can serve as a conduit allowing fluid passage from an inlet end to an outlet end. An electrode may be inserted therein via a separate inlet port 76112 or part of the (interior or exterior, as appropriate) surface of the conduit may be metalized during fabrication, to serve as the electrode. The flow path for reagent fluid to exit the flow chamber may include a conduit portion and the electrode conduit/manifold may deliver electrode solution to the reagent fluid outlet conduit, wherein the two fluids come into contact to provide the fluid-fluid interface that applies the reference electrode voltage to the flow cell.

In each instance, the electrode may be hollow and have the electrode solution delivered through its interior, or the electrode solution may be delivered over the exterior of the electrode. For example, as shown in FIG. 76B, the electrode may be hollow, such as being the interior surface of the manifold 76131, and it may have an exterior that is insulated from the flow cell using any suitable structure and material (not shown, to avoid obfuscation of the basic idea).

The electrode assembly thus may be built into the sensor chip itself or into the flow cell or its housing, coupled with a fluid inlet through which electrode solution may be introduced. The flow path for reagent fluid to exit the flow chamber may include a conduit portion 76A4 into which the electrode solution is presented, and wherein the two fluid flows come into contact to provide the fluid-fluid interface. The electrode solution may flow or be static.

Figure 76C:
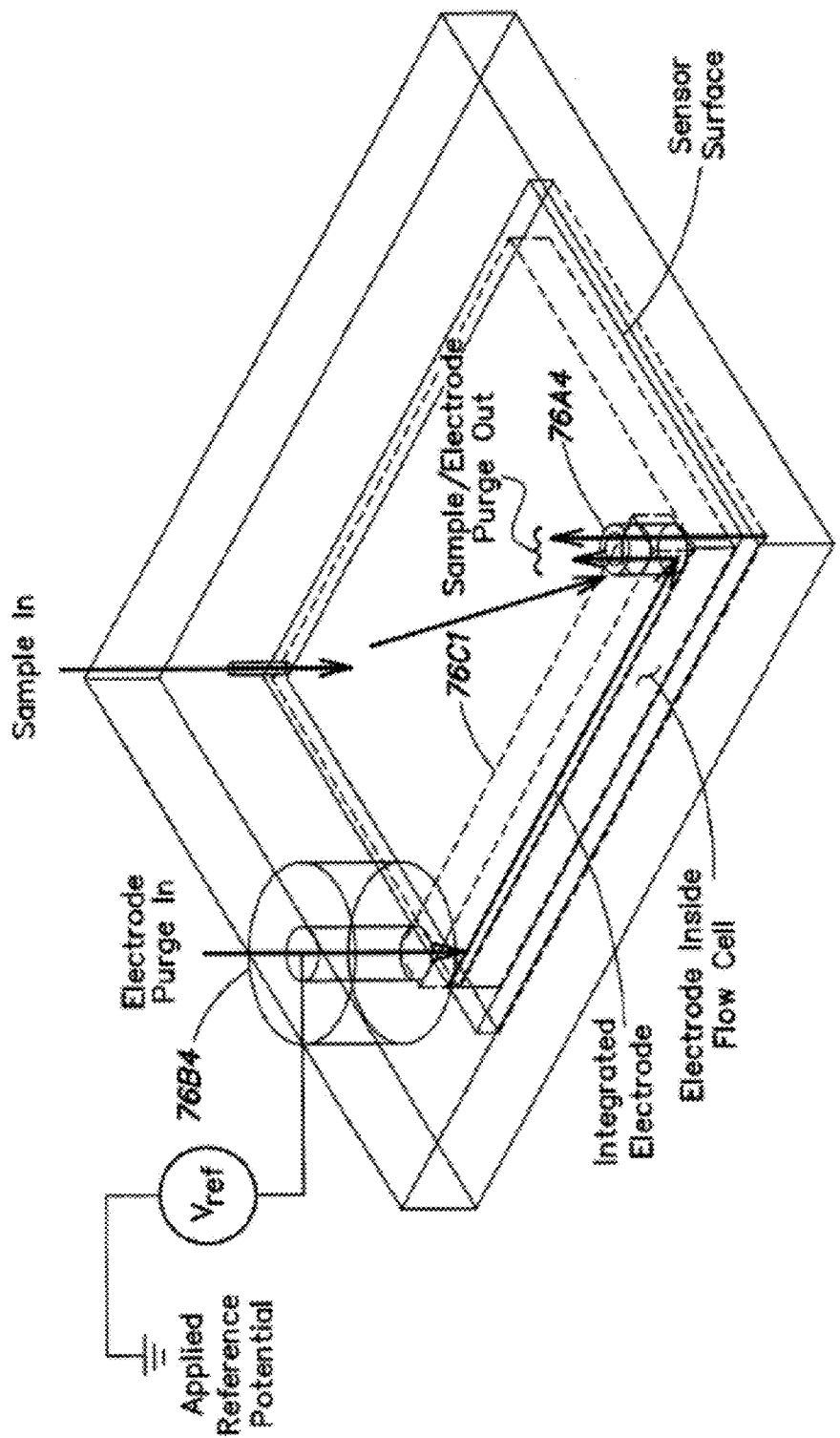
Figure 76D:
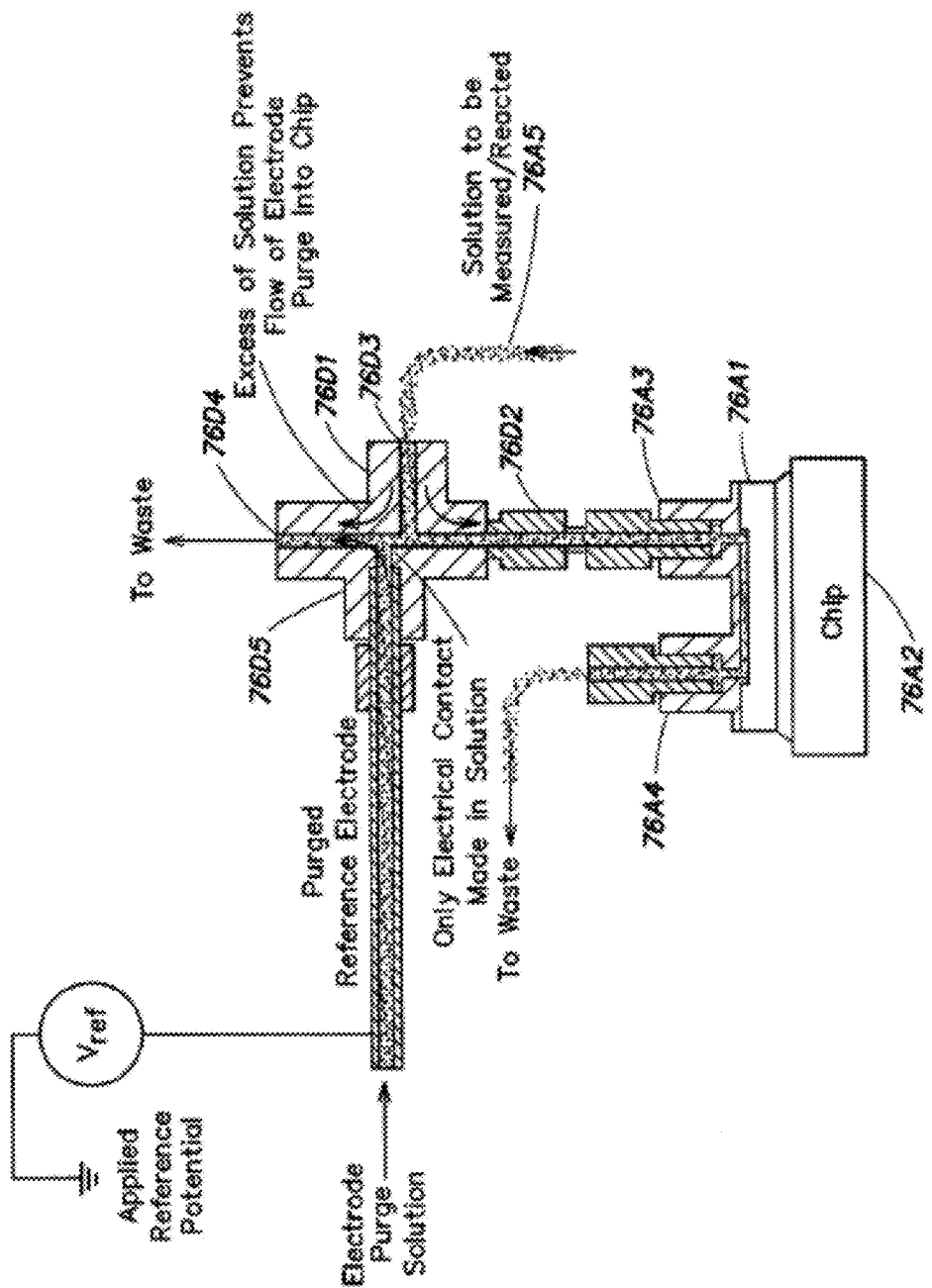
FIG. 76D is a diagrammatic illustration of a cross-section of a second example of a fluid-fluid reference electrode interface in which the reference electrode is introduced upstream in the reagent path from the flow cell.

As a further alternative embodiment, depicted in FIG. 76C, the electrode structure may be integrated into or disposed within the flow cell itself. This may be done in two distinctly different ways. First, the electrode solution may be introduced into the flow chamber and flowed from an inlet 76B4 into the flow cell (provided for that purpose) to an outlet port 76A4 through which both the electrode solution and the reagent flow exit the flow chamber. If both fluids are arranged to move through the chamber in a laminar flow, they will not intermix (or them will be little mixing and interaction) until they reach the outlet. So there need not be a barrier between the two fluids. Their entire region of contact will be the locus of fluid-fluid interfacing, which may provide considerably more surface for that interface than the other illustrated alternatives. Second, a fluid conduit may be provided adjacent to the flow chamber or even fully or partly within the flow chamber, with a non-conductive exterior. The electrode may extend along the interior of the conduit, between an electrode fluid inlet and a fluid outlet that permits the electrode solution to interface with the reagent flow, such as in a common outlet conduit 76A4.

In the foregoing examples, the reference potential is introduced either in or downstream of the flow cell. However, the same approach is possible with the electrode provided upstream of the flow cell, as shown diagrammatically in FIG. 76D. There, 76A3 is the inlet port to the flow cell and 76A4 is the outlet port, as in FIG. 76A. A cross-connector 76D1 having four ports has a first port 76D2 coupled onto the inlet port. A second port, 76D3, receives the solution to be reacted or measured (e.g., a reagent) via inlet conduit 76A5. A third port, 76D4, is used as a waste outlet port. The fourth port, 76D5, receives the electrode in the same manner as previously shown in FIG. 76A. Within the cross-connector, the electrode solution and the solution to be reacted/measured interact to transmit the reference potential into the flow cell. In contrast with some of the other alternative embodiments, however, at least some implementations of this embodiment may require that the solution to be measured/reacted must have a sufficiently high flow rate as to prevent flow of the electrode solution into the flow chamber. However, with judicious configuring of the cross-connector, it may still be possible to avoid the need to flow electrode solution continuously.

Further Developments in Fluidics

The delivery of multiple reagent solutions (and wash solutions) in sequence to a common volume (i.e., flow cell or flow chamber) requires selective switching (i.e., multiplexing) the fluid flows. The multiplexing of fluid flows typically introduces characteristics that are undesirable in that they produce less than ideal results, including potential contamination of reagents, for example, and intervals during which sensor response is unusable or unreliable, reducing potential throughput. The volume of interest, specifically where various reagents must commonly flow to reach the flow cell, is relatively large. This competes with the requirement of cleanliness, as a previously flowing reagent must be completely washed out of the common volume before the next reagent can flow through it to the flow cell. This takes time and consumes wash solution. The characteristic of high volume usually stems from the bulk of valve mechanics that is used to operate the multiplexing action. The presence of valve mechanisms in or near the common volume also competes with the requirement of cleanliness directly, as the valves often present high surface area and/or crevice-type volumes that can retain unwanted reagents. Hence, it would be desirable to provide an improved switching mechanism for reagent flow, to reduce the time required for switching fluids and to minimize cross-contamination.

As exemplified in the embodiment illustrated in FIGS. 78A-78E, instead of multiplexing multiple reagents right at the location of valves used to control their flow, the reagents may be multiplexed downstream of the valving, within a passive micro-fluidic multiplexer circuit that acts as a kind of union. The challenge of presenting a union to multiple reagents is to deliver only a single selected reagent to the chip (i.e., flow cell) input, while having no diffusion-transported effluent from any other reagent input. A simple nodal junction would not satisfy this requirement, as all incoming reagent lines, not being shuttered by valves directly at the junction, could freely diffuse into one another. The disclosed fluidic circuits overcome this difficulty by employing laminar flow or fluid resistance networks to discard diffuse effluent to a waste location.

Figure 78A:
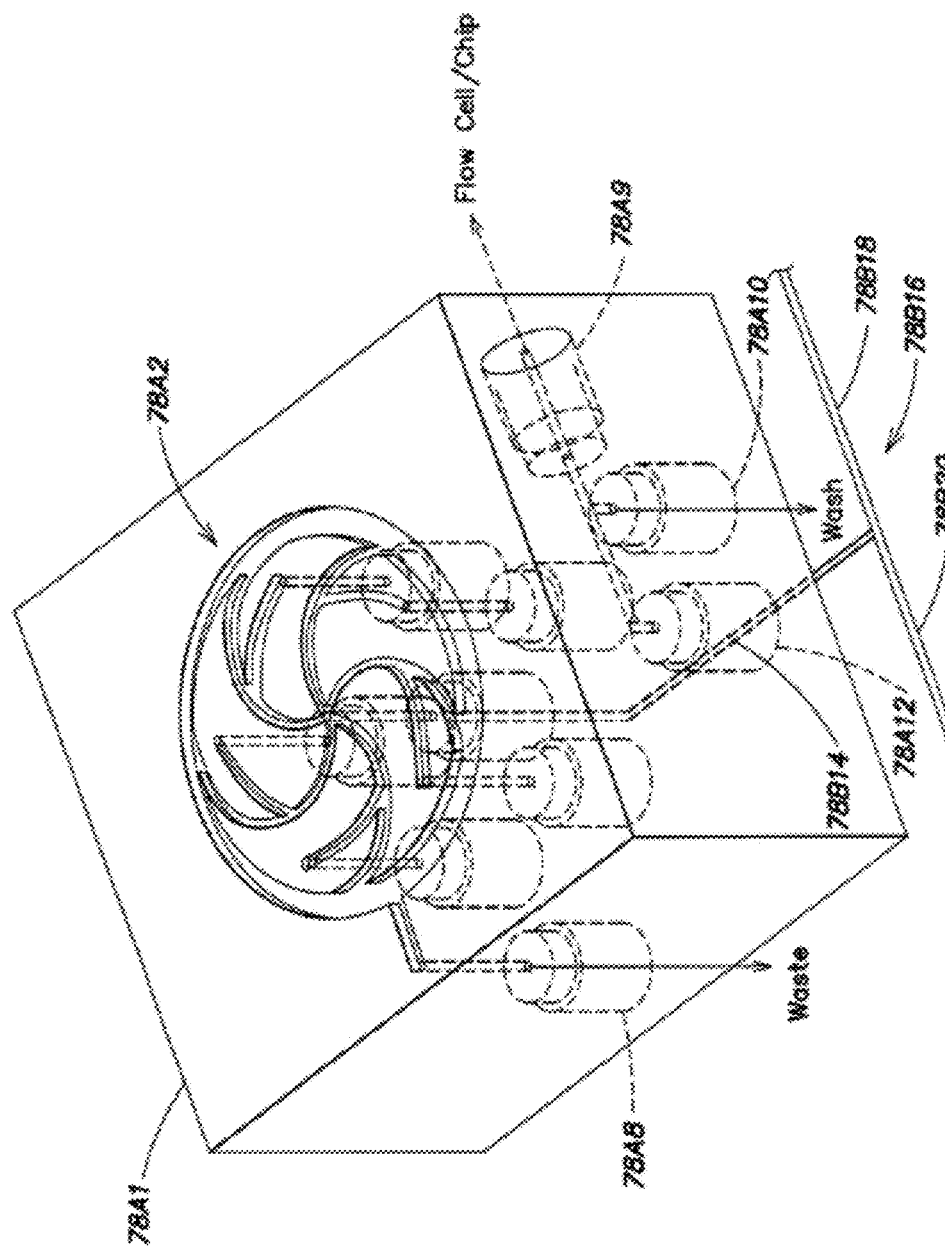
FIG. 78A is an isometric, see-through, diagrammatic illustration of one example of a flow multiplexer for supplying fluids to a flow cell as shown herein.
Figure 78B:
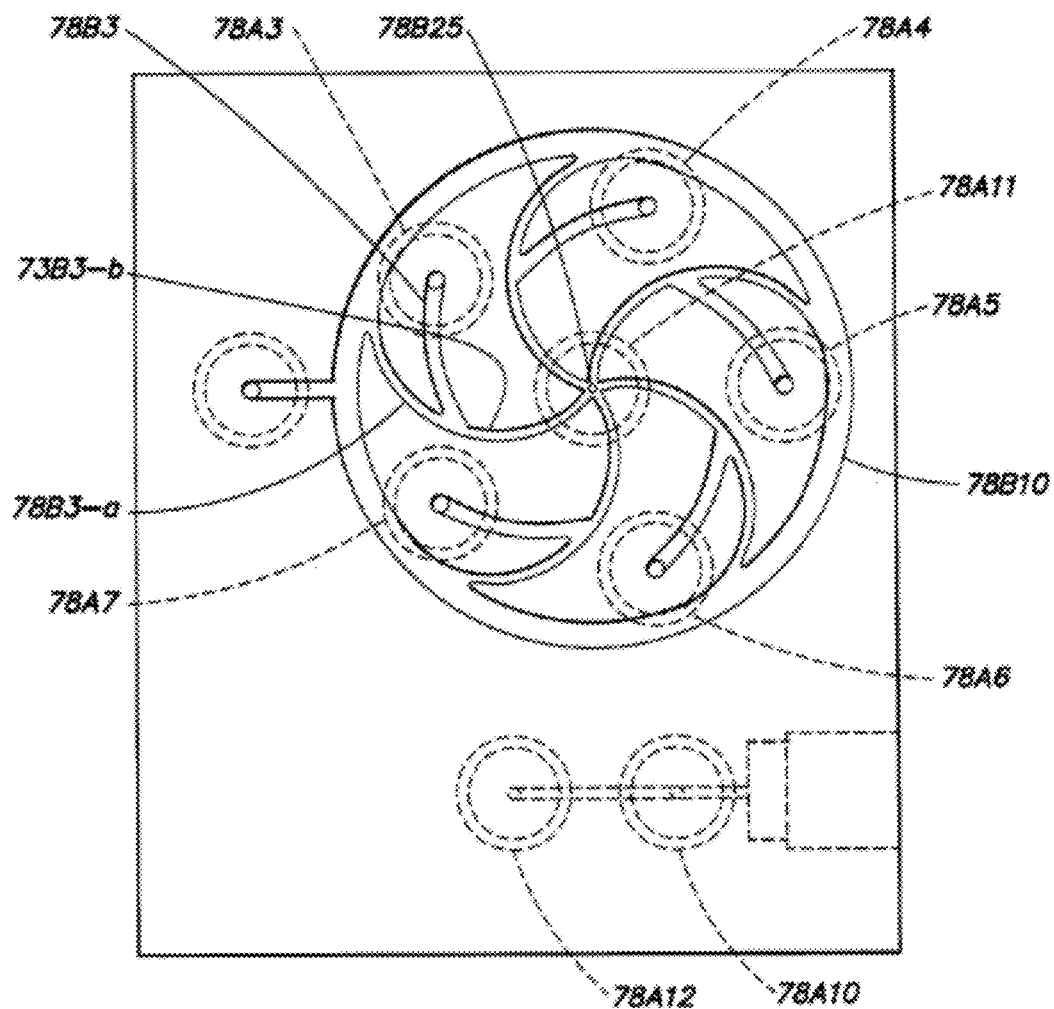
FIG. 78B is a top view of the apparatus of FIG. 78A.
Figure 78D:
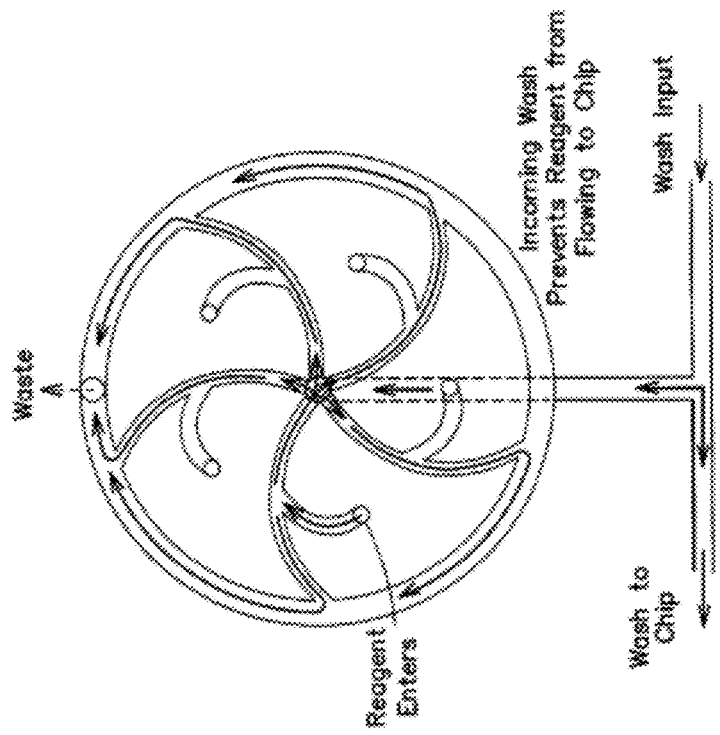
FIG. 78D is a diagrammatic illustration of flow through the multiplexer member of FIGS. 78A and 78B during ship washing and reagent priming modes
Figure 78C:
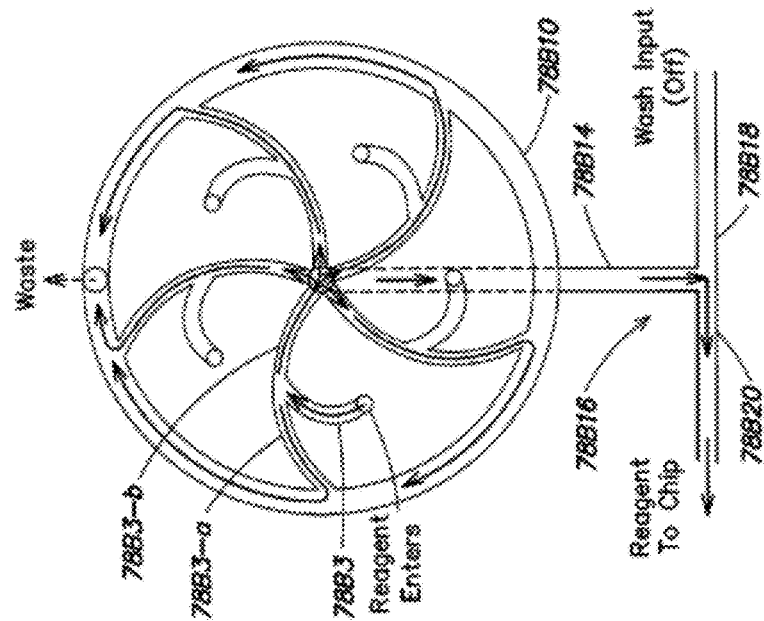
FIG. 78C is a diagrammatic illustration of flow through the multiplexer member of FIGS. 78A and 78B during reagent delivery mode.
Figure 78E:
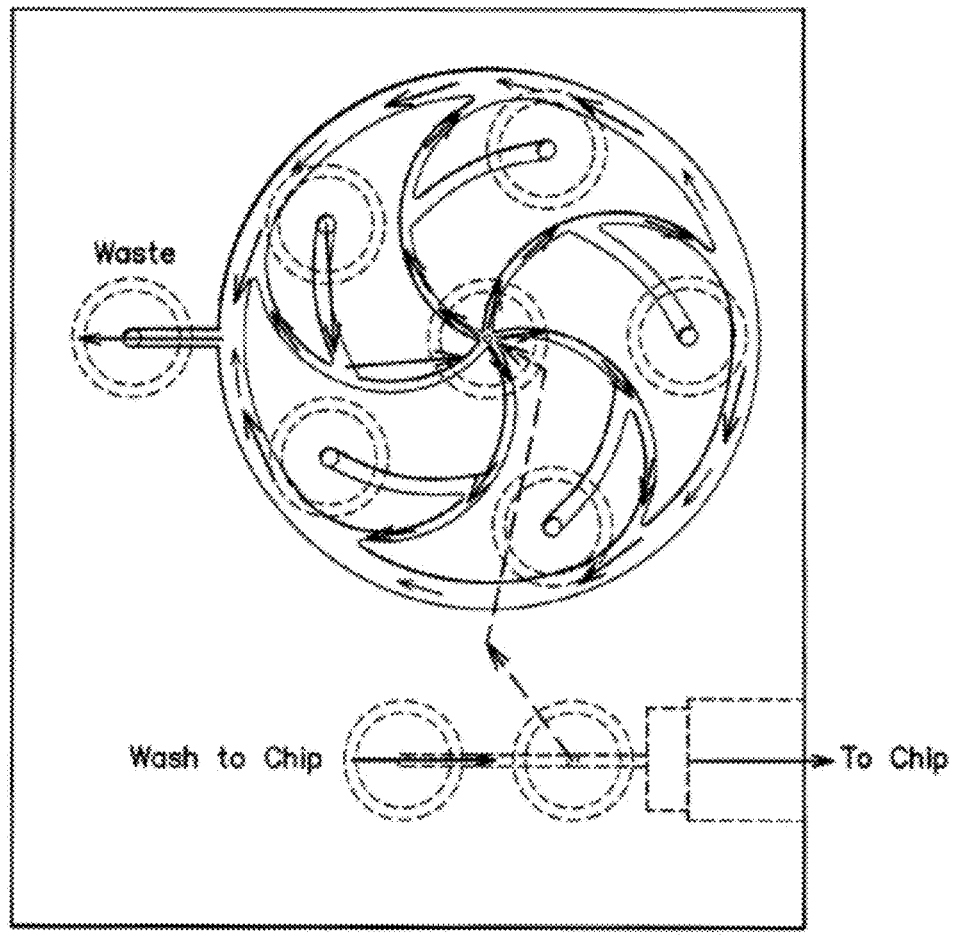
FIG. 78E is another diagrammatic illustration of wash solution flow through the multiplexer member.

The multiplexer circuit comprises a (optional) housing 778A1 supporting a fluid multiplexer member 78A2 and having reagent input ports 78A3-78A6, a wash input port 78A7, a waste output port 78A8, a chip (flow cell) output port 78A9, a wash solution inlet port 78A10, a multi-use central port 78A11 and a multi-purpose outlet supply port 778A12. (Each reagent is treated in like fashion and the structure of the multiplexer member is the same for each reagent and for the wash solution, so the pertinent structure will be discussed in detail only for one reagent, it being understood that such discussion applies as well to the structures for the other solutions.) Each reagent input feeds into the underside of a corresponding curved (e.g., semi-circular) laminar channel such as channel 78B3, in FIG. 78B. Channel 78B3 may, for example, be on the order of 0.5 mm on a cross-sectional side and a curvature 5 mm in diameter. The ends of the laminar channel feed into two restriction channels (e.g., 78B3-a and 78B3-b), with reduced cross sectional area and length of approximately 1 cm. A first one of the restriction channels, 78B3-a, connects to an outer, circular channel, 78B10, which feeds the fluid flow to the waste outlet 78A8. The second of the restriction channels, 78B3-b, leads to directly to a port 78A11 in the center of the structure, extending downwardly in the drawing. Referring to FIGS. 78C and 78D (which show the multiplexer in reflection relative to FIGS. 78A and 78B), port 78A11 connects to a first leg 78B14 of a T-shaped conduit structure 78B16, which has a second leg 78B18 that receives the wash solution input and a third leg 78B20 that supplies solutions to the flow cell fluid input.

On each of the solution feeds, a two-way valve is employed (not shown), upstream of the multiplexer member.

There are two modes of operation for the multiplexer circuit. In a first mode, a reagent is introduced via the multiplexer to the chip. In a second mode, a wash solution clears the multiplexer and the chip.

Figure 79:
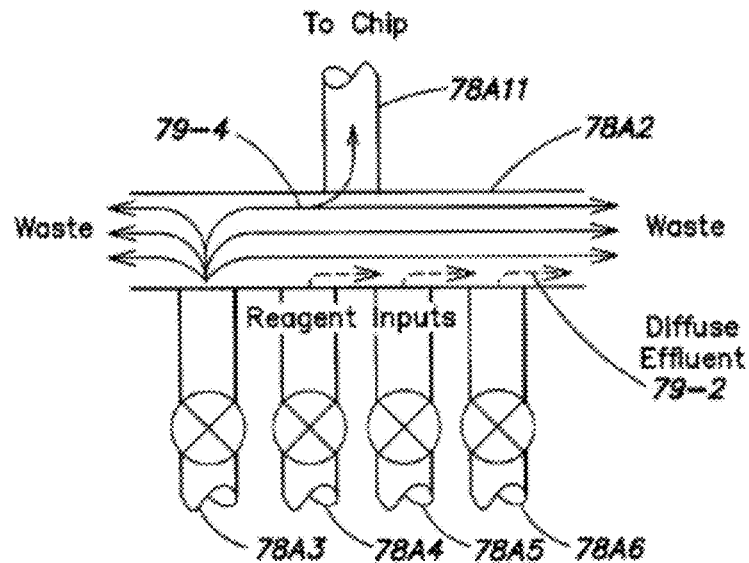
FIG. 79 is a diagrammatic illustration of flows in the apparatus of FIGS. 78A-78E.

In the first mode, the upstream valve on the wash solution input is turned off and no wash solution flows into conduit leg 78B18. Selection of a particular reagent is performed by opening its associated upstream valve. Downstream valves (also not shown, to avoid obfuscation) for both the chip and waste outlets are also opened, Two basic processes commence: a) referring to FIGS. 78C and 78E, the selected reagent entering via 78B3 is driven to the waste output in the multiplexer circuit, traveling in opposing directions from its point of entry and through both restriction channels 78B3-*a* and 78B3-*b*, and b) some typically smaller percentage of the reagent flows downward into port 78A11 into conduit 78B14 and thence upward into port 78A12 and through the chip output port 78A9 toward the chip. The restriction channels are intended to dominate the resistance of the system, albeit quite small, such that the reagent flow to waste is balanced between the two paths. While reagent traverses the laminar channel, it is possible for effluent from the other reagent inputs to diffuse into the reagent stream. However, as illustrated in FIG. 79, this diffuse effluent 79-2 remains in the lower lamina of the stream and continues on to the waste output along with the flow occurring via channel 78B3-*b*, That is, with no flows entering the other fluid inlet ports, the solution entering port 78A3, into channel 78B3, flows from channel 78B3-*b* to the waste port via the semicircular channels associated with each of the other inlet ports, sweeping out solutions that otherwise might diffuse into the incoming fluid. At the same time, a portion of the incoming reagent is directed toward the chip from the upper lamina, 79-4, where the concentration of effluent is close to zero, via aperture 78B25 into port 78A11 and thence as above described. A side view of this phenomenon is illustrated in FIG. 79.

Between reagent flows, wash solution is fed into the circuit, in the second mode. FIG. 78D illustrates the wash flow. Wash solution flows both to the chip via ports 78A10 and 78A9, and through the laminar channel structure to waste via port 78A8. In this way, both the chip and laminar channel structure are cleaned of the previous reagent material before a subsequent reagent is introduced. There is also a short priming period prior to reagent flow to the chip, where the reagent flows to waste while the chip is again washed. This brings the multiplexer to a state of stable concentration of the new reagent, while preventing reagent from immediately entering the chip.

The parameters indicated are merely suggested values, and may be adjusted through a large range.

When the reference electrode is place upstream of the flow cell, the port 78A9 provides a convenient location for its introduction.

The need for only two-way valves is advantageous from a simplicity point of view. Also, the valves can be located very remotely upstream of the multiplexer, and therefore can be placed in almost any location within the supporting instrument. The small physical size of the multiplexer, having no integrated valves or other bulky structures, suggests that it can be located directly at the chip location, greatly reducing the total common volume and providing high spatial and temporal gradients between wash solution and reagent.

Figure 80A:
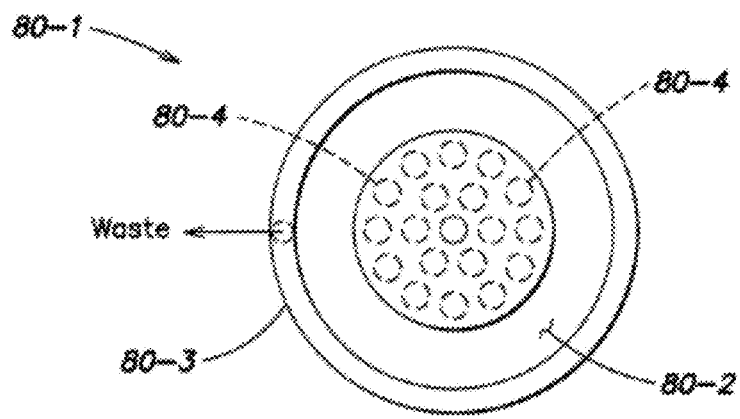
FIGS. 80A and 80B are, respectively, top and side views of an alternative "two-dimensional" fluid multiplexer.
Figure 80B:
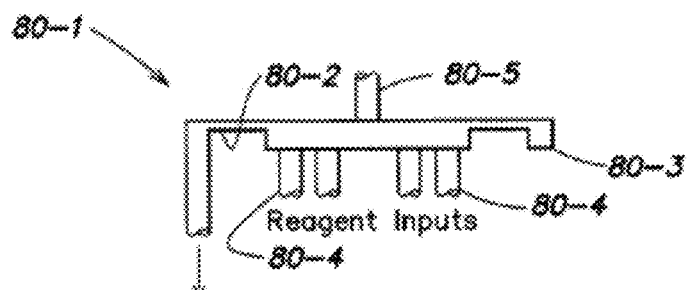

Also feasible is a "two-dimensional" (i.e., thin, disc-like) version of this circuit that would allow tighter packing of reagent inputs, as indicated in FIGS. 80A and 80B at 80-1. This would be particularly useful if a very large number of reagents were required. Instead of flowing in only two opposite directions of a linear channel, such a device will permit radial flow across a circular channel. A shallow restrictive ring 80-2 replaces the restriction channels. A relatively deep and low resistance ring on the outermost section can serve as the waste output. Reagent inputs are supplied at 80-4 and the output is taken at 80-5.

A variation of this two-dimensional structure can be made which does not rely on laminar flow to separate out the diffuse effluent. The reagent inputs are essentially packed in a single circle centered on the chip output. Instead of a free and open two-dimensional channel throughout the circuit, narrow channels connect the reagent inputs to both the chip output and waste ring. When a particular reagent input flows, it enters the central node and both exits to the chip and sweeps past the other reagent inputs on its way to the waste ring. Diffuse effluent from those ports enters the stream to waste, but cannot diffuse upstream toward the chip output. The relative fluidic resistances of the various channels can be adjusted for various performances characteristics (effluent isolation, waste rate minimization, etc.).

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "of" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

Sensor Calibration

In regard to FIG. 17, and as discussed above, the array controller 250 reads one or more analog output signals (e.g., Vout1 and Vout2) including multiplexed respective pixel voltage signals from the array 100 and then digitizes these respective pixel signals to provide measurement data to the computer 260. In turn, the computer 260 can store and/or process the measurement data. In an embodiment, the array controller 250 can be configured to perform or facilitate various calibration and diagnostic functions.

The array controller 250 can calibrate the gain of the sensors in the array 100 to provide an optimal number of sensors within an acquisition window of the array controller 250, according to an embodiment of the present invention. As referred to herein, the acquisition window is a voltage range for an analog-to-digital converter (e.g., ADC 254 of FIG. 17) that captures an output voltage for a maximal number of sensors at an optimal voltage for a reference electrode (e.g., reference electrode 76 of FIG. 17). For different analytes/solutions that flow over the sensors in the array, a shift in pH in the sensor system can occur and cause a shift in the electrical characteristics of the sensors. Due to the shift in electrical characteristics, one or more sensors in the array can fall outside of the acquisition window. A goal of method 8100 (discussed in detail below), among others, is to determine an optimal acquisition window for the array controller and/or the sensor array so as to maximize the number of sensors that are available for measurement in a chemical/biological experiment (e.g., DNA sequencing).

Figure 81:
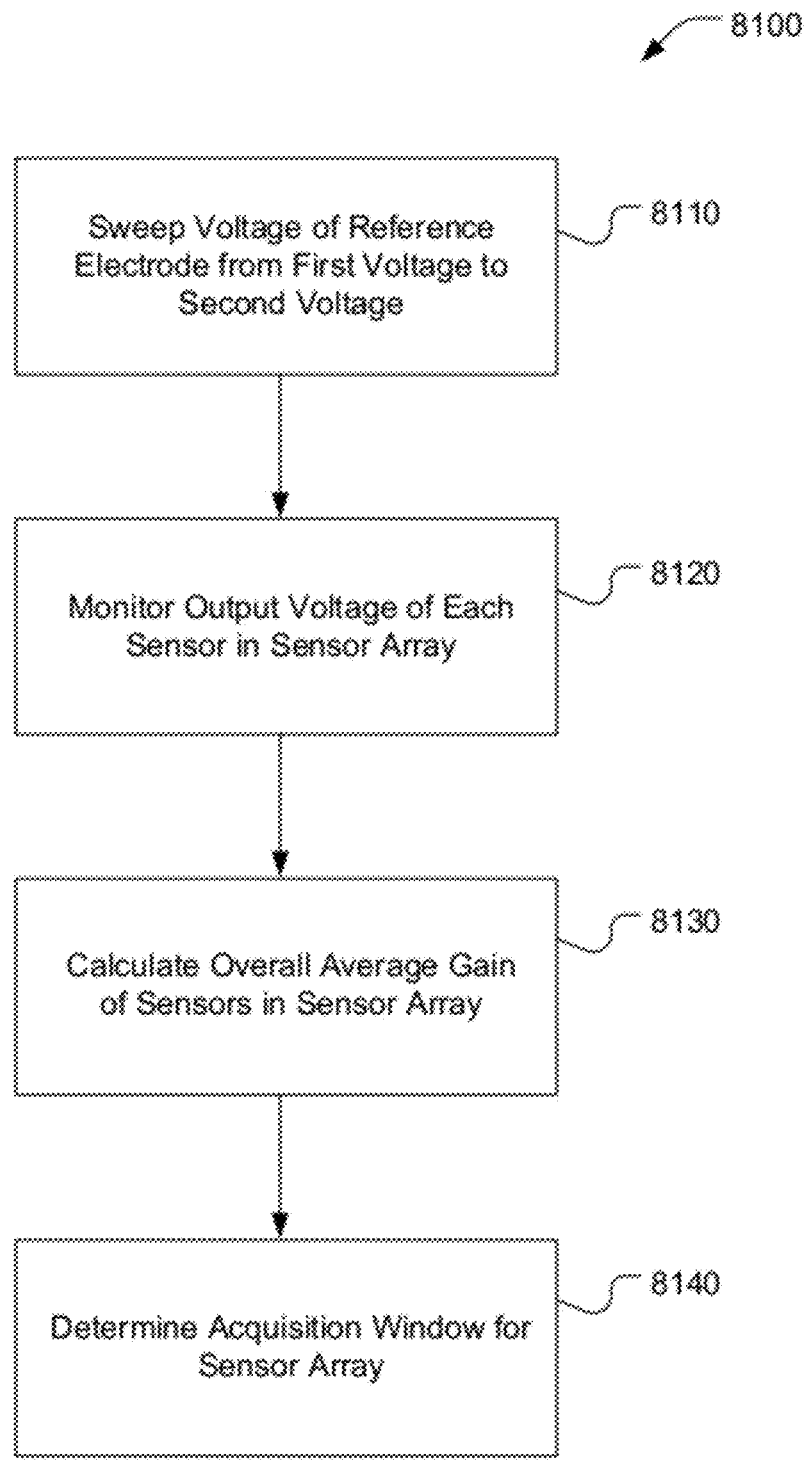
FIG. 81 is an illustration of an embodiment of a method for determining an acquisition window for a sensor array.

FIG. 81 is an illustration of an embodiment of a method 8100 for determining an acquisition window for a sensor array. The method 8100 can be applied to a system that includes a sensor array and an array controller such as, for example and without limitation, the system depicted in FIG. 17.

In step 8110, a voltage of a reference electrode is swept from a first voltage to a second voltage at a predetermined voltage increment. The reference electrode can be, for example, the reference electrode 76 of FIG. 17, where the reference electrode 76 is in fluid communication with the array 100 (as discussed in detail above). Further, in an embodiment, the first and second voltages can be defined by an operating range of the sensor array (e.g., array 100 of FIG. 17). The operating range of the sensor array can be, for example and without limitation, between −2.0 and +2.0 V. Here, the first voltage can be −2.0 V and the second voltage can be +2.0 V, where the predetermined voltage increment can be, for example and without limitation, 10, 50, or 100 mV. Based on the description herein, a person of ordinary skill in the art will recognize that the first and second voltages, as well as the predetermined voltage increment, can be other voltages.

In step 8120, the output voltage of each of the sensors in the array is monitored at one or more voltages within the first and second voltages (of step 8110). In an embodiment, at each reference electrode voltage increment, the gain of each of the sensors can be calculated. The gain of a particular sensor can be calculated by dividing a change in output voltage of the sensor ($\Delta V_{OUT}$) by a change in input voltage of the sensor ($\Delta V_{IN}$), according to an embodiment of the present invention. That is, for a particular reference electrode voltage increment ($V_{REF\_ELEC}$), the reference electrode voltage can be raised by another predetermined voltage increment ($\Delta V_{IN}$). In an embodiment, the other predetermined voltage increment ($\Delta V_{IN}$) is a smaller voltage increment than the predetermined voltage increment of step 8110. The other predetermined voltage increment ($\Delta V_{IN}$) can be, for example and without limitation, 1, 2, or 5 mV. Based on this adjusted reference electrode voltage ($V_{REF\_ELEC}+\Delta V_{IN}$), the output of the sensor can be monitored, where the change in output voltage of the sensor ($\Delta V_{OUT}$) is determined by the difference in the output voltage of the sensor at the particular reference electrode voltage ($V_{REF\_ELEC}$) and the adjusted reference electrode voltage ($V_{REF\_ELEC}+\Delta V_{IN}$). In essence, the reference electrode voltage serves as an input voltage (e.g., a gate voltage) to each of the sensors in the array.

For instance, at a reference electrode voltage of 100 mV ($V_{REF\_ELEC}$), the reference electrode voltage can be raised by another predetermined reference electrode voltage increment of 5 mV ($\Delta V_{IN}$). The gain of the sensor can be calculated by dividing a change in output voltage of the sensor by a change in input voltage of the sensor (e.g., Gain=$\Delta V_{OUT}/\Delta V_{IN}$). For the above example, the change in output voltage of the sensor ($\Delta V_{OUT}$) is determined by the difference in the output voltage of the sensor with the reference electrode voltage of 100 mV and the output voltage of the sensor with the reference electrode voltage of 105 mV. Assuming that the change in output voltage of the sensor is 3 mV, then the gain for the sensor would be 0.6 (i.e., Gain=$\Delta V_{OUT}/\Delta V_{IN}$=3 mV/5 mV=0.6).

In step 8130, an overall average gain of the sensors in the array is calculated at each of the one or more voltages (of step 8120). In an embodiment, the overall average gain of the sensors in the array can be calculated for each reference electrode voltage increment. For example, if the array includes 262,144 sensors (e.g., a sensor array with 512 rows by 512 columns), the overall average gain of the sensors at a particular reference electrode voltage can be calculated by dividing the sum of the individual gain values for the 262,144 sensors by 262,144. The individual gain value for each of the 262,144 sensors can be calculated based on the gain value description above (step 8120). Based on the description herein, a person of ordinary skill in the art will recognize that the number of sensors in the array can be more or less than 262,144 sensors, and that a sensor array with 262,144 is used for exemplary purposes.

In step 8140, an acquisition window is determined for the sensor array. In an embodiment, the acquisition window includes a maximum distribution of sensors that provide a maximal overall average gain at a particular reference electrode voltage. In an embodiment, the maximal overall average gain of the sensors in the array can occur within a range of reference electrode voltages such as, for example and without limitation, a voltage range within the first and second voltages (of step 8110). For instance, for a reference electrode voltage range of −200 to +200 mV, the maximal overall average gain of the sensors in the array can be at its highest. Alternatively, in an embodiment, the maximal overall average gain of the sensors can be within a predetermined gain range for the reference electrode voltage range. The predetermined gain range can include the highest overall average gain of the sensors. A goal of step 8140, among others, is to determine a particular reference electrode voltage where not only the overall average gain of the sensors is at a maximal value, but also a maximum number of sensors is available for measurement in a chemical/biological experiment (e.g., DNA sequencing).

The maximum number of sensors can be determined by sweeping a voltage window within the reference electrode voltage range that provides the maximal overall average gain, according to an embodiment of the present invention. For instance, if the reference electrode voltage range that provides the maximal overall average gain is between −200 and +200 mV, then the voltage window can be swept within this voltage range. In an embodiment, the voltage boundaries of the voltage window can be determined by a resolution of an analog-to-digital converter (e.g., ADC 254 of FIG. 17) used to sample the output signals of the sensors in the array. For instance, for an 8-bit ADC with a 1 mV resolution, the size of the voltage window can be 256 mV (i.e., $2^8$=256). As would be understood by a person of ordinary skill in the art, if a different voltage resolution is required, then the size of the voltage window can be adjusted. Alternatively, a different number of bits can be implemented in the ADC to achieve the different voltage resolution. Based on the description herein, a person of ordinary skill in the art will recognize that the resolution of the ADC can vary and is implementation-specific.

For exemplary purposes and to facilitate in the explanation of step 8140, a 256 mV voltage window and a reference electrode voltage range that provides the maximal overall average gain of −200 and +200 mV will be used. The center of the 256 mV voltage window can be swept at a predetermined voltage increment (e.g., 10, 20, 30, 40, or 50 mV) between the reference electrode voltage range of −200 to +200 mV, according to an embodiment of the present invention. For instance, at −200 mV, one end of the voltage window can be at −328 mV and the other end of the voltage window can be at −72 mV (e.g., |−328 mV−(−72 mV)|=256 mV).

Figure 82:
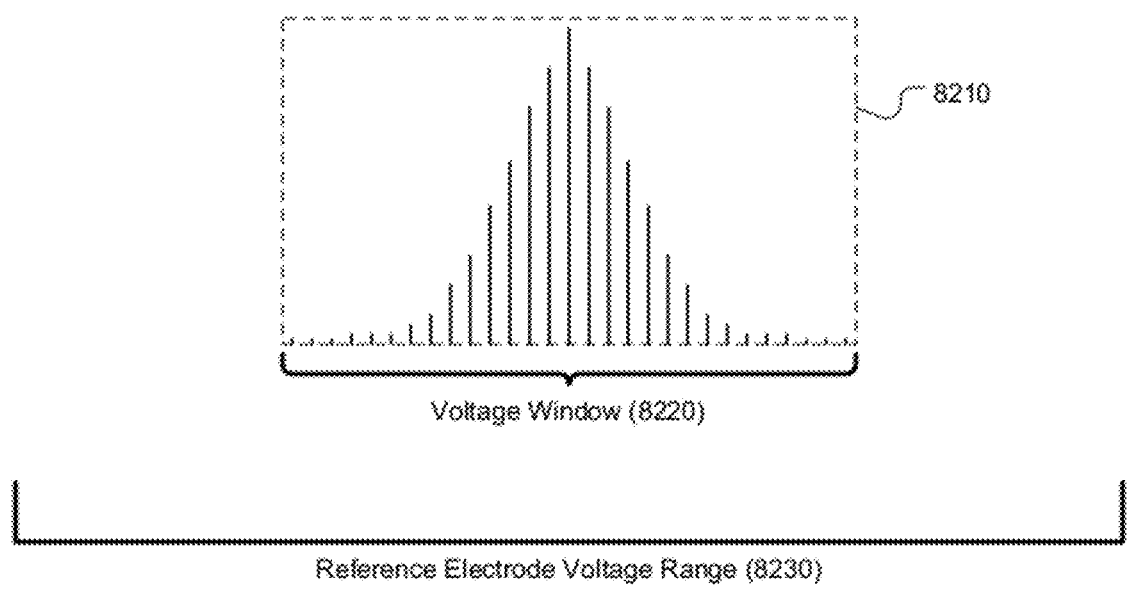
FIG. 82 is an illustration of an example sensor distribution with a voltage window at a particular reference electrode voltage.

At each voltage increment within the reference electrode voltage range, the distribution of sensors that provide an output signal can be determined, according to an embodiment of the present invention. FIG. 82 is an illustration of an example sensor distribution 8210 within a voltage window 8220 at a particular reference electrode value. FIG. 82 also illustrates a reference electrode voltage range 8230, in which the voltage window 8220 is swept. For step 8140, after the voltage window completes its sweep of the reference electrode voltage range, the acquisition window is determined by the voltage window with the reference electrode voltage that has the highest sensor distribution (e.g., maximum number of sensors that provide an output signal).

In summary, method 8100 of FIG. 81 determines a particular reference electrode voltage where not only the overall average gain of the sensors in an array is at a maximal value, but also a maximum number of sensors is available for measurement in a chemical/biological experiment (e.g., DNA sequencing). For an array controller (e.g., array controller 250 of FIG. 17) with multiple ADCs (e.g., ADC 254 of FIG. 17), method 8100 can be applied to each of the ADCs to determine an optimal acquisition window for a sensor array (e.g., array 100 of FIG. 17).

Example Computer System

Figure 83:
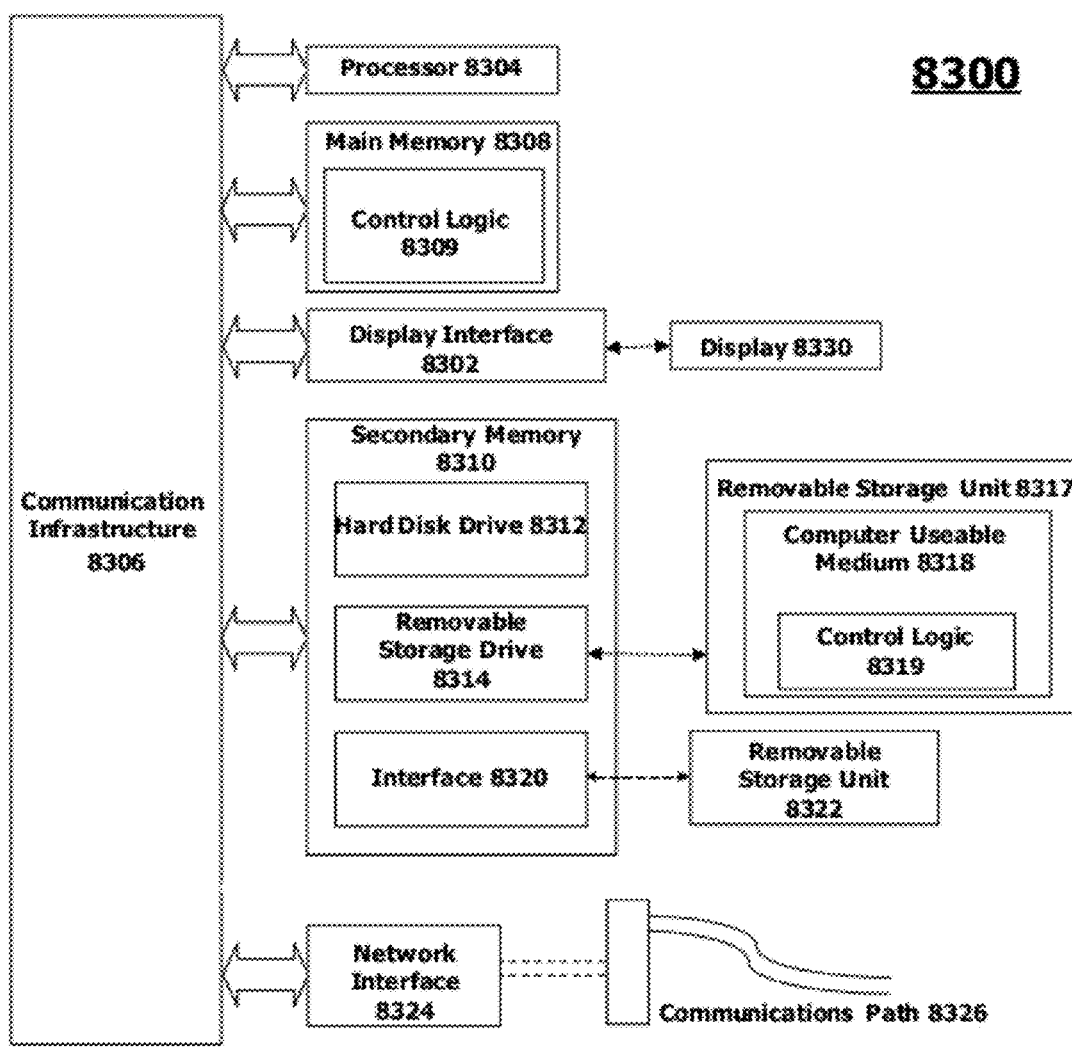
FIG. 83 is an illustration of an example computer system in which embodiments of the present invention can be implemented.

Various aspects of the embodiments described herein may be implemented in software, firmware, hardware, or a combination thereof. FIG. 83 is an illustration of an example computer system 8300 in which embodiments described herein, or portions thereof, can be implemented as computer-readable code. For example, the methods illustrated in the flowchart of FIG. 18B and flowchart 8100 of FIG. 81 can be implemented in computer system 8300. Various embodiments are described in terms of this example computer system 8300.

After reading the description herein, it will become apparent to a person skilled in the relevant art how to implement embodiments described herein using other computer systems and/or computer architectures. For instance, in an embodiment, computer system 8300 (or a portion thereof) may be a stand-alone computing system (e.g., array controller 250 of FIG. 17) that communicates with may 100 of FIG. 17 to perform the methods illustrated in the flowchart of FIG. 18B and flowchart 8100 of FIG. 81. In another embodiment, computer system 8300 (or a portion thereof) can be integrated as an on-chip controller on a device incorporating array 100 to perform the methods illustrated in the flowchart of FIG. 18B and flowchart 8100 of FIG. 81. In yet another embodiment, computer system 8300 (or a portion thereof) can be implemented as a stand-alone computer system and an on-chip controller that communicates with array 100 to perform the methods illustrated in the flowchart of FIG. 18B and flowchart 8100 of FIG. 81.

Computer system 8300 can be any commercially available and well known computer capable of performing the functions described herein, such as computers available from International Business Machines, Apple, Sun, HP, Dell, Compaq, Cray, etc.

Computer system 8300 includes one or more processors, such as processor 8304. Processor 8304 may be a special purpose or a general-purpose processor. Processor 8304 is connected to a communication infrastructure 8306 (e.g., a bus or network).

Computer system 8300 also includes a main memory 8308, preferably random access memory (RAM), and may also include a secondary memory 8310. Main memory 8308 has stored therein a control logic 8309 (computer software) and data. Secondary memory 8310 can include, for example, a hard disk drive 8312, a removable storage drive 8314, and/or a memory stick, Removable storage drive 8314 can comprise a floppy disk drive, a magnetic tape drive, an optical disk drive, a flash memory, or the like. The removable storage drive 8314 reads from and/or writes to a removable storage unit 8317 in a well-known manner, Removable storage unit 8318 can include a floppy disk, magnetic tape, optical disk, etc. which is read by and written to by removable storage drive 8318. As will be appreciated by persons skilled in the relevant art, removable storage unit 8317 includes a computer-usable storage medium 8318 having stored therein a control logic 8319 (e.g., computer software) and/or data.

In alternative implementations, secondary memory 8310 can include other similar devices for allowing computer programs or other instructions to be loaded into computer system 8300. Such devices can include, for example, a removable storage unit 8322 and an interface 8320. Examples of such devices can include a program cartridge and cartridge interface (such as those found in video game devices), a removable memory chip (e.g., EPROM or PROM) and associated socket, and other removable storage units 8322 and interfaces 8320 which allow software and data to be transferred from the removable storage unit 8322 to computer system 8300.

Computer system 8300 also includes a display 8330 that communicates with computer system 8300 via a display interface 8302. Although not shown in computer system 8300 of FIG. 83, as would be understood by a person skilled in the relevant art, computer system 8300 can communicate with other input/output devices such as, for example and without limitation, a keyboard, a pointing device, and a Bluetooth device.

Computer system 8300 can also include a communications interface 8324. Communications interface 8324 allows software and data to be transferred between computer system 8300 and external devices. Communications interface 8324 can include a modem, a network interface (such as an Ethernet card), a communications port, a PCMCIA slot and card, or the like. Software and data transferred via communications interface 8324 are in the form of signals, which may be electronic, electromagnetic, optical, or other signals capable of being received by communications interface 8324. These signals are provided to communications interface 8324 via a communications path 8326. Communications path 8326 carries signals and may be implemented using wire or cable, fiber optics, a phone line, a cellular phone link, a RF link or other communications channels.

In this document, the terms "computer program medium" and "computer-usable medium" are used to generally refer to media such as removable storage unit 8317, removable storage unit 8318, and a hard disk installed in hard disk drive 8312. Computer program medium and computer-usable medium can also refer to memories, such as main memory 8308 and secondary memory 8310, which can be memory semiconductors (e.g., DRAMs, etc.). These computer program products provide software to computer system 8300.

Computer programs (also called computer control logic) are stored on main memory 8308 and/or secondary memory 8310. Computer programs may also be received via communications interface 8324. Such computer programs, when executed, enable computer system 8300 to implement embodiments described herein. In particular, the computer programs, when executed, enable processor 8304 to implement processes described herein, such as the steps in the methods illustrated in the flowchart of FIG. 18B and flowchart 8100 of FIG. 81, discussed above. Accordingly, such computer programs represent controllers of the computer system 8300. Where embodiments are implemented using software, the software can be stored on a computer program product and loaded into computer system 8300 using removable storage drive 8314, interface 8320, hard drive 8312 or communications interface 8324.

Based on the description herein, a person skilled in the relevant art will recognize that the computer programs, when executed, can enable one or more processors to implement processes described above, such as the steps in the methods illustrated in the flowchart of FIG. 18B and flowchart 8100 of FIG. 81. In an embodiment, the one or more processors can be part of a computing device incorporated in a clustered computing environment or server farm. Further, in an embodiment, the computing process performed by the clustered computing environment such as, for example, the steps in the methods illustrated in the flowchart of FIG. 18B and flowchart 8100 may be carried out across multiple processors located at the same or different locations.

Based on the description herein, a person of skilled in the relevant art will recognize that the computer programs, when executed, can enable multiple processors to implement processes described above, such as the steps in the methods illustrated in the flowchart of FIG. 18B and flowchart 8100 of FIG. 81. In an embodiment, the computing process performed by the multiple processors can be carried out across multiple processors located at a different location from one another.

Embodiments are also directed to computer program products including software stored on any computer-usable medium (e.g., computer useable medium 8318 and 8331). Such software, when executed in one or more data processing device, causes a data processing device(s) to operate as described herein. Embodiments employ any computer-usable or -readable medium, known now or in the future. Examples of computer-usable mediums include, but are not limited to, primary storage devices (e.g., any type of random access memory), secondary storage devices (e.g., hard drives, floppy disks, CD ROMS, ZIP disks, tapes, magnetic storage devices, optical storage devices, MEMS, nanotechnological storage devices, etc.), and communication mediums (e.g., wired and wireless communications networks, local area networks, wide area networks, intranets, etc.).

Embodiments have been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

While various embodiments have been described above, it should be understood that they have been presented by way of example only, and not limitation. It will be understood by those skilled in the relevant art that various changes in form and details can be made therein without departing from the spirit and scope of the embodiments described herein. It should be understood that this description is not limited to these examples. This description is applicable to any elements operating as described herein. Accordingly, the breadth and scope of this description should not be limited by any of the above-described exemplary embodiments, but should be defined only in accordance with the following claims and their equivalents.

What is claimed is:

1. A method for calibrating a sensor array with a plurality of sensors, the method comprising:
   sweeping a voltage of a reference electrode from a first voltage to a second voltage, wherein the reference electrode is in fluid communication with the sensor array;
   monitoring an output voltage of each of the plurality of sensors at one or more voltages within the first and second voltages;
   calculating an overall average gain of the plurality of sensors at each of the one or more voltages; and
   determining an acquisition window for the sensor array, wherein the acquisition window comprises a maximum distribution of sensors that provide a maximal overall average gain at a particular reference electrode voltage.

2. The method of claim 1, wherein the sweeping the voltage of the reference electrode comprises sweeping the voltage of the reference electrode within an operating range of the sensor array.

3. The method of claim 1, wherein the sweeping the voltage of the reference electrode comprises sweeping the voltage of the reference electrode at a predetermined voltage increment from the first voltage to the second voltage.

4. The method of claim 1, wherein the calculating the overall average gain comprises dividing a sum of individual gain values for each of the plurality of sensors by the number of sensors in the plurality of sensors.

5. The method of claim 1, wherein the determining the acquisition window comprises determining a voltage range of the reference electrode, within the first and second voltages, that provides the maximal overall average gain.

6. The method of claim 5, wherein the determining the voltage range comprises determining the voltage range of the reference electrode with the highest overall average gain or the voltage range of the reference electrode that produces the overall average gain within a predetermined gain range.

7. The method of claim 5, wherein determining the acquisition window comprises sweeping a voltage window within the voltage range of the reference electrode that provides the maximal overall average gain.

8. The method of claim 7, wherein the sweeping the voltage window comprises determining a maximum distribution of sensors that provide the maximal overall average gain at the particular reference electrode voltage, and wherein the particular reference electrode voltage is within the voltage range of the reference electrode that provides the maximal overall average gain.

9. A computer program product comprising a computer-usable medium having computer program logic recorded thereon that, when executed by one or more processors, calibrates a sensor array with a plurality of sensors, the computer program logic comprising:
first computer readable program code that enables a processor to sweep a voltage of reference electrode from a first voltage to a second voltage, wherein the reference electrode is in fluid communication with the sensor array;
second computer readable program code that enables a processor to monitor an output voltage of each of the plurality of sensors at one or more voltages within the first and second voltages;
third computer readable program code that enables a processor to calculate an overall average gain of the plurality of sensors at each of the one or more voltages; and
fourth computer readable program code that enables a processor to determine an acquisition window for the sensor array, wherein the acquisition window comprises a maximum distribution of sensors that provide a maximal overall average gain at a particular reference electrode voltage.

10. The computer program product of claim 9, wherein the first computer readable program code comprises:
fifth computer readable program code that enables a process to sweep the voltage of the reference electrode within an operating range of the sensor array.

11. The computer program product code of claim 9, wherein the first computer readable program code comprises:
fifth computer readable program code that enables a processor to sweep the voltage of the reference electrode at a predetermined voltage increment from the first voltage to the second voltage.

12. The computer program product code of claim 9, wherein the third computer readable program code comprises:
fifth computer readable program code that enables a process to divide a sum of individual gain values for each of the plurality of sensors by the number of sensors in the plurality of sensors.

13. The computer program product code of claim 9, wherein the fourth computer readable program code comprises:
fifth computer readable program code that enables a processor to determine a voltage range of the reference electrode, within the first and second voltages, that provides the maximal overall average gain.

14. The computer program product code of claim 13, wherein the fifth computer readable program code comprises:
sixth computer readable program code that enables a processor to determine the voltage range of the reference electrode with the highest overall average gain or the voltage range of the reference electrode that produces the overall average gain within a predetermined gain range.

15. The computer program product code of claim 13, wherein the fourth computer readable program code comprises:
fifth computer readable program code that enables a processor to sweep a voltage window within the voltage range of the reference electrode that provides the maximal overall average gain.

16. The computer program product code of claim 15, wherein the fifth computer readable program code comprises:
sixth computer readable program code that enables a processor to determine the maximum distribution of sensors that provide the maximal overall average gain at the particular reference electrode voltage, and wherein the particular reference electrode voltage is within the voltage range of the reference electrode that provides the maximal overall average gain.

17. A system comprising:
a reference electrode;
a sensor array with a plurality of sensors, wherein the sensor array is in fluid communication with the reference electrode; and
an array controller coupled to the sensor array, wherein the array controller is configured to:
sweep a voltage of the reference electrode from a first voltage to a second voltage;
monitor an output voltage of each of the plurality of sensors at one or more voltages within the first and second voltages;
calculate an overall average gain of the plurality of sensors at each of the one or more voltages; and
determine an acquisition window for the sensor array, wherein the acquisition window comprises a maximum distribution of sensors that provide a maximal overall average gain at a particular reference electrode voltage.

18. The system of claim 17, wherein the array controller is configured to determine a voltage range of the reference electrode, within the first and second voltages, that provides the maximal overall average gain.

19. The system of claim 18, wherein the array controller is configured to sweep a voltage window within the voltage range of the reference electrode that provides the maximal overall average gain.

20. The system of claim 19, wherein the array controller is configured to determine a maximum distribution of sensors that provide the maximal overall average gain at the particular reference electrode voltage, and wherein the particular reference electrode voltage is within the voltage range of the reference electrode that provides the maximal overall average gain.

* * * * *

UNITED STATES PATENT AND TRADEMARK OFFICE
CERTIFICATE OF CORRECTION

PATENT NO. : 8,776,573 B2  Page 1 of 1
APPLICATION NO. : 13/333602
DATED : July 15, 2014
INVENTOR(S) : Todd Rearick et al.

It is certified that error appears in the above-identified patent and that said Letters Patent is hereby corrected as shown below:

ON THE TITLE PAGE

ITEM (57) ABSTRACT SECTION

10th line of the Abstract
        following "sensor" and before "can be" delete "may" and insert
        --array--.

Signed and Sealed this
Fourth Day of November, 2014

Michelle K. Lee
*Deputy Director of the United States Patent and Trademark Office*